United States Patent
Ameriks et al.

(10) Patent No.: US 11,993,601 B2
(45) Date of Patent: *May 28, 2024

(54) MONOACYLGLYCEROL LIPASE MODULATORS

(71) Applicant: Janssen Pharmaceutica NV, Beerse (BE)

(72) Inventors: Michael K. Ameriks, San Diego, CA (US); Gang Chen, San Diego, CA (US); Chaofeng Huang, San Diego, CA (US); Brian Ngo Laforteza, San Diego, CA (US); Suchitra Ravula, San Diego, CA (US); Wei Zhang, San Diego, CA (US)

(73) Assignee: Janssen Pharmaceutica NV

( * ) Notice: Subject to any disclaimer, the term of this patent is extended or adjusted under 35 U.S.C. 154(b) by 0 days.

This patent is subject to a terminal disclaimer.

(21) Appl. No.: 18/160,647

(22) Filed: Jan. 27, 2023

(65) Prior Publication Data

US 2023/0242531 A1 Aug. 3, 2023

Related U.S. Application Data

(63) Continuation of application No. 17/132,406, filed on Dec. 23, 2020, now Pat. No. 11,597,728, which is a continuation of application No. 16/586,263, filed on Sep. 27, 2019, now abandoned.

(60) Provisional application No. 62/738,684, filed on Sep. 28, 2018.

(51) Int. Cl.
 *C07D 471/18* (2006.01)
 *C07D 519/00* (2006.01)

(52) U.S. Cl.
 CPC .......... *C07D 471/18* (2013.01); *C07D 519/00* (2013.01)

(58) Field of Classification Search
 CPC .................... C07D 471/18; C07D 519/00
 See application file for complete search history.

(56) References Cited

U.S. PATENT DOCUMENTS

| | | | |
|---|---|---|---|
| 4,812,462 A | 3/1989 | Blankley et al. | |
| 4,816,463 A | 3/1989 | Blankley et al. | |
| 5,338,744 A | 8/1994 | Dudley et al. | |
| 8,431,704 B2 | 4/2013 | Love et al. | |
| 8,513,248 B2 | 8/2013 | Dean et al. | |
| 8,871,760 B2 | 10/2014 | Brotherton-pleiss et al. | |
| 8,933,236 B2 | 1/2015 | Chowdhury et al. | |
| 8,987,249 B2 | 3/2015 | Anderskewitz et al. | |
| 9,056,874 B2 | 6/2015 | Adams et al. | |
| 9,066,946 B2 | 6/2015 | Alcazar Vaca et al. | |
| 9,156,824 B2 | 10/2015 | Dally et al. | |
| 9,181,271 B2 | 11/2015 | Li et al. | |
| 9,233,974 B2 | 1/2016 | Link et al. | |
| 9,242,969 B2 | 1/2016 | Barsanti et al. | |
| 9,273,047 B2 | 3/2016 | Hunt et al. | |
| 9,273,947 B2 | 3/2016 | Kim et al. | |
| 9,290,476 B2 | 3/2016 | Leonard et al. | |
| 9,375,418 B2 | 6/2016 | Schmidt et al. | |
| 9,434,715 B2 | 9/2016 | Conza et al. | |
| 9,447,045 B2 | 9/2016 | Chen et al. | |
| 9,464,084 B2 | 10/2016 | Alcazar Vaca et al. | |
| 9,532,992 B2 | 1/2017 | Kuntz et al. | |
| 9,561,228 B2 | 2/2017 | Haq et al. | |
| 9,617,272 B2 | 4/2017 | Kumar et al. | |

(Continued)

FOREIGN PATENT DOCUMENTS

| CN | 101778850 A | 7/2010 |
|---|---|---|
| FR | 2857363 A1 | 1/2005 |

(Continued)

OTHER PUBLICATIONS

Ahn et al., "Enzymatic Pathways That Regulate Endocannabinoid Signaling in the Nervous System", Chem Rev., 2008, p. 1687-1707, vol. 108, No. 5.

(Continued)

*Primary Examiner* — Rebecca L Anderson

(57) ABSTRACT

Bridged compounds of Formula (I) and Formula (II), pharmaceutical compositions containing them, methods of making them, and methods of using them including methods for treating disease states, disorders, and conditions associated with MGL modulation, such as those associated with pain, psychiatric disorders, neurological disorders (including, but not limited to major depressive disorder, treatment resistant depression, anxious depression, bipolar disorder), cancers and eye conditions.

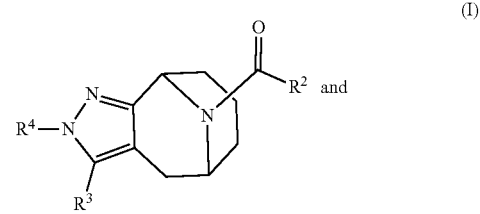

(I)

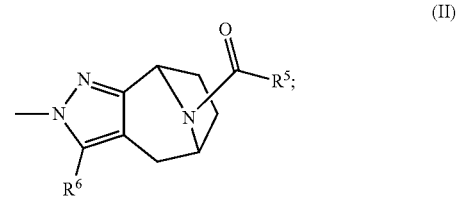

(II)

wherein $R^2$, $R^3$ $R^4$, $R^5$ and $R^6$ are defined herein.

20 Claims, No Drawings

(56) References Cited

U.S. PATENT DOCUMENTS

| | | |
|---|---|---|
| 9,637,456 B2 | 5/2017 | Amans et al. |
| 10,112,937 B2 | 10/2018 | Alcazar Vaca et al. |
| 10,150,765 B2 | 12/2018 | Alcazar Vaca et al. |
| 10,150,766 B2 | 12/2018 | Letavic et al. |
| 2005/0096345 A1 | 5/2005 | Thompson et al. |
| 2006/0217448 A1 | 9/2006 | Kelly et al. |
| 2006/0293337 A1 | 12/2006 | Evans et al. |
| 2008/0275052 A1 | 11/2008 | Dhar et al. |
| 2010/0035893 A1 | 2/2010 | Hoornaert |
| 2010/0144758 A1 | 6/2010 | Dillon et al. |
| 2011/0252717 A1 | 10/2011 | Graf Fernandez |
| 2011/0294790 A1 | 12/2011 | Mantegani et al. |
| 2012/0190680 A1 | 7/2012 | Bakthavatchalam et al. |
| 2014/0213554 A1 | 7/2014 | Wu et al. |
| 2014/0251902 A1 | 9/2014 | Solheim et al. |
| 2014/0275015 A1 | 9/2014 | Alcazar Vaca et al. |
| 2014/0275056 A1 | 9/2014 | Etavic et al. |
| 2014/0275096 A1 | 9/2014 | Ameriks et al. |
| 2014/0275120 A1 | 9/2014 | Alcazar Vaca et al. |
| 2015/0290190 A1 | 10/2015 | Ameriks et al. |
| 2015/0322062 A1 | 11/2015 | Alcazar Vaca et al. |
| 2016/0016962 A1 | 1/2016 | Ameriks et al. |
| 2016/0024082 A1 | 1/2016 | Alcazar Vaca et al. |
| 2016/0039809 A1 | 2/2016 | Alcazar Vaca et al. |
| 2016/0039836 A1 | 2/2016 | Letavic et al. |
| 2016/0046596 A1 | 2/2016 | Banerjee et al. |
| 2017/0081342 A1 | 3/2017 | Cheung et al. |
| 2018/0118749 A1 | 5/2018 | Andres Gil et al. |

FOREIGN PATENT DOCUMENTS

| | | |
|---|---|---|
| JP | 2012525351 A | 10/2012 |
| JP | 2013/505220 A | 2/2013 |
| WO | 2004/014374 A1 | 2/2004 |
| WO | 2004013144 A1 | 2/2004 |
| WO | 2006/023750 A2 | 3/2006 |
| WO | 2006/080884 A1 | 8/2006 |
| WO | 2006/110516 A1 | 10/2006 |
| WO | 2009/002423 A2 | 12/2008 |
| WO | 2009/023623 A1 | 2/2009 |
| WO | 2009095253 A1 | 8/2009 |
| WO | 2010/125101 A1 | 11/2010 |
| WO | 2010/125102 A1 | 11/2010 |
| WO | 2011050202 A1 | 4/2011 |
| WO | 2011/103715 A1 | 9/2011 |
| WO | 2011/121137 A1 | 10/2011 |
| WO | 2012/040048 A2 | 3/2012 |
| WO | 2012/054721 A1 | 4/2012 |
| WO | 2012054716 A1 | 4/2012 |
| WO | 2012145581 A1 | 10/2012 |
| WO | 2014/152589 A1 | 9/2014 |
| WO | 2014/152621 A1 | 9/2014 |
| WO | 2014152604 A1 | 9/2014 |
| WO | 2014/154897 A1 | 10/2014 |
| WO | 2015/025026 A1 | 2/2015 |
| WO | 2016/039977 A1 | 3/2016 |
| WO | 2016/039983 A1 | 3/2016 |
| WO | 2016040789 A1 | 3/2016 |
| WO | 2016158956 A1 | 10/2016 |
| WO | 2017087858 A1 | 5/2017 |
| WO | 2018134698 A1 | 7/2018 |
| WO | 2020065613 A1 | 4/2020 |
| WO | 2020065614 A1 | 4/2020 |
| WO | 2020211798 A1 | 10/2020 |
| WO | 2021064569 A1 | 4/2021 |
| WO | 2021/191359 A1 | 9/2021 |

OTHER PUBLICATIONS

Alekseev, et al., Use of the Graebe-Ullmann Reaction in the Synthesis of 8-Methyl-Y-Carboline and Isomeric Aromatic Aza-Y-Carbolines, Chemistry of Heterocyclic Compounds, 2012, pp. 1235-1250, vol. 48 Issue 8.

Alhouayek et al., "Increasing endogenous 2-arachidonoylglycerol levels counteracts colitis and related systemic inflammation", FASEB J., Aug. 2011, 2711-2721, vol. 25, No. 8.

Arbeloa, et al., P2X7 receptor blockade prevents ATP excitotoxicity in neurons and reduces brain damage after ischemia, Neurobiology of Disease, 2012, pp. 954-961, vol. 45.

Arulkumaran, et al., A potential therapeutic role for P2X7 receptor (P2X7R) antagonists in the treatment of inflammatory diseases, Expert Opin Investig, 2011, pp. 897-915, vol. 20 Issue 7.

Avignone, et al., Status Epilepticus Induces a Particular Microglial Activation State Characterized by Enhanced Purinergic Signaling, The Journal of Neuroscience, Sep. 10, 2008, pp. 9133-9144, vol. 28 Issue 37, Society for Neuroscience.

Bagshawe, "Antibody-Directed Enzyme prodrug Therapy : A Review", Drug Development Research, , vol. 34; pp. 220-230 (1995).

Bartlett, et al., The P2X7 Receptor Channel: Recent Development and the use of P2X7 antagonists in model of Disease, Pharmocol Rev, 2014, pp. 638-675, vol. 66.

Basso, et al., Behavioral profile of P2X7 receptor knockout mice in animal models of depression and anxiety: Relevance for neuropsychiatric disorders, Behavioural Brain Research, Oct. 18, 2008, pp. 83-90, vol. 198, Elsevier B.V.

Bedse et al., "Functional Redundancy Between Canonical Endocannabinoid Signaling Systems in the Modulation of Anxiety", Biol Psychiatry, Oct. 1, 2017, 488-499, vol. 82, No. 7.

Bedse et al., "Therapeutic endocannabinoid augmentation for mood and anxiety disorders: comparative profiling of FAAH, MAGL and dual inhibitors", Transl Psychiatry, Apr. 26, 2018, 92, vol. 8, No. 1.

Benito et al., "Cannabinoid CB2 Receptors in Human Brain Inflammation", British Journal of Pharmacology, 2008, 277-285, vol. 153.

Bennet, et al. (Editor), "Part XIV Oncology", Cecil Textbook of Medicine, vol. 1, 20th Edition: pp. 1004-1010 (1996).

Berge, S.M. et al., "Pharmaceutical Salts", J. Pharm. Sci., 1977, pp. 1-19, vol. 66 Issue 1.

Bernal-Chico et al., "Blockade of monoacylglycerol lipase inhibits oligodendrocyte excitotoxicity and prevents demyelination in vivo", Glia, Jan. 2015, 163-176, vol. 63, No. 1.

Bertolini, et al., "A New Rational Hypothesis for the Pharmacophore of the Active Metabolite of Leflunomide, a Potent Immunosuppressive Drug", Journal of Medicinal Chemistry, vol. 40 (13); pp. 2011-2016 (1997).

Bodor, Nicholas "Novel Approaches to the Design of Safer Drugs: Soft Drugs and Site-Specific Chemical Delivery Systems", Advances in Drug Research, vol. 13; pp. 256-331, (1984).

Bourzac, et al., Glucose Transporter 2 Expression is Down Regulated Following P2X7 Activation in Enterocytes, Journal of Cellular Physiology, 2013, pp. 120-129, vol. 228.

Buczynski and Parsons, "Quantification of brain endocannabinoid levels: methods, interpretations and pitfalls", Brit J Pharmacol, 2010, 423-442, vol. 160, No. 3.

Bundgaard, Hans "Design of Products", Design of Products, pp. 1-3, (1985).

Capuron, et al., Immune system to brain signaling: Neuropsychopharmacological implications, Pharmacology & Therapeutics, 2011, pp. 226-238, vol. 130, Elsevier Inc.

Carroll et al., "Synthesis and Pharmacological Characterization of Nicotinic Acetylcholine Receptor Properties of (+)- and (−)-Pyrido-[3,4-b]homotropanes", Journal of Medicinal Chemistry, 2006, 3244-3250, vol. 49, No. 11.

Cavuoto et al., "The Expression of Receptors for Endocannabinoids in Human and Rodent Skeletal Muscle", Biochemical and Biophysical Research Communications, 2007, 105-110, vol. 364.

Chen et al., "Monoacylglycerol Lipase Is a Therapeutic Target for Alzheimer's Disease", Cell Rep., Nov. 29, 2012, 1329-1339, vol. 2, No. 5.

Chessell, et al., Disruption of the P2X7 purinoceptor gene abolishes chronic inflammatory and neuropathic pain, Pain, Jan. 5, 2005, pp. 386-396, vol. 114, Elsevier B.V.

Chinnadurai et al., "Monoacylglycerol lipase inhibition as potential treatment for interstitial cystitis", Medical Hypotheses, Oct. 2019, 109321, vol. 131.

(56) References Cited

OTHER PUBLICATIONS

Christensen et al., "Efficacy and safety of the weight-loss drug rimonabant: a meta-analysis of randomised trials", The Lancet, 2007, 1706-1713, vol. 370.
Chu, et al., Inhibition of P2X7 receptor ameliorates transient global cerebral ischemia/reperfusion injury via modulating inflammatory responses in the rat hippocampus, Journal of Neuroinflammation, 2012, pp. 1-10, vol. 9 Issue 69.
Considine, G.D., Van Nostrand's Encyclopedia of Chemistry,, Encyclopedia of Chemistry, 2005, pp. 261, Chapter 5.
Covey et al., "Inhibition of endocannabinoid degradation rectifies motivational and dopaminergic deficits in the Q175 mouse model of Huntington's disease", Neuropsychopharmacology, 2018, 2056-2063, vol. 43.
Curry et al., "Monoacylglycerol Lipase Inhibitors Reverse Paclitaxel-Induced Nociceptive Behavior and Proinflammatory Markers in a Mouse Model of Chemotherapy-Induced Neuropathy", J Pharmacol Exp Ther., Jul. 2018, 169-183, vol. 366, No. 1.
Dantzer, Robert, Cytokine, Sickness Behavior, and Depression, Immunol Allergy Clin N Am, 2009, pp. 247-264, vol. 29.
Database Chemcats Ambinter Stock Screening Collection Accession No. 2040381923, Feb. 13, 2008.
Database Chemcats Ambinter Stock Screening Collection Accession No. 2040548370, Feb. 13, 2008.
Database Chemcats Ambinter Stock Screening Collection Accession No. 2046454718, Feb. 13, 2008.
Database Chemcats Ambinter Stock Screening Collection Database Accession No. 2040033692, Feb. 13, 2008.
Database Chemcats Aurora Screening Library Accession No. 2037938546, Sep. 6, 2007.
Database Chemcats Enamine Screening Library Accession No. 2035772210, Jan. 17, 2008.
Database Chemcats Ryan Scientific Screening Library Accession No. 2042634059, Jan. 25, 2008.
Database Chemcats Ryan Scientific Screening Library Accession No. 2042637020, Jan. 25, 2008.
Database Chemcats Ryan Scientific Screening Library Accession No. 2042676574, Jan. 25, 2008.
Database Chemcats Ryan Scientific Screening Library Accession No. 2043876860, Jan. 25, 2008.
Database Chemcats Ukrorgsynthesis Screening Collection Accession No. 2033253463, Mar. 6, 2007.
Delarasse, et al., The Purinergic Receptor P2X7 Triggers—Secretasedependent Processing of the Amyloid Precursor Protein, The Journal of Biological Chemistry, Nov. 16, 2010, pp. 2596-2606, vol. 286 Issue 4.
Dermer, Gerald B., "Another Anniversary For the War on Cancer",, Nature Publishing Group, Mar. 12, 1994, p. 320, vol. 12 No 2.
Devane et al., "Isolation and structure of a brain constituent that binds to the cannabinoid receptor", Science, 1992, 1946-1949, vol. 258.
Di Marzo et al., "Endocannabinoids and the regulation of their levels in health and disease", Curr Opin Lipidol, 2007, 129-140, vol. 18.
Di Marzo et al., "Plant, Synthetic, and Endogenous Cannabinoids in Medicine", Annu Rev Med., 2006, 553-574., vol. 57.
Diaz-Hernandez, et al., Altered P2X7-receptor level and function in mouse models of Huntington's disease and therapeutic efficacy of antagonist administration, The FASEB Journal, 2009, pp. 1893-1906, vol. 23.
Diaz-Hernandez, et al., In vivo P2X7 inhibition reduces amyloid plaques in Alzheimer's disease through GSK3 and secretases, Neurobiology of Aging, 2012, pp. 1816-1828, vol. 33.
Dinh et al., "Brain monoglyceride lipase participating in endocannabinoid inactivation", Proc Natl Acad Sci USA, Aug. 6, 2002, 10819-10824, vol. 99, No. 16.
Donnelly-Roberts, et al., [3H]A-804598 ([3H]2-cyano-1-[(1S)-1-phenylethyl]-3-quinolin-5-ylguanidine) is a novel, potent, and selective antagonist radioligand for P2X7 receptors, Neuropharmacology, 2009, pp. 223-229, vol. 56.
Duan, et al., P2X7 Receptors: Properties and Relevance to CNS Function, GLIA, 2006, pp. 738-746, vol. 54.
Dyatkin et al., Determination of the Absolute Configuration of a Key Tricyclic Component of a Novel Vasopressin Receptor Antagonist by Use of Vibrational Circular Dichroism, Chirality, 2002, pp. 215-219, vol. 14.
Engel, et al., Seizure suppression and neuroprotection by targeting the purinergic P2X7 receptor during status epilepticus in mice, The FASEB Journal, 2012, pp. 1616-1628, vol. 26.
Ferrari, et al., The P2X7 Receptor: A Key Player in IL-1 Processing and Release1, The Journal of Immunology,, 2006, pp. 3877-3883, vol. 176.
Fleisher, et al., "Improved oral drug delivery: solubility limitations overcome by the use of prodrugs", Advanced Drug Delivery Reviews, vol. 19; pp. 115-130 (1996).
Folkes et al., "An endocannabinoid-regulated basolateral amygdala-nucleus accumbens circuit modulates sociability", J Clin Invest., 2020, 1728-1742., vol. 130, Issue 4.
Freshney, et al., Culture of Animal Cells, Manual of Basic Technique, 1983, pp. 1-6, Chapter 1.
Friedle, et al., Recent Patents on Novel P2X7 Receptor Antagonists and their Potential for Reducing Central Nervous System Inflammation, Recent Patents on CNS Drug Discovery, 2010, pp. 35-45, vol. 5.
Furlan-Freguia, et al., P2X7 receptor signaling contributes to tissue factor-dependent thrombosis in mice, The Journal of Clinical Investigation, 2011, pp. 2932-2944, vol. 121 Issue 7.
Ghosh et al., "The monoacylglycerol lipase inhibitor JZL184 suppresses inflammatory pain in the mouse carrageenan model", Life Sci., Mar. 19, 2013, 498-505, vol. 92, No. 8-9.
Golub, et al., Molecular Classification of cancer: Class Discovery and class prediction by gene expression monitoring, Science, 1999, pp. 531-537, vol. 286.
Greene et al., "Chapter 7 Protection for the Amino Group", Protective Groups in Organic Synthesis, Third Edition, John Wiley Sons, 1999, pp. 518-525; 579-580; 620-621.
Grygorowicz, et al., Temporal expression of P2X7 purinergic receptor during the course of experimental autoimmune encephalomyelitis, Neurochemistry International, Sep. 9, 2010, pp. 823-829, vol. 57.
Guile, et al., Antagonists of the P2X7 Receptor. From Lead Identification to Drug Development, Journal of Medicinal Chemistry, May 28, 2009, pp. 3123-3141, vol. 52 Issue 10.
Guindon et al., "Peripheral antinociceptive effects of inhibitors of monoacylglycerol lipase in a rat model of Inflammatory pain", Br J Pharmacol., 2011, 1464-1478, vol. 163.
Gunosewoyo, et al., P2X purinergic receptor ligands recently patented compounds, Expert Opin. Ther Patents, 2010, pp. 625-646, vol. 20 Issue 5.
Hackam, et al., "Translation of Research Evidence From animals to Humans", JAMA, vol. 296 (14): pp. 1731-1732 (2006).
Hajrasouliha et al., "Endogenous cannabinoids contribute to remote ischemic preconditioning via cannabinoid CB2 receptors in the rat heart", Eur J Pharmacol, 2008, 246-252, vol. 579.
Hauer et al., "Glucocorticoid-endocannabinoid interaction in cardiac surgical patients: relationship to early cognitive dysfunction and late depression", Rev Neurosci., 2012, 681-690, vol. 23, No. 5-6.
Herkenam et al., "Cannabinoid receptor localization in brain", Proc. Nat. Acad. Sci., 1990, 1932-1936, vol. 87, No. 5.
Hernandez-Torres et al., "A Reversible and Selective Inhibitor of Monoacylglycerol Lipase Ameliorates Multiple Sclerosis", Angew Chem Int Ed Engl., Dec. 8, 2014, 13765-13770, vol. 53, No. 50.
Hill et al., "Circulating endocannabinoids and N-acyl ethanolamines are differentially regulated in major depression and following exposure to social stress", Psychoneuroendocrinology, Sep. 3, 2009, 1257-1262, vol. 34, No. 8.
Hill et al., "Reductions in circulating endocannabinoid levels in individuals with post-traumatic stress disorder following exposure to the World Trade Center attacks", Psychoneuroendocrinology, 2013, 2952-2961, vol. 38, No. 12.

(56) References Cited

OTHER PUBLICATIONS

Hill et al., "Serum Endocannabinoid Content is Altered in Females with Depressive Disorders: A Preliminary Report", Pharmacopsychiatry, Mar. 2008, 48-53, vol. 41, No. 2.
Hudson, Derek, Methodological Implications of Simultaneous Solid-Phase peptide Synthesis, J.Org.Chem, 1988, pp. 617-624, vol. 53.
International Search Report and Written Opinion for International Application No. PCT/EP2021/057764 dated Jun. 8, 2021.
International Search Report and Written Opinion for International Application No. PCT/IB2019/058240 dated Jan. 10, 2020.
International Search Report and Written Opinion for International Application No. PCT/IB2019/058241 dated Jan. 10, 2020.
International Search Report and Written Opinion for International Application No. PCT/IB2020/059099 dated Nov. 24, 2020.
Ji, et al., P2X7 deficiency attenuates hypertension and renal injury in deoxycorticosterone acetate-salt hypertension, Am J Physiol Renal Physiol, 2012, pp. F1207-F1215, vol. 303.
Jordan, "Tamoxifen: A Most Unlikely Pioneering Medicine", Nature Reviews, vol. 2: pp. 205-213, (Mar. 2003).
Jung et al., "Uncoupling of the endocannabinoid signalling complex in a mouse model of fragile X syndrome", Nature Communications, 2012, 1080., vol. 3.
Katz et al., "Endocannabinoid Degradation Inhibition Improves Neurobehavioral Function, Blood-Brain Barrier Integrity, and Neuroinflammation following Mild Traumatic Brain Injury", J Neurotrauma, Mar. 1, 2015, 297-306, vol. 32, Issue 5.
Keating, et al., P2X7 Receptor-Dependent Intestinal Afferent Hypersensitivity in a Mouse Model of Postinfectious Irritable Bowel Syndrome, The Journal of Immunology, Jun. 22, 2011, pp. 1467-1474, vol. 187.
Keller, et al., "Radiosynthesis and Preclinical Evaluation of [18F]F-DPA, A Novel Pyrazolo[1,5a]pyrimidine Acetamide TSPO Radioligand, in Healthy Sprague Dawley Rats", Molecular Imaging and Biology, 2017, pp. 736-745, vol. 19.
Killeen, et al., Signaling through purinergic receptors for ATP induce human cutaneous innate and adaptive th17 responses:implications in the pathogenesis of psoriasis, The Journal of Immunology, 2013, pp. 4324-4336, vol. 190.
Kim, et al., Blockade of P2X receptor prevents astroglial death in the dentate gyrus following pilocarpine-induced status epilepticus, Neurological research, 2009, pp. 982-988, vol. 31.
Kinsey et al., "Blockade of Endocannabinoid-Degrading Enzymes Attenuates Neuropathic Pain", J Pharmacol Exp Ther., Sep. 2009, 902-910, vol. 330, No. 3.
Larsen, et al., "A text book of Drug Design and Development", Index; pp. 1-18 (1991).
Ligresti et al., "From endocannabinoid profiling to 'endocannabinoid therapeutics'", Curr Opin Chem Biol., Jun. 2009, 321-331, vol. 13, No. 3.
Long et al., "Characterization of Monoacylglycerol Lipase Inhibition Reveals Differences in Central and Peripheral Endocannabinoid Metabolism", Chem Biol., Jul. 31, 2009, 744-753, vol. 16, No. 7.
Long et al., "Selective blockade of 2-arachidonoylglycerol hydrolysis produces cannabinoid behavioral effects", Nat Chem Biol., Jan. 2009, 37-44, vol. 5, No. 1.
Manske, R.H.F. and Kulka, M., "The Skraup Synthesis of Quinolines", Org. Reaction, 1953, 59-98, vol. 7.
Marcellino, et al., On the role of P2X7 receptors in dopamine nerve cell degeneration in a rat model of Parkinson's disease: studies with the P2X7 receptor antagonist A-438079, J Neural Transm, Apr. 13, 2010, pp. 681-687, vol. 117.
Martins, et al., The role of P2X7 purinergic receptors in inflammatory and nociceptive changes accompanying cyclophosphamide-induced hemorrhagic cystitis in mice, British Journal of Pharmacology, 2012, pp. 183-196, vol. 165.
Matsuda et al., "Structure of a cannabinoid recepter and functional expresion of the cloned cDNA", Nature, 1990, 561-564, vol. 346.
Mechoulam et al., "Identification of an endogenous 2-monoglyceride, present in canine gut, that binds to cannabinoid receptors", Biochem Pharmacol, 1995, 83-90, vol. 50.

Miller et al., "Controlled-deactivation cb1 receptor ligands as a novel strategy to lower intraocular pressure", Pharmaceuticals, 2018, 1-8, vol. 11, No. 50.
Muller, et al., Apotential role for P2X7r in allergic airway inflammation in mice and humans, American Journal of Respiratory Cell and molecular Biology, 2011, pp. 456-464, vol. 44.
Mulvihill et al., "Therapeutic potential of monoacylglycerol lipase inhibitors", Life Sci., Mar. 19, 2013, 492-497, vol. 92, No. 8-9.
Munro et al., "Molecular characterization of a peripheral receptor for cannabinoids", Nature, 1993, 61-65, vol. 365.
Nikitenko, A.A., et al., "Selective Hydrolysis of Ethyl 5,6-Dihydro-4H-pyrrolo[1,2-b]pyrazole-2-carboxylate and Ethyl 5,6-Dihydro-4H-pyrrolo[1,2-b]pyrazole-3-carboxylate as a Key Step in the Large-Scale Synthesis of Bicyclic Heteroaryl Carboxyaldehydes", Org. Process Res. Dev., 2006, 712-716, vol. 10, No. 4.
Nithipatikom et al., "2-Arachidonoylglycerol: a novel inhibitor of androgen-independent prostate cancer cell invasion", Cancer Res., Dec. 15, 2004, 8826-8830, vol. 64, No. 24.
Nithipatikom et al., "A new class of inhibitors of 2-arachidonoylglycerol hydrolysis and invasion of prostate cancer cells", Biochem Biophys Res Commun., Jul. 15, 2005, 1028-1033, vol. 332, No. 4.
Nithipatikom et al., "Anti-proliferative effect of a putative endocannabinoid, 2-arachidonylglyceryl ether in prostate carcinoma cells", Prostaglandins Other Lipid Mediat., Feb. 9, 2011, 34-43, vol. 94, No. 1-2.
Nomura et al., "Endocannabinoid Hydrolysis Generates Brain Prostaglandins That Promote Neuroinflammation", Science, Nov. 11, 2011, 809-813, vol. 334, No. 6057.
Oyanguren-Desez, et al., Gain-of-function of P2X7 receptor gene variants in multiple sclerosis, Cell Calcium, Sep. 8, 2011, pp. 468-472, vol. 50.
Pacher et al., "Pleiotropic effects of the CB2 cannabinoid receptor activation on human monocyte migration: Implications for atherosclerosis and inflammatory diseases", Amer J Physiol, 2008, H1133-H1134, vol. 294.
Parvathenani, et al., P2X7 Mediates Superoxide Production in Primary Microglia and Is Up-regulated in a Transgenic Mouse Model of Alzheimer's Disease, The Journal of Biological Chemistry, Jan. 27, 2003, pp. 13309-13317, vol. 278 Issue 15.
Pasquarelli et al., "Contrasting effects of selective MAGL and FAAH inhibition on dopamine depletion and GDNF expression in a chronic MPTP mouse model of Parkinson's disease", Neurochem Int., Nov. 2017, 14-24, vol. 110.
Pasquarelli et al., "Evaluation of monoacylglycerol lipase as a therapeutic target in a transgenic mouse model of ALS", Neuropharmacology, Sep. 15, 2017, 157-169, vol. 124.
Patel et al., "The endocannabinoid system as a target for novel anxiolytic drugs", Neurosci Biobehav Rev., May 2017, 56-66, vol. 76, Part A.
Paulekuhn, et al., Trends in Active Pharmaceutical Ingredient Salt Selection based on Analysis of the Orange Book Database, Journal of Medicinal Chemistry, Aug. 20, 2007, pp. 6665-6672, vol. 50 Issue 26.
Pike, Victor W., "Hypervalent aryliodine compounds as precursors for radiofluorination", J. Label Compd Radiopharm., 2018, pp. 196-227, vol. 61.
Piomelli, "The molecular logic of endocannabinoid signalling", Nat Rev Neurosci, 2003, 873-884, vol. 4.
Piro et al., "A Dysregulated Endocannabinoid-Eicosanoid Network Supports Pathogenesis in a Mouse Model of Alzheimer's Disease", Cell Rep., Jun. 28, 2012, 617-623, vol. 1, No. 6.
Ramesh et al., "Blockade of Endocannabinoid Hydrolytic Enzymes Attenuates Precipitated Opioid Withdrawal Symptoms in Mice", J Pharmacol Exp Ther., Oct. 2011, 173-185, vol. 339, No. 1.
Robinson, et al., "Discovery of the Hemifumarate and (r-L-Alanyloxy)methyl Ether as Prodrugs of an Antirheumatic Oxindole: Prodrugs for the Enolic OH Group", Journal of Medicinal Chemistry, vol. 39 (1); pp. 10-18 (1996).
Romagnoli, et al., The P2X 7 receptor as a therapeutic target, Expert Opin. Ther., 2008, pp. 647-661, vol. 15 Issue 5.

(56) References Cited

OTHER PUBLICATIONS

Rudolph, et al., Novel methyl substituted 1-(5,6-dihydro-[1,2,4]triazolo [4,3-a]pyrazin-7(8H)-yl)methanones are P2X7 antagonists, Bioorganic & Medicinal Chemistry Letters, Jun. 9, 2015, pp. 3157-3163, vol. 25.

Sanz, et al., Activation of Microglia by Amyloid Requires P2X7 Receptor Expression1, The Journal of Immunology, 2009, pp. 4378-4385, vol. 182.

Schlosburg et al., "Chronic monoacylglycerol lipase blockade causes functional antagonism of the endocannabinoid system", Nat Neurosci., Sep. 13, 2010, 1113-1119, vol. 9.

Shan, et al., "Prodrug Strategies Based on Intramolecular Cyclization Reactions", Journal of Pharmaceutical Sciences, vol. 86 (7): pp. 765-767 (Jul. 1977).

Sharp, et al., P2x7 deficiency suppresses development of experimental autoimmune encephalomyelitis, Journal of Neuroinflammation, Aug. 8, 2008, pp. 1-13, vol. 5 Issue 33.

Simone, Part XIV—Oncology, Textbook of Medicine, 1996, 20th edition, pp. 1004-1010, vol. 1.

Skaper, et al., The P2X7 purinergic receptor: from physiology to neurological disorders, The FASEB Journal, 2010, pp. 337-345, vol. 24.

Solini, et al., Enhanced P2X7 Activity in Human Fibroblasts From Diabetic Patients A Possible Pathogenetic Mechanism for Vascular Damage in Diabetes, Arterioscler Thromb Vasc Biol., 2004, pp. 1240-1245, vol. 24.

Stahl, et al., "Handbook Of Pharmaceutical Salts", International Union Of pure And Applied Chemistry, Index; pp. 1-3, (2002).

Sticht, et al., "Inhibition of monoacylglycerol lipase attenuates vomiting in Suncus murinus and 2-arachidonoyl glycerol attenuates nausea in rats", Br J Pharmacol., Apr. 2012, 2425-2435, vol. 165, No. 8.

Straiker et al., "Monoacylglycerol Lipase Limits the Duration of Endocannabinoid-Mediated Depolarization-Induced Suppression of Excitation in Autaptic Hippocampal Neurons", Mol Pharmacol., Dec. 2009, 1220-1227, vol. 76, No. 6.

Sugiura et al., "2-Arachidonoylgylcerol: A Possible Endogenous Cannabinoid Receptor Ligand in Brain", Biochem Biophys Res Commun, 1995, 89-97, vol. 215.

Sugiura et al., "Biosynthesis and degradation of anandamide and 2-arachidonoylglycerol and their possible physiological significance", Prostaglandins Leukot Essent Fatty Acid, Feb.-Mar. 2002, 173-192, vol. 66, No. 2-3.

Suguira et al., "Biochemistry, pharmacology and physiology of 2-arachidonoylglycerol, an endogenous cannabinoid receptor ligand", Prog Lipid Res, 2006, 405-446, vol. 45, No. 5.

Surprenant, et al., Signaling at Purinergic P2X Receptors, Annu. Rev. Physiol, Oct. 13, 2008, pp. 333-359, vol. 71.

Terrone et al., "Inhibition of monoacylglycerol lipase terminates diazepam-resistant status epilepticus in mice and its effects are potentiated by a ketogenic diet", Epilepsia, Jan. 2018, 79-91, vol. 59, No. 1.

Thiboutot, et al., Inflammasome Activation by propionibacterium acnes: the Story of IL-1 in Acne continues to unfold, Journal Of Investigative Dermatology, 2014, pp. 595-597, vol. 134.

Tuo et al., "Therapeutic Potential of Fatty Acid Amide Hydrolase, Monoacylglycerol Lipase, and N-Acylethanolamine Acid Amidase Inhibitors", J Med Chem., Jan. 12, 2017, 4-46, vol. 60, No. 1.

Vergani, et al., Effects of the purinergic Inhibitor Oxidized ATP in a model of Islet Allograft rejection, Diabetes, 2013, pp. 1665-1675, vol. 62.

Vergani, et al., Long term Heart Transplant Survival by targeting the Ionotropic Purinergic receptor P2X7, Circulation, 2013, pp. 463-475, vol. 127.

Von Ruden et al., "Inhibition of monoacylglycerol lipase mediates a cannabinoid 1-receptor dependent delay of kindling progression in mice", Neurobiol Dis., May 2015, 238-245, vol. 77.

Walter et al., "ATP Induces a Rapid and Pronounced Increase in 2-Arachidonoylglycerol Production by Astrocytes, a Response Limited by Monoacylglycerol Lipase", J Neurosci., Sep. 15, 2004, 8068-8074, vol. 24, No. 37.

Wang et al., "Treating a novel plasticity defect rescues episodic memory in Fragile X model mice", Mol Psychiatry, 2018, 1798-1806, vol. 23, No. 8.

Wenzel et al., "Novel multi-target directed ligand-based strategies for reducing neuroinflammation in Alzheimer's disease", Life Sci., Aug. 15, 2018, 314-322, vol. 207.

Wilkerson et al., "The Selective Monoacylglycerol Lipase Inhibitor MJN110 Produces Opioid-Sparing Effects in a Mouse Neuropathic Pain Model", J Pharmacol Exp Ther., Apr. 2016, 145-156, vol. 357, No. 1.

Wilson et al., "A high-throughput-compatible assay for determining the activity of fatty acid amide hydrolase", Anal Biochem., Jul. 15, 2003, 270-275, vol. 318, No. 2.

Yi et al., "Reductions in circulating endocannabinoid 2-arachidonoylglycerol levels in healthy human subjects exposed to chronic stressors", Progress in Neuro-Psychopharmacology and Biological Psychiatry, 2016, 92-97, vol. 67, No. 3.

Zhang et al., "Inhibition of monoacylglycerol lipase prevents chronic traumatic encephalopathy-like neuropathology in a mouse model of repetitive mild closed head injury", J Cereb Blood Flow Metab., Mar. 31, 2015, 706, vol. 35, Issue No. 4.

MONOACYLGLYCEROL LIPASE MODULATORS

CROSS-REFERENCE TO RELATED APPLICATIONS

This application is a continuation of U.S. Ser. No. 17/132,406 filed Dec. 23, 2020, pending, which is a continuation of U.S. Ser. No. 16/586,263 filed Sep. 27, 2019, which claims priority to U.S. Patent Application No. 62/738,684, filed on Sep. 28, 2018, the disclosures of which are incorporated herein by reference in their entirety.

FIELD OF THE INVENTION

The present invention is related to certain bridged chemical entities having MGL (monoacylglycerol lipase) modulating properties, pharmaceutical compositions comprising these chemical entities, chemical processes for preparing these chemical entities and their use in the treatment of diseases, disorders or conditions associated with MGL receptor activity in subjects, in particular humans.

BACKGROUND OF THE INVENTION

*Cannabis Sativa* and analogs of $\Delta^9$-tetrahydrocannabinol have been used since the days of folk medicine for therapeutic purposes. The endocannabinoid system consists of two G-protein coupled receptors, cannabinoid receptor type 1 (CB1) (Matsuda et al., *Nature*, 1990, 346, 561-4) and cannabinoid receptor type 2 (CB2) (Munro et al., *Nature*, 1993, 365, 61-5). CB1 receptor is one of the most abundant G-protein coupled receptor expressed in the brain (Herkenam et al., *Proc. Nat. Acad. Sci.*, 1990, 87 (5), 1932-1936). CB1 is also expressed peripherally in the liver, gastrointestinal tract, pancreas, adipose tissue and skeletal muscles (Di Marzo et al., *Curr Opin Lipidol*, 2007, 18, 129-140). CB2 is predominantly expressed in immune cells such as monocytes (Pacher et al., *Amer J Physiol*, 2008, 294, H1133-H1134) and under certain conditions (inflammation) in the brain ((Benito et al., *Brit J Pharmacol*, 2008, 153, 277-285) and in skeletal (Cavuoto et al., *Biochem Biophys Res Commun*, 2007, 364, 105-110) and cardiac muscles (Hajrasouliha et al., *Eur J Pharmacol*, 2008, 579, 246-252).

In 1992, N-arachidonoylethanolamine (AEA or anandamide) was found to be an endogenous ligand for cannabinoid receptors (Devane et al., *Science*, 1992, 258, 1946-9). Subsequently, 2-arachidonoylglycerol (2-AG) was also identified as an additional endogenous ligand for the cannabinoid receptors (Mechoulam et al., *Biochem Pharmacol*, 1995, 50, 83-90; Sugiura et al., *Biochem Biophys Res Commun*, 1995, 215, 89-97). Concentrations of 2-AG were reported to be at least 100 times higher than these of anandamide in the rat brain (Buczynski and Parsons, *Brit J Pharmacol*, 2010, 160 (3), 423-42). Therefore 2-AG may play more essential physiological roles than anandamide in the brain endocannabinoid system (Sugiura et al. *Prostaglandins Leukot Essent Fatty Acids*, 2002, February-March, 66(2-3):173-92). The endocannabinoid 2-AG is a full agonist for CB1 and CB2 receptors, while anandamide is a partial agonist for both receptors (Suguira et al., *Prog Lipid Res*, 2006, 45(5):405-46). Unlike many classical neurotransmitters, endocannabinoids signal through a retrograde mechanism. They are synthesized on demand in postsynaptic neurons and then rapidly degraded following binding to presynaptic cannabinoid receptors (Ahn et al., *Chem Rev.* 2008, 108(5):1687-707). Monoacylglycerol lipase (MGLL, also known as MAG lipase and MGL) is the serine hydrolase responsible for the degradation of 2-AG into arachidonic acid and glycerol in the central nervous system (Mechoulam et al., *Biochem Pharmacol*, 1995, 50, 83-90; Sugiura et al., *Biochem Biophys Res Commun*, 1995, 215, 89-97; Long et al., *Nat Chem Biol.* 2009 January; 5(1):37-44;), Schlosburg et al, *Nat Neurosci.*, 2010, September; 13(9):1113-9) and peripheral tissues (Long et al., *Chem Biol.*, 2009 Jul. 31; 16(7):744-53). Anandamide is hydrolyzed by fatty acid amide hydrolase (FAAH) (Piomelli, *Nat Rev Neurosci*, 2003, 4, 873-884). MGL exists in both soluble and membrane bound forms (Dinh et al., *Proc Natl Acad Sci USA.*, 2002, Aug. 6; 99(16):10819-24). In the brain MGL is located in presynaptic neurons (Straiker et al., *Mol Pharmacol.*, 2009, December; 76(6):1220-7) and astrocytes (Walter et al., *J Neurosci.*, 2004, Sep. 15; 24(37):8068-74) within regions associated with high CB1 receptor density. Compared to wild-type controls, genetic ablation of MGL expression produces 10-fold increase in brain 2-AG levels without affecting anandamide concentration (Schlosburg et al., *Nat Neurosci.*, 2010, September; 13(9):1113-9).

Thus, MGL modulation offers an interesting strategy for potentiating the cannabinoid system. The primary advantage of this approach is that only brain regions where endocannabinoids are actively produced will be modulated, potentially minimizing the side effects associated with exogenous CB1 agonists. Pharmacological inactivation of MGL by covalent inhibitors in animals increase 2-AG content in brain and peripheral tissues and has been found to produce antinociceptive, anxiolytic and anti-inflammatory effects that are dependent on CB1 and/or CB2 receptors (Long et al., *Nat Chem Biol.*, 2009, January, 5(1):37-44; Ghosh et al., *Life Sci.*, 2013, Mar. 19, 92(8-9):498-505; Bedse et al., *Biol Psychiatry.*, 2017, Oct. 1, 82(7):488-499; Bernal-Chico et al., *Glia.*, 2015, January, 63(1):163-76; Patel et al. *Neurosci Biobehav Rev.*, 2017, May, 76(Pt A):56-66; Betse et al., *Transl Psychiatry.*, 2018, Apr. 26, 8(1):92). In addition to the role of MGL in terminating 2-AG signaling, MGL modulation, including MGL inhibition also promotes CB1/2-independent effects on neuroinflammation (Nomura et al., *Science.*, 2011, Nov. 11; 334(6057):809-13. MGL modulation, including MGL inhibition leads to reduction in proinflammatory prostanoid signaling in animal models of traumatic brain injury (Katz et al., *J Neurotrauma.*, 2015, Mar. 1; 32(5):297-306; Zhang et al., *J Cereb Blood Flow Metab.*, 2015, Mar. 31; 35(4):706), neurodegeneration including Alzheimer's disease (Piro et al., *Cell Rep.*, 2012, Jun. 28, 1(6):617-23; Wenzel et al., *Life Sci.*, 2018, Aug. 15, 207: 314-322; Chen et al., *Cell Rep.*, 2012, Nov. 29, 2(5):1329-39), Parkinson's disease (Nomura et al., *Science*, 2011, Nov. 11, 334(6057), 809-13; Pasquarelli et al., *Neurochem Int.*, 2017, November, 110:14-24), amyotrophic lateral sclerosis (Pasquarelli et al., *Neuropharmacology*, 2017, Sep. 15, 124: 157-169), multiple sclerosis (Hernadez-Torres et al., *Angew Chem Int Ed Engl.*, 2014, Dec. 8, 53(50):13765-70; Bernal-Chico et al., *Glia.*, 2015, January, 63(1):163-76), Huntington's disease (Covey et al., *Neuropsychopharmacology*, 2018, 43, 2056-2063), Tourette syndrome and status epilepticus (Terrone et al., *Epilepsia.*, 2018, January, 59(1), 79-91; von Ruden et al., *Neurobiol Dis.*, 2015, May; 77:238-45).

Therefore, by potentiating the cannabinoid system and attenuating proinflammatory cascades, MGL modulation, including MGL inhibition offers a compelling therapeutic approach for the treatment of a vast array of complex diseases. Importantly, MGL modulation, including MGL inhibition in animals does not produces the full spectrum of neurobehavioral effects observed with $\Delta^9$-tetrahydrocannabinol and other CB1 agonists (Tuo et al., *J Med Chem.,* 2017, Jan. 12, 60(1), 4-46; Mulvihill et al., *Life Sci.,* 2013, Mar. 19, 92(8-9), 492-7).

Endocannabinoid hypoactivity is a risk factor for the treatment of depression, anxiety and post-traumatic stress disorders. Millennia of human use of *Cannabis sativa,* and a brief period in which humans were treated with the endocannabinoid antagonist, rimonabant, provide support for that hypothesis. 2-AG levels are decreased in individuals with major depression (Hill et al., *Pharmacopsychiatry.,* 2008, March; 41(2): 48-53; Hill et al., *Psychoneuroendocrinology.,* 2009, September; 34(8): 1257-1262). Low circulating 2-AG levels predict rates of depression (Hauer et al., *Rev Neurosci.,* 2012, 23(5-6):681-90). Reduced circulating 2-AG has been found in patient with post-traumatic stress disorder (PTSD) (Hill et al., *Psychoneuroendocrinology,* 2013, 38 (12), 2952-2961). Healthy volunteers exposed to chronic stressors exhibited progressively diminished circulating 2-AG levels which correlated with the onset of reductions in measures of positive emotions (Yi et al., *Progress in Neuro-Psychopharmacology and Biological Psychiatry,* 2016, 67 (3), 92-97). The CB1 receptor inverse agonist/antagonist Rimonabant has been withdrawn from the market due to the high incidence of severe depression and suicidal ideation (Christensen et al., *The Lancet,* 2007, 370, 1706-1713). Therefore, MGL modulators are potentially useful for the treatment of mood disorders, anxiety and PTSD.

Cannabinoid receptor agonists are clinically used to treat pain, spasticity, emesis and anorexia (Di Marzo, et al., *Annu Rev Med.,* 2006, 57:553-74; Ligresti et al., *Curr Opin Chem Biol.,* 2009, June; 13(3):321-31). Therefore, MGL modulators, including MGL inhibitors are also potentially useful for these indications. MGL exerts CB1-dependant antinociceptive effects in animal models of noxious chemical, inflammatory, thermal and neuropathic pain (Guindon et al., *Br J Pharmacol.,* 2011, August; 163(7):1464-78; Kinsey et al., *J Pharmacol Exp Ther.,* 2009, September; 330(3):902-10; Long et al., *Nat Chem Biol.,* 2009, January; 5(1):37-44). MGL blockade reduces mechanical and acetone induced cold allodynia in mice subjected to chronic constriction injury of the sciatic nerve (Kinsey et al., *J Pharmacol Exp Ther.,* 2009, September; 330(3):902-10). MGL inhibition produces opiate-sparing events with diminished tolerance, constipation, and cannabimimetic side effects (Wilkerson et al., *J Pharmacol Exp Ther.,* 2016, April; 357(1):145-56). MGL blockade is protective in model of inflammatory bowel disease (Alhouayek et al., *FASEB J.,* 2011, August; 25(8): 2711-21). MGL inhibition also reverse Paclitaxel-induced nociceptive behavior and proinflammatory markers in a mouse model of chemotherapy-induced neuropathy (Curry et al., *J Pharmacol Exp Ther.,* 2018, July; 366(1):169-18). MGL inhibitors are also potentially useful for the treatment of chronic inflammatory condition of the urinary bladder like interstitial cystitis (Chinnadurai et al., *Med Hypotheses* 2019, October; 131: 109321).

Inhibition of 2-AG hydrolysis exerts anti-proliferative activity and reduction in prostate cancer cell invasiveness (Nithipatikom et al., *Cancer Res.,* 2004, Dec. 15, 64(24): 8826-30; Nithipatikom et al., *Biochem Biophys Res Commun.,* 2005, Jul. 15,332(4):1028-33; Nithipatikom et al., *Prostaglandins Other Lipid Mediat.,* 2011, February, 94(1-2):34-43). MGL is upregulated in aggressive human cancer cells and primary tumors where it has a unique role of providing lipolytic sources of free fatty acids for synthesis of oncogenic signaling lipids that promote cancer aggressiveness. Thus, beyond the physiological roles of MGL in mediated endocannabinoid signaling, MGL in cancer plays a distinct role in modulating the fatty acid precursor pools for synthesis of protumorigenic signaling lipids in malignant human cancer cells.

MGL blockade shows anti-emetic and anti-nausea effects in a lithium chloride model of vomiting in shrews (Sticht et al., *Br J Pharmacol.,* 2012, April, 165(8):2425-35).

MGL modulators, including MGL inhibitors may have utility in modulating drug dependence of opiates. MGL blockade reduce the intensity of naloxone-precipitated morphine withdrawal symptoms in mice. MGL blockade also attenuated spontaneous withdrawal signs in morphine-dependent mice (Ramesh et al., *J Pharmacol Exp Ther.,* 2011, October, 339(1):173-85).

MGL modulators are also potentially useful for the treatment of eye conditions, including but not limited to, glaucoma and disease states arising from elevated intraocular pressure (Miller et al., *Pharmaceuticals,* 2018, 11, 50).

SUMMARY OF THE INVENTION

Embodiments of the present invention relate to chemical entities, pharmaceutical compositions containing them, methods of making and purifying them, and methods for using them the treatment of diseases, disorders, and conditions associated with the MGL modulation.

An additional embodiment of the invention is a method of treating a subject suffering from or diagnosed with a disease, disorder, or condition associated with the MGL modulation using at least one chemical entity of the invention.

Additional embodiments, features, and advantages of the invention will be apparent from the following detailed description and through practice of the invention.

Embodiments of this invention are compounds of Formula (I),

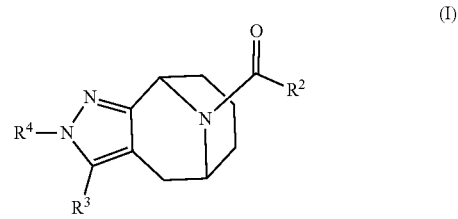

wherein
$R^2$ is selected from the group consisting of:

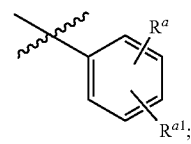

(b) 6-membered heteroaryl selected from the group consisting of: pyridazin-4-yl; pyrazin-2-yl; pyrimidinyl; pyrimidinyl substituted with $C_{1-4}$alkyl or $OC_{1-4}$alkyl; and pyridinyl, wherein the pyridinyl is substituted with one or two substituents each independently selected from the group consisting of: halo, $C_{1-4}$alkyl, $OC_{1-4}$alkyl, $OC_{1-4}$haloalkyl, $C_{3-6}$cycloalkyl, $NH_2$, CN, $N(CH_3)_2$,

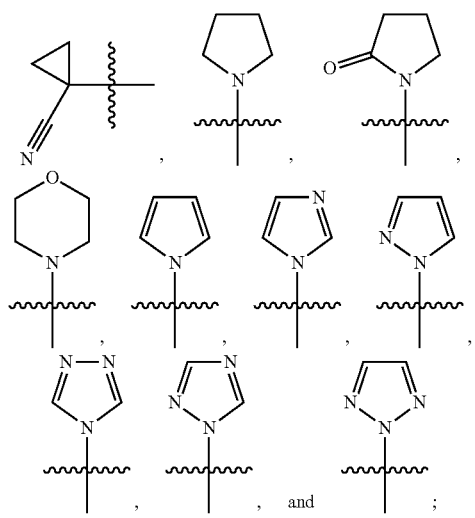
(c) 5-membered heteroaryl selected from the group consisting of:
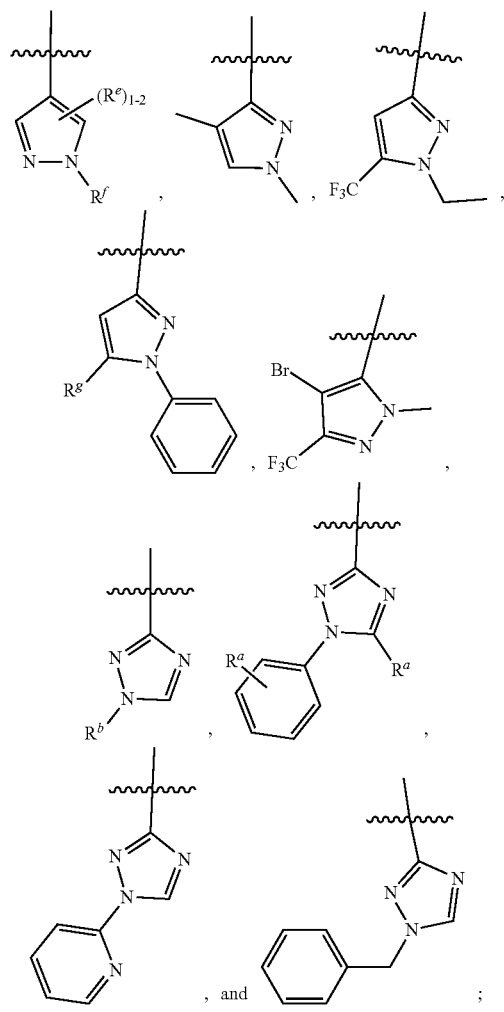
(d) 5,6-fused bicyclic heteroaryl or 6,5-fused bicyclic heteroaryl selected from the group consisting of:
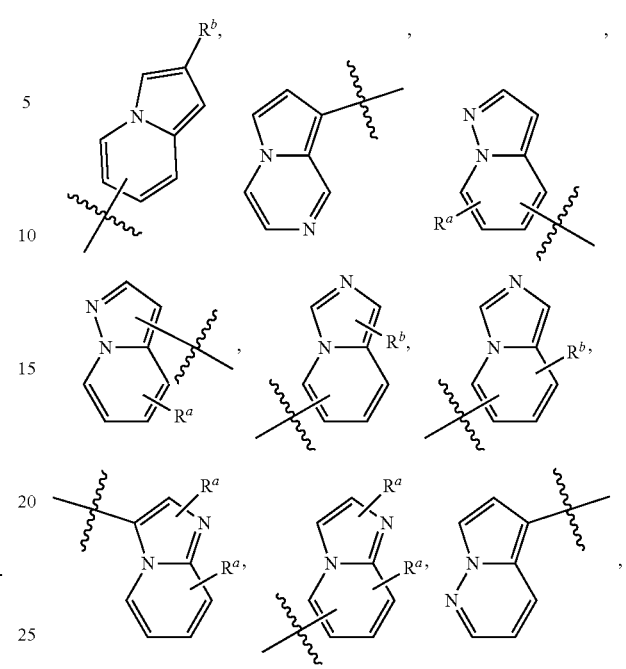
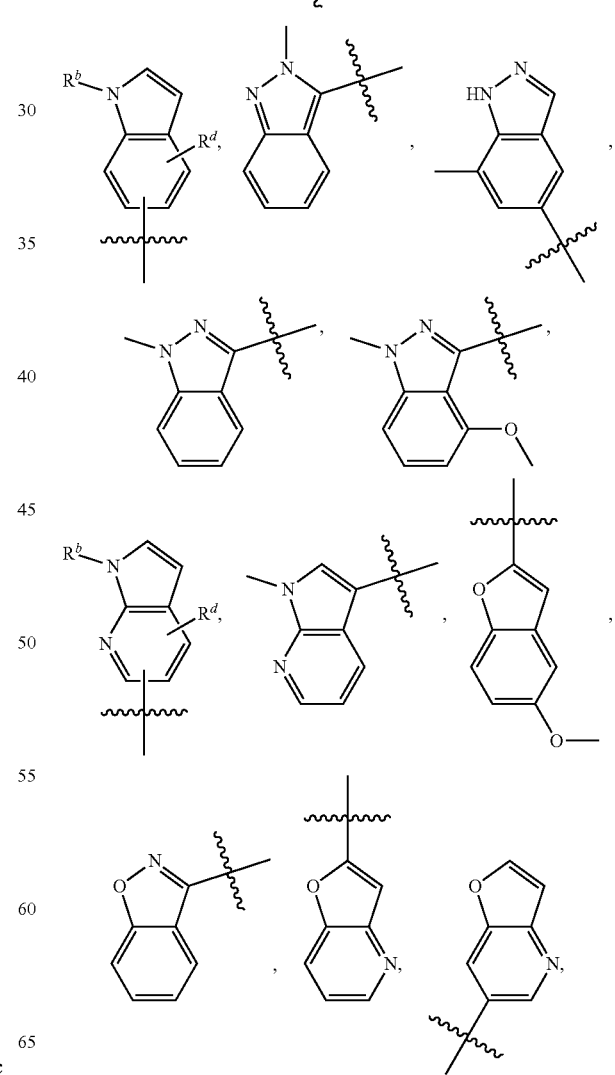

-continued
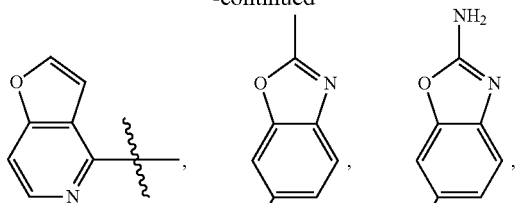
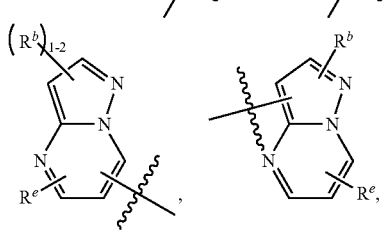
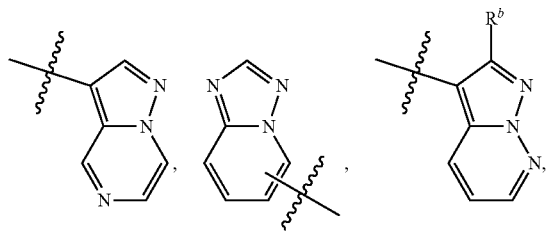
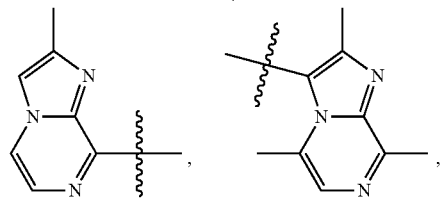
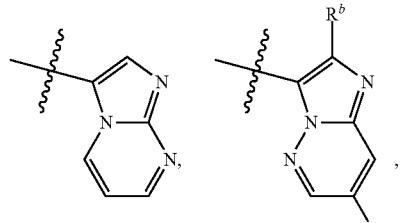
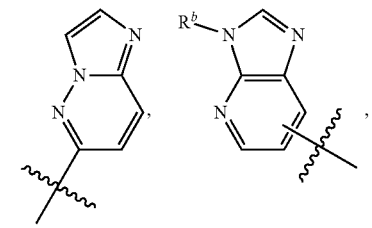
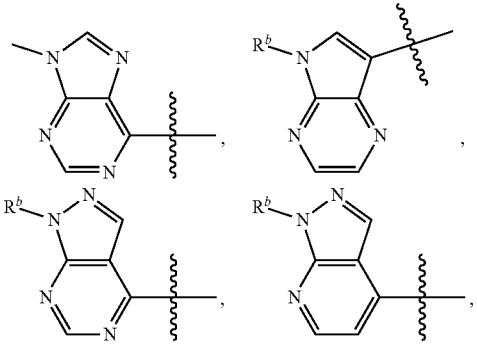
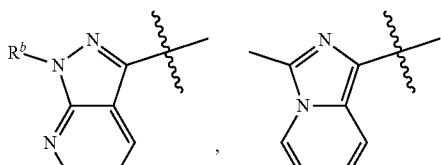
(e) 6,6-fused bicyclic heteroaryl selected from the group consisting of:
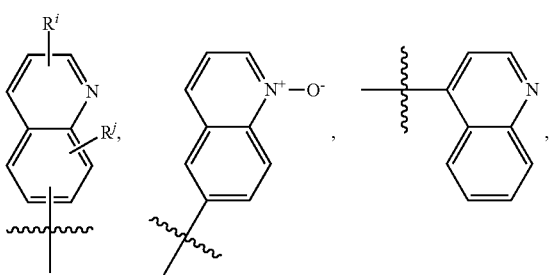
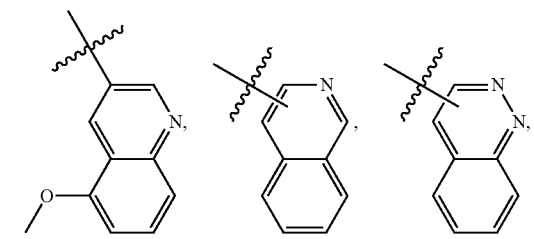
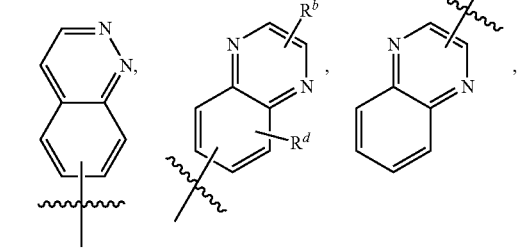
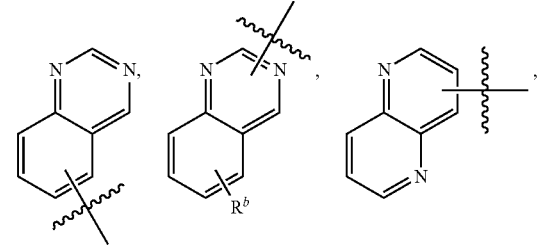

-continued

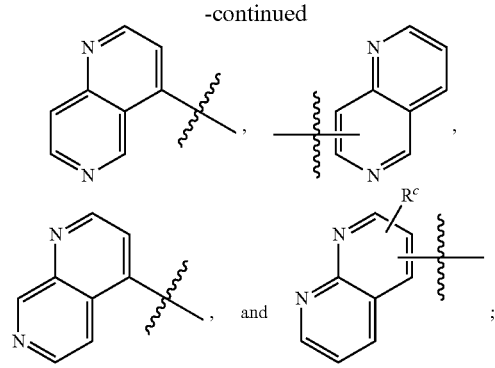

and
(f)

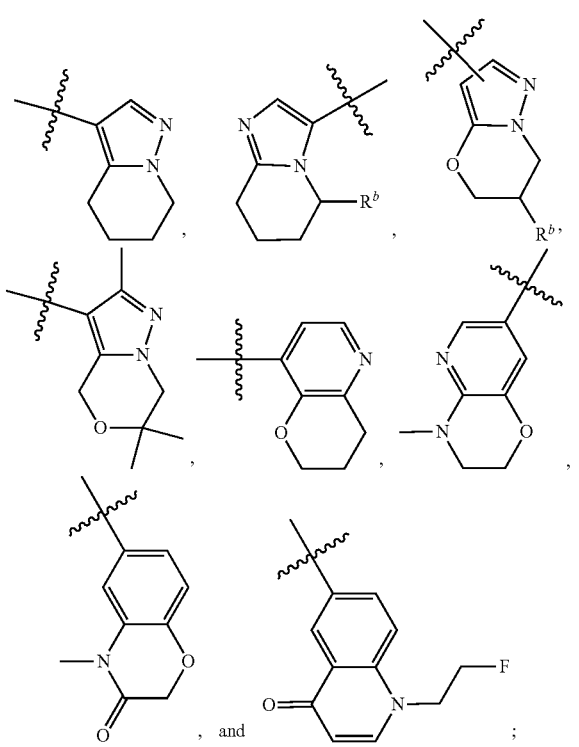

wherein
$R^a$ is selected from the group consisting of: H, halo, $C_{1-4}$alkyl, $OC_{1-4}$alkyl, $C_{1-4}$haloalkyl and $OC_{1-4}$haloalkyl;
$R^{a1}$ is selected from the group consisting of: $C_{1-4}$alkyl; $OC_{1-4}$alkyl; $OC_{1-4}$haloalkyl; $N(C=O)CH_3$; oxazol-2-yl; pyrimidin-2-yl; and 5-membered heteroaryl ring containing two, three, or four nitrogen members, wherein the 5-membered heteroaryl ring is optionally substituted with one $R^a$ member;
$R^b$ is H or $C_{1-4}$akyl;
$R^c$ is H or $C_{1-4}$haloalkyl;
$R^d$ is H or halo;
$R^e$ is selected from the group consisting of: H, halo, $C_{1-4}$akyl, $C_{1-4}$haloalkyl, $OC_{1-4}$alkyl, and $C_{3-6}$cycloalkyl;
$R^f$ is selected from the group consisting of: H, $C_{1-4}$alkyl, $CH_2CH_2OH$, $C_{1-4}$haloalkyl, cyclopropyl, phenyl, and phenyl substituted with $CF_3$;

$R^g$ is selected from the group consisting of: H, $OC_{1-4}$alkyl and $C_{1-4}$haloalkyl;
$R^i$ is selected from the group consisting of: H, halo, $C_{1-4}$alkyl, $C_{1-4}$haloalkyl, OH, $OC_{1-4}$alkyl, $OC_{1-4}$haloalkyl, and $C_{3-6}$cycloalkyl;
$R^j$ is selected from the group consisting of: H, halo, $OCH_3$, OH, $NH_2$, and $NO_2$;
$R^3$ is selected from the group consisting of:
(g) phenyl, wherein phenyl is independently substituted with one, two, or three members selected from the group consisting of: halo, $C_{1-4}$alkyl, $C_{1-4}$haloalkyl, and $OC_{1-4}$alkyl;
(h) 5-(trifluoromethyl)-2-thienyl or 1-methylindol-2-yl; and
(i) cyclopropyl; and
$R^4$ is $C_{1-4}$alkyl or $C_{3-4}$cycloalkyl;
and pharmaceutically acceptable salts, isotopes, N-oxides, solvates, and stereoisomers thereof.

Embodiments of this invention are also compounds of Formula (II),

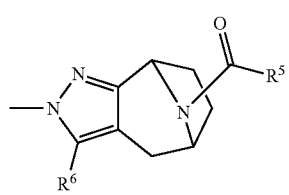

(II)

wherein
$R^5$ is selected from the group consisting of:
(a) phenyl optionally independently substituted with one or two members selected from the group consisting of: halo, $OC_{1-4}$alkyl, and

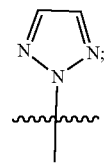

(b) 6-membered heteroaryl selected from the group consisting of:

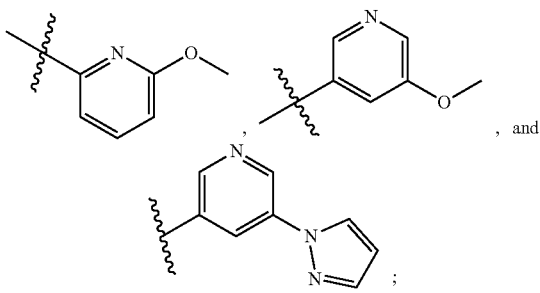

(c) 5-membered heteroaryl selected from the group consisting of:

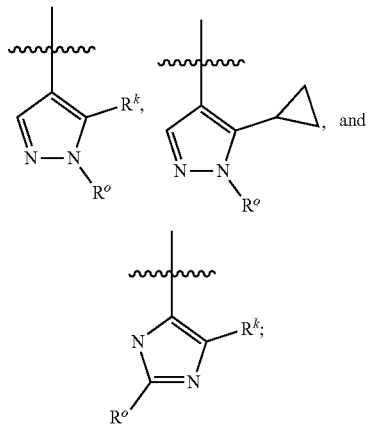

and (d) 5,6-fused bicyclic heteroaryl or 6,5-fused bicyclic heteroaryl selected from the group consisting of:

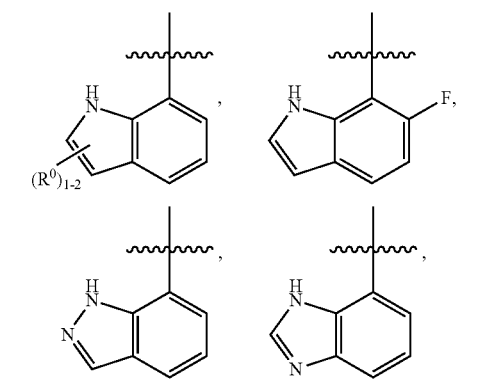

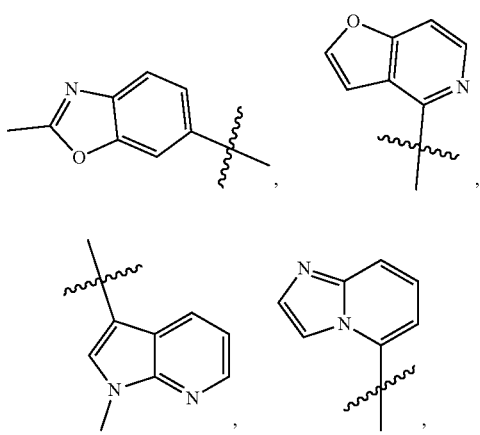

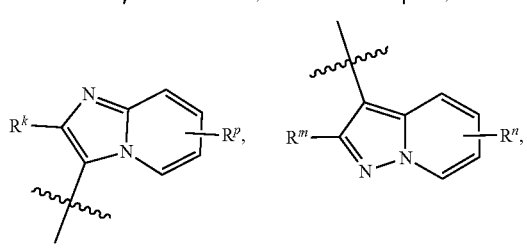

-continued

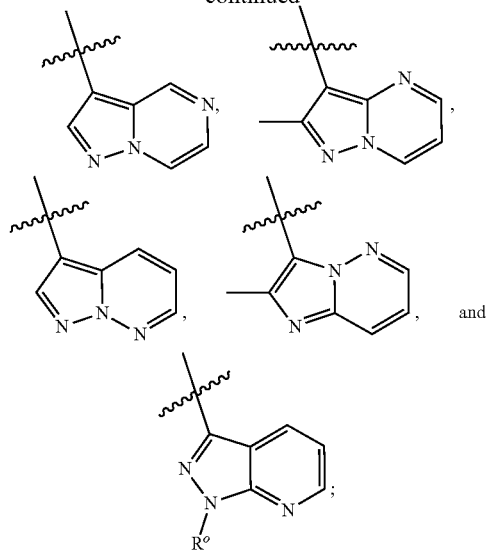

and (e) 6,6-fused bicyclic heteroaryl selected from the group consisting of:

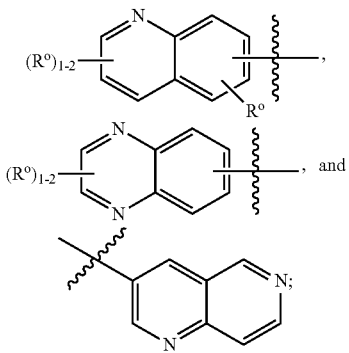

(f)

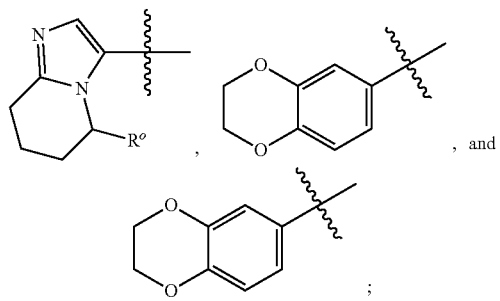

wherein
$R^k$ is selected from the group consisting of: H, halo, $C_{1-4}$alkyl, and $C_{1-4}$haloalkyl;
$R^m$ is selected from the group consisting of: H, $C_{1-4}$alkyl, and $C_{1-4}$haloalkyl;
$R^n$ is H or $OC_{1-4}$alkyl;
$R^o$ is H or $C_{1-4}$alkyl;
$R^p$ is selected from the group consisting of: H, halo, $C_{1-4}$alkyl, $C_{1-4}$haloalkyl, and $OC_{1-4}$alkyl; and R[6] is phenyl, wherein phenyl is independently substituted with one, two, or three members selected from the group consisting of: halo, $C_{1-4}$alkyl, $C_{1-4}$haloalkyl, and $OC_{1-4}$alkyl;

and pharmaceutically acceptable salts, isotopes, N-oxides, solvates, and stereoisomers thereof.

DETAILED DESCRIPTION OF THE INVENTION

As used herein, the terms "including", "containing" and "comprising" are used in their open, non-limiting sense.

Unless qualified specifically in particular instances of use, the term "alkyl" refers to a straight- or branched-chain alkyl group having from 1 to 8 carbon atoms in the chain. Examples of alkyl groups include methyl (Me), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples. "$C_1$-$C_4$alkyl" refers to straight- or branched-chain alkyl group having from 1 to 4 carbon atoms in the chain.

The term "cycloalkyl" refers to a saturated or partially saturated, monocyclic, fused polycyclic, or spiro polycyclic carbocycle having from 3 to 12 ring atoms per carbocycle. Illustrative examples of cycloalkyl groups include the following entities, in the form of properly bonded moieties:

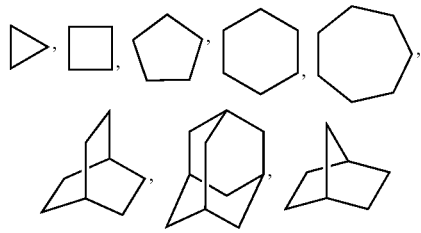

The term "halogen" or "halo" represents chlorine, fluorine, bromine, or iodine.

The term "haloalkyl" refers to a straight- or branched-chain alkyl group having from 1 to 6 carbon atoms in the chain optionally substituting hydrogens with halogens. The term "$C_1$-$C_4$ haloalkyl" as used here refers to a straight- or branched-chain alkyl group having from 1 to 4 carbon atoms in the chain, optionally substituting hydrogens with halogens. Examples of "haloalkyl" groups include trifluoromethyl ($CF_3$), difluoromethyl ($CF_2H$), monofluoromethyl ($CH_2F$), pentafluoroethyl ($CF_2CF_3$), tetrafluoroethyl ($CHFCF_3$), monofluoroethyl ($CH_2CH_2F$), trifluoroethyl ($CH_2CF_3$), tetrafluorotrifluoromethylethyl ($CF(CF_3)_2$), and groups that in light of the ordinary skill in the art and the teachings provided herein would be considered equivalent to any one of the foregoing examples.

The term "aryl" refers to a monocyclic, aromatic carbocycle (ring structure having ring atoms that are all carbon) having 6 atoms per ring (Carbon atoms in the aryl groups are sp2 hybridized.)

The term "phenyl" represents the following moiety:

The term "heteroaryl" as used herein, refers to an aromatic monocyclic or multicyclic ring system comprising 5 to 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is monocyclic and has 5 or 6 ring atoms and at least one nitrogen ring atom. A heteroaryl group is joined via a ring carbon atom and any nitrogen atom of a heteroaryl can be optionally oxidized to the corresponding N-oxide. The term "heteroaryl" also encompasses a heteroaryl group, as defined above, which has been fused to a benzene ring.

The term "5-membered heteroaryl" as used herein, refers to a heteroaryl group, as defined above, which has 5 ring atoms. Non-limiting examples of illustrative 5-membered heteroaryls include:

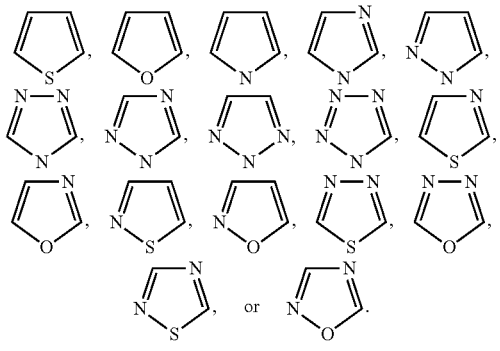

The term "6-membered heteroaryl" as used herein, refers to a heteroaryl group, as defined above, which has 6 ring atoms. Non-limiting examples of illustrative 6-membered heteroaryls include:

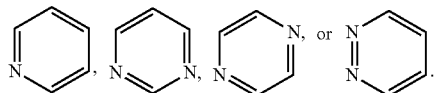

The term "5,6-fused bicyclic heteroaryl or 6,5-fused bicyclic heteroaryl" as used herein, refers to a heteroaryl group, as defined above, which has 9 ring atoms. Non-limiting examples of illustrative 5,6-fused bicyclic heteroaryl or 6,5-fused bicyclic heteroaryl include:

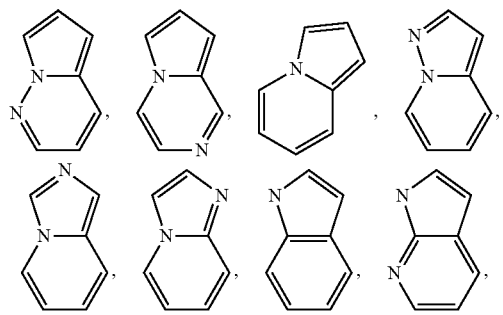

-continued

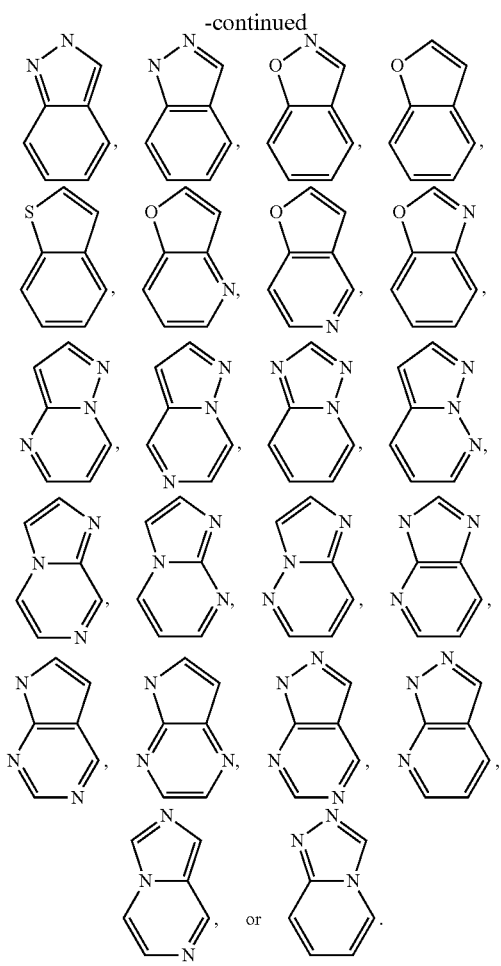

The term "6,6-fused bicyclic heteroaryl" as used herein, refers to a heteroaryl group, as defined above, which has 9 ring atoms. Non-limiting examples of illustrative 6,6-fused bicyclic heteroaryl include:

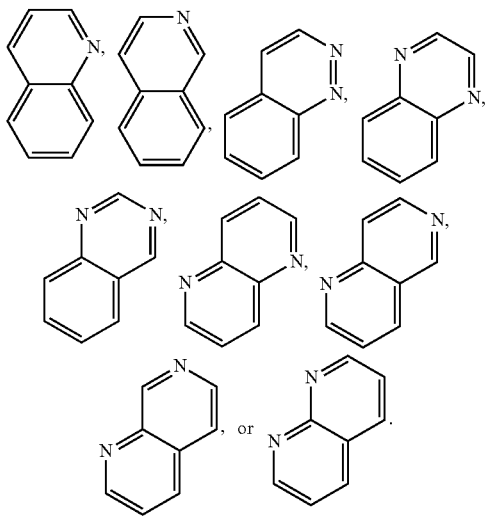

Those skilled in the art will recognize that the species of heteroaryl, cycloalkyl, aryl groups listed or illustrated above are not exhaustive, and that additional species within the scope of these defined terms may also be selected.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system.

The term "variable point of attachment" means that a group is allowed to be attached at more than one alternative position in a structure. The attachment will always replace a hydrogen atom on one of the ring atoms. In other words, all permutations of bonding are represented by the single diagram, as shown in the illustrations below.

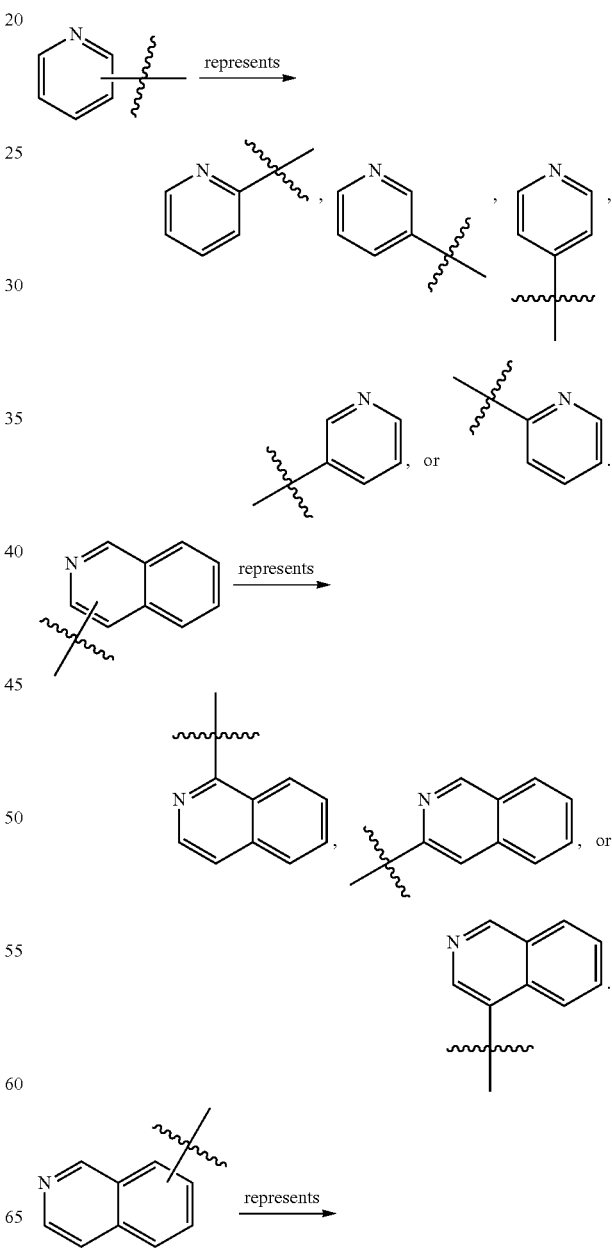

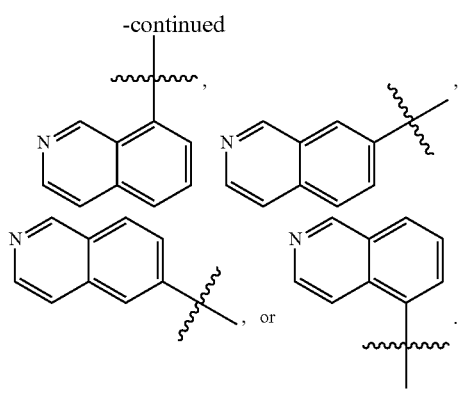

Those skilled in the art will recognize that that if more than one such substituent is present for a given ring, the bonding of each substituent is independent of all of the others. The groups listed or illustrated above are not exhaustive.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system.

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof, are considered within the scope of such formula. The compounds of this invention may possess one or more asymmetric centers; such compounds can therefore be produced as individual (R)- or (S)-stereoisomers or as mixtures thereof. Thus, any formula given herein is intended to represent a racemate, one or more of its enantiomeric forms, one or more of its diastereomeric forms, and mixtures thereof. Additionally, any formula given herein is intended to refer also to any one of hydrates, solvates, polymorphs and of such compounds, and mixtures thereof, even if such forms are not listed explicitly.

The term "R" at a stereocenter designates that the stereocenter is purely of the R-configuration as defined in the art; likewise, the term "S" means that the stereocenter is purely of the S-configuration. As used herein, the term "RS" refers to a stereocenter that exists as a mixture of the R- and S-configurations.

Compounds containing one stereocenter drawn without a stereo bond designation are a mixture of 2 enantiomers. Compounds containing 2 stereocenters both drawn without stereo bond designations are a mixture of 4 diastereomers. Compounds with 2 stereocenters both labeled "RS" and drawn with stereo bond designations are a 2-component mixture with relative stereochemistry as drawn. Unlabeled stereocenters drawn without stereo bond designations are a mixture of the R- and S-configurations. For unlabeled stereocenters drawn with stereo bond designations, the absolute stereochemistry is as depicted.

Reference to a compound herein stands for a reference to any one of: (a) the actually recited form of such compound, and (b) any of the forms of such compound in the medium in which the compound is being considered when named. For example, reference herein to a compound such as R—COOH, encompasses reference to any one of, for example, R—COOH(s), R—COOH(sol), and R—COO-(sol). In this example, R—COOH(s) refers to the solid compound, as it could be for example in a tablet or some other solid pharmaceutical composition or preparation; R—COOH(sol) refers to the undissociated form of the compound in a solvent; and R—COO-(sol) refers to the dissociated form of the compound in a solvent, such as the dissociated form of the compound in an aqueous environment, whether such dissociated form derives from R—COOH, from a salt thereof, or from any other entity that yields R—COO— upon dissociation in the medium being considered. In another example, an expression such as "exposing an entity to compound of formula R—COOH" refers to the exposure of such entity to the form, or forms, of the compound R—COOH that exists, or exist, in the medium in which such exposure takes place. In still another example, an expression such as "reacting an entity with a compound of formula R—COOH" refers to the reacting of (a) such entity in the chemically relevant form, or forms, of such entity that exists, or exist, in the medium in which such reacting takes place, with (b) the chemically relevant form, or forms, of the compound R—COOH that exists, or exist, in the medium in which such reacting takes place. In this regard, if such entity is for example in an aqueous environment, it is understood that the compound R—COOH is in such same medium, and therefore the entity is being exposed to species such as R—COOH(aq) and/or R—COO-(aq), where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation. No further examples in this regard are provided herein because these interactions and transformations in a given medium are known by any one of ordinary skill in the art.

Any formula given herein is also intended to represent unlabeled forms as well as isotopicallylabeled forms of the compounds. Isotopicallylabeled compounds have structures depicted by the formulas given herein except that one or more atoms are replaced by an atom having a selected atomic mass or mass number in an enriched form. Examples of isotopes that can be incorporated into compounds of the invention in a form that exceeds natural abundances include isotopes of hydrogen, carbon, nitrogen, oxygen, phosphorous, fluorine, chlorine, and iodine, such as $^{2}$H (or chemical symbol D), $^{3}$H (or chemical symbol T), $^{11}$C, $^{13}$C, $^{14}$C, $^{15}$N, $^{18}$O, $^{17}$O $^{31}$P, $^{32}$P, 35S, $^{18}$F, $^{36}$Cl, and $^{125}$I, respectively. Such isotopicallylabelled compounds are useful in metabolic studies (preferably with $^{14}$C), reaction kinetic studies (with, for example $^{2}$H or $^{3}$H), detection or imaging techniques [such as positron emission tomography (PET) or single-photon emission computed tomography (SPECT)] including drug or substrate tissue distribution assays, or in radioactive treatment of patients. In particular, an $^{18}$F or $^{11}$C labeled compound may be particularly preferred for PET or SPECT studies. Further, substitution with heavier isotopes such as deuterium (i.e., $^2$H, or D) may afford certain therapeutic advantages resulting from greater metabolic stability, for example increased in vivo half-life or reduced dosage requirements. Isotopicallylabeled compounds of this invention can generally be prepared by carrying out the procedures disclosed in the schemes or in the examples and preparations described below by substituting a readily available isotopicallylabeled reagent for a non-isotopically labeled reagent.

When referring to any formula given herein, the selection of a particular moiety from a list of possible species for a specified variable is not intended to define the same choice of the species for such variable appearing elsewhere. In other words, where a variable appears more than once, the choice of the species from a specified list is independent of the choice of the species for the same variable elsewhere in the formula, unless stated otherwise.

The term Cn-m alkyl refers to an aliphatic chain, whether straight or branched, with a total number N of carbon members in the chain that satisfies n≤N≤m, with m>n.

When the same plurality of substituents is assigned to various groups, the specific individual substituent assignment to each of such groups is meant to be independently made with respect to the specific individual substituent assignments to the remaining groups. By way of illustration, but not as a limitation, if each of groups Q and R can be H or F, the choice of H or F for Q is made independently of the choice of H or F for R, so the choice of assignment for Q does not determine or condition the choice of assignment for R, or vice-versa, unless it is expressly indicated otherwise. Illustrative claim recitation in this regard would read as "each of Q and R is independently H or F", or "each of Q and R is independently selected from the group consisting of H and F".

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

In another example, a zwitterionic compound would be encompassed herein by referring to a compound that is known to form a zwitterion, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI.27369 by the Chemical Entities of Biological Interest (ChEBI) dictionary of molecular entities. As generally well known, a zwitterion or zwitterionic compound is a neutral compound that has formal unit charges of opposite sign. Sometimes these compounds are referred to by the term "inner salts". Other sources refer to these compounds as "dipolar ions", although the latter term is regarded by still other sources as a misnomer. As a specific example, aminoethanoic acid (the amino acid glycine) has the formula $H_2NCH_2COOH$, and it exists in some media (in this case in neutral media) in the form of the zwitterion $^+H_3NCH_2COO^-$. Zwitterions, zwitterionic compounds, inner salts and dipolar ions in the known and well-established meanings of these terms are within the scope of this invention, as would in any case be so appreciated by those of ordinary skill in the art. Because there is no need to name each and every embodiment that would be recognized by those of ordinary skill in the art, no structures of the zwitterionic compounds that are associated with the compounds of this invention are given explicitly herein. They are, however, part of the embodiments of this invention. No further examples in this regard are provided herein because the interactions and transformations in a given medium that lead to the various forms of a given compound are known by any one of ordinary skill in the art.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

By way of a first example on substituent terminology, if substituent $S^1_{example}$ is one of $S_1$ and $S_2$, and substituent $S^2_{example}$ is one of $S_3$ and $S_4$, then these assignments refer to embodiments of this invention given according to the choices $S^1_{example}$ is $S_1$ and $S^2_{example}$ is $S_3$; $S^1_{example}$ is $S_1$ and $S^2_{example}$ is $S_4$; $S^1_{example}$ is $S_2$ and $S^2_{example}$ is $S_3$; $S^1_{example}$ is $S_2$ and $S^2_{example}$ is $S_4$; and equivalents of each one of such choices. The shorter terminology "$S^1_{example}$ is one of $S_1$ and $S_2$, and $S^2_{example}$ is one of $S_3$ and $S_4$," is accordingly used herein for the sake of brevity, but not by way of limitation. The foregoing first example on substituent terminology, which is stated in generic terms, is meant to illustrate the various substituent assignments described herein.

Furthermore, when more than one assignment is given for any member or substituent, embodiments of this invention comprise the various groupings that can be made from the listed assignments, taken independently, and equivalents thereof. By way of a second example on substituent terminology, if it is herein described that substituent $S_{example}$ is one of $S_1$, $S_2$, and $S_3$, this listing refers to embodiments of this invention for which $S_{example}$ is $S_1$; $S_{example}$ is $S_2$; $S_{example}$ is $S_3$; $S_{example}$ is one of $S_1$ and $S_2$; $S_{example}$ is one of $S_1$ and $S_3$; $S_{example}$ is one of $S_2$ and $S_3$; $S_{example}$ is one of $S_1$, $S_2$ and $S_3$; and $S_{example}$ is any equivalent of each one of these choices. The shorter terminology "$S_{example}$ is one of $S_1$, $S_2$, and $S_3$" is accordingly used herein for the sake of brevity, but not by way of limitation. The foregoing second example on substituent terminology, which is stated in generic terms, is meant to illustrate the various substituent assignments described herein.

The nomenclature "$C_i$-$C_j$" with j>i, when applied herein to a class of substituents, is meant to refer to embodiments of this invention for which each and every one of the number of carbon members, from i to j including i and j, is independently realized. By way of example, the term $C_1$-$C_3$ refers independently to embodiments that have one carbon member ($C_1$), embodiments that have two carbon members ($C_2$), and embodiments that have three carbon members ($C_3$).

A "pharmaceutically acceptable salt" is intended to mean a salt of an acid or base of a compound represented by Formula (I) (as well as compounds of Formula (II)) that is non-toxic, biologically tolerable, or otherwise biologically suitable for administration to the subject. See, generally, S. M. Berge, et al., "Pharmaceutical Salts", *J. Pharm. Sci.*, 1977, 66:1-19, and *Handbook of Pharmaceutical Salts, Properties, Selection, and Use*, Stahl and Wermuth, Eds., Wiley-VCH and VHCA, Zurich, 2002. Preferred pharmaceutically acceptable salts are those that are pharmacologically effective and suitable for contact with the tissues of patients without undue toxicity, irritation, or allergic response.

A compound of Formula (I) (as well as compounds of Formula (II)) may possess a sufficiently acidic group, a sufficiently basic group, or both types of functional groups, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

Compounds of Formula (I) (as well as compounds of Formula (II)) may contain at least one nitrogen of basic character, so desired pharmaceutically acceptable salts may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents.

Compounds of Formula (I) (as well as compounds of Formula (II)) may contain a carboxylic acid moiety, a desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinarylevel of skill in this technology. Illustrative examples of suitable salts include organic salts derived from amino acids, such as glycine and arginine, ammonia, carbonates, bicarbonates, primary, secondary, and tertiary amines, and cyclic amines, such as benzylamines, pyrrolidines, piperidine, morpholine, piperazine, N-methyl-glucamine and tromethamine and inorganic salts derived from sodium, calcium, potassium, magnesium, manganese, iron, copper, zinc, aluminum, and lithium.

The compounds of the invention, including their pharmaceutically acceptable salts, whether alone or in combination, (collectively, "active agent" or "active agents") of the present invention are useful as MGL-modulators in the methods of the invention. Such methods for modulating MGL comprise the use of a therapeutically effective amount of at least one chemical entity of the invention.

In some embodiments, the MGL modulator is an inhibitor and is used in a subject diagnosed with or suffering from a disease, disorder, or condition associated with MGL receptor activity, such as those described herein. Symptoms or disease states are intended to be included within the scope of "disease, disorders or conditions."

Accordingly, the invention relates to methods of using the active agents described herein to treat subjects diagnosed with or suffering from a disease, disorder, or condition associated with the MGL receptor activity. The term "treat" or "treating" as used herein is intended to refer to administration of an active agent or composition of the invention to a subject for the purpose of effecting a therapeutic or prophylactic benefit through modulation of MGL receptor activity. Treating includes reversing, ameliorating, alleviating, inhibiting the progress of, lessening the severity of, or preventing a disease, disorder, or condition, or one or more symptoms of such disease, disorder or condition associated with the MGL modulation. The term "subject" refers to a mammalian patient in need of such treatment, such as a human.

The term "composition" refers to a product that includes the specified ingredients in therapeutically effective amounts, as well as any product that results, directly, or indirectly, from combinations of the specified ingredients in the specified amounts.

The term "MGL inhibitor" is intended to encompass a compound that interacts with MGL to substantially reduce or eliminate its catalytic activity, thereby increasing the concentrations of its substrate(s). The term "MGL-modulated" is used to refer to the condition of being affected by the modulation of the MGL enzyme including the condition of being affected by the inhibition of the MGL enzyme. The disclosure is directed to methods for treating, ameliorating and/or preventing diseases, conditions, or disorders associated with pain (including inflammatory pain), and also psychiatric disorders, neurological disorders, cancers and eye conditions by the administration of therapeutically effective amounts of MGL modulators to subjects in need thereof.

The term "modulators" include both inhibitors and activators, where "inhibitors" refer to compounds that decrease, prevent, inactivate, desensitize, or down-regulate the MGL expression or activity, and "activators" are compounds that increase, activate, facilitate, sensitize, or up-regulate MGL expression or activity.

As used herein, unless otherwise noted, the term "affect" or "affected" (when referring to a disease, condition or disorder that is affected by inhibition of MGL) includes a reduction in the frequency and/or severity of one or more symptoms or manifestations of said disease, condition or disorder; and/or include the prevention of the development of one or more symptoms or manifestations of said disease, condition or disorder or the development of the disease, condition or disorder.

In treatment methods according to the invention, a therapeutically effective amount of at least one active agent according to the invention is administered to a subject suffering from or diagnosed as having such a disease, disorder, or condition. A "therapeutically effective amount" means an amount or dose sufficient to generally bring about the desired therapeutic or prophylactic benefit in subjects in need of such treatment for the designated disease, disorder, or condition. Effective amounts or doses of the active agents of the present invention may be ascertained by routine methods such as modeling, dose escalation studies or clinical trials, and by taking into consideration routine factors, e.g., the mode or route of administration or drug delivery, the pharmacokinetics of the agent, the severity and course of the disease, disorder, or condition, the subject's previous or ongoing therapy, the subject's health status and response to drugs, and the judgment of the treating physician. For a 70-kg human, an illustrative range for a suitable dosage amount is from about 1 to 1000 mg/day in single or multiple dosage units (e.g., BID, TID, QID or as required by modality).

Once improvement of the subject's disease, disorder, or condition has occurred, the dose may be adjusted for preventive or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Subjects may, however, require intermittent treatment on a long-term basis upon any recurrence of symptoms.

In addition, the compounds of the invention are envisaged for use alone, in combination with one or more of other compounds of this invention, or in combination with additional active ingredients in the treatment of the conditions discussed below. The additional active ingredients may be co-administered separately with at least one compound of the invention, with active agents of the invention or included with such an agent in a pharmaceutical composition according to the invention. In an illustrative embodiment, additional active ingredients are those that are known or discovered to be effective in the treatment of conditions, disorders, or diseases associated with the MGL modulation, such as another MGL inhibitor or a compound active against another target associated with the particular condition, disorder, or disease. The combination may serve to increase efficacy (e.g., by including in the combination a compound potentiating the potency or effectiveness of an agent according to the invention), decrease one or more side effects, or decrease the required dose of the active agent according to the invention.

When referring to inhibiting the target, an "effective amount" means an amount sufficient to affect MGL modulation.

The active agents of the invention are envisaged for use, alone or in combination with one or more additional active ingredients, to formulate pharmaceutical compositions of the invention. A pharmaceutical composition of the invention comprises a therapeutically effective amount of at least one active agent in accordance with the invention.

Pharmaceutically acceptable excipients commonly used in pharmaceutical compositions are substances that are non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of such excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the active agents may be prepared using pharmaceutically acceptable excipients and compounding techniques known or that become available to those of ordinary skill in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. The compositions may be formulated for any one of a plurality of administration routes, such as intravenous infusion, topical administration, or oral administration. Preferably, the compositions may be formulated for oral administration.

For oral administration, the active agents of the invention can be provided in the form of tablets or capsules, or as a solution, emulsion, or suspension. To prepare the oral compositions, the active agents may be formulated to yield a dosage of, e.g., for a 70-kg human, an illustrative range for a suitable dosage amount is from about 1 to 1000 mg/day in single or multiple dosage units.

Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin or (hydroxypropyl)methyl cellulose capsules. To prepare hard gelatin capsules, active ingredient(s) may be mixed with a solid, semi-solid, or liquid diluent. Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, compositions may be formulated for rectal administration as a suppository, enema or foam. For parenteral use, including intravenous, intramuscular, intraperitoneal, or subcutaneous routes, the agents of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 µg/kg/minute of agent admixed with a pharmaceutical carrier over a period ranging from several minutes to several days.

For topical administration, the agents may be mixed with a pharmaceutical carrier at a concentration of about 0.01% to about 20% of drug to vehicle, preferably 0.1% to 10%. Another mode of administering the agents of the invention may utilize a patch formulation to affect transdermal delivery.

Active agents may alternatively be administered in methods of this invention by inhalation, via the nasal or oral routes, e.g., in a spray formulation also containing a suitable carrier.

In a further embodiment, the invention is directed to a method of treating a subject suffering from or diagnosed with a disease, disorder, or condition associated with MGL modulation, comprising administering to the subject in need of such treatment a therapeutically effective amount of the active agent.

The compounds of Formula (I) (as well as compounds of Formula (II)) are useful in methods for treating, ameliorating and/or preventing a disease, a condition or a disorder that is affected by the inhibition of MGL. Such methods comprise administering to a subject, including an animal, a mammal, and a human in need of such treatment, amelioration and/or prevention, a therapeutically effective amount of a compound of Formula (I) (as well as compounds of Formula (II)), or an enantiomer, diastereomer, solvate or pharmaceutically acceptable salt thereof.

In particular, the compounds of Formula (I) (as well as compounds of Formula (II)), or pharmaceutically acceptable salts, isotopes, N-oxides, solvates and stereoisomers thereof, are useful for treating, ameliorating and/or preventing diseases, conditions, or disorders causing pain, psychiatric disorders, neurological disorders, cancers and eyes conditions. More particularly, the compounds of Formula (I) (as well as compounds of Formula (II)), or pharmaceutically acceptable salts, isotopes, N-oxides, solvates and stereoisomers thereof, are useful for treating, ameliorating and/or preventing inflammatory pain, major depressive disorder, treatment resistant depression, anxious depression or bipolar disorder by administering to a subject in need thereof a therapeutically effective amount of a compound of Formula (I) (as well as compounds of Formula (II)), or a pharmaceutically acceptable salt, isotope, N-oxide, solvate or stereoisomer thereof as herein defined.

1) Pain

Examples of inflammatory pain include, but are not limited to, pain due to a disease, condition, disorder, or a pain state including inflammatory bowel disease, visceral pain, migraine, post-operative pain, osteoarthritis, rheumatoid arthritis, back pain, lower back pain, joint pain, abdominal pain, chest pain, labor, musculoskeletal diseases, skin diseases, toothache, pyresis, burn, sunburn, snake bite, venomous snake bite, spider bite, insect sting, neurogenic bladder, interstitial cystitis, urinary tract infection, rhinitis, contact dermatitis/hypersensitivity, itch, eczema, pharyngitis, mucositis, enteritis, irritable bowel syndrome, cholecystitis, pancreatitis, postmastectomy pain syndrome, menstrual pain, endometriosis, pain due to physical trauma, headache, sinus headache, tension headache, or arachnoiditis.

One type of inflammatory pain is inflammatory hyperalgesia/hypersensitivity. Examples of inflammatory hyperalgesia include a disease, condition, disorder, or pain state including inflammation, osteoarthritis, rheumatoid arthritis, back pain, joint pain, abdominal pain, musculoskeletal diseases, skin diseases, post-operative pain, headaches, toothache, burn, sunburn, insect sting, neurogenic bladder, urinary incontinence, interstitial cystitis, urinary tract infection, cough, asthma, chronic obstructive pulmonary disease, rhinitis, contact dermatitis/hypersensitivity and/or dermal allergy, itch, eczema, pharyngitis, enteritis, irritable bowel syndrome, inflammatory bowel diseases including Crohn's Disease, ulcerative colitis, benign prostatic hypertrophy, and nasal hypersensitivity.

In an embodiment, the present invention is directed to a method for treating, ameliorating and/or preventing inflammatory visceral hyperalgesia in which an enhanced visceral irritability exists, comprising, consisting of, and/or consisting essentially of the step of administering to a subject in need of such treatment a therapeutically effective amount of a compound of Formula (I) (as well as compounds of Formula (II)) or a pharmaceutically acceptable salt, isotope, N-oxide, solvate or stereoisomer thereof. In a further embodiment, the present invention is directed to a method for treating inflammatory somatic hyperalgesia in which a hypersensitivity to thermal, mechanical and/or chemical stimuli exists, comprising administering to a subject in need of such treatment a therapeutically effective amount of a compound of Formula (I) (as well as compounds of Formula (II)), or a pharmaceutically acceptable salt, isotope, N-oxide, solvate or stereoisomer thereof.

A further embodiment of the present invention is directed to a method for treating, ameliorating and/or preventing neuropathic pain. Examples of a neuropathic pain include pain due to a disease, condition, disorder, or pain state including cancer, neurological disorders, spine and peripheral nerve surgery, brain tumor, traumatic brain injury (TBI), spinal cord trauma, chronic pain syndrome, fibromyalgia, chronic fatigue syndrome, lupus, sarcoidosis, peripheral neuropathy, bilateral peripheral neuropathy, diabetic neuropathy, central pain, neuropathies associated with spinal cord injury, stroke, amyotrophic lateral sclerosis (ALS), Parkinson's disease, multiple sclerosis, sciatic neuritis, mandibular joint neuralgia, peripheral neuritis, polyneuritis, stump pain, phantom limb pain, bony fractures, oral neuropathic pain, Charcot's pain, complex regional pain syndrome I and II (CRPS I/II), radiculopathy, Guillain-Barre syndrome, meralgia paresthetica, burning-mouth syndrome, optic neuritis, postfebrile neuritis, migrating neuritis, segmental neuritis, Gombault's neuritis, neuronitis, cervicobrachial neuralgia, cranial neuralgia, geniculate neuralgia, glossopharyngeal neuralgia, migrainous neuralgia, idiopathic neuralgia, intercostals neuralgia, mammary neuralgia, Morton's neuralgia, nasociliary neuralgia, occipital neuralgia, postherpetic neuralgia, causalgia, red neuralgia, Sluder's neuralgia, splenopalatine neuralgia, supraorbital neuralgia, trigeminal neuralgia, vulvodynia, vidian neuralgia or chemotherapy-induced neuropathy.

One type of neuropathic pain is neuropathic cold allodynia, which can be characterized by the presence of a neuropathy-associated allodynic state in which a hypersensitivity to cooling stimuli exists. Examples of neuropathic cold allodynia include allodynia due to a disease, condition, disorder or pain state including neuropathic pain (neuralgia), pain arising from spine and peripheral nerve surgery or trauma, traumatic brain injury (TBI), trigeminal neuralgia, postherpetic neuralgia, causalgia, peripheral neuropathy, diabetic neuropathy, central pain, stroke, peripheral neuritis, polyneuritis, complex regional pain syndrome I and II (CRPS I/II) and radiculopathy.

In a further embodiment, the present invention is directed to a method for treating, ameliorating and/or preventing neuropathic cold allodynia in which a hypersensitivity to a cooling stimuli exists, comprising administering to a subject in need of such treatment a therapeutically effective amount of a compound of Formula (I) (as well as compounds of Formula (II)) or a pharmaceutically acceptable salt, isotope, N-oxide, solvate or stereoisomer thereof.

2) Psychiatric Disorders

Examples of psychiatric disorders include, but are not limited to, anxieties such as, social anxiety, post-traumatic stress disorder, phobias, social phobia, special phobias, panic disorder, obsessive-compulsive disorder, acute stress disorder, separation anxiety disorder, and generalized anxiety disorder, as well as depression such as, major depression, bipolar disorder, seasonal affective disorder, post-natal depression, manic depression, and bipolar depression, mood disorders and mood affective disorders that can be treated according to the present invention include, but are not limited to, bipolar disorder I depressed, hypomanic, manic and mixed form; bipolar disorder II; depressive disorders, such as single depressive episode or recurrent major depressive disorder, minor depressive disorder, treatment-resistant depression, anxious depression, bipolar disorder, depressive disorder with postpartum onset, depressive disorders with psychotic symptoms; persistent mood disorders, such as cyclothymia, dysthymia, euthymia; and premenstrual dysphoric disorder; psychoses.

3) Neurological Disorders

Examples of neurological disorder include, but are not limited to, tremors, dyskinesias, dystonias, spasticity, Tourette's Syndrome; neuromyelitis optica, Parkinson's disease; Alzheimer's disease; senile dementia; Huntington's disease; Epilepsy/seizure disorders and sleep disorders.

4) Cancers:

Examples of cancers include, but are not limited to, benign skin tumors, prostate tumors, ovarian tumors and cerebral tumors (glioblastomas, medulloepitheliomas, medulloblastomas, neuroblastomas, tumors of embryonic origin, astrocytomas, astroblastomas, ependymomas, oligodendrogliomas, neuroepitheliomas, epiphyseal tumor, ependymoblastomas, malignant meningiomas, sarcomatosis, malignant melanomas, schwannomas).

5) Eye Conditions

Examples of eye conditions include, but are not limited to, ocular hypertension, glaucoma, degeneration and apoptosis of retinal ganglion cells and neuroretinal cells.

Other embodiments of this invention provide for a method for modulating MGL receptor activity, including when such receptor is in a subject, comprising exposing MGL receptor to a therapeutically effective amount of at least one compound selected from compounds of the invention.

Embodiments of this invention are compounds of Formula (I),

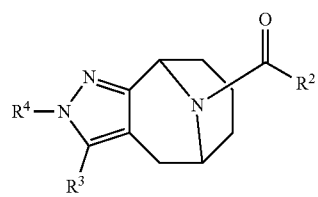
(I)

wherein
$R^2$ is selected from the group consisting of:

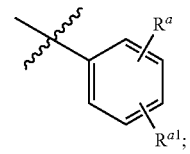

(b) 6-membered heteroaryl selected from the group consisting of: pyridazin-4-yl; pyrazin-2-yl; pyrimidinyl; pyrimidinyl substituted with $C_{1-4}$alkyl or $OC_{1-4}$alkyl; and pyridinyl, wherein the pyridinyl is substituted with one or two substituents each independently selected from the group consisting of: halo, $C_{1-4}$alkyl, $OC_{1-4}$alkyl, $OC_{1-4}$haloalkyl, $C_{3-6}$cycloalkyl, $NH_2$, CN, $N(CH_3)_2$,

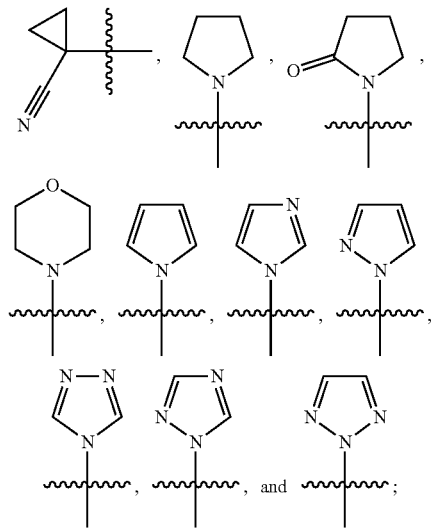

(c) 5-membered heteroaryl selected from the group consisting of:

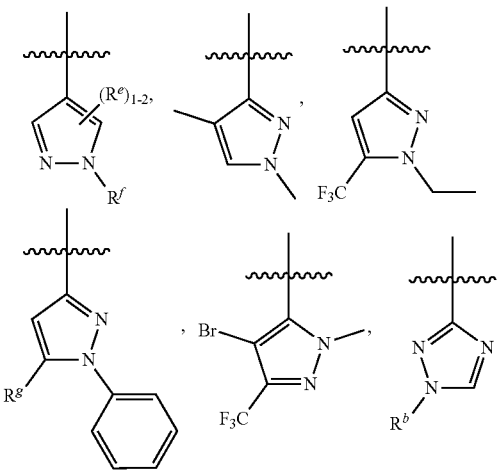

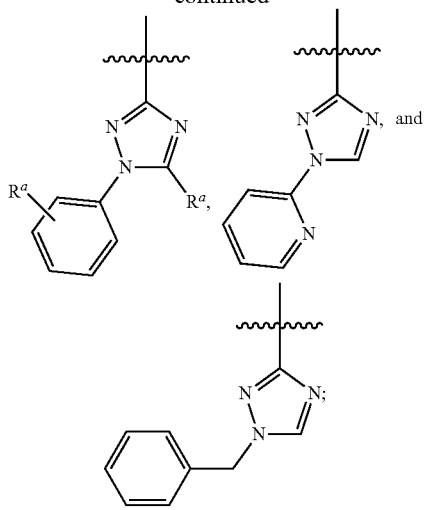
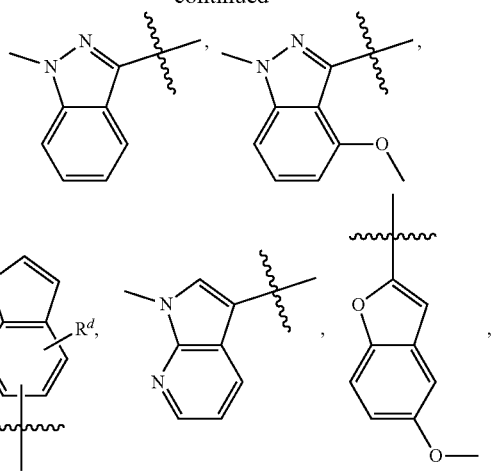
(d) 5,6-fused bicyclic heteroaryl or 6,5-fused bicyclic heteroaryl selected from the group consisting of:
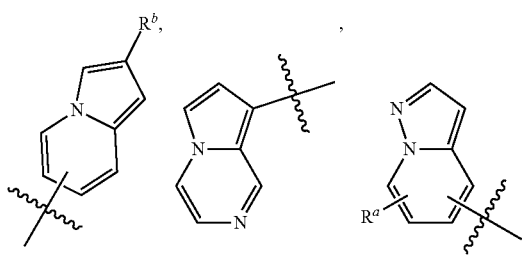
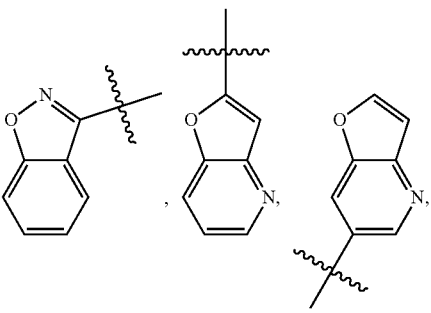
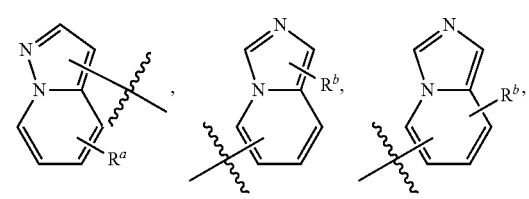
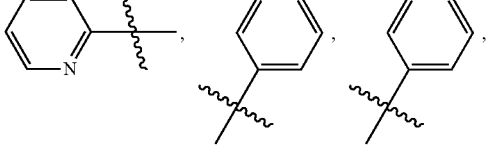
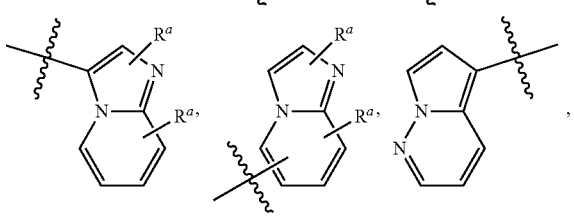
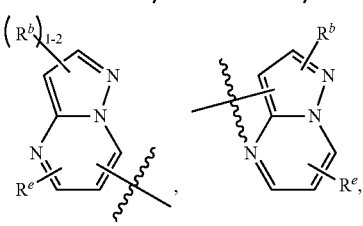
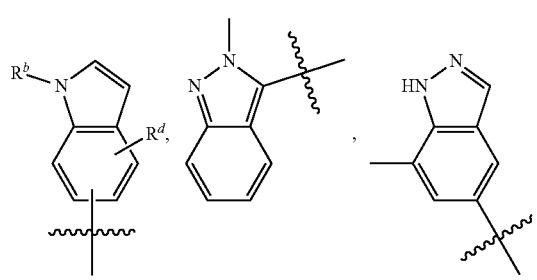
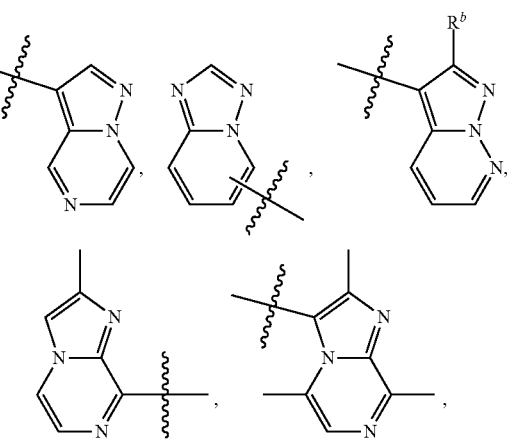

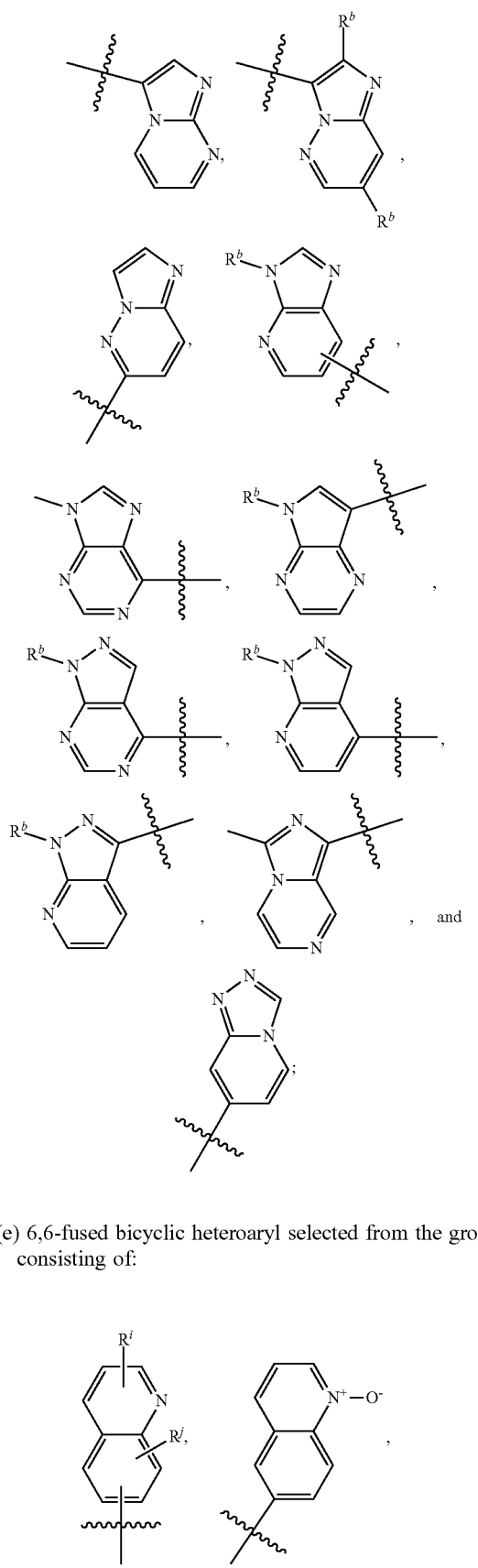
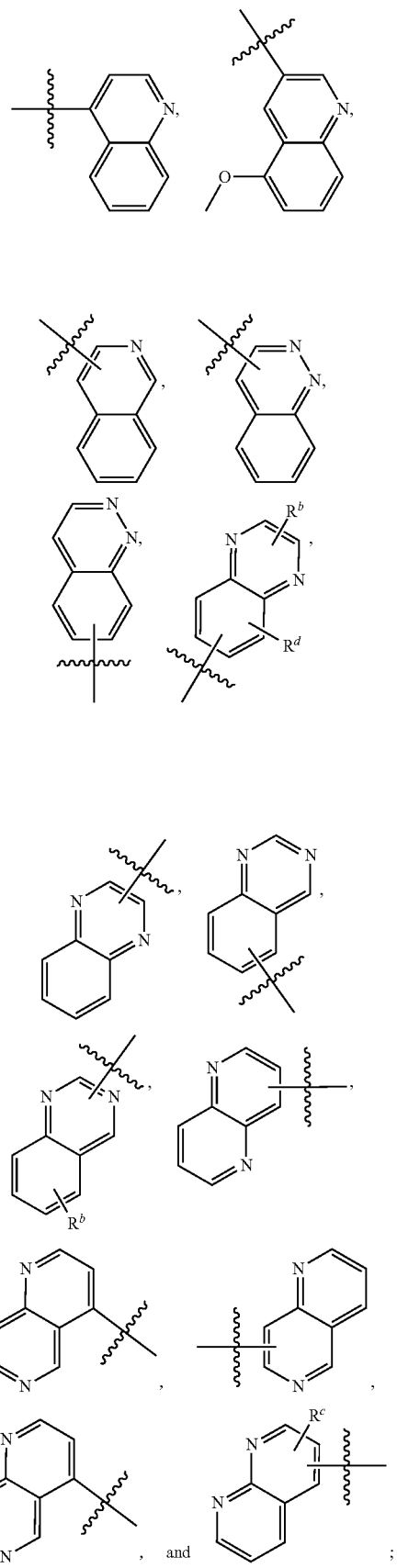
(e) 6,6-fused bicyclic heteroaryl selected from the group consisting of:

and
(f)

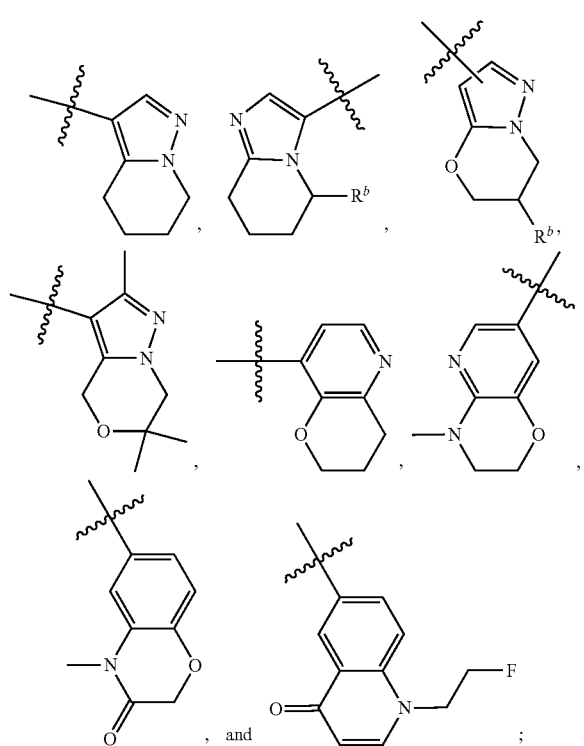

wherein
$R^a$ is selected from the group consisting of: H, halo, $C_{1-4}$alkyl, $OC_{1-4}$alkyl, $C_{1-4}$haloalkyl and $OC_{1-4}$haloalkyl;
$R^{a1}$ is selected from the group consisting of: $C_{1-4}$alkyl; $OC_{1-4}$alkyl; $OC_{1-4}$haloalkyl; $N(C{=}O)CH_3$; oxazol-2-yl; pyrimidin-2-yl; and 5-membered heteroaryl ring containing two, three, or four nitrogen members, wherein the 5-membered heteroaryl ring is optionally substituted with one $R^a$ member;
$R^b$ is H or $C_{1-4}$akyl;
$R^c$ is H or $C_{1-4}$haloalkyl;
$R^d$ is H or halo;
$R^e$ is selected from the group consisting of: H, halo, $C_{1-4}$akyl, $C_{1-4}$haloalkyl, $OC_{1-4}$alkyl, and $C_{3-6}$cycloalkyl;
$R^f$ is selected from the group consisting of: H, $C_{1-4}$alkyl, $CH_2CH_2OH$, $C_{1-4}$haloalkyl, cyclopropyl, phenyl, and phenyl substituted with $CF_3$;
$R^g$ is selected from the group consisting of: H, $OC_{1-4}$alkyl and $C_{1-4}$haloalkyl;
$R^i$ is selected from the group consisting of: H, halo, $C_{1-4}$alkyl, $C_{1-4}$haloalkyl, OH, $OC_{1-4}$alkyl, $OC_{1-4}$haloalkyl, and $C_{3-6}$cycloalkyl;
$R^j$ is selected from the group consisting of: H, halo, $OCH_3$, OH, $NH_2$, and $NO_2$;
$R^3$ is selected from the group consisting of:
(g) phenyl, wherein phenyl is independently substituted with one, two, or three members selected from the group consisting of: halo, $C_{1-4}$alkyl, $C_{1-4}$haloalkyl, and $OC_{1-4}$alkyl;
(h) 5-(trifluoromethyl)-2-thienyl or 1-methylindol-2-yl; and
(i) cyclopropyl; and
$R^4$ is $C_{1-4}$alkyl or $C_{3-4}$cycloalkyl;
and pharmaceutically acceptable salts, isotopes, N-oxides, solvates, and stereoisomers thereof.

An additional embodiment of the invention is a compound of Formula (I) wherein $R^2$ is

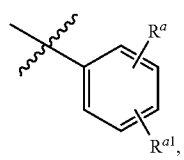

where $R^a$ is H, halo, $C_{1-4}$alkyl, or $OC_{1-4}$alkyl; and $R^{a1}$ is $C_{1-4}$alkyl, $OC_{1-4}$alkyl, $OC_{1-4}$haloalkyl, or $(C{=}O)NHCH_3$.

An additional embodiment of the invention is a compound of Formula (I) wherein $R^2$ is

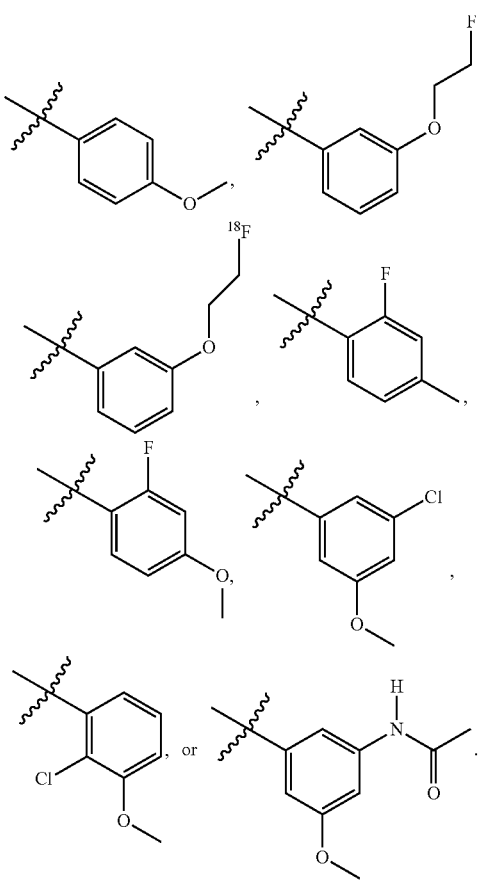

An additional embodiment of the invention is a compound of Formula (I) wherein $R^2$ is

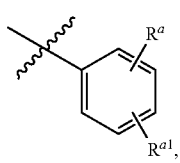

where $R^a$ is H, halo, $C_{1-4}$alkyl, $OC_{1-4}$alkyl, or $C_{1-4}$haloalkyl; and $R^{a1}$ is

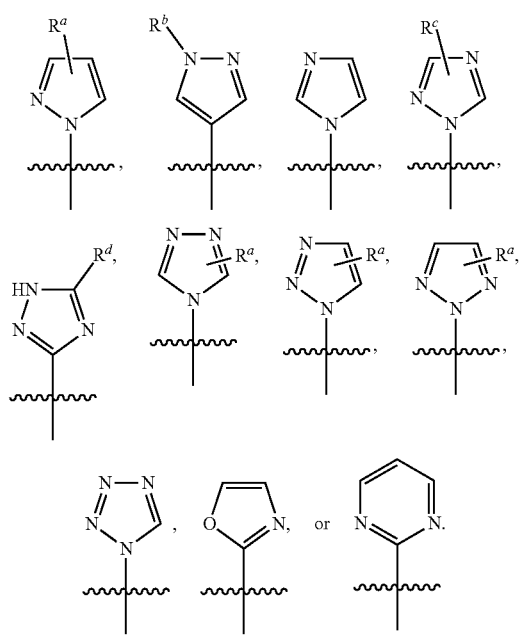

An additional embodiment of the invention is a compound of Formula (I) wherein $R^{a1}$ is

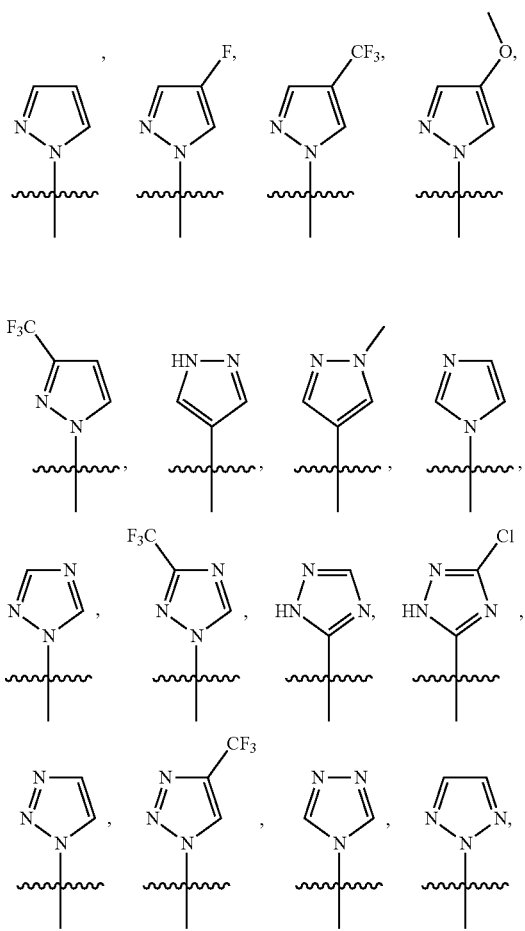

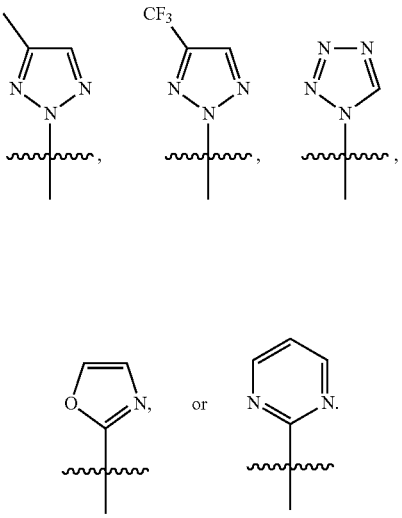

An additional embodiment of the invention is a compound of Formula (I) wherein $R^a$ is H, Cl, F, $CH_3$, $CF_3$, or $OCH_3$.

An additional embodiment of the invention is a compound of Formula (I) wherein $R^b$ is H or $CH_3$.

An additional embodiment of the invention is a compound of Formula (I) wherein $R^c$ is H or $CF_3$.

An additional embodiment of the invention is a compound of Formula (I) wherein $R^d$ is H, Cl, or F.

An additional embodiment of the invention is a compound of Formula (I) wherein $R^2$ is

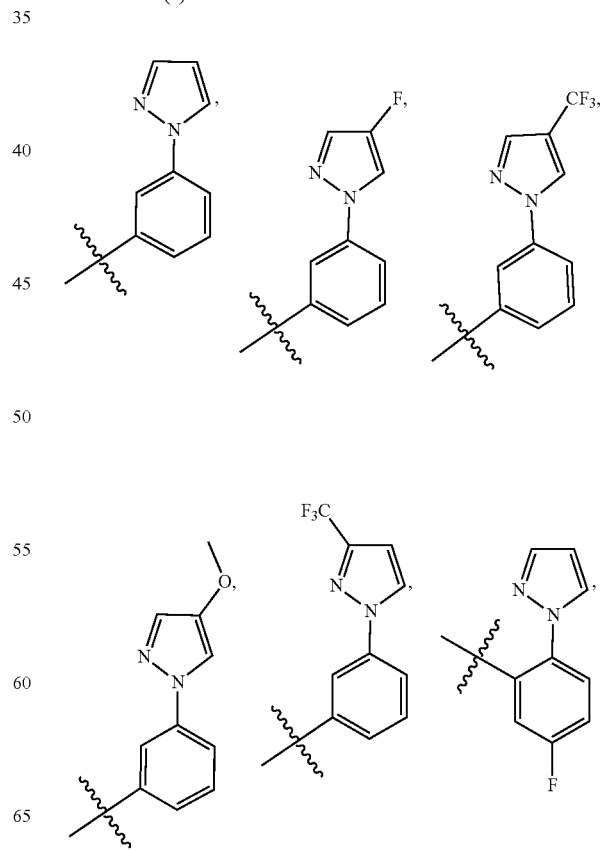

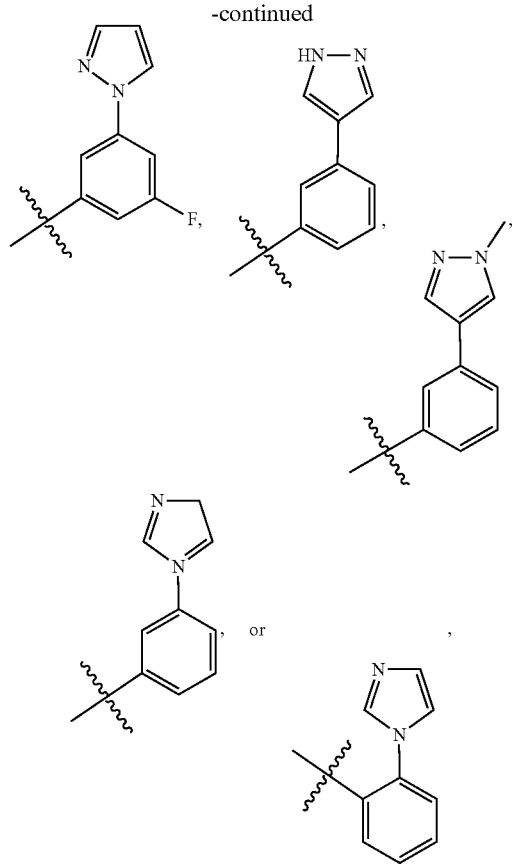
An additional embodiment of the invention is a compound of Formula (I) wherein R² is
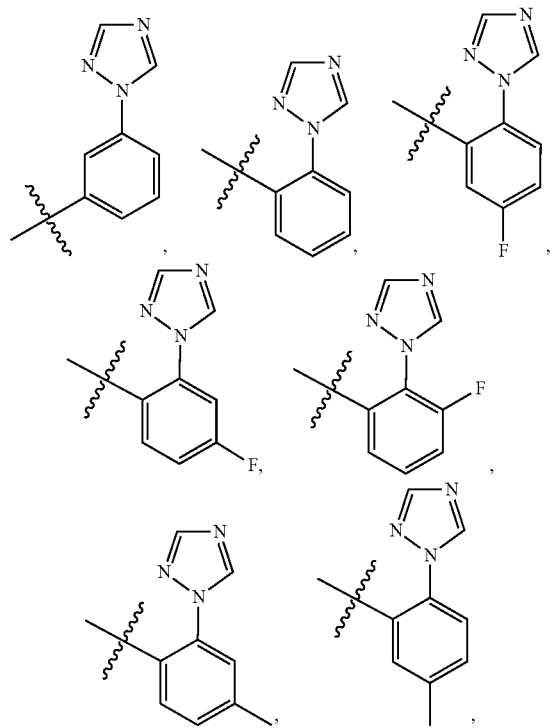
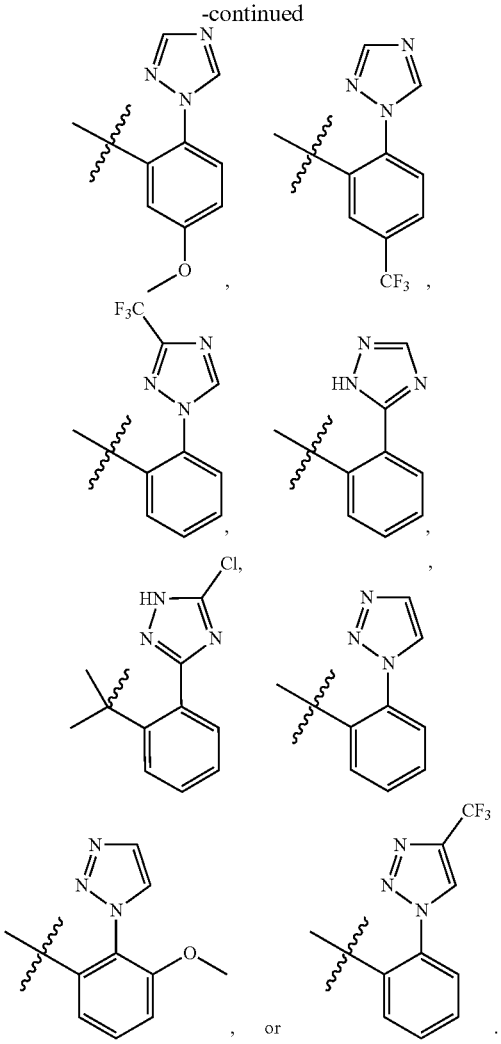
An additional embodiment of the invention is a compound of Formula (I) wherein R² is
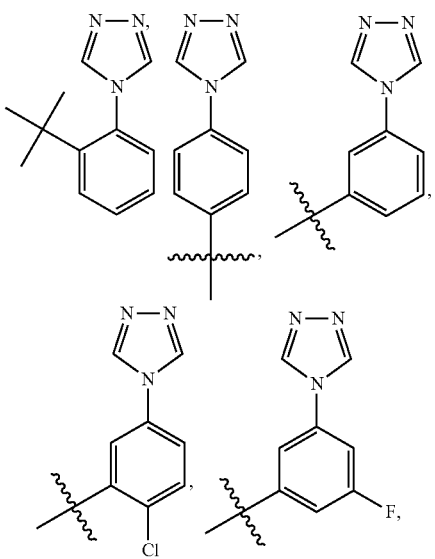

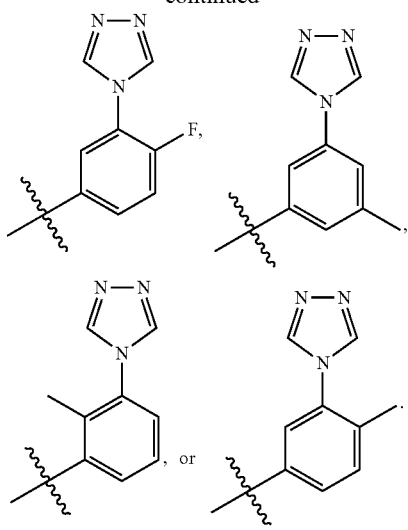
An additional embodiment of the invention is a compound of Formula (I) wherein R² is
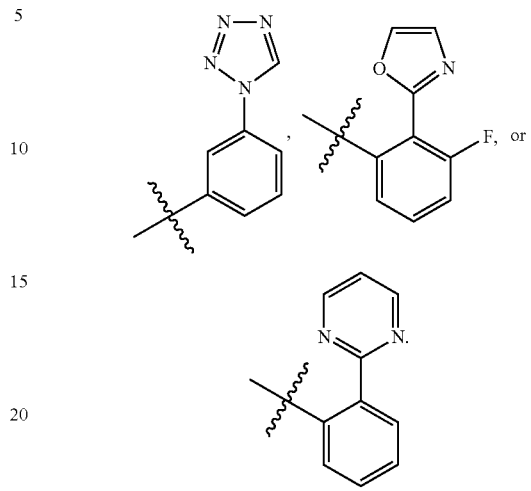
An additional embodiment of the invention is a compound of Formula (I) wherein R² is
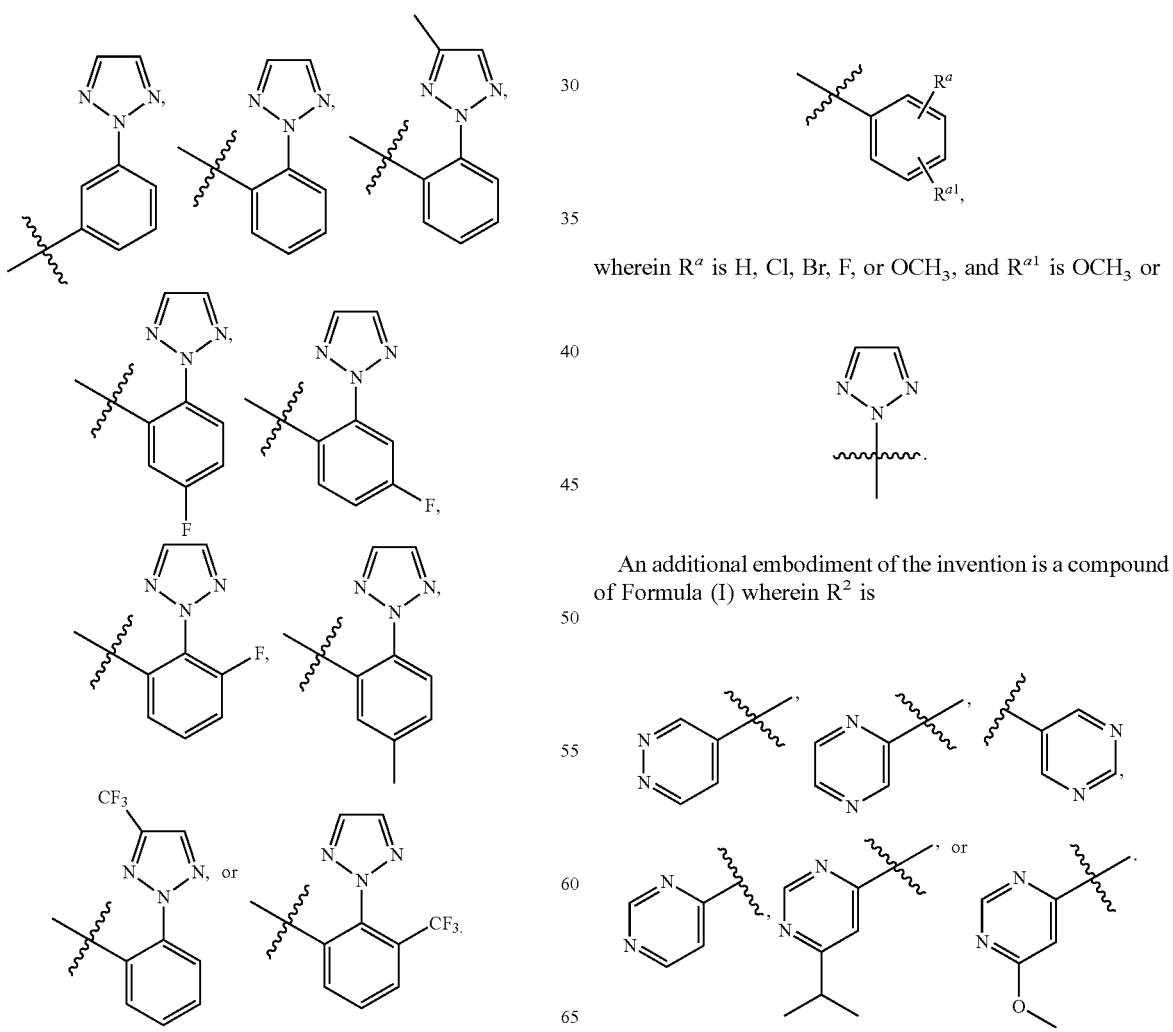
wherein $R^a$ is H, Cl, Br, F, or OCH₃, and $R^{a1}$ is OCH₃ or
An additional embodiment of the invention is a compound of Formula (I) wherein R² is An additional embodiment of the invention is a compound of Formula (I) wherein R² is
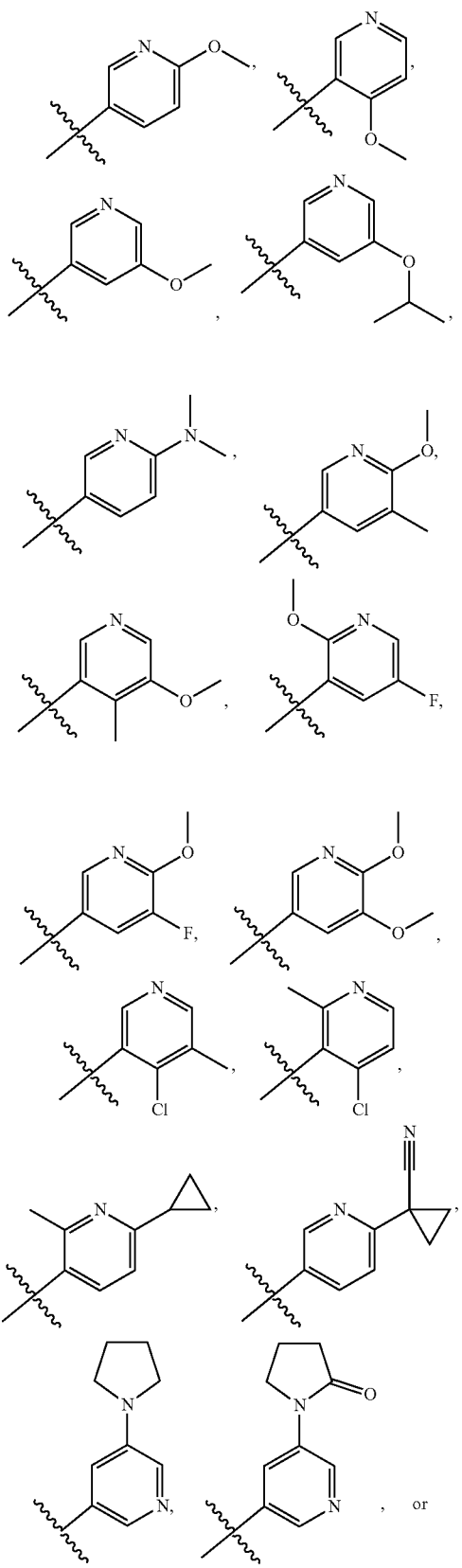
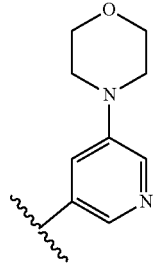
An additional embodiment of the invention is a compound of Formula (I) wherein R² is
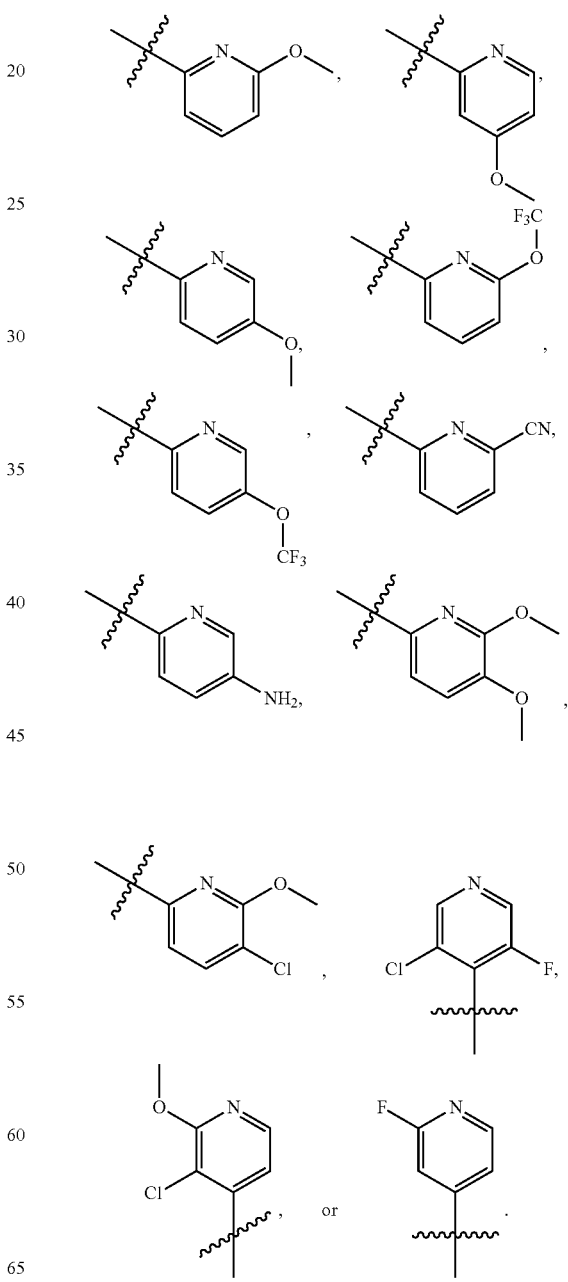

An additional embodiment of the invention is a compound of Formula (I) wherein R² is
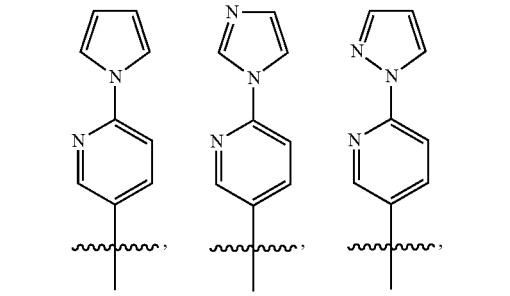
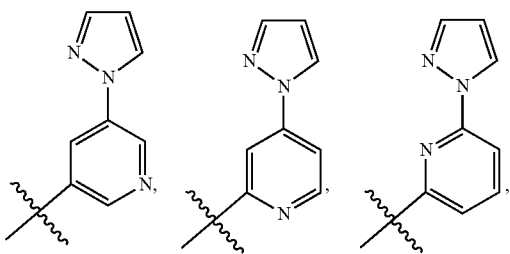
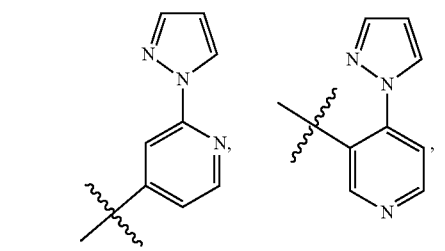
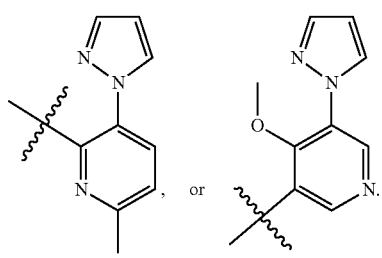
An additional embodiment of the invention is a compound of Formula (I) wherein R² is
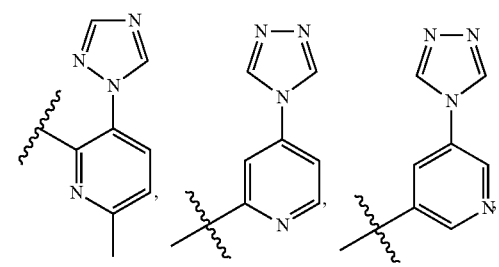
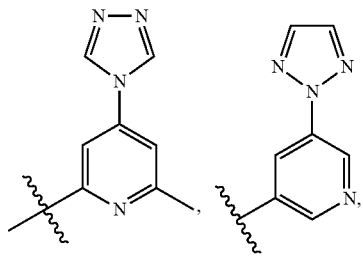
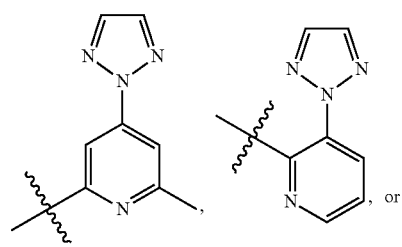
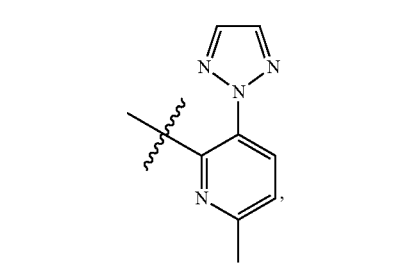
An additional embodiment of the invention is a compound of Formula (I) wherein R² is
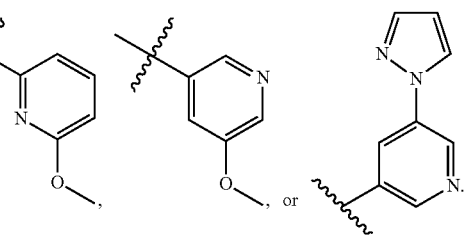
An additional embodiment of the invention is a compound of Formula (I) wherein R² is
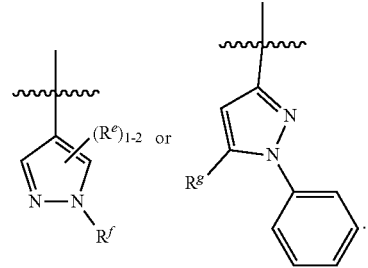

An additional embodiment of the invention is a compound of Formula (I) wherein $R^2$ is:

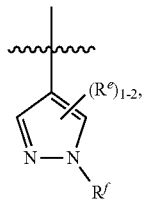

and $R^e$ is independently selected from the group consisting of: H, halo, $C_{1-4}$akyl, $C_{1-4}$haloalkyl, $OC_{1-4}$alkyl, and cyclopropyl.

An additional embodiment of the invention is a compound of Formula (I) wherein $R^2$ is:

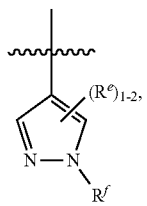

and $R^f$ is selected from the group consisting of: H, $C_{1-4}$alkyl, $CH_2CH_2OH$, $CH_2CF_3$, cyclopropyl, phenyl, and phenyl substituted with $CF_3$.

An additional embodiment of the invention is a compound of Formula (I) wherein $R^2$ is

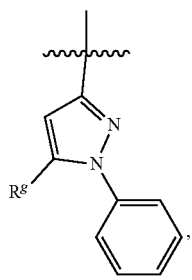

and $R^g$ is H, $OCH_3$ or $CF_3$.

An additional embodiment of the invention is a compound of Formula (I) wherein $R^2$ is

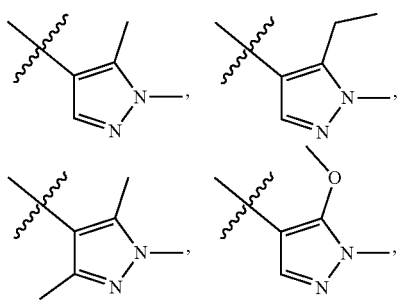

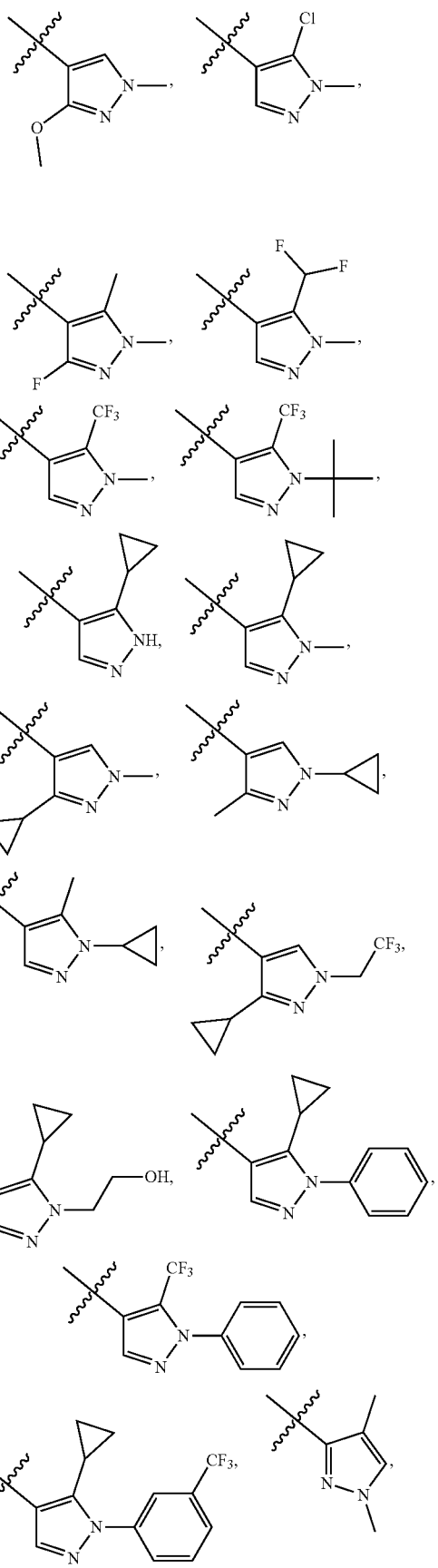

-continued

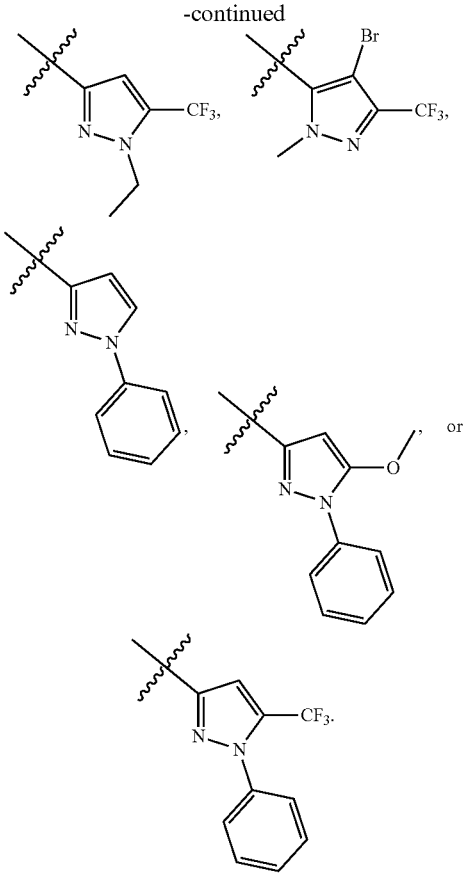

An additional embodiment of the invention is a compound of Formula (I) wherein R² is

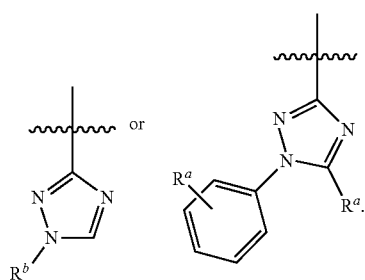

An additional embodiment of the invention is a compound of Formula (I) wherein R² is

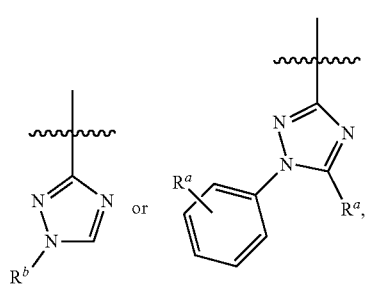

and R$^a$ is independently selected from the group consisting of: H, Cl, F, C$_{1-4}$alkyl, OC$_{1-4}$alkyl, and C$_{1-4}$haloalkyl; and R$^b$ is CH$_3$ or CH(CH$_3$)$_2$.

An additional embodiment of the invention is a compound of Formula (I) wherein R² is

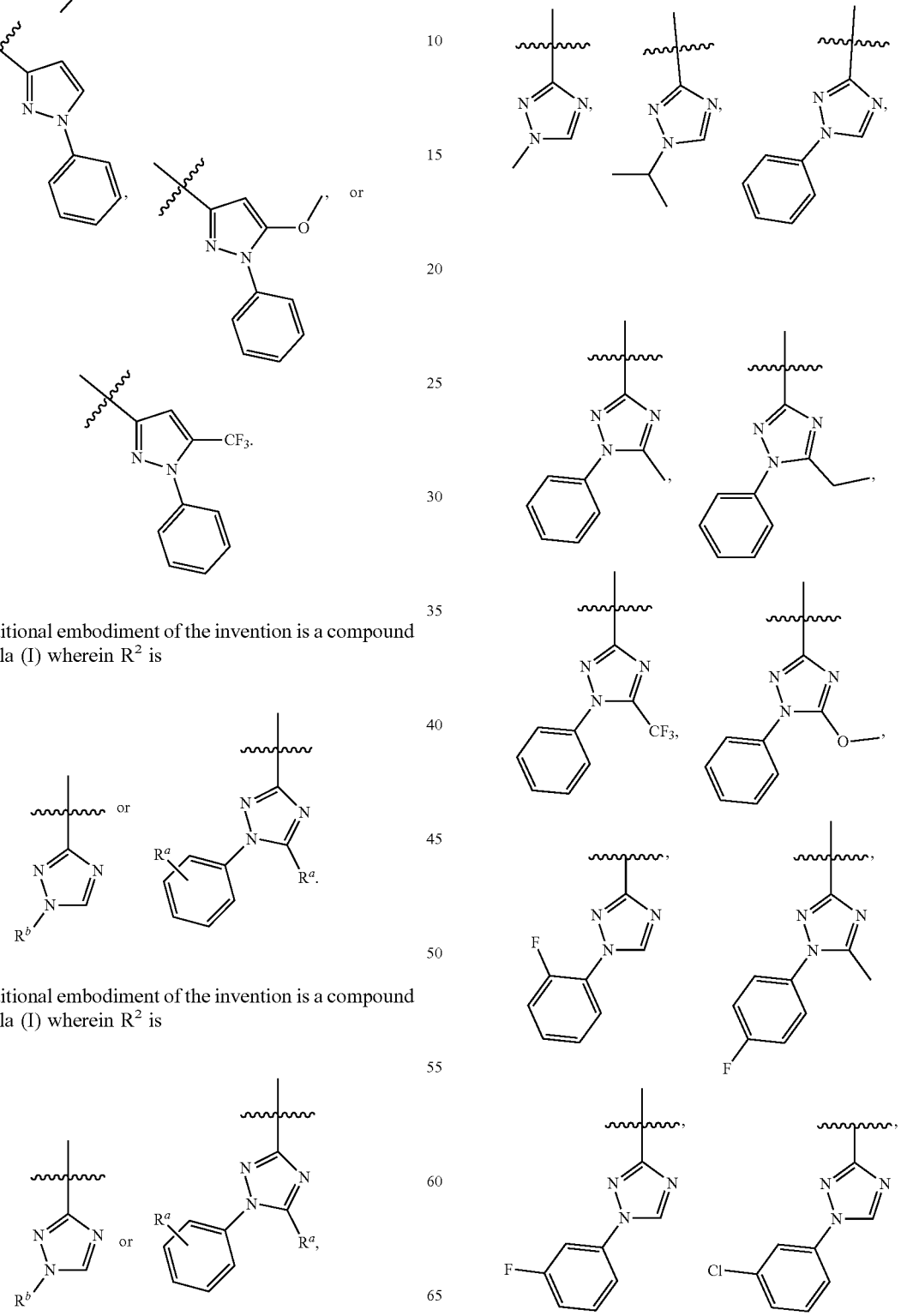

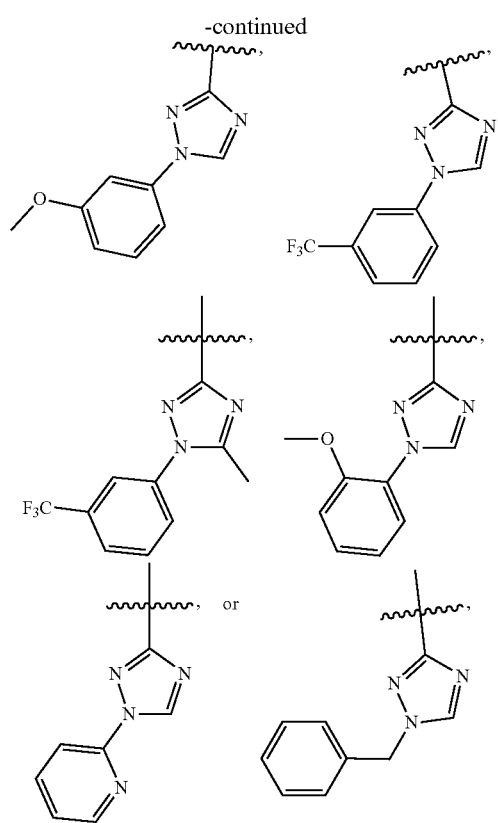
An additional embodiment of the invention is a compound of Formula (I) wherein R² is
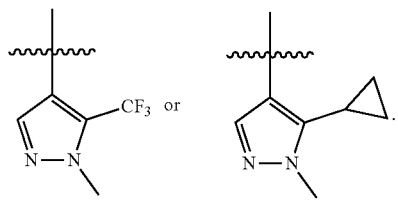
An additional embodiment of the invention is a compound of Formula (I) wherein R² is
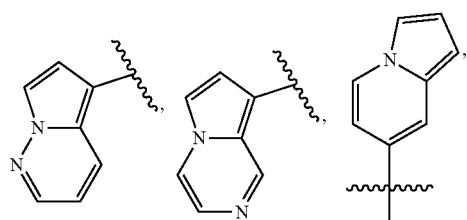
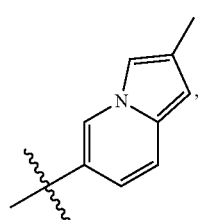
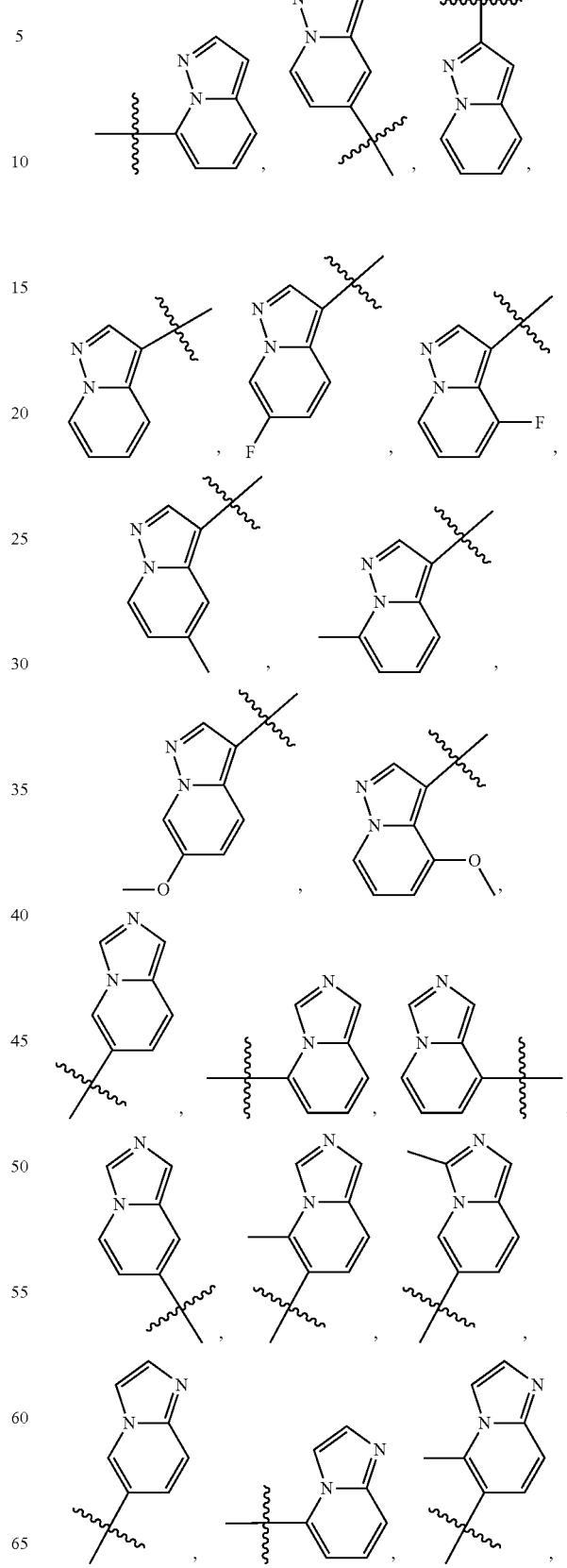

-continued
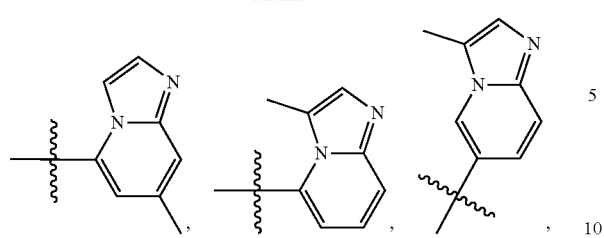
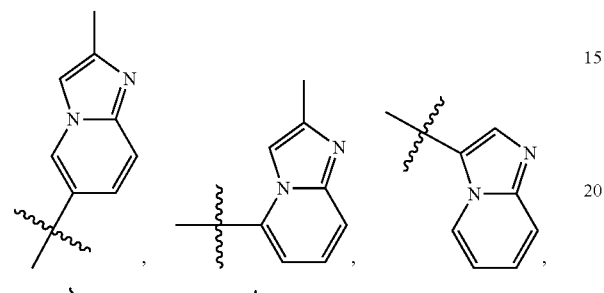
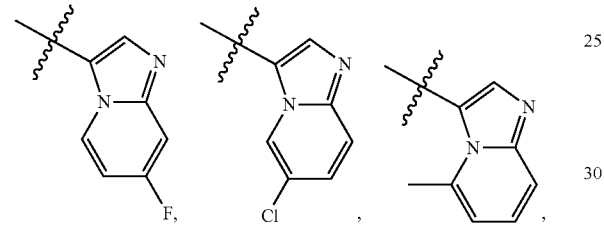
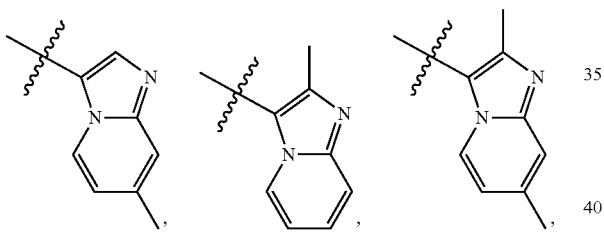
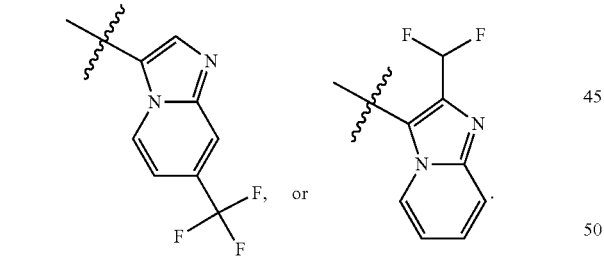
An additional embodiment of the invention is a compound of Formula (I) wherein R² is
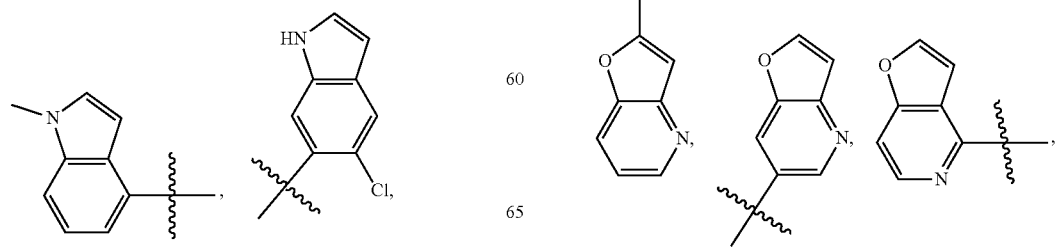
-continued
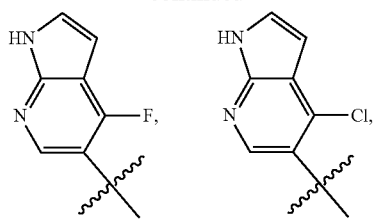
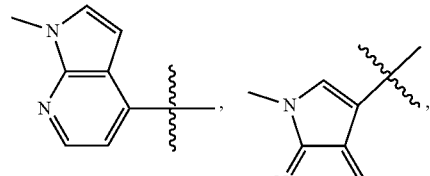
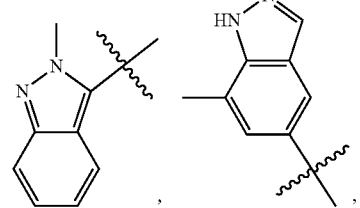
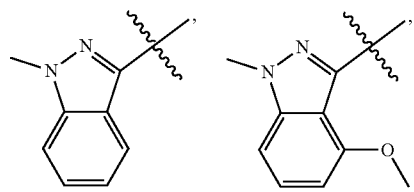
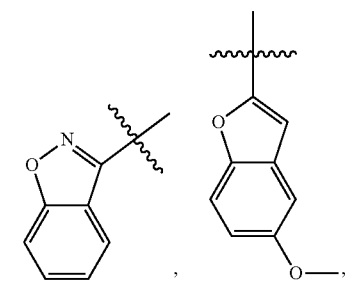
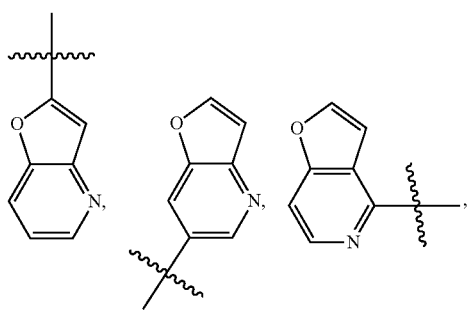

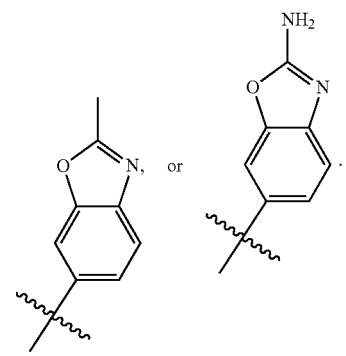
An additional embodiment of the invention is a compound of Formula (I) wherein R² is
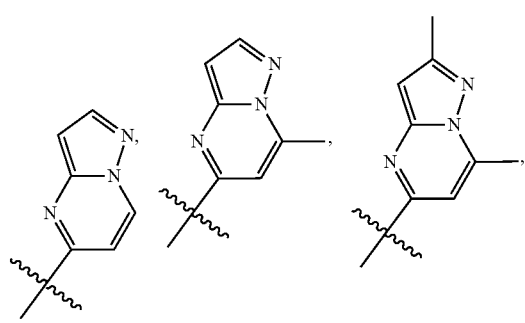
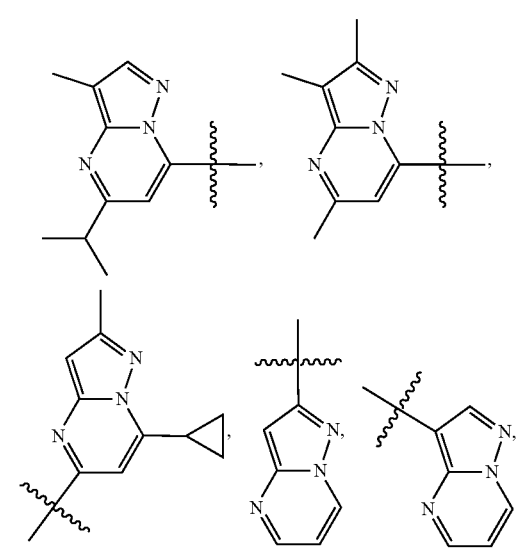
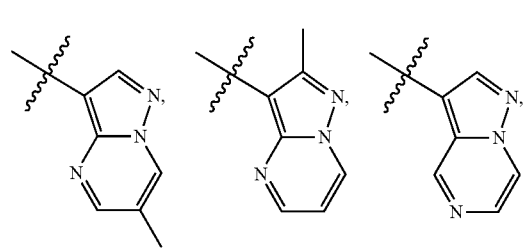
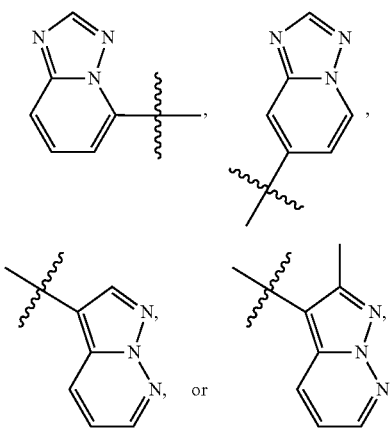
An additional embodiment of the invention is a compound of Formula (I) wherein R² is
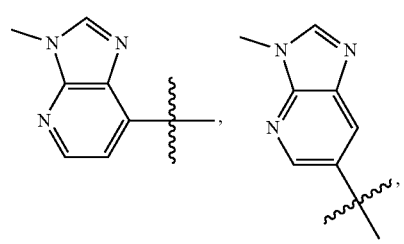
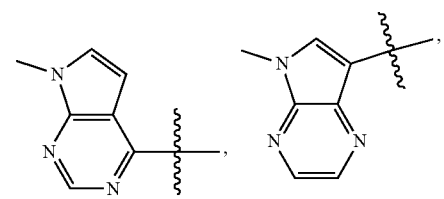
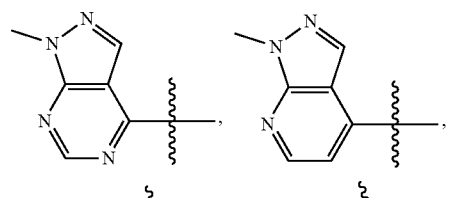
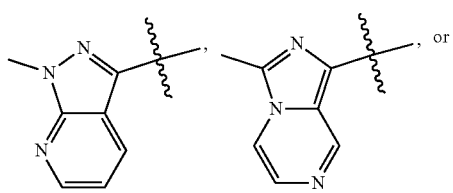
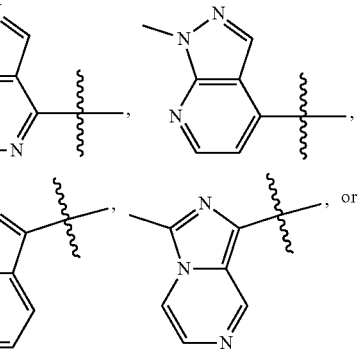
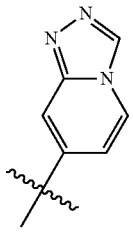

An additional embodiment of the invention is a compound of Formula (I) wherein R² is
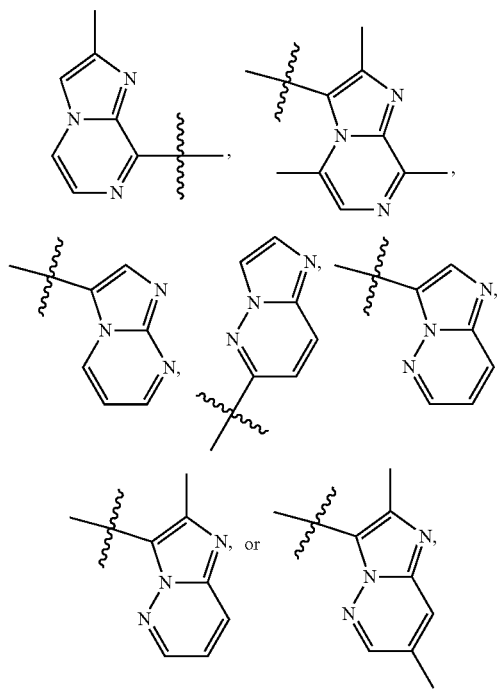
An additional embodiment of the invention is a compound of Formula (I) wherein R² is
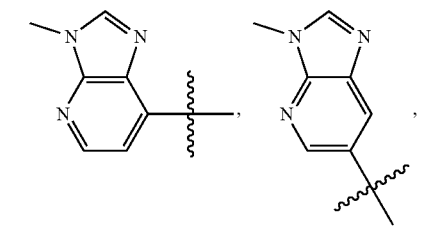
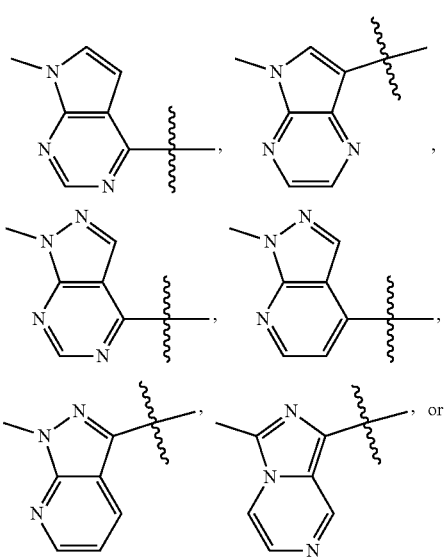
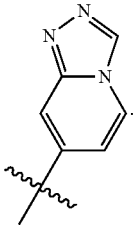
An additional embodiment of the invention is a compound of Formula (I) wherein R² is
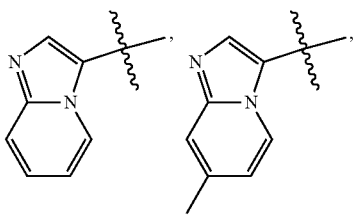
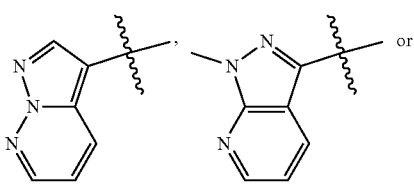
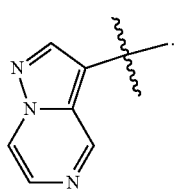
An additional embodiment of the invention is a compound of Formula (I) wherein R² is
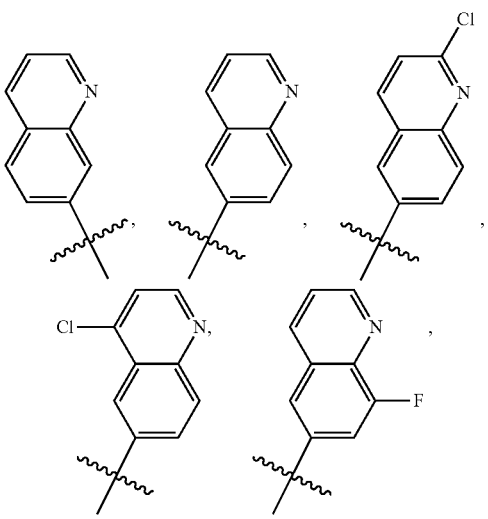

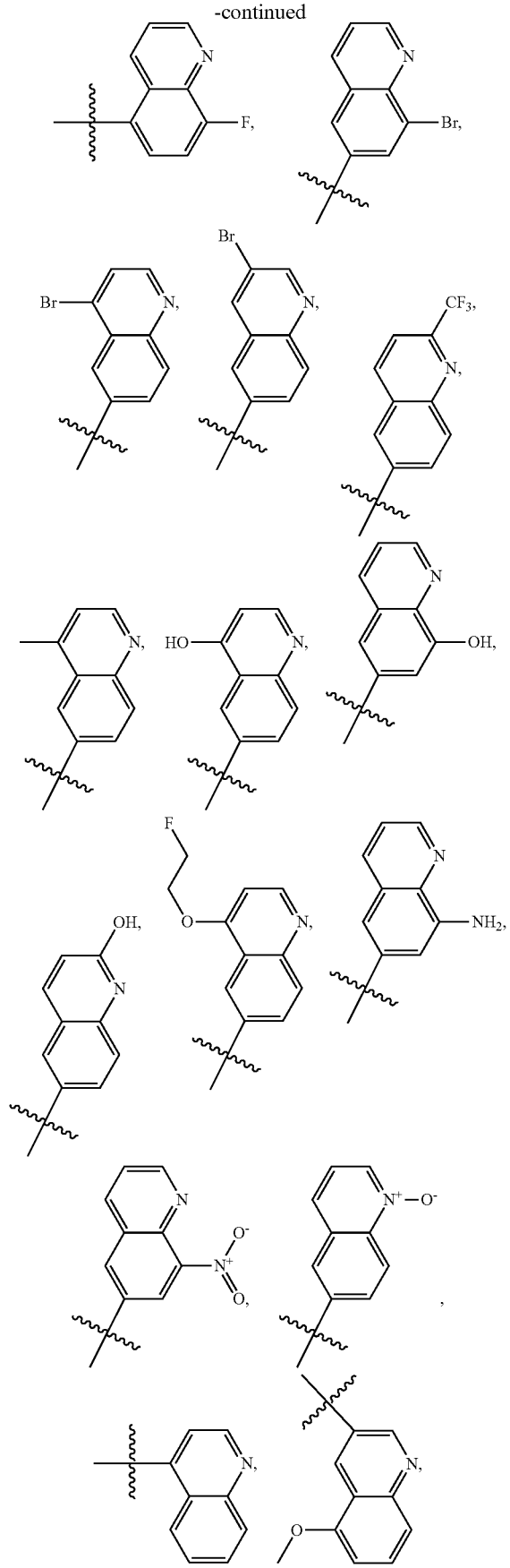
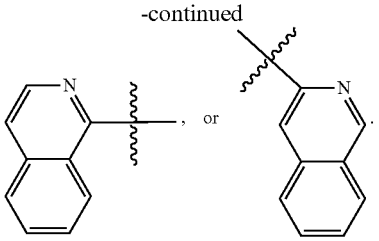
An additional embodiment of the invention is a compound of Formula (I) wherein $R^2$ is
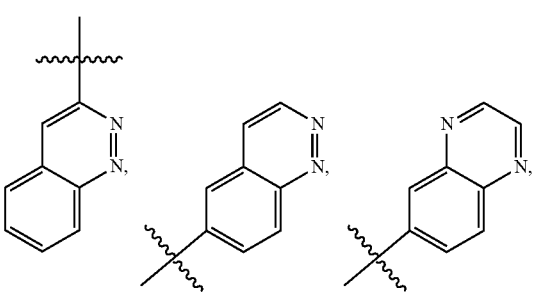
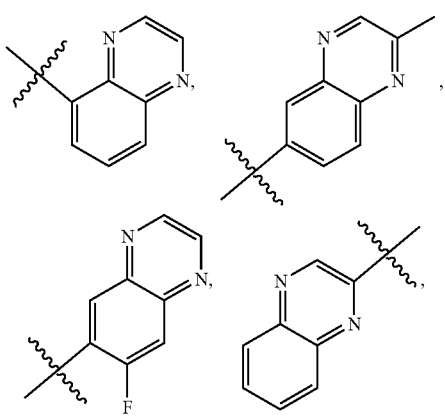
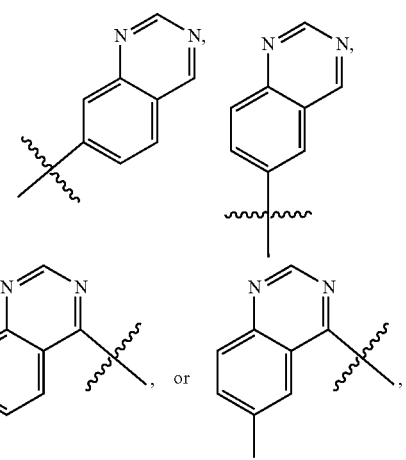

An additional embodiment of the invention is a compound of Formula (I) wherein R² is
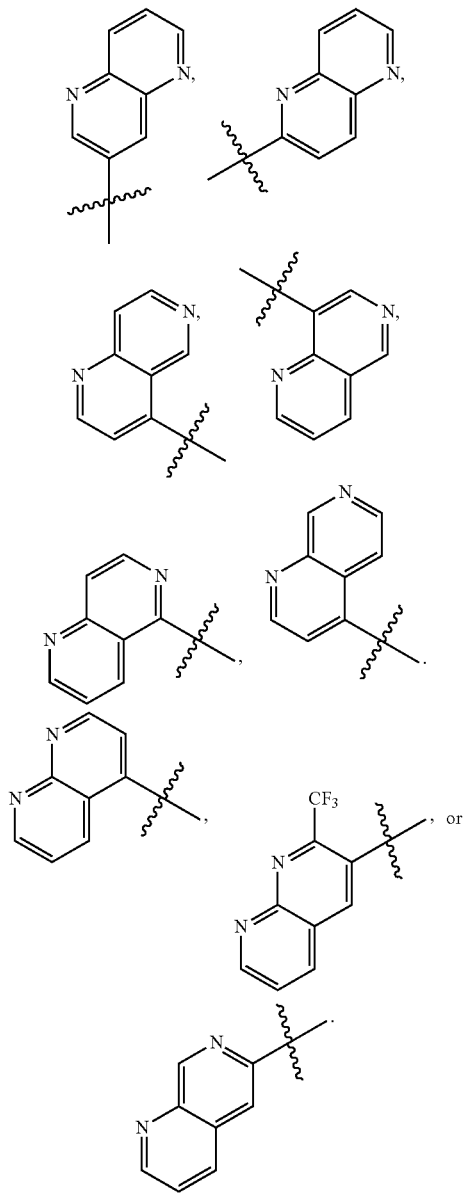
An additional embodiment of the invention is a compound of Formula (I) wherein R² is
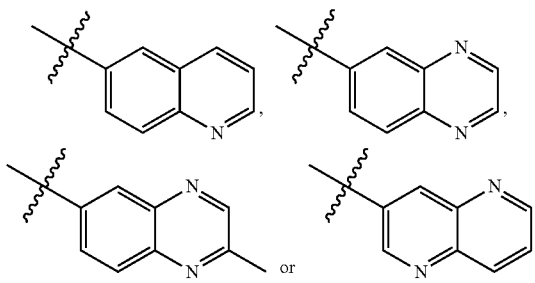
An additional embodiment of the invention is a compound of Formula (I) wherein R² is
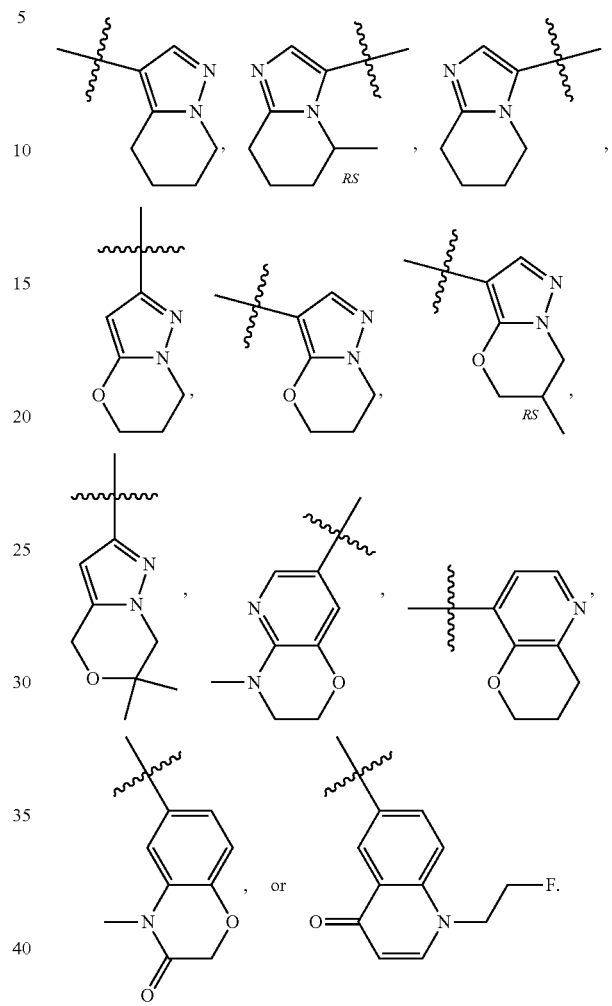
An additional embodiment of the invention is a compound of Formula (I) wherein R³ is
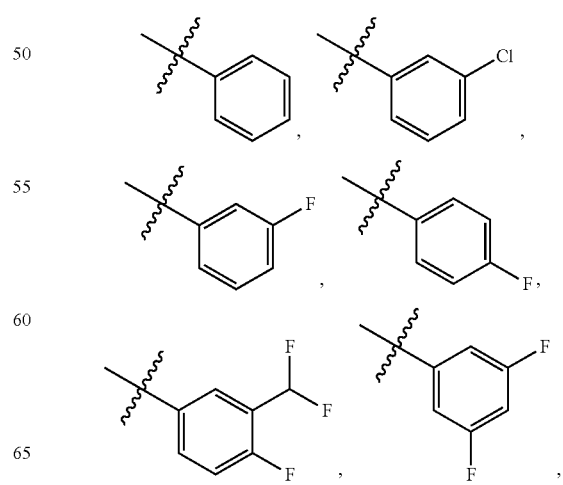

-continued

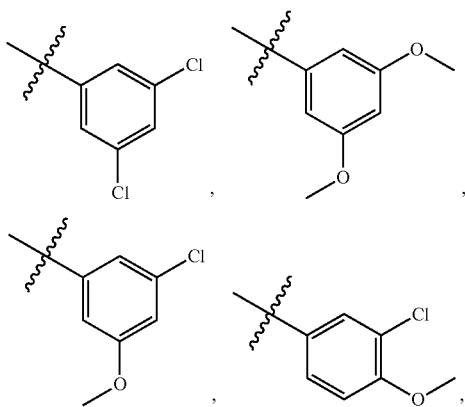

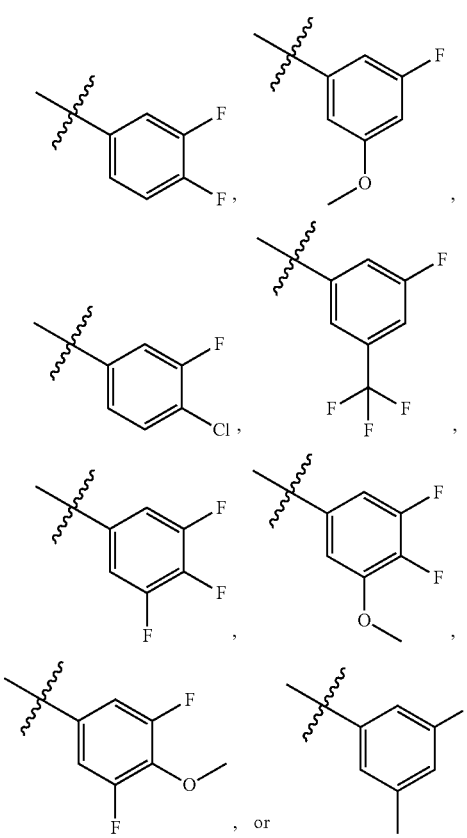

An additional embodiment of the invention is a compound of Formula (I) wherein $R^3$ is cyclopropyl and $R^4$ is $CH_3$.

An additional embodiment of the invention is a compound of Formula (I) wherein $R^3$ is 5-(trifluoromethyl)-2-thienyl or 1-methylindol-2-yl; and $R^4$ is $CH_3$.

An additional embodiment of the invention is a compound of Formula (I) wherein $R^3$ is 3-chlorophenyl, 3-fluorophenyl, 4-fluorophenyl, 3,5-difluorophenyl, 3,5-dichlorophenyl, 3,4-difluorophenyl, and 4-chloro-3-fluorophenyl.

An additional embodiment of the invention is a compound of Formula (I) wherein $R^4$ is $CH_3$.

An additional embodiment of the invention is a compound of Formula (I) wherein $R^4$ is cyclopropyl.

An additional embodiment of the invention is a compound of Formula (I) wherein $R^2$ is

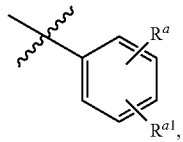

wherein $R^a$ is F, Cl, or $OCH_3$, $R^{a1}$ is $OCH_3$, $CH_3$, or 2H-1,2,3-triazol-2-yl and $R^4$ is $CH_3$.

An additional embodiment of the invention is a compound of Formula (I) having the Formula (IA):

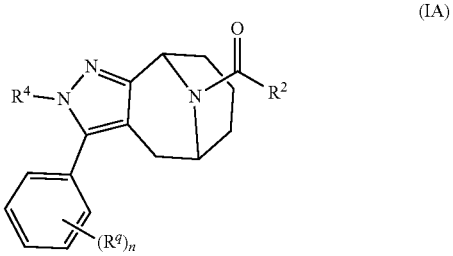

(IA)

wherein
$R^2$ is selected from the group consisting of:

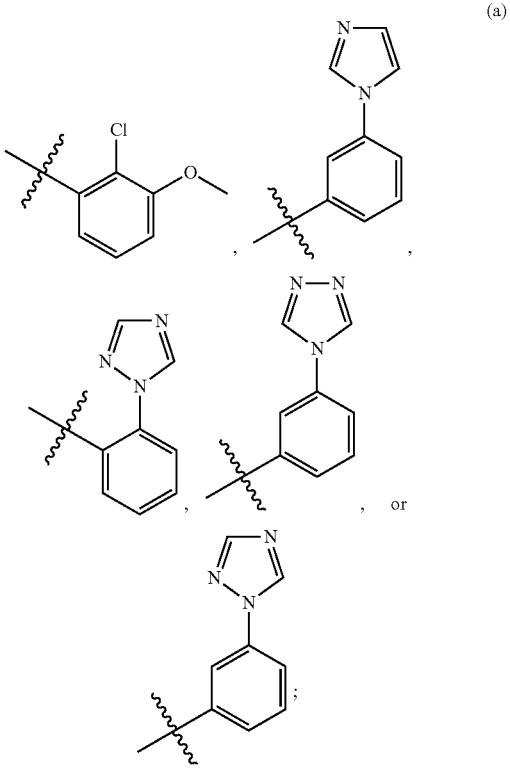

(a)

(b)

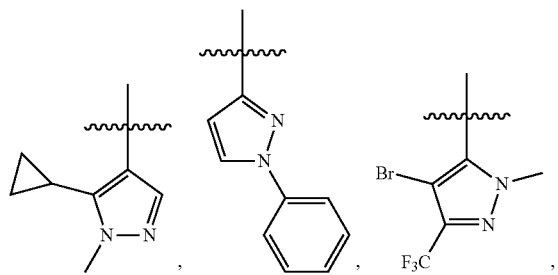

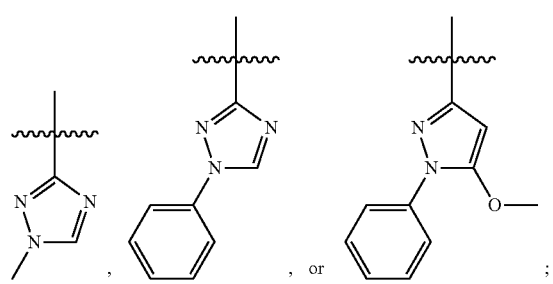

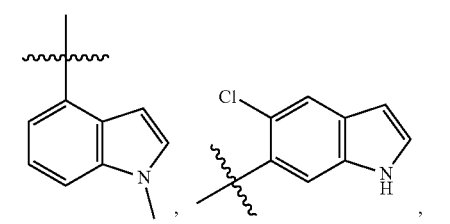

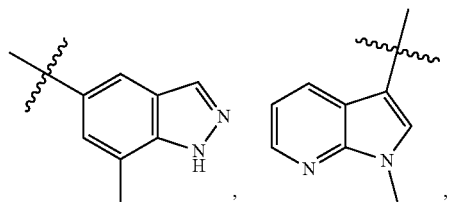

(c)

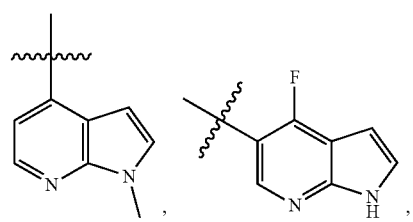

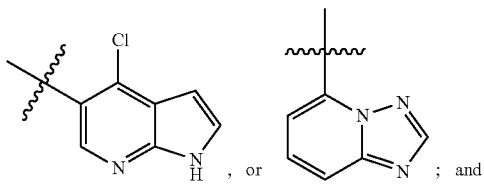

(d)

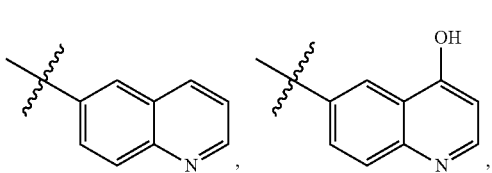

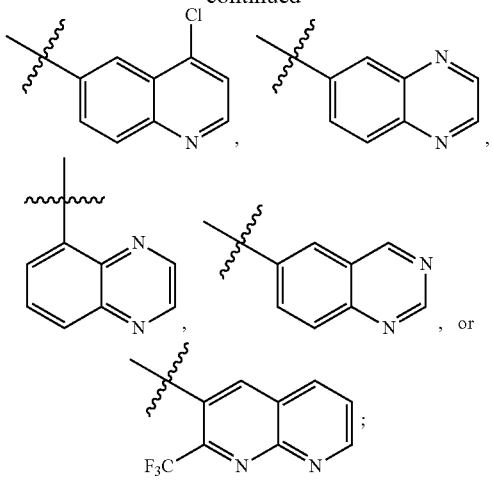

$R^4$ is $CH_3$ or cyclopropyl;

$R^q$ is halo, or $CHF_2$; and n is 0, 1, or 2;

and pharmaceutically acceptable salts, isotopes, N-oxides, solvates, and stereoisomers thereof.

An additional embodiment of the invention is a compound of Formula (I) having the Formula (IB):

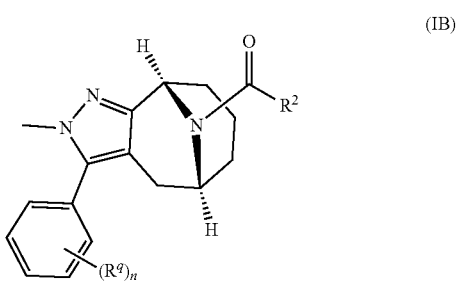

(IB)

wherein $R^2$ is phenyl optionally independently substituted with one or two members selected from the group consisting of: halo, $C_{1-4}$alkyl, $C_{1-4}$haloalkyl, $OC_{1-4}$alkyl, $OC_{1-4}$haloalkyl, $NH(C=O)(CH_3)$,

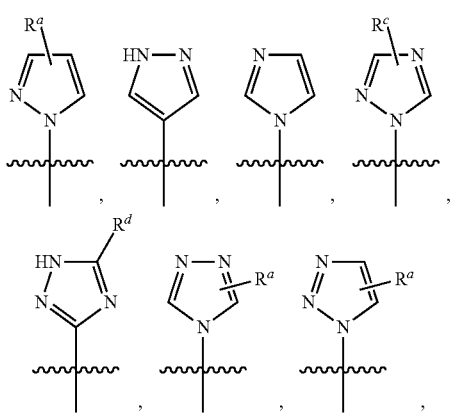

-continued

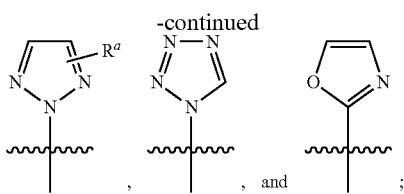

wherein $R^a$ is selected from the group consisting of: H, halo, $C_{1-4}$alkyl, $OC_{1-4}$alkyl, and $C_{1-4}$haloalkyl;

$R^b$ is $C_{1-4}$akyl;

$R^c$ is H or $CF_3$;

$R^d$ is H or halo;

each $R^q$ is independently selected from the group consisting of: Cl, F, $CF_3$, and $OCH_3$; and n is 0, 1, 2, or 3;

and pharmaceutically acceptable salts, isotopes, N-oxides, solvates, and stereoisomers thereof.

An additional embodiment of the invention is a compound of Formula (I) having the Formula (IC):

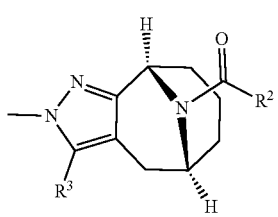

(IC)

wherein $R^2$ is selected from the group consisting of:

(a) 5-membered heteroaryl selected from the group consisting of:

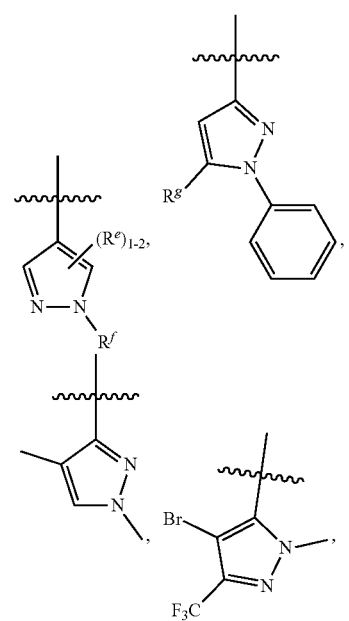

-continued

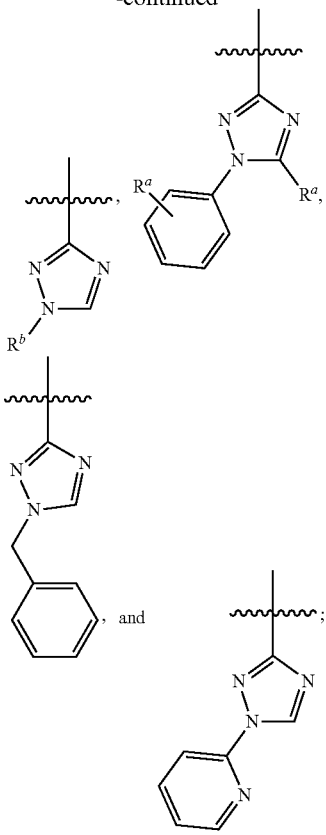

and (b) 6-membered heteroaryl selected from the group consisting of: pyridazin-4-yl; pyrazin-2-yl; pyrimidinyl; pyrimidinyl substituted with $C_{1-4}$alkyl or $OC_{1-4}$alkyl; and pyridinyl, wherein the pyridinyl is substituted with one or two substituents each independently selected from the group consisting of: halo, $C_{1-4}$alkyl, $OC_{1-4}$alkyl, $OC_{1-4}$haloalkyl, cyclopropyl, $NH_2$, CN, $N(CH_3)_2$,

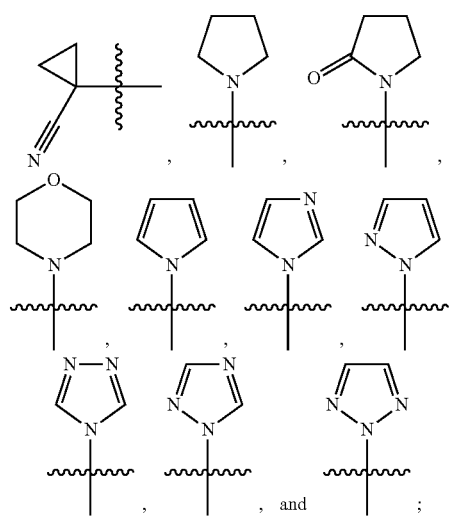

wherein
- $R^a$ is selected from the group consisting of: H, halo, $OC_{1-4}$alkyl, and $C_{1-4}$haloalkyl;
- $R^b$ is $C_{1-4}$akyl;
- $R^e$ is selected from the group consisting of: F, $C_{1-4}$akyl, $CF_2H$, $CF_3$, $OCH_3$, and cyclopropyl;
- $R^f$ is selected from the group consisting of: H, $C_{1-4}$alkyl, cyclopropyl, and phenyl;
- $R^g$ is H or $CF_3$; and
- $R^3$ is phenyl substituted with one, two, or three members each independently selected from the group consisting of: Cl and F;

and pharmaceutically acceptable salts, isotopes, N-oxides, solvates, and stereoisomers thereof.

An additional embodiment of the invention is a compound of Formula (I) having the Formula (IC), wherein $R^2$ is:

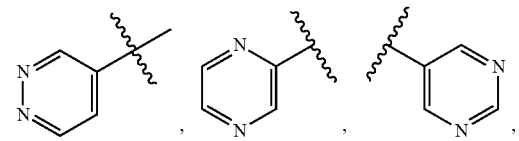

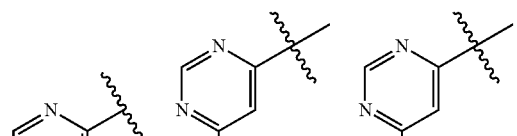

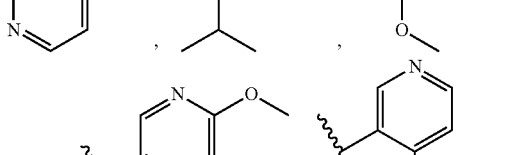

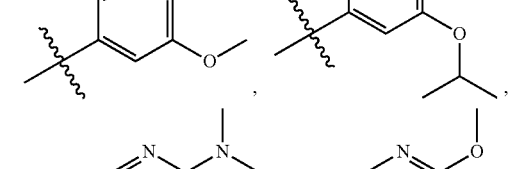

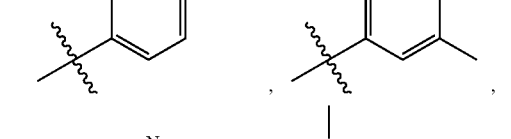

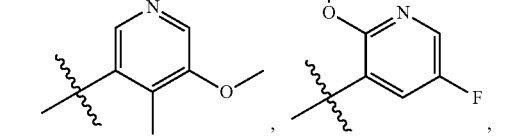

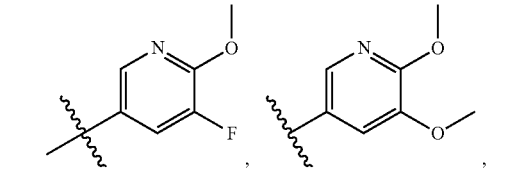

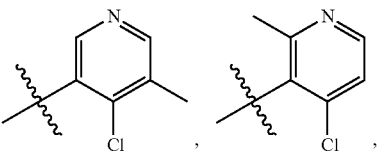

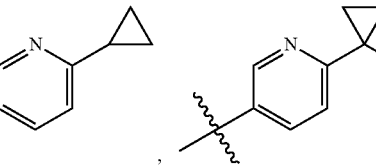

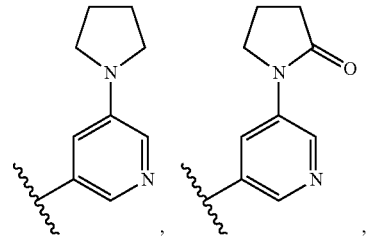

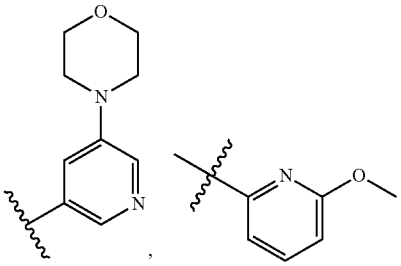

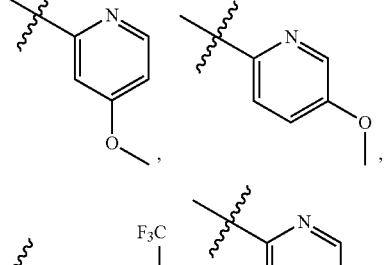

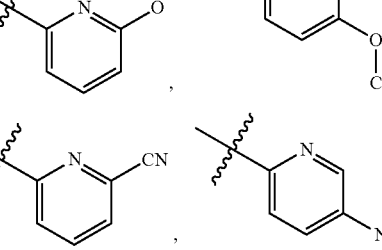

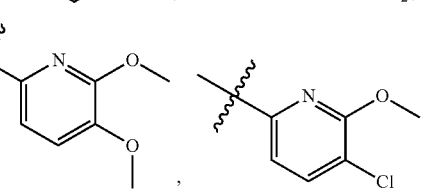

-continued
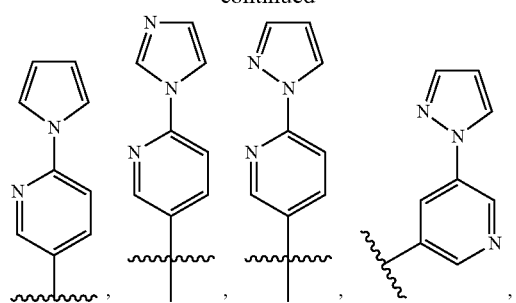
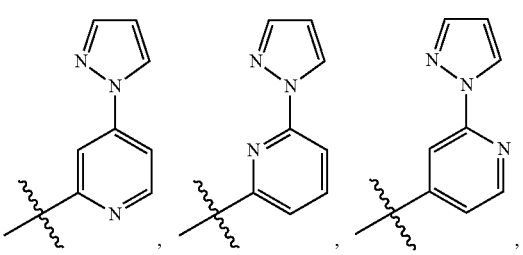
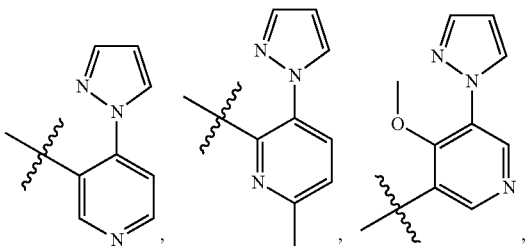
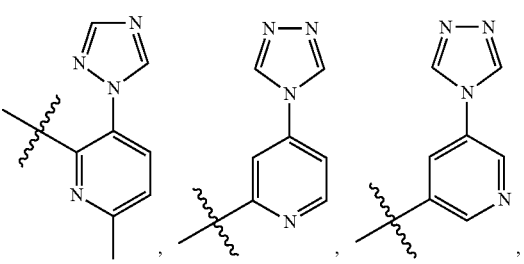
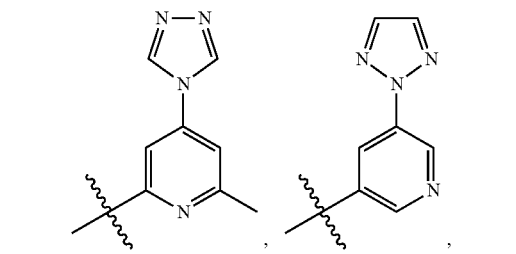
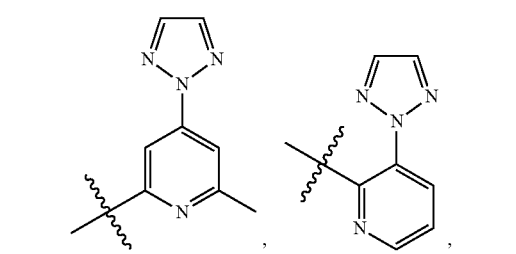
-continued
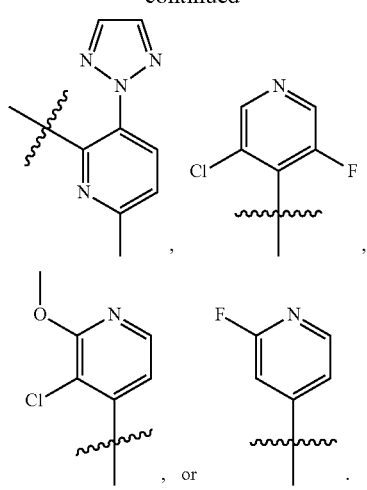
An additional embodiment of the invention is a compound of Formula (I) having the Formula (IC), wherein $R^2$ is:
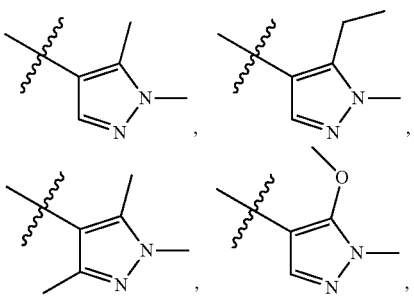
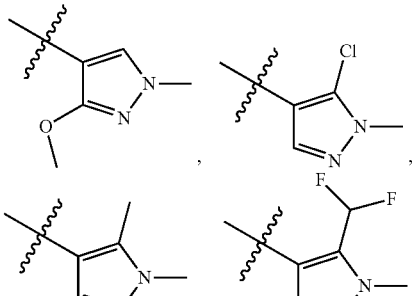
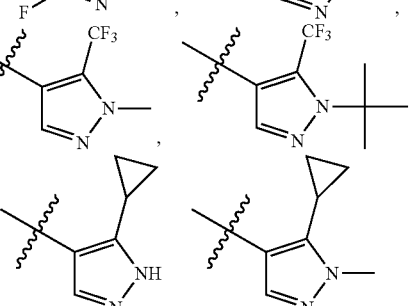
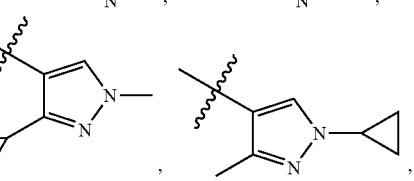

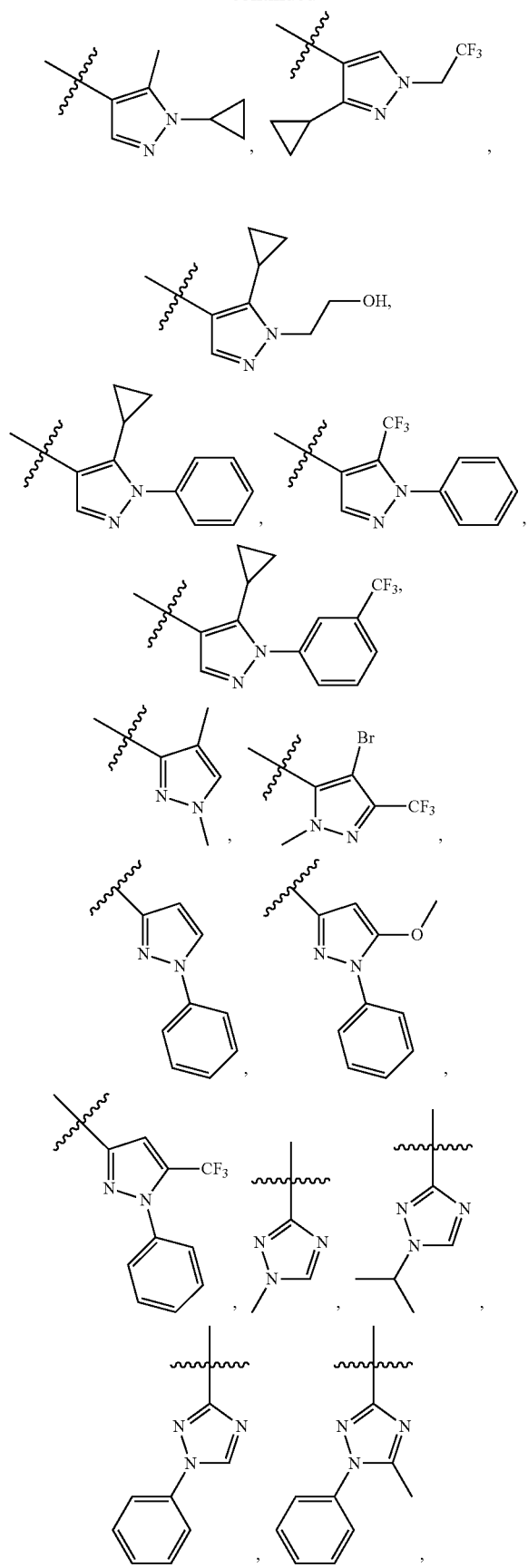
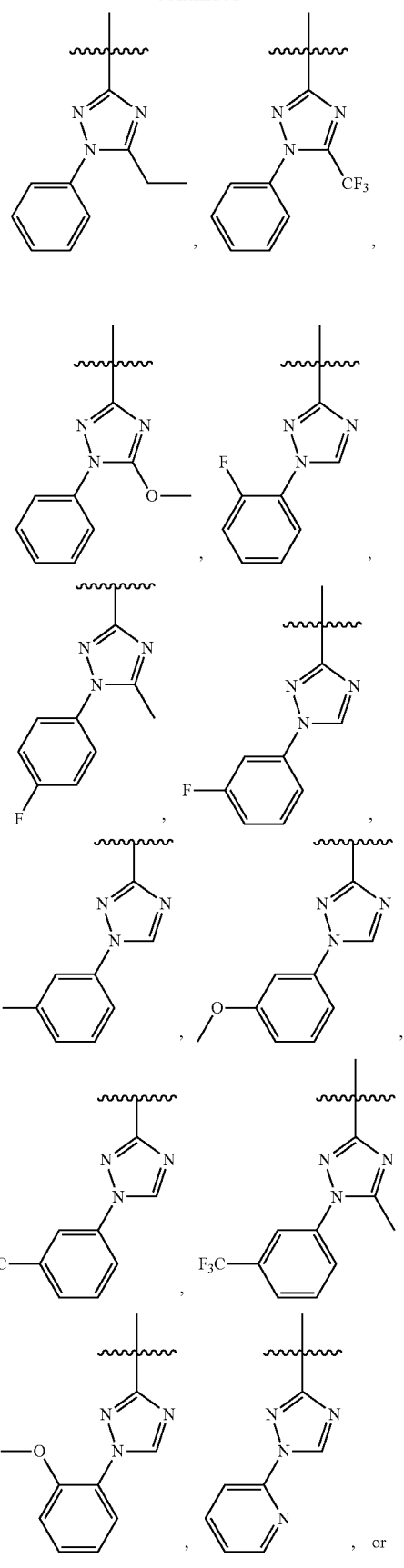

-continued
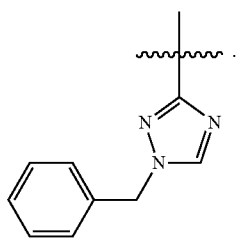
An additional embodiment of the invention is a compound of Formula (I) having the Formula (ID):
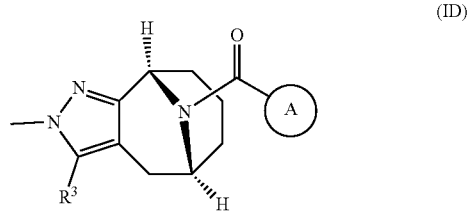
(ID)
wherein
Ring A is selected from the group consisting of:
(a) 6,6-fused bicyclic heteroaryl selected from the group consisting of:
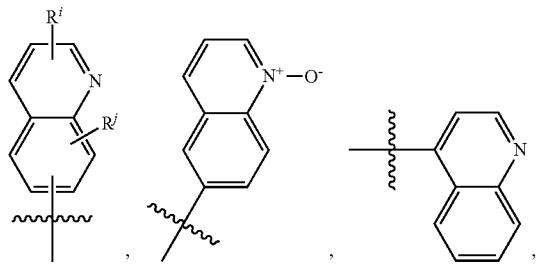
,
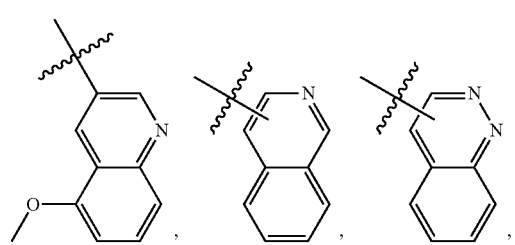
,
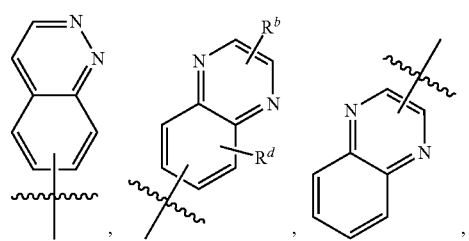
,
-continued
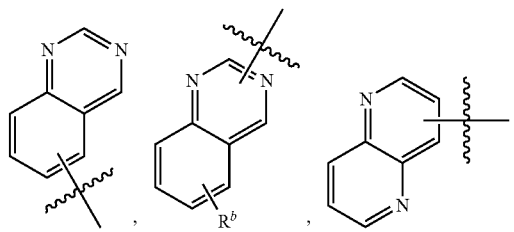
,
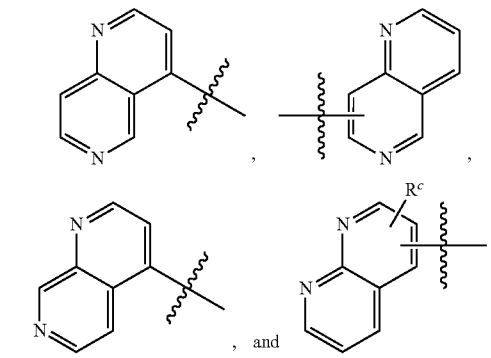
, and
and
(b) 5,6-fused bicyclic heteroaryl or 6,5-fused bicyclic heteroaryl selected from the group consisting of.
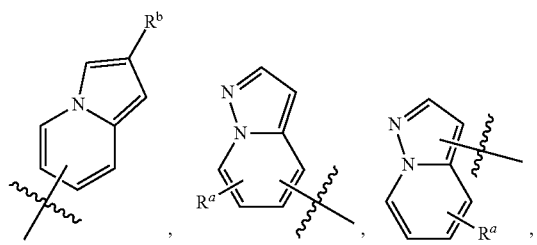
,
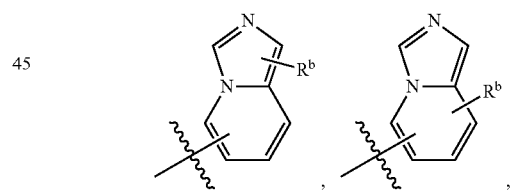
,
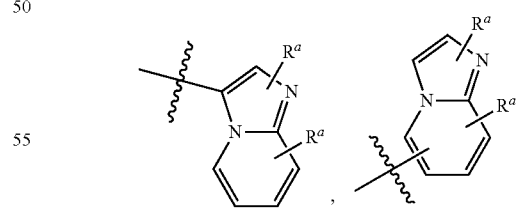
,
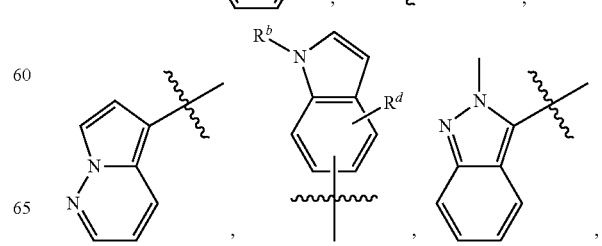
,

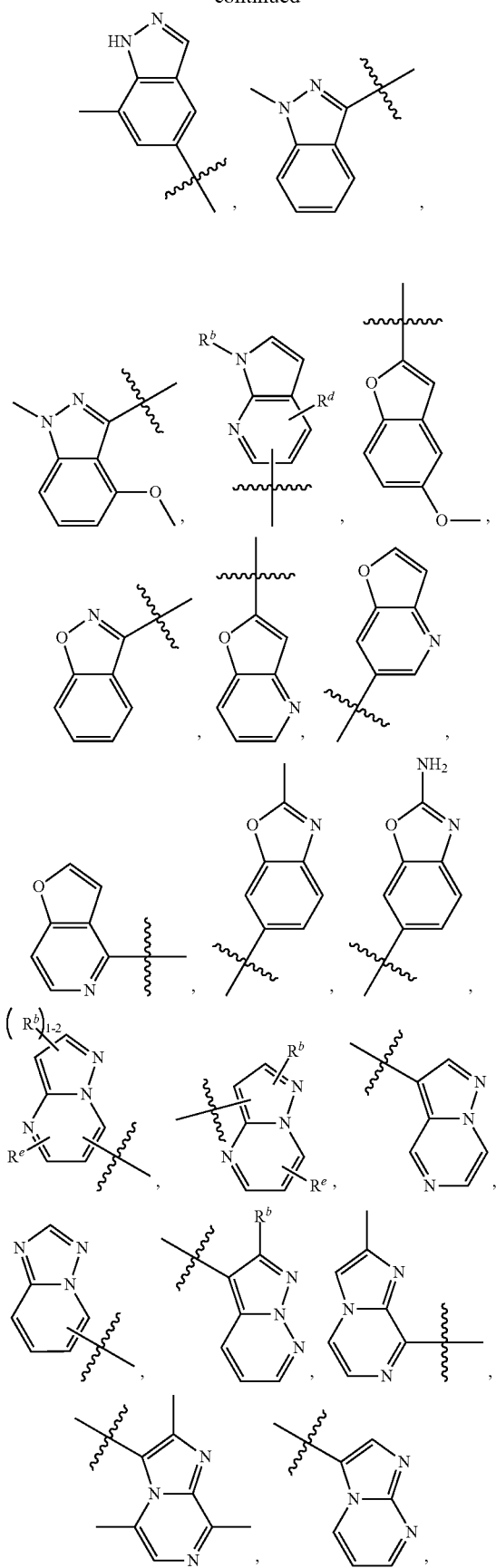

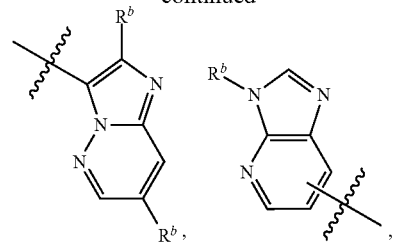

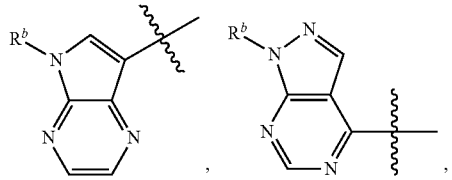

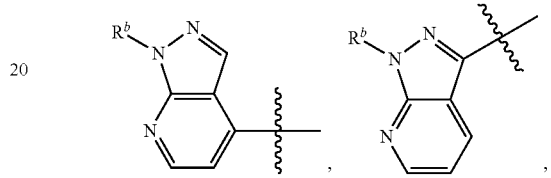

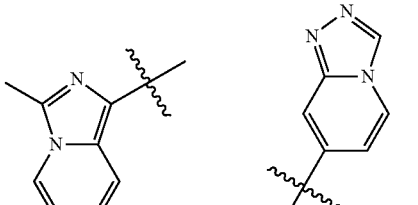

, and wherein $R^a$ is selected from the group consisting of: H, Cl, F, CH$_3$, OCH$_3$, CF$_3$, and CF$_2$H;

$R^b$ is H or CH$_3$;

$R^c$ is H or CF$_3$;

$R^d$ is selected from the group consisting of: H, Cl, and F;

$R^e$ is selected from the group consisting of: H, C$_{1-4}$alkyl, and cyclopropyl;

$R^i$ is selected from the group consisting of: H, Cl, Br, CH$_3$, CF$_3$, OH, and OCH$_2$CH$_2$F;

$R^j$ is selected from the group consisting of: H, halo, OCH$_3$, OH, NH$_2$, and NO$_2$; and $R^3$ is cyclopropyl, 1-methyl-1H-indol-2-yl, or phenyl substituted with one, two, or three members each independently selected from the group consisting of: Cl, F, CH$_3$, OCH$_3$, and CF$_3$;

and pharmaceutically acceptable salts, isotopes, N-oxides, solvates, and stereoisomers thereof.

An additional embodiment of the invention is a compound of Formula (I) having the Formula (ID), wherein $R^3$ is:

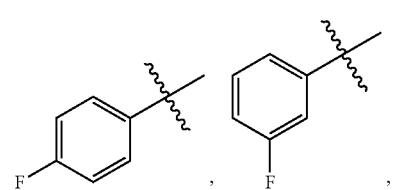

-continued
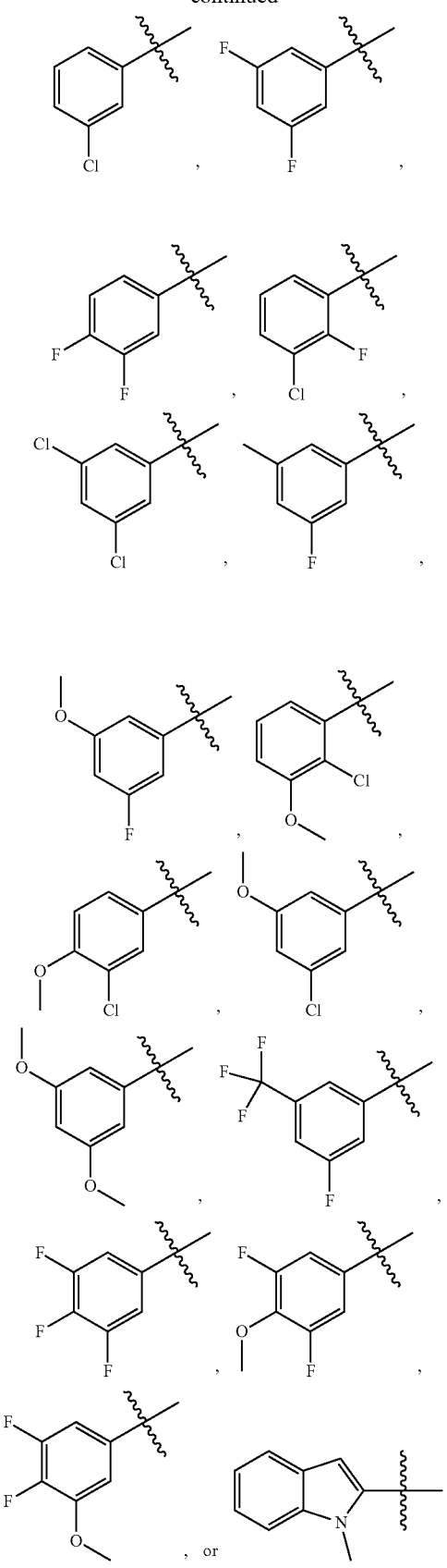
An additional embodiment of the invention is a compound of Formula (I) having the Formula (ID), wherein Ring A is:
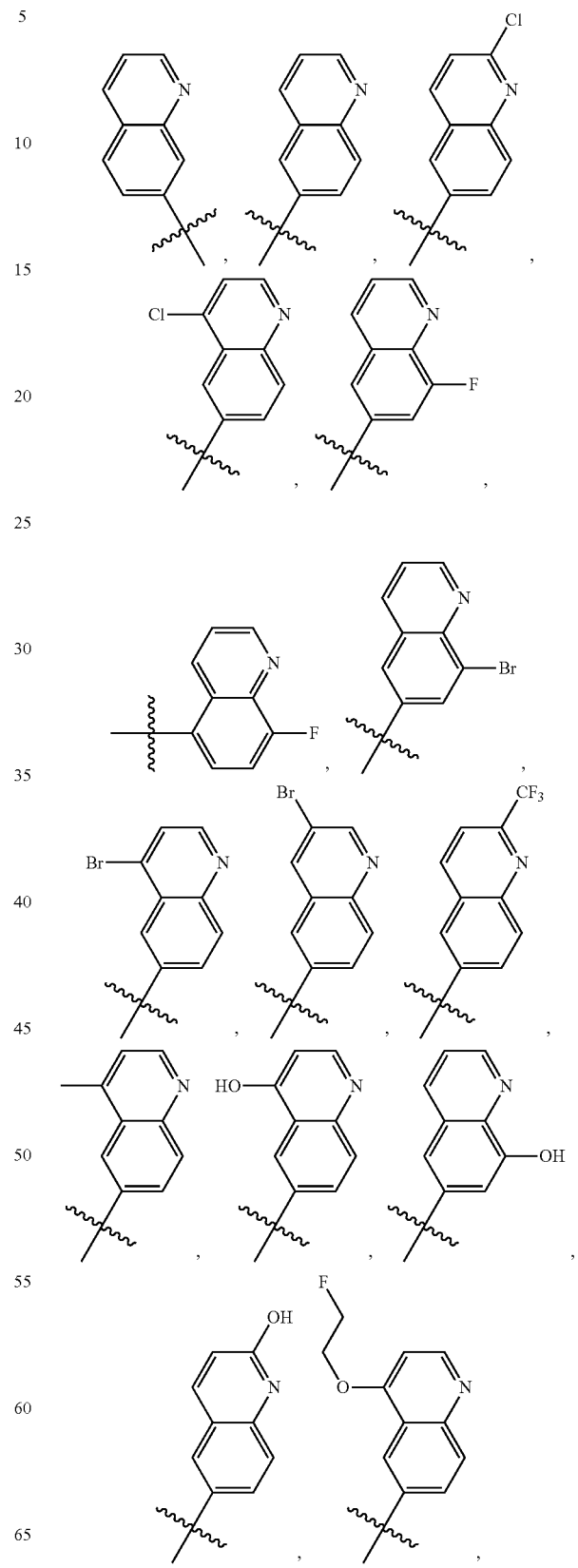

-continued
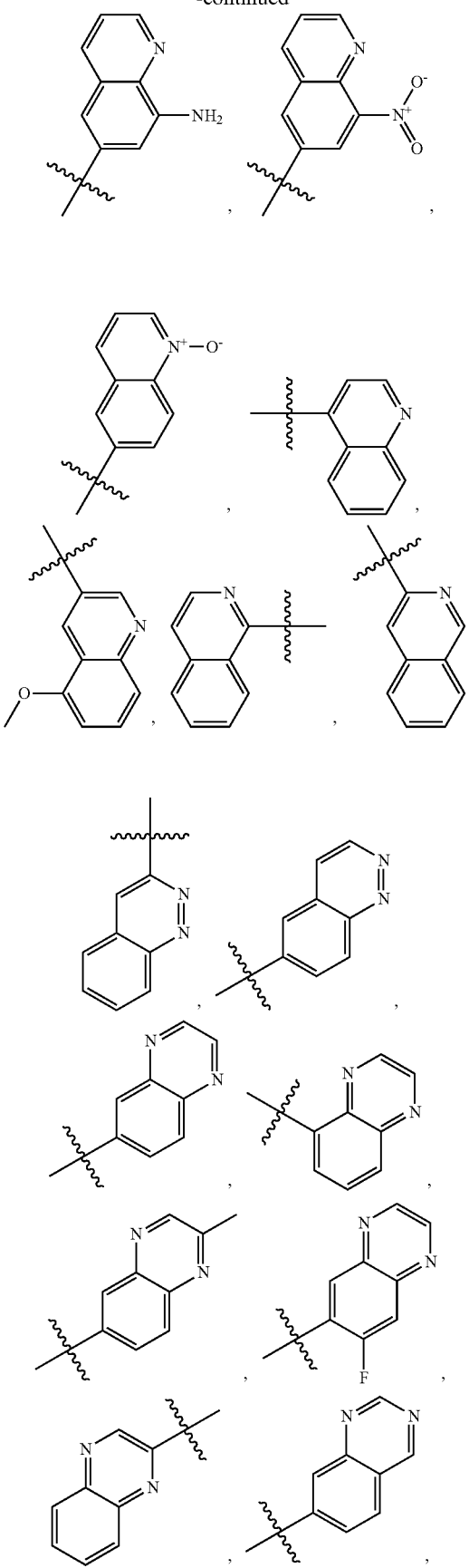
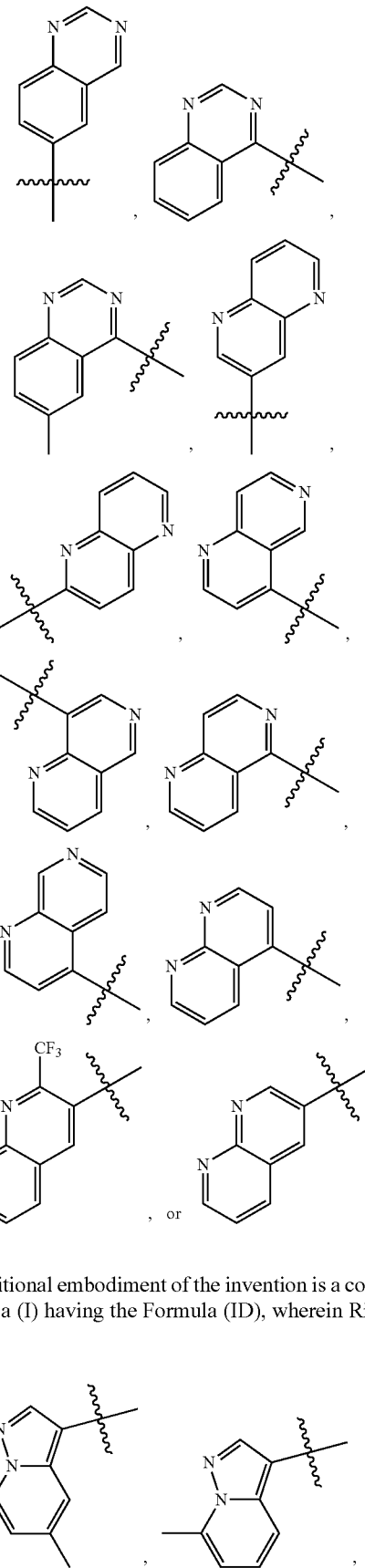
An additional embodiment of the invention is a compound of Formula (I) having the Formula (ID), wherein Ring A is:
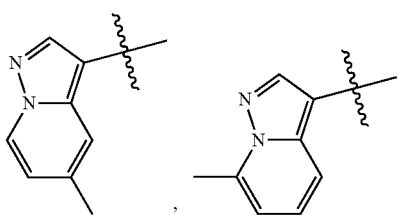

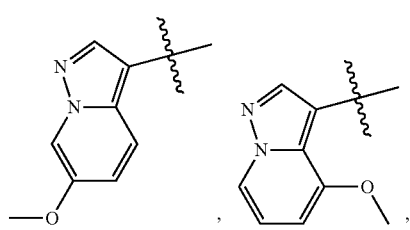
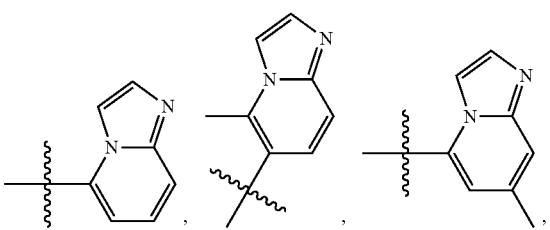
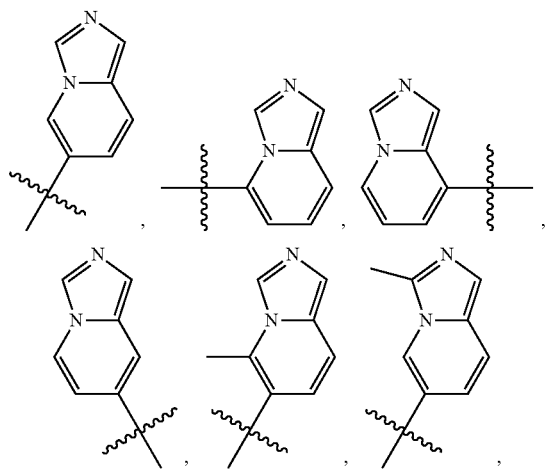
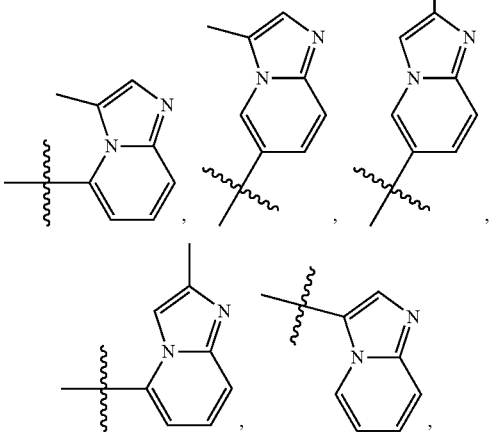
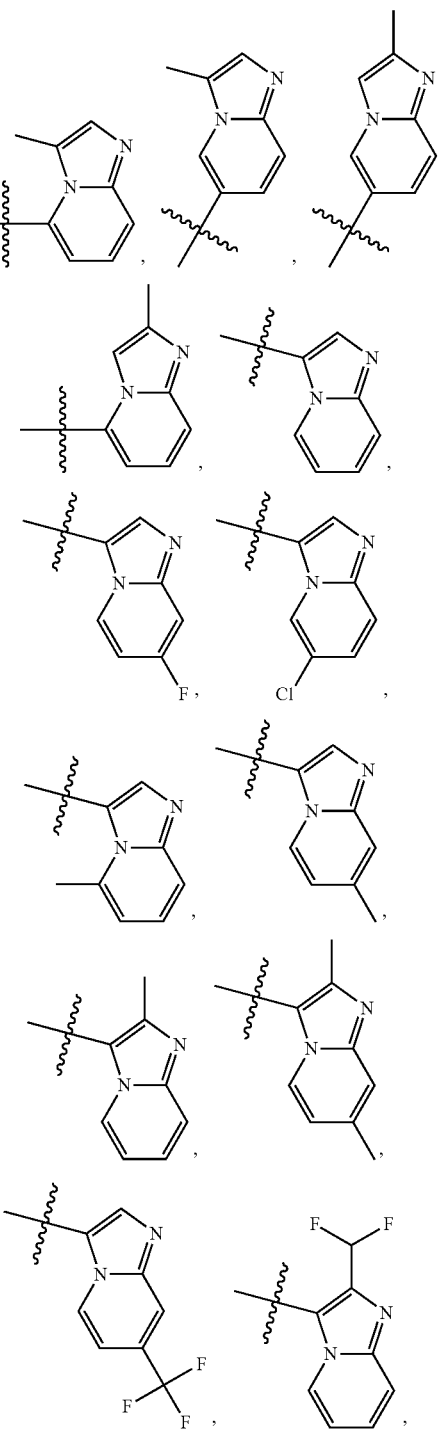

-continued
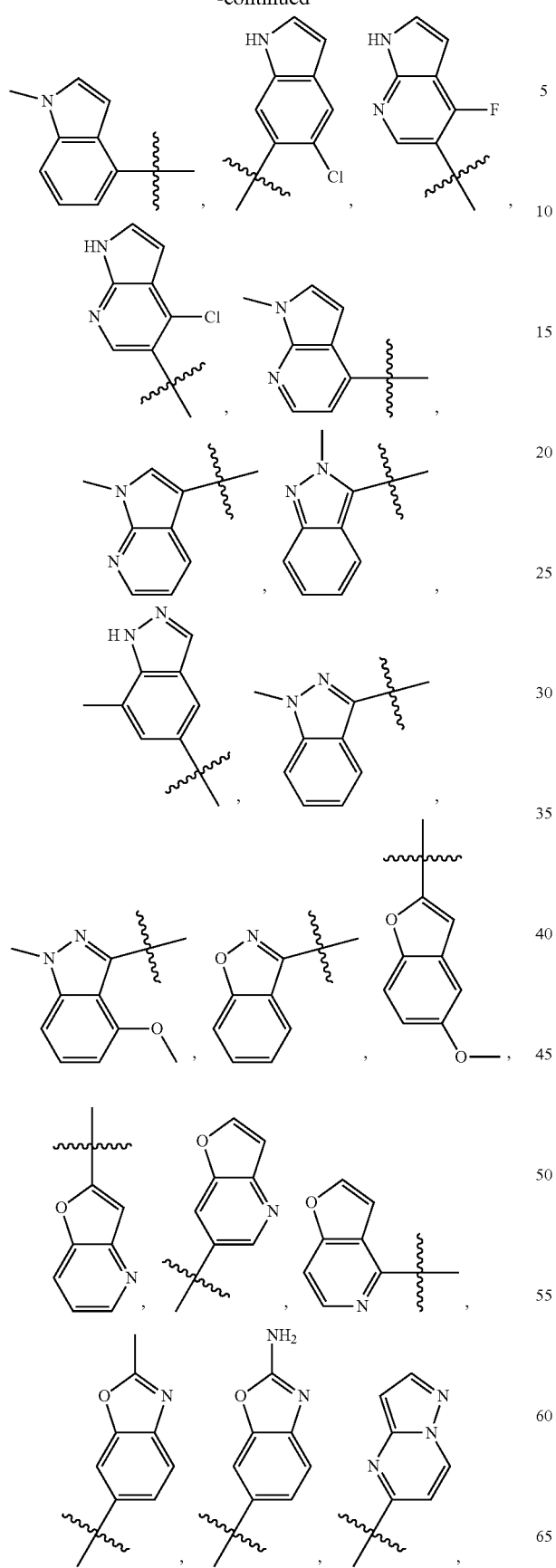
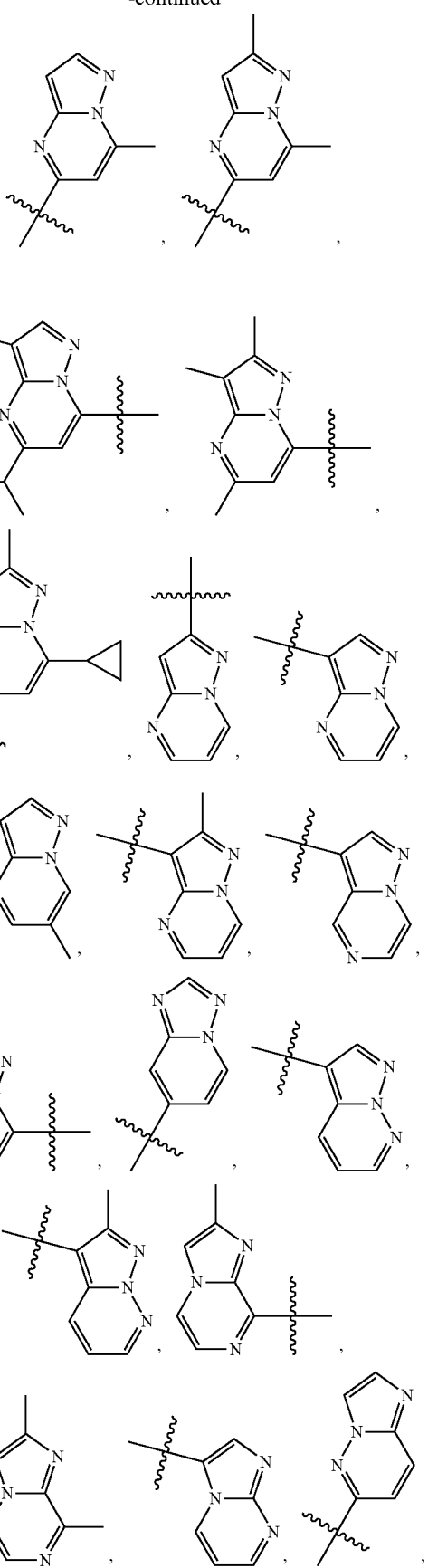

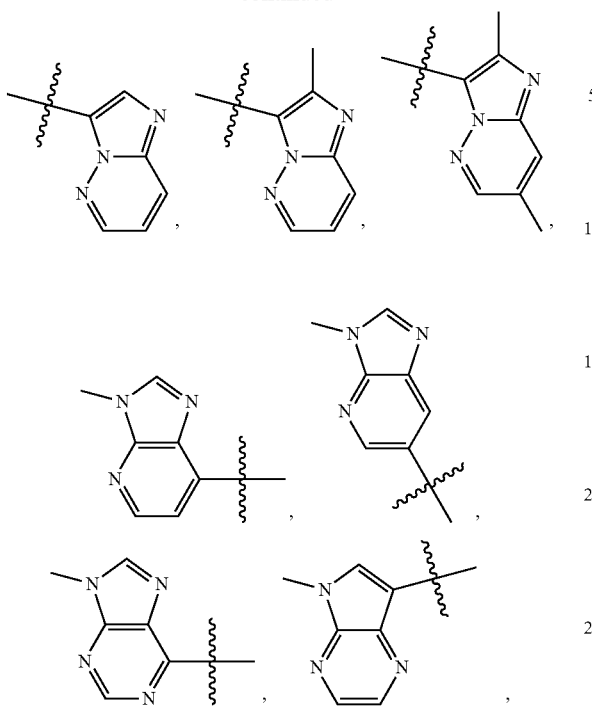

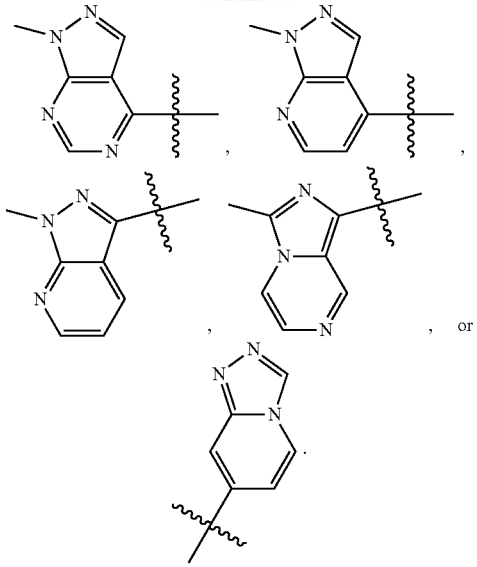

An additional embodiment of the invention is a compound selected from the group consisting of compounds of Formula (I), Formula (IA), Formula (IB), Formula (IC), Formula (ID), and a combination thereof.

A further embodiment of the current invention is a compound as shown below in Table 1.

TABLE 1

| Ex # | Compound Name |
|---|---|
| 1 | racemic-((5R,9S)-2-Methyl-3-phenyl-4,5,6,7,8,9-hexahydro-2H-5,9-epiminocycloocta[c]pyrazol-10-yl)(quinolin-6-yl)methanone; |
| 2 | ((5R,9S)-3-Cyclopropyl-2-methyl-4,5,6,7,8,9-hexahydro-2H-5,9-epiminocycloocta[c]pyrazol-10-yl)(quinolin-6-yl)methanone; |
| 3 | racemic-(2-Chloro-3-methoxyphenyl)((5R,9S)-2-methyl-3-phenyl-4,5,6,7,8,9-hexahydro-2H-5,9-epiminocycloocta[c]pyrazol-10-yl)methanone; |
| 4 | (2-Chloro-3-methoxyphenyl)((5R,9S)-2-methyl-3-phenyl-4,5,6,7,8,9-hexahydro-2H-5,9-epiminocycloocta[c]pyrazol-10-yl)methanone; |
| 5 | (2-Chloro-3-methoxyphenyl)((5S,9R)-2-methyl-3-phenyl-4,5,6,7,8,9-hexahydro-2H-5,9-epiminocycloocta[c]pyrazol-10-yl)methanone; |
| 6 | racemic-(2-(1H-1,2,4-Triazol-1-yl)phenyl)((5R,9S)-2-methyl-3-phenyl-4,5,6,7,8,9-hexahydro-2H-5,9-epiminocycloocta[c]pyrazol-10-yl)methanone; |
| 7 | racemic-(3-(4H-1,2,4-Triazol-4-yl)phenyl)((5R,9S)-2-methyl-3-phenyl-4,5,6,7,8,9-hexahydro-2H-5,9-epiminocycloocta[c]pyrazol-10-yl)methanone; |
| 8 | racemic-(4-(1H-1,2,4-Triazol-1-yl)phenyl)((5R,9S)-2-methyl-3-phenyl-4,5,6,7,8,9-hexahydro-2H-5,9-epiminocycloocta[c]pyrazol-10-yl)methanone; |
| 9 | racemic-(3-(1H-Imidazol-1-yl)phenyl)((5R,9S)-2-methyl-3-phenyl-4,5,6,7,8,9-hexahydro-2H-5,9-epiminocycloocta[c]pyrazol-10-yl)methanone; |
| 10 | racemic-(1-Methyl-1H-1,2,4-triazol-3-yl)((5R,9S)-2-methyl-3-phenyl-4,5,6,7,8,9-hexahydro-2H-5,9-epiminocycloocta[c]pyrazol-10-yl)methanone; |
| 11 | racemic-(5-Chloro-1-methyl-1H-pyrazol-4-yl)((5R,9S)-2-methyl-3-phenyl-4,5,6,7,8,9-hexahydro-2H-5,9-epiminocycloocta[c]pyrazol-10-yl)methanone; |
| 12 | racemic-(5-Methoxy-1-methyl-1H-pyrazol-4-yl)((5R,9S)-2-methyl-3-phenyl-4,5,6,7,8,9-hexahydro-2H-5,9-epiminocycloocta[c]pyrazol-10-yl)methanone; |
| 13 | racemic-(4-Bromo-1-methyl-3-(trifluoromethyl)-1H-pyrazol-5-yl)((5R,9S)-2-methyl-3-phenyl-4,5,6,7,8,9-hexahydro-2H-5,9-epiminocycloocta[c]pyrazol-10-yl)methanone; |
| 14 | racemic-(5-Cyclopropyl-1-methyl-1H-pyrazol-4-yl)((5R,9S)-2-methyl-3-phenyl-4,5,6,7,8,9-hexahydro-2H-5,9-epiminocycloocta[c]pyrazol-10-yl)methanone; |
| 15 | racemic-((5R,9S)-2-Methyl-3-phenyl-4,5,6,7,8,9-hexahydro-2H-5,9-epiminocycloocta[c]pyrazol-10-yl)(1-phenyl-1H-1,2,4-triazol-3-yl)methanone; |
| 16 | racemic-((5R,9S)-2-Methyl-3-phenyl-4,5,6,7,8,9-hexahydro-2H-5,9-epiminocycloocta[c]pyrazol-10-yl)(1-phenyl-1H-pyrazol-3-yl)methanone; |
| 17 | racemic-(5-Methoxy-1-phenyl-1H-pyrazol-3-yl)((5R,9S)-2-methyl-3-phenyl-4,5,6,7,8,9-hexahydro-2H-5,9-epiminocycloocta[c]pyrazol-10-yl)methanone; |
| 18 | racemic-(1-Methyl-1H-indol-4-yl)((5R,9S)-2-methyl-3-phenyl-4,5,6,7,8,9-hexahydro-2H-5,9-epiminocycloocta[c]pyrazol-10-yl)methanone; |

TABLE 1-continued

| Ex # | Compound Name |
|---|---|
| 19 | racemic-(5-Chloro-1H-indol-6-yl)((5R,9S)-2-methyl-3-phenyl-4,5,6,7,8,9-hexahydro-2H-5,9-epiminocycloocta[c]pyrazol-10-yl)methanone; |
| 20 | racemic-(7-Methyl-1H-indazol-5-yl)((5R,9S)-2-methyl-3-phenyl-4,5,6,7,8,9-hexahydro-2H-5,9-epiminocycloocta[c]pyrazol-10-yl)methanone; |
| 21 | racemic-(1-Methyl-1H-pyrrolo[2,3-b]pyridin-4-yl)((5R,9S)-2-methyl-3-phenyl-4,5,6,7,8,9-hexahydro-2H-5,9-epiminocycloocta[c]pyrazol-10-yl)methanone; |
| 22 | racemic-(4-Chloro-1H-pyrrolo[2,3-b]pyridin-5-yl)((5R,9S)-2-methyl-3-phenyl-4,5,6,7,8,9-hexahydro-2H-5,9-epiminocycloocta[c]pyrazol-10-yl)methanone; |
| 23 | racemic-(4-Fluoro-1H-pyrrolo[2,3-b]pyridin-5-yl)((5R,9S)-2-methyl-3-phenyl-4,5,6,7,8,9-hexahydro-2H-5,9-epiminocycloocta[c]pyrazol-10-yl)methanone; |
| 24 | racemic-(1-Methyl-1H-pyrrolo[2,3-b]pyridin-3-yl)((5R,9S)-2-methyl-3-phenyl-4,5,6,7,8,9-hexahydro-2H-5,9-epiminocycloocta[c]pyrazol-10-yl)methanone; |
| 25 | racemic-[1,2,4]Triazolo[1,5-a]pyridin-5-yl((5R,9S)-2-methyl-3-phenyl-4,5,6,7,8,9-hexahydro-2H-5,9-epiminocycloocta[c]pyrazol-10-yl)methanone; |
| 27 | racemic-(4-Chloroquinolin-6-yl)((5R,9S)-2-methyl-3-phenyl-4,5,6,7,8,9-hexahydro-2H-5,9-epiminocycloocta[c]pyrazol-10-yl)methanone; |
| 28 | racemic-(4-Hydroxyquinolin-6-yl)((5R,9S)-2-methyl-3-phenyl-4,5,6,7,8,9-hexahydro-2H-5,9-epiminocycloocta[c]pyrazol-10-yl)methanone; |
| 29 | racemic-((5R,9S)-2-Methyl-3-phenyl-4,5,6,7,8,9-hexahydro-2H-5,9-epiminocycloocta[c]pyrazol-10-yl)(quinoxalin-5-yl)methanone; |
| 30 | racemic-((5R,9S)-2-Methyl-3-phenyl-4,5,6,7,8,9-hexahydro-2H-5,9-epiminocycloocta[c]pyrazol-10-yl)(quinoxalin-6-yl)methanone; |
| 31 | racemic-((5R,9S)-2-Methyl-3-phenyl-4,5,6,7,8,9-hexahydro-2H-5,9-epiminocycloocta[c]pyrazol-10-yl)(quinazolin-6-yl)methanone; |
| 32 | racemic-((5R,9S)-2-Methyl-3-phenyl-4,5,6,7,8,9-hexahydro-2H-5,9-epiminocycloocta[c]pyrazol-10-yl)(2-(trifluoromethyl)-1,8-naphthyridin-3-yl)methanone; |
| 33 | racemic-(2-Chloro-3-methoxyphenyl)((5R,9S)-3-(4-fluorophenyl)-2-methyl-4,5,6,7,8,9-hexahydro-2H-5,9-epiminocycloocta[c]pyrazol-10-yl)methanone; |
| 34 | (2-(2H-1,2,3-Triazol-2-yl)phenyl)((5R,9S)-3-(4-fluorophenyl)-2-methyl-4,5,6,7,8,9-hexahydro-2H-5,9-epiminocycloocta[c]pyrazol-10-yl)methanone; |
| 35 | racemic-(1,4-Dimethyl-1H-pyrazol-3-yl)((5R,9S)-3-(4-fluorophenyl)-2-methyl-4,5,6,7,8,9-hexahydro-2H-5,9-epiminocycloocta[c]pyrazol-10-yl)methanone; |
| 36 | ((5R,9S)-3-(4-Fluorophenyl)-2-methyl-4,5,6,7,8,9-hexahydro-2H-5,9-epiminocycloocta[c]pyrazol-10-yl)(1-methyl-1H-pyrazolo[3,4-b]pyridin-3-yl)methanone; |
| 37 | racemic-((5R,9S)-3-(4-Fluorophenyl)-2-methyl-4,5,6,7,8,9-hexahydro-2H-5,9-epiminocycloocta[c]pyrazol-10-yl)(quinolin-6-yl)methanone; |
| 38 | ((5R,9S)-3-(4-Fluorophenyl)-2-methyl-4,5,6,7,8,9-hexahydro-2H-5,9-epiminocycloocta[c]pyrazol-10-yl)(quinolin-6-yl)methanone; |
| 39 | racemic-(2-Chloro-3-methoxyphenyl)((5R,9S)-3-(3-fluorophenyl)-2-methyl-4,5,6,7,8,9-hexahydro-2H-5,9-epiminocycloocta[c]pyrazol-10-yl)methanone; |
| 40 | racemic-((5R,9S)-3-(3-Fluorophenyl)-2-methyl-4,5,6,7,8,9-hexahydro-2H-5,9-epiminocycloocta[c]pyrazol-10-yl)(1-phenyl-1H-1,2,4-triazol-3-yl)methanone; |
| 41 | ((5R,9S)-3-(3-Fluorophenyl)-2-methyl-4,5,6,7,8,9-hexahydro-2H-5,9-epiminocycloocta[c]pyrazol-10-yl)(furo[3,2-b]pyridin-6-yl)methanone; |
| 42 | racemic-((5R,9S)-3-(3-Fluorophenyl)-2-methyl-4,5,6,7,8,9-hexahydro-2H-5,9-epiminocycloocta[c]pyrazol-10-yl)(quinolin-6-yl)methanone; |
| 43 | ((5S,9R)-3-(3-Fluorophenyl)-2-methyl-4,5,6,7,8,9-hexahydro-2H-5,9-epiminocycloocta[c]pyrazol-10-yl)(quinolin-6-yl)methanone; |
| 44 | ((5R,9S)-3-(3-Fluorophenyl)-2-methyl-4,5,6,7,8,9-hexahydro-2H-5,9-epiminocycloocta[c]pyrazol-10-yl)(quinolin-6-yl)methanone; |
| 45 | racemic-((5R,9S)-2-Cyclopropyl-3-(3-fluorophenyl)-4,5,6,7,8,9-hexahydro-2H-5,9-epiminocycloocta[c]pyrazol-10-yl)(quinolin-6-yl)methanone; |
| 46 | (3-(1H-1,2,4-Triazol-1-yl)phenyl)((5R,9S)-3-(3-chlorophenyl)-2-methyl-4,5,6,7,8,9-hexahydro-2H-5,9-epiminocycloocta[c]pyrazol-10-yl)methanone; |
| 47 | (3-(1H-Pyrazol-4-yl)phenyl)((5R,9S)-3-(3-chlorophenyl)-2-methyl-4,5,6,7,8,9-hexahydro-2H-5,9-epiminocycloocta[c]pyrazol-10-yl)methanone; |
| 48 | (3-(1H-Pyrazol-1-yl)phenyl)((5R,9S)-3-(3-chlorophenyl)-2-methyl-4,5,6,7,8,9-hexahydro-2H-5,9-epiminocycloocta[c]pyrazol-10-yl)methanone; |
| 49 | (3-(1H-Tetrazol-1-yl)phenyl)((5R,9S)-3-(3-chlorophenyl)-2-methyl-4,5,6,7,8,9-hexahydro-2H-5,9-epiminocycloocta[c]pyrazol-10-yl)methanone; |
| 50 | (2-Chloro-5-(4H-1,2,4-triazol-4-yl)phenyl)((5R,9S)-3-(3-chlorophenyl)-2-methyl-4,5,6,7,8,9-hexahydro-2H-5,9-epiminocycloocta[c]pyrazol-10-yl)methanone; |
| 51 | (4-(4H-1,2,4-Triazol-4-yl)phenyl)((5R,9S)-3-(3-chlorophenyl)-2-methyl-4,5,6,7,8,9-hexahydro-2H-5,9-epiminocycloocta[c]pyrazol-10-yl)methanone; |
| 52 | ((5R,9S)-3-(3-Chlorophenyl)-2-methyl-4,5,6,7,8,9-hexahydro-2H-5,9-epiminocycloocta[c]pyrazol-10-yl)(1-isopropyl-1H-1,2,4-triazol-3-yl)methanone; |
| 53 | ((5R,9S)-3-(3-Chlorophenyl)-2-methyl-4,5,6,7,8,9-hexahydro-2H-5,9-epiminocycloocta[c]pyrazol-10-yl)(1-(2-fluorophenyl)-1H-1,2,4-triazol-3-yl)methanone; |
| 54 | ((5R,9S)-3-(3-Chlorophenyl)-2-methyl-4,5,6,7,8,9-hexahydro-2H-5,9-epiminocycloocta[c]pyrazol-10-yl)(1-(pyridin-2-yl)-1H-1,2,4-triazol-3-yl)methanone; |

TABLE 1-continued

| Ex # | Compound Name |
|---|---|
| 55 | ((5R,9S)-3-(3-Chlorophenyl)-2-methyl-4,5,6,7,8,9-hexahydro-2H-5,9-epiminocycloocta[c]pyrazol-10-yl)(1-(3-fluorophenyl)-1H-1,2,4-triazol-3-yl)methanone; |
| 56 | (1-(3-Chlorophenyl)-1H-1,2,4-triazol-3-yl)((5R,9S)-3-(3-chlorophenyl)-2-methyl-4,5,6,7,8,9-hexahydro-2H-5,9-epiminocycloocta[c]pyrazol-10-yl)methanone; |
| 57 | ((5R,9S)-3-(3-Chlorophenyl)-2-methyl-4,5,6,7,8,9-hexahydro-2H-5,9-epiminocycloocta[c]pyrazol-10-yl)(1-phenyl-5-(trifluoromethyl)-1H-pyrazol-4-yl)methanone; |
| 58 | ((5R,9S)-3-(3-Chlorophenyl)-2-methyl-4,5,6,7,8,9-hexahydro-2H-5,9-epiminocycloocta[c]pyrazol-10-yl)(5-methyl-1-(3-(trifluoromethyl)phenyl)-1H-1,2,4-triazol-3-yl)methanone; |
| 59 | ((5R,9S)-3-(3-Chlorophenyl)-2-methyl-4,5,6,7,8,9-hexahydro-2H-5,9-epiminocycloocta[c]pyrazol-10-yl)(1-(3-(trifluoromethyl)phenyl)-1H-1,2,4-triazol-3-yl)methanone; |
| 60 | (1-Benzyl-1H-1,2,4-triazol-3-yl)((5R,9S)-3-(3-chlorophenyl)-2-methyl-4,5,6,7,8,9-hexahydro-2H-5,9-epiminocycloocta[c]pyrazol-10-yl)methanone; |
| 61 | Benzo[d]isoxazol-3-yl((5R,9S)-3-(3-chlorophenyl)-2-methyl-4,5,6,7,8,9-hexahydro-2H-5,9-epiminocycloocta[c]pyrazol-10-yl)methanone; |
| 62 | ((5R,9S)-3-(3-chlorophenyl)-2-methyl-4,5,6,7,8,9-hexahydro-2H-5,9-epiminocycloocta[c]pyrazol-10-yl)(1-methyl-1H-indazol-3-yl)methanone; |
| 63 | racemic-((5R,9S)-3-(3-Chlorophenyl)-2-methyl-4,5,6,7,8,9-hexahydro-2H-5,9-epiminocycloocta[c]pyrazol-10-yl)(quinolin-6-yl)methanone; |
| 64 | ((5R,9S)-3-(3-Chlorophenyl)-2-methyl-4,5,6,7,8,9-hexahydro-2H-5,9-epiminocycloocta[c]pyrazol-10-yl)(quinoxalin-6-yl)methanone; |
| 65 | ((5R,9S)-3-(3,5-Difluorophenyl)-2-methyl-4,5,6,7,8,9-hexahydro-2H-5,9-epiminocycloocta[c]pyrazol-10-yl)(4-(2-fluoroethoxy)quinolin-6-yl)methanone; |
| 66 | ((5R,9S)-3-(3,5-Difluorophenyl)-2-methyl-4,5,6,7,8,9-hexahydro-2H-5,9-epiminocycloocta[c]pyrazol-10-yl)(3-(2-fluoroethoxy)phenyl)methanone; |
| 67 | ((5R,9S)-3-(3,5-Difluorophenyl)-2-methyl-4,5,6,7,8,9-hexahydro-2H-5,9-epiminocycloocta[c]pyrazol-10-yl)(3-(2-(fluoro-18F)ethoxy)phenyl)methanone; |
| 68 | racemic-(2-(2H-1,2,3-Triazol-2-yl)phenyl)((5R,9S)-3-(3,5-difluorophenyl)-2-methyl-4,5,6,7,8,9-hexahydro-2H-5,9-epiminocycloocta[c]pyrazol-10-yl)methanone; |
| 69 | (2-(1H-1,2,4-Triazol-5-yl)phenyl)((5R,9S)-3-(3,5-difluorophenyl)-2-methyl-4,5,6,7,8,9-hexahydro-2H-5,9-epiminocycloocta[c]pyrazol-10-yl)methanone; |
| 70 | (2-(5-Chloro-1H-1,2,4-triazol-3-yl)phenyl)((5R,9S)-3-(3,5-difluorophenyl)-2-methyl-4,5,6,7,8,9-hexahydro-2H-5,9-epiminocycloocta[c]pyrazol-10-yl)methanone; |
| 71 | ((5R,9S)-3-(3,5-Difluorophenyl)-2-methyl-4,5,6,7,8,9-hexahydro-2H-5,9-epiminocycloocta[c]pyrazol-10-yl)(3-(1-methyl-1H-pyrazol-4-yl)phenyl)methanone; |
| 72 | (3-(4H-1,2,4-Triazol-4-yl)phenyl)((5R,9S)-3-(3,5-difluorophenyl)-2-methyl-4,5,6,7,8,9-hexahydro-2H-5,9-epiminocycloocta[c]pyrazol-10-yl)methanone; |
| 73 | ((5R,9S)-3-(3,5-Difluorophenyl)-2-methyl-4,5,6,7,8,9-hexahydro-2H-5,9-epiminocycloocta[c]pyrazol-10-yl)(5-methyl-2-(2H-1,2,3-triazol-2-yl)phenyl)methanone; |
| 74 | ((5R,9S)-3-(3,5-Difluorophenyl)-2-methyl-4,5,6,7,8,9-hexahydro-2H-5,9-epiminocycloocta[c]pyrazol-10-yl)(3-fluoro-2-(2H-1,2,3-triazol-2-yl)phenyl)methanone; |
| 75 | ((5R,9S)-3-(3,5-Difluorophenyl)-2-methyl-4,5,6,7,8,9-hexahydro-2H-5,9-epiminocycloocta[c]pyrazol-10-yl)(3-fluoro-2-(oxazol-2-yl)phenyl)methanone; |
| 76 | racemic-((5R,9S)-3-(3,5-Difluorophenyl)-2-methyl-4,5,6,7,8,9-hexahydro-2H-5,9-epiminocycloocta[c]pyrazol-10-yl)(2-(pyrimidin-2-yl)phenyl)methanone; |
| 77 | racemic-((5R,9S)-3-(3,5-Difluorophenyl)-2-methyl-4,5,6,7,8,9-hexahydro-2H-5,9-epiminocycloocta[c]pyrazol-10-yl)(5-methoxy-1-methyl-1H-pyrazol-4-yl)methanone; |
| 78 | racemic-((5R,9S)-3-(3,5-Difluorophenyl)-2-methyl-4,5,6,7,8,9-hexahydro-2H-5,9-epiminocycloocta[c]pyrazol-10-yl)(1-ethyl-5-(trifluoromethyl)-1H-pyrazol-3-yl)methanone; |
| 79 | racemic-(5-Cyclopropyl-1H-pyrazol-4-yl)((5R,9S)-3-(3,5-difluorophenyl)-2-methyl-4,5,6,7,8,9-hexahydro-2H-5,9-epiminocycloocta[c]pyrazol-10-yl)methanone; |
| 80 | racemic-(5-Cyclopropyl-1-(2-hydroxyethyl)-1H-pyrazol-4-yl)((5R,9S)-3-(3,5-difluorophenyl)-2-methyl-4,5,6,7,8,9-hexahydro-2H-5,9-epiminocycloocta[c]pyrazol-10-yl)methanone; |
| 81 | racemic-(3-Cyclopropyl-1-(2,2,2-trifluoroethyl)-1H-pyrazol-4-yl)((5R,9S)-3-(3,5-difluorophenyl)-2-methyl-4,5,6,7,8,9-hexahydro-2H-5,9-epiminocycloocta[c]pyrazol-10-yl)methanone; |
| 82 | racemic-(5-Cyclopropyl-1-phenyl-1H-pyrazol-4-yl)((5R,9S)-3-(3,5-difluorophenyl)-2-methyl-4,5,6,7,8,9-hexahydro-2H-5,9-epiminocycloocta[c]pyrazol-10-yl)methanone; |
| 83 | racemic-(5-Cyclopropyl-1-(3-(trifluoromethyl)phenyl)-1H-pyrazol-4-yl)((5R,9S)-3-(3,5-difluorophenyl)-2-methyl-4,5,6,7,8,9-hexahydro-2H-5,9-epiminocycloocta[c]pyrazol-10-yl)methanone; |
| 84 | racemic-((5R,9S)-3-(3,5-Difluorophenyl)-2-methyl-4,5,6,7,8,9-hexahydro-2H-5,9-epiminocycloocta[c]pyrazol-10-yl)(5-methyl-1-phenyl-1H-1,2,4-triazol-3-yl)methanone; |

TABLE 1-continued

| Ex # | Compound Name |
|---|---|
| 85 | racemic-((5R,9S)-3-(3,5-Difluorophenyl)-2-methyl-4,5,6,7,8,9-hexahydro-2H-5,9-epiminocycloocta[c]pyrazol-10-yl)(1-(4-fluorophenyl)-5-methyl-1H-1,2,4-triazol-3-yl)methanone; |
| 86 | racemic-((5R,9S)-3-(3,5-Difluorophenyl)-2-methyl-4,5,6,7,8,9-hexahydro-2H-5,9-epiminocycloocta[c]pyrazol-10-yl)(5-ethyl-1-phenyl-1H-1,2,4-triazol-3-yl)methanone; |
| 87 | ((5R,9S)-3-(3,5-Difluorophenyl)-2-methyl-4,5,6,7,8,9-hexahydro-2H-5,9-epiminocycloocta[c]pyrazol-10-yl)(2-fluoropyridin-4-yl)methanone; |
| 88 | ((5R,9S)-3-(3,5-Difluorophenyl)-2-methyl-4,5,6,7,8,9-hexahydro-2H-5,9-epiminocycloocta[c]pyrazol-10-yl)(5-methoxypyridin-3-yl)methanone; |
| 89 | (5-Aminopyridin-2-yl)((5R,9S)-3-(3,5-difluorophenyl)-2-methyl-4,5,6,7,8,9-hexahydro-2H-5,9-epiminocycloocta[c]pyrazol-10-yl)methanone; |
| 90 | ((5R,9S)-3-(3,5-Difluorophenyl)-2-methyl-4,5,6,7,8,9-hexahydro-2H-5,9-epiminocycloocta[c]pyrazol-10-yl)(5-methoxybenzofuran-2-yl)methanone; |
| 91 | ((5R,9S)-3-(3,5-Difluorophenyl)-2-methyl-4,5,6,7,8,9-hexahydro-2H-5,9-epiminocycloocta[c]pyrazol-10-yl)(2-methylbenzo[d]oxazol-6-yl)methanone; |
| 92 | (2-Aminobenzo[d]oxazol-6-yl)((5R,9S)-3-(3,5-difluorophenyl)-2-methyl-4,5,6,7,8,9-hexahydro-2H-5,9-epiminocycloocta[c]pyrazol-10-yl)methanone; |
| 93 | ((5R,9S)-3-(3,5-Difluorophenyl)-2-methyl-4,5,6,7,8,9-hexahydro-2H-5,9-epiminocycloocta[c]pyrazol-10-yl)(furo[3,2-b]pyridin-2-yl)methanone; |
| 94 | ((5R,9S)-3-(3,5-Difluorophenyl)-2-methyl-4,5,6,7,8,9-hexahydro-2H-5,9-epiminocycloocta[c]pyrazol-10-yl)(furo[3,2-c]pyridin-4-yl)methanone; |
| 95 | ((5R,9S)-3-(3,5-Difluorophenyl)-2-methyl-4,5,6,7,8,9-hexahydro-2H-5,9-epiminocycloocta[c]pyrazol-10-yl)(1-methyl-1H-pyrazolo[3,4-b]pyridin-3-yl)methanone; |
| 96 | racemic-((5R,9S)-3-(3,5-Difluorophenyl)-2-methyl-4,5,6,7,8,9-hexahydro-2H-5,9-epiminocycloocta[c]pyrazol-10-yl)(quinolin-6-yl)methanone; |
| 97 | ((5R,9S)-3-(3,5-Difluorophenyl)-2-methyl-4,5,6,7,8,9-hexahydro-2H-5,9-epiminocycloocta[c]pyrazol-10-yl)(quinolin-6-yl)methanone; |
| 98 | ((5S,9R)-3-(3,5-Difluorophenyl)-2-methyl-4,5,6,7,8,9-hexahydro-2H-5,9-epiminocycloocta[c]pyrazol-10-yl)(quinolin-6-yl)methanone; |
| 99 | ((5R,9S)-3-(3,5-Difluorophenyl)-2-methyl-4,5,6,7,8,9-hexahydro-2H-5,9-epiminocycloocta[c]pyrazol-10-yl)(isoquinolin-3-yl)methanone; |
| 100 | ((5R,9S)-3-(3,5-Difluorophenyl)-2-methyl-4,5,6,7,8,9-hexahydro-2H-5,9-epiminocycloocta[c]pyrazol-10-yl)(quinolin-7-yl)methanone; |
| 101 | (4-Bromoquinolin-6-yl)((5R,9S)-3-(3,5-difluorophenyl)-2-methyl-4,5,6,7,8,9-hexahydro-2H-5,9-epiminocycloocta[c]pyrazol-10-yl)methanone; |
| 102 | (3-Bromoquinolin-6-yl)((5R,9S)-3-(3,5-difluorophenyl)-2-methyl-4,5,6,7,8,9-hexahydro-2H-5,9-epiminocycloocta[c]pyrazol-10-yl)methanone; |
| 103 | (8-Bromoquinolin-6-yl)((5R,9S)-3-(3,5-difluorophenyl)-2-methyl-4,5,6,7,8,9-hexahydro-2H-5,9-epiminocycloocta[c]pyrazol-10-yl)methanone; |
| 104 | (2-Chloroquinolin-6-yl)((5R,9S)-3-(3,5-difluorophenyl)-2-methyl-4,5,6,7,8,9-hexahydro-2H-5,9-epiminocycloocta[c]pyrazol-10-yl)methanone; |
| 105 | ((5R,9S)-3-(3,5-Difluorophenyl)-2-methyl-4,5,6,7,8,9-hexahydro-2H-5,9-epiminocycloocta[c]pyrazol-10-yl)(8-fluoroquinolin-5-yl)methanone; |
| 106 | ((5R,9S)-3-(3,5-Difluorophenyl)-2-methyl-4,5,6,7,8,9-hexahydro-2H-5,9-epiminocycloocta[c]pyrazol-10-yl)(8-fluoroquinolin-6-yl)methanone; |
| 107 | ((5R,9S)-3-(3,5-Difluorophenyl)-2-methyl-4,5,6,7,8,9-hexahydro-2H-5,9-epiminocycloocta[c]pyrazol-10-yl)(2-(trifluoromethyl)quinolin-6-yl)methanone; |
| 108 | ((5R,9S)-3-(3,5-Difluorophenyl)-2-methyl-4,5,6,7,8,9-hexahydro-2H-5,9-epiminocycloocta[c]pyrazol-10-yl)(8-hydroxyquinolin-6-yl)methanone; |
| 109 | ((5R,9S)-3-(3,5-Difluorophenyl)-2-methyl-4,5,6,7,8,9-hexahydro-2H-5,9-epiminocycloocta[c]pyrazol-10-yl)(5-methoxyquinolin-3-yl)methanone; |
| 110 | ((5R,9S)-3-(3,5-Difluorophenyl)-2-methyl-4,5,6,7,8,9-hexahydro-2H-5,9-epiminocycloocta[c]pyrazol-10-yl)(8-nitroquinolin-6-yl)methanone; |
| 111 | (8-Aminoquinolin-6-yl)((5R,9S)-3-(3,5-difluorophenyl)-2-methyl-4,5,6,7,8,9-hexahydro-2H-5,9-epiminocycloocta[c]pyrazol-10-yl)methanone; |
| 112 | ((5R,9S)-3-(3,5-Difluorophenyl)-2-methyl-4,5,6,7,8,9-hexahydro-2H-5,9-epiminocycloocta[c]pyrazol-10-yl)(quinazolin-7-yl)methanone; |
| 113 | ((5R,9S)-3-(3,5-Difluorophenyl)-2-methyl-4,5,6,7,8,9-hexahydro-2H-5,9-epiminocycloocta[c]pyrazol-10-yl)(quinoxalin-6-yl)methanone; |
| 114 | ((5R,9S)-3-(3,5-Difluorophenyl)-2-methyl-4,5,6,7,8,9-hexahydro-2H-5,9-epiminocycloocta[c]pyrazol-10-yl)(quinazolin-6-yl)methanone; |
| 115 | ((5R,9S)-3-(3,5-Difluorophenyl)-2-methyl-4,5,6,7,8,9-hexahydro-2H-5,9-epiminocycloocta[c]pyrazol-10-yl)(2-methylquinoxalin-6-yl)methanone; |
| 116 | ((5R,9S)-3-(3,5-Difluorophenyl)-2-methyl-4,5,6,7,8,9-hexahydro-2H-5,9-epiminocycloocta[c]pyrazol-10-yl)(7-fluoroquinoxalin-6-yl)methanone; |
| 117 | ((5R,9S)-3-(3,5-Difluorophenyl)-2-methyl-4,5,6,7,8,9-hexahydro-2H-5,9-epiminocycloocta[c]pyrazol-10-yl)(1,6-naphthyridin-5-yl)methanone; |
| 118 | ((5R,9S)-3-(3,5-Difluorophenyl)-2-methyl-4,5,6,7,8,9-hexahydro-2H-5,9-epiminocycloocta[c]pyrazol-10-yl)(1,8-naphthyridin-3-yl)methanone; |
| 119 | ((5R,9S)-3-(3,5-Difluorophenyl)-2-methyl-4,5,6,7,8,9-hexahydro-2H-5,9-epiminocycloocta[c]pyrazol-10-yl)(1,8-naphthyridin-4-yl)methanone; |
| 120 | ((5R,9S)-3-(3,5-Difluorophenyl)-2-methyl-4,5,6,7,8,9-hexahydro-2H-5,9-epiminocycloocta[c]pyrazol-10-yl)(1,7-naphthyridin-4-yl)methanone; |
| 121 | ((5R,9S)-3-(3,5-Difluorophenyl)-2-methyl-4,5,6,7,8,9-hexahydro-2H-5,9-epiminocycloocta[c]pyrazol-10-yl)(1,6-naphthyridin-4-yl)methanone; |

TABLE 1-continued

| Ex # | Compound Name |
|---|---|
| 122 | ((5R,9S)-3-(3,5-Difluorophenyl)-2-methyl-4,5,6,7,8,9-hexahydro-2H-5,9-epiminocycloocta[c]pyrazol-10-yl)(1,5-naphthyridin-2-yl)methanone; |
| 123 | 6-((5R,9S)-3-(3,5-Difluorophenyl)-2-methyl-4,5,6,7,8,9-hexahydro-2H-5,9-epiminocycloocta[c]pyrazole-10-carbonyl)-1-(2-fluoroethyl)quinolin-4(1H)-one; |
| 124 | 6-((5R,9S)-3-(3,5-Difluorophenyl)-2-methyl-4,5,6,7,8,9-hexahydro-2H-5,9-epiminocycloocta[c]pyrazole-10-carbonyl)-4-methyl-2H-benzo[b][1,4]oxazin-3(4H)-one; |
| 125 | ((5R,9S)-3-(3,5-Difluorophenyl)-2-methyl-4,5,6,7,8,9-hexahydro-2H-5,9-epiminocycloocta[c]pyrazol-10-yl)(4-methyl-3,4-dihydro-2H-pyrido[3,2-b][1,4]oxazin-7-yl)methanone; |
| 126 | (2-(2H-1,2,3-Triazol-2-yl)phenyl)((5R,9S)-3-(3,4-difluorophenyl)-2-methyl-4,5,6,7,8,9-hexahydro-2H-5,9-epiminocycloocta[c]pyrazol-10-yl)methanone; |
| 127 | racemic-((5R,9S)-3-(3,4-Difluorophenyl)-2-methyl-4,5,6,7,8,9-hexahydro-2H-5,9-epiminocycloocta[c]pyrazol-10-yl)(quinolin-6-yl)methanone; |
| 128 | ((5R,9S)-3-(3,4-Difluorophenyl)-2-methyl-4,5,6,7,8,9-hexahydro-2H-5,9-epiminocycloocta[c]pyrazol-10-yl)(quinolin-6-yl)methanone; |
| 129 | racemic-((5R,9S)-3-(3,4-Difluorophenyl)-2-methyl-4,5,6,7,8,9-hexahydro-2H-5,9-epiminocycloocta[c]pyrazol-10-yl)(quinoxalin-6-yl)methanone; |
| 130 | ((5R,9S)-3-(3-Fluoro-5-methoxyphenyl)-2-methyl-4,5,6,7,8,9-hexahydro-2H-5,9-epiminocycloocta[c]pyrazol-10-yl)(quinoxalin-6-yl)methanone; |
| 131 | ((5R,9S)-3-(4-Chloro-3-fluorophenyl)-2-methyl-4,5,6,7,8,9-hexahydro-2H-5,9-epiminocycloocta[c]pyrazol-10-yl)(quinoxalin-6-yl)methanone; |
| 132 | ((5R,9S)-3-(3-Chloro-4-methoxyphenyl)-2-methyl-4,5,6,7,8,9-hexahydro-2H-5,9-epiminocycloocta[c]pyrazol-10-yl)(quinoxalin-6-yl)methanone; |
| 133 | (2-(2H-1,2,3-Triazol-2-yl)phenyl)((5R,9S)-3-(3-chloro-4-methoxyphenyl)-2-methyl-4,5,6,7,8,9-hexahydro-2H-5,9-epiminocycloocta[c]pyrazol-10-yl)methanone; |
| 134 | ((5R,9S)-3-(3-Chloro-4-methoxyphenyl)-2-methyl-4,5,6,7,8,9-hexahydro-2H-5,9-epiminocycloocta[c]pyrazol-10-yl)(1-methyl-1H-pyrazolo[3,4-b]pyridin-3-yl)methanone; |
| 135 | ((5R,9S)-3-(3-Chloro-4-methoxyphenyl)-2-methyl-4,5,6,7,8,9-hexahydro-2H-5,9-epiminocycloocta[c]pyrazol-10-yl)(quinolin-6-yl)methanone; |
| 136 | ((5R,9S)-3-(3-Chloro-5-methoxyphenyl)-2-methyl-4,5,6,7,8,9-hexahydro-2H-5,9-epiminocycloocta[c]pyrazol-10-yl)(2-methylbenzo[d]oxazol-6-yl)methanone; |
| 137 | ((5R,9S)-3-(3-Chloro-5-methoxyphenyl)-2-methyl-4,5,6,7,8,9-hexahydro-2H-5,9-epiminocycloocta[c]pyrazol-10-yl)(quinolin-6-yl)methanone; |
| 138 | ((5R,9S)-3-(3-Chloro-5-methoxyphenyl)-2-methyl-4,5,6,7,8,9-hexahydro-2H-5,9-epiminocycloocta[c]pyrazol-10-yl)(quinoxalin-6-yl)methanone; |
| 139 | ((5R,9S)-3-(3,5-Dimethoxyphenyl)-2-methyl-4,5,6,7,8,9-hexahydro-2H-5,9-epiminocycloocta[c]pyrazol-10-yl)(2-methylbenzo[d]oxazol-6-yl)methanone; |
| 140 | ((5R,9S)-3-(3,5-Dimethoxyphenyl)-2-methyl-4,5,6,7,8,9-hexahydro-2H-5,9-epiminocycloocta[c]pyrazol-10-yl)(quinoxalin-6-yl)methanone; |
| 141 | (3-(4H-1,2,4Ttriazol-4-yl)phenyl)((5R,9S)-3-(3,5-dichlorophenyl)-2-methyl-4,5,6,7,8,9-hexahydro-2H-5,9-epiminocycloocta[c]pyrazol-10-yl)methanone; |
| 142 | ((5R,9S)-3-(3,5-Dichlorophenyl)-2-methyl-4,5,6,7,8,9-hexahydro-2H-5,9-epiminocycloocta[c]pyrazol-10-yl)(4-methyl-3,4-dihydro-2H-pyrido[3,2-b][1,4]oxazin-7-yl)methanone; |
| 143 | ((5R,9S)-3-(3,5-Dichlorophenyl)-2-methyl-4,5,6,7,8,9-hexahydro-2H-5,9-epiminocycloocta[c]pyrazol-10-yl)(5-methoxy-1-methyl-1H-pyrazol-4-yl)methanone; |
| 144 | (5-Cyclopropyl-1-methyl-1H-pyrazol-4-yl)((5R,9S)-3-(3,5-dichlorophenyl)-2-methyl-4,5,6,7,8,9-hexahydro-2H-5,9-epiminocycloocta[c]pyrazol-10-yl)methanone; |
| 145 | ((5R,9S)-3-(3,5-Dichlorophenyl)-2-methyl-4,5,6,7,8,9-hexahydro-2H-5,9-epiminocycloocta[c]pyrazol-10-yl)(1-phenyl-1H-1,2,4-triazol-3-yl)methanone; |
| 146 | ((5R,9S)-3-(3,5-Dichlorophenyl)-2-methyl-4,5,6,7,8,9-hexahydro-2H-5,9-epiminocycloocta[c]pyrazol-10-yl)(5-methoxypyridin-3-yl)methanone; |
| 147 | ((5R,9S)-3-(3,5-Dichlorophenyl)-2-methyl-4,5,6,7,8,9-hexahydro-2H-5,9-epiminocycloocta[c]pyrazol-10-yl)(6-methyl-3-(2H-1,2,3-triazol-2-yl)pyridin-2-yl)methanone; |
| 148 | ((5R,9S)-3-(3,5-Dichlorophenyl)-2-methyl-4,5,6,7,8,9-hexahydro-2H-5,9-epiminocycloocta[c]pyrazol-10-yl)(2-methylbenzo[d]oxazol-6-yl)methanone; |
| 149 | ((5R,9S)-3-(3,5-Dichlorophenyl)-2-methyl-4,5,6,7,8,9-hexahydro-2H-5,9-epiminocycloocta[c]pyrazol-10-yl)(furo[3,2-b]pyridin-2-yl)methanone; |
| 150 | ((5R,9S)-3-(3,5-Dichlorophenyl)-2-methyl-4,5,6,7,8,9-hexahydro-2H-5,9-epiminocycloocta[c]pyrazol-10-yl)(imidazo[1,5-a]pyridin-8-yl)methanone; |
| 151 | ((5R,9S)-3-(3,5-Dichlorophenyl)-2-methyl-4,5,6,7,8,9-hexahydro-2H-5,9-epiminocycloocta[c]pyrazol-10-yl)(imidazo[1,2-a]pyridin-3-yl)methanone; |
| 152 | (4-Methoxy-2-(2H-1,2,3-triazol-2-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 153 | ((5R,9S)-3-(3,5-Dichlorophenyl)-2-methyl-4,5,6,7,8,9-hexahydro-2H-5,9-epiminocycloocta[c]pyrazol-10-yl)(quinoxalin-6-yl)methanone; |
| 154 | racemic-((5R,9S)-3-(3-(Difluoromethyl)-4-fluorophenyl)-2-methyl-4,5,6,7,8,9-hexahydro-2H-5,9-epiminocycloocta[c]pyrazol-10-yl)(quinolin-6-yl)methanone; |

TABLE 1-continued

| Ex # | Compound Name |
|---|---|
| 155 | racemic-((5R,9S)-3-(3-(Difluoromethyl)-4-fluorophenyl)-2-methyl-4,5,6,7,8,9-hexahydro-2H-5,9-epiminocycloocta[c]pyrazol-10-yl)(quinoxalin-6-yl)methanone; |
| 156 | ((5R,9S)-3-(3-Fluoro-5-(trifluoromethyl)phenyl)-2-methyl-4,5,6,7,8,9-hexahydro-2H-5,9-epiminocycloocta[c]pyrazol-10-yl)(quinoxalin-6-yl)methanone; |
| 157 | (3-Chloro-5-methoxyphenyl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 158 | N-(3-Methoxy-5-((5R,9S)-2-methyl-3-(3,4,5-trifluorophenyl)-4,5,6,7,8,9-hexahydro-2H-5,9-epiminocycloocta[c]pyrazole-10-carbonyl)phenyl)acetamide; |
| 159 | (3-(4H-1,2,4-Triazol-4-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 160 | (2-(4H-1,2,4-Triazol-4-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 161 | (3-Fluoro-2-(1H-1,2,4-triazol-1-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 162 | (4-Fluoro-2-(1H-1,2,4-triazol-1-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 163 | (5-Fluoro-2-(1H-1,2,4-triazol-1-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 164 | (4-Methyl-2-(1H-1,2,4-triazol-1-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 165 | (5-Methyl-2-(1H-1,2,4-triazol-1-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 166 | (2-(1H-1,2,4-Triazol-1-yl)-5-(trifluoromethyl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 167 | ((5R,9S)-2-Methyl-3-(3,4,5-trifluorophenyl)-4,5,6,7,8,9-hexahydro-2H-5,9-epiminocycloocta[c]pyrazol-10-yl)(2-(3-(trifluoromethyl)-1H-1,2,4-triazol-1-yl)phenyl)methanone; |
| 168 | (2-(1H-Imidazol-1-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 169 | (5-Fluoro-2-(1H-pyrazol-1-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 170 | (3-(1-Methyl-1H-pyrazol-4-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 171 | (3-(4-Fluoro-1H-pyrazol-1-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 172 | ((5R,9S)-2-Methyl-3-(3,4,5-trifluorophenyl)-4,5,6,7,8,9-hexahydro-2H-5,9-epiminocycloocta[c]pyrazol-10-yl)(3-(4-(trifluoromethyl)-1H-pyrazol-1-yl)phenyl)methanone; |
| 173 | (3-(4-Methoxy-1H-pyrazol-1-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 174 | ((5R,9S)-2-Methyl-3-(3,4,5-trifluorophenyl)-4,5,6,7,8,9-hexahydro-2H-5,9-epiminocycloocta[c]pyrazol-10-yl)(3-(3-(trifluoromethyl)-1H-pyrazol-1-yl)phenyl)methanone; |
| 175 | (3-(2H-1,2,3-Triazol-2-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 176 | (5-Fluoro-2-(2H-1,2,3-triazol-2-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 177 | (3-Methyl-2-(2H-1,2,3-triazol-2-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 178 | (3-Methoxy-2-(2H-1,2,3-triazol-2-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 179 | (4-Methoxy-2-(2H-1,2,3-triazol-2-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 180 | (5-Methoxy-2-(2H-1,2,3-triazol-2-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 181 | (2-(2H-1,2,3-Triazol-2-yl)-4-(trifluoromethyl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; |

TABLE 1-continued

| Ex # | Compound Name |
|---|---|
| 182 | (2-(2H-1,2,3-Triazol-2-yl)-5-(trifluoromethyl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 183 | (2-(1H-1,2,3-Triazol-1-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 184 | (3-Methoxy-2-(1H-1,2,3-triazol-1-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 185 | ((5R,9S)-2-Methyl-3-(3,4,5-trifluorophenyl)-4,5,6,7,8,9-hexahydro-2H-5,9-epiminocycloocta[c]pyrazol-10-yl)(4,5,6,7-tetrahydropyrazolo[1,5-a]pyridin-3-yl)methanone; |
| 186 | (3,4-Dihydro-2H-pyrano[3,2-b]pyridin-7-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 187 | (6,7-Dihydro-5H-pyrazolo[5,1-b][1,3]oxazin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 188 | ((5R,9S)-2-Methyl-3-(3,4,5-trifluorophenyl)-4,5,6,7,8,9-hexahydro-2H-5,9-epiminocycloocta[c]pyrazol-10-yl)(6-methyl-6,7-dihydro-5H-pyrazolo[5,1-b][1,3]oxazin-3-yl)methanone; |
| 189 | (6,7-Dihydro-5H-pyrazolo[5,1-b][1,3]oxazin-2-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 190 | ((5R,9S)-2-Methyl-3-(3,4,5-trifluorophenyl)-4,5,6,7,8,9-hexahydro-2H-5,9-epiminocycloocta[c]pyrazol-10-yl)(1-methyl-5-(trifluoromethyl)-1H-pyrazol-4-yl)methanone; |
| 191 | (1-(tert-Butyl)-5-(trifluoromethyl)-1H-pyrazol-4-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 192 | (5-Ethyl-1-phenyl-1H-1,2,4-triazol-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 193 | ((5R,9S)-2-Methyl-3-(3,4,5-trifluorophenyl)-4,5,6,7,8,9-hexahydro-2H-5,9-epiminocycloocta[c]pyrazol-10-yl)(1-phenyl-5-(trifluoromethyl)-1H-pyrazol-3-yl)methanone; |
| 194 | ((5R,9S)-2-Methyl-3-(3,4,5-trifluorophenyl)-4,5,6,7,8,9-hexahydro-2H-5,9-epiminocycloocta[c]pyrazol-10-yl)(1-phenyl-5-(trifluoromethyl)-1H-1,2,4-triazol-3-yl)methanone; |
| 195 | (5-Methoxy-1-phenyl-1H-1,2,4-triazol-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 196 | (1-(3-Fluorophenyl)-1H-1,2,4-triazol-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 197 | (1-(4-Fluorophenyl)-5-methyl-1H-1,2,4-triazol-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 198 | (1-(2-Methoxyphenyl)-1H-1,2,4-triazol-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 199 | (1-(3-Methoxyphenyl)-1H-1,2,4-triazol-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 200 | (4-Methoxypyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 201 | (6-Methoxypyridin-2-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 202 | (4-Methoxypyridin-2-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 203 | (5-Methoxypyridin-2-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 204 | (6-Methoxypyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 205 | (5-Isopropoxypyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 206 | ((5R,9S)-2-Methyl-3-(3,4,5-trifluorophenyl)-4,5,6,7,8,9-hexahydro-2H-5,9-epiminocycloocta[c]pyrazol-10-yl)(6-(trifluoromethoxy)pyridin-2-yl)methanone; |
| 207 | ((5R,9S)-2-Methyl-3-(3,4,5-trifluorophenyl)-4,5,6,7,8,9-hexahydro-2H-5,9-epiminocycloocta[c]pyrazol-10-yl)(5-(trifluoromethoxy)pyridin-2-yl)methanone; |
| 208 | 6-((5R,9S)-2-Methyl-3-(3,4,5-trifluorophenyl)-4,5,6,7,8,9-hexahydro-2H-5,9-epiminocycloocta[c]pyrazole-10-carbonyl)picolinonitrile; |
| 209 | ((5R,9S)-2-Methyl-3-(3,4,5-trifluorophenyl)-4,5,6,7,8,9-hexahydro-2H-5,9-epiminocycloocta[c]pyrazol-10-yl)(pyrazin-2-yl)methanone; |
| 210 | ((5R,9S)-2-Methyl-3-(3,4,5-trifluorophenyl)-4,5,6,7,8,9-hexahydro-2H-5,9-epiminocycloocta[c]pyrazol-10-yl)(pyrimidin-4-yl)methanone; |

TABLE 1-continued

| Ex # | Compound Name |
|---|---|
| 211 | ((5R,9S)-2-Methyl-3-(3,4,5-trifluorophenyl)-4,5,6,7,8,9-hexahydro-2H-5,9-epiminocycloocta[c]pyrazol-10-yl)(pyridazin-4-yl)methanone; |
| 212 | ((5R,9S)-2-Methyl-3-(3,4,5-trifluorophenyl)-4,5,6,7,8,9-hexahydro-2H-5,9-epiminocycloocta[c]pyrazol-10-yl)(pyrimidin-5-yl)methanone; |
| 213 | (5-(1H-Pyrazol-1-yl)pyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 214 | (6-(1H-Pyrazol-1-yl)pyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 215 | (6-(1H-Pyrrol-1-yl)pyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 216 | (6-(1H-Imidazol-1-yl)pyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 217 | (6-Methyl-3-(2H-1,2,3-triazol-2-yl)pyridin-2-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 218 | ((5R,9S)-2-Methyl-3-(3,4,5-trifluorophenyl)-4,5,6,7,8,9-hexahydro-2H-5,9-epiminocycloocta[c]pyrazol-10-yl)(5-(pyrrolidin-1-yl)pyridin-3-yl)methanone; |
| 219 | 1-(5-((5R,9S)-2-Methyl-3-(3,4,5-trifluorophenyl)-4,5,6,7,8,9-hexahydro-2H-5,9-epiminocycloocta[c]pyrazole-10-carbonyl)pyridin-3-yl)pyrrolidin-2-one; |
| 220 | ((5R,9S)-2-Methyl-3-(3,4,5-trifluorophenyl)-4,5,6,7,8,9-hexahydro-2H-5,9-epiminocycloocta[c]pyrazol-10-yl)(5-morpholinopyridin-3-yl)methanone; |
| 221 | ((5R,9S)-2-Methyl-3-(3,4,5-trifluorophenyl)-4,5,6,7,8,9-hexahydro-2H-5,9-epiminocycloocta[c]pyrazol-10-yl)(2-methylindolizin-6-yl)methanone; |
| 222 | ((5R,9S)-2-Methyl-3-(3,4,5-trifluorophenyl)-4,5,6,7,8,9-hexahydro-2H-5,9-epiminocycloocta[c]pyrazol-10-yl)(2-methylbenzo[d]oxazol-6-yl)methanone; |
| 223 | ((5R,9S)-2-Methyl-3-(3,4,5-trifluorophenyl)-4,5,6,7,8,9-hexahydro-2H-5,9-epiminocycloocta[c]pyrazol-10-yl)(pyrazolo[1,5-a]pyridin-3-yl)methanone; |
| 224 | ((5R,9S)-2-Methyl-3-(3,4,5-trifluorophenyl)-4,5,6,7,8,9-hexahydro-2H-5,9-epiminocycloocta[c]pyrazol-10-yl)(5-methylpyrazolo[1,5-a]pyridin-3-yl)methanone; |
| 225 | ((5R,9S)-2-Methyl-3-(3,4,5-trifluorophenyl)-4,5,6,7,8,9-hexahydro-2H-5,9-epiminocycloocta[c]pyrazol-10-yl)(pyrazolo[1,5-a]pyridin-5-yl)methanone; |
| 226 | ((5R,9S)-2-Methyl-3-(3,4,5-trifluorophenyl)-4,5,6,7,8,9-hexahydro-2H-5,9-epiminocycloocta[c]pyrazol-10-yl)(pyrazolo[1,5-a]pyridin-6-yl)methanone; |
| 227 | ((5R,9S)-2-Methyl-3-(3,4,5-trifluorophenyl)-4,5,6,7,8,9-hexahydro-2H-5,9-epiminocycloocta[c]pyrazol-10-yl)(pyrazolo[1,5-a]pyridin-2-yl)methanone; |
| 228 | Imidazo[1,2-a]pyridin-5-yl((5R,9S)-2-methyl-3-(3,4,5-trifluorophenyl)-4,5,6,7,8,9-hexahydro-2H-5,9-epiminocycloocta[c]pyrazol-10-yl)methanone; |
| 229 | Imidazo[1,5-a]pyridin-5-yl((5R,9S)-2-methyl-3-(3,4,5-trifluorophenyl)-4,5,6,7,8,9-hexahydro-2H-5,9-epiminocycloocta[c]pyrazol-10-yl)methanone; |
| 230 | Imidazo[1,5-a]pyridin-6-yl((5R,9S)-2-methyl-3-(3,4,5-trifluorophenyl)-4,5,6,7,8,9-hexahydro-2H-5,9-epiminocycloocta[c]pyrazol-10-yl)methanone; |
| 231 | Imidazo[1,2-a]pyridin-6-yl((5R,9S)-2-methyl-3-(3,4,5-trifluorophenyl)-4,5,6,7,8,9-hexahydro-2H-5,9-epiminocycloocta[c]pyrazol-10-yl)methanone; |
| 232 | ((5R,9S)-2-Methyl-3-(3,4,5-trifluorophenyl)-4,5,6,7,8,9-hexahydro-2H-5,9-epiminocycloocta[c]pyrazol-10-yl)(7-methylimidazo[1,2-a]pyridin-3-yl)methanone; |
| 233 | (1-Methyl-1H-pyrrolo[2,3-b]pyridin-4-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 234 | (1-Methyl-1H-pyrrolo[2,3-b]pyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 235 | ((5R,9S)-2-Methyl-3-(3,4,5-trifluorophenyl)-4,5,6,7,8,9-hexahydro-2H-5,9-epiminocycloocta[c]pyrazol-10-yl)(pyrrolo[1,2-b]pyridazin-5-yl)methanone; |
| 236 | ((5R,9S)-2-Methyl-3-(3,4,5-trifluorophenyl)-4,5,6,7,8,9-hexahydro-2H-5,9-epiminocycloocta[c]pyrazol-10-yl)(pyrrolo[1,2-a]pyrazin-8-yl)methanone; |
| 237 | (4-Methoxy-1-rnethyl-1H-indazol-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 238 | (1-Methyl-1H-pyrazolo[3,4-b]pyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 239 | ((5R,9S)-2-Methyl-3-(3,4,5-trifluorophenyl)-4,5,6,7,8,9-hexahydro-2H-5,9-epiminocycloocta[c]pyrazol-10-yl)(pyrazolo[1,5-b]pyridazin-3-yl)methanone; |
| 240 | ((5R,9S)-2-Methyl-3-(3,4,5-trifluorophenyl)-4,5,6,7,8,9-hexahydro-2H-5,9-epiminocycloocta[c]pyrazol-10-yl)(pyrazolo[1,5-a]pyrimidin-2-yl)methanone; |
| 241 | ((5R,9S)-2-Methyl-3-(3,4,5-trifluorophenyl)-4,5,6,7,8,9-hexahydro-2H-5,9-epiminocycloocta[c]pyrazol-10-yl)(pyrazolo[1,5-a]pyrimidin-3-yl)methanone; |
| 242 | ((5R,9S)-2-Methyl-3-(3,4,5-trifluorophenyl)-4,5,6,7,8,9-hexahydro-2H-5,9-epiminocycloocta[c]pyrazol-10-yl)(6-methylpyrazolo[1,5-a]pyrimidin-3-yl)methanone; |
| 243 | ((5R,9S)-2-Methyl-3-(3,4,5-trifluorophenyl)-4,5,6,7,8,9-hexahydro-2H-5,9-epiminocycloocta[c]pyrazol-10-yl)(pyrazolo[1,5-a]pyrimidin-5-yl)methanone; |
| 244 | ((5R,9S)-2-Methyl-3-(3,4,5-trifluorophenyl)-4,5,6,7,8,9-hexahydro-2H-5,9-epiminocycloocta[c]pyrazol-10-yl)(pyrazolo[1,5-a]pyrazin-3-yl)methanone; |

TABLE 1-continued

| Ex # | Compound Name |
|---|---|
| 245 | Imidazo[1,2-b]pyridazin-6-yl((5R,9S)-2-rnethyl-3-(3,4,5-trifluorophenyl)-4,5,6,7,8,9-hexahydro-2H-5,9-epiminocycloocta[c]pyrazol-10-yl)methanone; |
| 246 | Imidazo[1,2-b]pyridazin-3-yl((5R,9S)-2-methyl-3-(3,4,5-trifluorophenyl)-4,5,6,7,8,9-hexahydro-2H-5,9-epiminocycloocta[c]pyrazol-10-yl)methanone; |
| 247 | [1,2,4]Triazolo[1,5-a]pyridin-7-yl((5R,9S)-2-methyl-3-(3,4,5-trifluorophenyl)-4,5,6,7,8,9-hexahydro-2H-5,9-epiminocycloocta[c]pyrazol-10-yl)methanone; |
| 248 | ((5R,9S)-2-Methyl-3-(3,4,5-trifluorophenyl)-4,5,6,7,8,9-hexahydro-2H-5,9-epiminocycloocta[c]pyrazol-10-yl)(5-methyl-5H-pyrrolo[2,3-b]pyrazin-7-yl)methanone; |
| 249 | Imidazo[1,2-a]pyrimidin-3-yl((5R,9S)-2-methyl-3-(3,4,5-trifluorophenyl)-4,5,6,7,8,9-hexahydro-2H-5,9-epiminocycloocta[c]pyrazol-10-yl)methanone; |
| 250 | ((5R,9S)-2-Methyl-3-(3,4,5-trifluorophenyl)-4,5,6,7,8,9-hexahydro-2H-5,9-epiminocycloocta[c]pyrazol-10-yl)(quinolin-4-yl)methanone; |
| 251 | Isoquinolin-1-yl((5R,9S)-2-methyl-3-(3,4,5-trifluorophenyl)-4,5,6,7,8,9-hexahydro-2H-5,9-epiminocycloocta[c]pyrazol-10-yl)methanone; |
| 252 | ((5R,9S)-2-Methyl-3-(3,4,5-trifluorophenyl)-4,5,6,7,8,9-hexahydro-2H-5,9-epiminocycloocta[c]pyrazol-10-yl)(quinolin-6-yl)methanone; |
| 253 | ((5R,9S)-2-Methyl-3-(3,4,5-trifluorophenyl)-4,5,6,7,8,9-hexahydro-2H-5,9-epiminocycloocta[c]pyrazol-10-yl)(quinolin-7-yl)methanone; |
| 254 | ((5R,9S)-2-Methyl-3-(3,4,5-trifluorophenyl)-4,5,6,7,8,9-hexahydro-2H-5,9-epiminocycloocta[c]pyrazol-10-yl)(quinazolin-4-yl)methanone; |
| 255 | ((5R,9S)-2-Methyl-3-(3,4,5-trifluorophenyl)-4,5,6,7,8,9-hexahydro-2H-5,9-epiminocycloocta[c]pyrazol-10-yl)(quinoxalin-6-yl)methanone; |
| 256 | ((5R,9S)-2-Methyl-3-(3,4,5-trifluorophenyl)-4,5,6,7,8,9-hexahydro-2H-5,9-epiminocycloocta[c]pyrazol-10-yl)(2-methylquinoxalin-6-yl)methanone; |
| 257 | ((5R,9S)-2-Methyl-3-(3,4,5-trifluorophenyl)-4,5,6,7,8,9-hexahydro-2H-5,9-epiminocycloocta[c]pyrazol-10-yl)(quinoxalin-2-yl)methanone; |
| 258 | Cinnolin-3-yl((5R,9S)-2-methyl-3-(3,4,5-trifluorophenyl)-4,5,6,7,8,9-hexahydro-2H-5,9-epiminocycloocta[c]pyrazol-10-yl)methanone; |
| 259 | Cinnolin-6-yl((5R,9S)-2-methyl-3-(3,4,5-trifluorophenyl)-4,5,6,7,8,9-hexahydro-2H-5,9-epiminocycloocta[c]pyrazol-10-yl)methanone; |
| 260 | ((5R,9S)-2-Methyl-3-(3,4,5-trifluorophenyl)-4,5,6,7,8,9-hexahydro-2H-5,9-epiminocycloocta[c]pyrazol-10-yl)(1,5-naphthyridin-2-yl)methanone; |
| 261 | ((5R,9S)-2-Methyl-3-(3,4,5-trifluorophenyl)-4,5,6,7,8,9-hexahydro-2H-5,9-epiminocycloocta[c]pyrazol-10-yl)(1,5-naphthyridin-3-yl)methanone; |
| 262 | ((5R,9S)-2-Methyl-3-(3,4,5-trifluorophenyl)-4,5,6,7,8,9-hexahydro-2H-5,9-epiminocycloocta[c]pyrazol-10-yl)(1,6-naphthyridin-8-yl)methanone; |
| 263 | (2-(2H-1,2,3-Triazol-2-yl)phenyl)((5R,9S)-3-(3,5-difluoro-4-methoxyphenyl)-2-methyl-4,5,6,7,8,9-hexahydro-2H-5,9-epiminocycloocta[c]pyrazol-10-yl)methanone; |
| 264 | ((5R,9S)-3-(3,5-Difluoro-4-methoxyphenyl)-2-methyl-4,5,6,7,8,9-hexahydro-2H-5,9-epiminocycloocta[c]pyrazol-10-yl)(1-methyl-1H-pyrazolo[3,4-b]pyridin-3-yl)methanone; |
| 265 | ((5R,9S)-3-(3,5-Difluoro-4-methoxyphenyl)-2-methyl-4,5,6,7,8,9-hexahydro-2H-5,9-epiminocycloocta[c]pyrazol-10-yl)(quinolin-6-yl)methanone; |
| 266 | (2-(2H-1,2,3-Triazol-2-yl)phenyl)((5R,9S)-3-(3,5-difluoro-4-methoxyphenyl)-2-methyl-4,5,6,7,8,9-hexahydro-2H-5,9-epiminocycloocta[c]pyrazol-10-yl)methanone; |
| 267 | ((5R,9S)-3-(3,4-Difluoro-5-methoxyphenyl)-2-methyl-4,5,6,7,8,9-hexahydro-2H-5,9-epiminocycloocta[c]pyrazol-10-yl)(1-methyl-1H-pyrazolo[3,4-b]pyridin-3-yl)methanone; |
| 268 | ((5R,9S)-3-(3,4-Difluoro-5-methoxyphenyl)-2-methyl-4,5,6,7,8,9-hexahydro-2H-5,9-epiminocycloocta[c]pyrazol-10-yl)(quinolin-6-yl)methanone; |
| 269 | ((5R,9S)-2-Methyl-3-(1-methyl-1H-indol-2-yl)-4,5,6,7,8,9-hexahydro-2H-5,9-epiminocycloocta[c]pyrazol-10-yl)(quinolin-6-yl)methanone; and |
| 270 | racemic-((5R,9S)-2-Methyl-3-(5-(trifluoromethyl)thiophen-2-yl)-4,5,6,7,8,9-hexahydro-2H-5,9-epiminocycloocta[c]pyrazol-10-yl)(quinolin-6-yl)methanone; | and pharmaceutically acceptable salts, isotopes, N-oxides, solvates, and stereoisomers thereof.

TABLE 2

| Ex # | Compound Name |
|---|---|
| 271 | (4-Methoxyphenyl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 272 | (2-Fluoro-4-methylphenyl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 273 | (2-Fluoro-4-methoxyphenyl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 274 | (3-Fluoro-5-(1H-pyrazol-1-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; |

TABLE 2-continued

| Ex # | Compound Name |
|---|---|
| 275 | (3-Fluoro-5-(4H-1,2,4-triazol-4-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 276 | (4-Fluoro-3-(4H-1,2,4-triazol-4-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 277 | ((5R,9S)-2-Methyl-3-(3,4,5-trifluorophenyl)-4,5,6,7,8,9-hexahydro-2H-5,9-epiminocycloocta[c]pyrazol-10-yl)(4-methyl-3-(4H-1,2,4-triazol-4-yl)phenyl)methanone; |
| 278 | ((5R,9S)-2-Methyl-3-(3,4,5-trifluorophenyl)-4,5,6,7,8,9-hexahydro-2H-5,9-epiminocycloocta[c]pyrazol-10-yl)(3-methyl-5-(4H-1,2,4-triazol-4-yl)phenyl)methanone; |
| 279 | ((5R,9S)-2-Methyl-3-(3,4,5-trifluorophenyl)-4,5,6,7,8,9-hexahydro-2H-5,9-epiminocycloocta[c]pyrazol-10-yl)(2-methyl-3-(4H-1,2,4-triazol-4-yl)phenyl)methanone; |
| 280 | (2-(2H-1,2,3-Triazol-2-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 281 | (4-Fluoro-2-(2H-1,2,3-triazol-2-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 282 | (3-Fuoro-2-(2H-1,2,3-triazol-2-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 283 | (5-Fluoro-2-(2H-1,2,3-triazol-2-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 284 | (5-Methyl-2-(2H-1,2,3-triazol-2-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 285 | (2-(2H-1,2,3-Triazol-2-yl)-3-(trifluoromethyl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 286 | (2-(4-Methyl-2H-1,2,3-triazol-2-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 287 | ((5R,9S)-2-Methyl-3-(3,4,5-trifluorophenyl)-4,5,6,7,8,9-hexahydro-2H-5,9-epiminocycloocta[c]pyrazol-10-yl)(2-(4-(trifluoromethyl)-2H-1,2,3-triazol-2-yl)phenyl)methanone; |
| 288 | (5-Methoxy-2-(1H-1,2,4-triazol-1-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 289 | ((5R,9S)-2-Methyl-3-(3,4,5-trifluorophenyl)-4,5,6,7,8,9-hexahydro-2H-5,9-epiminocycloocta[c]pyrazol-10-yl)(2-(4-(trifluoromethyl)-1H-1,2,3-triazol-1-yl)phenyl)methanone; |
| 290 | (6-Isopropylpyrimidin-4-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 291 | (6-Methoxypyrimidin-4-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 292 | (6-(Dimethylamino)pyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 293 | (5-Methoxy-4-methylpyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 294 | (6-Methoxy-5-methylpyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 295 | (5-Fluoro-6-methoxypyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 296 | (5-Fluoro-2-methoxypyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 297 | (5,6-Dimethoxypyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 298 | (5,6-Dimethoxypyridin-2-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 299 | (3-Chloro-2-methoxypyridin-4-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 300 | (5-Chloro-6-methoxypyridin-2-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 301 | (4-Chloro-2-methylpyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 302 | (4-Chloro-5-methylpyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 303 | (3-Chloro-5-fluoropyridin-4-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 304 | (6-Cyclopropyl-2-methylpyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 305 | 1-(5-((5R,9S)-2-Methyl-3-(3,4,5-trifluorophenyl)-4,5,6,7,8,9-hexahydro-2H-5,9-epiminocycloocta[c]pyrazole-10-carbonyl)pyridin-2-yl)cyclopropane-1-carbonitrile; |

TABLE 2-continued

| Ex # | Compound Name |
|---|---|
| 306 | (2-(1H-Pyrazol-1-yl)pyridin-4-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 307 | (4-(1H-Pyrazol-1-yl)pyridin-2-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 308 | (4-(1H-Pyrazol-1-yl)pyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 309 | (6-(1H-Pyrazol-1-yl)pyridin-2-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 310 | (6-Methyl-3-(1H-pyrazol-1-yl)pyridin-2-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 311 | (4-Methoxy-5-(1H-pyrazol-1-yl)pyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 312 | (6-Methyl-3-(1H-1,2,4-triazol-1-yl)pyridin-2-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 313 | (5-(4H-1,2,4-Triazol-4-yl)pyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 314 | (4-(4H-1,2,4-Triazol-4-yl)pyridin-2-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 315 | ((5R,9S)-2-Methyl-3-(3,4,5-trifluorophenyl)-4,5,6,7,8,9-hexahydro-2H-5,9-epiminocycloocta[c]pyrazol-10-yl)(6-methyl-4-(4H-1,2,4-triazol-4-yl)pyridin-2-yl)methanone; |
| 316 | (5-(2H-1,2,3-Triazol-2-yl)pyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 317 | (3-(2H-1,2,3-Triazol-2-yl)pyridin-2-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 318 | ((5R,9S)-2-Methyl-3-(3,4,5-trifluorophenyl)-4,5,6,7,8,9-hexahydro-2H-5,9-epiminocycloocta[c]pyrazol-10-yl)(6-methyl-4-(2H-1,2,3-triazol-2-yl)pyridin-2-yl)methanone; |
| 319 | (1,5-Dimethyl-1H-pyrazol-4-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 320 | (5-Ethyl-1-methyl-1H-pyrazol-4-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 321 | ((5R,9S)-2-Methyl-3-(3,4,5-trifluorophenyl)-4,5,6,7,8,9-hexahydro-2H-5,9-epiminocycloocta[c]pyrazol-10-yl)(1,3,5-trimethyl-1H-pyrazol-4-yl)methanone; |
| 322 | (5-Methoxy-1-methyl-1H-pyrazol-4-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 323 | (3-Methoxy-1-methyl-1H-pyrazol-4-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 324 | (3-Fluoro-1,5-dimethyl-1H-pyrazol-4-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 325 | (5-(Difluoromethyl)-1-methyl-1H-pyrazol-4-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 326 | (1-Cyclopropyl-5-methyl-1H-pyrazol-4-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 327 | (1-Cyclopropyl-3-methyl-1H-pyrazol-4-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 328 | (3-Cyclopropyl-1-methyl-1H-pyrazol-4-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 329 | Indolizin-7-yl((5R,9S)-2-methyl-3-(3,4,5-trifluorophenyl)-4,5,6,7,8,9-hexahydro-2H-5,9-epiminocycloocta[c]pyrazol-10-yl)methanone; |
| 330 | (4-Fluoropyrazolo[1,5-a]pyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 331 | (6-Fluoropyrazolo[1,5-a]pyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 332 | ((5R,9S)-2-Methyl-3-(3,4,5-trifluorophenyl)-4,5,6,7,8,9-hexahydro-2H-5,9-epiminocycloocta[c]pyrazol-10-yl)(7-methylpyrazolo[1,5-a]pyridin-3-yl)methanone; |
| 333 | (4-Methoxypyrazolo[1,5-a]pyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; |

TABLE 2-continued

| Ex # | Compound Name |
|---|---|
| 334 | (6-Methoxypyrazolo[1,5-a]pyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 335 | Imidazo[1,5-a]pyridin-7-yl((5R,9S)-2-methyl-3-(3,4,5-trifluorophenyl)-4,5,6,7,8,9-hexahydro-2H-5,9-epiminocycloocta[c]pyrazol-10-yl)methanone; |
| 336 | ((5R,9S)-2-Methyl-3-(3,4,5-trifluorophenyl)-4,5,6,7,8,9-hexahydro-2H-5,9-epiminocycloocta[c]pyrazol-10-yl)(5-methylimidazo[1,5-a]pyridin-6-yl)methanone; |
| 337 | ((5R,9S)-2-Methyl-3-(3,4,5-trifluorophenyl)-4,5,6,7,8,9-hexahydro-2H-5,9-epiminocycloocta[c]pyrazol-10-yl)(3-methylimidazo[1,5-a]pyridin-6-yl)methanone; |
| 338 | ((5R,9S)-2-Methyl-3-(3,4,5-trifluorophenyl)-4,5,6,7,8,9-hexahydro-2H-5,9-epiminocycloocta[c]pyrazol-10-yl)(5-methylimidazo[1,2-a]pyridin-6-yl)methanone; |
| 339 | ((5R,9S)-2-Methyl-3-(3,4,5-trifluorophenyl)-4,5,6,7,8,9-hexahydro-2H-5,9-epiminocycloocta[c]pyrazol-10-yl)(7-methylimidazo[1,2-a]pyridin-5-yl)methanone; |
| 340 | ((5R,9S)-2-Methyl-3-(3,4,5-trifluorophenyl)-4,5,6,7,8,9-hexahydro-2H-5,9-epiminocycloocta[c]pyrazol-10-yl)(3-methylimidazo[1,2-a]pyridin-5-yl)methanone; |
| 341 | ((5R,9S)-2-Methyl-3-(3,4,5-trifluorophenyl)-4,5,6,7,8,9-hexahydro-2H-5,9-epiminocycloocta[c]pyrazol-10-yl)(3-methylimidazo[1,2-a]pyridin-6-yl)methanone; |
| 342 | ((5R,9S)-2-Methyl-3-(3,4,5-trifluorophenyl)-4,5,6,7,8,9-hexahydro-2H-5,9-epiminocycloocta[c]pyrazol-10-yl)(2-methylimidazo[1,2-a]pyridin-6-yl)methanone; |
| 343 | ((5R,9S)-2-Methyl-3-(3,4,5-trifluorophenyl)-4,5,6,7,8,9-hexahydro-2H-5,9-epiminocycloocta[c]pyrazol-10-yl)(2-methylimidazo[1,2-a]pyridin-5-yl)methanone; |
| 344 | Imidazo[1,2-a]pyridin-3-yl((5R,9S)-2-methyl-3-(3,4,5-trifluorophenyl)-4,5,6,7,8,9-hexahydro-2H-5,9-epiminocycloocta[c]pyrazol-10-yl)methanone; |
| 345 | (7-Fluoroimidazo[1,2-a]pyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 346 | (7-Chloroimidazo[1,2-a]pyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 347 | ((5R,9S)-2-Methyl-3-(3,4,5-trifluorophenyl)-4,5,6,7,8,9-hexahydro-2H-5,9-epiminocycloocta[c]pyrazol-10-yl)(2-methylimidazo[1,2-a]pyridin-3-yl)methanone; |
| 348 | (2,7-Dimethylimidazo[1,2-a]pyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 349 | ((5R,9S)-3-(3-Fluoro-5-methylphenyl)-2-methyl-4,5,6,7,8,9-hexahydro-2H-5,9-epiminocycloocta[c]pyrazol-10-yl)(2-methylimidazo[1,2-a]pyridin-3-yl)methanone; |
| 350 | ((5R,9S)-2-Methyl-3-(3,4,5-trifluorophenyl)-4,5,6,7,8,9-hexahydro-2H-5,9-epiminocycloocta[c]pyrazol-10-yl)(5-methylimidazo[1,2-a]pyridin-3-yl)methanone; |
| 351 | ((5R,9S)-2-Methyl-3-(3,4,5-trifluorophenyl)-4,5,6,7,8,9-hexahydro-2H-5,9-epiminocycloocta[c]pyrazol-10-yl)(7-(trifluoromethyl)imidazo[1,2-a]pyridin-3-yl)methanone; |
| 352 | (2-(Difluoromethyl)imidazo[1,2-a]pyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 353 | (2-Methyl-2H-indazol-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 354 | (2,7-Dimethylpyrazolo[1,5-a]pyrimidin-5-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 355 | ((5R,9S)-2-Methyl-3-(3,4,5-trifluorophenyl)-4,5,6,7,8,9-hexahydro-2H-5,9-epiminocycloocta[c]pyrazol-10-yl)(7-methylpyrazolo[1,5-a]pyrimidin-6-yl)methanone; |
| 356 | (5-Isopropyl-3-methylpyrazolo[1,5-a]pyrimidin-7-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 357 | ((5R,9S)-2-Methyl-3-(3,4,5-trifluorophenyl)-4,5,6,7,8,9-hexahydro-2H-5,9-epiminocycloocta[c]pyrazol-10-yl)(2,3,5-trimethylpyrazolo[1,5-a]pyrimidin-7-yl)methanone; |
| 358 | (7-Cyclopropyl-2-methylpyrazolo[1,5-a]pyrimidin-5-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 359 | ((5R,9S)-2-Methyl-3-(3,4,5-trifluorophenyl)-4,5,6,7,8,9-hexahydro-2H-5,9-epiminocycloocta[c]pyrazol-10-yl)(2-methylpyrazolo[1,5-a]pyrimidin-3-yl)methanone; |
| 360 | ((5R,9S)-2-Methyl-3-(3,4,5-trifluorophenyl)-4,5,6,7,8,9-hexahydro-2H-5,9-epiminocycloocta[c]pyrazol-10-yl)(2-methylpyrazolo[1,5-b]pyridazin-3-yl)methanone; |

TABLE 2-continued

| Ex # | Compound Name |
| --- | --- |
| 361 | ((5R,9S)-2-Methyl-3-(3,4,5-trifluorophenyl)-4,5,6,7,8,9-hexahydro-2H-5,9-epiminocycloocta[c]pyrazol-10-yl)(2-methylimidazo[1,2-a]pyrazin-8-yl)methanone; |
| 362 | ((5R,9S)-2-Methyl-3-(3,4,5-trifluorophenyl)-4,5,6,7,8,9-hexahydro-2H-5,9-epiminocycloocta[c]pyrazol-10-yl)(2,5,8-trimethylimidazo[1,2-a]pyrazin-3-yl)methanone; |
| 363 | ((5R,9S)-2-Methyl-3-(3,4,5-trifluorophenyl)-4,5,6,7,8,9-hexahydro-2H-5,9-epiminocycloocta[c]pyrazol-10-yl)(2-methylimidazo[1,2-b]pyridazin-3-yl)methanone; |
| 364 | (2,7-Dimethylimidazo[1,2-b]pyridazin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 365 | ((5R,9S)-2-Methyl-3-(3,4,5-trifluorophenyl)-4,5,6,7,8,9-hexahydro-2H-5,9-epiminocycloocta[c]pyrazol-10-yl)(3-methyl-3H-imidazo[4,5-b]pyridin-7-yl)methanone; |
| 366 | ((5R,9S)-2-Methyl-3-(3,4,5-trifluorophenyl)-4,5,6,7,8,9-hexahydro-2H-5,9-epiminocycloocta[c]pyrazol-10-yl)(3-methyl-3H-imidazo[4,5-b]pyridin-6-yl)methanone; |
| 367 | ((5R,9S)-2-Methyl-3-(3,4,5-trifluorophenyl)-4,5,6,7,8,9-hexahydro-2H-5,9-epiminocycloocta[c]pyrazol-10-yl)(7-methyl-7H-pyrrolo[2,3-d]pyrimidin-4-yl)methanone; |
| 368 | (1-Methyl-1H-pyrazolo[3,4-b]pyridin-4-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 369 | (1-Methyl-1H-pyrazolo[3,4-d]pyrimidin-4-yl)((5R,9S)-2-methyl-3-(3,4,5-trifluorophenyl)-4,5,6,7,8,9-hexahydro-2H-5,9-epiminocycloocta[c]pyrazol-10-yl)methanone; |
| 370 | [1,2,4]Triazolo[4,3-a]pyridin-7-yl((5R,9S)-2-methyl-3-(3,4,5-trifluorophenyl)-4,5,6,7,8,9-hexahydro-2H-5,9-epiminocycloocta[c]pyrazol-10-yl)methanone; |
| 371 | ((5R,9S)-2-Methyl-3-(3,4,5-trifluorophenyl)-4,5,6,7,8,9-hexahydro-2H-5,9-epiminocycloocta[c]pyrazol-10-yl)(3-methylimidazo[1,5-a]pyrazin-1-yl)methanone; |
| 372 | ((5R,9S)-3-(3-Fluoro-5-methylphenyl)-2-methyl-4,5,6,7,8,9-hexahydro-2H-5,9-epiminocycloocta[c]pyrazol-10-yl)(quinolin-6-yl)methanone; |
| 373 | ((5R,9S)-2-Methyl-3-(3,4,5-trifluorophenyl)-4,5,6,7,8,9-hexahydro-2H-5,9-epiminocycloocta[c]pyrazol-10-yl)(4-methylquinolin-6-yl)methanone; |
| 374 | ((5R,9S)-3-(3,5-Difluorophenyl)-2-methyl-4,5,6,7,8,9-hexahydro-2H-5,9-epiminocycloocta[c]pyrazol-10-yl)(2-hydroxyquinolin-6-yl)methanone; |
| 375 | 6-((5R,9S)-3-(3,5-Difluorophenyl)-2-methyl-4,5,6,7,8,9-hexahydro-2H-5,9-epiminocycloocta[c]pyrazole-10-carbonyl) quinoline 1-oxide; |
| 376 | ((5R,9S)-3-(3,5-Difluorophenyl)-2-methyl-4,5,6,7,8,9-hexahydro-2H-5,9-epiminocycloocta[c]pyrazol-10-yl)(quinolin-6-yl-4-t)methanone; |
| 377 | ((5R,9S)-2-Methyl-3-(3,4,5-trifluorophenyl)-4,5,6,7,8,9-hexahydro-2H-5,9-epiminocycloocta[c]pyrazol-10-yl)(6-methylquinazolin-4-yl)methanone; |
| 378 | ((5R,9S)-2-Methyl-3-(3,4,5-trifluorophenyl)-4,5,6,7,8,9-hexahydro-2H-5,9-epiminocycloocta[c]pyrazol-10-yl)(quinoxalin-6-yl-2-d)methanone; |
| 379 | ((5R,9S)-2-Methyl-3-(3,4,5-trifluorophenyl)-4,5,6,7,8,9-hexahydro-2H-5,9-epiminocycloocta[c]pyrazol-10-yl)(quinoxalin-6-yl-2,3-d2)methanone; |
| 380 | ((5R,9S)-2-Methyl-3-(3,4,5-trifluorophenyl)-4,5,6,7,8,9-hexahydro-2H-5,9-epiminocycloocta[c]pyrazol-10-yl)(5-methyl-5,6,7,8-tetrahydroimidazo[1,2-a]pyridin-3-yl)methanone; |
| 381 | ((5R,9S)-2-Methyl-3-(3,4,5-trifluorophenyl)-4,5,6,7,8,9-hexahydro-2H-5,9-epiminocycloocta[c]pyrazol-10-yl)(5,6,7,8-tetrahydroimidazo[1,2-a]pyridin-3-yl)methanone; and |
| 382 | ((5R,9S)-2-Methyl-3-(3,4,5-trifluorophenyl)-4,5,6,7,8,9-hexahydro-2H-5,9-epiminocycloocta[c]pyrazol-10-yl)(2,6,6-trimethyl-6,7-dihydro-4H-pyrazolo[5,1-c][1,4]oxazin-3-yl)methanone; | and pharmaceutically acceptable salts, isotopes, N-oxides, solvates, and stereoisomers thereof.

A further embodiment of the current invention is a compound selected from the group consisting of:

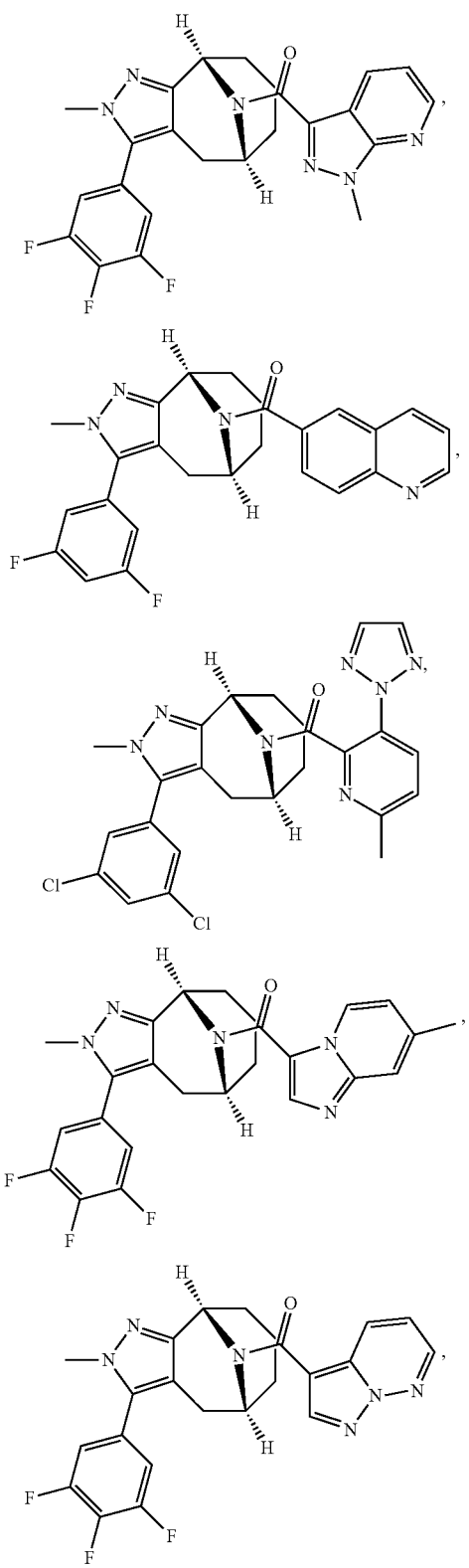 [SMILES: Cn1nc2c(c1-c1cc(F)c(F)c(F)c1)C[C@@H]1CCC[C@H]2N1C(=O)c1nn(C)c2ncccc12 ; Cn1nc2c(c1-c1cc(F)cc(F)c1)C[C@@H]1CCC[C@H]2N1C(=O)c1ccc2ncccc2c1 ; Cc1ccc(-n2nccn2)c(C(=O)N2[C@H]3CCC[C@@H]2c2nn(C)c(-c4cc(Cl)cc(Cl)c4)c2C3)n1 ; Cc1ccn2c(C(=O)N3[C@H]4CCC[C@@H]3c3nn(C)c(-c5cc(F)c(F)c(F)c5)c3C4)cnc2c1 ; Cn1nc2c(c1-c1cc(F)c(F)c(F)c1)C[C@@H]1CCC[C@H]2N1C(=O)c1cnn2ncccc12]

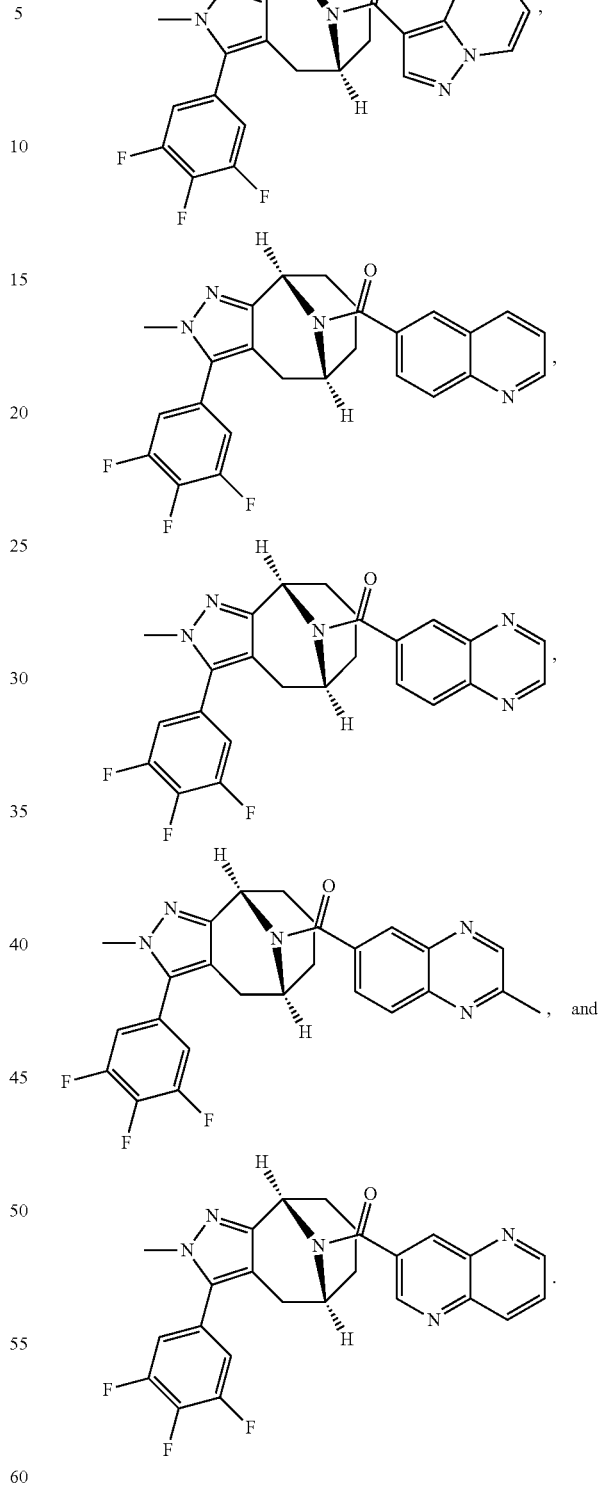

and pharmaceutically acceptable salts, isotopes, N-oxides, solvates, and stereoisomers thereof.

An additional embodiment of the invention is a pharmaceutical composition comprising: (A) a therapeutically effective amount of at least one compound selected from compounds of Formula (I):

wherein

R² is selected from the group consisting of:

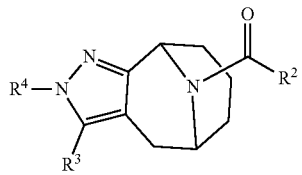

(b) 6-membered heteroaryl selected from the group consisting of: pyridazin-4-yl; pyrazin-2-yl; pyrimidinyl; pyrimidinyl substituted with $C_{1-4}$alkyl or $OC_{1-4}$alkyl; and pyridinyl, wherein the pyridinyl is substituted with one or two substituents each independently selected from the group consisting of: halo, $C_{1-4}$alkyl, $OC_{1-4}$alkyl, $OC_{1-4}$haloalkyl, $C_{3-6}$cycloalkyl, $NH_2$, CN, $N(CH_3)_2$,

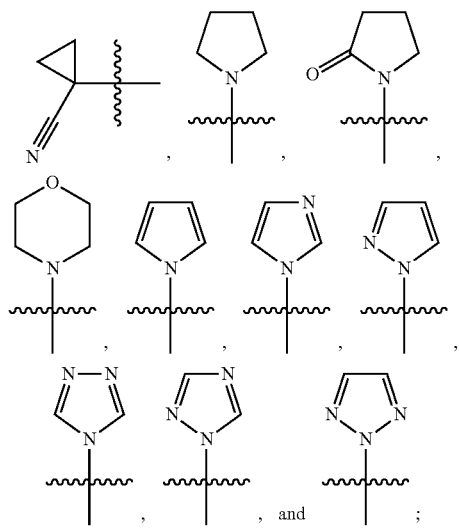

(c) 5-membered heteroaryl selected from the group consisting of:

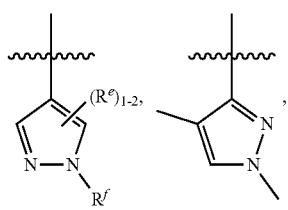

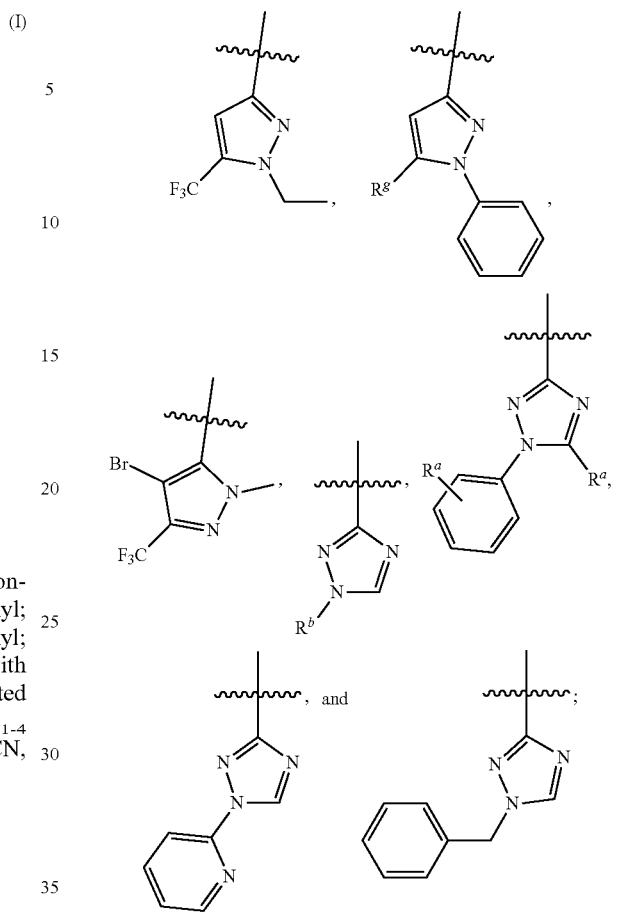

(d) 5,6-fused bicyclic heteroaryl or 6,5-fused bicyclic heteroaryl selected from the group consisting of:

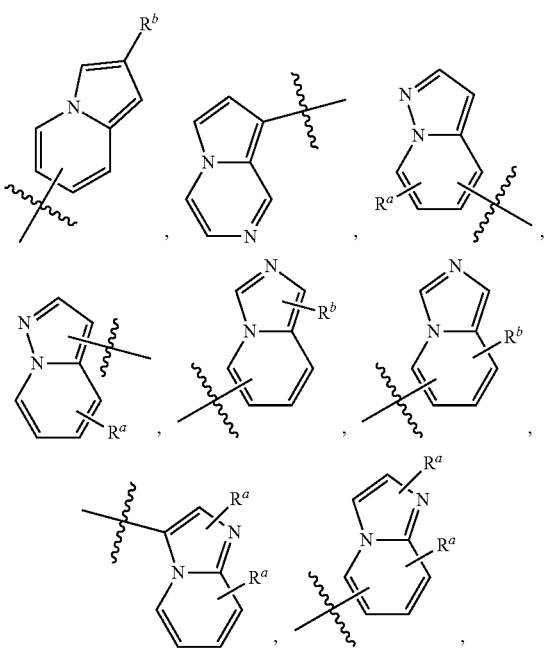

115
-continued
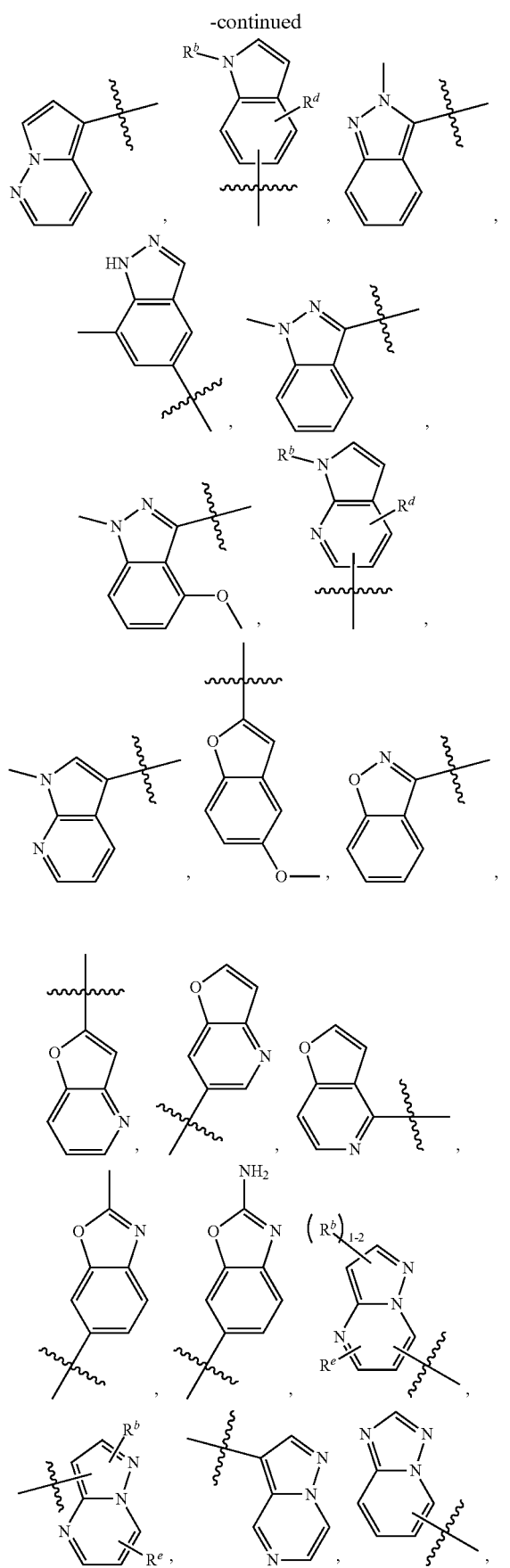
116
-continued
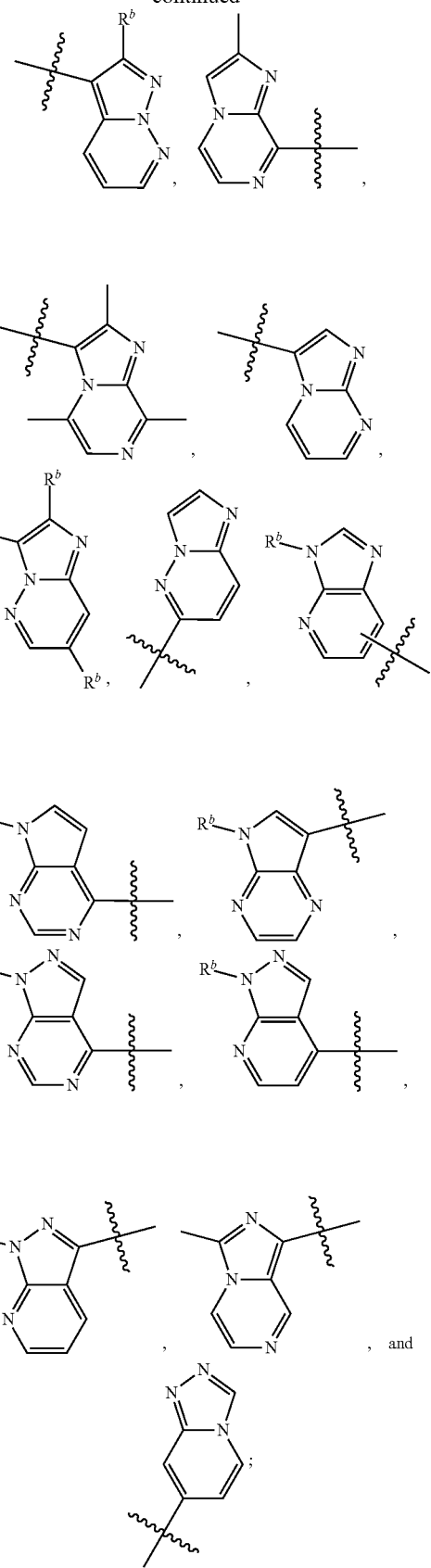

(e) 6,6-fused bicyclic heteroaryl selected from the group consisting of:

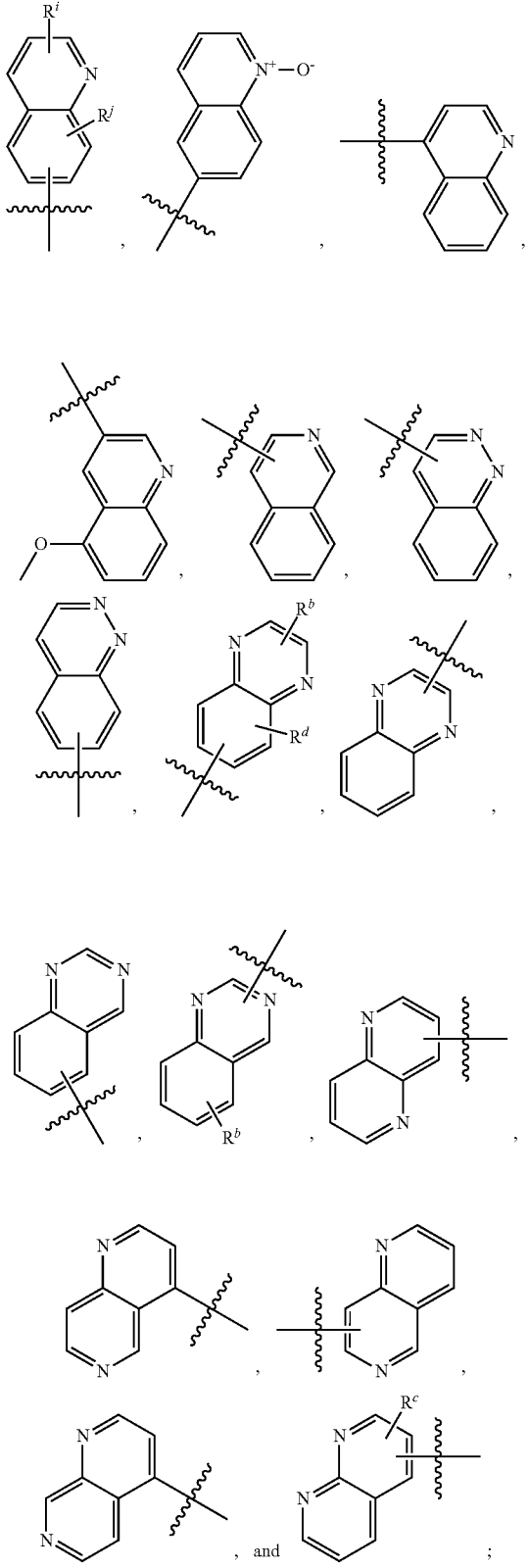

and (f)

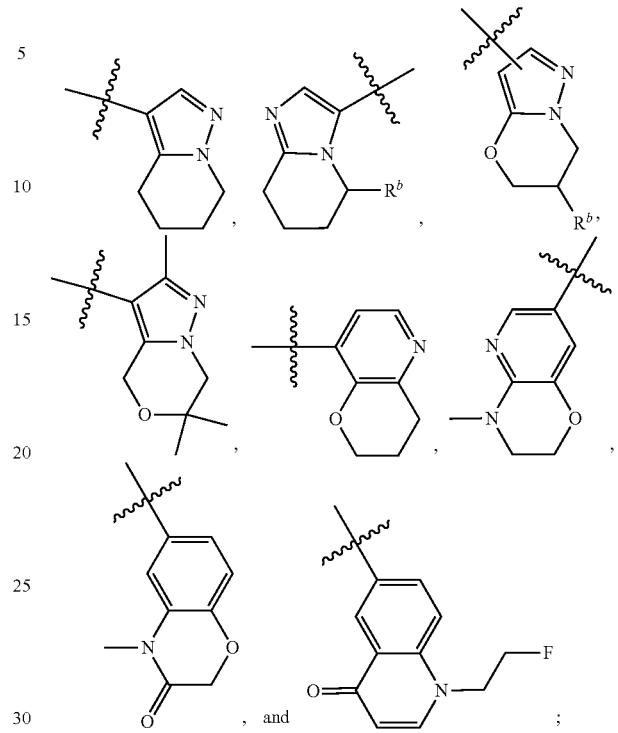

$R^a$ is selected from the group consisting of: H, halo, $C_{1-4}$alkyl, $OC_{1-4}$alkyl, $C_{1-4}$haloalkyl and $OC_{1-4}$haloalkyl;

$R^{a1}$ is selected from the group consisting of: $C_{1-4}$alkyl; $OC_{1-4}$alkyl; $OC_{1-4}$haloalkyl; $N(C=O)CH_3$; oxazol-2-yl; pyrimidin-2-yl; and 5-membered heteroaryl ring containing two, three, or four nitrogen members, wherein the 5-membered heteroaryl ring is optionally substituted with one $R^a$ member;

$R^b$ is H or $C_{1-4}$akyl;

$R^c$ is H or $C_{1-4}$haloalkyl;

$R^d$ is H or halo;

$R^e$ is selected from the group consisting of: H, halo, $C_{1-4}$akyl, $C_{1-4}$haloalkyl, $OC_{1-4}$alkyl, and $C_{3-6}$cycloalkyl;

$R^f$ is selected from the group consisting of: H, $C_{1-4}$alkyl, $CH_2CH_2OH$, $C_{1-4}$haloalkyl, cyclopropyl, phenyl, and phenyl substituted with $CF_3$;

$R^g$ is selected from the group consisting of: H, $OC_{1-4}$alkyl and $C_{1-4}$haloalkyl;

$R^i$ is selected from the group consisting of: H, halo, $C_{1-4}$alkyl, $C_{1-4}$haloalkyl, OH, $OC_{1-4}$alkyl, $OC_{1-4}$haloalkyl, and $C_{3-6}$cycloalkyl;

$R^j$ is selected from the group consisting of: H, halo, $OCH_3$, OH, $NH_2$, and $NO_2$;

$R^3$ is selected from the group consisting of:

(g) phenyl, wherein phenyl is independently substituted with one, two, or three members selected from the group consisting of: halo, $C_{1-4}$alkyl, $C_{1-4}$haloalkyl, and $OC_{1-4}$alkyl;

(h) 5-(trifluoromethyl)-2-thienyl or 1-methylindol-2-yl; and (i) cyclopropyl; and $R^4$ is $C_{1-4}$alkyl or $C_{3-4}$cycloalkyl;

and pharmaceutically acceptable salts, isotopes, N-oxides, solvates, and stereoisomers of compounds of Formula (I);

and (B) at least one pharmaceutically acceptable excipient.

An additional embodiment of the invention is a pharmaceutical composition comprising a therapeutically effective amount of at least one compound of Formula (IA), as well as pharmaceutically acceptable salts, N-oxides or solvates of compounds of Formula (IA), pharmaceutically acceptable prodrugs of compounds of Formula (IA), and pharmaceutically active metabolites of Formula (IA); and at least one pharmaceutically acceptable excipient.

An additional embodiment of the invention is a pharmaceutical composition comprising a therapeutically effective amount of at least one compound of Formula (IB), as well as pharmaceutically acceptable salts, N-oxides or solvates of compounds of Formula (IB), pharmaceutically acceptable prodrugs of compounds of Formula (IB), and pharmaceutically active metabolites of Formula (IB); and at least one pharmaceutically acceptable excipient.

An additional embodiment of the invention is a pharmaceutical composition comprising a therapeutically effective amount of at least one compound of Formula (IC), as well as pharmaceutically acceptable salts, N-oxides or solvates of compounds of Formula (IC), pharmaceutically acceptable prodrugs of compounds of Formula (IC), and pharmaceutically active metabolites of Formula (IB); and at least one pharmaceutically acceptable excipient.

An additional embodiment of the invention is a pharmaceutical composition comprising a therapeutically effective amount of at least one compound of Formula (ID), as well as pharmaceutically acceptable salts, N-oxides or solvates of compounds of Formula (ID), pharmaceutically acceptable prodrugs of compounds of Formula (ID), and pharmaceutically active metabolites of Formula (ID); and at least one pharmaceutically acceptable excipient.

An additional embodiment of the invention is a pharmaceutical composition comprising a therapeutically effective amount of at least one compound in Table 1 (as well as Table 2), as well as pharmaceutically acceptable salts, N-oxides or solvates of compounds of Table 1 (as well as Table 2), pharmaceutically acceptable prodrugs of compounds of Table 1, and pharmaceutically active metabolites of Table 1 (as well as Table 2); and at least one pharmaceutically acceptable excipient.

Also within the scope of the invention are enantiomers and diastereomers of the compounds of Formula (I) (as well as Formulas (IA), (IB), (IC) and (ID)). Also within the scope of the invention are the pharmaceutically acceptable salts, N-oxides or solvates of the compounds of Formula (I) (as well as Formulas (IA), (IB), (IC) and (ID)). Also within the scope of the invention are the pharmaceutically acceptable prodrugs of compounds of Formula (I) (as well as Formulas (IA), (IB), (IC) and (ID)), and pharmaceutically active metabolites of the compounds of Formula (I) (as well as Formulas (IA), (IB), (IC) and (ID)).

Also within the scope of the invention are isotopic variations of compounds of Formula (I) (as well as Formulas (IA), (IB), (IC) and (ID)), such as, e.g., deuterated compounds of Formula (I). Also within the scope of the invention are the pharmaceutically acceptable salts, N-oxides or solvates of the isotopic variations of the compounds of Formula (I) (as well as Formulas (IA), (IB), (IC) and (ID)). Also within the scope of the invention are the pharmaceutically acceptable prodrugs of the isotopic variations of the compounds of Formula (I) (as well as Formulas (IA), (IB), (IC) and (ID)), and pharmaceutically active metabolites of the isotopic variations of the compounds of Formula (I) (as well as Formulas (IA), (IB), (IC) and (ID)).

An additional embodiment of the invention is a method of treating a subject suffering from or diagnosed with a disease, disorder, or condition mediated by MGL receptor activity, comprising administering to a subject in need of such treatment a therapeutically effective amount of at least one compound selected from compounds of Formula (I):

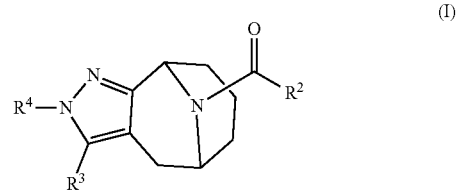

wherein $R^2$ is selected from the group consisting of:

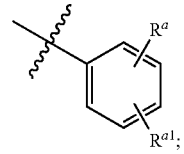

(b) 6-membered heteroaryl selected from the group consisting of: pyridazin-4-yl; pyrazin-2-yl; pyrimidinyl; pyrimidinyl substituted with $C_{1-4}$alkyl or $OC_{1-4}$alkyl; and pyridinyl, wherein the pyridinyl is substituted with one or two substituents each independently selected from the group consisting of: halo, $C_{1-4}$alkyl, $OC_{1-4}$alkyl, $OC_{1-4}$haloalkyl, $C_{3-6}$cycloalkyl, $NH_2$, CN, $N(CH_3)_2$,

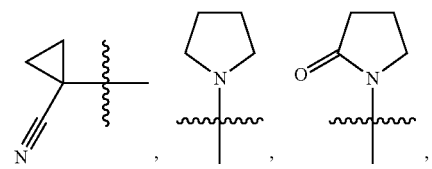

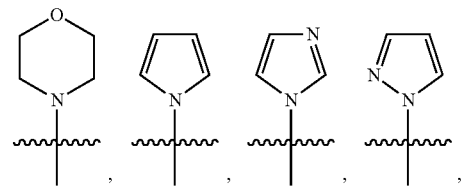

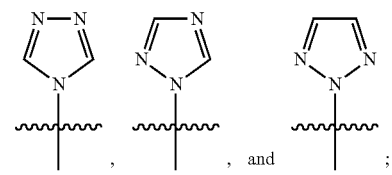

(c) 5-membered heteroaryl selected from the group consisting of:
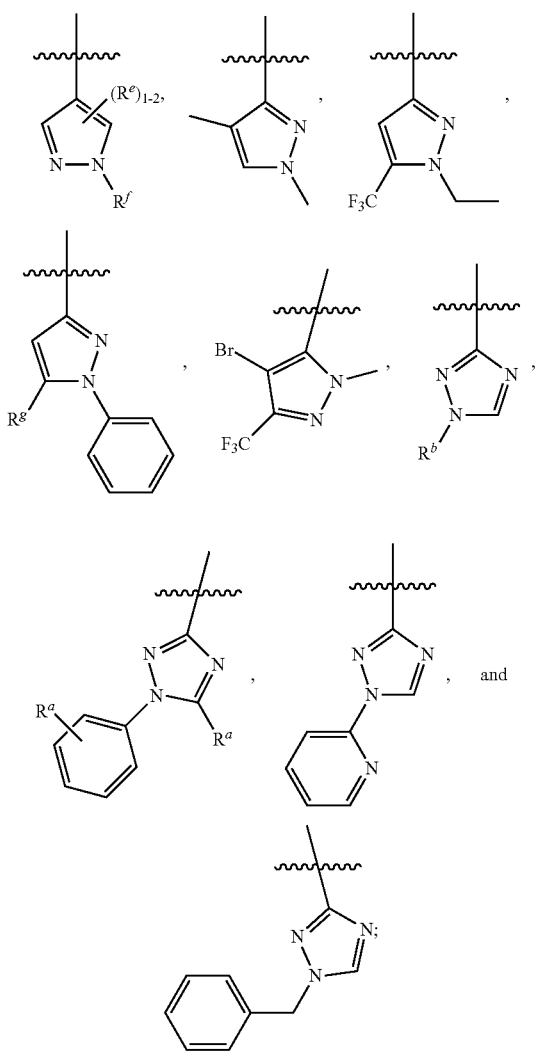
and
(d) 5,6-fused bicyclic heteroaryl or 6,5-fused bicyclic heteroaryl selected from the group consisting of:
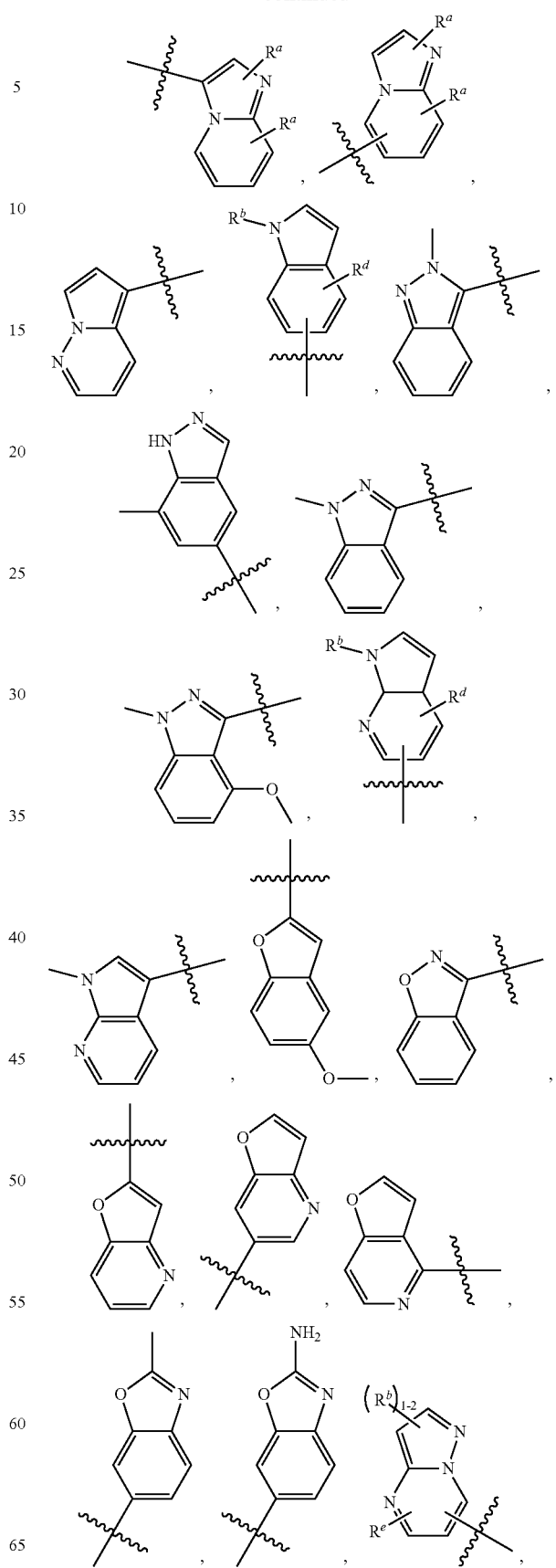

-continued
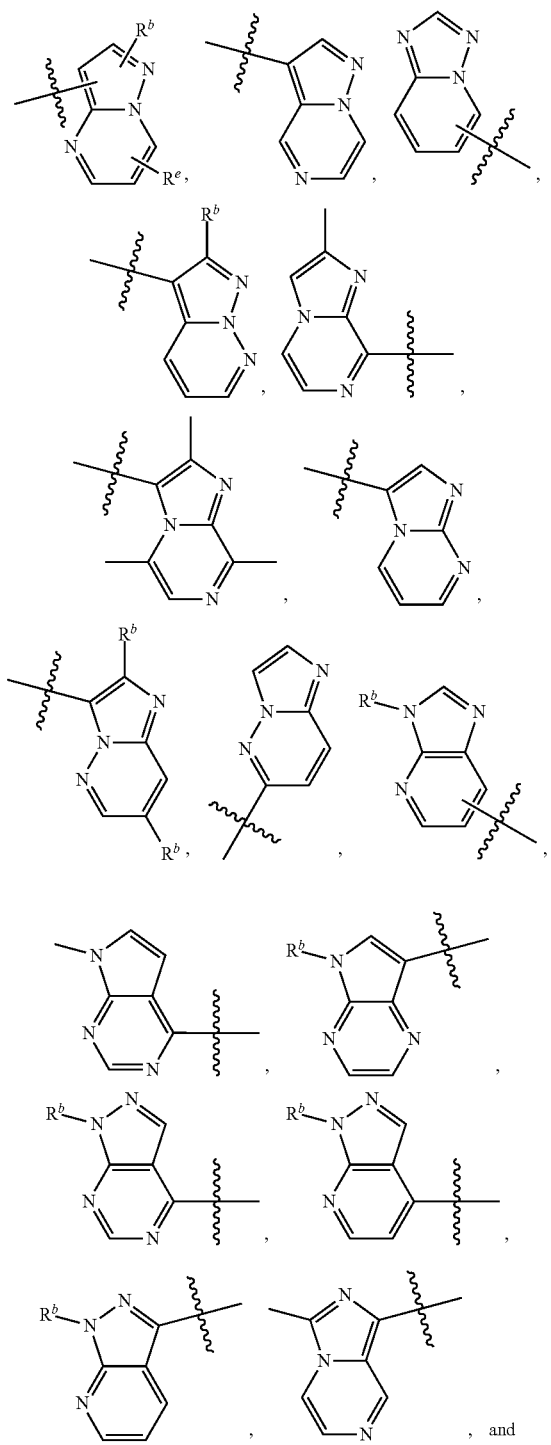
(e) 6,6-fused bicyclic heteroaryl selected from the group consisting of:
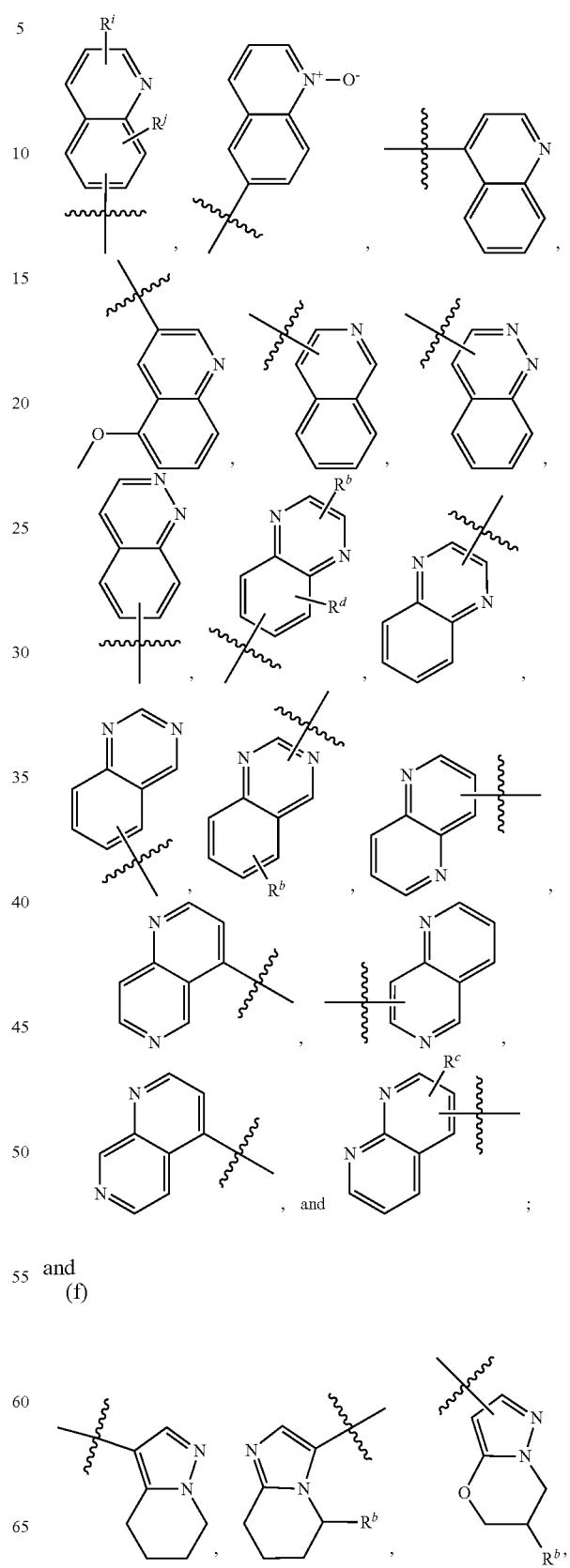
and
(f)

-continued

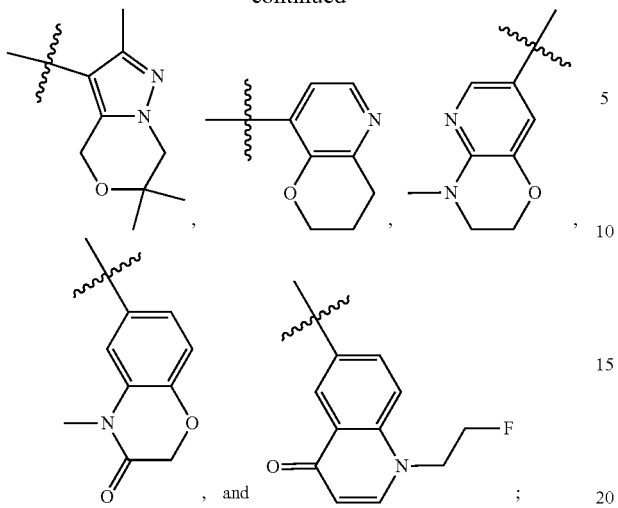

$R^a$ is selected from the group consisting of: H, halo, $C_{1-4}$alkyl, $OC_{1-4}$alkyl, $C_{1-4}$haloalkyl and $OC_{1-4}$haloalkyl;

$R^{a1}$ is selected from the group consisting of: $C_{1-4}$alkyl; $OC_{1-4}$alkyl; $OC_{1-4}$haloalkyl; $N(C=O)CH_3$; oxazol-2-yl; pyrimidin-2-yl; and 5-membered heteroaryl ring containing two, three, or four nitrogen members, wherein the 5-membered heteroaryl ring is optionally substituted with one $R^a$ member;

$R^b$ is H or $C_{1-4}$akyl;

$R^c$ is H or $C_{1-4}$haloalkyl;

$R^d$ is H or halo;

$R^e$ is selected from the group consisting of: H, halo, $C_{1-4}$akyl, $C_{1-4}$haloalkyl, $OC_{1-4}$alkyl, and $C_{3-6}$cycloalkyl;

$R^f$ is selected from the group consisting of: H, $C_{1-4}$alkyl, $CH_2CH_2OH$, $C_{1-4}$haloalkyl, cyclopropyl, phenyl, and phenyl substituted with $CF_3$;

$R^g$ is selected from the group consisting of: H, $OC_{1-4}$alkyl and $C_{1-4}$haloalkyl;

$R^i$ is selected from the group consisting of: H, halo, $C_{1-4}$alkyl, $C_{1-4}$haloalkyl, OH, $OC_{1-4}$alkyl, $OC_{1-4}$haloalkyl, and $C_{3-6}$cycloalkyl;

$R^j$ is selected from the group consisting of: H, halo, $OCH_3$, OH, $NH_2$, and $NO_2$;

$R^3$ is selected from the group consisting of:

(g) phenyl, wherein phenyl is independently substituted with one, two, or three members selected from the group consisting of: halo, $C_{1-4}$alkyl, $C_{1-4}$haloalkyl, and $OC_{1-4}$alkyl;

(h) 5-(trifluoromethyl)-2-thienyl or 1-methylindol-2-yl; and (i) cyclopropyl; and $R^4$ is $C_{1-4}$alkyl or $C_{3-4}$cycloalkyl;

and pharmaceutically acceptable salts, isotopes, N-oxides, solvates, and stereoisomers thereof, to a subject in need thereof.

An additional embodiment of the invention is a method of treating a subject suffering from or diagnosed with a disease, disorder, or condition mediated by MGL receptor activity, comprising administering to a subject in need of such treatment a therapeutically effective amount of at least one compound selected from compounds of Formula (I) (as well as Formulas (IA), (IB), (IC) and (ID)), enantiomers and diastereomers of the compounds of Formula (I), isotopic variations of the compounds of Formula (I), and pharmaceutically acceptable salts of all of the foregoing.

Embodiments of this invention are compounds of Formula (II),

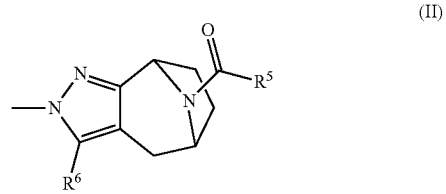

(II)

wherein $R^5$ is selected from the group consisting of:

(a) phenyl optionally independently substituted with one or two members selected from the group consisting of: halo, $OC_{1-4}$alkyl, and

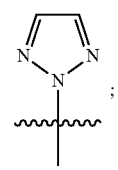

;

(b) 6-membered heteroaryl selected from the group consisting of:

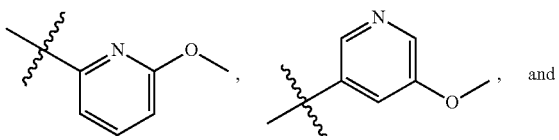

and

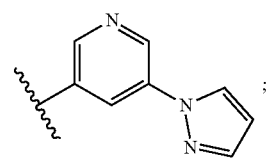

;

(c) 5-membered heteroaryl selected from the group consisting of:

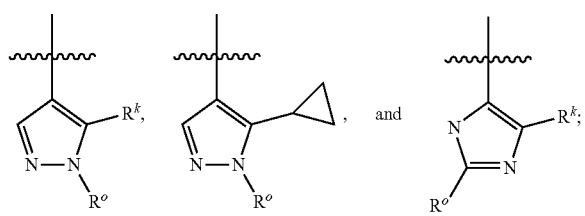

(d) 5,6-fused bicyclic heteroaryl or 6,5-fused bicyclic heteroaryl selected from the group consisting of:

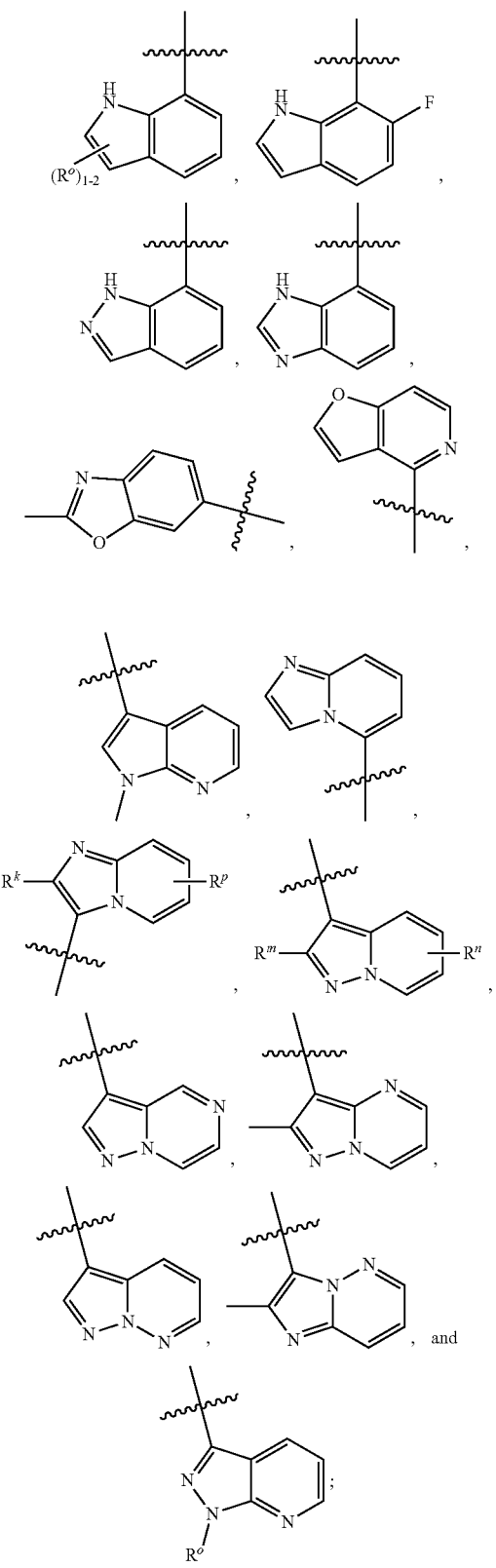

(e) 6,6-fused bicyclic heteroaryl selected from the group consisting of:

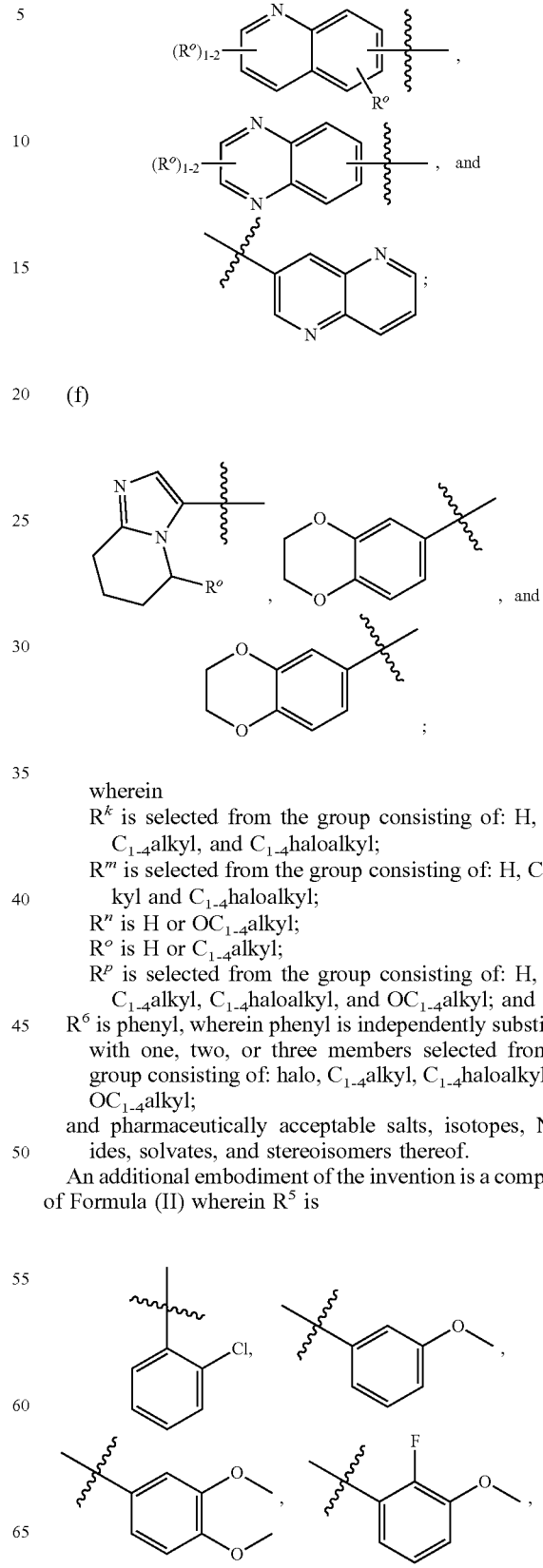

(f)

wherein
$R^k$ is selected from the group consisting of: H, halo, $C_{1-4}$alkyl, and $C_{1-4}$haloalkyl;
$R^m$ is selected from the group consisting of: H, $C_{1-4}$alkyl and $C_{1-4}$haloalkyl;
$R^n$ is H or $OC_{1-4}$alkyl;
$R^o$ is H or $C_{1-4}$alkyl;
$R^p$ is selected from the group consisting of: H, halo, $C_{1-4}$alkyl, $C_{1-4}$haloalkyl, and $OC_{1-4}$alkyl; and
$R^6$ is phenyl, wherein phenyl is independently substituted with one, two, or three members selected from the group consisting of: halo, $C_{1-4}$alkyl, $C_{1-4}$haloalkyl, and $OC_{1-4}$alkyl;
and pharmaceutically acceptable salts, isotopes, N-oxides, solvates, and stereoisomers thereof.

An additional embodiment of the invention is a compound of Formula (II) wherein $R^5$ is

129

-continued

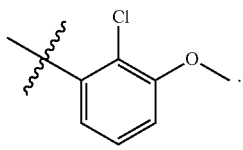

An additional embodiment of the invention is a compound of Formula (II) wherein $R^5$ is

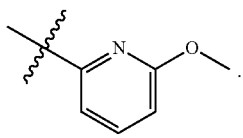 [SMILES: *c1cccc(OC)n1]

An additional embodiment of the invention is a compound of Formula (II) wherein $R^5$ is

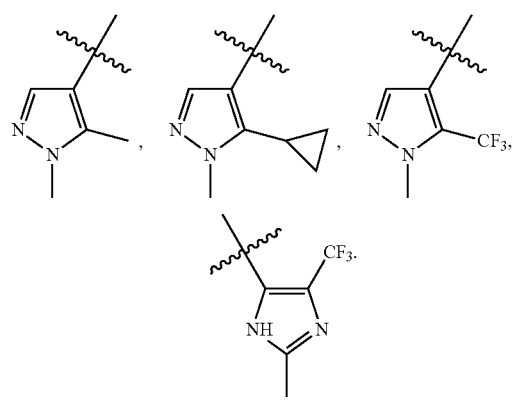

An additional embodiment of the invention is a compound of Formula (II) wherein $R^5$ is

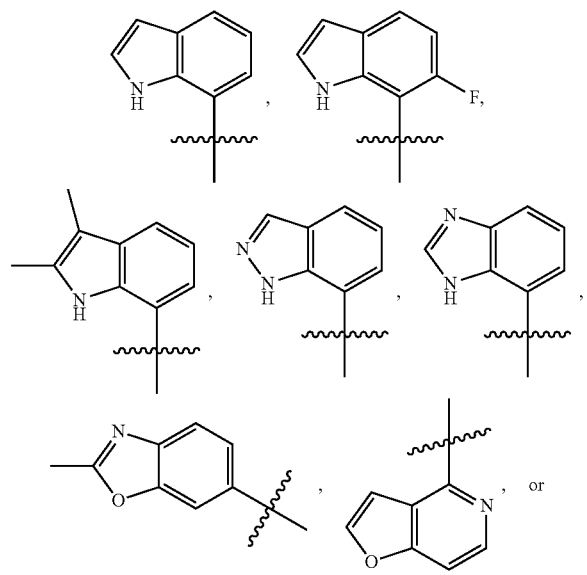

130

-continued

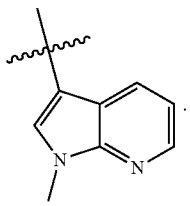

An additional embodiment of the invention is a compound of Formula (II) wherein $R^5$ is

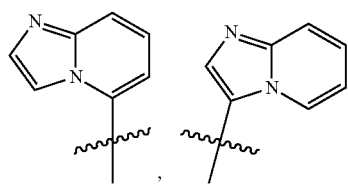

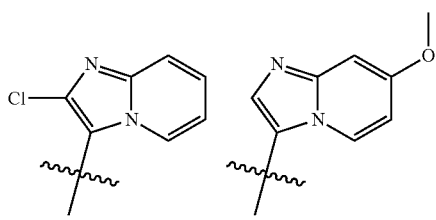

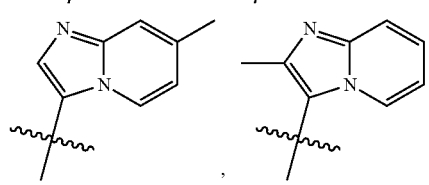

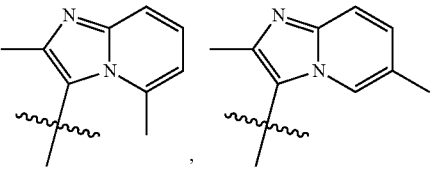

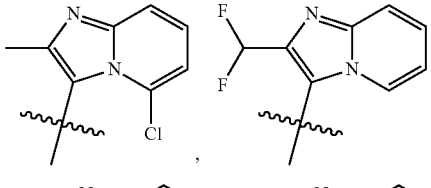

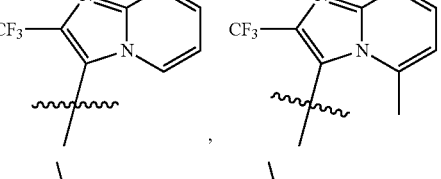

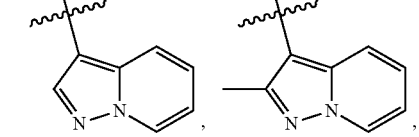

-continued

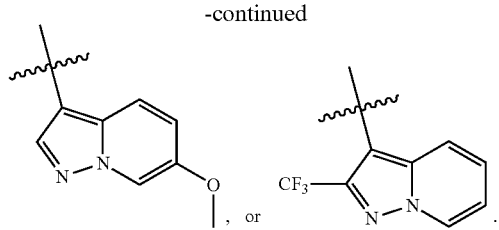, or

An additional embodiment of the invention is a compound of Formula (II) wherein R⁵ is

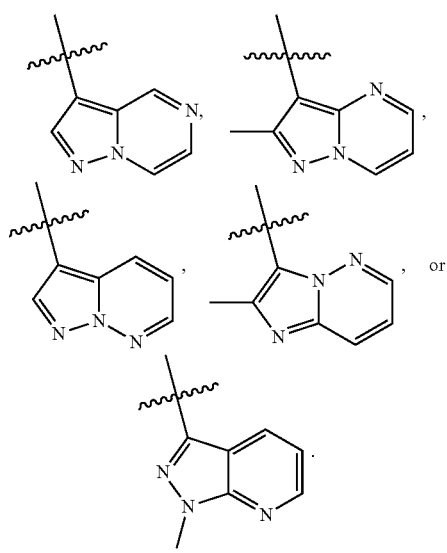, or

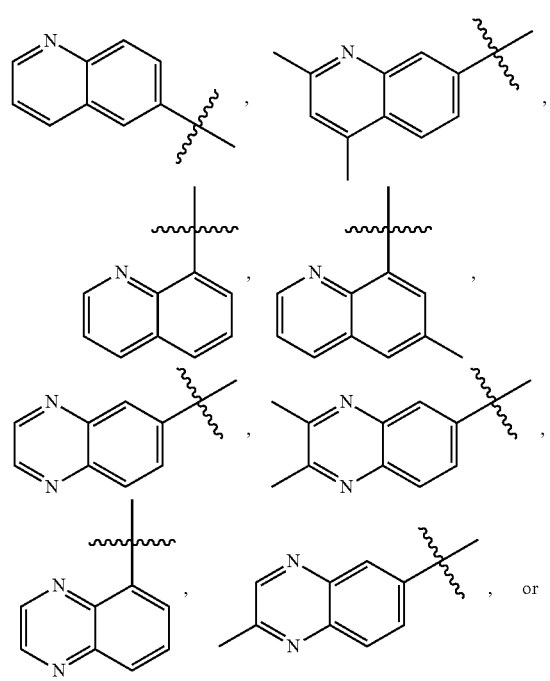

An additional embodiment of the invention is a compound of Formula (II) wherein R⁵ is

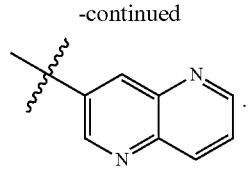

An additional embodiment of the invention is a compound of Formula (II) wherein R⁵ is

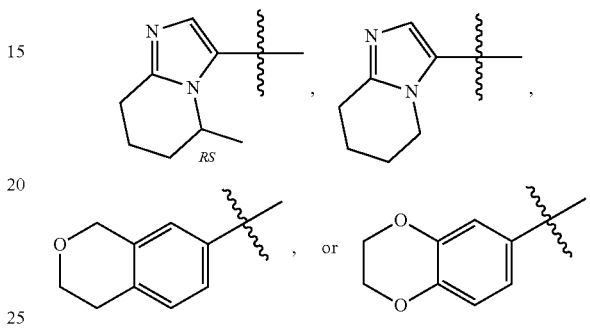, or

An additional embodiment of the invention is a compound of Formula (11) wherein R⁶ is

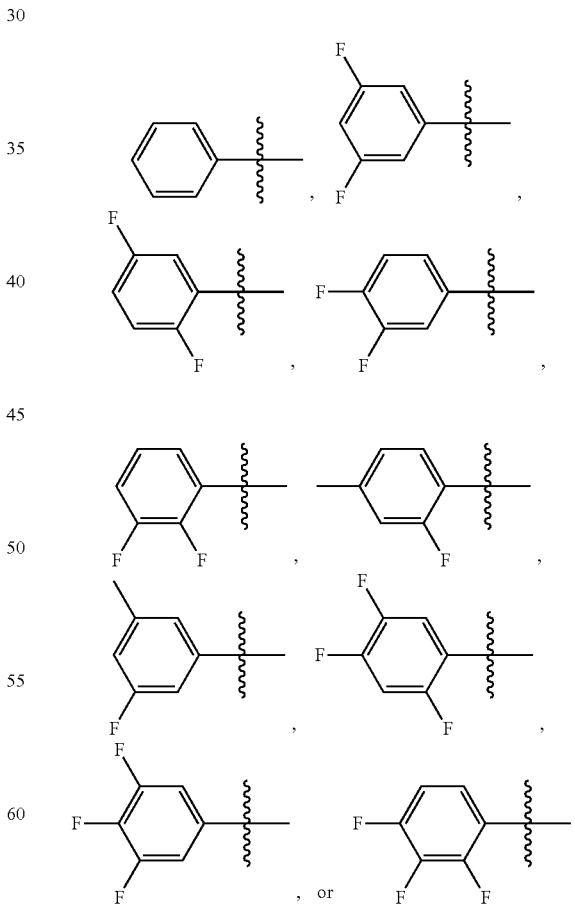, or

A further embodiment of the current invention is a compound as shown below in Table 3.

TABLE 3

| Ex # | Compound Name |
|---|---|
| 26 | racemic-((5R,8S)-2-Methyl-3-phenyl-2,4,5,6,7,8-hexahydro-5,8-epiminocyclohepta[c]pyrazol-9-yl)(quinolin-6-yl)methanone; |
| 383 | (3-Chlorophenyl)((5R,8S)-2-methyl-3-(3,4,5-trifluorophenyl)-2,4,5,6,7,8-hexahydro-5,8-epiminocyclohepta[c]pyrazol-9-yl)methanone; |
| 384 | (3-Methoxyphenyl)((5R,8S)-2-methyl-3-(3,4,5-trifluorophenyl)-2,4,5,6,7,8-hexahydro-5,8-epiminocyclohepta[c]pyrazol-9-yl)methanone; |
| 385 | ((5R,8S)-3-(2,5-Difluorophenyl)-2-methyl-2,4,5,6,7,8-hexahydro-5,8-epiminocyclohepta[c]pyrazol-9-yl)(3-methoxyphenyl)methanone; |
| 386 | (3-Methoxyphenyl)((5R,8S)-2-methyl-3-(2,4,5-trifluorophenyl)-2,4,5,6,7,8-hexahydro-5,8-epiminocyclohepta[c]pyrazol-9-yl)methanone; |
| 387 | ((5R,8S)-3-(2,3-Difluorophenyl)-2-methyl-2,4,5,6,7,8-hexahydro-5,8-epiminocyclohepta[c]pyrazol-9-yl)(3-methoxyphenyl)methanone; |
| 388 | (2,3-Dimethoxyphenyl)((5R,8S)-2-methyl-3-(3,4,5-trifluorophenyl)-2,4,5,6,7,8-hexahydro-5,8-epiminocyclohepta[c]pyrazol-9-yl)methanone; |
| 389 | (2-Fluoro-3-methoxyphenyl)((5R,8S)-2-methyl-3-(3,4,5-trifluorophenyl)-2,4,5,6,7,8-hexahydro-5,8-epiminocyclohepta[c]pyrazol-9-yl)methanone; |
| 390 | (2-Chloro-3-methoxyphenyl)((5R,8S)-2-methyl-3-(3,4,5-trifluorophenyl)-2,4,5,6,7,8-hexahydro-5,8-epiminocyclohepta[c]pyrazol-9-yl)methanone; |
| 391 | (6-Methoxypyridin-2-yl)((5R,8S)-2-methyl-3-(3,4,5-trifluorophenyl)-2,4,5,6,7,8-hexahydro-5,8-epiminocyclohepta[c]pyrazol-9-yl)methanone; |
| 392 | (1,5-Dimethyl-1H-pyrazol-4-yl)((5R,8S)-2-methyl-3-(3,4,5-trifluorophenyl)-2,4,5,6,7,8-hexahydro-5,8-epiminocyclohepta[c]pyrazol-9-yl)methanone; |
| 393 | (5-Cyclopropyl-1-methyl-1H-pyrazol-4-yl)((5R,8S)-3-(3-fluoro-5-methylphenyl)-2-methyl-2,4,5,6,7,8-hexahydro-5,8-epiminocyclohepta[c]pyrazol-9-yl)methanone; |
| 394 | (5-Cyclopropyl-1-methyl-1H-pyrazol-4-yl)((5R,8S)-2-methyl-3-phenyl-2,4,5,6,7,8-hexahydro-5,8-epiminocyclohepta[c]pyrazol-9-yl)methanone; |
| 395 | (5-Cyclopropyl-1-methyl-1H-pyrazol-4-yl)((5R,8S)-3-(3,4-difluorophenyl)-2-methyl-2,4,5,6,7,8-hexahydro-5,8-epiminocyclohepta[c]pyrazol-9-yl)methanone; |
| 396 | (5-Cyclopropyl-1-methyl-1H-pyrazol-4-yl)((5R,8S)-3-(2,4-difluorophenyl)-2-methyl-2,4,5,6,7,8-hexahydro-5,8-epiminocyclohepta[c]pyrazol-9-yl)methanone; |
| 397 | (5-Cyclopropyl-1-methyl-1H-pyrazol-4-yl)((5R,8S)-3-(3,5-difluorophenyl)-2-methyl-2,4,5,6,7,8-hexahydro-5,8-epiminocyclohepta[c]pyrazol-9-yl)methanone; |
| 398 | (5-Cyclopropyl-1-methyl-1H-pyrazol-4-yl)((5R,8S)-2-methyl-3-(2,3,4-trifluorophenyl)-2,4,5,6,7,8-hexahydro-5,8-epiminocyclohepta[c]pyrazol-9-yl)methanone; |
| 399 | (5-Cyclopropyl-1-methyl-1H-pyrazol-4-yl)((5R,8S)-2-methyl-3-(3,4,5-trifluorophenyl)-2,4,5,6,7,8-hexahydro-5,8-epiminocyclohepta[c]pyrazol-9-yl)methanone; |
| 400 | ((5R,8S)-2-Methyl-3-(3,4,5-trifluorophenyl)-2,4,5,6,7,8-hexahydro-5,8-epiminocyclohepta[c]pyrazol-9-yl)(2-methyl-4-(trifluoromethyl)-1H-imidazol-5-yl)methanone; |
| 401 | (1H-Indol-7-yl)((5R,8S)-2-methyl-3-(3,4,5-trifluorophenyl)-2,4,5,6,7,8-hexahydro-5,8-epiminocyclohepta[c]pyrazol-9-yl)methanone; |
| 402 | (6-Fluoro-1H-indol-7-yl)((5R,8S)-2-methyl-3-(3,4,5-trifluorophenyl)-2,4,5,6,7,8-hexahydro-5,8-epiminocyclohepta[c]pyrazol-9-yl)methanone; |
| 403 | (2,3-Dimethyl-1H-indol-7-yl)((5R,8S)-2-methyl-3-(3,4,5-trifluorophenyl)-2,4,5,6,7,8-hexahydro-5,8-epiminocyclohepta[c]pyrazol-9-yl)methanone; |
| 404 | (1H-Indazol-7-yl)((5R,8S)-2-methyl-3-(3,4,5-trifluorophenyl)-2,4,5,6,7,8-hexahydro-5,8-epiminocyclohepta[c]pyrazol-9-yl)methanone; |
| 405 | (1H-Benzo[d]imidazol-7-yl)((5R,8S)-2-methyl-3-(3,4,5-trifluorophenyl)-2,4,5,6,7,8-hexahydro-5,8-epiminocyclohepta[c]pyrazol-9-yl)methanone; |
| 406 | ((5R,8S)-2-Methyl-3-(3,4,5-trifluorophenyl)-2,4,5,6,7,8-hexahydro-5,8-epiminocyclohepta[c]pyrazol-9-yl)(2-methylbenzo[d]oxazol-6-yl)methanone; |
| 407 | Furo[3,2-c]pyridin-4-yl((5R,8S)-2-methyl-3-(3,4,5-trifluorophenyl)-2,4,5,6,7,8-hexahydro-5,8-epiminocyclohepta[c]pyrazol-9-yl)methanone; |
| 408 | (1-Methyl-1H-pyrrolo[2,3-b]pyridin-3-yl)((5R,8S)-2-methyl-3-phenyl-2,4,5,6,7,8-hexahydro-5,8-epiminocyclohepta[c]pyrazol-9-yl)methanone; |
| 409 | (1-Methyl-1H-pyrrolo[2,3-b]pyridin-3-yl)((5R,8S)-2-methyl-3-(3,4,5-trifluorophenyl)-2,4,5,6,7,8-hexahydro-5,8-epiminocyclohepta[c]pyrazol-9-yl)methanone; |
| 410 | Imidazo[1,2-a]pyridin-5-yl((5R,8S)-2-methyl-3-(3,4,5-trifluorophenyl)-2,4,5,6,7,8-hexahydro-5,8-epiminocyclohepta[c]pyrazol-9-yl)methanone; |
| 411 | Imidazo[1,2-a]pyridin-3-yl((5R,8S)-2-methyl-3-(3,4,5-trifluorophenyl)-2,4,5,6,7,8-hexahydro-5,8-epiminocyclohepta[c]pyrazol-9-yl)methanone; |
| 412 | (2-Chloroimidazo[1,2-a]pyridin-3-yl)((5R,8S)-2-methyl-3-(3,4,5-trifluorophenyl)-2,4,5,6,7,8-hexahydro-5,8-epiminocyclohepta[c]pyrazol-9-yl)methanone; |
| 413 | (7-Methoxyimidazo[1,2-a]pyridin-3-yl)((5R,8S)-2-methyl-3-(3,4,5-trifluorophenyl)-2,4,5,6,7,8-hexahydro-5,8-epiminocyclohepta[c]pyrazol-9-yl)methanone; |
| 414 | ((5R,8S)-2-Methyl-3-(3,4,5-trifluorophenyl)-2,4,5,6,7,8-hexahydro-5,8-epiminocyclohepta[c]pyrazol-9-yl)(2-methylimidazo[1,2-a]pyridin-3-yl)methanone; |
| 415 | (2,5-Dimethylimidazo[1,2-a]pyridin-3-yl)((5R,8S)-2-methyl-3-(3,4,5-trifluorophenyl)-2,4,5,6,7,8-hexahydro-5,8-epiminocyclohepta[c]pyrazol-9-yl)methanone; |
| 416 | (2,6-Dimethylimidazo[1,2-a]pyridin-3-yl)((5R,8S)-2-methyl-3-(3,4,5-trifluorophenyl)-2,4,5,6,7,8-hexahydro-5,8-epiminocyclohepta[c]pyrazol-9-yl)methanone; |
| 417 | ((5R,8S)-2-Methyl-3-(3,4,5-trifluorophenyl)-2,4,5,6,7,8-hexahydro-5,8-epiminocyclohepta[c]pyrazol-9-yl)(2-methylimidazo[1,2-a]pyridin-3-yl)methanone |

TABLE 3-continued

| Ex # | Compound Name |
|---|---|
| 418 | (5-Chloro-2-methylimidazo[1,2-a]pyridin-3-yl)((5R,8S)-2-methyl-3-(3,4,5-trifluorophenyl)-2,4,5,6,7,8-hexahydro-5,8-epiminocyclohepta[c]pyrazol-9-yl)methanone; |
| 419 | (2-(Difluoromethyl)imidazo[1,2-a]pyridin-3-yl)((5R,8S)-2-methyl-3-(3,4,5-trifluorophenyl)-2,4,5,6,7,8-hexahydro-5,8-epiminocyclohepta[c]pyrazol-9-yl)methanone; |
| 420 | ((5R,8S)-2-Methyl-3-(3,4,5-trifluorophenyl)-2,4,5,6,7,8-hexahydro-5,8-epiminocyclohepta[c]pyrazol-9-yl)(2-(trifluoromethyl)imidazo[1,2-a]pyridin-3-yl)methanone; |
| 421 | (5-Methyl-2-(trifluoromethyl)imidazo[1,2-a]pyridin-3-yl)((5R,8S)-2-methyl-3-(3,4,5-trifluorophenyl)-2,4,5,6,7,8-hexahydro-5,8-epiminocyclohepta[c]pyrazol-9-yl)methanone; |
| 422 | ((5R,8S)-2-Methyl-3-(3,4,5-trifluorophenyl)-2,4,5,6,7,8-hexahydro-5,8-epiminocyclohepta[c]pyrazol-9-yl)(pyrazolo[1,5-a]pyridin-3-yl)methanone; |
| 423 | ((5R,8S)-2-Methyl-3-(3,4,5-trifluorophenyl)-2,4,5,6,7,8-hexahydro-5,8-epiminocyclohepta[c]pyrazol-9-yl)(2-methylpyrazolo[1,5-a]pyridin-3-yl)methanone |
| 424 | (6-Methoxypyrazolo[1,5-a]pyridin-3-yl)((5R,8S)-2-methyl-3-(3,4,5-trifluorophenyl)-2,4,5,6,7,8-hexahydro-5,8-epiminocyclohepta[c]pyrazol-9-yl)methanone; |
| 425 | ((5R,8S)-2-Methyl-3-(3,4,5-trifluorophenyl)-2,4,5,6,7,8-hexahydro-5,8-epiminocyclohepta[c]pyrazol-9-yl)(2-(trifluoromethyl)pyrazolo[1,5-a]pyridin-3-yl)methanone; |
| 426 | ((5R,8S)-2-Methyl-3-(3,4,5-trifluorophenyl)-2,4,5,6,7,8-hexahydro-5,8-epiminocyclohepta[c]pyrazol-9-yl)(pyrazolo[1,5-a]pyrazin-3-yl)methanone; |
| 427 | ((5R,8S)-2-Methyl-3-(3,4,5-trifluorophenyl)-2,4,5,6,7,8-hexahydro-5,8-epiminocyclohepta[c]pyrazol-9-yl)(pyrazolo[1,5-a]pyrimidin-3-yl)methanone; |
| 428 | ((5R,8S)-2-Methyl-3-(3,4,5-trifluorophenyl)-2,4,5,6,7,8-hexahydro-5,8-epiminocyclohepta[c]pyrazol-9-yl)(2-methylimidazo[1,2-b]pyridazin-3-yl)methanone; |
| 429 | ((5R,8S)-2-Methyl-3-(3,4,5-trifluorophenyl)-2,4,5,6,7,8-hexahydro-5,8-epiminocyclohepta[c]pyrazol-9-yl)(2-methylpyrazolo[1,5-a]pyrimidin-3-yl)methanone; |
| 430 | (1-Methyl-1H-pyrazolo[3,4-b]pyridin-3-yl)((5R,8S)-2-methyl-3-(3,4,5-trifluorophenyl)-2,4,5,6,7,8-hexahydro-5,8-epiminocyclohepta[c]pyrazol-9-yl)methanone; |
| 431 | ((5R,8S)-2-Methyl-3-phenyl-2,4,5,6,7,8-hexahydro-5,8-epiminocyclohepta[c]pyrazol-9-yl)(quinolin-6-yl)methanone; |
| 432 | ((5R,8S)-2-Methyl-3-(3,4,5-trifluorophenyl)-2,4,5,6,7,8-hexahydro-5,8-epiminocyclohepta[c]pyrazol-9-yl)(quinolin-8-yl)methanone; |
| 433 | ((5S,8R)-2-Methyl-3-(3,4,5-trifluorophenyl)-2,4,5,6,7,8-hexahydro-5,8-epiminocyclohepta[c]pyrazol-9-yl)(quinolin-6-yl)methanone; |
| 434 | ((5R,8S)-2-Methyl-3-(3,4,5-trifluorophenyl)-2,4,5,6,7,8-hexahydro-5,8-epiminocyclohepta[c]pyrazol-9-yl)(quinolin-6-yl)methanone; |
| 435 | (2,4-Dimethylquinolin-7-yl)((5R,8S)-2-methyl-3-(3,4,5-trifluorophenyl)-2,4,5,6,7,8-hexahydro-5,8-epiminocyclohepta[c]pyrazol-9-yl)methanone; |
| 436 | ((5R,8S)-2-Methyl-3-(3,4,5-trifluorophenyl)-2,4,5,6,7,8-hexahydro-5,8-epiminocyclohepta[c]pyrazol-9-yl)(6-methylquinolin-8-yl)methanone; |
| 437 | ((5R,8S)-2-Methyl-3-(3,4,5-trifluorophenyl)-2,4,5,6,7,8-hexahydro-5,8-epiminocyclohepta[c]pyrazol-9-yl)(quinoxalin-6-yl)methanone; |
| 438 | (2,3-Dimethylquinoxalin-6-yl)((5R,8S)-2-methyl-3-(3,4,5-trifluorophenyl)-2,4,5,6,7,8-hexahydro-5,8-epiminocyclohepta[c]pyrazol-9-yl)methanone; |
| 439 | ((5R,8S)-2-Methyl-3-phenyl-2,4,5,6,7,8-hexahydro-5,8-epiminocyclohepta[c]pyrazol-9-yl)(quinoxalin-5-yl)methanone; |
| 440 | ((5R,8S)-2-Methyl-3-(3,4,5-trifluorophenyl)-2,4,5,6,7,8-hexahydro-5,8-epiminocyclohepta[c]pyrazol-9-yl)(1,5-naphthyridin-3-yl)methanone; |
| 441 | ((5R,8S)-2-Methyl-3-(3,4,5-trifluorophenyl)-2,4,5,6,7,8-hexahydro-5,8-epiminocyclohepta[c]pyrazol-9-yl)(5-methyl-5,6,7,8-tetrahydroimidazo[1,2-a]pyridin-3-yl)methanone; |
| 442 | ((5R,8S)-2-Methyl-3-(3,4,5-trifluorophenyl)-2,4,5,6,7,8-hexahydro-5,8-epiminocyclohepta[c]pyrazol-9-yl)(5,6,7,8-tetrahydroimidazo[1,2-a]pyridin-3-yl)methanone; |
| 443 | Isochroman-7-yl((5R,8S)-2-methyl-3-(3,4,5-trifluorophenyl)-2,4,5,6,7,8-hexahydro-5,8-epiminocyclohepta[c]pyrazol-9-yl)methanone; and |
| 444 | (2,3-Dihydrobenzo[b][1,4]dioxin-6-yl)((5R,8S)-2-methyl-3-(3,4,5-trifluorophenyl)-2,4,5,6,7,8-hexahydro-5,8-epiminocyclohepta[c]pyrazol-9-yl)methanone; | and pharmaceutically acceptable salts, isotopes, N-oxides, solvates, and stereoisomers thereof.

An additional embodiment of the invention is a pharmaceutical composition comprising:

(A) a therapeutically effective amount of at least one compound selected from compounds of Formula (II),

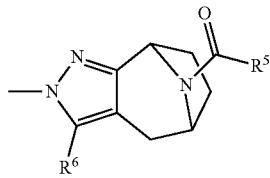
(II)

wherein

R⁵ is selected from the group consisting of:

(a) phenyl optionally independently substituted with one or two members selected from the group consisting of: halo, OC$_{1-4}$alkyl, and

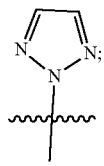

(b) 6-membered heteroaryl selected from the group consisting of:

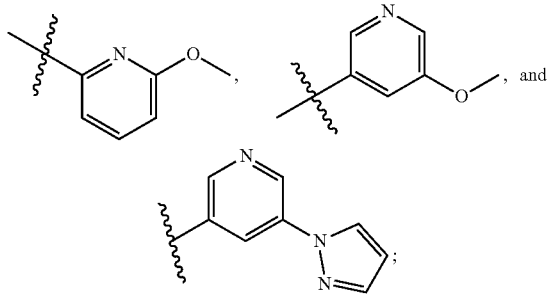

(c) 5-membered heteroaryl selected from the group consisting of:

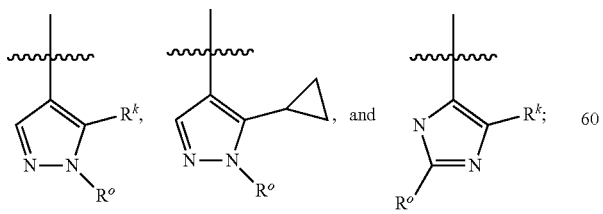

(d) 5,6-fused bicyclic heteroaryl or 6,5-fused bicyclic heteroaryl selected from the group consisting of:

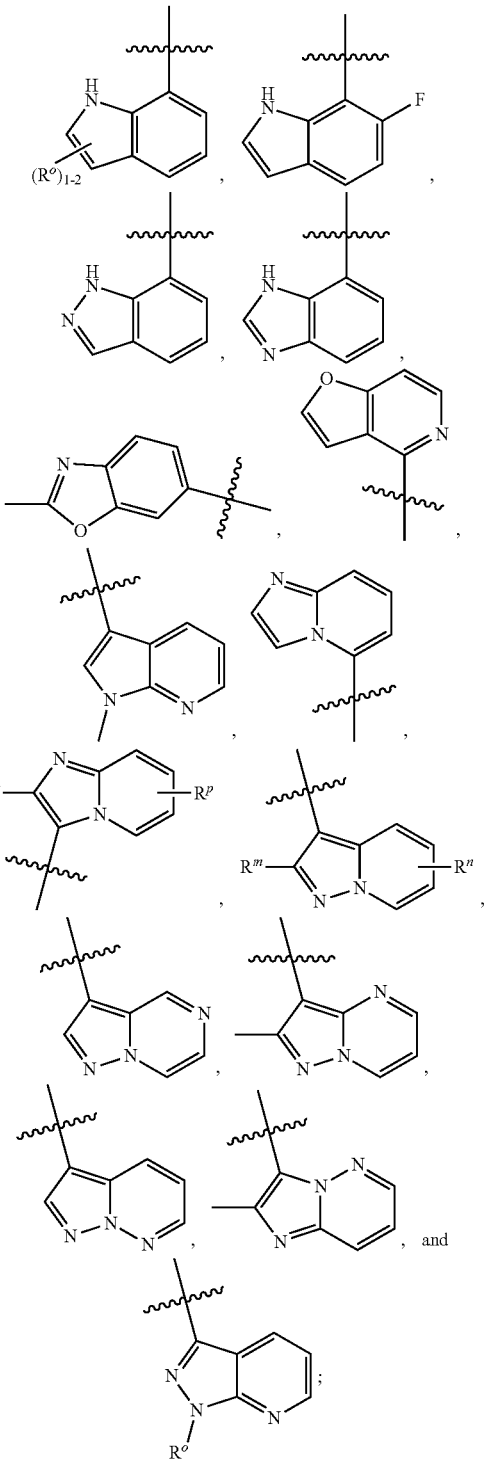

(e) 6,6-fused bicyclic heteroaryl selected from the group consisting of:

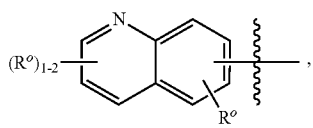

-continued

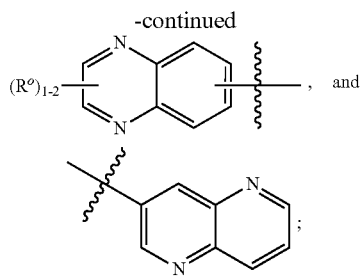, and (f)

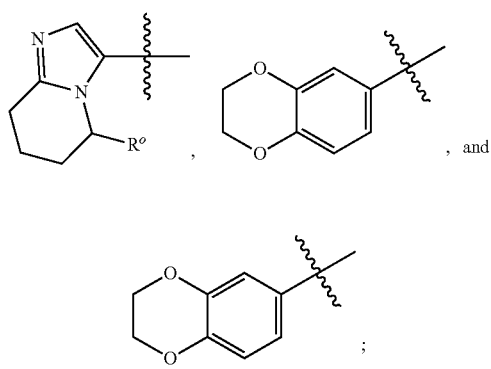

wherein $R^k$ is selected from the group consisting of: H, halo, $C_{1-4}$alkyl, and $C_{1-4}$haloalkyl;

$R^m$ is selected from the group consisting of: H, $C_{1-4}$alkyl and $C_{1-4}$haloalkyl;

$R^n$ is H or $OC_{1-4}$alkyl;

$R^o$ is H or $C_{1-4}$alkyl;

$R^p$ is selected from the group consisting of: H, halo, $C_{1-4}$alkyl, $C_{1-4}$haloalkyl, and $OC_{1-4}$alkyl; and $R^6$ is phenyl, wherein phenyl is independently substituted with one, two, or three members selected from the group consisting of: halo, $C_{1-4}$alkyl, $C_{1-4}$haloalkyl, and $OC_{1-4}$alkyl;

and pharmaceutically acceptable salts, isotopes, N-oxides, solvates, and stereoisomers of compounds of Formula (II);

and (B) at least one pharmaceutically acceptable excipient.

An additional embodiment of the invention is a pharmaceutical composition comprising a therapeutically effective amount of at least one compound in Table 3, as well as pharmaceutically acceptable salts, N-oxides or solvates of compounds of Table 3, pharmaceutically acceptable prodrugs of compounds of Table 3, and pharmaceutically active metabolites of Table 3; and at least one pharmaceutically acceptable excipient.

An additional embodiment of the invention is a method of treating a subject suffering from or diagnosed with a disease, disorder, or condition mediated by MGL receptor activity, comprising administering to a subject in need of such treatment a therapeutically effective amount of at least one compound selected from compounds of Formula (II):

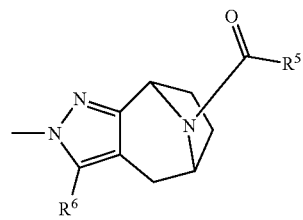

(II)

wherein
$R^5$ is selected from the group consisting of:
(a) phenyl optionally independently substituted with one or two members selected from the group consisting of: halo, $OC_{1-4}$alkyl, and

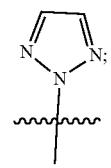

(b) 6-membered heteroaryl selected from the group consisting of:

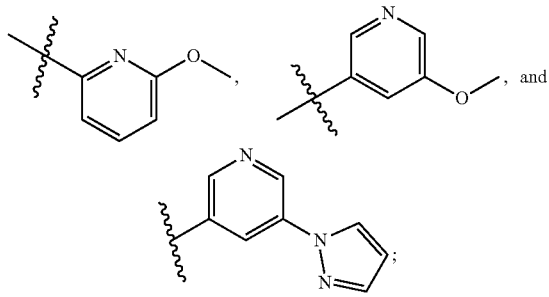

(c) 5-membered heteroaryl selected from the group consisting of:

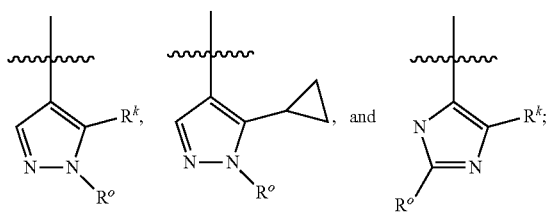

(d) 5,6-fused bicyclic heteroaryl or 6,5-fused bicyclic heteroaryl selected from the group consisting of:

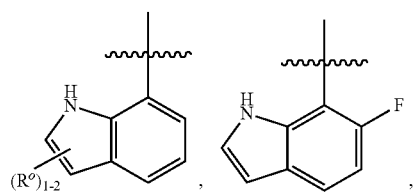

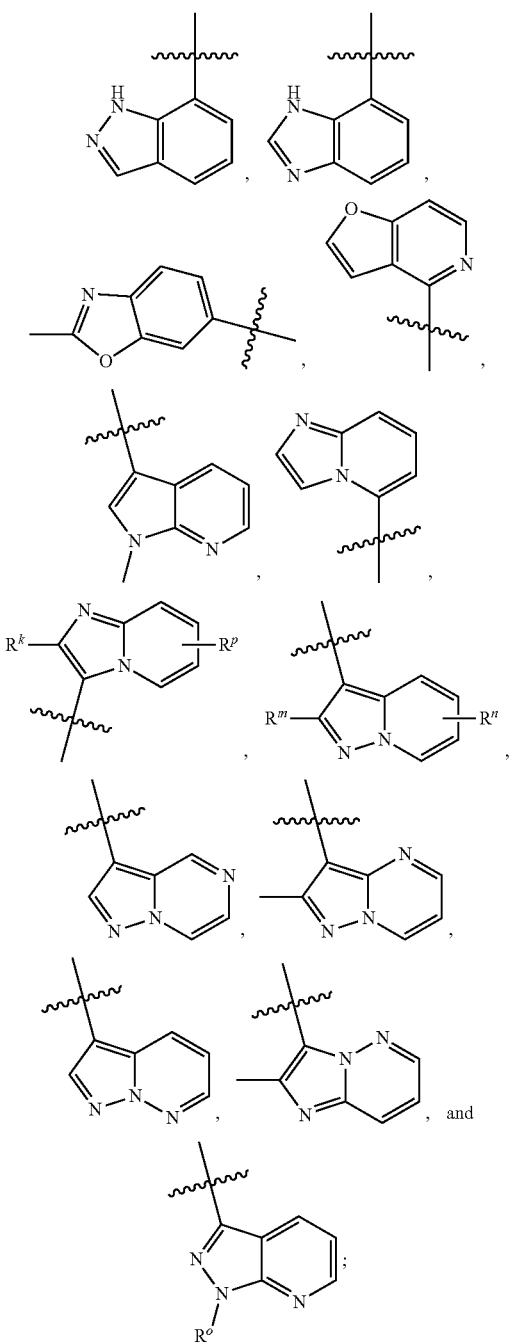

(e) 6,6-fused bicyclic heteroaryl selected from the group consisting of:

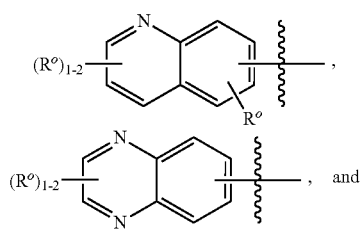

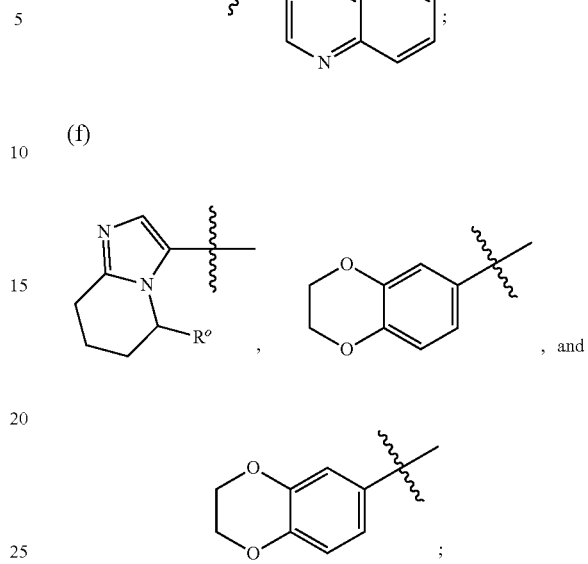

(f)

wherein $R^k$ is selected from the group consisting of: H, halo, $C_{1-4}$alkyl, and $C_{1-4}$haloalkyl;

$R^m$ is selected from the group consisting of: H, $C_{1-4}$alkyl and $C_{1-4}$haloalkyl;

$R^n$ is H or $OC_{1-4}$alkyl;

$R^o$ is H or $C_{1-4}$alkyl;

$R^p$ is selected from the group consisting of: H, halo, $C_{1-4}$alkyl, $C_{1-4}$haloalkyl, and $OC_{1-4}$alkyl; and $R^6$ is phenyl, wherein phenyl is independently substituted with one, two, or three members selected from the group consisting of: halo, $C_{1-4}$alkyl, $C_{1-4}$haloalkyl, and $OC_{1-4}$alkyl;

and pharmaceutically acceptable salts, isotopes, N-oxides, solvates, and stereoisomers thereof, to a subject in need thereof.

Exemplary compounds useful in methods of the invention will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I). Reactions may be performed between the melting point and the reflux temperature of the solvent, and preferably between 0° C. and the reflux temperature of the solvent. Reactions may be heated employing conventional heating or microwave heating. Reactions may also be conducted in sealed pressure vessels above the normal reflux temperature of the solvent.

Abbreviations and acronyms used herein include the following:

TABLE

| Term | Acronym |
| --- | --- |
| Acetonitrile | ACN, MeCN |
| Aqueous | aq |
| Atmosphere | atm |
| Broad | br |
| Diatomaceous Earth | Celite ® |
| Dimethylsulfoxide | DMSO |
| Diethyl ether | Ether, $Et_2O$ |
| Ethyl Acetate | EtOAc, or EA |
| Ethanol | EtOH |
| Electrospray ionization | ESI |
| Normal-phase silica gel chromatography | FCC |
| Grams | g |
| Hours | H, hr, hrs |
| High-pressure liquid chromatography | HPLC |
| Hertz | Hz |
| Isopropyl alcohol | iPrOH, IPA |
| Liquid chromatography and mass spectrometry | LCMS |
| Molar | M |
| Mass to charge ratio | m/z |
| Methanol | MeOH |
| Milligrams | mg |
| Minute | min |
| Milliliter | mL |
| Microliter | μL |
| Millimoles | mmol |
| Mass spectrometry | MS |
| Normal | N |
| Nuclear magnetic resonance | NMR |
| $CF_3SO_3$— or triflate | OTf |
| Parts per million | ppm |
| Precipitate | ppt |
| Polytetrafluoroethylene | PTFE |
| Retention time | $R_t$ |
| Room temperature | rt |
| Saturated | sat |
| Supercritical Fluid Chromatography | SFC |
| Temperature | T |
| Thin layer chromatography | TLC |
| Volume in milliliters of solvent per gram of substrate | V, or volumes |

PREPARATIVE EXAMPLES

Exemplary compounds useful in methods of the invention will now be described by reference to the illustrative synthetic schemes for their general preparation below and the specific examples to follow.

SCHEME 1

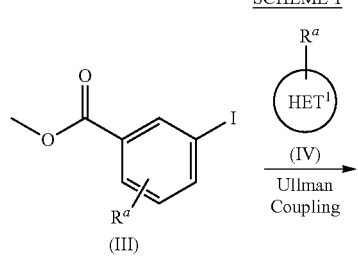

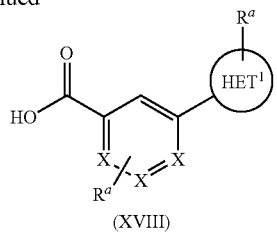

(XVIII)

According to SCHEME 1, Ullmann-type copper-mediated displacement of an optionally substituted aryl halide compound of formula (III), where $R^a$ is independently selected from the group consisting of: halo, $C_{1-4}$alkyl, $C_{1-4}$haloalkyl, and $OC_{1-4}$alkyl; with an nitrogen containing nucleophile such as a 5 membered heteroaryl containing 2 or 3 nitrogen members of formula (IV), where $R^a$ is independently selected from the group consisting of: halo, $C_{1-4}$alkyl, $C_{1-4}$haloalkyl, and $OC_{1-4}$alkyl; in the presence of a copper catalyst such as copper powder, copper (I) iodide, and the like; an inorganic base such as cesium carbonate, potassium carbonate, $K_3PO_4$, and the like; an auxiliary bidentate amine ligand such as trans-N,N-dimethylcyclohexane-1,2-diamine; in an inert high boiling solvent such as nitrobenzene, toluene, xylene, N-methylpyrrolidone (NMP), N,N-dimethylformamide (DMF), and the like, at temperatures ranging from 100-200° C.; employing conventional or microwave heating; provides a compound of formula (XVIII), where X is CH. For example, 3-iodobenzoic acid is reacted with 3-(trifluoromethyl)pyrazole, a base such as cesium carbonate, a copper catalyst such as CuI, a ligand such as trans-N,N-dimethylcyclohexane-1,2-diamine, in a suitable solvent such as DMF, at temperatures ranging from 100-140° C., under microwave irradiation, to provide 3-[3-(trifluoromethyl)pyrazol-1-yl]benzoic acid.

SCHEME 2

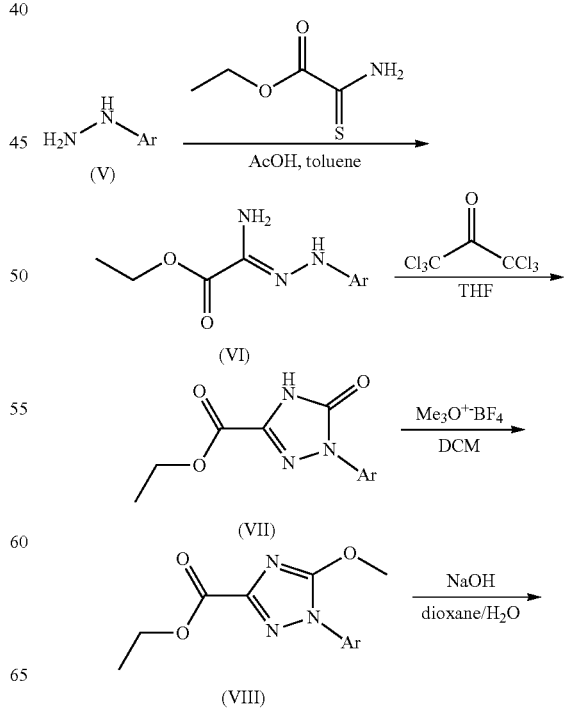

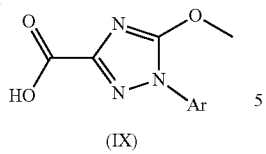
(IX)

According to SCHEME 2, condensation of the aryl hydrazine of formula (V), where Ar is and optionally substituted phenyl; with ethyl 2-amino-2-thioxoacetate; in a mixture of acetic acid and toluene; provides amino intermediate compound of formula (VI). Amino intermediate compound of formula (VI) is subsequently cyclized with triphosgene to yield ethyl 5-oxo-1-aryl-1H-1,2,4-triazole3-carboxylate of formula (VII). The aryl ether of formula (VIII) is synthesized by treatment of 1,2,4-triazolone of formula (VII) with alkyl oxonium salts, such as trimethyloxonium tetrafluoroborate or triethyloxonium tetrafluoroborate; in a suitable solvent such as dichloromethane (DCM), and the like, at temperatures ranging from 0° C. to room temperature. Saponification of the ester compound of formula (VIII) using a base such as aqueous lithium or sodium hydroxide in a polar solvent such as tetrahydrofuran (THF), dioxane, methanol (MeOH), ethanol (EtOH) or a mixture thereof, provides an acid compound of formula (IX).

SCHEME 3

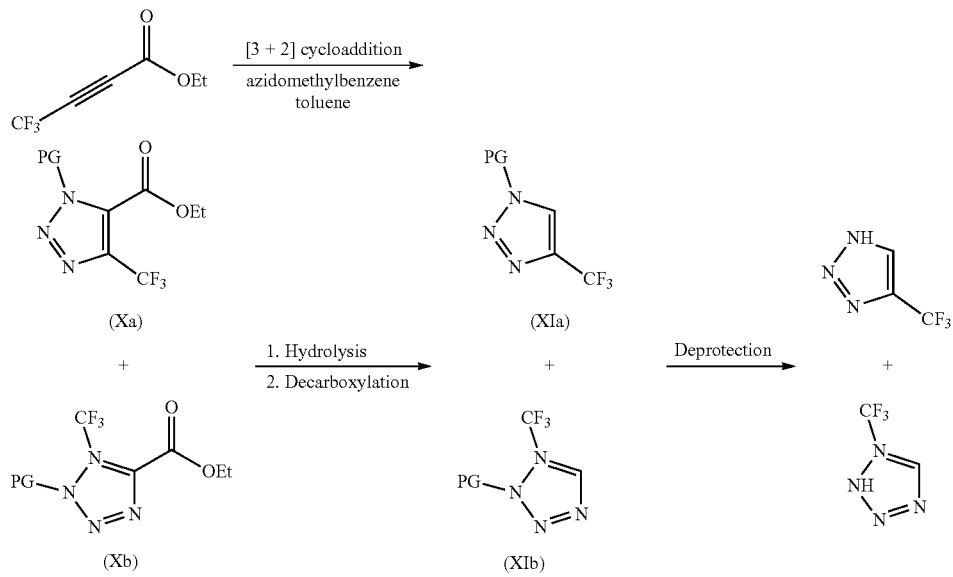

According to SCHEME 3, triazoles of formula (Xa) and (Xb) are prepared in a [3+2]cycloaddition reaction between a azidomethylbenzene and 4,4,4-trifluoro-2-butynoic acid ester; in a suitable solvent such as toluene, and the like; at a temperature of about 115° C.; for a period of 16 to 24 h; to provide a mixture of isomeric triazole compounds. Hydrolysis of the ester moiety in compounds of formula (Xa) and (Xb) is achieved employing conditions previously described. Decarboxylation is achieved employing silver carbonate; in a suitable solvent such as dimethyl sulfoxide (DMSO), and the like; in the presence of acetic acid: at a temperature of 120° C.; for a period of 18 h; to provide compounds of formula (XIa) and (XIb), where PG is benzyl.

Cleavage of the benzyl protecting group of compounds of formula (XIa) and (XIb), is achieved according to procedures known to one skilled in the art and employing established methodologies, such as those described in T. W. Greene and P. G. M. Wuts, "Protective Groups in Organic Synthesis," 3 ed., John Wiley & Sons, 1999, pgs 579-580; 620-621. For example, when PG is benzyl, deprotection is achieved employing Selcat-Q-6 10% palladium on carbon, Pd/C, and the like; under 1 atm of $H_2$; in a suitable solvent such as 1,4-dioxane, EtOH, MeOH, Ethyl Acetate (EtOAc), or a mixture thereof, preferably 1,4-dioxane; with or without the presence HCl, for a period of 24 to 78 hr, to provide 4-(trifluoromethyl)-1H-1,2,3-triazole and 5-(trifluoromethyl)-1H-1,2,3-triazole.

SCHEME 4

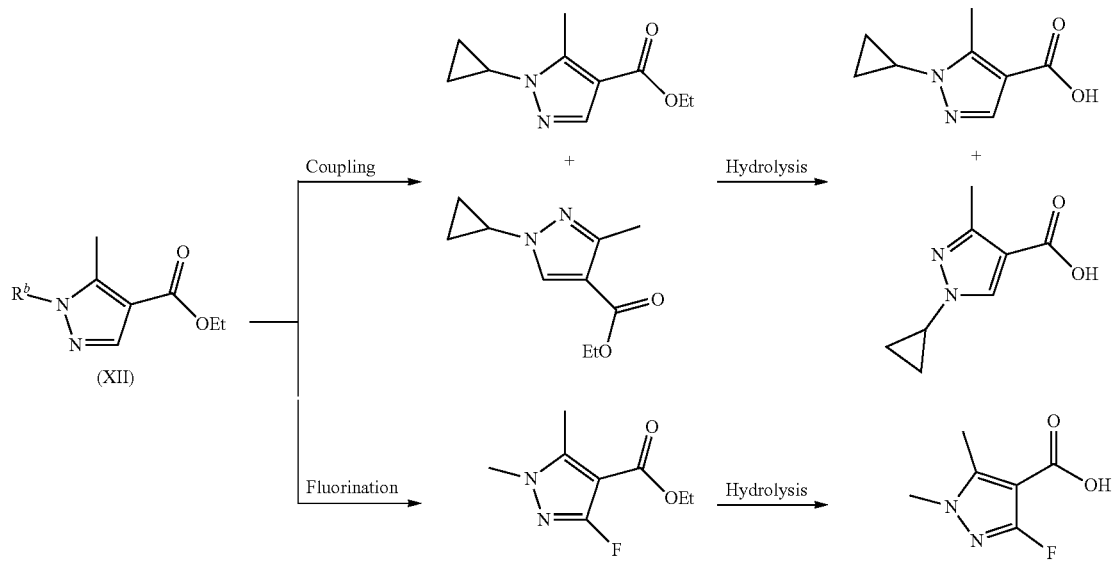

According to SCHEME 4, a compound of formula (XII) where $R^b$ is H, is reacted in a metal-mediated cross coupling reaction; with a suitably substituted cycloalkyl boronic acid, boronic ester, and the like; a copper catalyst such as Cu(OAc)$_2$, a ligand such as 2,2'-bipyridine, and the like; a base such as K$_2$CO$_3$, Cs$_2$CO$_3$, lithium bis(trimethylsilyl) amide (LHMDS), sodium tert-butoxide (NaOtBu), K$_3$PO$_4$, and the like; in a suitable solvent such as toluene, THF, DMF, dioxane, 1,2-dichloroethane, or a mixture thereof; provide a mixture of isomeric compounds ethyl 1-cyclopropyl-5-methyl-1H-pyrazole-4-carboxylate and ethyl 1-cyclopropyl-3-methyl-1H-pyrazole-4-carboxylate. Hydrolysis of ethyl 1-cyclopropyl-5-methyl-1H-pyrazole-4-carboxylate and ethyl 1-cyclopropyl-3-methyl-1H-pyrazole-4-carboxylate employing methods previously described provides 1-cyclopropyl-5-methyl-1H-pyrazole-4-carboxylic acid and 1-cyclopropyl-3-methyl-1H-pyrazole-4-carboxylic acid.

A compound of formula (XII), where $R^b$ is CH$_3$, is fluorinated using an electrophilic fluorine source such as, N-fluorobenzenesulfonimide (NFSI), a base such as lithium diisopropylamide (LDA); in a suitable solvent such as THF, and the like; at temperatures ranging from −78° C. to rt; for a period of 18-24 h; to provide ethyl 3-fluoro-1,5-dimethyl-1H-pyrazole-4-carboxylate. Subsequent acid hydrolysis of ethyl 3-fluoro-1,5-dimethyl-1H-pyrazole-4-carboxylate with HCl, at a temperature of about 110° C., for a period of 3 h, provides 3-fluoro-1,5-dimethyl-1H-pyrazole-4-carboxylic acid.

SCHEME 5

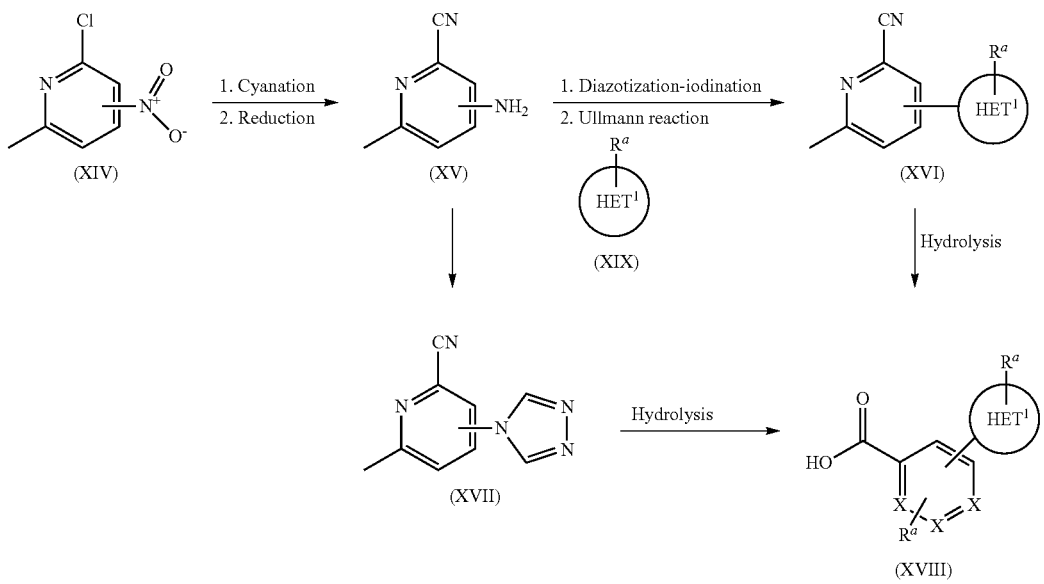

According to SCHEME 5, a compound of formula (XIV), undergoes a palladium-catalyzed cyanation employing conditions known to one skilled in the art. For example, a compound of formula (XIV), is reacted with a palladium catalyst such as tetrakis(triphenylphosphine)palladium(0), and the like; zinc cyanide as the nucleophile; in a suitable solvent such as N,N-dimethylformamide (DMF), and the like; at a temperature of about 80° C.; for a period of 18-24 h; to provide a cyano compound. Reduction of the nitro group is achieved employing iron in acetic acid to provide a compound of formula (XV). The aryl amine compound of formula (XV) undergoes a two-step diazotization-iodination reaction employing conditions known to one skilled in the art. For example, diazotization of the aryl amine is achieved using hydrochloric or sulfuric acid in the presence of sodium nitrite; subsequent iodination reaction with KI affords an iodo compound. Reaction of the iodo intermediate in an Ullmann-type copper-mediated displacement reaction with a commercially available or synthetically accessible 5-membered heteroaryl ring containing 2 or 3 nitrogen members of formula (XIX) to provide a compound of formula (XVI). A nitrile compound of formula (XVI) is hydrolyzed with a base such as sodium hydroxide, potassium hydroxide, and the like; in suitable solvent such as 1,4-dioxane and water; to provide a compound of formula (XVIII), where X is CH or N (wherein only one X can be N); HET¹ is a 5 membered heteroaryl containing 2 or 3 nitrogen members, and $R^a$ is H, halo, $C_{1-4}$alkyl, $C_{1-4}$haloalkyl, and $OC_{1-4}$alkyl.

In an alternate method, a compound of formula (XVIII), where X is CH or N (wherein only one X can be N); is prepared in two steps from a compound of formula (XV). A compound of formula (XV), is reacted with diformylhydrazine; in the presence of trimethylsilyl chloride as a Lewis acid; a base such as triethylamine; in a suitable solvent such as pyridine; at a temperature of about 100° C.; for a period of about 16 h; provides the 1,2,4-triazol-4-yl intermediate compound. Basic hydrolysis of the nitrile compound of formula (XVII) is achieved with a hydroxide base such as NaOH or KOH, in suitable solvent such as 1,4-dioxane and water, to provide a compound of formula (XVIII), where X is CH or N (wherein only one X can be N), and HET¹ is 1,2,4-triazol-4-yl.

SCHEME 6

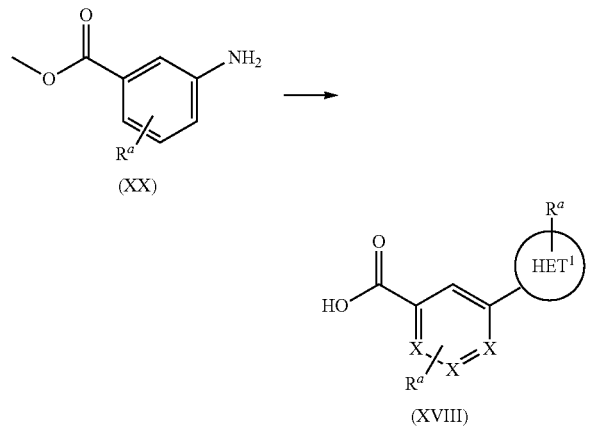

According to SCHEME 6, a compound of formula (XVIII), where X is CH, HET¹ is 1,2,4-triazol-4-yl, is prepared in two steps from a compound of formula (XX) where $R^a$ is halo or $C_{1-4}$alkyl. In a first step, a compound of formula (XX) where $R^a$ is halo or $C_{1-4}$alkyl is reacted with diformylhydrazine, in the presence of trimethylsilyl chloride as a Lewis acid, triethylamine, in a suitable solvent such as pyridine, at a temperature of about 100° C., for a period of about 16 h, to provide the 1,2,4-triazol-4-yl intermediate; in a second step, saponification is achieved according to conditions known to one skilled in the art, or as previously described.

In a similar fashion, methyl 4-aminopyridine-2-carboxylate and methyl 5-aminonicotinate may be used instead a compound of formula (XX), to provide compounds of formula (XVIII), where only one X is N.

SCHEME 7

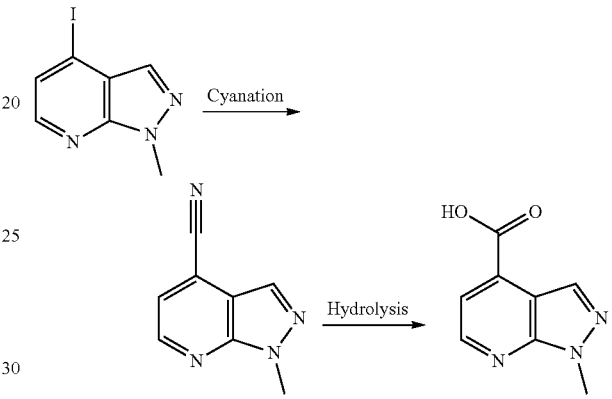

According to SCHEME 7, commercially available or synthetically accessible 4-iodo-1-methyl-1H-pyrazolo[3,4-b]pyridine is reacted in a copper-catalyzed cyanation using CuCN which can function as both copper catalyst and cyanating reagent; with or without the addition of CuI; in a suitable solvent such as DMSO, and the like; at a temperature of about 120° C.; for a period of 20 to 48 h; to provide 1-methyl-1H-pyrazolo[3,4-b]pyridine-4-carbonitrile. Hydrolysis of the nitrile to the corresponding acid is achieved according to procedures previously described.

In a similar fashion 5-bromo-7-methylimidazo[1,2-a]pyridine is converted to (7-methylimidazo[1,2-a]pyridin-5-yl)(λ¹-oxidaneyl)methanone

SCHEME 8

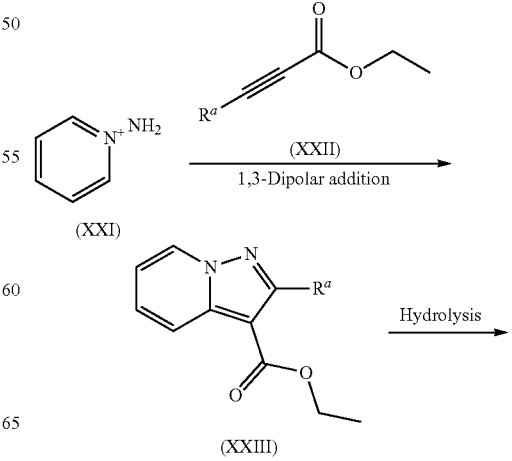

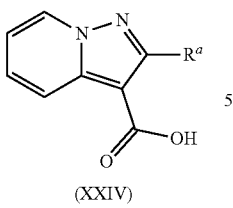

(XXIV)

According to SCHEME 8, 1-aminopyridin-1-ium is reacted in a 1,3-dipolar addition reaction with a compound of formula (XXII), where $R^a$ is H, $C_{1-4}$alkyl or $C_{1-4}$haloalkyl; in the presence of a base such as TEA, and the like; 2,3-dichloro-5,6-dicyano-p-benzoquinone (DDQ); in a suitable solvent such as DMF, and the like; at temperatures ranging from 0° C. to rt; for a period of 16-24 h; provides a compound of formula (XXIII). Hydrolysis of the ester to the corresponding acid is achieved according to procedures previously described.

SCHEME 9

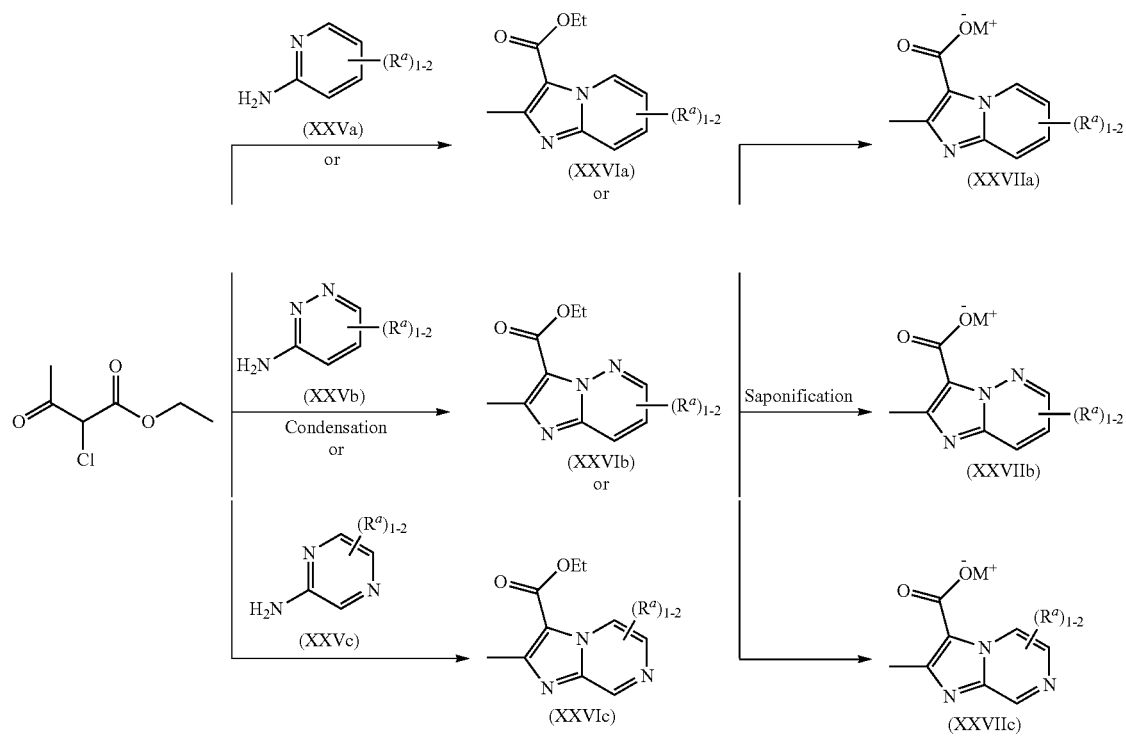

According to SCHEME 9, compounds of formulas (XXVIa, XXVIb, and XXVIc) are prepared under conditions known to one skilled in the art, by condensation of commercially available or synthetically accessible substituted pyridine, pyridazine and pyrazine amines of formulas (XXVa, XXVb, and XXVc) where $R^a$ is as defined in claim 1, using ethyl 2-chloro-3-oxobutanoate in a suitable solvent such as 1,2-dimethoxy ethane (DME), and the like; at temperature of 90° C., for a period of about 2-16 hours. Saponification of the esters (XXVIa, XXVIb, and XXVIc) to the corresponding acid is achieved employing conditions known to one skilled in the art. For example, using a suitable base such as potassium trimethylsilanolate (TMSOK), NaOH, LiGH, and the like, in a suitable solvent such as water/THF/MeOH, at a temperature of about 60° C., for a period of about 24 h, to provide compounds of formulas (XXVIIa, XXVIIb, and XXVIIc), where M is potassium, Na, or Li, preferably potassium.

SCHEME 10

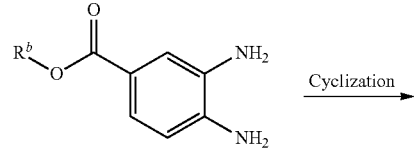

Cyclization

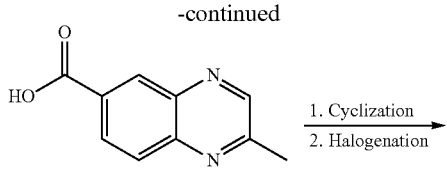

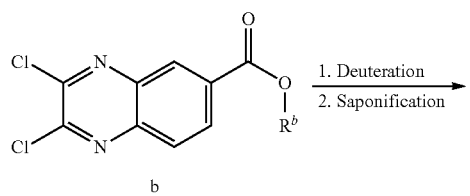

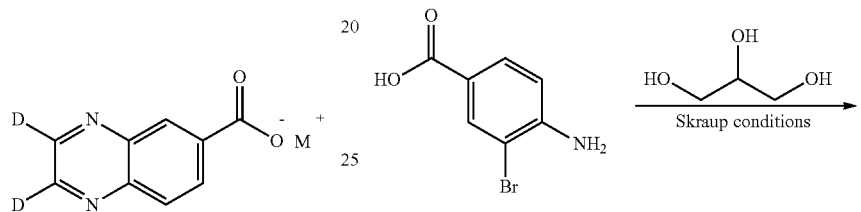

According to SCHEME 10, 2-methylquinoxaline-6-carboxylic acid (where $R^b$ is H) is prepared by condensation of commercially available or synthetically accessible 2-amino-4-aminobenzoic acid with 1,2-dioxoalkanes such as 2-oxopropanal, and the like; in a suitable solvent such as EtOH and the like, at a temperature of 80° C., for a period of about 16-24 hours, to provide 2-methylquinoxaline-6-carboxylic acid.

In a similar fashion, methyl 3,4-diaminobenzoate (where $R^b$ is $CH_3$) is condensed with diethyl oxalate, in a suitable solvent such as EtOH and the like; at a temperature of about 140° C.; for a period of about 16-24 hours; affords methyl 2,3-dihydroxyquinoxaline-6-carboxylate.

Subsequent chlorination with chlorinating reagent, such as thionyl chloride, and the like; neat, or in a suitable solvent such as toluene, and the like; followed by catalytic amount of DMF; at reflux temperature; affords methyl 2,3-dichloroquinoxaline-6-carboxylate. Palladium catalyzed reductive deuteration of methyl 2,3-dichloroquinoxaline-6-carboxylate using commercially available deuterated reagent such as sodium borodeuteride; in presence of a palladium catalyst such as 1,1'-bis(diphenylphosphino)ferrocenedichloropalladium(II) (PdCl$_2$(dppf)) and the like; a base such as $N^1$, $N^1$, $N^2$, $N^2$-tetramethylethane-1,2-diamine (TMEDA), and the like; in a suitable solvent such as THF, and the like; at room temperature; for a period of 1-3 hour; affords methyl quinoxaline-6-carboxylate-2,3-d$_2$. Saponification of the ester to the corresponding acid is achieved employing conditions known to one skilled in the art, for example, using a suitable base such as NaOH, LiGH, KOH, and the like, preferably Li; in a suitable solvent such as water/THF/MeOH, at room temperature, for a period of about 1 h, affords quinoxaline-6-carboxylic-2,3-d$_2$ acid (where M is Li). Potassium, sodium and lithium salts are isolated depending on the base used in the saponification.

SCHEME 11

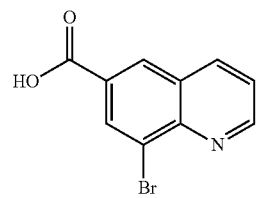

According to SCHEME 11, treatment of 4-amino-3-bromobenzoic acid with excess glycerol under Skraup conditions known to one skilled in the art (R. H. F. Manske and M. Kulka, "The Skraup Synthesis of Quinolines"; Org. Reaction, vol. 7, p. 59-98, 1953), affords 6-carboxy-8-bromoquinoline. For example, reaction of 4-amino-3-bromobenzoic acid is heated at 140° C., with sulfuric acid, glycerol, an oxidizing agent such as nitrobenzene, in the presence of ferrous sulfate, to provide 6-carboxy-8-bromoquinoline.

SCHEME 12

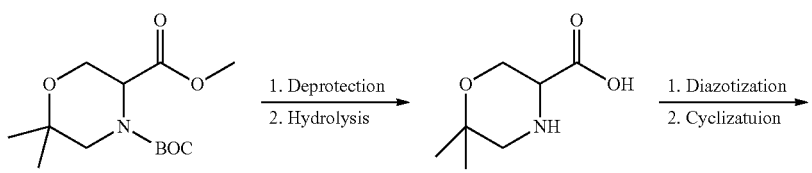

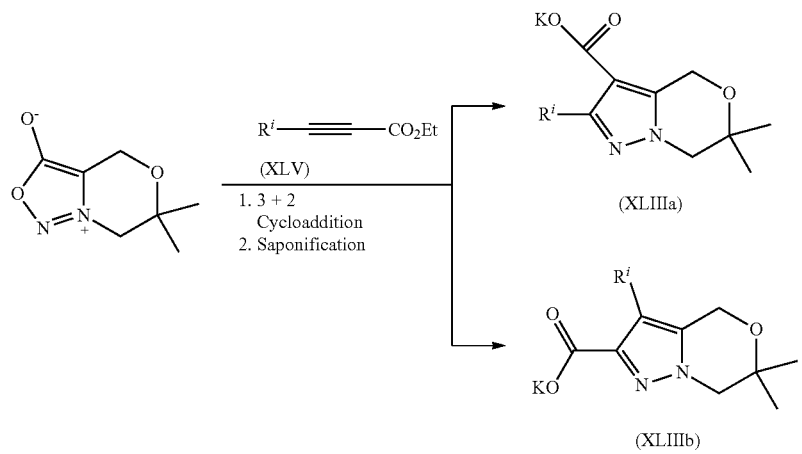

According to SCHEME 12, 6,6-dimethylmorpholine-3-carboxylic acid is prepared in two steps from 4-(tert-butyl) 3-methyl 6,6-dimethylmorpholine-3,4-dicarboxylate. In a first step, deprotection of BOC group is achieved according to procedures known to one skilled in the art and employing established methodologies, such as those described in T. W. Greene and P. G. M. Wuts, "Protective Groups in Organic Synthesis," 3 ed., John Wiley & Sons, 1999, pgs 518-525. For example, deprotection under acidic conditions such as trifluoroacetic acid (TFA)/CH$_2$Cl$_2$, HCl/Dioxane, and the like, at room temperature for a period of 2 h. Subsequent hydrolysis in situ, with suitable base such as NaOH and the like, in a solvent such as MeOH/water provides 6,6-dimethylmorpholine-3-carboxylic acid. Diazotization of 6,6-dimethylmorpholine-3-carboxylic acid is achieved employing sodium nitrite; in water; under acidic conditions such as conc. HCl; at temperatures ranging from 0° C. to room temperature; for a period of 16 h. The resulting nitroso acid is treated with trifluoroacetic anhydride (TFAA) in a suitable solvent such as acetonitrile (ACN) and the like; at room temperature; for a period of 2 h; to provide 6,6-dimethyl-6,7-dihydro-4H-[1,2,3]oxadiazolo[4,3-c][1,4]oxazin-8-ium-3-olate (Reference: Nikitenko, A. A., et al., Org. Process Res. Dev., 2006, 10 (4), pp 712-716) 6,6-Dimethyl-6,7-dihydro-4H-[1,2,3]oxadiazolo[4,3-c][1,4]oxazin-8-ium-3-olate undergoes a [3+2] cycloaddition reaction with an alkynoate of formula (XLV), where R$^i$ is C$_{1-4}$alkyl; in a suitable solvent such as xylene, and the like; at a temperature of about 140° C.; for a period of 2 h. Subsequent saponification of the resulting two regioisomeric esters to the corresponding acids is achieved employing conditions previously described. For example, employing a suitable base such as NaOH, LiGH, KOH, and the like; in a suitable solvent such as water, THF, MeOH, or a mixture thereof; at a temperature of about 60° C.; for a period of about 24 h; to provide compounds of formulas (XLIIIa) and (XLIIIb), where M is K, Na, or Li.

SCHEME 13

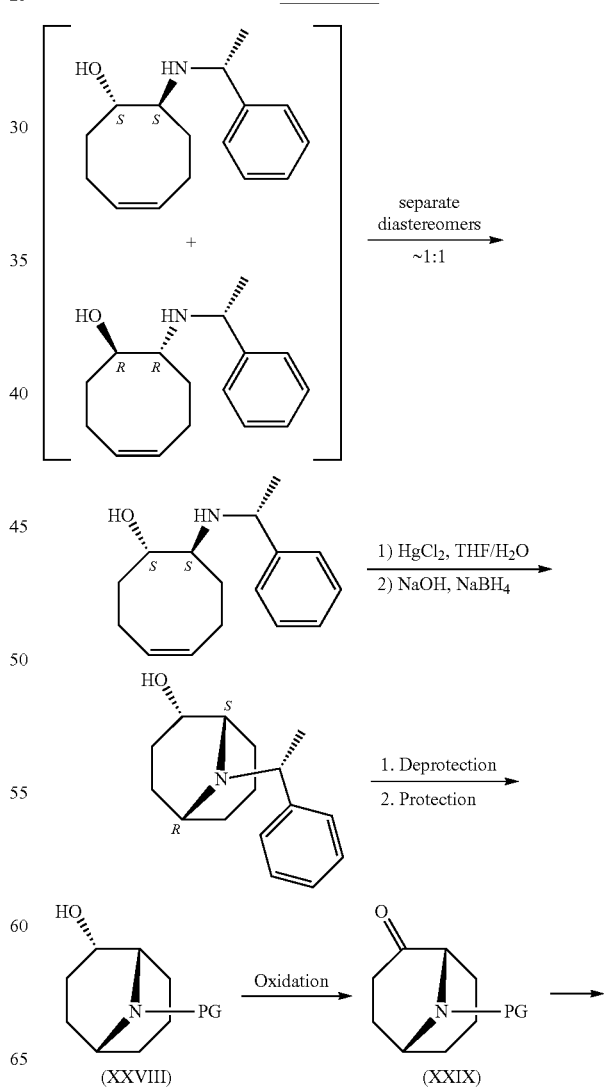

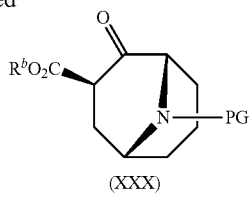

(XXX)

According to SCHEME 13, (1S,8S)-(+)-trans-8-[(R)-phenylethylamino)cyclooct-4-enol and (1R,8R)-(−)-trans-8-[(R)-phenylethylamino]cyclooct-4-enol are prepared according to methods as described in Carroll, F. I., et al., "Synthesis and Pharmacological Characterization of Nicotinic Acetylcholine Receptor Properties of (+)- and (−)-Pyrido-[3,4-b]homotropanes", Journal of Medicinal Chemistry, 49(11), 3244-3250; 2006.

(1S,8S,Z)-8-(((R)-1-phenylethyl)amino)cyclooct-4-en-1-ol is converted to (1S,2S,5R)-9-((R)-1-phenylethyl)-9-azabicyclo[3.3.1]nonan-2-ol in two steps. In a first step, reaction of (1S,8S,Z)-8-(((R)-1-phenylethyl)amino)cyclooct-4-en-1-ol with mercury(II) chloride, in a suitable solvent such as diethyl ether, tetrahydrofuran, dioxane, water, or a mixture thereof, at room temperature, for a period of 12-24 h, provides a mercurial chloride complex at the alkenyl moiety. In a second step, reduction of the aforementioned mercurial chloride complex is accomplished by reaction with 3 M sodium hydroxide, and a reducing agent such as sodium borohydride, at a temperature of about 0° C., to provide the cyclized (1S,2S,5R)-9-((R)-1-phenylethyl)-9-azabicyclo[3.3.1]nonan-2-ol product.

The chiral (R)-methylbenzyl is deprotected employing hydrogenation conditions known to one skilled in the art and employing established methodologies, such as those described in T. W. Greene and P. G. M. Wuts, "Protective Groups in Organic Synthesis," 3 ed., John Wiley & Sons, 1999; pgs 579-580; 620-621. For example, employing $H_2$ in the presence of a catalyst such as Pd/C, and the like, in a suitable solvent such as MeOH, and the like, to provide (1S,2S,5R)-9-azabicyclo[3.3.1]nonan-2-ol.

The amine moiety of (1S,2S,5R)-9-azabicyclo[3.3.1]nonan-2-ol is protected with a carbamate protecting group such as tert-butyloxycarbonyl (BOC). For example, reaction of (1S,2S,5R)-9-azabicyclo[3.3.1]nonan-2-ol, with BOC-anhydride, at room temperature, for a period of about 4-7 h, provides a compound of formula (XXVIII), where PG is BOC.

A compound of formula (XXVIII) is converted to compound of formula (XXIX) under oxidative conditions, such as Swern (Moffott-Swern) oxidation. For example, a compound of formula (XXVIII) is treated with DMSO, oxalyl chloride, triethylamine, in a suitable solvent such as DCM, and the like, to provide a compound of formula (XXIX). In a preferred method, the reaction is run initially at −78° C. and then warmed to room temperature and stirred overnight.

A compound of formula (XXIX) is converted to compound (XXX) by treatment with a strong base such as lithium bis(trimethylsilyl)amide (LiHMDS/LHMDS), and the like, in a suitable solvent such as THF, and the like, at a temperature of about −78° C., for a period of about 30 minutes. The resulting lithium enolate is trapped by methyl or ethyl cyanoformate, at a temperature of about −78° C., for a period of 1-3 h, to furnish the 3-keto ester compound of formula (XXX), where PG is BOC and $R^b$ is $C_{1-4}$alkyl.

SCHEME 14

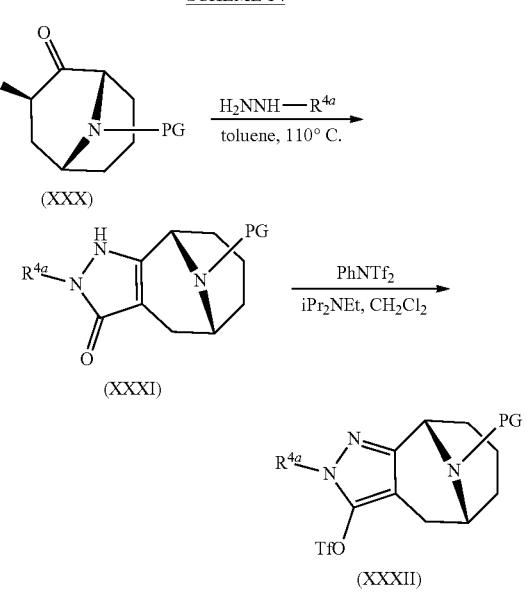

According to SCHEME 14, a keto-ester compound of formula (XXX) is reacted with a commercially available or synthetically accessible hydrazine of formula $R^{4a}NHNH_2$, in an inert solvent such as toluene, and the like, at a temperature of about 100° C., to provide a pyrazolone compound of formula (XXXI), where $R^{4a}$ is $C_{1-4}$alkyl or $C_{3-6}$cycloalkyl.

Derivation of pyrazolone compound of formula (XXXI), with a sulfonate-based leaving group such as trifluoromethanesulfonyl (triflate), is achieved by is by reaction with a triflating agent such as trifluoromethanesulfonic anhydride ($Tf_2O$), a base such as triethylamine (TEA), pyridine, and the like, in a suitable solvent such as DCM and the like. Milder triflating agents such as N-phenylbis(trifluoromethanesulfonimide) ($Tf_2NPh$), a base such as TEA, DIEA, and the like, in a suitable solvent such as DCM, and the like; are used for better selectivity, to provide a compound of formula (XXXII).

racemic-(5R,8S)-2-Methyl-3-phenyl-2,4,5,6,7,8-hexahydro-5,8-epiminocyclohepta[c]pyrazole is prepared according to methods analogous to those described above.

SCHEME 15

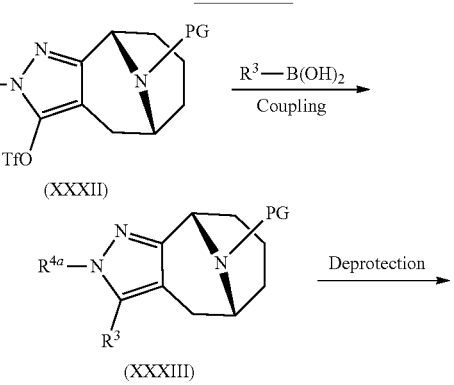

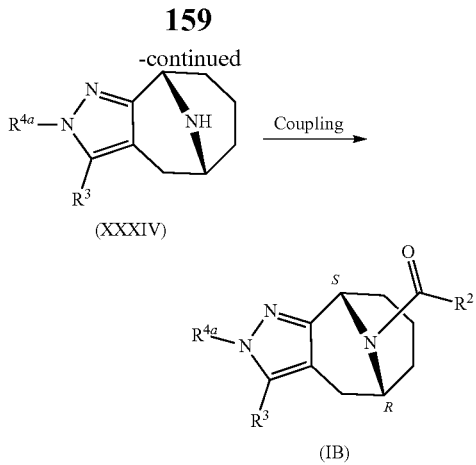

(XXXIV)

(IB)

According to SCHEME 15, a compound of formula (XXXII) is reacted in a metal mediated cross coupling reaction to provide a compound of formula (XXXIII), where $R^{4a}$ is H or $C_{1-4}$alkyl, PG is BOC, and $R^3$ is phenyl optionally substituted with one, two or three members independently selected from the group consisting of: halo, or $C_{1-4}$haloalkyl; or thiophene substituted with $CF_3$. For example, a compound of formula (XXXII), where $R^{4a}$ is H or $C_{1-4}$alkyl, and PG; is reacted with a suitably substituted commercially available or synthetically accessible alkyl, cycloalkyl, aryl or heteroaryl boronic acid, boronate ester, and the like, in the presence of a palladium catalyst such as [1,1′-bis(di-tert-butylphosphino)ferrocene]dichloropalladium(II) (PdCl$_2$(dtbpf)), tetrakis(triphenylphosphine)palladium(0) (Pd(PPh$_3$)$_4$), [1,1′-bis(diphenylphosphino)ferrocene]dichloropalladium(II) (PdCl$_2$(dppf)), palladium(II)bis(triphenylphosphine) dichloride (Pd(PPh$_3$)$_2$Cl$_2$), and the like, a base such as K$_3$PO$_4$, aq. Na$_2$CO$_3$, Na$_2$CO$_3$, Cs$_2$CO$_3$, and the like, in a suitable solvent such as 1,2-dimethoxyethane, 1,4-dioxane, DMF, water, or a mixture thereof, at a temperature ranging from 60 to 180° C., employing microwave or conventional heating, for a period of about 30 min to 16 h, to provide a compound of formula (XXXIII).

In an alternate method, tert-butyl (5R,9S)-2-methyl-3-(((trifluoromethyl)sulfonyl)oxy)-4,5,6,7,8,9-hexahydro-2H-5,9-epiminocycloocta[c]pyrazole-10-carboxylate is reacted in a metal mediated coupling reaction with a commercially available or synthetically accessible aryl or heteroaryl boronic acid, boronate ester, of formula R$^3$—B(OH)$_2$, where $R^3$ is phenyl optionally substituted with one, two or three members independently selected from the group consisting of: halo, $C_{1-4}$haloalkyl, $OC_{1-4}$alkyl; or 1-methyl-1H-indol-2-yl; employing a catalyst such as chloro(2-dicyclohexylphosphino-2′,4′,6′-triisopropyl-1,1′-biphenyl)[2-(2′-amino-1,1′-biphenyl)]palladium(II) (XPhos Pd G2), and the like; a base such as K$_3$PO$_4$, aq. Na$_2$CO$_3$, Na$_2$CO$_3$, Cs$_2$CO$_3$, and the like, in a suitable solvent such as 1,2-dimethoxyethane, 1,4-dioxane, dimethylformamide (DMF), water, or a mixture thereof, at a temperature ranging from 60 to 180° C., employing microwave or conventional heating, for a period of about 30 min to 16 h, to provide a compound of formula (XXXIII).

Cleavage of the BOC protecting group on a compound of formula (XXXIII) is achieved according to procedures known to one skilled in the art and employing established methodologies, such as those described in T. W. Greene and P. G. M. Wuts, "Protective Groups in Organic Synthesis," 3 ed., John Wiley & Sons, 1999, pgs 518-525. For example, under acidic conditions such as TFA/CH$_2$Cl$_2$, HCl/Dioxane, and the like, provides a compound of formula (XXXIV).

A compound of Formula (IB) is prepared by conventional amide bond forming techniques such as coupling reactions which are well known to those skilled in the art (such as HATU (1-[bis(dimethylamino)methylene]-1H-1,2,3-triazolo[4,5-b]pyridinium 3-oxid hexafluorophosphate), BOP (benzotriazol-1-yloxy-tris(dimethylamino)phosphonium hexafluorophosphate), or conversion of the acid to an acid chloride). For example, reaction of a compound of formula (XXXIV) where $R^{4a}$ is H or $C_{1-4}$alkyl, and $R^3$ is as described in claim 1; with a commercially available or synthetically accessible acid, where the acid is activated with an appropriate activating reagent, for example a carbodiimide, such as N,N′-dicyclohexylcarbodiimide (DCC) or 1-ethyl-3-(3-dimethylaminopropyl)carbodiimide (EDC, EDAC or EDCI) optionally in the presence of hydroxybenzotriazole (HOBt) and/or a catalyst such as 4-dimethylaminopyridine (DMAP); a halotrisaminophosphonium salt such as (benzotriazol-1-yloxy)tris(dimethylamino)phosphonium hexafluorophosphate (BOP), or bromotripyrrolidinophosphonium hexafluorophosphate (PyBroP®); a suitable pyridinium salt such as 2-chloro-1-methyl pyridinium chloride; or another suitable coupling agent such as N,N,N′,N′-tetramethyl-O-(1H-benzotriazol-1-yl)uronium hexafluorophosphate (HBTU), 1-[bis(dimethylamino)methylene]-1H-1,2,3-triazolo[4,5-b]pyridinium 3-oxid hexafluorophosphate (HATU), 2,4,6-tripropyl-1,3,5,2,4,6-trioxatriphosphorinane-2,4,6-trioxide (T3P®) and the like.

Coupling reactions are conducted in a suitable solvent such as DCM, THF, DMF and the like, optionally in the presence of a tertiary amine such as N-methylmorpholine, N-ethyldiisopropylamine (DIEA, DIPEA), or triethylamine (TEA), at a temperature ranging from about 0° C. to rt, to provide compound a of Formula (IB).

A compound of Formula (IB) (as well as a compound of Formula (I)), where $R^2$ is a heteroaryl substituted with a reactive functional group such as a hydroxyl group, is alkylated with a suitable alkyl halide such as 1-iodoethane, fluoro-2-iodoethane, and the like. For example, a compound of Formula (IB) (as well as a compound of Formula (I)), where $R^2$ is 4-hydroxyquinoline, is reacted with fluoro-2-iodoethane; a suitable base such as Cs$_2$CO$_3$, K$_2$CO$_3$, and the like: in a suitable solvent such as N,N-dimethylformamide to provide a compound of Formula (IA) (as well as a compound of Formula (I)) where $R^2$ is 4-(2-fluoroethoxy)quinoline.

A compound of Formula (IB) (as well as a compound of Formula (I)), where $R^2$ is quinoline, is oxidized to the N-oxide compound of Formula (IB) (as well as a compound of Formula (I)), employing m-chloroperoxybenzoic acid (m-CPBA), in a suitable solvent such as DCM, chloroform, and the like, at temperatures ranging from 0° C. to room temperature, for a period of 30 minutes to 1 hr.

A compound of Formula (IB) (as well as a compound of Formula (I)), where $R^2$ is a bromo substituted quinoline is tritiated employing conditions known to one skilled in the art. For example, (4-bromoquinolin-6-yl)((5R,9S)-3-(3,5-difluorophenyl)-2-methyl-4,5,6,7,8,9-hexahydro-2H-5,9-epiminocycloocta[c]pyrazol-10-yl)methanone is reacted with Pd/C, in a suitable solvent such as MeOH, and the like, in the presence of 1 atm of tritium gas, to provide ((5R,9S)-3-(3,5-difluorophenyl)-2-methyl-4,5,6,7,8,9-hexahydro-2H-5,9-epiminocycloocta[c]pyrazol-10-yl)(quinolin-6-yl-4-t) methanone.

A compound of Formula (IB) (as well as a compound of Formula (I)), where $R^2$ is a heteroaryl substituted with a reactive functional group such as Br, is reacted under catalytic hydrogenation dehalogenation reaction conditions such as Pd/C and hydrogen gas under conditions known to one skilled in the art.

SCHEME 15

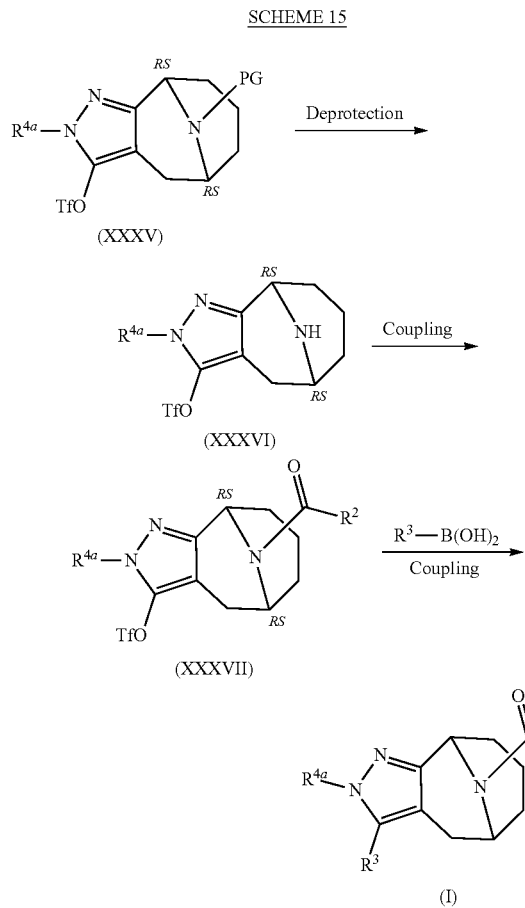

According to SCHEME 15, a compound of Formula (I) is prepared from a compound of formula (XXXV) in three steps. In a first step, deprotection of the BOC protecting group as previously described, followed by amide bond coupling then subsequent Suzuki coupling as previously described provides a compound of Formula (I).

SCHEME 16

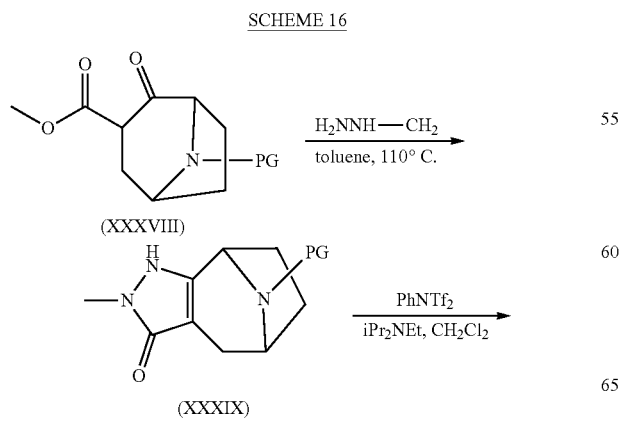

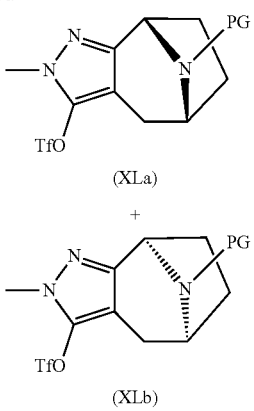

According to SCHEME 16, a compound of formula (XXXVIII) is prepared in a manner as described in JOC 2002, 67, 3479-3486, where PG is BOC. A keto-ester compound of formula (XXXVIII) is reacted with a commercially available or synthetically accessible methylhydrazine, in an inert solvent such as toluene, and the like, at a temperature of about 100° C., to provide a compound of formula (XXXIX), where PG is Boc.

Derivation of a compound of formula (XXIX), with a sulfonate-based leaving group such as trifluoromethanesulfonyl (triflate), is achieved by is by reaction with a triflating agent such as trifluoromethanesulfonic anhydride (Tf$_2$O), a base such as triethylamine (TEA), pyridine, and the like, in a suitable solvent such as DCM and the like. Milder triflating agents such as N-phenylbis(trifluoromethanesulfonimide) (Tf$_2$NPh), a base such as TEA, DIEA, and the like, in a suitable solvent such as DCM, and the like; are used for better selectivity, to provide a compound of formula (XLa) and (XLb), where PG is BOC. Single enantiomers were isolated by Chiral SFC purification of (XLa) and (XLb).

SCHEME 17

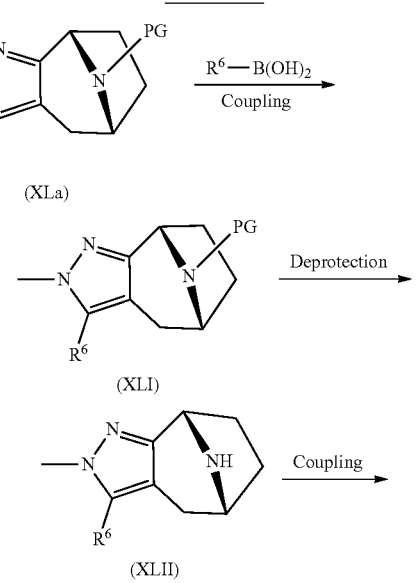

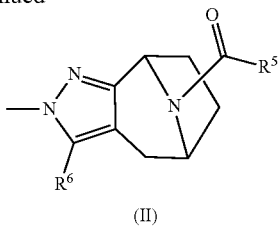

(II)

According to SCHEME 17, a single enantiomer compound of formula (XLa) (as well as XLb, or the racemic mixture), is reacted in a coupling reaction with a suitably substituted commercially available or synthetically accessible alkyl, cycloalkyl, aryl or heteroaryl boronic acid, boronate ester, and the like, in the presence of a palladium catalyst, under Suzuki coupling conditions previously described to provide a compound of formula (XLI). Deprotection of the protecting group is achieved according to methods previously described. Subsequent amide coupling of a compound of formula (XLII), with a suitably substituted commercially available or synthetically accessible acid, provides a compound of Formula (II).

Compounds of Formula (I) (as well as compounds of Formula (IA), (IB), (IC), (ID), or (II)) may be converted to their corresponding salts using methods known to one of ordinary skill in the art. For example, an amine of Formula (I) is treated with trifluoroacetic acid, HCl, or citric acid in a solvent such as $Et_2O$, $CH_2Cl_2$, THF, MeOH, chloroform, or isopropanol to provide the corresponding salt form. Alternately, trifluoroacetic acid or formic acid salts are obtained as a result of reverse phase HPLC purification conditions. Crystalline forms of pharmaceutically acceptable salts of compounds of Formula (I) (as well as compounds of Formula (IA), (IB), (IC), (ID), or (II)) may be obtained in crystalline form by recrystallization from polar solvents (including mixtures of polar solvents and aqueous mixtures of polar solvents) or from non-polar solvents (including mixtures of non-polar solvents).

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention.

Compounds prepared according to the schemes described above may be obtained as single forms, such as single enantiomers, by form-specific synthesis, or by resolution. Compounds prepared according to the schemes above may alternately be obtained as mixtures of various forms, such as racemic (1:1) or non-racemic (not 1:1) mixtures. Where racemic and non-racemic mixtures of enantiomers are obtained, single enantiomers may be isolated using conventional separation methods known to one of ordinary skill in the art, such as chiral chromatography, recrystallization, diastereomeric salt formation, derivatization into diastereomeric adducts, biotransformation, or enzymatic transformation. Where regioisomeric or diastereomeric mixtures are obtained, as applicable, single isomers may be separated using conventional methods such as chromatography or crystallization.

The following specific examples are provided to further illustrate the invention and various preferred embodiments.

EXAMPLES

In obtaining the compounds described in the examples below and the corresponding analytical data, the following experimental and analytical protocols were followed unless otherwise indicated.

Unless otherwise stated, reaction mixtures were magnetically stirred at room temperature (rt) under a nitrogen atmosphere. Where solutions were "dried," they were generally dried over a drying agent such as $Na_2SO_4$ or $MgSO_4$. Where mixtures, solutions, and extracts were "concentrated", they were typically concentrated on a rotary evaporator under reduced pressure. Reactions under microwave irradiation conditions were carried out in a Biotage Initiator or CEM (Microwave Reactor) Discover instrument.

Normal-phase silica gel chromatography (FCC) was performed on silica gel ($SiO_2$) using prepacked cartridges.

Preparative reverse-phase high performance liquid chromatography (RP HPLC) was performed on either:

METHOD A. An Agilent HPLC with an Xterra Prep RP18 column (5 µM, 30×100 or 50×150 mm) or an XBridge C18 OBD column (5 µM, 30×100 or 50×150 mm), and a mobile phase of 5% ACN in 20 mM $NH_4OH$ was held for 2 min, then a gradient of 5-99% ACN over 15 min, then held at 99% ACN for 5 min, with a flow rate of 40 or 80 mL/min.

or

METHOD B. A Shimadzu LC-8A Series HPLC with an Inertsil ODS-3 column (3 m, 30×100 mm, T=45° C.), mobile phase of 5% ACN in $H_2O$ (both with 0.05% TFA) was held for 1 min, then a gradient of 5-99% ACN over 6 min, then held at 99% ACN for 3 min, with a flow rate of 80 mL/min. or METHOD C. A Shimadzu LC-8A Series HPLC with an XBridge C18 OBD column (5 m, 50×100 mm), mobile phase of 5% ACN in $H_2O$ (both with 0.05% TFA) was held for 1 min, then a gradient of 5-99% ACN over 14 min, then held at 99% ACN for 10 min, with a flow rate of 80 mL/min.

or

METHOD D. A Gilson HPLC with an XBridge C18 column (5 µm, 100×50 mm), mobile phase of 5-99% ACN in 20 mM $NH_4OH$ over 10 min and then hold at 99% ACN for 2 min, at a flow rate of 80 mL/min.

METHOD E: An Agilent HPLC with a Gemini-NX C18 column (5 µM, 30×100 mm) and a mobile phase of 0-90% ACN in 10 mM $(NH_4)HCO_3$ over 16 min, with a flow rate of 30 mL/min Preparative supercritical fluid high performance liquid chromatography (SFC) was performed either on a Jasco preparative SFC system, an APS 1010 system from Berger instruments, or a SFC-PICLAB-PREP 200 (PIC SOLUTION, Avignon, France). The separations were conducted at 100 to 150 bar with a flow rate ranging from 40 to 60 mL/min. The column was heated to 35 to 40° C.

Mass spectra (MS) were obtained on an Agilent series 1100 MSD using electrospray ionization (ESI) in positive mode unless otherwise indicated. Calculated (calcd.) mass corresponds to the exact mass.

Nuclear magnetic resonance (NMR) spectra were obtained on Bruker model DRX spectrometers. Definitions for multiplicity are as follows: s=singlet, d=doublet, t=triplet, q=quartet, m=multiplet, br=broad. It will be understood that for compounds comprising an exchangeable proton, said proton may or may not be visible on an NMR spectrum depending on the choice of solvent used for running the NMR spectrum and the concentration of the compound in the solution.

Chemical names were generated using ChemDraw Ultra 17.1 (CambridgeSoft Corp., Cambridge, MA) or OEMetaChem V1.4.0.4 (Open Eye).

Compounds designated as R* or S* are enantiopure compounds where the absolute configuration was not determined.

Intermediate 1: racemic-(5R,9S)-2-Methyl-3-phenyl-4,5,6,7,8,9-hexahydro-2H-5,9-epiminocycloocta[c]pyrazole

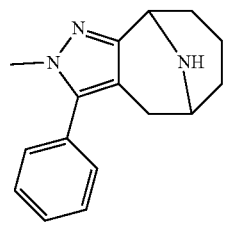 [SMILES: Cn1nc2c(c1-c1ccccc1)CC1CCCC2N1]

Step A: racemic-tert-Butyl (5R,9S)-2-methyl-3-oxo-2,3,4,5,6,7,8,9-octahydro-1H-5,9-epiminocycloocta[c]pyrazole-10-carboxylate. To a solution of racemic-9-(tert-butyl) 3-ethyl (1S,5R)-2-oxo-9-azabicyclo[3.3.1] nonane-3,9-dicarboxylate (2.5 g, 8.4 mmol) in toluene (30.0 mL) was added methylhydrazine (0.66 mL, 12.6 mmol) and the resulting mixture was heated at 110° C. for 3 h. After cooling to rt, concentrated the solvent in vacuo and the crude residue was purified (FCC, SiO$_2$; 0-10% MeOH/DCM) to give the title compound as an oil (2.3 g, 91% yield). MS (ESI): mass calcd. for $C_{15}H_{23}N_3O_3$, 293.1; m/z found, 294.1 [M+H]$^+$.

Step B: racemic-tert-Butyl (5R,9S)-2-methyl-3-(((trifluoromethyl)sulfonyl) oxy)-4,5,6,7,8,9-hexahydro-2H-5,9-epiminocycloocta[c]pyrazole-10-carboxylate. To a solution of racemic-tert-butyl (5R,9S)-2-methyl-3-oxo-2,3,4,5,6,7,8,9-octahydro-1H-5,9-epiminocycloocta[c]pyrazole-10-carboxylate (2.0 g, 6.8 mmol) in dichloromethane (DCM) (30.0 mL) was added N,N-diisopropylethylamine (DIEA/DIPEA/Hünigs Base) (1.3 mL, 7.5 mmol) followed by the addition of 1,1,1-trifluoro-N-phenyl-N-((trifluoromethyl)sulfonyl) methanesulfonamide (2.7 g, 7.5 mmol). The reaction mixture was stirred at rt for 5 h, concentrated the solvent in vacuo and the crude residue was purified (FCC, SiO$_2$; 0-20% EtOAc/hexanes@220 nm wavelength) to afford the title compound as an oil (2.5 g, 86% yield). MS (ESI): mass calcd. for $C_{16}H_{22}F_3N_3O_5S$, 425.1; m/z found, 369.9 [M+2H-tertbutyl]$^+$.

Step C: racemic-tert-Butyl (5R,9S)-2-methyl-3-phenyl-4,5,6,7,8,9-hexahydro-2H-5,9-epiminocycloocta[c]pyrazole-10-carboxylate. A solution of racemic-tert-butyl (5R,9S)-2-methyl-3-(((trifluoromethyl)sulfonyl)oxy)-4,5,6,7,8,9-hexahydro-2H-5,9-epiminocycloocta[c]pyrazole-10-carboxylate (750 mg, 1.8 mmol), phenylboronic acid (645 mg, 5.3 mmol), potassium phosphate (1.1 g, 5.3 mmol), and 1,1'-ferrocenediyl-bis(diphenylphosphine) (dppf) (60 mg, 0.1 mmol) in dioxane (6.0 mL) was degassed with nitrogen for 10 minutes. [1,1'-Bis(diphenylphosphino)ferrocene]dichloropalladium(II) (PdCl$_2$(dppf)) (195 mg, 0.3 mmol) was added at once and the resulting mixture was degassed with nitrogen for an additional 10 minutes. The reaction mixture was heated in microwave reactor at 140° C. for 30 minutes. After cooling to rt, the crude mixture was diluted with brine and extracted with DCM (×3). The combined organic extracts were dried over Na$_2$SO$_4$, concentrated in vacuo and purified (FCC, SiO$_2$; 0-50% EtOAc/hexanes) to afford product as a white solid (605 mg, 97% yield). MS (ESI): mass calcd. for $C_{21}H_{27}N_3O_2$, 353.2; m/z found, 354.1 [M+H]$^+$.

Step D. racemic-(5R,9S)-2-Methyl-3-phenyl-4,5,6,7,8,9-hexahydro-2H-5,9-epiminocycloocta[c]pyrazole. To a solution of racemic-tert-butyl (5R,9S)-2-methyl-3-phenyl-4,5,6,7,8,9-hexahydro-2H-5,9-epiminocycloocta[c]pyrazole-10-carboxylate in dichloromethane (DCM) (2.0 mL) was added trifluoroacetic acid (2.0 mL) and the mixture was stirred at room temperature for 1 h. The solvent was concentrated in vacuo to obtain the title compound as white solid (475 mg, 95% yield). MS (ESI): mass calcd. for $C_{13}H_{15}N_3$, 253.1; m/z found, 254.1 [M+H]$^+$.

Intermediate 2: tert-Butyl (5R,9S)-2-methyl-3-(((trifluoromethyl)sulfonyl) oxy)-4,5,6,7,8,9-hexahydro-2H-5,9-epiminocycloocta[c]pyrazole-10-carboxylate

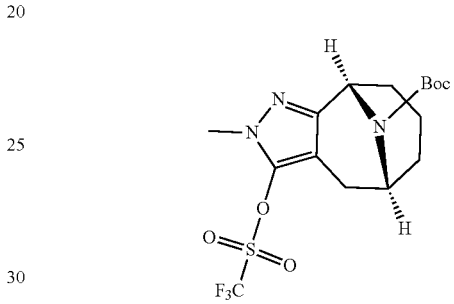

Method A:

Step A: (4Z)-9-Oxabicyclo[6.1.0]non-4-ene. To a solution of 1,5-cyclooctadiene (125 g, 116 mmol) in tetrahydrofuran (175 mL) was added a solution of 3-chloroperoxybenzoic acid (m-CPBA) (55%, 300 g, 956 mmol) in chloroform (1.75 L) dropwise, and the reaction was stirred at room temperature for 42 h. The reaction mixture was washed with 20% sodium bisulfite (4×1 L), saturated sodium bicarbonate (4×1 L) and brine (2×1 L). The organic layer was dried over sodium sulfate, filtered and evaporated. The mixture was distilled under vacuum (bp=40° C. at 2 mm Hg) to give the title compound (74.2 g, 51% yield) as a colorless liquid. MS (ESI): mass calcd. for $C_8H_{12}O$, 124.1; m/z found, 123.0 [M−H]$^-$.

Step B: (1S,8S,Z)-8-(((R)-1-Phenylethyl)amino)cyclooct-4-en-1-ol. To a solution of ytterbium(III) trifluoromethanesulfonate hydrate (12.5 g, 20.2 mmol) in distilled tetrahydrofuran (200 mL) was added (R)-(+)-α-methylbenzyl amine (77 mL, 604 mmol, 0.95 g/mL) and 1,2-epoxy-5-cyclooctene (50 g, 403 mmol) in distilled tetrahydrofuran (300 mL). The reaction mixture was stirred in a sealed tube at 100° C. for 48 h, poured into water (500 mL), and the volatiles were evaporated. The aqueous layer was extracted with dichloromethane (3×500 mL) and the combined organic layers were dried over sodium sulfate, filtered, and evaporated to give the title compound (120 g, crude) as a yellow oil. The reaction was repeated on a 99 g scale (798 mmol). The crude products from both reactions were combined and converted to the hydrochloride salt in 2 batches. To 20 g of the crude product was added hydrogen chloride (3.88 M in diethyl ether, 82 mL, 318 mmol). The precipitate was collected and the first crop (3.34 g, 11.8 mmol, 14%) was isolated as a white crystalline solid. To the remaining crude product (280 g, 114 mmol) in ethyl acetate (560 mL) was added hydrogen chloride (3.88 M in diethyl ether, 560 mL, 2173 mmol). The suspension was stirred at room temperature for 30 min and the precipitate was collected. The solid was suspended in ethyl acetate saturated with water (5.6 L) and stirred at 50° C. for 30 min. After cooling to room temperature, the precipitate was collected and the second crop (78 g, 277 mmol, 24% yield) was isolated as a white crystalline solid. MS (ESI): mass calcd. for $C_{16}H_{23}NO$, 245.2; m/z found, m/z=246.2 [M+H]$^+$. $^1$H NMR (400 MHz, CDCl$_3$) δ 7.46-7.18 (m, 6H), 4.33-4.09 (m, 2H), 3.88 (br. s., 4H), 3.42 (s, 1H), 3.02-2.82 (m, 1H), 2.05-1.85 (m, 2H), 1.79-1.60 (m, 2H), 1.50 (d, J=6.8 Hz, 2H), 1.38-1.27 (m, 2H)

Step C: (1S,2S,5R)-9-((R)-1-phenylethyl)-9-azabicyclo [3.3.1]nonan-2-ol. To a solution of mercury(II) chloride (104 g, 383 mmol) in tetrahydrofuran (750 mL) and water (320 mL) was added a solution of (1S,8S,Z)-8-[[(1R)-1-phenylethyl]amino]cyclooct-4-en-1-ol (98.0 g, 348 mmol) in tetrahydrofuran (350 mL) and sodium hydroxide (3 M, 116 mL, 348 mmol) and the reaction was stirred at room temperature for 1 d. To the reaction mixture was added sodium hydroxide (3 M, 280 mL, 840 mmol) and a solution of sodium borohydride (13.0 g, 344 mmol) in sodium hydroxide (3 M, 70 mL, 210 mmol) at 0° C. and the reaction was stirred at room temperature for 1 d to give the title compound (98 g), which was used in the next step without further purification.

LCMS: 58%, t$_R$=2.019 min, m/z=246.1 [M+H]$^+$.

Step D: tert-Butyl (1S,2S,5R)-2-hydroxy-9-azabicyclo [3.3.1]nonane-9-carboxylate. A mixture of (1R,2S,5R)-9-[(1R)-1-phenylethyl]-9-azabicyclo[3.3.1]nonan-4-ol (98.0 g, crude) and 10% palladium on carbon (42.5 g) in methanol (2.5 L) was stirred at room temperature for 2 h under hydrogen. To the reaction mixture was added di-tert-butyl dicarbonate (175 g, 802 mmol) and triethylamine (56 mL, 402 mmol) and the reaction was stirred at room temperature for 18 h. The reaction mixture was filtered through a pad of Celite®; and the Celite® was washed with methanol (2×500 mL). The combined filtrates were concentrated under reduced pressure and the residue was purified by silica gel column chromatography eluting with ethyl acetate. The residue was purified by gradient silica gel column chromatography eluting with heptane:ethyl acetate (100:0→3:1) to give a first crop of the title compound (43.4 g, 180 mmol, 44% yield) as a yellow oil. $^1$H NMR (500 MHz, DMSO-d$_6$) δ 4.94-4.87 (m, 1H), 4.08-3.87 (m, 2H), 3.66-3.53 (m, 1H), 1.96-1.31 (m, 10H), 1.39 (s, 9H).

Step E: tert-Butyl (1R,5R)-2-oxo-9-azabicyclo[3.3.1] nonane-9-carboxylate. To a solution of oxalyl chloride (12.9 mL, 152 mmol) in dichloromethane (560 mL) was added dimethyl sulfoxide (21.5 mL, 303 mmol) dropwise at −78° C. To the reaction mixture was added a solution of tert-butyl (1R,2S,5R)-2-hydroxy-9-azabicyclo[3.3.1]nonane-9-carboxylate (24.5 g, 102 mmol) in dichloromethane (140 mL) and the reaction was stirred at −78° C. for 30 min. Triethylamine (TEA)(85 mL, 61 mmol) was added and the reaction was allowed to warm to room temperature and stirred for 2 h. The reaction mixture was washed with water (3×300 mL), dried over sodium sulfate, filtered and evaporated. The residue was purified by silica gel column chromatography eluting with heptane:ethyl acetate (4:1) to afford the title compound (19.5 g, 82 mmol, 80% yield) as a white crystalline solid. $[α]_D^{25}$+116.0° (c 0.110, MeOH). MS (ESI): mass calcd. for $C_{13}H_{21}NO_3$, 239.2; m/z found, 262.1 [M+Na]*. $^1$H NMR (500 MHz, DMSO-d$_6$) δ 4.49-4.35 (m, 1H), 4.34-4.23 (m, 1H), 2.43-2.24 (m, 3H), 1.83-1.74 (m, 1H), 1.71-1.56 (m, 2H), 1.57-1.33 (m, 4H), 1.43, 1.39 (s, 9H).

Step F: 9-(tert-Butyl) 3-ethyl (1S,5R)-2-oxo-9-azabicyclo [3.3.1]nonane-3,9-dicarboxylate. To a solution of tert-butyl (1R,5R)-2-oxo-9-azabicyclo[3.3.1]nonane-9-carboxylate (8.2 g, 34.3 mmol) in distilled tetrahydrofuran (180 mL) was added lithium bis(trimethylsilyl)amide (LiHMDS) (1 M in tetrahydrofuran, 41.2 mL, 41.2 mmol) at −78° C. and the reaction was stirred at −78° C. for 30 min. To the reaction mixture was added a solution of ethyl cyanoformate (4.4 mL, 44.5 mmol) in distilled tetrahydrofuran (20 mL) and the reaction was stirred at −78° C. for 1 h. The reaction was quenched with saturated ammonium chloride (200 mL). The aqueous layer was extracted with dichloromethane (2×200 mL). The combined organic layers were washed with water (2×150 mL), dried over sodium sulfate, filtered and evaporated. The residue was purified by silica gel column chromatography eluting with heptane:ethyl acetate (4:1) to afford the title compound (5.5 g, 18 mmol, 51% yield) as a pale yellow oil. $[α]_D^{25}$ −45.0° (c 0.185, MeOH). MS (ESI): mass calcd. for $C_{16}H_{25}NO_5$, 311.2; m/z found, 256.1 [M+2H-tBu]$^+$. $^1$H NMR (300 MHz, DMSO-d$_6$) δ 11.83 (s, 1H), 4.52-4.37 (m, 1H), 4.36-4.25 (m, 1H), 4.20 (q, J=7.1 Hz, 2H), 2.66-2.49 (m, 1H), 2.09 (d, J=16.5 Hz, 1H), 1.76-1.45 (m, 6H), 1.39 (s, 9H), 1.24 (t, J=7.1 Hz, 3H).

Step G: tert-Butyl (5R,9S)-2-methyl-3-oxo-2,3,4,5,6,7,8, 9-octahydro-1H-5,9-epiminocycloocta[c]pyrazole-10-carboxylate. To a mixture of 9-(tert-butyl) 3-ethyl (1S,5R)-2-oxo-9-azabicyclo[3.3.1]nonane-3,9-dicarboxylate (20.4 g, 65.5 mmol) in acetic acid (AcOH) (260 mL) was added methylhydrazine (5.2 mL, 99.3 mmol, 0.88 g/mL) and the reaction was stirred at 80° C. for 8 h. The reaction mixture was evaporated and the residue was purified by silica gel column chromatography eluting with ethyl acetate:methanol (10:1) to give the title compound (15.4 g, 52.5 mmol, 80% yield). MS (ESI): mass calcd. for $C_{15}H_{23}N_3O_3$, 293.2; m/z found, 294.2 [M+H]$^+$.

Step H: tert-Butyl (5R,9S)-2-methyl-3-(((trifluoromethyl) sulfonyl)oxy)-4,5,6,7,8,9-hexahydro-2H-5,9-epiminocycloocta[c]pyrazole-10-carboxylate. To a solution of tert-butyl (5R,9S)-2-methyl-3-oxo-2,3,4,5,6,7,8,9-octahydro-1H-5,9-epiminocycloocta[c]pyrazole-10-carboxylate (20.0 g, 68.2 mmol) in dichloromethane (300 mL) was added N,N-diisopropylethylamine (13 mL, 75.1 mmol), and N-phenyl-bis(trifluoromethanesulfonimide) (26.8 g, 75.0 mmol) and the reaction was stirred at room temperature for 18 h. The reaction mixture was washed with saturated sodium bicarbonate (2×200 mL), 10% potassium bisulfate (2×200 mL) and brine (1×200 mL), dried over sodium sulfate, filtered and evaporated. The residue was purified by gradient silica column chromatography eluting with heptane:ethyl acetate (6:1→4:1). The residue was dissolved in ethyl acetate (100 mL) and evaporated. The less pure fractions were combined and evaporated. The residue was dissolved in dichloromethane (100 mL), washed with saturated sodium bicarbonate (3×150 mL), dried over sodium sulfate, filtered and evaporated.

The products were combined to give the title compound (16.4 g, 39 mmol, 56% yield) as a colorless oil. MS (ESI): mass calcd. for $C_{16}H_{22}F_3N_3O_5S$, 425.1; m/z found, 370.1 [M+2H-tbutyl]+. $^1$H NMR (500 MHz, DMSO-d$_6$) δ 5.06 (d, J=18.9 Hz, 1H), 4.48 (d, J=31.6 Hz, 1H), 3.73 (s, 3H), 2.84 (dd, J=16.3, 7.4 Hz, 1H), 2.44 (d, J=16.3 Hz, 1H), 1.78-1.61 (m, 3H), 1.59-1.41 (m, 2H), 1.38 (s, 9H), 1.27-1.16 (m, 1H). Optical rotation: $[α]_D^{25}$+10.0° (c 0.15, MeOH).

Method B:

The title compound was prepared by Chiral SFC purification of racemic-tert-butyl (5R,9S)-2-methyl-3-(((trifluoromethyl)sulfonyl) oxy)-4,5,6,7,8,9-hexahydro-2H-5,9-epiminocycloocta[c]pyrazole-10-carboxylate (Step B, Intermediate 1) using stationary phase: Lux Cellulose-2 5 μm 250*30 mm, Mobile phase: 85% $CO_2$, 15% iPrOH (single enantiomer; 0.93 min retention time). MS (ESI): mass calcd. for $C_{16}H_{22}F_3N_3O_5S$, 425.1; m/z found, 370.0 [M+2H-tbutyl]$^+$. $^1$H NMR (500 MHz, DMSO-d$_6$) δ 5.06 (d, J=18.9 Hz, 1H), 4.48 (d, J=31.6 Hz, 1H), 3.73 (s, 3H), 2.84 (dd, J=16.3, 7.4 Hz, 1H), 2.44 (d, J=16.3 Hz, 1H), 1.78-1.61 (m, 3H), 1.59-1.41 (m, 2H), 1.38 (s, 9H), 1.27-1.16 (m, 1H).

Intermediate 3: tert-Butyl (5S,9R)-2-methyl-3-(((trifluoromethyl)sulfonyl) oxy)-4,5,6,7,8,9-hexahydro-2H-5,9-epiminocycloocta[c]pyrazole-10-carboxylate

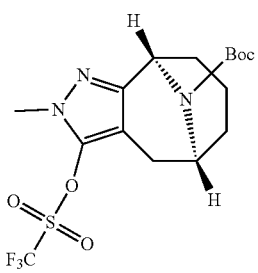 [SMILES: Cn1nc2c(c1OS(=O)(=O)C(F)(F)F)C[C@@H]1CCC[C@H]2N1CC(=O)OC(C)(C)C]

The title compound was obtained from the same chiral SFC purification of Intermediate 2 (Method B) used to provide the title compound (single enantiomer; 0.48 min retention time). MS (ESI): mass calcd. for $C_{16}H_{22}F_3N_3O_5S$, 425.1; m/z found, 370.0 [M+2H-tbutyl]$^+$.

Intermediate 4: racemic-(5R,9S)-3-(3-Fluorophenyl)-2-methyl-4,5,6,7,8,9-hexahydro-2H-5,9-epiminocycloocta[c]pyrazole

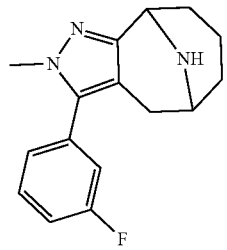

The title compound is prepared in a manner analogous to Intermediate 1 using (3-fluorophenyl) boronic acid instead of phenylboronic acid in Step C. MS(ESI): mass calcd. for $C_{16}H_{18}FN_3$, 271.1; m/z found, 272.1 [M+H]$^+$.

Intermediate 5: racemic-(5R,9S)-3-(4-Fluorophenyl)-2-methyl-4,5,6,7,8,9-hexahydro-2H-5,9-epiminocycloocta[c]pyrazole

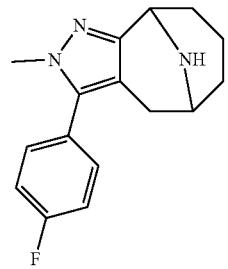 [SMILES: Cn1nc2c(c1-c1ccc(F)cc1)CC1CCCC2N1]

The title compound is prepared in a manner analogous to Intermediate 1 using (4-fluorophenyl) boronic acid instead of phenylboronic acid in Step C. MS(ESI): mass calcd. for $C_{16}H_{18}FN_3$, 271.1; m/z found, 272.1 [M+H]$^+$.

Intermediate 6: racemic-(5R,9S)-3-(3-Chlorophenyl)-2-methyl-4,5,6,7,8,9-hexahydro-2H-5,9-epiminocycloocta[c]pyrazole

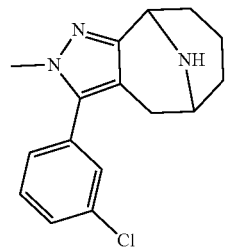 [SMILES: Cn1nc2c(c1-c1cccc(Cl)c1)CC1CCCC2N1]

The title compound was prepared in a manner analogous to Intermediate 1 using (3-chlorophenyl) boronic acid instead of phenylboronic acid in Step C. MS (ESI): mass calcd. for $C_{16}H_{18}ClN_3$, 287.1; m/z found, 288.1 [M+H]$^+$.

Intermediate 7: racemic-(5R,9S)-3-(3,5-Difluorophenyl)-2-methyl-4,5,6,7,8,9-hexahydro-2H-5,9-epiminocycloocta[c]pyrazole

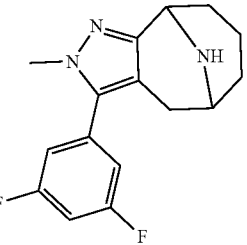

The title compound was prepared in a manner analogous to Intermediate 1 using (3,5-difluorophenyl) boronic acid instead of phenylboronic acid in Step C. MS (ESI): mass calcd. for $C_{16}H_{18}ClN_3$, 289.1; m/z found, 290.1 [M+H]$^+$.

Intermediate 8: racemic-(5R,9S)-3-(3,4-Difluorophenyl)-2-methyl-4,5,6,7,8,9-hexahydro-2H-5,9-epiminocycloocta[c]pyrazole

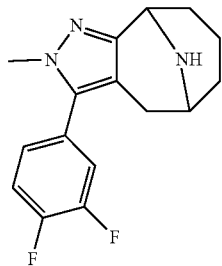 [SMILES: Cn1nc2c(c1-c1ccc(F)c(F)c1)CC1CCCC2N1]

The title compound was prepared in a manner analogous to Intermediate 1 using (3,4-difluorophenyl) boronic acid instead of phenylboronic acid in Step C. MS (ESI): mass calcd. for $C_{16}H_{18}ClN_3$, 289.1; m/z found, 290.1 [M+H]$^+$.

Intermediate 9: racemic-(5R,9S)-2-Methyl-3-(5-(trifluoromethyl) thiophen-2-yl)-4,5,6,7,8,9-hexahydro-2H-5,9-epiminocycloocta[c]pyrazole

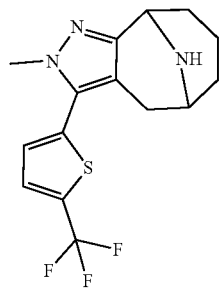 [SMILES: Cn1nc2c(c1-c1ccc(C(F)(F)F)s1)CC1CCCC2N1]

The title compound was prepared in a manner analogous to Intermediate 1 using (5-(trifluoromethyl) thiophen-2-yl) boronic acid instead of phenylboronic acid in Step C. MS (ESI): mass calcd. for $C_{16}H_{18}ClN_3$, 327.1; m/z found, 328.1 [M+H]$^+$.

Intermediate 10: racemic-(5R,9S)-3-(3-(Difluoromethyl)-4-fluorophenyl)-2-methyl-4,5,6,7,8,9-hexahydro-2H-5,9-epiminocycloocta[c]pyrazole

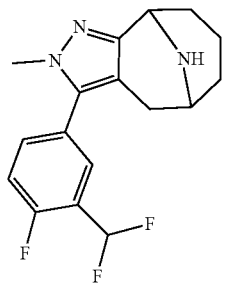 [SMILES: Cn1nc2c(c1-c1ccc(F)c(C(F)F)c1)CC1CCCC2N1]

The title compound was prepared in a manner analogous to Intermediate 1 using (3-(difluoromethyl)-4-fluorophenyl) boronic acid instead of phenylboronic acid in Step C. MS (ESI): mass calcd. for $C_{16}H_{18}ClN_3$, 327.1; m/z found, 328.1 [M+H]$^+$.

Intermediate 11: racemic-(5R,9S)-2-Cyclopropyl-3-(3-fluorophenyl)-4,5,6,7,8,9-hexahydro-2H-5,9-epiminocycloocta[c]pyrazole

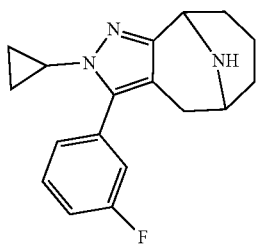 [SMILES: Fc1cccc(-c2c3c(nn2C2CC2)C2CCCC(C3)N2)c1]

The title compound was prepared in a manner analogous to Intermediate 1 using cyclopropylhydrazine hydrochloride instead of methylhydrazine in Step A and (3-fluorophenyl) boronic acid instead of phenylboronic acid in Step C. MS (ESI): mass calcd. for $C_{18}H_{20}FN_3$, 297.1; m/z found, 298.1 [M+H]$^+$.

Intermediate 12: (5R,9S)-3-(3,5-Difluorophenyl)-2-methyl-4,5,6,7,8,9-hexahydro-2H-5,9-epiminocycloocta[c]pyrazole

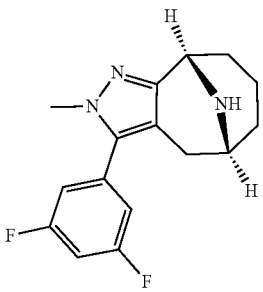 [SMILES: Cn1nc2c(c1-c1cc(F)cc(F)c1)C[C@H]1CCC[C@@H]2N1]

Step A: tert-Butyl (5R,9S)-3-(3,5-difluorophenyl)-2-methyl-4,5,6,7,8,9-hexahydro-2H-5,9-epiminocycloocta[c]pyrazole-10-carboxylate. A microwave vial was charged with a solution of tert-butyl (5R,9S)-2-methyl-3-(((trifluoromethyl)sulfonyl)oxy)-4,5,6,7,8,9-hexahydro-2H-5,9-epiminocycloocta[c]pyrazole-10-carboxylate (Intermediate 2) (500 mg, 1.2 mmol), (3,5-difluorophenyl)boronic acid (223 mg, 1.4 mmol), chloro(2-dicyclohexylphosphino-2',4',6'-triisopropyl-1,1'-biphenyl)[2-(2'-amino-1,1'-biphenyl)]palladium(II) (XPhos Pd G2) (93 mg, 0.12 mmol), and sat. aq. Na$_2$CO$_3$ (8.0 mL) in dioxane (2.0 mL). The vial was evacuated and degassed with N$_2$ (×3), then capped and sealed. The mixture was heated in a microwave reactor at 110° C. for 30 minutes. After cooling to rt, the crude mixture was diluted with brine and extracted with DCM (×3). The combined organic extracts were dried over Na$_2$SO$_4$, concentrated in vacuo and purified (FCC, SiO$_2$; 0-100% EtOAc/hexanes) to afford product as a white solid (356 mg, 78% yield). MS (ESI): mass calcd. for $C_{21}H_{25}F_2N_3O_2$, 389.1; m/z found, 334.0 [M+2H-tbutyl]$^+$.

Step B: (5R,9S)-3-(3,5-Difluorophenyl)-2-methyl-4,5,6,7,8,9-hexahydro-2H-5,9-epiminocycloocta[c]pyrazole. To a solution of tert-butyl (5R,9S)-3-(3,5-difluorophenyl)-2-methyl-4,5,6,7,8,9-hexahydro-2H-5,9-epiminocycloocta[c]pyrazole-10-carboxylate in DCM (2.0 mL) was added trifluoroacetic acid (2.0 mL) and the mixture was stirred at rt for 1 h. The solvent was concentrated in vacuo and purified by reverse-phase HPLC using a XBridge C18 column (5 μm, 100×4.6 mm), mobile phase of 10-100% ACN in 20 mM NH$_4$OH, to afford the title compound as white solid (225 mg, 86% yield). MS (ESI): mass calcd. for C$_{16}$H$_{17}$F$_2$N$_3$, 289.1; m/z found, 290.1[M+H]$^+$. $^1$H NMR (500 MHz, DMSO-d$_6$) δ 7.36-7.28 (m, 1H), 7.28-7.20 (m, 2H), 3.95 (t, J=3.3 Hz, 1H), 3.78 (s, 3H), 2.86 (dd, J=16.1, 7.3 Hz, 1H), 2.34 (d, J=16.1 Hz, 2H), 1.86-1.64 (m, 2H), 1.62-1.44 (m, 2H), 1.40-1.21 (m, 2H).

Intermediate 13: (5R,9S)-3-(3-Fluorophenyl)-2-methyl-4,5,6,7,8,9-hexahydro-2H-5,9-epiminocycloocta[c]pyrazole

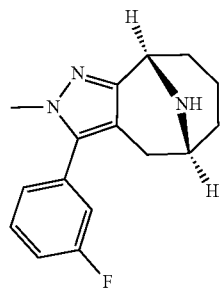 [SMILES: Cn1nc2c(c1-c1cccc(F)c1)C[C@H]1CCC[C@@H]2N1]

The title compound was prepared in a manner analogous to Intermediate 12 using (3-fluorophenyl) boronic acid instead of (3,5-difluorophenyl) boronic acid. MS (ESI): mass calcd. for C$_{16}$H$_{18}$FN$_3$, 271.1; m/z found, 272.1 [M+H]$^+$.

Intermediate 14: (5R,9S)-3-(3-Chlorophenyl)-2-methyl-4,5,6,7,8,9-hexahydro-2H-5,9-epiminocycloocta[c]pyrazole

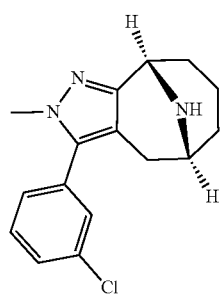 [SMILES: Cn1nc2c(c1-c1cccc(Cl)c1)C[C@H]1CCC[C@@H]2N1]

The title compound was prepared in a manner analogous to Intermediate 12 using (3-chlorophenyl) boronic acid instead of (3,5-difluorophenyl) boronic acid. MS (ESI): mass calcd. for C$_{16}$H$_{18}$ClFN$_3$, 287.1; m/z found, 288.1 [M+H]$^+$. $^1$H NMR (500 MHz, DMSO-d$_6$) δ 7.59-7.57 (m, 1H), 7.57-7.54 (m, 1H), 7.54-7.51 (m, 1H), 7.48-7.44 (m, 1H), 4.43-4.36 (m, 1H), 3.79 (s, 3H), 3.68-3.61 (m, 1H), 2.97 (dd, J=16.4, 7.4 Hz, 1H), 2.55 (d, J=16.4 Hz, 1H), 1.97-1.81 (m, 2H), 1.74-1.65 (m, 1H), 1.65-1.56 (m, 1H), 1.47-1.39 (m, 1H), 1.37-1.25 (m, 1H).

Intermediate 15: (5R,9S)-3-(3-Fluoro-5-methoxyphenyl)-2-methyl-4,5,6,7,8,9-hexahydro-2H-5,9-epiminocycloocta[c]pyrazole

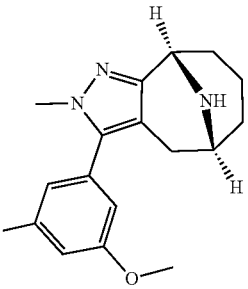

The title compound was prepared in a manner analogous to Intermediate 12 using (3-fluoro-5-methoxyphenyl) boronic acid instead of (3,5-difluorophenyl) boronic acid. MS (ESI): mass calcd. for C$_{17}$H$_{20}$FN$_3$O, 301.1; m/z found, 302.1 [M+H]$^+$.

Intermediate 16: (5R,9S)-3-(3-Fluoro-5-(trifluoromethyl) phenyl)-2-methyl-4,5,6,7,8,9-hexahydro-2H-5,9-epiminocycloocta[c]pyrazole

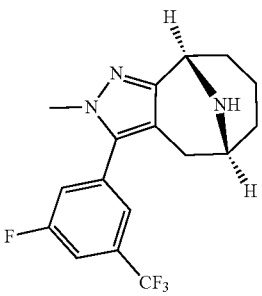 [SMILES: Cn1nc2c(c1-c1cc(F)cc(C(F)(F)F)c1)C[C@H]1CCC[C@@H]2N1]

The title compound was prepared in a manner analogous to Intermediate 12 using (3-fluoro-5-(trifluoromethyl) phenyl) boronic acid instead of (3,5-difluorophenyl) boronic acid. MS (ESI): mass calcd. for C$_{17}$H$_{17}$F$_4$N$_3$, 339.1; m/z found, 340.1 [M+H]$^+$.

Intermediate 17: (5R,9S)-3-(3-Chloro-5-methoxyphenyl)-2-methyl-4,5,6,7,8,9-hexahydro-2H-5,9-epiminocycloocta[c]pyrazole

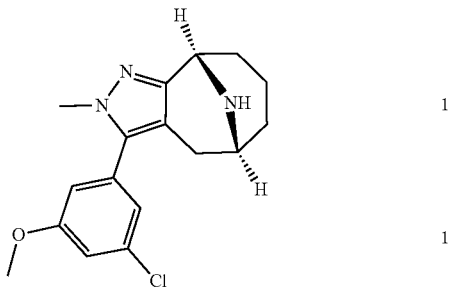

The title compound was prepared in a manner analogous to Intermediate 12 using (3-chloro-5-methoxyphenyl) boronic acid instead of (3,5-difluorophenyl) boronic acid. MS (ESI): mass calcd. for $C_{17}H_{20}ClN_3O$, 317.1; m/z found, 318.1 [M+H]$^+$.

Intermediate 18: (5R,9S)-3-(3-Chloro-4-methoxyphenyl)-2-methyl-4,5,6,7,8,9-hexahydro-2H-5,9-epiminocycloocta[c]pyrazole

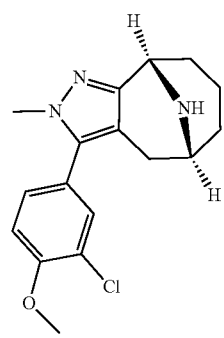 [SMILES: COc1ccc(-c2c3c(nn2C)[C@@H]2CCC[C@H](C3)N2)cc1Cl]

The title compound was prepared in a manner analogous to Intermediate 12 using (3-chloro-4-methoxyphenyl) boronic acid instead of (3,5-difluorophenyl) boronic acid. MS (ESI): mass calcd. for $C_{17}H_{20}ClN_3O$, 317.1; m/z found, 318.1 [M+H]$^+$.

Intermediate 19: (5R,9S)-3-(3,5-Dichlorophenyl)-2-methyl-4,5,6,7,8,9-hexahydro-2H-5,9-epiminocycloocta[c]pyrazole

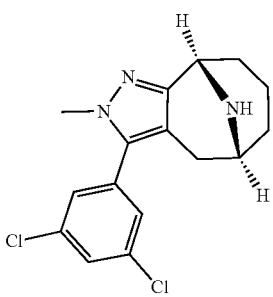 [SMILES: Cn1nc2c(c1-c1cc(Cl)cc(Cl)c1)C[C@H]1CCC[C@@H]2N1]

The title compound was prepared in a manner analogous to Intermediate 12 using (3,5-dichlorophenyl) boronic acid instead of (3,5-difluorophenyl) boronic acid. MS (ESI): mass calcd. for $C_{16}H_{17}Cl_2N_3$, 321.1; m/z found, 322.1 [M+H]$^+$.

Intermediate 20: (5R,9S)-3-(4-Chloro-3-fluorophenyl)-2-methyl-4,5,6,7,8,9-hexahydro-2H-5,9-epiminocycloocta[c]pyrazole

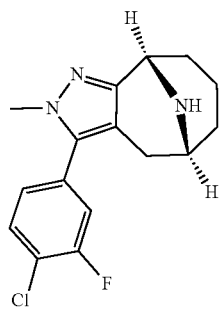 [SMILES: Cn1nc2c(c1-c1ccc(Cl)c(F)c1)C[C@H]1CCC[C@@H]2N1]

The title compound was prepared in a manner analogous to Intermediate 12 using (4-chloro-3-fluorophenyl) boronic acid instead of (3,5-difluorophenyl) boronic acid. MS (ESI): mass calcd. for $C_{16}H_{17}ClFN_3$, 305.1; m/z found, 306.1 [M+H]$^+$.

Intermediate 21: (5R,9S)-3-(3,4-Difluoro-5-methoxyphenyl)-2-methyl-4,5,6,7,8,9-hexahydro-2H-5,9-epiminocycloocta[c]pyrazole

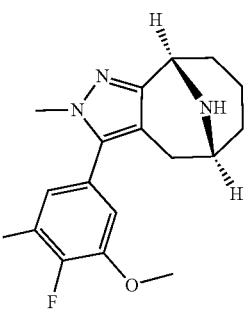

The title compound was prepared in a manner analogous to Intermediate 12 using (3,4-difluoro-5-methoxyphenyl) boronic acid instead of (3,5-difluorophenyl) boronic acid. MS (ESI): mass calcd. for $C_{17}H_{19}F_2N_3O$, 319.1; m/z found, 320.1 [M+H]$^+$.

Intermediate 22: (5R,9S)-3-(3,5-Difluoro-4-methoxyphenyl)-2-methyl-4,5,6,7,8,9-hexahydro-2H-5,9-epiminocyclooctα[c]pyrazole

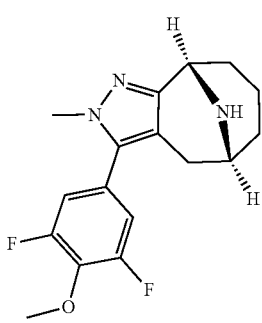 [SMILES: COc1c(F)cc(-c2c3c(nn2C)[C@@H]2CCC[C@H](C3)N2)cc1F]

The title compound was prepared in a manner analogous to Intermediate 12 using (3,5-difluoro-4-methoxyphenyl) boronic acid instead of (3,5-difluorophenyl) boronic acid. MS (ESI): mass calcd. for $C_{17}H_{19}F_2N_3O$, 319.1; m/z found, 320.1 $[M+H]^+$.

Intermediate 23: (5R,9S)-3-(3,5-Dimethoxyphenyl)-2-methyl-4,5,6,7,8,9-hexahydro-2H-5,9-epiminocyclooctα[c]pyrazole

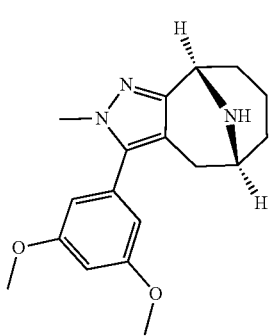 [SMILES: COc1cc(OC)cc(-c2c3c(nn2C)[C@@H]2CCC[C@H](C3)N2)c1]

The title compound was prepared in a manner analogous to Intermediate 12 using (3,5-dimethoxyphenyl) boronic acid instead of (3,5-difluorophenyl) boronic acid. MS (ESI): mass calcd. for $C_{18}H_{23}N_3O_2$, 313.1; m/z found, 314.1 $[M+H]^+$.

Intermediate 24: (5R,9S)-3-(3,4-Difluorophenyl)-2-methyl-4,5,6,7,8,9-hexahydro-2H-5,9-epiminocyclooctα[c]pyrazole

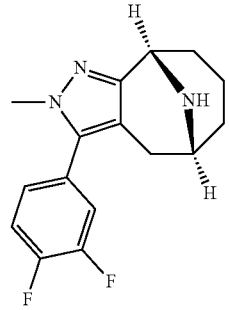 [SMILES: Cn1nc2c(c1-c1ccc(F)c(F)c1)C[C@H]1CCC[C@@H]2N1]

The title compound was prepared in a manner analogous to Intermediate 12 using (3,4-difluorophenyl) boronic acid instead of (3,5-difluorophenyl) boronic acid. MS (ESI): mass calcd. for $C_{16}H_{17}F_2N_3$, 289.1; m/z found, 290.1 $[M+H]^+$.

Intermediate 25: (5R,9S)-2-Methyl-3-(3,4,5-trifluorophenyl)-4,5,6,7,8,9-hexahydro-2H-5,9-epiminocyclooctα[c]pyrazole

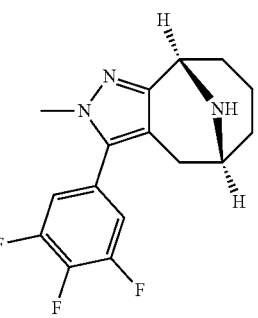

The title compound was prepared in a manner analogous to Intermediate 12 using (3,4,5-trifluorophenyl) boronic acid instead of (3,5-difluorophenyl) boronic acid in Step A, employing either conventional or microwave heating. MS (ESI): mass calcd. for $C_{16}H_{16}F_3N_3$, 307.1; m/z found, 308.1 $[M+H]^+$.

Intermediate 26: (5S,9R)-2-Methyl-3-phenyl-4,5,6,7,8,9-hexahydro-2H-5,9-epiminocyclooctα[c]pyrazole

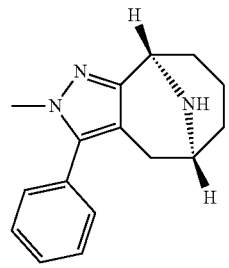 [SMILES: Cn1nc2c(c1-c1ccccc1)C[C@@H]1CCC[C@H]2N1]

The title compound is prepared in a manner analogous to Intermediate 1 using tert-butyl (5S,9R)-2-methyl-3-(((trifluoromethyl)sulfonyl)oxy)-4,5,6,7,8,9-hexahydro-2H-5,9-epiminocycloocta[c]pyrazole-10-carboxylate (Intermediate 3) instead of racemic-(5R,9S)-2-methyl-3-phenyl-4,5,6,7,8,9-hexahydro-2H-5,9-epiminocycloocta[c]pyrazole (Step C, Intermediate 1). MS(ESI): mass calcd. for $C_{16}H_{19}N_3$, 253.1; m/z found, 254.1 $[M+H]^+$.

Intermediate 27: (5R,9S)-2-Methyl-3-phenyl-4,5,6,7,8,9-hexahydro-2H-5,9-epiminocycloocta[c]pyrazole

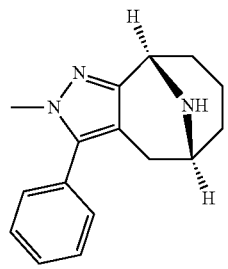 [SMILES: Cn1nc2c(c1-c1ccccc1)C[C@H]1CCC[C@@H]2N1]

The title compound is prepared in a manner analogous to Intermediate 1 using tert-butyl (5R,9S)-2-methyl-3-(((trifluoromethyl)sulfonyl) oxy)-4,5,6,7,8,9-hexahydro-2H-5,9-epiminocycloocta[c]pyrazole-10-carboxylate (Intermediate 2) instead of racemic-(5R,9S)-2-methyl-3-phenyl-4,5,6,7,8,9-hexahydro-2H-5,9-epiminocycloocta[c]pyrazole (Step C, Intermediate 1). MS(ESI): mass calcd. for $C_{16}H_{19}N_3$, 253.1; m/z found, 254.1 $[M+H]^+$.

Intermediate 28: (5S,9R)-3-(3-Fluorophenyl)-2-methyl-4,5,6,7,8,9-hexahydro-2H-5,9-epiminocycloocta[c]pyrazole

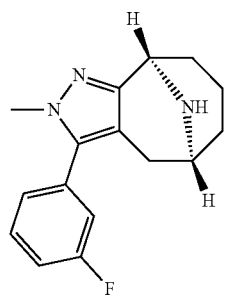 [SMILES: Cn1nc2c(c1-c1cccc(F)c1)C[C@@H]1CCC[C@H]2N1]

The title compound is prepared in a manner analogous to Intermediate 1 using (3-fluorophenyl) boronic acid instead of phenylboronic acid in Step C and tert-butyl (5S,9R)-2-methyl-3-(((trifluoromethyl)sulfonyl)oxy)-4,5,6,7,8,9-hexahydro-2H-5,9-epiminocycloocta[c]pyrazole-10-carboxylate (Intermediate 3) instead of racemic-(5R,9S)-2-methyl-3-phenyl-4,5,6,7,8,9-hexahydro-2H-5,9-epiminocycloocta[c]pyrazole (Step C, Intermediate 1). MS(ESI): mass calcd. for $C_{16}H_{18}FN_3$, 271.1; m/z found, 272.1 $[M+H]^+$.

Intermediate 29: (5S,9R)-3-(3,5-Difluorophenyl)-2-methyl-4,5,6,7,8,9-hexahydro-2H-5,9-epiminocycloocta[c]pyrazole

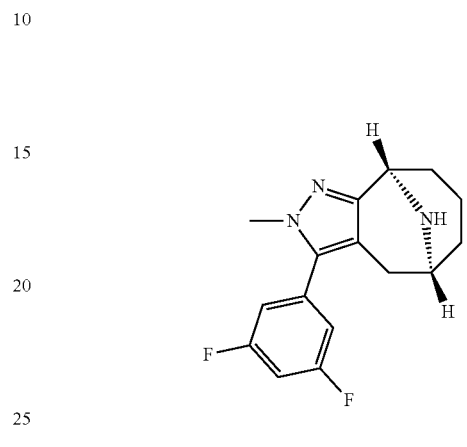

The title compound is prepared in a manner analogous to Intermediate 1 using (3,5-difluorophenyl)boronic acid instead of phenylboronic acid in Step C and tert-butyl (5S,9R)-2-methyl-3-(((trifluoromethyl)sulfonyl)oxy)-4,5,6,7,8,9-hexahydro-2H-5,9-epiminocycloocta[c]pyrazole-10-carboxylate (Intermediate 3) instead of racemic-(5R,9S)-2-methyl-3-phenyl-4,5,6,7,8,9-hexahydro-2H-5,9-epiminocycloocta[c]pyrazole (Step C, Intermediate 1). MS(ESI): mass calcd. for $C_{16}H_{17}F_2N_3$, 289.1; m/z found, 290.1 $[M+H]^+$.

Intermediate 30: (5R,9S)-3-(4-Fluorophenyl)-2-methyl-4,5,6,7,8,9-hexahydro-2H-5,9-epiminocycloocta[c]pyrazole

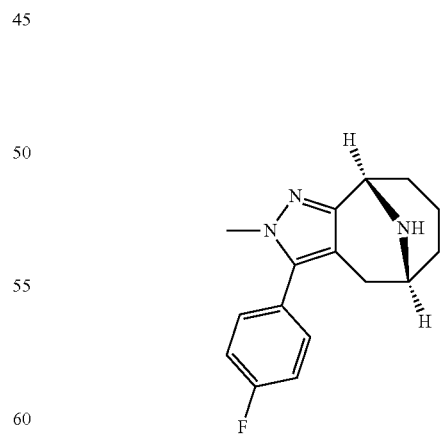

The title compound was prepared in a manner analogous to Intermediate 12 using (4-fluorophenyl) boronic acid instead of (3,5-difluorophenyl) boronic acid. MS (ESI): mass calcd. for $C_{16}H_{18}FN_3$, 271.1; m/z found, 272.1 $[M+H]^+$.

Intermediate 31: (5R,9S)-3-Cyclopropyl-2-methyl-4,5,6,7,8,9-hexahydro-2H-5,9-epiminocycloocta[c]pyrazole

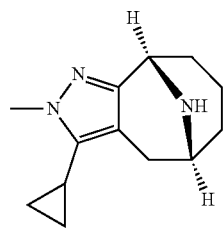 [SMILES: Cn1nc2c(c1C1CC1)C[C@H]1CCC[C@@H]2N1]

The title compound was prepared in a manner analogous to Intermediate 12 using cyclopropylboronic acid instead of (3,5-difluorophenyl) boronic acid. MS (ESI): mass calcd. for $C_{13}H_{19}N_3$, 217.1; m/z found, 218.1 $[M+H]^+$.

Intermediate 32: (5R,9S)-2-Methyl-3-(1-methyl-1H-indol-2-yl)-4,5,6,7,8,9-hexahydro-2H-5,9-epiminocycloocta[c]pyrazole

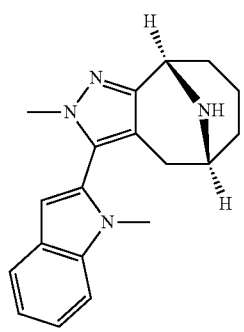 [SMILES: Cn1nc2c(c1-c1cc3ccccc3n1C)C[C@H]1CCC[C@@H]2N1]

The title compound was prepared in a manner analogous to Intermediate 12 using -methyl-2-(4,4,5,5-tetramethyl-1,3,2-dioxaborolan-2-yl)-1H-indole instead of (3,5-difluorophenyl) boronic acid. MS (ESI): mass calcd. for $C_{19}H_{22}N_4$, 306.1; m/z found, 307.1 $[M+H]^+$.

Intermediate 33: 2-Methylquinoxaline-6-carboxylic acid

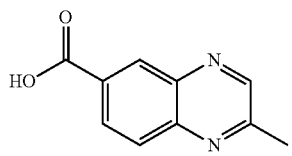

To a solution of 3,4 diaminobenzoic acid (500 mg, 3.3 mmol) in ethanol (4.0 mL) was added 2-oxopropanal (0.45 mL, 6.6 mmol) and the mixture was refluxed at 80° C. for 16 hours. The reaction mixture was cooled to rt and concentrated under reduced pressure. The crude mixture was used without purification. MS (ESI): mass calcd. for $C_{10}H_{18}N_2O_2$, 188.0 m/z found, 189.0 $[M+H]^+$. $^1$H NMR (500 MHz, DMSO-$d_6$) δ 13.38 (s, 1H), 8.96 (s, 1H), 8.62-8.49 (m, 1H), 8.31-8.19 (m, 1H), 8.17-7.95 (m, 1H), 2.75 (d, J=1.6 Hz, 3H).

Intermediate 34: racemic-(5R,8S)-2-Methyl-3-phenyl-2,4,5,6,7,8-hexahydro-5,8-epiminocyclohepta[c]pyrazole

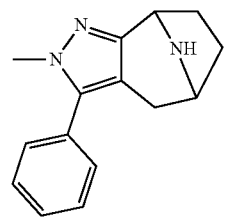 [SMILES: Cn1nc2c(c1-c1ccccc1)CC1CCC2N1]

Step A: racemic-tert-Butyl (5R,8S)-2-methyl-3-(((trifluoromethyl)sulfonyl)oxy)-2,4,5,6,7,8-hexahydro-5,8-epiminocyclohepta[c]pyrazole-9-carboxylate. The title compound is prepared in a manner analogous to Intermediate 1, Steps A-B, using 8-(tert-butyl) 3-ethyl 2-oxo-8-azabicyclo[3.2.1]octane-3,8-dicarboxylate (Intermediate 35, product from Step E) instead of racemic-9-(tert-butyl) 3-ethyl (1S,5R)-2-oxo-9-azabicyclo[3.3.1] nonane-3,9-dicarboxylate in Step A. MS(ESI): mass calcd. for $C_{15}H_{20}F_3N_3O_5S$, 411.1; m/z found, 356.0 [M+2H-tbutyl]$^+$.

Step B: racemic-(5R,8S)-2-Methyl-3-phenyl-2,4,5,6,7,8-hexahydro-5,8-epiminocyclohepta[c]pyrazole. The title compound was prepared in a manner analogous to Intermediate 12, Steps A-B, using racemic-tert-butyl(5R,8S)-2-methyl-3-(((trifluoromethyl)sulfonyl)oxy)-2,4,5,6,7,8-hexahydro-5, 8-epiminocyclohepta[c]pyrazole-9-carboxylate instead of tert-butyl (5R,9S)-2-methyl-3-(((trifluoromethyl)sulfonyl)oxy)-4,5,6,7,8,9-hexahydro-2H-5,9-epiminocycloocta[c]pyrazole-10-carboxylate (Intermediate 2) and phenylboronic acid instead of (3,5-difluorophenyl) boronic acid in Step A. MS (ESI): mass calcd. for $C_{15}H_{17}N_3$, 239.1; m/z found, 240.1 $[M+H]^+$.

Intermediate 35: tert-Butyl (5R,8S)-2-methyl-3-(((trifluoromethyl)sulfonyl)oxy)-2,4,5,6,7,8-hexahydro-5,8-epiminocyclohepta[c]pyrazole-9-carboxylate

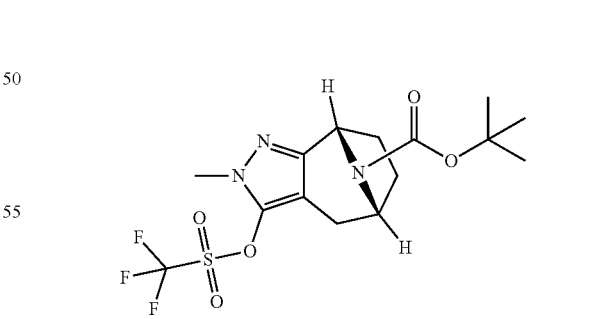

Step A: Ethyl 5-formyl-1H-pyrrole-2-carboxylate. A cooled (0° C.) solution of dichloroethane (DCE) (250 mL) and POCl$_3$ (18.7 mL, 201 mmol) was slowly charged with N,N-dimethylformamide (DMF) (17.7 mL, 230 mmol), this suspension was stirred at 0° C. for 15 min. Then the reaction mixture was charged with a solution of ethyl 1H-pyrrole-2-carboxylate (20 g, 144 mmol) dissolved in dichloroethane (DCE) (50 mL) and stirred at 0° C. for 30 min warming to rt overnight. The completed reaction was cooled to 0° C. and a 50 mL solution of sodium acetate tri-hydrate (~43 g) was added. The resulting mixture was heated to 75° C. for 30 min and then cooled to rt. The aq. layer was extracted with methyl tert-butyl ether (MTBE, TBME) washed with Aq. NaHCO$_3$, brine, dried over Na$_2$SO$_4$, filtered and concentrated. Purification (FCC, eluting with 0-10% EtOAc/Hex) afforded the title compound (18.1 g, 75%). MS (ESI): mass calcd. for C$_8$H$_9$NO$_3$, 167.1; m/z found, 168.1 [M+H]$^+$. $^1$H NMR (500 MHz, CDCl$_3$) δ 10.04-9.67 (s, 1H), 9.74-9.59 (s, 1H), 7.02-6.86 (d, J=2.5 Hz, 2H), 4.49-4.30 (m, 2H), 1.45-1.31 (m, 2H).

Step B: Ethyl (E)-5-(3-ethoxy-3-oxoprop-1-en-1-yl)-1H-pyrrole-2-carboxylate. A cooled (0° C.) solution of NaH (8.7 g, 217 mmol) in THF (200 mL) was charged with triethylphosphono acetate (61.7 g, 234 mmol). The reaction mixture was stirred at 0° C. for 3 hours, then ethyl 5-formyl-1H-pyrrole-2-carboxylate (27.9 g, 167 mmol) was added. The reaction mixture was stirred at rt overnight. The reaction mixture was quench with aq. NH$_4$Cl (200 mL) and extracted into Et$_2$O (×3), washed with brine, dried over Na$_2$SO$_4$, filtered and concentrated under reduced pressure. The crude material was recrystallized form 10% EtOAc/Hex to give the title compound (39.5 g, 99.8%). MS (ESI): mass calcd. for C$_{12}$H$_{15}$NO$_4$, 237.1; m/z found, 238.1 [M+H]$^+$. $^1$H NMR (500 MHz, CDCl$_3$) δ 9.93 (s, 1H), 7.56 (d, J=16.0 Hz, 1H), 6.98-6.81 (m, 1H), 6.63-6.43 (m, 1H), 6.32 (d, J=16.0 Hz, 1H), 4.39 (q, J=7.1 Hz, 2H), 4.25 (q, J=7.1 Hz, 2H), 1.39 (t, J=7.1 Hz, 3H), 1.32 (t, J=7.2 Hz, 3H).

Step C: Ethyl 5-(3-ethoxy-3-oxopropyl)pyrrolidine-2-carboxylate. To a flask was added ethyl (E)-5-(3-ethoxy-3-oxoprop-1-en-1-yl)-1H-pyrrole-2-carboxylate (39.5 g, 167 mmol mmol) the Rhodium on Alumnia (27.4 g, 13.3 mmol) and this was suspended in acetic acid (80 mL) and was evacuated and back filled with N$_2$. The flask was then fitted with a H$_2$ bladder and evacuated and back filled with H$_2$ twice. The reaction mixture was stirred at rt for 48 hrs. The crude reaction mixture was passed through a Celite®, washed with DCM, then concentrated under reduced pressure. Water (400 mL) was added to the reaction mixture, and the reaction mixture was extracted into DCM (×3). The organic layers were combined, washed with aq. NaHCO$_3$, brine, dried (Na$_2$SO$_4$), filtered and concentrated under reduced pressure to afford the title product as a tinted oil (38.6 g, 95%). MS (ESI): mass calcd. for C$_{12}$H$_{21}$NO$_4$, 243.1; m/z found, 244.1 [M+H]$^+$.

Step D: 1-(tert-Butyl) 2-ethyl 5-(3-ethoxy-3-oxopropyl)pyrrolidine-1,2-dicarboxylate. A solution of ethyl 5-(3-ethoxy-3-oxopropyl)pyrrolidine-2-carboxylate (38.6 g, 158 mmol) and Boc-anhydride (di-tert-butyl decarbonate) (38 g, 175 mmol) in DCM (317 mL) was slowly charged with TEA (44.1 mL, 317 mmol). The resulting reaction mixture was stirred at rt overnight. The reaction mixture was diluted with DCM (200 mL) and washed with water, brine, dried over Na$_2$SO$_4$, filtered and concentrated to give the title product (54.8 g, 100.6%). MS (ESI): mass calcd. for C$_{17}$H$_{29}$NO$_6$, 343.2; m/z found, 244.1 [M+2H-CO$_2$tBu]$^+$.

Step E: 8-(tert-Butyl) 3-ethyl 2-oxo-8-azabicyclo[3.2.1]octane-3,8-dicarboxylate. A solution of 1-(tert-butyl) 2-ethyl 5-(3-ethoxy-3-oxopropyl)pyrrolidine-1,2-dicarboxylate (54.8 g, 160 mmol) in THF (1.3 L) and potassium tert-butoxide (KOtBu) (21.5 g, 191 mmol) was heated at 60° C. for 3 h. The reaction mixture was cooled and concentrated under reduced pressure. The crude product was resuspended in DCM (800 mL) and washed with sat. NH$_4$Cl. The aq. layer was re-extracted with EtOAc (×2). The combined organic layers were washed with brine, dried over Na$_2$SO$_4$, filtered and concentrated under reduced pressure. Purification (FCC, SiO$_2$, eluting with 0-10% EtOAc/hex) afforded the title compound (37.8 g, 79.7%). MS (ESI): mass calcd. for C$_{15}$H$_{23}$NO$_5$, 297.2; m/z found, 242.1 [M+2H-tBu]$^+$.

Step F: racemic-tert-Butyl 2-methyl-3-oxo-1,2,3,4,5,6,7,8-octahydro-5,8-epiminocyclohepta[c]pyrazole-9-carboxylate. A solution of 8-(tert-butyl) 3-ethyl 2-oxo-8-azabicyclo[3.2.1]octane-3,8-dicarboxylate (1.76 g, 5.9 mmol) in toluene (33 mL) was charged with methylhydrazine (467 mL). The resulting mixture was heated at 110° C. for 2 hours. The cooled reaction was concentrated under reduced pressure. Purification (FCC, SiO$_2$, eluting with 0-10% MeOH/DCM) afforded the title compound as a clear oil. MS (ESI): mass calcd. for C$_{14}$H$_{21}$N$_3$O$_3$, 279.2; m/z found, 280.2 [M+1]$^+$.

Step G: tert-butyl (5R,8S)-2-Methyl-3-(((trifluoromethyl)sulfonyl)oxy)-2,4,5,6,7,8-hexahydro-5,8-epiminocyclohepta[c]pyrazole-9-carboxylate and tert-butyl (5S,8R)-2-Methyl-3-(((trifluoromethyl)sulfonyl)oxy)-2,4,5,6,7,8-hexahydro-5,8-epiminocyclohepta[c]pyrazole-9-carboxylate. To a solution of racemic-tert-butyl 2-methyl-3-oxo-1,2,3,4,5,6,7,8-octahydro-5,8-epiminocyclohepta[c]pyrazole-9-carboxylate (9.48 g, 34 mmol) in DCM (152 mL) was added N-phenyl-bis(trifluoromethansulfonimide) (13.5 g, 37 mmol) followed by DIEA (6.4 mL, 37 mmol). The resulting solution was stirred at rt for 18 h. The completed reaction was concentrated under reduced pressure. Purification (FCC, SiO$_2$, eluting with 0-20% EtOAc/Hex) afforded the title racemic mixture of compounds (11.2 g, 80%). MS (ESI): mass calcd. for C$_{15}$H$_{20}$F$_3$N$_3$O$_5$S, 411.1; m/z found, 356.0 [M+2H-tbutyl]$^+$.

Single enantiomers were isolated by Chiral SFC purification of racemic-tert-butyl 2-methyl-3-(((trifluoromethyl)sulfonyl)oxy)-2,4,5,6,7,8-hexahydro-5, 8-epiminocyclohepta[c]pyrazole-9-carboxylate using stationary phase: Chiralpak IC 5 µm 250*30 mm, Mobile phase: 93% CO$_2$, 7% iPrOH, giving tert-butyl (5R,8S)-2-methyl-3-(((trifluoromethyl)sulfonyl)oxy)-2,4,5,6,7,8-hexahydro-5,8-epiminocyclohepta[c]pyrazole-9-carboxylate (single enantiomer; 1.05 min retention time) MS (ESI): mass calcd. for C$_{15}$H$_{20}$F$_3$N$_3$O$_5$S, 411.1; m/z found, 356.0 [M+2H-tbutyl]$^+$ and Intermediate 104: tert-butyl (5S,8R)-2-methyl-3-(((trifluoromethyl)sulfonyl)oxy)-2,4,5,6,7,8-hexahydro-5,8-epiminocyclohepta[c]pyrazole-9-carboxylate (single enantiomer; 1.13 min retention time) MS (ESI): mass calcd. for C$_{15}$H$_{20}$F$_3$N$_3$O$_{5s}$, 411.1; m/z found, 356.0 [M+2H-tbutyl]$^+$.

Intermediate 36: 8-Bromoquinoline-6-carboxylic acid

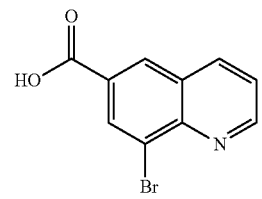

To a mixture of 4-amino-3-bromobenzoic acid (500 mg, 2.31 mmol) in concentrated sulfuric acid (650 μL) was added glycerol (1.75 g, 19.0 mmol), 4-nitrobenzoic acid (391 mg, 2.34 mmol), boric acid (215 mg, 3.48 mmol) and iron(II) sulfate heptahydrate (234 mg, 0.842 mmol), and the reaction was stirred at 140° C. for 42 h. The reaction mixture was cooled to room temperature and the pH was adjusted to 10 with 10% sodium hydroxide. The aqueous layer was extracted with ethyl acetate (2×100 mL) and the combined organic layers were dried over sodium sulfate, filtered and evaporated to give the title compound (150 mg, 25% yield) as a yellow powder. MS (ESI): mass calcd. for $C_{10}H_6BrNO_2$, 251.0; m/z found, 252.0 $[M+H]^+$.

Intermediate 37:
1-(3-Chlorophenyl)-1,2,4-triazole-3-carboxylic acid

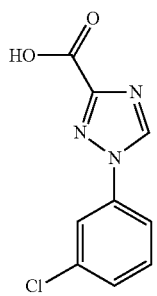 [SMILES: O=C(O)c1ncn(-c2cccc(Cl)c2)n1]

Step A: Methyl 1-(3-chlorophenyl)-1,2,4-triazole-3-carboxylate. To a mixture of methyl-1H-1,2,4-triazole-5-carboxylate (300 mg, 2.36 mmol), (3-chlorophenyl)boronic acid (370 mg, 2.37 mmol) and copper(II) acetate (429 mg, 2.36 mmol) in dichloromethane (5 mL) was added pyridine (570 μL, 7.08 mmol), and the reaction was stirred at room temperature for 3 days. The reaction mixture was filtered through a pad of Celite® and the filtrate was washed with 10% potassium bisulfate (1×5 mL), saturated sodium bicarbonate (1×5 mL) and brine (3×5 mL).

The organic layer was dried over magnesium sulfate, filtered and evaporated. The resulting residue was triturated with diethyl ether (5 mL) to give the title compound (120 mg, 21% yield) as a white powder. MS (ESI): mass calcd. for $C_{10}H_8ClN_3O_2$, 237.0; m/z found, 238.1 $[M+H]^+$.

Step B: 1-(3-Chlorophenyl)-1,2,4-triazole-3-carboxylic acid. To a solution of methyl 1-(3-chlorophenyl)-1,2,4-triazole-3-carboxylate (120 mg, 0.505 mmol) in 1,4-dioxane (1 mL) was added an aqueous solution of sodium hydroxide (500 μL, 1.00 mmol, 2 M) and the reaction was stirred at room temperature for 1 h. The reaction mixture was acidified to pH 5 with 6 M hydrochloric acid and the precipitate was collected to afford the title compound (99 mg, 87% yield) as a white powder. MS (ESI): mass calcd. for $C_9H_6ClN_3O_2$, 223.0; m/z found, 224.1 $[M+H]^+$.

Intermediate 38: 1-(3-(Trifluoromethyl)phenyl)-1H-1,2,4-triazole-3-carboxylic acid

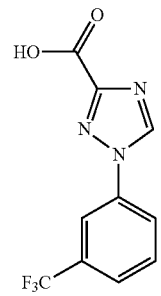

The title compound was prepared in a manner analogous to Intermediate 37 using (3-(trifluoromethyl)phenyl)boronic acid instead of (3-chlorophenyl)boronic acid. MS (ESI): mass calcd. for $C_{10}H_6F_3N_3O_2$, 257.0; m/z found, 258.1 $[M+H]^+$.

Intermediate 39:
1-(2-Fluorophenyl)-1H-1,2,4-triazole-3-carboxylic acid

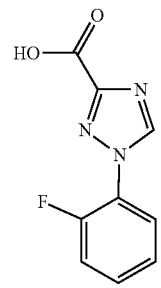

The title compound was prepared in a manner analogous to Intermediate 37 using (2-fluorophenyl)boronic acid instead of (3-chlorophenyl)boronic acid. MS (ESI): mass calcd. for $C_9H_6FN_3O_2$, 207.0; m/z found, 208.1 $[M+H]^+$.

Intermediate 40: 5-Methyl-1-(3-(trifluoromethyl)phenyl)-1H-1,2,4-triazole-3-carboxylic acid

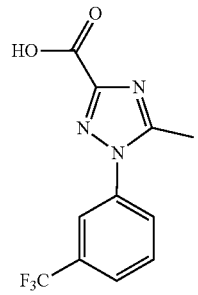 [SMILES: Cc1nc(C(=O)O)nn1-c1cccc(C(F)(F)F)c1]

The title compound was prepared in a manner analogous to Intermediate 37 using (3-(trifluoromethyl)phenyl)boronic acid instead of (3-chlorophenyl)boronic acid and methyl 5-methyl-1H-1,2,4-triazole-3-carboxylate instead of methyl-1H-1,2,4-triazole-5-carboxylate. MS (ESI): mass calcd. for $C_{11}H_8N_3F_3N_3O_2$, 271.1; m/z found, 272.1 [M+H]$^+$.

Intermediate 41: 1-(3-Methoxyphenyl)-1,2,4-triazole-3-carboxylic acid

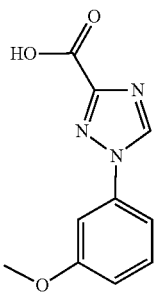 [SMILES: COc1cccc(-n2cnc(C(=O)O)n2)c1]

The title compound was prepared in a manner analogous to Intermediate 37 using (3-methoxyphenyl)boronic acid instead of (3-chlorophenyl)boronic acid. MS (ESI): mass calcd. for $C_{10}H_9N_3O_3$, 219.1; m/z found, 220.1 [M+H]$^+$.

Intermediate 42: 1-(2-Methoxyphenyl)-1,2,4-triazole-3-carboxylic acid

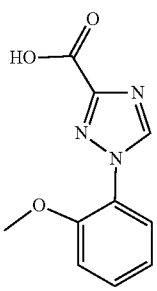 [SMILES: COc1ccccc1-n1cnc(C(=O)O)n1]

The title compound was prepared in a manner analogous to Intermediate 37 using (2-methoxyphenyl)boronic acid instead of (3-chlorophenyl)boronic acid. MS (ESI): mass calcd. for $C_{10}H_9N_3O_3$, 219.1; m/z found, 220.1 [M+H]$^+$.

Intermediate 43: 2-(1H-Imidazol-1-yl)benzoic acid

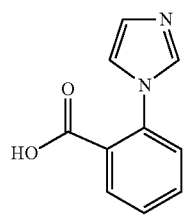 [SMILES: O=C(O)c1ccccc1-n1ccnc1]

The title compound was prepared in a manner analogous to Intermediate 37 using (2-(methoxycarbonyl)phenyl)boronic acid instead of (3-chlorophenyl)boronic acid and imidazole instead of methyl-1H-1,2,4-triazole-5-carboxylate. MS (ESI): mass calcd. for $C_{10}H_8N_2O_2$, 188.1; m/z found, 189.1 [M+H]$^+$.

Intermediate 44: 3-[3-(Trifluoromethyl)pyrazol-1-yl]benzoic acid

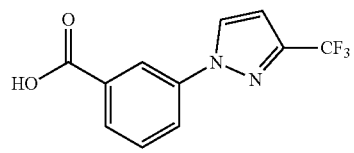 [SMILES: O=C(O)c1cccc(-n2ccc(C(F)(F)F)n2)c1]

A mixture of 3-iodobenzoic acid (300 mg, 1.21 mmol), 3-(trifluoromethyl)pyrazole (247 mg, 1.82 mmol), cesium carbonate (670 mg, 2.06 mmol), trans-N,N-dimethylcyclohexane-1,2-diamine (32 μL, 0.203 mmol) and copper(I) iodide (25 mg, 0.131 mmol) in N,N-dimethylformamide (1.25 mL) was stirred at 100° C. for 30 min, then at 140° C. for 70 min under microwave irradiation. The reaction mixture was taken up in water (5 mL), acidified to pH 3 with 1 M hydrochloric acid and extracted with ethyl acetate (3×5 mL). The combined organic layers were dried over sodium sulfate, filtered and evaporated. The crude product was purified by preparative HPLC (Method E) to afford the title compound (140 mg, 45% yield) as a tan powder. MS (ESI): mass calcd. for $C_{11}H_7F_3N_2O_2$, 256.0; m/z found, 257.1 [M+H]$^+$.

Intermediate 45: 2-(2H-1,2,3-Triazol-2-yl)-5-(trifluoromethyl)benzoic acid

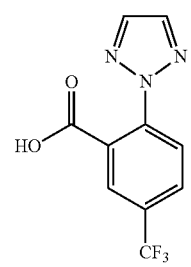 [SMILES: O=C(O)c1cc(C(F)(F)F)ccc1-n1nccn1]

The title compound was prepared in a manner analogous to Intermediate 44 using 2-iodo-5-(trifluoromethyl)benzoic acid instead of 3-iodobenzoic acid and 1,2,3-triazole instead of 3-(trifluoromethyl)pyrazole. MS (ESI): mass calcd. for $C_{10}H_6F_3N_3O_2$, 257.0; m/z found, 258.1 [M+H]$^+$.

Intermediate 46:
5-Methoxy-2-(2H-1,2,3-triazol-2-yl)benzoic acid

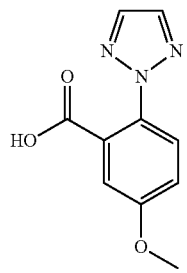

The title compound was prepared in a manner analogous to Intermediate 44 using 2-iodo-5-methoxybenzoic acid instead of 3-iodobenzoic acid and 1,2,3-triazole instead of 3-(trifluoromethyl)pyrazole. MS (ESI): mass calcd. for $C_{10}H_9N_3O_3$, 219.1; m/z found, 220.1 [M+H]$^+$.

Intermediate 47:
3-Methoxy-2-(2H-1,2,3-triazol-2-yl)benzoic acid

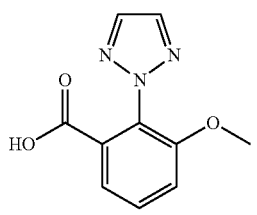 [SMILES: COc1cccc(C(=O)O)c1-n1nccn1]

The title compound was prepared in a manner analogous to Intermediate 44 using 2-iodo-3-methoxybenzoic acid instead of 3-iodobenzoic acid and 1,2,3-triazole instead of 3-(trifluoromethyl)pyrazole. MS (ESI): mass calcd. for $C_{10}H_9N_3O_3$, 219.1; m/z found, 220.1 [M+H]$^+$.

Intermediate 48:
3-Methoxy-2-(1H-1,2,3-triazol-1-yl)benzoic acid

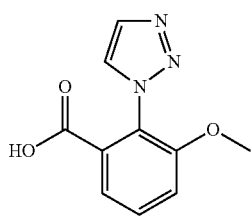 [SMILES: COc1cccc(C(=O)O)c1-n1ccnn1]

The title compound was prepared in a manner analogous to Intermediate 44 using 2-iodo-3-methoxybenzoic acid instead of 3-iodobenzoic acid and 1,2,3-triazole instead of 3-(trifluoromethyl)pyrazole. MS (ESI): mass calcd. for $C_{10}H_9N_3O_3$, 219.1; m/z found, 220.1 [M+H]$^+$.

Intermediate 49: 2-(2H-1,2,3-Triazol-2-yl)benzoic acid

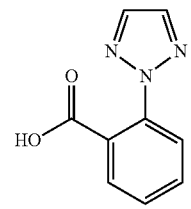

The title compound was prepared in a manner analogous to Intermediate 44 using 2-iodobenzoic acid instead of 3-iodobenzoic acid and 1,2,3-triazole instead of 3-(trifluoromethyl)pyrazole. MS (ESI): mass calcd. for $C_9H_7N_3O_2$, 189.1; m/z found, 190.1 [M+H]$^+$.

Intermediate 50: 2-(1H-1,2,3-Triazol-1-yl)benzoic acid

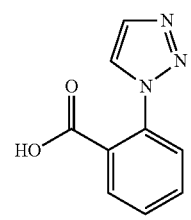 [SMILES: O=C(O)c1ccccc1-n1ccnn1]

The title compound was prepared in a manner analogous to Intermediate 44 using 2-iodobenzoic acid instead of 3-iodobenzoic acid and 1,2,3-triazole instead of 3-(trifluoromethyl)pyrazole. MS (ESI): mass calcd. for $C_9H_7N_3O_2$, 189.1; m/z found, 190.1 [M+H]$^+$.

Intermediate 51: 3-(2H-1,2,3-Triazol-2-yl)benzoic acid

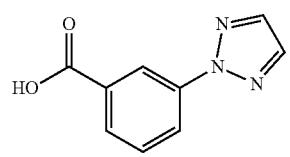 [SMILES: O=C(O)c1cccc(-n2nccn2)c1]

The title compound was prepared in a manner analogous to Intermediate 44 using 1,2,3-triazole instead of 3-(trifluoromethyl)pyrazole. MS (ESI): mass calcd. for $C_9H_7N_3O_2$, 189.1; m/z found, 190.1 [M+H]$^+$.

Intermediate 52: 2-(1H-1,2,4-Triazol-1-yl)-5-(trifluoromethyl)benzoic acid

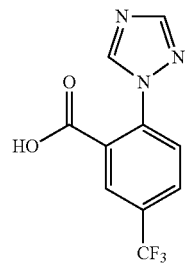 [SMILES: O=C(O)c1cc(C(F)(F)F)ccc1-n1cncn1]

The title compound was prepared in a manner analogous to Intermediate 44 using 2-iodo-5-(trifluoromethyl)benzoic acid instead of 3-iodobenzoic acid and 1,2,4-triazole instead of 3-(trifluoromethyl)pyrazole. MS (ESI): mass calcd. for $C_{10}H_6F_3N_3O_2$, 257.0; m/z found, 258.0 [M+H]$^+$.

Intermediate 53: 2-(3-(Trifluoromethyl)-1H-1,2,4-triazol-1-yl)benzoic acid

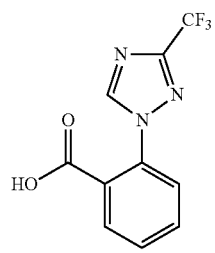 [SMILES: O=C(O)c1ccccc1-n1cnc(C(F)(F)F)n1]

The title compound was prepared in a manner analogous to Intermediate 44 using 2-iodobenzoic acid instead of 3-iodobenzoic acid and 3-(trifluoromethyl)-1H-1,2,4-triazole instead of 3-(trifluoromethyl)pyrazole. MS (ESI): mass calcd. for $C_{10}H_6F_3N_3O_2$, 257.0; m/z found, 258.1 [M+H]$^+$.

Intermediate 54: 3-Fluoro-2-(1H-1,2,4-triazol-1-yl)benzoic acid

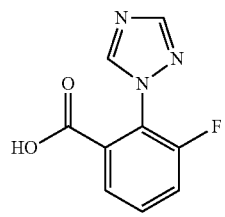

The title compound was prepared in a manner analogous to Intermediate 44 using 3-fluoro-2-iodobenzoic acid instead of 3-iodobenzoic acid and 1,2,4-triazole instead of 3-(trifluoromethyl)pyrazole. MS (ESI): mass calcd. for $C_9H_6FN_3O_2$, 207.0; m/z found, 208.1 [M+H]$^+$.

Intermediate 55: 4-Fluoro-2-(1H-1,2,4-triazol-1-yl)benzoic acid

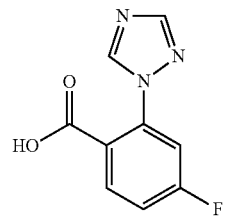 [SMILES: O=C(O)c1ccc(F)cc1-n1cncn1]

The title compound was prepared in a manner analogous to Intermediate 44 using 4-fluoro-2-iodobenzoic acid instead of 3-iodobenzoic acid and 1,2,4-triazole instead of 3-(trifluoromethyl)pyrazole. MS (ESI): mass calcd. for $C_9H_6FN_3O_2$, 207.0; m/z found, 208.1 [M+H]$^+$.

Intermediate 56: 5-Fluoro-2-(1H-1,2,4-triazol-1-yl)benzoic acid

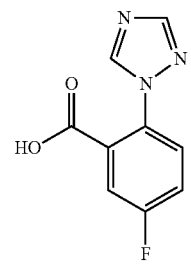 [SMILES: O=C(O)c1cc(F)ccc1-n1cncn1]

The title compound was prepared in a manner analogous to Intermediate 44 using 5-fluoro-2-iodobenzoic acid instead of 3-iodobenzoic acid and 1,2,4-triazole instead of 3-(trifluoromethyl)pyrazole. MS (ESI): mass calcd. for $C_9H_6FN_3O_2$, 207.0; m/z found, 208.1 [M+H]$^+$.

Intermediate 57: 4-Methyl-2-(1H-1,2,4-triazol-1-yl)benzoic acid

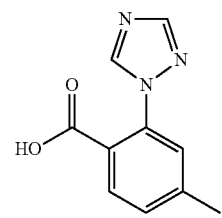

The title compound was prepared in a manner analogous to Intermediate 44 using 2-iodo-4-methylbenzoic acid instead of 3-iodobenzoic acid and 1,2,4-triazole instead of 3-(trifluoromethyl)pyrazole. MS (ESI): mass calcd. for $C_{10}H_9N_3O_2$, 203.1; m/z found, 202.1 [M−H]$^-$

Intermediate 58:
5-Methyl-2-(1H-1,2,4-triazol-1-yl)benzoic acid

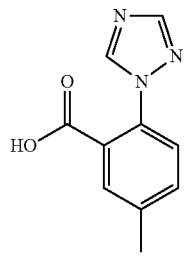

The title compound was prepared in a manner analogous to Intermediate 44 using 2-iodo-5-methylbenzoic acid instead of 3-iodobenzoic acid and 1,2,4-triazole instead of 3-(trifluoromethyl)pyrazole. MS (ESI): mass calcd. for $C_{10}H_9N_3O_2$, 203.1; m/z found, 204.1 [M+H]$^+$.

Intermediate 59:
3-(4-(Trifluoromethyl)pyrazol-1-yl)benzoic acid

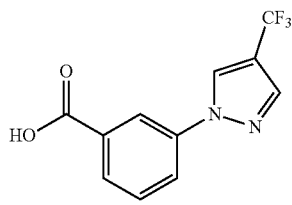 [SMILES: O=C(O)c1cccc(-n2cc(C(F)(F)F)cn2)c1]

The title compound was prepared in a manner analogous to Intermediate 44 using 4-(trifluoromethyl)pyrazole instead of 3-(trifluoromethyl)pyrazole. MS (ESI): mass calcd. for $C_{11}H_7F_3N_2O_2$, 256.0; m/z found, 257.1 [M+H]$^+$.

Intermediate 60:
3-(4-Fluoro-1H-pyrazol-1-yl)benzoic acid

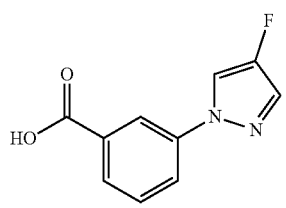 [SMILES: O=C(O)c1cccc(-n2cc(F)cn2)c1]

The title compound was prepared in a manner analogous to Intermediate 44 using 4-fluoropyrazole instead of 3-(trifluoromethyl)pyrazole. MS (ESI): mass calcd. for $C_{10}H_7F_1N_2O_2$, 206.0; m/z found, 207.1 [M+H]$^+$.

Intermediate 61:
3-(4-Methoxy-1H-pyrazol-1-yl)benzoic acid

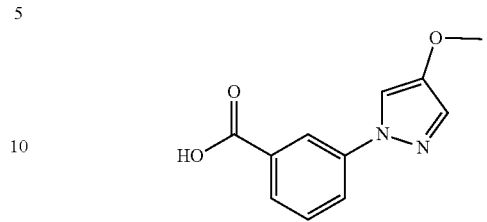

The title compound was prepared in a manner analogous to Intermediate 44 using 4-methoxypyrazole instead of 3-(trifluoromethyl)pyrazole. MS (ESI): mass calcd. for $C_{11}H_{10}N_2O_3$, 218.1; m/z found, 219.1 [M+H]$^+$.

Intermediate 62:
5-Methoxy-1-phenyl-1,2,4-triazole-3-carboxylic acid

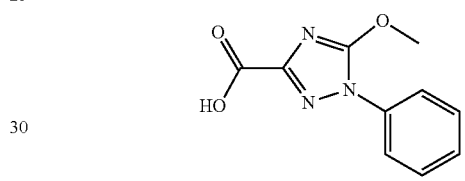

Step A: Ethyl (2Z)-2-amino-2-(phenylhydrazono)acetate. To a solution of ethyl 2-amino-2-thioxoacetate (615 mg, 4.62 mmol) in a mixture of toluene (10 mL) and acetic acid (1 mL) was added phenylhydrazine (455 µL, 4.62 mmol). The reaction was stirred at room temperature for 1 h. The reaction mixture was poured into 1 M sodium carbonate (20 mL) and extracted with ethyl acetate (3×10 mL). The combined organic layers were washed with 1 M sodium carbonate (2×10 mL) and brine (1×10 mL), dried over sodium sulfate, filtered and evaporated to give the title compound (652 mg) as a yellow oil, which was used directly in the next step. MS (ESI): mass calcd. for $C_{10}H_{13}N_3O_2$, 207.1; m/z found, 208.1 [M+H]$^+$.

Step B: Ethyl 5-oxo-1-phenyl-4H-1,2,4-triazole-3-carboxylate. To a solution of ethyl (2Z)-2-amino-2-(phenylhydrazono)acetate (600 mg, crude) in distilled tetrahydrofuran (20 mL) was added triphosgene (860 mg, 2.90 mmol) at 0° C. The reaction mixture was stirred at 0° C. for 2 h, then at room temperature for 18 h. The reaction mixture was diluted with water (20 mL) and extracted with ethyl acetate (2×20 mL). The combined organic layers were washed with brine (2×10 mL), dried over sodium sulfate, filtered and evaporated. Purification (FCC, SiO$_2$, n-heptane:ethyl acetate (100:0→50:50) afforded the title compound (295 mg, 43% yield) as a white powder. MS (ESI): mass calcd. for $C_{11}H_{11}N_3O_3$, 233.1; m/z found, 234.1 [M+H]$^+$.

Step C: Ethyl 5-methoxy-1-phenyl-1,2,4-triazole-3-carboxylate. To a solution of ethyl 5-oxo-1-phenyl-4H-1,2,4-triazole-3-carboxylate (260 mg, 1.11 mmol) in dichloromethane (10 mL) was added trimethyloxonium tetrafluoroborate (34 mg, 0.232 mmol) at 0° C. The reaction mixture was stirred at room temperature for 24 h. The reaction mixture was quenched with 1 M sodium carbonate (10 mL) and extracted with dichloromethane (2×10 mL).

The combined organic layers were washed with brine (2×10 mL), dried over sodium sulfate, filtered and evaporated. Purification (FCC, SiO$_2$, n-heptane-ethyl acetate (100:0→50:50) afforded the title compound (155 mg, 56% yield) as a pale yellow powder. MS (ESI): mass calcd. for C$_{12}$H$_{13}$N$_3$O$_3$, 247.1; m/z found, 248.1 [M+H]$^+$.

Step D: 5-Methoxy-1-phenyl-1,2,4-triazole-3-carboxylic acid. To a solution of ethyl 5-methoxy-1-phenyl-1,2,4-triazole-3-carboxylate (150 mg, 0.607 mmol) in 1,4-dioxane (1 mL) was added sodium hydroxide (1 M, 1 mL, 1.00 mmol) and the reaction was stirred at room temperature for 1 h. The reaction mixture was diluted with ethyl acetate (3 mL), and the aqueous layer was acidified to pH 5 with 2 M hydrochloric acid and extracted with ethyl acetate (2×2 mL). The combined organic layers were dried over sodium sulfate, filtered and evaporated to afford the title compound (113 g, 84% yield) as a white powder. MS (ESI): mass calcd. for C$_{10}$H$_9$N$_3$O$_3$, 219.1; m/z found, 220.1 [M+H]$^+$.

Intermediate 63: (5R,9S)-3-(3-Fluoro-5-methylphenyl)-2-methyl-4,5,6,7,8,9-hexahydro-2H-5,9-epiminocycloocta[c]pyrazole

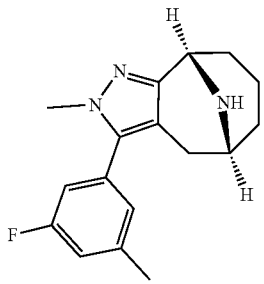 [SMILES: Cc1cc(F)cc(-c2c3c(nn2C)[C@@H]2CCC[C@H](C3)N2)c1]

The title compound was prepared in a manner analogous to Intermediate 12 using (3-fluoro-5-methylphenyl) boronic acid instead of (3,5-difluorophenyl) boronic acid in Step A. MS (ESI): mass calcd. for C$_{17}$H$_{20}$FN$_3$, 285.2; m/z found, 286.1 [M+H]$^+$.

Intermediate 64: 3-Fluoro-5-pyrazol-1-yl-benzoic acid

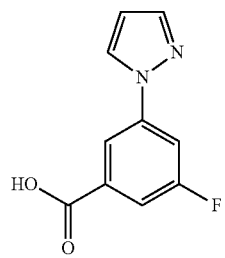

A mixture of methyl 3-bromo-5-fluorobenzoate (300 mg, 1.29 mmol), pyrazole (132 mg, 1.94 mmol), cesium carbonate (713 mg, 2.19 mmol), trans-N,N'-dimethylcyclohexane-1,2-diamine (35 µL, 0.222 mmol, 0.902 g/mL) and copper(I) iodide (25 mg, 0.131 mmol) in N,N-dimethylformamide (1 mL) was stirred at 140° C. for 120 min under microwave irradiation. The reaction mixture was diluted with ethyl acetate (5 mL) and water (5 mL). The aqueous layer was acidified to pH 3 with 1 M hydrochloric acid. The precipitate was collected and washed with water (2×5 mL) to afford the title compound (245 mg, 1.19 mmol, 92%) as a tan powder. MS (ESI): mass calcd. for C$_{10}$H$_7$FN$_2$O$_2$, 206.1; m/z found, 207.2 [M+H]$^+$. $^1$H NMR (500 MHz, DMSO-d$_6$) δ 13.56 (br s, 1H), 8.67 (d, J=2.6 Hz, 1H), 8.28-8.25 (m, 1H), 8.03 (dt, J=10.1, 2.3 Hz, 1H), 7.81 (d, J=1.7 Hz, 1H), 7.61-7.56 (m, 1H), 6.62-6.59 (m, 1H).

Intermediate 65: 5-Methoxy-2-(1H-1,2,4-triazol-1-yl)benzoic acid

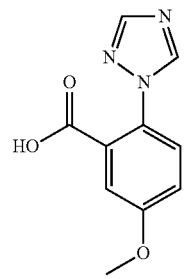 [SMILES: COc1ccc(-n2cncn2)c(C(=O)O)c1]

The title compound was prepared in a manner analogous to Intermediate 44 using 2-iodo-5-methoxybenzoic acid instead of 3-iodobenzoic acid and 1,2,4-triazole instead of 3-(trifluoromethyl)pyrazole. MS (ESI): mass calcd. for C$_{10}$H$_9$N$_3$O$_3$, 219.1; m/z found, 220.2 [M+H]$^+$.

Intermediate 66: 2-[4-(Trifluoromethyl)triazol-2-yl]benzoic acid

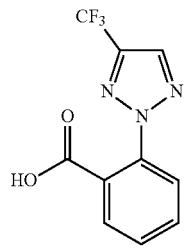 [SMILES: O=C(O)c1ccccc1-n1ncc(C(F)(F)F)n1]

Step A: Ethyl 3-benzyl-5-(trifluoromethyl)triazole-4-carboxylate and ethyl 1-benzyl-5-(trifluoromethyl)triazole-4-carboxylate. To a solution of azidomethylbenzene (1.2 g, 9.01 mmol) in toluene (40 mL) was added ethyl 4,4,4-trifluoro-2-butynoate (3.0 g, 18.1 mmol). The reaction mixture was stirred at 115° C. for 16 h and evaporated to give a mixture of the title compounds (2.65 g, 8.86 mmol, 98%) as a yellow oil. MS (ESI): mass calcd. for C$_{13}$H$_{12}$F$_3$N$_3$O$_2$, 299.1; m/z found, 300.1 [M+H]$^+$.

Step B: 3-Benzyl-5-(trifluoromethyl)triazole-4-carboxylic acid and 1-benzyl-5-(trifluoromethyl)triazole-4-carboxylic acid. To a mixture of ethyl 3-benzyl-5-(trifluoromethyl)triazole-4-carboxylate and ethyl 1-benzyl-5-(trifluoromethyl)triazole-4-carboxylate (2.65 g, 8.86 mmol) in 1,4-dioxane (14 mL) and water (14 mL) was added sodium hydroxide (720 mg, 18 mmol). The reaction mixture was stirred at room temperature for 16 h. The reaction mixture was quenched with 6 M hydrochloric acid (3 mL) and evaporated. The residue was taken up in water (10 mL) and extracted with dichloromethane (3×20 mL). The combined organic layers were dried over sodium sulfate, filtered and evaporated. The residue was triturated with diisopropyl ether to give a first crop of a mixture of the title compounds (680 mg, 2.51 mmol, 28%) as a white powder.

The trituration solvent was evaporated to give a second crop of a mixture of the title compounds (670 mg, 2.47 mmol, 28%) as a white powder. MS (ESI): mass calcd. for $C_{11}H_8F_3N_3O_2$, 271.1; m/z found, 272.1 $[M+H]^+$.

Step C: 1-Benzyl-4-(trifluoromethyl)triazole and 1-benzyl-5-(trifluoromethyl)triazole. To a mixture of 3-benzyl-5-(trifluoromethyl)triazole-4-carboxylic acid and 1-benzyl-5-(trifluoromethyl)triazole-4-carboxylic acid (1 g, 3.69 mmol) in dimethyl sulfoxide (50 mL) was added silver carbonate (305 mg, 1.11 mmol) and acetic acid (36 µL, 0.629 mmol, 1.049 g/mL). The reaction mixture was stirred at 120° C. for 18 h and acidified to pH 3 with 1 M aq. hydrochloric acid. The mixture was diluted with water (50 mL) and extracted with ethyl acetate (2×50 mL). The combined organic layers were washed with water (3×25 mL), dried over magnesium sulfate, filtered and evaporated to give a mixture of the title compounds (300 mg, 1.32 mmol, 36%) as a yellow powder. MS (ESI): mass calcd. for $C_{10}H_8F_3N_3O_3$, 227.1; m/z found, 228.1 $[M+H]^+$.

Step D: 4-(Trifluoromethyl)-1H-triazole. To a solution of a mixture of 1-benzyl-4-(trifluoromethyl)triazole and 1-benzyl-5-(trifluoromethyl)triazole (750 mg, 3.3 mmol) in 1,4-dioxane (20 mL) was added Selcat-Q-6 10% palladium on carbon (351 mg, 0.33 mmol) and hydrogen chloride (4.2 M in 1,4 dioxane, 2.36 mL, 9.91 mmol). The reaction mixture was stirred at room temperature for 78 h under hydrogen (1 bar) to give the title compound (35 mL, 0.094 M stock solution) as a pale yellow liquid.

Step E: 2-[4-(Trifluoromethyl)triazol-2-yl]benzoic acid. A mixture of 2-iodobenzoic acid (200 mg, 0.806 mmol), 4-(trifluoromethyl)-1H-triazole (0.094 M stock solution in 1,4-dioxane, 11 mL, 1.034 mmol), cesium carbonate (445 mg, 1.366 mmol), trans-N,N'-dimethylcyclohexane-1,2-diamine (22 µL, 0.140 mmol) and copper(I) iodide (15 mg, 0.079 mmol) in N,N-dimethylformamide (5 mL) was stirred at 140° C. for 30 min under microwave irradiation. The reaction mixture was cooled to room temperature. The reaction mixture was cooled to room temperature, filtered and washed with 1,4-dioxane (5 mL). The combined filtrates were evaporated. The reaction was repeated twice, on 50 and 72 mg scale. The crude products were combined and purified by preparative HPLC (Method E) to afford the title compound (44 mg, 0.171 mmol, 13%) as a pale yellow oil and 2-[4-(trifluoromethyl)triazol-1-yl]benzoic acid (Intermediate 67) (27 mg, 0.105 mmol, 8%) as a pale yellow oil. MS (ESI): mass calcd. for $C_{10}H_6F_3N_3O_2$, 257.0; m/z found, 258.1 $[M+H]^+$. $^1H$ NMR (300 MHz, DMSO-$d_6$) δ 13.40 (br s, 1H), 8.72 (s, 1H), 7.91 (d, J=7.3 Hz, 1H), 7.85-7.78 (m, 2H), 7.78-7.64 (m, 1H).

Intermediate 67: 2-[4-(Trifluoromethyl)triazol-1-yl]benzoic acid

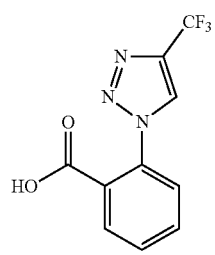 [SMILES: O=C(O)c1ccccc1-n1cc(C(F)(F)F)nn1]

The title compound was isolated from Intermediate 66, step E.

MS (ESI): mass calcd. for $C_{10}H_6F_3N_3O_2$, 257.0; m/z found, 258.1 $[M+H]^+$. $^1H$ NMR (300 MHz, DMSO-$d_6$) δ 13.33 (br s, 1H), 9.36 (s, 1H), 8.04 (d, J=7.4 Hz, 1H), 7.90-7.64 (m, 3H).

Intermediate 68: 3-Fluoro-5-(4H-1,2,4-triazol-4-yl)benzoic acid

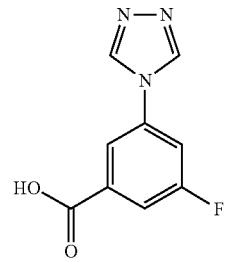 [SMILES: O=C(O)c1cc(F)cc(-n2cnnc2)c1]

Step A: Methyl 3-fluoro-5-(1,2,4-triazol-4-yl)benzoate. To a solution of methyl 3-amino-5-fluorobenzoate (250 mg, 1.48 mmol) in pyridine (8 mL) was added 1,2-diformylhydrazine (325 mg, 3.69 mmol) and triethylamine (1 mL, 7.16 mmol). To the mixture was added chlorotrimethylsilane (375 µL, 2.96 mmol) dropwise. The reaction mixture was stirred at 100° C. for 16 h and evaporated. The residue was diluted with dichloromethane (8 mL) and water (10 mL). The aqueous layer was extracted with dichloromethane (2×10 mL). The combined organic layers were washed with 10% potassium bisulfate (1×15 mL) and 1 M sodium hydroxide (1×15 mL), dried over sodium sulfate, filtered and evaporated to give the title compound (131 mg, 0.592 mmol, 40%) as a white powder. MS (ESI): mass calcd. for $C_{10}H_8FN_3O_2$, 221.1; m/z found, 222.1 $[M+H]^+$.

Step B: 3-Fluoro-5-(1,2,4-triazol-4-yl)benzoic acid. To a solution of methyl 3-fluoro-5-(1,2,4-triazol-4-yl)benzoate (130 mg, 0.588 mmol) in 1,4-dioxane (1 mL) and water (1 mL) was added sodium hydroxide (48 mg, 1.20 mmol) and the reaction was stirred at room temperature for 16 h.

The reaction was quenched with 6 M hydrochloric acid (0.20 mL). The precipitate was collected and washed with water (1×1 mL) to afford the title compound (80 mg, 0.386 mmol, 65%) as a white powder. MS (ESI): mass calcd. for $C_9H_6FN_3O_2$, 207.0; m/z found, 208.1 $[M+H]^+$.

Intermediate 69: 4-Fluoro-3-(4H-1,2,4-triazol-4-yl)benzoic acid

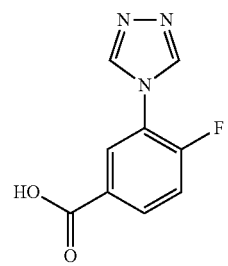 [SMILES: O=C(O)c1ccc(F)c(-n2cnnc2)c1]

The title compound was prepared in a manner analogous to Intermediate 68 using methyl 3-amino-4-fluorobenzoate instead of methyl 3-amino-5-fluorobenzoate in Step A. MS (ESI): mass calcd. for $C_9H_6FN_3O_2$, 207.0; m/z found, 206.0 [M−H]⁻.

Intermediate 70:
3-Methyl-5-(4H-1,2,4-triazol-4-yl)benzoic acid

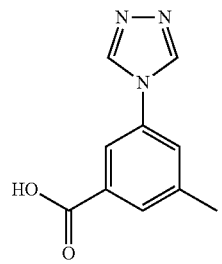

The title compound was prepared in a manner analogous to Intermediate 68 using methyl 3-amino-5-methylbenzoate instead of methyl 3-amino-5-fluorobenzoate in Step A. MS (ESI): mass calcd. for $C_{10}H_9N_3O_2$, 203.1; m/z found, 204.1 [M+H]⁺.

Intermediate 71:
2-Methyl-3-(4H-1,2,4-triazol-4-yl)benzoic acid

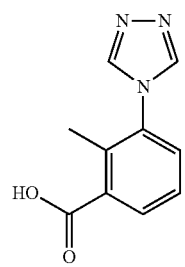

The title compound was prepared in a manner analogous to Intermediate 68 using methyl 3-amino-2-methylbenzoate instead of methyl 3-amino-5-fluorobenzoate in Step A. MS (ESI): mass calcd. for $C_{10}H_9N_3O_2$, 203.1; m/z found, 204.1 [M+H]⁺.

Intermediate 72:
4-Methyl-3-(4H-1,2,4-triazol-4-yl)benzoic acid

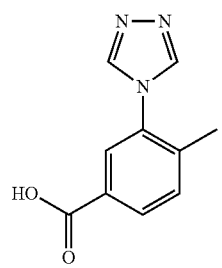

The title compound was prepared in a manner analogous to Intermediate 68 using methyl 3-amino-4-methylbenzoate instead of methyl 3-amino-5-fluorobenzoate in Step A. MS (ESI): mass calcd. for $C_{10}H_9N_3O_2$, 203.1; m/z found, 204.1 [M+H]⁺.

Intermediate 73:
2-(4-Methyl-2H-1,2,3-triazol-2-yl)benzoic acid

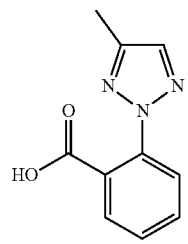

The title compound was prepared in a manner analogous to Intermediate 44 using 2-iodobenzoic acid instead of 3-iodobenzoic acid and 4-methyl-2H-1,2,3-triazole instead of 3-(trifluoromethyl)pyrazole. MS (ESI): mass calcd. for $C_{10}H_9N_3O_2$, 203.1; m/z found, 204.1 [M+H]⁺.

Intermediate 74:
4-Fluoro-2-(2H-1,2,3-triazol-2-yl)benzoic acid

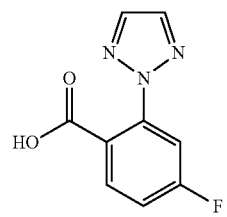 [SMILES: O=C(O)c1ccc(F)cc1-n1nccn1]

The title compound was prepared in a manner analogous to Intermediate 44 using 4-fluoro-2-iodobenzoic acid instead of 3-iodobenzoic acid and 1,2,3-triazole instead of 3-(trifluoromethyl)pyrazole. MS (ESI): mass calcd. for $C_9H_6FN_3O_2$, 207.0; m/z found, 208.1 [M+H]⁺.

Intermediate 75:
3-Fluoro-2-(2H-1,2,3-triazol-2-yl)benzoic acid

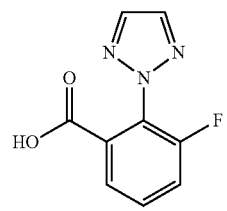 [SMILES: O=C(O)c1cccc(F)c1-n1nccn1]

The title compound was prepared in a manner analogous to Intermediate 44 using 3-fluoro-2-iodobenzoic acid instead of 3-iodobenzoic acid and 1,2,3-triazole instead of 3-(trifluoromethyl)pyrazole. MS (ESI): mass calcd. for $C_9H_6FN_3O_2$, 207.0; m/z found, 208.1 [M+H]⁺.

Intermediate 76: 5-Methyl-2-(2H-1,2,3-triazol-2-yl)benzoic acid

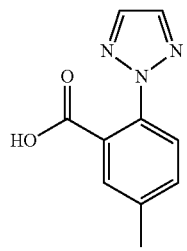

The title compound was prepared in a manner analogous to Intermediate 44 using 2-iodo-5-methylbenzoic acid instead of 3-iodobenzoic acid and 1,2,3-triazole instead of 3-(trifluoromethyl)pyrazole. MS (ESI): mass calcd. for $C_{10}H_9N_3O_2$, 203.1; m/z found, 204.2 [M+H]$^+$.

Intermediate 77: 2-(2H-1,2,3-Triazol-2-yl)-3-(trifluoromethyl)benzoic acid

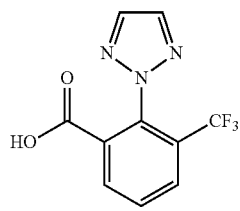 [SMILES: O=C(O)c1cccc(C(F)(F)F)c1-n1nccn1]

The title compound was prepared in a manner analogous to Intermediate 44 using 2-iodo-3-(trifluoromethyl)benzoic acid instead of 3-iodobenzoic acid and 1,2,3-triazole instead of 3-(trifluoromethyl)pyrazole. MS (ESI): mass calcd. for $C_{10}H_6F_3N_3O_2$, 257.0; m/z found, 258.1 [M+H]$^+$.

Intermediate 78: 4-(1H-Pyrazol-1-yl)picolinic acid

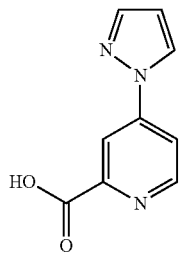 [SMILES: O=C(O)c1cc(-n2cccn2)ccn1]

The title compound was prepared in a manner analogous to Intermediate 64, using methyl 4-iodopicolinate instead of methyl 3-bromo-5-fluorobenzoate. MS (ESI): mass calcd. for $C_9H_7N_3O_2$, 189.1; m/z found, 190.1 [M+H]$^+$.

Intermediate 79: Indolizine-7-carboxylic acid

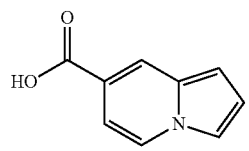 [SMILES: O=C(O)c1ccn2cccc2c1]

The title compound was prepared in a manner analogous to Intermediate 66, Step B, using methyl indolizine-7-carboxylate instead of ethyl 3-benzyl-5-(trifluoromethyl)triazole-4-carboxylate. MS (ESI): mass calcd. for $C_9H_7NO_2$, 161.1; m/z found, 162.1 [M+H]$^+$. $^1$H NMR (300 MHz, DMSO-d$_6$) δ 12.73 (br s, 1H), 8.29 (d, J=7.2 Hz, 1H), 8.16-8.09 (m, 1H), 7.78-7.69 (m, 1H), 6.94 (dd, J=7.3, 1.8 Hz, 1H), 6.88 (dd, J=4.0, 2.6 Hz, 1H), 6.78-6.71 (m, 1H).

Intermediate 80: 2-(1H-Pyrazol-1-yl)isonicotinic acid

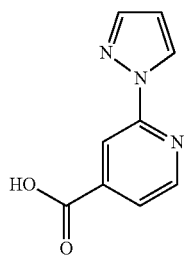 [SMILES: O=C(O)c1ccnc(-n2cccn2)c1]

The title compound was prepared in a manner analogous to Intermediate 64, using methyl 2-iodoisonicotinate instead of methyl 3-bromo-5-fluorobenzoate. MS (ESI): mass calcd. for $C_9H_7N_3O_2$, 189.1; m/z found, 190.1 [M+H]$^+$.

Intermediate 81: 4-Methoxy-5-(1H-pyrazol-1-yl)nicotinic acid

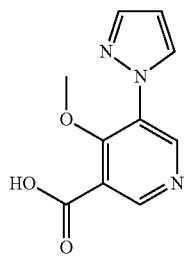 [SMILES: COc1c(C(=O)O)cncc1-n1cccn1]

Step A: Methyl 4-hydroxypyridine-3-carboxylate. To a mixture of 4-hydroxynicotinic acid (2.09 g, 15 mmol) in methanol (41 mL, 101 mmol, 0.792 g/mL) was added sulfuric acid (80 µL, 1.5 mmol, 1.84 g/mL). The reaction mixture was stirred at 65° C. for 16 h. The reaction mixture was neutralized with saturated sodium carbonate (3 mL) and the precipitate was collected to give the title compound (1.98 g, 12.9 mmol, 86%) as an off-white powder. MS (ESI): mass calcd. for $C_7H_7NO_3$, 153.0; m/z found, 154.1 [M+H]$^+$.

Step B: Methyl 4-hydroxy-5-iodo-pyridine-3-carboxylate. To a suspension of methyl 4-hydroxypyridine-3-carboxylate (1.11 g, 7.25 mmol) in acetonitrile (5 mL) and acetic acid (3 mL) was added N-iodosuccinimide (1.63 g, 7.24 mmol) and the reaction mixture was stirred at 60° C. for 16 h. The reaction mixture was evaporated. The residue was diluted with acetone (10 mL) and the precipitate was collected to give the title compound (828 mg, 2.97 mmol, 41%) as an off-white powder. MS (ESI): mass calcd. for $C_7H_6INO_3$, 278.9; m/z found, 280.0 $[M+H]^+$.

Step C: Methyl 5-iodo-4-methoxy-pyridine-3-carboxylate. To a suspension of methyl 4-hydroxy-5-iodo-pyridine-3-carboxylate (811 mg, 2.91 mmol) in dichloromethane (15 mL) was added trimethyloxonium tetrafluoroborate (1075 mg, 7.25 mmol). The reaction mixture was stirred at room temperature for 20 h. To the reaction mixture was added trimethyloxonium tetrafluoroborate (1075 mg, 7.25 mmol). The reaction mixture was stirred at room temperature for 24 h. The reaction mixture was diluted with water (40 mL). The aqueous layer was extracted with dichloromethane (3×50 mL). The combined organic layers were washed with water (2×20 mL). The organic layer was dried over magnesium sulfate, filtered and evaporated to give the title compound (260 mg, 0.887 mmol, 30%) as an off-white powder. MS (ESI): mass calcd. for $C_8H_8INO_3$, 293.0; m/z found, 294.0 $[M+H]^+$.

Step D: 4-Methoxy-5-pyrazol-1-yl-pyridine-3-carboxylic acid. To a solution of methyl 5-iodo-4-methoxy-pyridine-3-carboxylate (100 mg, 0.341 mmol) in dimethyl sulfoxide (1 mL) was added pyrazole (116 mg, 1.70 mmol), copper(I) oxide (5.0 mg, 0.0349 mmol) and cesium carbonate (222 mg, 0.681 mmol). The reaction mixture was stirred at 110° C. for 40 h under argon. The reaction mixture was purified by preparative HPLC (Method E) to afford the title compound (15 mg, 0.068 mmol, 20%) as an off-white powder. MS (ESI): mass calcd. for $C_{10}H_9N_3O_3$, 219.1; m/z found, 220.2 $[M+H]^+$.

Intermediate 82: 4-(1H-Pyrazol-1-yl)nicotinic acid

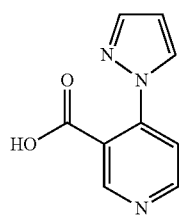

Step A: Methyl 4-pyrazol-1-ylpyridine-3-carboxylate. To a mixture of 4-bromo-nicotinic acid methyl ester hydrobromide (220 mg, 0.741 mmol), pyrazole (76 mg, 1.12 mmol), cesium carbonate (725 mg, 2.23 mmol), trans-N,N'-dimethylcyclon-hexane-1,2-diamine (20 µL, 0.127 mmol, 0.902 g/mL) and copper(I) iodide (14 mg, 0.0735 mmol) in N,N-dimethylformamide (2 mL) was stirred at 140° C. for 20 min under microwave irradiation. The reaction mixture was diluted with water (10 mL) and extracted with ethyl acetate (3×10 mL). The combined organic layers were dried over magnesium sulfate, filtered and evaporated. The residue was purified by silica gel column chromatography eluting with ethyl acetate to give the title compound (60 mg, 0.295 mmol, 39%) as a yellow oil. MS (ESI): mass calcd. for $C_{10}H_9N_3O_2$, 203.1; m/z found, 204.2 $[M+H]^+$.

Step B: 4-Pyrazol-1-ylpyridine-3-carboxylic acid. To a mixture of methyl 4-pyrazol-1-ylpyridine-3-carboxylate (60 mg, 0.295 mmol) in water (800 µL) and 1,4-dioxane (800 µL) was added sodium hydroxide (30 mg, 0.75 mmol). The reaction mixture was stirred at 80° C. at 2 h. The reaction mixture was quenched with 6 M hydrochloric acid (0.15 mL) and evaporated to afford the title compound (80 mg) as a crude white powder. The title compound was used crude without further purification.

Intermediate 83:
6-Methyl-3-(1H-1,2,4-triazol-1-yl)picolinic acid

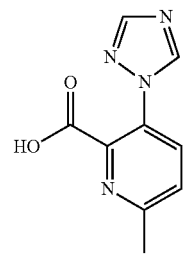

Step A: 6-Methyl-3-nitro-pyridine-2-carbonitrile. To a suspension of 2-chloro-6-methyl-3-nitropyridine (1.0 g, 5.795 mmol) in N,N-dimethylformamide (10 mL) was added zinc cyanide (749 mg, 6.378 mmol) and tetrakis(triphenylphosphine)palladium(0) (1004 mg, 0.869 mmol). The reaction mixture was stirred at 80° C. for 22 h under argon and evaporated under reduced pressure. The reaction was repeated on the same scale. The crude products were combined and purified by gradient silica gel column chromatography eluting with n-heptane:ethyl acetate (100:00→70:30) to give the title compound (700 mg, 4.29 mmol, 37%) as a yellow oil. MS (ESI): mass calcd. for $C_7H_5N_3O_2$, 163.0; m/z found, 164.1 $[M+H]^+$.

Step B: 3-Amino-6-methyl-pyridine-2-carbonitrile. To a solution of 6-methyl-3-nitro-pyridine-2-carbonitrile (640 mg, 3.92 mmol) in acetic acid (10 mL) was added iron (548 mg, 9.81 mmol) at 0° C. The reaction mixture was allowed to warm to room temperature and stirred for 2 h. The reaction mixture was diluted with dichloromethane (20 mL) and filtered through a pad of Celite®. The Celite® was washed with dichloromethane (3×10 mL). The combined filtrates were evaporated and the residue was taken up in water (15 mL), made basic to pH 9 with saturated sodium carbonate (5 mL) and extracted with dichloromethane (3×50 mL). The combined organic layers were dried over magnesium sulfate, filtered and evaporated to give the title compound (451 mg, 3.39 mmol, 86%) as an orange powder. MS (ESI): mass calcd. for $C_7H_7N_3$, 133.1; m/z found, 134.2 $[M+H]^+$. $^1H$ NMR (500 MHz, DMSO-$d_6$) δ 7.20 (d, J=8.6 Hz, 1H), 7.14 (d, J=8.7 Hz, 1H), 6.03 (br s, 2H), 2.29 (s, 3H).

Step C: 3-Iodo-6-methyl-pyridine-2-carbonitrile. To a suspension of 3-amino-6-methyl-pyridine-2-carbonitrile (750 mg, 5.63 mmol) in water (10 mL) was added hydrochloric acid (6 M, 5.6 mL, 33.6 mmol) and the mixture was cooled to 0° C. Aqueous sodium nitrite (2 M, 4.2 mL, 8.4 mmol) was added dropwise over 5 min at 0° C. and the reaction was stirred at 0° C. for 30 min. Aqueous potassium iodide (2 M, 6.2 mL, 12.4 mmol) was added dropwise over 10 min, maintaining the temperature between 0-5° C. The reaction mixture was stirred at 0° C. for 30 min. The reaction mixture was diluted with saturated aqueous sodium carbonate (5 mL) and extracted with ethyl acetate (3×10 mL). The combined organic layers were dried over magnesium sulfate, filtered and evaporated. The residue was purified by gradient silica gel column chromatography eluting with n-heptane-ethyl acetate (9:1→4:1) to afford the title compound (925 mg, 3.79 mmol, 67%) as an off-white powder. MS (ESI): mass calcd. for $C_7H_5IN_2$, 244.0; m/z found, 245.0 $[M+H]^+$.

Step D: 6-Methyl-3-(1,2,4-triazol-1-yl)pyridine-2-carbonitrile. To a solution of 3-iodo-6-methyl-pyridine-2-carbonitrile (250 mg, 1.02 mmol) and 1,2,4-triazole (106 mg, 1.53 mmol) in N,N-dimethylformamide (1.5 mL) was added cesium carbonate (567 mg, 1.74 mmol), trans-N,N-dimethylcyclohexane-1,2-diamine (28 μL, 0.178 mmol, 0.902 g/mL) and copper(I) iodide (20 mg, 0.105 mmol). The reaction mixture was stirred at 140° C. for 40 min under microwave irradiation and poured into water (8 mL). The mixture was extracted with ethyl acetate (3×10 mL) and the combined organic layers were dried over magnesium sulfate, filtered and evaporated. The residue was purified by silica gel column chromatography eluting with ethyl acetate to give the title compound (50 mg, 0.270 mmol, 26%) as a pale yellow powder. MS (ESI): mass calcd. for $C_9H_7N_5$, 185.1; m/z found, 186.2 $[M+H]^+$.

Step E: 6-Methyl-3-(1,2,4-triazol-1-yl)pyridine-2-carboxylic acid. To a mixture of 6-methyl-3-(1,2,4-triazol-1-yl)pyridine-2-carbonitrile (50 mg, 0.27 mmol) in water (675 μL) and 1,4-dioxane (675 μL) was added sodium hydroxide (27 mg, 0.675 mmol). The reaction mixture was stirred at 60° C. for 1 h then at 80° C. for 23 h. The reaction mixture was quenched with 6 M hydrochloric acid (0.115 mL) and evaporated to afford the title compound (88 mg, crude) as a pale-yellow powder containing ca. 35 wt % sodium chloride. MS (ESI): mass calcd. for $C_9H_8N_4O_2$, 204.1; m/z found, 161.1 $[M+2H—CO_2]^+$. $^1H$ NMR (300 MHz, DMSO-$d_6$) δ 8.92 (s, 1H), 8.16 (s, 1H), 7.84 (d, J=8.2 Hz, 1H), 7.49-7.34 (m, 1H), 7.30 (d, J=8.2 Hz, 1H), 2.50-2.47 (m, 3H).

Intermediate 84:
6-Methyl-3-(1H-pyrazol-1-yl)picolinic acid

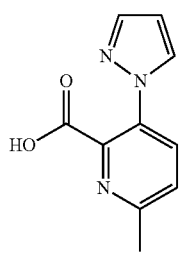

The title compound was prepared in a manner analogous to Intermediate 83 using pyrazole instead of 1,2,4-triazole in Step D. MS (ESI): mass calcd. for $C_{10}H_9N_3O_2$, 203.1; m/z found, 202.1 $[M-H]^-$.

Intermediate 85: 3-(2H-1,2,3-Triazol-2-yl)picolinic acid

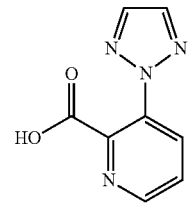 [SMILES: O=C(O)c1ncccc1-n1nccn1]

The title compound was prepared in a manner analogous to Intermediate 83, Steps D-E using 3-bromopicolinonitrile instead of 3-iodo-6-methyl-pyridine-2-carbonitrile, using 1H-1,2,3-triazole instead of 1,2,4-triazole; and using conventional heating instead of microwave heating. MS (ESI): mass calcd. for $C_8H_6N_4O_2$, 190.1; m/z found, 191.1 $[M+H]^+$.

Intermediate 86:
6-Methyl-4-(2H-1,2,3-triazol-2-yl)picolinic acid

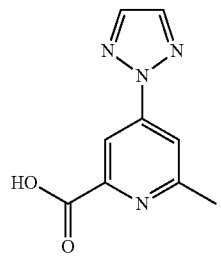

Step A: 4-Amino-6-methyl-pyridine-2-carbonitrile. To a solution of 6-methyl-4-nitropyridine-2-carbonitrile (1.0 g, 6.13 mmol) in acetic acid (20 mL) was added iron (856 mg, 15.3 mmol). The reaction mixture was stirred at room temperature for 1 h. The reaction mixture was filtered through a pad of Celite® and the Celite® was washed with ethyl acetate (3×50 mL). The combined filtrates were washed with saturated sodium carbonate (3×30 mL) and brine (1×30 mL). The organic layer was dried over magnesium sulfate, filtered and evaporated to give the title compound (760 mg, 5.71 mmol, 93%) as a tan powder. MS (ESI): mass calcd. for $C_7H_7N_3$, 133.1; m/z found, 134.2 $[M+H]^+$.

Step B: 4-Iodo-6-methyl-pyridine-2-carbonitrile. To the suspension of 4-amino-6-methyl-pyridine-2-carbonitrile (650 mg, 4.88 mmol) in water (7 mL) was added hydrochloric acid (6 M, 4.89 mL, 29.3 mmol) and the mixture was cooled to 0° C. To the mixture was added sodium nitrite (2 M, 3.66 mL, 7.32 mmol) dropwise over 1 min at 0° C. and the reaction mixture was stirred at 0° C. for 30 min. To the reaction mixture was added 2 M aqueous potassium iodide (5.37 mL, 10.7 mmol) dropwise over 1 min at 0° C. The reaction mixture was stirred at 0° C. for 30 min. To the reaction mixture was quenched with saturated sodium carbonate (50 mL) and extracted with ethyl acetate (3×50 mL). The combined organic layers were dried over magnesium sulfate, filtered and evaporated. The residue was purified by silica gel column chromatography eluting with n-hexane: ethyl acetate (4:1) to afford the title compound (320 mg, 1.31 mmol, 27%) as a yellow powder. MS (ESI): mass calcd. for $C_7H_{11}IN_2$, 244.0; m/z found, 245.0 $[M+H]^+$.

Step C: 6-Methyl-4-(2H-1,2,3-triazol-2-yl)picolinic acid. The title compound was prepared in a manner analogous to Intermediate 83 using 4-iodo-6-methyl-pyridine-2-carbonitrile instead of 3-iodo-6-methyl-pyridine-2-carbonitrile in Step D and using conventional heating instead of microwave heating. MS (ESI): mass calcd. for $C_9H_8N_4O_2$, 204.1; m/z found, 205.1 $[M+H]^+$.

Intermediate 87: 4-(4H-1,2,4-Triazol-4-yl)picolinic acid

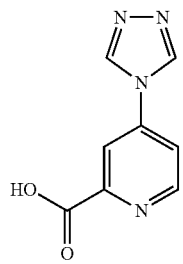 [SMILES: O=C(O)c1cc(-n2cnnc2)ccn1]

The title compound was prepared in a manner analogous to Intermediate 68 using methyl 4-aminopyridine-2-carboxylate instead of methyl 3-amino-5-fluorobenzoate in Step A. MS (ESI): mass calcd. for $C_8H_6N_4O_2$, 190.1; m/z found, 191.1 $[M+H]^+$.

Intermediate 88: 5-(4H-1,2,4-Triazol-4-yl)nicotinic acid

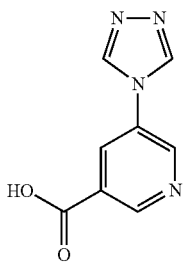 [SMILES: O=C(O)c1cncc(-n2cnnc2)c1]

The title compound was prepared in a manner analogous to Intermediate 68 using methyl 5-aminonicotinate instead of methyl 3-amino-5-fluorobenzoate in Step A. MS (ESI): mass calcd. for $C_8H_6N_4O_2$, 190.1; m/z found, 191.1 $[M+H]^+$.

Intermediate 89: 6-Methyl-4-(4H-1,2,4-triazol-4-yl)picolinic acid

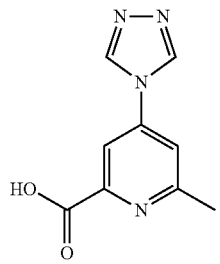

Step A: 4-Amino-6-methyl-pyridine-2-carbonitrile. To a solution of 6-methyl-4-nitropyridine-2-carbonitrile (1.0 g, 6.13 mmol) in acetic acid (20 mL) was added iron powder (3.08 g, 55.2 mmol) at 50° C. and the reaction was stirred at 50° C. for 30 min, filtered and evaporated. The residue was purified by silica gel column chromatography eluting with n-heptane:ethyl acetate (1:1) to give the title compound (160 mg, 1.20 mmol, 19%) as a white powder.

Step B: 6-Methyl-4-(1,2,4-triazol-4-yl)pyridine-2-carbonitrile. To a solution of 4-amino-6-methyl-pyridine-2-carbonitrile (150 mg, 1.13 mmol) in pyridine (5 mL) was added 1,2-diformylhydrazine (248 mg, 2.82 mmol) and triethylamine (786 μL, 5.63 mmol). To the mixture was added chlorotrimethylsilane (1.43 mL, 11.3 mmol) dropwise, and the reaction was stirred at 100° C. for 16 h. The reaction mixture was filtered and evaporated and the residue was purified by silica gel column chromatography eluting with chloroform:methanol (10:1) to give the title compound (65 mg, 0.351 mmol, 31%) as a white powder. MS (ESI): mass calcd. for $C_9H_7N_5$, 185.1; m/z found, 186.1 $[M+H]^+$.

Step C: 6-Methyl-4-(1,2,4-triazol-4-yl)pyridine-2-carboxylic acid hydrochloride. To a mixture of 6-methyl-4-(1,2,4-triazol-4-yl)pyridine-2-carbonitrile (50 mg, 0.270 mmol) in water (600 μL) and 1,4-dioxane (600 μL) was added sodium hydroxide (50 mg, 1.25 mmol). The reaction mixture was stirred at 80° C. for 1 h. The reaction was quenched with 6 M hydrochloric acid (0.3 mL) and the mixture was evaporated. The residue was triturated with water (1 mL) to afford the title compound (21 mg, 0.087 mmol, 32%) as a white powder. MS (ESI): mass calcd. for $C_9H_8N_4O_2$, 204.1; m/z found, 205.1 $[M+H]^+$.

Intermediate 90: 5-(Triazol-2-yl)pyridine-3-carboxylic acid

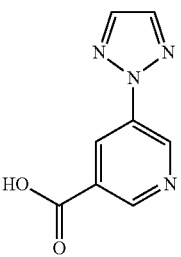 [SMILES: O=C(O)c1cncc(-n2nccn2)c1]

Step A: 5-(Triazol-2-yl)pyridine-3-carboxylic acid and 5-(triazol-1-yl)pyridine-3-carboxylic acid. To a mixture of methyl 5-iodopyridine-3-carboxylate (200 mg, 0.76 mmol), 1H-1,2,3-triazole (80 mg, 1.16 mmol), cesium carbonate (420 mg, 1.29 mmol), trans-N,N'-dimethylcyclohexane-1,2-diamine (20 μL, 0.127 mmol, 0.902 g/mL) and copper(I) iodide (20 mg, 0.105 mmol) in N,N-dimethylformamide (2 mL) was stirred at 140° C. for 3 h. The reaction mixture was filtered and the filtrate was evaporated to give a mixture of the title compounds (320 mg, crude) as a brown powder. MS (ESI): mass calcd. for $C_8H_6N_4O_2$, 190.1; m/z found, 189.2 [M–H]$^-$.

Step B: Methyl 5-(triazol-2-yl)pyridine-3-carboxylate and methyl 5-(triazol-1-yl)pyridine-3-carboxylate. To the suspension of the crude acid mixture (320 mg, 1.68 mmol) in dry tetrahydrofuran (5 mL) was added a 1.0 M ethereal solution of diazomethane (5 mL, 5 mmol, 1 M). The reaction mixture was stirred at room temperature for 1 h. The reaction mixture was diluted with water (5 mL) and extracted with ethyl acetate (3×5 mL). The combined organic layers were washed with water (1×5 mL), dried over sodium sulfate, filtered and evaporated. The crude product was purified by preparative HPLC to give methyl 5-(triazol-2-yl)pyridine-3-carboxylate (11 mg, 0.054 mmol, 3%) as a white powder. MS m/z=205.1 [M+H]$^+$.

Fractions from the same preparative HPLC (Method E) were collected to give methyl 5-(triazol-1-yl)pyridine-3-carboxylate (8 mg, 0.039 mmol, 2%) as a white powder. MS (ESI): mass calcd. for $C_9H_8N_4O_2$, 204.1; m/z found, 205.1 [M+H]$^+$.

Step C: 5-(Triazol-2-yl)pyridine-3-carboxylic acid. To a solution of methyl 5-(triazol-2-yl)pyridine-3-carboxylate (11 mg, 0.0539 mmol) in 1,4-dioxane (500 μL) was added a solution of sodium hydroxide (6 mg, 0.15 mmol) in water (130 μL). The reaction mixture was stirred at room temperature for 16 h. The reaction mixture was acidified to pH 4 with 1 M hydrochloric acid (100 μL). The mixture was evaporated to afford the title compound (18 mg, 0.095 mmol, crude) as a light brown powder. $^1$H NMR (500 MHz, DMSO-$d_6$) δ 13.82 (br s, 1H), 9.45 (d, J=2.5 Hz, 1H), 9.10 (d, J=1.7 Hz, 1H), 8.76-8.71 (m, 1H), 8.27 (s, 2H).

Intermediate 91:
3-Fluoro-1,5-dimethyl-1H-pyrazole-4-carboxylic acid

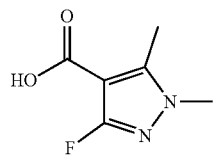

Step A: Ethyl 3-fluoro-1,5-dimethyl-1H-pyrazole-4-carboxylate. To a solution ethyl 1,5-dimethyl-1H-pyrazole-4-carboxylate (50 mg, 0.30 mmol) in THF (2.5 mL) at −78° C. was added lithium diisopropylamide (LDA) (2.0 M in THF/heptane/ethylbenzene) (0.30 mL, 0.60 mmol) and the mixture stirred at −78° C. for 30 min before adding a solution of N-fluorodibenzenesulfonimide (NFSI) (187 mg, 0.60 mmol) in THF (0.5 mL). The reaction was maintained at −78° C. for an additional 30 min, the cold bath removed, and the mixture stirred at room temperature overnight. The reaction was quenched with sat. aq. NH$_4$Cl and then diluted with EtOAc and H$_2$O. The layers were separated and the aqueous layer extracted with EtOAc (×3). The combined organic layers were then washed with brine, dried over Na$_2$SO$_4$, filtered, and concentrated in vacuo. The crude residue was purified by silica gel chromatography (0-10% MeOH in DCM) to afford a yellow solid (33.5 mg, 61% yield). MS (ESI): mass calcd. for $C_8H_{11}FN_2O_2$, 186.1; m/z found, 187.1 [M+H]$^+$. $^1$H NMR (400 MHz, Chloroform-d) δ 4.29 (q, J=7.1 Hz, 2H), 3.67 (s, 3H), 2.38 (s, 3H), 1.34 (t, J=7.1 Hz, 3H).

Step B: 3-Fluoro-1,5-dimethyl-1H-pyrazole-4-carboxylic acid. A solution of ethyl 3-fluoro-1,5-dimethyl-1H-pyrazole-4-carboxylate (9.7 mg, 52.1 μmol) in 37% aq. HCl (1.62 mL) was heated to 110° C. for 3 h before being cooled to room temperature and diluted with H$_2$O. The mixture was carefully neutralized using 10 N aq. NaOH and then extracted with EtOAc (×3). The combined organic layers were then dried over Na$_2$SO$_4$, filtered, and concentrated in vacuo to afford a yellow solid which was used directly in the next step without further purification. MS (ESI): mass calcd. for $C_6H_7FN_2O_2$, 158.0; m/z found, 159.1 [M+H]$^+$. $^1$H NMR (400 MHz, Methanol-$d_4$) δ 3.68 (d, J=1.5 Hz, 3H), 2.34 (s, 3H).

Intermediate 92:
1-Cyclopropyl-5-methyl-pyrazole-4-carboxylic acid

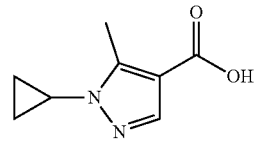

Step A: Ethyl 1-cyclopropyl-5-methyl-pyrazole-4-carboxylate and ethyl 2-cyclopropyl-5-methyl-pyrazole-4-carboxylate. To a solution of ethyl 3-methyl-1H-pyrazole-4-carboxylate (1.55 g, 10.1 mmol) in 1,2-dichloroethane (60 mL) was added cyclopropylboronic acid (1.73 g, 20.1 mmol), copper(II) acetate (3.65 g, 20.1 mmol), potassium carbonate (2.78 g, 20.1 mmol), and 2,2'-bipyridine (3.14 g, 20.1 mmol). The reaction mixture was stirred at room temperature for 5 d. To reaction mixture was diluted with water (100 mL) and extracted with chloroform (2×60 mL). The combined organic layers were washed with brine (1×10 mL), dried over magnesium sulfate, filtered and evaporated. The residue was purified by gradient silica gel column chromatography eluting with n-heptane-ethyl acetate (20:1→1:1) to give a 60:40 mixture of the title compounds (290 mg, 1.493 mmol, 15%) as a colorless liquid.

Ethyl 1-cyclopropyl-5-methyl-pyrazole-4-carboxylate: MS (ESI): mass calcd. for $C_{10}H_{14}N_2O_2$, 194.1; m/z found, 195.2 [M+H]$^+$. $^1$H NMR (300 MHz, DMSO-$d_6$) δ 7.69 (s, 1H), 4.20 (q, J=6.8 Hz, 2H), 3.64-3.48 (m, 1H), 2.57 (s, 3H), 1.26 (t, J=7.1 Hz, 3H), 1.13-1.03 (m, 4H). Fractions from the same column were collected and purified by silica gel column chromatography eluting with n-heptane-ethyl acetate (100:1→1:1) to give pure ethyl 2-cyclopropyl-5-methyl-pyrazole-4-carboxylate (90 mg, 0.463 mmol, 5%) as a colorless liquid. MS (ESI): mass calcd. for $C_{10}H_{14}N_2O_2$, 194.1; m/z found, 195.2 [M+H]$^+$.

$^1$H NMR (500 MHz, DMSO-$d_6$) δ 8.21 (s, 1H), 4.18 (q, J=7.1 Hz, 2H), 3.74-3.66 (m, 1H), 2.30 (s, 3H), 1.25 (t, J=7.1 Hz, 3H), 1.09-1.01 (m, 2H), 0.96-0.90 (m, 2H).

Step B: 1-Cyclopropyl-5-methyl-pyrazole-4-carboxylic acid. To a mixture of ethyl 1-cyclopropyl-5-methyl-pyrazole-4-carboxylate and ethyl 2-cyclopropyl-5-methyl-pyrazole-4-carboxylate (260 mg, 1.34 mmol) in water (1.5 mL)

and 1,4-dioxane (1.5 mL) was added sodium hydroxide (120 mg, 3 mmol). The reaction mixture was stirred at 80° C. at 18 h. The reaction mixture was evaporated. The residue was taken up in water (2 mL) and acidified to pH 4 with 1 M hydrochloric acid. The precipitate was collected to afford the title compound (35 mg, 0.211 mmol, 16%) as a white powder. MS (ESI): mass calcd. for $C_8H_{10}N_2O_2$, 166.1; m/z found, 167.1 [M+H]$^+$. $^1$H NMR (500 MHz, DMSO-$d_6$) δ 12.19 (br s, 1H), 7.65 (s, 1H), 3.59-3.50 (m, 1H), 2.55 (s, 3H), 1.08-0.98 (m, 4H). Structure confirmed by NOESY.

Intermediate 93: 1-Cyclopropyl-3-methyl-pyrazole-4-carboxylic acid

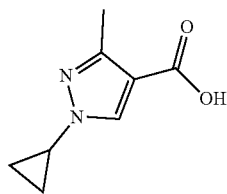

To a mixture of ethyl 2-cyclopropyl-5-methyl-pyrazole-4-carboxylate (Intermediate 92, Step A). (70 mg, 0.36 mmol) in water (1 mL) and 1,4-dioxane (1 mL) was added sodium hydroxide (32 mg, 0.80 mmol). The reaction mixture was stirred at 80° C. at 2 h. The reaction mixture was evaporated and the residue was taken up in water (2 mL). The mixture was acidified to pH 4 with 1 M hydrochloric acid. The precipitate was collected to afford the title compound (25 mg, 0.150 mmol, 42%) as a white powder. MS (ESI): mass calcd. for $C_8H_{10}N_2O_2$, 166.1; m/z found, 167.2 [M+H]$^+$. $^1$H NMR (300 MHz, DMSO-$d_6$) δ 12.11 (br s, 1H), 8.14 (s, 1H), 3.78-3.58 (m, 1H), 2.28 (s, 3H), 1.14-0.80 (m, 4H). Structure confirmed by NOESY.

Intermediate 94: 1-Methyl-1H-pyrazolo[3,4-b]pyridine-4-carboxylic acid

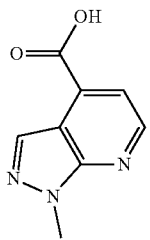

Step A: 4-Iodo-1-methyl-pyrazolo[3,4-b]pyridine. To a solution of 4-iodo-1H-pyrazolo[3,4-b]pyridine (405 mg, 1.65 mmol) in N,N-dimethylformamide (4 mL) was added sodium hydride (60% in mineral oil, 80 mg, 2.0 mmol) at 0° C. and the reaction was stirred at 0° C. for 15 min. To the reaction mixture was added iodomethane (115 μL, 1.85 mmol, 2.28 g/mL) and the reaction was stirred at 0° C. for 45 min. The reaction mixture was poured into water (20 mL) and extracted with ethyl acetate (3×15 mL). The combined organic layers were dried over magnesium sulfate, filtered and evaporated. The residue was purified by silica gel column chromatography eluting with n-heptane:ethyl acetate (9:1) to afford the title compound (200 mg, 0.772 mmol, 47%) as a white powder. MS (ESI): mass calcd. for $C_7H_6IN_3$, 259.0; m/z found, 260.0 [M+H]$^+$.

Step B: 1-Methylpyrazolo[3,4-b]pyridine-4-carbonitrile. To a solution of 4-iodo-1-methyl-pyrazolo[3,4-b]pyridine (150 mg, 0.579 mmol) in dimethyl sulfoxide (1.5 mL) was added copper(I) cyanide (62 mg, 0.692 mmol). The reaction mixture was stirred at 120° C. for 20 h under argon and poured into water (15 mL). The precipitate was collected to give the crude title compound (165 mg) as an orange powder. MS (ESI): mass calcd. for $C_8H_6N_4$, 158.1; m/z found, 157.1 [M–H]$^-$.

Step C: 1-Methylpyrazolo[3,4-b]pyridine-4-carboxylic acid. To a mixture of 1-methylpyrazolo[3,4-b]pyridine-4-carbonitrile (150 mg, 0.948 mmol) in water (1 mL) and 1,4-dioxane (1 mL) was added sodium hydroxide (1 M, 960 μL, 0.96 mmol). The reaction mixture was stirred at 80° C. at 20 h and the reaction mixture was filtered. The filtrate was diluted with water (5 mL) and extracted with ethyl acetate (2×5 mL). The aqueous layer was acidified to pH 4 with 1 M hydrochloric acid. The precipitate was collected to afford the title compound (35 mg, 0.198 mmol, 21%) as a tan powder. MS (ESI): mass calcd. for $C_8H_7N_3O_2$, 177.1; m/z found, 178.1 [M+H]$^+$.

Intermediate 95: 7-Methylimidazo[1,2-a]pyridine-5-carboxylic acid

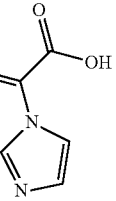

Step A: 7-Methylimidazo[1,2-a]pyridine-5-carbonitrile. To a solution of 5-bromo-7-methylimidazo[1,2-a]pyridine (300 mg, 1.42 mmol) in dimethyl sulfoxide (3 mL) was added copper(I) cyanide (152 mg, 1.70 mmol). The reaction mixture was stirred at 120° C. for 20 h. To the reaction mixture was added copper(I) iodide (54 mg, 0.284 mmol). The reaction mixture was stirred at 120° C. for 20 h. The reaction mixture was poured into water (20 mL). The precipitate was collected and triturated with warm chloroform (3×20 mL). The filtrate was evaporated to give the title compound (103 mg, 0.655 mmol, 46%) as a tan powder. MS (ESI): mass calcd. for $C_9H_7N_3$, 157.1; m/z found, 158.1 [M+H]$^+$.

Step B: 7-Methylimidazo[1,2-a]pyridine-5-carboxylic acid. To a mixture of 7-methylimidazo[1,2-a]pyridine-5-carbonitrile (93 mg, 0.592 mmol) in water (1.5 mL) and 1,4-dioxane (1.5 mL) was added sodium hydroxide (59 mg, 1.48 mmol). The reaction mixture was stirred at 50° C. for 1 h. The mixture was acidified to pH 4 with 1 M hydrochloric acid. The mixture was evaporated. The residue was triturated with methanol (2×3 mL) and the filtrate was evaporated to afford the title compound (120 mg, crude) as a pale yellow powder. MS (ESI): mass calcd. for $C_9H_8N_2O_2$, 176.1; m/z found, 177.1 [M+H]$^+$. $^1$H NMR (500 MHz, DMSO-$d_6$) δ 8.86 (d, J=2.0 Hz, 1H), 8.16-8.09 (m, 1H), 8.00-7.96 (m, 1H), 7.96-7.93 (m, 1H), 3.72-3.17 (m, 1H), 2.54 (s, 3H).

Intermediate 96: Potassium 7-fluoroimidazo[1,2-a]pyridine-3-carboxylate

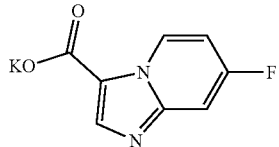

To a solution of ethyl 7-fluoroimidazo[1,2-a] pyridine-3-carboxylate (100 mg, 0.5 mmol) in THF (4.0 mL) was added potassium trimethylsilanolate (92.4 mg, 0.72 mmol) and the resulting mixture was stirred at rt for 16 h. The reaction mixture was then filtered and washed with THF to obtain the title compound as white solid which was taken to next step without purification. MS (ESI): mass calcd. for $C_8H_4FKN_2O_2$, 218.0 m/z found, 181.1[M-K+2H]$^+$.

Intermediate 97: Potassium 2,7-dimethylimidazo[1,2-b]pyridazine-3-carboxylate

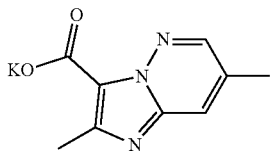

Step A: Ethyl 2,7-dimethylimidazo[1,2-b] pyridazine-3-carboxylate. To a solution of 5-methylpyridazin-3-amine (250 mg, 2.3 mmol) in 1,2-dimethoxyethane (2.2 mL, 20.8 mmol) was added ethyl 2-chloro-3-oxobutanoate (2.3 mL, 2.7 mmol) and the mixture was heated to 90° C. for 1 h. The reaction mixture was concentrated under reduced pressure, diluted with EtOAc, washed the organic layer with water (×2). The combined organic extracts were dried over anhydrous $Na_2SO_4$ and concentrated under vacuo. Purification by flash chromatography ($SiO_2$; 0-100% EtOAc/hexanes) afforded the title compound as a white solid (86.4 mg, 20% yield). MS (ESI): mass calcd. for $C_{11}H_{13}N_3O_2$, 219.1 m/z found, 220.1[M+H]$^+$. $^1$H NMR (400 MHz, DMSO-d$_6$) δ 8.57 (d, J=2.1 Hz, 1H), 7.98-7.90 (m, 1H), 4.35 (q, J=7.1 Hz, 2H), 2.60 (s, 3H), 2.41 (d, J=1.2 Hz, 3H), 1.34 (t, J=7.1 Hz, 3H).

Step B: Potassium 2,7-dimethylimidazo[1,2-b]pyridazine-3-carboxylate. The title compound was prepared in a manner analogous to Intermediate 96 using ethyl 2,7-dimethylimidazo[1,2-b]pyridazine-3-carboxylate (Step A) instead of ethyl 7-fluoroimidazo[1,2-a] pyridine-3-carboxylate and stirring the reaction mixture at 60° C. instead of room temperature. MS (ESI): mass calcd. for $C_9H_8KN_3O_2$, 229.0; m/z found, 192.0 [M-K+2H]$^+$.

Intermediate 98: Potassium 2,5,8-trimethylimidazo[1,2-a]pyrazine-3-carboxylate

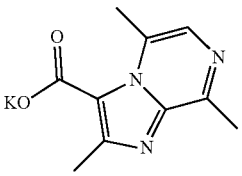

The title compound was prepared in a manner analogous to Intermediate 97 using 3,6-dimethylpyrazin-2-amine instead of 5-methylpyridazin-3-amine in step A. MS (ESI): mass calcd. for $C_{10}H_{10}KN_3O_2$, 243.0; m/z found, 206.1 [M-K+2H]$^+$.

Intermediate 99: Sodium 3-methylimidazo[1,5-a]pyrazine-1-carboxylate

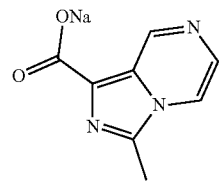

To a solution of methyl 3-methylimidazo[1,5-a] pyrazine-1-carboxylate (53 mg, 0.28 mmol) in ethanol (3.0 mL) was added a solution of sodium hydroxide (33 mg, 0.83 mmol) in water (1.0 ml). The resulting mixture was stirred at 80° C. for 16 h. The reaction mixture was then filtered and washed with ethyl acetate to obtain the title compound as white solid which was taken to next step without purification. MS (ESI): mass calcd. for $C_8H_6N_3NaO_2$, 199.0 m/z found, 178.1 [M-Na+2H]$^+$.

Intermediate 100: 2-(Trifluoromethyl)pyrazolo[1,5-a]pyridine-3-carboxylic acid

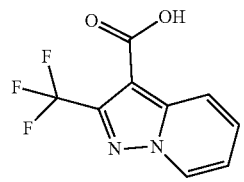 [SMILES: O=C(O)c1c(C(F)(F)F)nn2ccccc12]

Step A: Ethyl 2-(trifluoromethyl)pyrazolo[1,5-a]pyridine-3-carboxylate. A solution of 1-aminopyridin-1-ium (1 g, 10.5 mmol) in DMF (10 mL) was cooled to 0° C. in an ice bath and charged with ethyl 4,4,4-trifluorobut-2-ynoate (1.5 mL, 10.5 mmol) followed by TEA (1.5 mL, 10.5 mmol) and 2,3-dichloro-5,6-dicyano-p-benzoquinone (DDQ) (2.39 g, 10.5 mmol). The resulting mixture was stirred at rt overnight. The reaction was cooled to 0° C. in an ice bath and charged with 2,3-dichloro-5,6-dicyano-p-benzoquinone (2.39 g, 10.5 mmol) which was stirred overnight warming to rt. The reaction mixture was poured into water and extracted into DCM (2×). The combined organic layers were washed with brine, dried over Na$_2$SO$_4$, filtered, concentrated under reduced pressure and purified (FCC, SiO$_2$; 0-30% EtOAc/hexanes) to afford the title product (220 mg, 8%). MS (ESI): mass calcd. for C$_{11}$H$_9$F$_3$N$_2$O$_2$, 258.0; m/z found, 259.0 [M+H]$^+$.

Step B: 2-(Trifluoromethyl)pyrazolo[1,5-a]pyridine-3-carboxylic acid.

A solution of ethyl 2-(trifluoromethyl)pyrazolo[1,5-a]pyridine-3-carboxylate (220 mg, 0.852 mmol) in THF/EtOH/H$_2$O (1:1:1, 3 mL) was charged with LiGH (82 mg, 3.4 mmol). The resulting solution was stirred at rt overnight. The completed reaction was concentrated and resuspended in water. The mixture was acidified with 1N HCl and extracted into EtOAc (3×). The organic layer was dried over Na$_2$SO$_4$, filtered and concentrated to give the title compound that was carried forward without further purification (216 mg, 100%). MS (ESI): mass calcd. for C$_9$H$_5$F$_3$N$_2$O$_2$, 230.0; m/z found, 231.0 [M+H]$^+$.

Intermediate 101: Lithium quinoxaline-6-carboxylic-2,3-d$_2$ acid

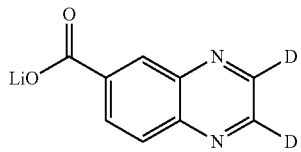

Step A: Methyl 2,3-dihydroxyquinoxaline-6-carboxylate. A solution of methyl 3,4-diaminobenzoate (1.0 g, 6.0 mmol) in diethyl oxalate (20.0 mL) was heated to 140° C. in an oil bath for 16 h. The resulting mixture was cooled to room temperature and the solids were collected by filtration, then dried under vacuum to afford the title compound as yellow solid (780 mg, 60% yield). MS (ESI): mass calcd. for C$_{10}$H$_8$N$_2$O$_4$, 220.1 m/z found, 221.1[M+H]$^+$. $^1$H NMR (500 MHz, DMSO-d$_6$) δ 12.10 (d, J=74.3 Hz, 2H), 7.78-7.62 (m, 2H), 7.20 (d, J=8.4 Hz, 1H), 3.84 (s, 3H).

Step B: Methyl 2,3-dichloroquinoxaline-6-carboxylate. To a solution of methyl 2,3-dihydroxyquinoxaline-6-carboxylate (590 mg, 2.7 mmol) in toluene (16.0 mL) was added thionyl chloride (3.8 mL, 53.6 mmol) followed by N,N-dimethylformamide (0.25 mL, 3.2 mmol). The resulting solution was heated to reflux temperature for 3 h. After cooling the mixture, concentrated the solvent under vacuum and triturated with ethyl acetate. The resulting brown solid was filtered and dried on vacuum to afford the title compound (308 mg, 45% yield). MS (ESI): mass calcd. for C$_{10}$H$_6$Cl$_2$N$_2$O$_2$, 257.1 m/z found, 257.9 [M+H]$^+$.

Step C: Methyl quinoxaline-6-carboxylate-2,3-d$_2$. To a solution of methyl 2,3-dichloroquinoxaline-6-carboxylate (208 mg, 0.81 mmol) in THF (16.0 mL) was added PdCl$_2$ (dppf) (30 mg, 0.04 mmol), N$^1$, N$^1$, N$^2$, N$^2$-tetramethylethane-1,2-diamine (0.21 mL, 1.37 mmol) and sodium borodeuteride (68 mg, 1.62 mmol). The mixture was degassed with nitrogen and then stirred at rt for 2 h. The reaction mixture was diluted with water and extracted with ethyl acetate (×2). The combined organic extracts were dried over Na$_2$SO$_4$ and concentrated. Purification by flash chromatography (SiO$_2$; 0-100% EtOAc/hexanes) afforded the title compound as a white solid (72.5 mg, 47% yield). MS (ESI): mass calcd. for C$_{10}$H$_6$D$_2$N$_2$O$_2$, 190.2 m/z found, 191.0 [M+H]$^+$. $^1$H NMR (400 MHz, DMSO-d$_6$) δ 8.65 (dd, J=1.9, 0.6 Hz, 1H), 8.33 (dd, J=8.7, 1.9 Hz, 1H), 8.23 (dd, J=8.7, 0.6 Hz, 1H), 3.97 (s, 3H).

Step D: Lithium quinoxaline-6-carboxylate-2,3-d$_2$ To a solution of methyl quinoxaline-6-carboxylate-2,3-d$_2$ (68 mg, 0.36 mmol) in THE (2.4 mL) was added a solution of lithium hydroxide (17.0 mg, 0.72 mmol) in water (1.0 mL). The mixture was stirred at rt for 1 h, then concentrated to afford the title compound as white solid which was further taken to next step without purification (quantitative yield). MS (ESI): mass calcd. for C$_9$H$_3$D$_2$LiN$_2$O$_2$, 182.1 m/z found, 177.1 [M+H]$^+$.

Intermediate 102: Lithium quinoxaline-6-carboxylic-2-d acid

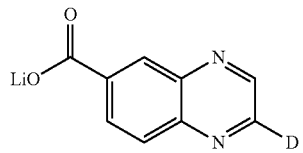

The title compound was prepared in a manner analogous to Intermediate 101, using ethyl 2-oxoacetate and ethanol instead of diethyl oxalate and stirring the reaction at rt instead of heating in step A. MS (ESI): mass calcd. for, C$_9$H$_4$DLiN$_2$O$_2$ 181.1 m/z found, 175.9[M-Li+2H]$^+$.

Intermediate 103: Potassium 2,6,6-trimethyl-6,7-dihydro-4H-pyrazolo[5,1-c][1,4]oxazine-3-carboxylate

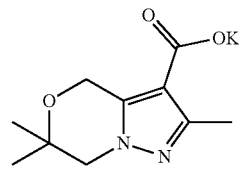

Step A: 6,6-Dimethylmorpholine-3-carboxylic acid. To a solution of 4-(tert-butyl) 3-methyl 6,6-dimethylmorpholine-3,4-dicarboxylate (5 g, 18.3 mmol) in DCM (18.3 mL) was added trifluoroacetic acid (6.0 mL) and the mixture was stirred at rt for 2 h. Concentrated the solvent, dissolved the crude residue in methanol (MeOH) (9.2 mL) followed by addition of sodium hydroxide (3.0 g, 73.2 mmol) in water. Concentrated solvent using a rotary evaporator and the crude product was taken to next step without purification. MS (ESI): mass calcd. for C$_7$H$_{13}$NO$_3$, 159.1 m/z found, 160.2 [M+H]$^+$.

Step B: 6,6-Dimethyl-6,7-dihydro-4H-[1,2,3]oxadiazolo[4,3-c][1,4]oxazin-8-ium-3-olate. To a solution of 6,6-dimethylmorpholine-3-carboxylic acid (2.9 g, 18.3 mmol) in water (1.8 mL, 95.2 mmol) was added sodium nitrite (1.9 g, 27.4 mmol) and hydrochloric acid (37% in water) (1.24 mL, 14.8 mmol). The mixture was stirred at rt for 16 h, diluted with water and extracted 3× with 20% iPrOH/chloroform mixture. The combined organic extracts were dried over anhydrous Na$_2$SO$_4$ and concentrated under vacuo. The crude residue was then dissolved in acetonitrile (7.5 mL) followed by addition of 2,2,2-trifluoroacetic anhydride (1.5 mL, 11.1 mmol). The resulting mixture was stirred at rt for 2 h. The reaction mixture was quenched with potassium carbonate (2.0 g, 14.8 mmol), added water and filtered to obtain the title compound as crystalline precipitate extracted 3× with 20% iPrOH/chloroform. The solid was used in next step without further purification. MS (ESI): mass calcd. for $C_7H_{12}N_2O_4$, 170.2; m/z found, 171.1 [M+H]$^+$. $^1$H NMR (500 MHz, DMSO-d$_6$) δ ppm 4.6 (s, 2H) 4.3 (s, 2H) 1.3 (s, 6H).

Step C: Ethyl 2,6,6-trimethyl-6,7-dihydro-4H-pyrazolo[5,1-c] [1,4]oxazine-3-carboxylate:

To a solution of 6,6-dimethyl-6,7-dihydro-4H-[1,2,3] oxadiazolo[4,3-c] [1,4]oxazin-8-ium-3-olate (200 mg, 1.2 mmol) in xylene (4.0 mL) was added ethyl but-2-ynoate (0.28 mL, 2.4 mmol) and the mixture was stirred at 145° C. for 16 h. Concentrated the solvent and purified by flash chromatography (SiO$_2$; 0-100% EtOAc/hexanes) to obtain the title compound as major regioisomer (91 mg, 33% yield). MS (ESI): mass calcd. for $C_{12}H_{18}N_2O_3$, 238.3; m/z found, 239.1 [M+H]$^+$. $^1$H NMR (500 MHz, DMSO-d$_6$) δ 4.88 (s, 2H), 4.17 (q, J=7.1 Hz, 2H), 3.89 (s, 2H), 2.32 (s, 3H), 1.28 (s, 1H), 1.27-1.24 (m, 8H).

Step D: Potassium 2,6,6-trimethyl-6,7-dihydro-4H-pyrazolo[5,1-c][1,4]oxazine-3-carboxylate: The title compound was prepared in a manner analogous to Intermediate 96 using ethyl 2,6,6-trimethyl-6,7-dihydro-4H-pyrazolo[5,1-c] [1,4] oxazine-3-carboxylate (Step C) instead of ethyl 7-fluoroimidazo[1,2-a] pyridine-3-carboxylate and stirring the reaction mixture at 60° C. for 24 h instead of room temperature. MS (ESI): mass calcd. for $C_{10}H_{13}KN_2O_3$, 248.1; m/z found, 211.1 [M-K+2H]$^+$.

Intermediate 104: tert-Butyl (5S,8R)-2-methyl-3-(((trifluoromethyl)sulfonyl)oxy)-2,4,5,6,7,8-hexahydro-5,8-epiminocyclohepta[c]pyrazole-9-carboxylate

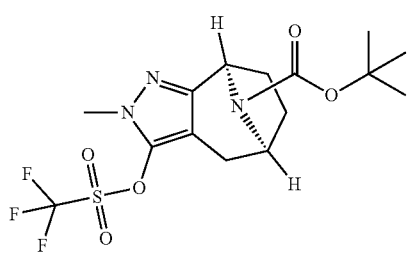 [SMILES: Cn1nc2c(c1OS(=O)(=O)C(F)(F)F)C[C@@H]1CC[C@H]2N1C(=O)OC(C)(C)C]

The title compound was obtained from the same chiral SFC purification of racemic-tert-butyl (5R,8S)-2-methyl-3-(((trifluoromethyl)sulfonyl)oxy)-2,4,5,6,7,8-hexahydro-5,8-epiminocyclohepta[c]pyrazole-9-carboxylate (Intermediate 35) used to provide the title compound (single enantiomer; 1.13 min retention time). MS (ESI): mass calcd. for $C_{15}H_{20}F_3N_3O_5S$, 411.1; m/z found, 356.0 [M+2H-tbutyl]$^+$.

Intermediate 105: (5R,8S)-2-Methyl-3-(3,4,5-trifluorophenyl)-2,4,5,6,7,8-hexahydro-5,8-epiminocyclohepta[c]pyrazole 2,2,2-trifluoroacetate

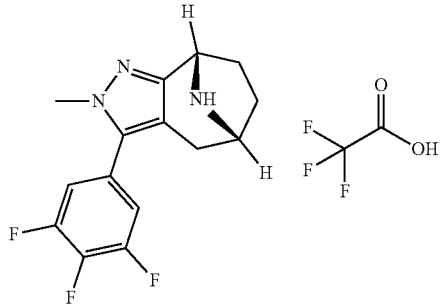

Step A: tert-Butyl (5R,8S)-2-methyl-3-(3,4,5-trifluorophenyl)-2,4,5,6,7,8-hexahydro-5,8-epiminocyclohepta[c] pyrazole-9-carboxylate. A microwave vial with tert-butyl (5R,8S)-2-methyl-3-(((trifluoromethyl)sulfonyl)oxy)-2,4,5, 6,7,8-hexahydro-5,8-epiminocyclohepta[c]pyrazole-9-carboxylate (Intermediate 35) (500 mg, 1.22 mmol), (3,4,5-trifluorophenyl)boronic acid (257 mg, 1.46 mmol), sodium carbonate (386 mg, 3.65 mmol) and XPhos Pd G2 (96 mg, 0.12 mmol) in 1,4-dioxane (17 mL) and water (2 mL) was purged with N$_2$ for 5 min. The resulting mixture was heated in a microwave reactor for 30 min at 110° C. The completed reaction was diluted with water and extracted into DCM (3×). The combined organics were dried over Na$_2$SO$_4$, filtered, concentrated under reduced pressure and purified (FCC, SiO$_2$; 0-30% EtOAc/hexanes) to afford the title product (465 mg, 97%). MS (ESI): mass calcd. for $C_{20}H_{22}F_3N_3O_2$, 393.2; m/z found, 338.0 [M+2H-tbutyl]$^+$.

Step B: (5R,8S)-2-Methyl-3-(3,4,5-trifluorophenyl)-2,4, 5,6,7,8-hexahydro-5,8-epiminocyclohepta[c]pyrazole 2,2,2-trifluoroacetate. A solution of tert-butyl (5R,8S)-2-methyl-3-(3,4,5-trifluorophenyl)-2,4,5,6,7,8-hexahydro-5,8-epiminocyclohepta[c]pyrazole-9-carboxylate (950 mg, 2.42 mmol) in DCM (10 mL) was charged with trifluoroacetic acid (TFA) (3.5 mL, 45.8 mmol) and stirred at rt for 30 min. The completed reaction was concentrated and carried forward without further purification (983 mg, 100%). MS (ESI): mass calcd. for $C_{15}H_{14}F_3N_3$, 293.3; m/z found, 294.0 [M+H]$^+$.

Intermediate 106: (5R,8S)-2-Methyl-3-phenyl-2,4,5, 6,7,8-hexahydro-5,8-epiminocyclohepta[c]pyrazole 2,2,2-trifluoroacetate

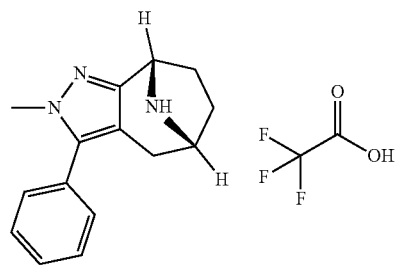

The title compound was prepared in a manner analogous to Intermediate 105 using phenyl boronic acid instead of (3,4,5-trifluorophenyl)boronic acid in Step A. MS (ESI): mass calcd. for $C_{15}H_{17}N_3$, 239.1; m/z found, 240.1 $[M+H]^+$.

Intermediate 107: (5R,8S)-2-Methyl-2,4,5,6,7,8-hexahydro-5,8-epiminocyclohepta[c]pyrazol-3-yl trifluoromethanesulfonate 2,2,2-trifluoroacetate

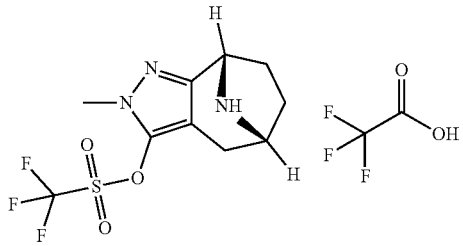

A solution of tert-butyl (5R,8S)-2-methyl-3-(((trifluoromethyl)sulfonyl)oxy)-2,4,5,6,7,8-hexahydro-5,8-epiminocyclohepta[c]pyrazole-9-carboxylate (Intermediate 104) (235 mg, 0.571 mmol) in DCM (5 mL) was charged with TFA (0.85 mL, 11.07 mmol) and stirred at rt for 30 min. The completed reaction was concentrated and carried forward without further purification (177 mg, 100%). MS (ESI): mass calcd. for $C_{10}H_{12}F_3N_3O_3S$, 311.1; m/z found, 312.0 $[M+H]^+$.

Intermediate 108: (5R,8S)-9-(3-Methoxybenzoyl)-2-methyl-2,4,5,6,7,8-hexahydro-5,8-epiminocyclohepta[c]pyrazol-3-yl trifluoromethanesulfonate

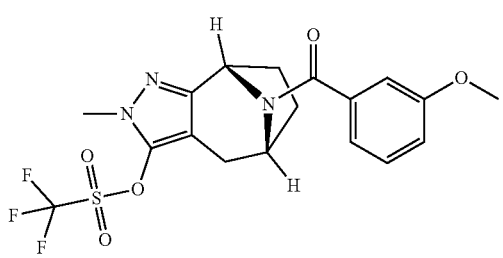 [SMILES: COc1cccc(C(=O)N2[C@@H]3CC[C@H]2c2nn(C)c(OS(=O)(=O)C(F)(F)F)c2C3)c1]

A solution of (5R,8S)-2-methyl-2,4,5,6,7,8-hexahydro-5,8-epiminocyclohepta[c]pyrazol-3-yl trifluoromethanesulfonate 2,2,2-trifluoroacetate (Intermediate 107) (90 mg, 0.289 mmol), 3-methoxybenzoic acid (58 mg, 0.379 mmol) and HATU (330 mg, 0.867 mmol) in DMF (11 mL) was charged with DIEA (200 µL, 1.16 mmol). The resulting solution was stirred at rt overnight.

The completed reaction was diluted with water and extracted into DCM (×2), the combined organics were dried over $Na_2SO_4$, filtered, concentrated under reduced pressure and purified (FCC, $SiO_2$; 0-10% MeOH/DCM) to afford the title product (62 mg, 48%). MS (ESI): mass calcd. for $C_{18}H_{18}F_3N_3O_5S$, 445.1; m/z found, 446.0 $[M+H]^+$.

Intermediate 109: (5R,8S)-9-(5-Cyclopropyl-1-methyl-1H-pyrazole-4-carbonyl)-2-methyl-2,4,5,6,7,8-hexahydro-5,8-epiminocyclohepta[c]pyrazol-3-yl trifluoromethanesulfonate

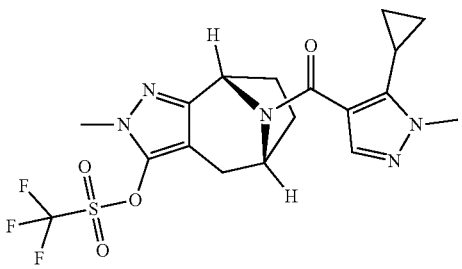 [SMILES: Cn1nc2c(c1OS(=O)(=O)C(F)(F)F)C[C@H]1CC[C@@H]2N1C(=O)c1cnn(C)c1C1CC1]

The title compound was prepared in a manner analogous to Intermediate 108 using 5-cyclopropyl-1-methyl-1H-pyrazole-4-carboxylic acid instead of 3-methoxybenzoic acid. MS (ESI): mass calcd. for $C_{18}H_{20}F_3N_5O_4S$, 459.1; m/z found, 460.0 $[M+H]^+$.

Intermediate 110: (5R,8S)-2-Methyl-9-(quinoline-6-carbonyl)-2,4,5,6,7,8-hexahydro-5,8-epiminocyclohepta[c]pyrazol-3-yl trifluoromethanesulfonate

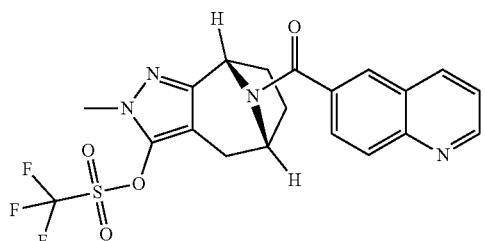

The title compound was prepared in a manner analogous to Intermediate 108 using quinoline-6-carboxylic acid instead of 3-methoxybenzoic acid. MS (ESI): mass calcd. for $C_{18}H_{17}F_3N_4O_4S$, 466.1; m/z found, 467.0 $[M+H]^+$.

Intermediate 111: (5S,8R)-2-Methyl-3-(3,4,5-trifluorophenyl)-2,4,5,6,7,8-hexahydro-5,8-epiminocyclohepta[c]pyrazole 2,2,2-trifluoroacetate

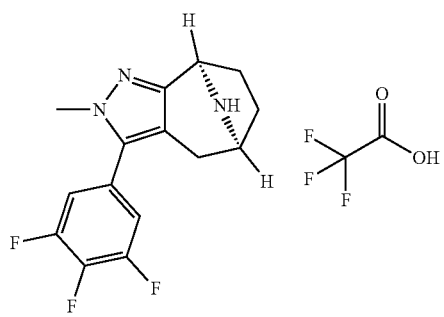

The title compound was prepared in a manner analogous to Intermediate 105 using tert-butyl (5S,8R)-2-methyl-3-

(((trifluoromethyl)sulfonyl)oxy)-2,4,5,6,7,8-hexahydro-5,8-epiminocyclohepta[c]pyrazole-9-carboxylate instead of (5R,8S)-2-methyl-3-(3,4,5-trifluorophenyl)-2,4,5,6,7,8-hexahydro-5,8-epiminocyclohepta[c]pyrazole 2,2,2-trifluoroacetate in step A. MS (ESI): mass calcd. for $C_{15}H_{14}F_3N_3$, 293.3; m/z found, 294.1 [M+H]$^+$.

Intermediate 112:
5-Fluoro-2-(2H-1,2,3-triazol-2-yl)benzoic acid

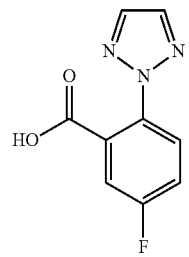 [SMILES: O=C(O)c1cc(F)ccc1-n1nccn1]

The title compound was prepared in a manner analogous to Intermediate 44 using 5-fluoro-2-iodobenzoic acid instead of 3-iodobenzoic acid and 1,2,3-triazole instead of 3-(trifluoromethyl)pyrazole. MS (ESI): mass calcd. for $C_9H_6FN_3O_2$, 207.0; m/z found, 208.2 [M+H]$^+$. $^1$H NMR (500 MHz, DMSO-$d_6$) δ 13.34 (br s, 1H), 8.05 (s, 2H), 7.78 (dd, J=8.8, 4.9 Hz, 1H), 7.59 (dd, J=8.6, 2.9 Hz, 1H), 7.55 (td, J=8.4, 3.0 Hz, 1H).

Example 1: racemic-((5R,9S)-2-Methyl-3-phenyl-4,5,6,7,8,9-hexahydro-2H-5,9-epiminocycloocta[c]pyrazol-10-yl) (quinolin-6-yl)methanone

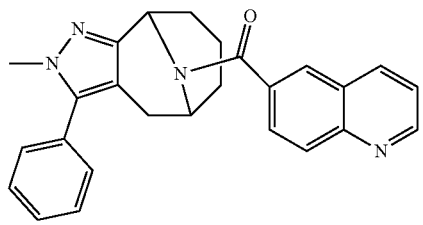 [SMILES: Cn1nc2c(c1-c1ccccc1)CC1CCCC2N1C(=O)c1ccc2ncccc2c1]

To a solution of racemic-(5R,9S)-2-methyl-3-phenyl-4,5,6,7,8,9-hexahydro-2H-5,9-epiminocycloocta[c]pyrazole (Intermediate 1) (25 mg, 0.01 mmol) in DCM (2.0 mL) was added 1-[bis(dimethylamino)methylene]-1H-1,2,3-triazolo[4,5-b]pyridinium 3-oxid hexafluorophosphate (HATU) (45 mg, 0.12 mmol) followed by N,N-diisopropylethylamine (DIPEA or DIEA) (0.05 mL, 0.3 mmol) and quinoline-6-carboxylic acid (18.8 mg, 0.11 mmol) and the mixture was stirred for 1 h at rt. The reaction mixture was then diluted with water and extracted with DCM (×2). The combined organics were washed with brine, dried over Na$_2$SO$_4$, filtered, and concentrated in vacuo. The crude product was purified by reverse-phase HPLC using a XBridge C18 column (5 μm, 100×4.6 mm), mobile phase of 10-100% ACN in 20 mM NH$_4$OH, to afford the title compound as white solid (16.2 mg, 40% yield). MS (ESI): mass calcd. for $C_{26}H_{24}N_4O$, 408.2; m/z found, 409.2 [M+H]$^+$. $^1$H NMR (400 MHz, DMSO-$d_6$) δ 9.07-8.89 (m, 1H), 8.48 (d, J=8.4 Hz, 1H), 8.20-8.02 (m, 2H), 7.88-7.73 (m, 1H), 7.68-7.39 (m, 6H), 5.17-4.81 (m, 1H), 4.11 (s, 1H), 3.76 (d, J=40.8 Hz, 3H), 3.23-2.93 (m, 1H), 2.49-2.31 (m, 1H), 2.14-1.38 (m, 6H).

Example 2: ((5R,9S)-3-Cyclopropyl-2-methyl-4,5,6,7,8,9-hexahydro-2H-5,9-epiminocycloocta[c]pyrazol-10-yl) (quinolin-6-yl)methanone

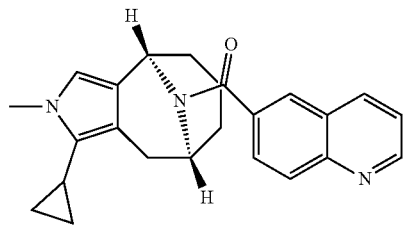 [SMILES: Cn1cc2c(c1C1CC1)C[C@@H]1CCC[C@H]2N1C(=O)c1ccc2ncccc2c1]

The title compound was prepared in a manner analogous to Example 1, using (5R,9S)-3-cyclopropyl-2-methyl-4,5,6,7,8,9-hexahydro-2H-5,9-epiminocycloocta[c]pyrazole (Intermediate 31) instead of racemic-(5R,9S)-2-methyl-3-phenyl-4,5,6,7,8,9-hexahydro-2H-5,9-epiminocycloocta[c]pyrazole (Intermediate 1). MS (ESI): mass calcd. for $C_{23}H_{24}N_4O$, 372.2; m/z found, 373.0 [M+H]$^+$. $^1$H NMR (500 MHz, DMSO-$d_6$) δ 9.07-8.81 (m, 1H), 8.56-8.40 (m, 1H), 8.16-7.93 (m, 2H), 7.83-7.50 (m, 2H), 5.69-5.56 (m, 1H), 4.78-4.57 (m, 1H), 3.81-3.69 (m, 3H), 3.40-3.38 (m, 2H), 1.92-1.22 (m, 7H), 0.97-0.85 (m, 2H), 0.80-0.60 (m, 2H).

Example 3: racemic-(2-Chloro-3-methoxyphenyl)((5R,9S)-2-methyl-3-phenyl-4,5,6,7,8,9-hexahydro-2H-5,9-epiminocycloocta[c]pyrazol-10-yl)methanone

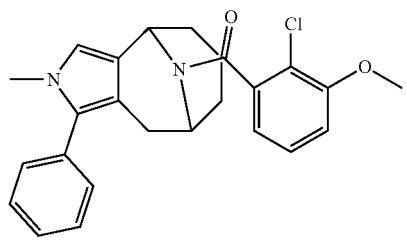 [SMILES: COc1cccc(C(=O)N2C3CCCC2c2cn(C)c(-c4ccccc4)c2C3)c1Cl]

The title compound was prepared in a manner analogous to Example 1, using 2-chloro-3-methoxybenzoic acid instead of quinoline-6-carboxylic acid. MS (ESI): mass calcd. for $C_{24}H_{24}ClN_3O_2$, 421.1; m/z found, 422.1 [M+H]$^+$.

Example 4: (2-Chloro-3-methoxyphenyl) ((5R,9S)-2-methyl-3-phenyl-4,5,6,7,8,9-hexahydro-2H-5,9-epiminocycloocta[c]pyrazol-10-yl) methanone

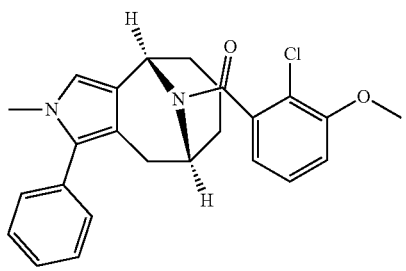

The title compound was prepared in a manner analogous to Example 1, using (5R,9S)-2-methyl-3-phenyl-4,5,6,7,8,9-hexahydro-2H-5,9-epiminocycloocta[c]pyrazole (Intermediate 27) instead of racemic-(5R,9S)-2-methyl-3-phenyl-4,5,6,7,8,9-hexahydro-2H-5,9-epiminocycloocta[c]pyrazole (Intermediate 1) and 2-chloro-3-methoxybenzoic acid instead of quinoline-6-carboxylic acid. MS (ESI): mass calcd. for $C_{24}H_{24}ClN_3O_2$, 421.1; m/z found, 422.1 [M+H]$^+$. $^1$H NMR (500 MHz, DMSO-d$_6$) δ 7.56-7.30 (m, 6H), 7.24-7.16 (m, 1H), 7.10-6.62 (m, 1H), 5.82-5.67 (m, 1H), 3.92-3.86 (m, 3H), 3.85-3.66 (m, 4H), 3.14-2.67 (m, 1H), 2.38 (dd, J=19.2, 16.0 Hz, 1H), 1.95-1.34 (m, 6H).

Example 5: (2-Chloro-3-methoxyphenyl) ((5S,9R)-2-methyl-3-phenyl-4,5,6,7,8,9-hexahydro-2H-5,9-epiminocycloocta[c]pyrazol-10-yl) methanone

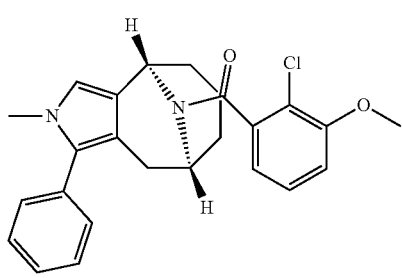 [SMILES: COc1cccc(C(=O)N2[C@H]3CCC[C@@H]2c2cn(C)c(-c4ccccc4)c2C3)c1Cl]

The title compound was prepared in a manner analogous to Example 1, using (5S,9R)-2-methyl-3-phenyl-4,5,6,7,8,9-hexahydro-2H-5,9-epiminocycloocta[c]pyrazole (Intermediate 26) instead of racemic-(5R,9S)-2-methyl-3-phenyl-4,5,6,7,8,9-hexahydro-2H-5,9-epiminocycloocta[c]pyrazole (Intermediate 1) and 2-chloro-3-methoxybenzoic acid instead of quinoline-6-carboxylic acid. MS (ESI): mass calcd. for $C_{24}H_{24}ClN_3O_2$, 421.1; m/z found, 422.1 [M+H]$^+$.

Example 6: racemic-(2-(1H-1,2,4-Triazol-1-yl) phenyl)((5R,9S)-2-methyl-3-phenyl-4,5,6,7,8,9-hexahydro-2H-5,9-epiminocycloocta[c]pyrazol-10-yl) methanone

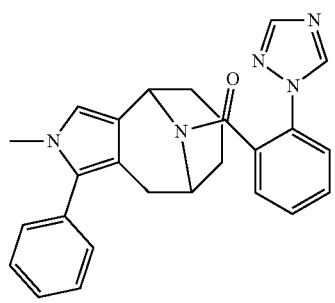 [SMILES: CN(C(=O)c1ccccc1-n1cncn1)C1CCCCCc2c1cn(C)c2-c1ccccc1]

The title compound was prepared in a manner analogous to Example 1, using 2-(1H-1,2,4-triazol-1-yl) benzoic acid instead of quinoline-6-carboxylic acid. MS (ESI): mass calcd. for $C_{25}H_{24}N_6O$, 424.2; m/z found, 425.2 [M+H]$^+$. $^1$H NMR (500 MHz, DMSO-d$_6$) δ 9.02-8.64 (m, 1H), 8.49-8.23 (m, 1H), 7.75-7.39 (m, 9H), 5.64 (s, 1H), 3.86-3.58 (m, 4H), 3.08-2.77 (m, 1H), 2.35 (dd, J=16.2, 8.4 Hz, 1H), 1.80-1.28 (m, 6H).

Example 7: racemic-(3-(4H-1,2,4-Triazol-4-yl) phenyl)((5R,9S)-2-methyl-3-phenyl-4,5,6,7,8,9-hexahydro-2H-5,9-epiminocycloocta[c]pyrazol-10-yl) methanone

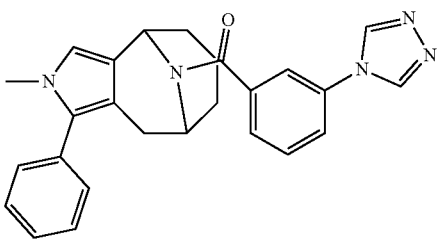 [SMILES: CN(C(=O)c1cccc(-n2cnnc2)c1)C1CCCCCc2c1cn(C)c2-c1ccccc1]

The title compound was prepared in a manner analogous to Example 1, using 3-(4H-1,2,4-triazol-4-yl) benzoic acid instead of quinoline-6-carboxylic acid. MS (ESI): mass calcd. for $C_{25}H_{24}N_6O$, 424.2; m/z found, 425.1 [M+H]$^+$. $^1$H NMR (500 MHz, DMSO-d$_6$) δ 9.21 (d, J=1.1 Hz, 2H), 7.93-7.76 (m, 2H), 7.71-7.59 (m, 1H), 7.58-7.35 (m, 6H), 5.79-5.68 (m, 1H), 4.03 (td, J=7.0, 6.6, 4.6 Hz, 1H), 3.76 (d, J=40.0 Hz, 3H), 3.11-2.92 (m, 1H), 2.47-2.33 (m, 1H), 1.96-1.33 (m, 6H).

Example 8: racemic-(4-(1H-1,2,4-Triazol-1-yl) phenyl) ((5R,9S)-2-methyl-3-phenyl-4,5,6,7,8,9-hexahydro-2H-5,9-epiminocycloocta[c]pyrazol-10-yl) methanone

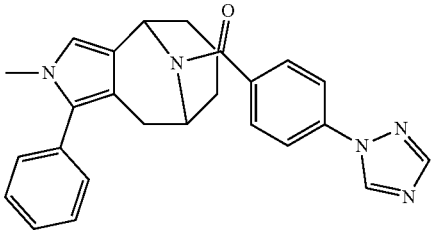 [SMILES: CN(C(=O)c1ccc(-n2cncn2)cc1)C1CCCCCc2c1cn(C)c2-c1ccccc1]

The title compound was prepared in a manner analogous to Example 1, using 4-(1H-1,2,4-triazol-1-yl) benzoic acid instead of quinoline-6-carboxylic acid. MS (ESI): mass calcd. for $C_{25}H_{24}N_6O$, 424.2; m/z found, 425.2 [M+H]$^+$. $^1$H NMR (400 MHz, DMSO-d$_6$) δ 9.39 (s, 1H), 8.26 (d, J=2.7 Hz, 1H), 8.08-7.88 (m, 2H), 7.77-7.60 (m, 1H), 7.58-7.32 (m, 6H), 5.74 (s, 1H), 4.06 (s, 1H), 3.86-3.68 (m, 3H), 3.24-2.88 (m, 1H), 2.42 (d, J=16.2 Hz, 1H), 2.02-1.40 (m, 6H).

Example 9: racemic-(3-(1H-Imidazol-1-yl) phenyl) ((5R,9S)-2-methyl-3-phenyl-4,5,6,7,8,9-hexahydro-2H-5,9-epiminocycloocta[c]pyrazol-10-yl) methanone

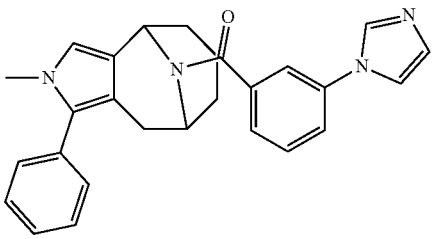 [SMILES: CN(C(=O)c1cccc(-n2ccnc2)c1)C1CCCCCc2c1cn(C)c2-c1ccccc1]

The title compound was prepared in a manner analogous to Example 1, using 3-(1H-imidazol-1-yl) benzoic acid instead of quinoline-6-carboxylic acid. MS (ESI): mass calcd. for $C_{26}H_{25}N_5O$, 423.2; m/z found, 424.2 [M+H]$^+$. $^1$H NMR (400 MHz, DMSO-d$_6$) δ 8.35 (dd, J=3.0, 1.8 Hz, 1H), 7.90-7.31 (m, 10H), 7.11 (dd, J=3.1, 1.9 Hz, 1H), 5.74 (s, 1H), 4.04 (s, 1H), 3.83-3.67 (m, 3H), 3.19-2.90 (m, 1H), 2.40 (d, J=16.1 Hz, 1H), 2.03-1.36 (m, 6H).

Example 10: racemic-(1-Methyl-1H-1,2,4-triazol-3-yl)((5R,9S)-2-methyl-3-phenyl-4,5,6,7,8,9-hexahydro-2H-5,9-epiminocycloocta[c]pyrazol-10-yl) methanone

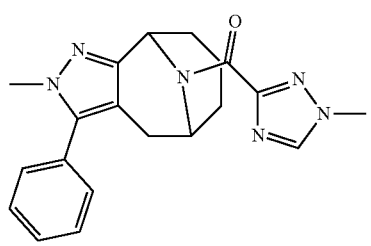 [SMILES: Cn1cnc(C(=O)N2C3CCCC2c2nn(C)c(-c4ccccc4)c2C3)n1]

The title compound was prepared in a manner analogous to Example 1, using 1-methyl-1H-1,2,4-triazole-3-carboxylic acid instead of quinoline-6-carboxylic acid. MS (ESI): mass calcd. for $C_{20}H_{22}N_6O$, 362.2; m/z found, 363.2 [M+H]$^+$. $^1$H NMR (500 MHz, DMSO-d$_6$) δ 8.58 (dd, J=21.7, 0.7 Hz, 1H), 7.61-7.35 (m, 5H), 5.55 (d, J=172.8 Hz, 1H), 5.07-4.44 (m, 1H), 3.95-3.87 (m, 3H), 3.81-3.70 (m, 3H), 3.17-2.89 (m, 1H), 2.47-2.28 (m, 1H), 1.93-1.36 (m, 6H).

Example 11: racemic-(5-Chloro-1-methyl-1H-pyrazol-4-yl)((5R,9S)-2-methyl-3-phenyl-4,5,6,7,8,9-hexahydro-2H-5,9-epiminocycloocta[c]pyrazol-10-yl)methanone

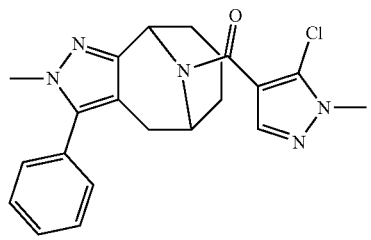 [SMILES: Cn1ncc(C(=O)N2C3CCCC2c2nn(C)c(-c4ccccc4)c2C3)c1Cl]

The title compound was prepared in a manner analogous to Example 1, using 5-chloro-1-methyl-1H-pyrazole-4-carboxylic acid instead of quinoline-6-carboxylic acid. MS (ESI): mass calcd. for $C_{21}H_{22}ClN_5O$, 395.2; m/z found, 396.2 [M+H]$^+$. $^1$H NMR (300 MHz, DMSO-d$_6$) δ 7.74 (s, 1H), 7.57-7.37 (m, 5H), 5.73-5.56 (m, 1H), 4.33-4.18 (m, 1H), 3.82 (s, 3H), 3.78 (s, 3H), 3.14-2.93 (m, 1H), 2.65-2.31 (m, 1H), 2.07-1.55 (m, 4H), 1.56-1.30 (m, 2H).

Example 12: racemic-(5-Methoxy-1-methyl-1H-pyrazol-4-yl)((5R,9S)-2-methyl-3-phenyl-4,5,6,7,8,9-hexahydro-2H-5,9-epiminocycloocta[c]pyrazol-10-yl)methanone

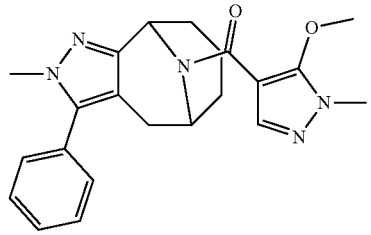 [SMILES: COc1c(C(=O)N2C3CCCC2c2nn(C)c(-c4ccccc4)c2C3)cnn1C]

The title compound was prepared in a manner analogous to Example 1, using 5-methoxy-1-methyl-1H-pyrazole-4-carboxylic acid instead of quinoline-6-carboxylic acid. MS (ESI): mass calcd. for $C_{22}H_{25}N_5O_2$, 391.2; m/z found, 392.2 [M+H]$^+$. $^1$H NMR (500 MHz, DMSO-d$_6$) δ 7.56-7.46 (m, 4H), 7.46-7.40 (m, 2H), 5.69-5.58 (m, 1H), 4.47-4.35 (m, 1H), 3.92 (s, 3H), 3.77 (s, 3H), 3.59 (s, 3H), 3.14-3.04 (m, 1H), 2.50-2.41 (m, 1H), 1.85-1.57 (m, 4H), 1.54-1.34 (m, 2H).

Example 13: racemic-(4-Bromo-1-methyl-3-(trifluoromethyl)-1H-pyrazol-5-yl) ((5R,9S)-2-methyl-3-phenyl-4,5,6,7,8,9-hexahydro-2H-5,9-epiminocycloocta[c]pyrazol-10-yl)methanone

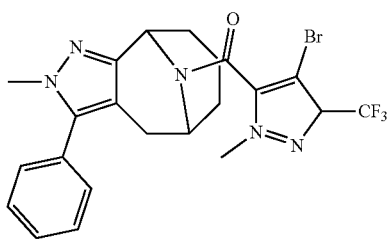

The title compound was prepared in a manner analogous to Example 1, using 4-bromo-1-methyl-3-(trifluoromethyl)-1H-pyrazole-5-carboxylic acid instead of quinoline-6-carboxylic acid. MS (ESI): mass calcd. for $C_{22}H_{21}BrF_3N_5O$, 507.1; m/z found, 508.1 [M+H]$^+$. $^1$H NMR (500 MHz, DMSO-d$_6$) δ 7.60-7.38 (m, 5H), 5.75 (d, J=18.7 Hz, 1H), 4.04-3.71 (m, 6H), 3.31-2.85 (m, 2H), 2.64-2.52 (m, 1H), 2.05-1.32 (m, 6H).

Example 14: racemic-(5-Cyclopropyl-1-methyl-1H-pyrazol-4-yl) ((5R,9S)-2-methyl-3-phenyl-4,5,6,7,8,9-hexahydro-2H-5,9-epiminocycloocta[c]pyrazol-10-yl)methanone

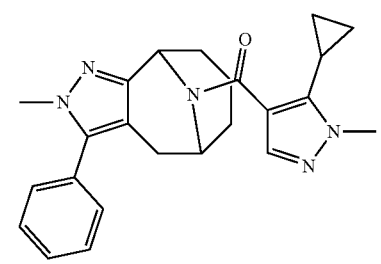 [SMILES: Cn1nc2c(c1-c1ccccc1)CC1CCCC2N1C(=O)c1cnn(C)c1C1CC1]

The title compound was prepared in a manner analogous to Example 1, using 4-chloroquinoline-6-carboxylic acid instead of quinoline-6-carboxylic acid. MS (ESI): mass calcd. for $C_{24}H_{27}N_5O$, 401.2; m/z found, 402.1 [M+H]$^+$. $^1$H NMR (400 MHz, DMSO-d$_6$) δ 7.55-7.30 (m, 6H), 5.72 (d, J=26.3 Hz, 1H), 4.94 (d, J=32.7 Hz, 1H), 3.88-3.79 (m, 3H), 3.81-3.68 (m, 3H), 3.11-2.88 (m, 1H), 2.46-2.28 (m, 1H), 1.88-1.36 (m, 7H), 0.96-0.78 (m, 2H), 0.65-0.33 (m, 2H).

Example 15: racemic-((5R,9S)-2-Methyl-3-phenyl-4,5,6,7,8,9-hexahydro-2H-5,9-epiminocycloocta[c]pyrazol-10-yl) (1-phenyl-1H-1,2,4-triazol-3-yl)methanone

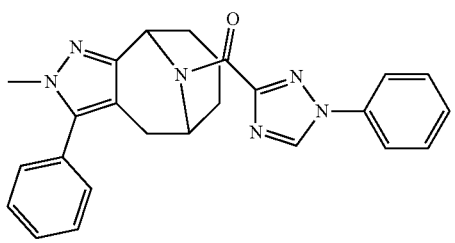 [SMILES: Cn1nc2c(c1-c1ccccc1)CC1CCCC2N1C(=O)c1ncn(-c2ccccc2)n1]

The title compound was prepared in a manner analogous to Example 1, using 1-phenyl-1H-1,2,4-triazole-3-carboxylic acid instead of quinoline-6-carboxylic acid. MS (ESI): mass calcd. for $C_{25}H_{24}N_6O$, 424.2; m/z found, 425.1 [M+H]$^+$. $^1$H NMR (500 MHz, DMSO-d$_6$) δ 9.41 (d, J=18.5 Hz, 1H), 7.96-7.79 (m, 2H), 7.64-7.56 (m, 2H), 7.55-7.40 (m, 6H), 5.57 (d, J=203.7 Hz, 1H), 5.10-4.52 (m, 1H), 3.76 (d, J=29.6 Hz, 3H), 3.18-2.96 (m, 1H), 2.56 (d, J=16.2 Hz, 1H), 2.06-1.39 (m, 6H).

Example 16: racemic-((5R,9S)-2-Methyl-3-phenyl-4,5,6,7,8,9-hexahydro-2H-5,9-epiminocycloocta[c]pyrazol-10-yl) (1-phenyl-1H-pyrazol-3-yl)methanone

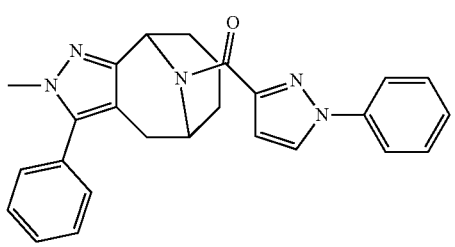 [SMILES: Cn1nc2c(c1-c1ccccc1)CC1CCCC2N1C(=O)c1ccn(-c2ccccc2)n1]

The title compound was prepared in a manner analogous to Example 1, using 1-phenyl-1H-pyrazole-3-carboxylic acid instead of quinoline-6-carboxylic acid. MS (ESI): mass calcd. for $C_{26}H_{25}N_5O$, 423.2; m/z found, 424.1 [M+H]$^+$. $^1$H NMR (500 MHz, DMSO-d$_6$) δ 8.60 (dd, J=13.8, 2.5 Hz, 1H), 7.95-7.79 (m, 2H), 7.62-7.30 (m, 8H), 6.84 (dd, J=2.5, 1.4 Hz, 1H), 6.03-5.68 (m, 1H), 5.19-5.01 (m, 1H), 3.85-3.62 (m, 3H), 3.15-3.01 (m, 1H), 2.57-2.53 (m, 1H), 1.91-1.38 (m, 6H).

Example 17: racemic-(5-Methoxy-1-phenyl-1H-pyrazol-3-yl) ((5R,9S)-2-methyl-3-phenyl-4,5,6,7,8,9-hexahydro-2H-5,9-epiminocycloocta[c]pyrazol-10-yl) methanone

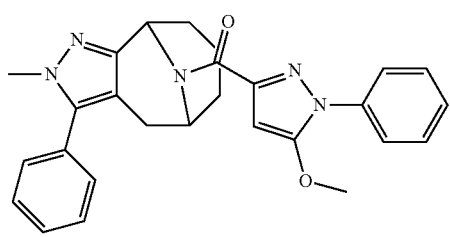 [SMILES: COc1cc(C(=O)N2C3CCCC2c2nn(C)c(-c4ccccc4)c2C3)nn1-c1ccccc1]

The title compound was prepared in a manner analogous to Example 1, using 5-methoxy-1-phenyl-1H-pyrazole-3-carboxylic acid instead of quinoline-6-carboxylic acid. MS (ESI): mass calcd. for $C_{27}H_{27}N_5O_2$, 453.2; m/z found, 454.1 [M+H]$^+$. $^1$H NMR (400 MHz, DMSO-d$_6$) δ 7.74-7.57 (m, 2H), 7.58-7.30 (m, 8H), 6.22 (s, 1H), 6.10-5.71 (m, 1H), 5.12 (d, J=72.4 Hz, 1H), 4.00-3.92 (m, 3H), 3.81-3.65 (m, 3H), 3.14-2.96 (m, 1H), 2.07-1.38 (m, 7H).

Example 18: racemic-(1-Methyl-1H-indol-4-yl) ((5R,9S)-2-methyl-3-phenyl-4,5,6,7,8,9-hexahydro-2H-5,9-epiminocycloocta[c]pyrazol-10-yl)methanone

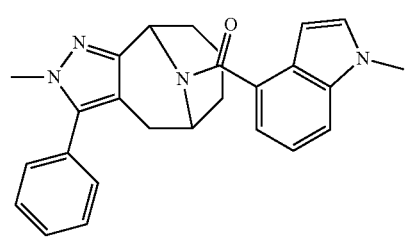

The title compound was prepared in a manner analogous to Example 1, using 1-methyl-1H-indole-4-carboxylic acid instead of quinoline-6-carboxylic acid. MS (ESI): mass calcd. for $C_{26}H_{26}N_4O$, 410.2; m/z found, 411.1 [M+H]$^+$. $^1$H NMR (400 MHz, DMSO-d$_6$) δ 7.57-7.38 (m, 6H), 7.27-7.14 (m, 1H), 6.98 (d, J=7.0 Hz, 1H), 6.32 (d, J=23.4 Hz, 1H), 5.78 (d, J=21.0 Hz, 1H), 4.14-3.76 (m, 6H), 3.69 (s, 1H), 3.22-2.78 (m, 2H), 2.31 (d, J=16.1 Hz, 1H), 2.02-1.33 (m, 6H).

Example 19: racemic-(5-Chloro-1H-indol-6-yl) ((5R,9S)-2-methyl-3-phenyl-4,5,6,7,8,9-hexahydro-2H-5,9-epiminocycloocta[c]pyrazol-10-yl) methanone

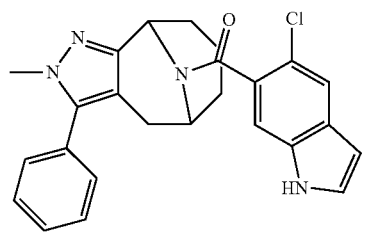 [SMILES: Cn1nc2c(c1-c1ccccc1)CC1CCCC2N1C(=O)c1cc2[nH]ccc2cc1Cl]

The title compound was prepared in a manner analogous to Example 1, using 5-chloro-1H-indole-6-carboxylic acid instead of quinoline-6-carboxylic acid. MS (ESI): mass calcd. for $C_{25}H_{23}ClN_4O$, 430.1; m/z found, 431.1 [M+H]$^+$. $^1$H NMR (400 MHz, DMSO-d$_6$) δ 11.48-11.13 (m, 1H), 7.82-7.61 (m, 1H), 7.57-7.37 (m, 5H), 7.18 (d, J=63.8 Hz, 1H), 6.60-6.42 (m, 1H), 5.92-5.67 (m, 1H), 5.21-4.45 (m, 1H), 3.85-3.68 (m, 3H), 3.24-2.73 (m, 2H), 2.45-2.32 (m, 1H), 2.04-1.27 (m, 6H).

Example 20: racemic-(7-Methyl-1H-indazol-5-yl) ((5R,9S)-2-methyl-3-phenyl-4,5,6,7,8,9-hexahydro-2H-5,9-epiminocycloocta[c]pyrazol-10-yl) methanone

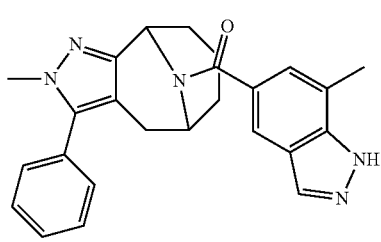

The title compound was prepared in a manner analogous to Example 1, using 7-methyl-1H-indazole-5-carboxylic acid instead of quinoline-6-carboxylic acid. MS (ESI): mass calcd. for $C_{25}H_{25}N_5O$, 411.2; m/z found, 412.1 [M+H]$^+$. $^1$H NMR (400 MHz, DMSO-d$_6$) δ 13.32 (s, 1H), 8.14 (d, J=10.6 Hz, 1H), 7.70-7.39 (m, 6H), 7.18 (s, 1H), 5.70 (s, 1H), 4.96 (d, J=20.3 Hz, 1H), 4.19 (s, 1H), 3.75 (d, J=36.8 Hz, 3H), 3.23-2.92 (m, 2H), 2.41 (d, J=16.3 Hz, 1H), 2.07-1.31 (m, 7H).

Example 21: racemic-(1-Methyl-1H-pyrrolo[2,3-b]pyridin-4-yl)((5R,9S)-2-methyl-3-phenyl-4,5,6,7,8,9-hexahydro-2H-5,9-epiminocycloocta[c]pyrazol-10-yl)methanone

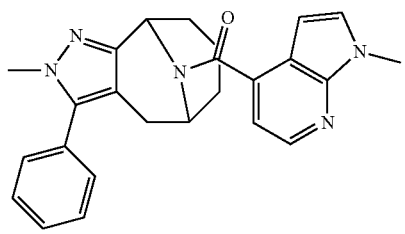

The title compound was prepared in a manner analogous to Example 1, using 1-methyl-1H-pyrrolo[2,3-b] pyridine-4-carboxylic acid instead of quinoline-6-carboxylic acid. MS (ESI): mass calcd. for $C_{25}H_{25}N_5O$, 411.2; m/z found, 412.1 [M+H]$^+$. $^1$H NMR (400 MHz, DMSO-d$_6$) δ 8.33 (dd, J=11.6, 4.8 Hz, 1H), 7.63-7.34 (m, 5H), 7.03 (dd, J=18.7, 4.8 Hz, 1H), 6.35 (dd, J=36.5, 3.5 Hz, 1H), 5.81 (s, 1H), 5.19-4.53 (m, 1H), 3.97-3.65 (m, 6H), 3.22-2.78 (m, 2H), 2.34 (d, J=16.1 Hz, 1H), 2.04-1.34 (m, 6H).

Example 22: racemic-(4-Chloro-1H-pyrrolo[2,3-b]pyridin-5-yl) ((5R,9S)-2-methyl-3-phenyl-4,5,6,7,8,9-hexahydro-2H-5,9-epiminocycloocta[c]pyrazol-10-yl)methanone

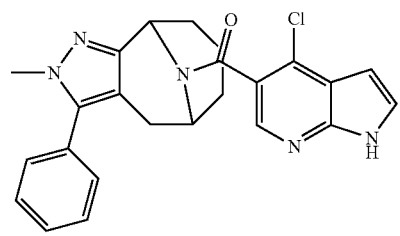 [SMILES: Cn1nc2c(c1-c1ccccc1)CC1CCCC2N1C(=O)c1cnc2[nH]ccc2c1Cl]

The title compound was prepared in a manner analogous to Example 1, using 4-chloro-1H-pyrrolo[2,3-b] pyridine-5-carboxylic acid instead of quinoline-6-carboxylic acid. MS (ESI): mass calcd. for $C_{24}H_{22}ClN_5O$, 431.1; m/z found, 432.1 [M+H]$^+$. $^1$H NMR (500 MHz, DMSO-d$_6$) δ 8.37-7.86 (m, 1H), 7.76-7.62 (m, 1H), 7.59-7.32 (m, 5H), 6.68-6.43 (m, 1H), 5.80 (d, J=41.6 Hz, 1H), 4.15-3.83 (m, 1H), 3.82-3.69 (m, 3H), 3.20-2.85 (m, 2H), 2.48-2.16 (m, 1H), 2.00-1.32 (m, 6H).

Example 23: racemic-(4-Fluoro-1H-pyrrolo[2,3-b]pyridin-5-yl) ((5R,9S)-2-methyl-3-phenyl-4,5,6,7,8,9-hexahydro-2H-5,9-epiminocycloocta[c]pyrazol-10-yl)methanone

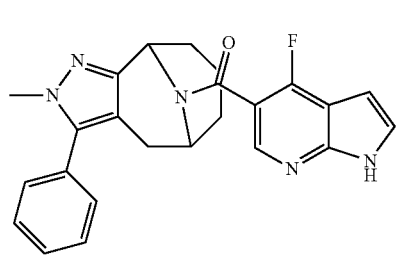 [SMILES: Cn1nc2c(c1-c1ccccc1)CC1CCCC2N1C(=O)c1cnc2[nH]ccc2c1F]

The title compound was prepared in a manner analogous to Example 1, using 4-fluoro-1H-pyrrolo[2,3-b] pyridine-5-carboxylic acid instead of quinoline-6-carboxylic acid. MS (ESI): mass calcd. for $C_{24}H_{22}FN_5O$, 415.1; m/z found, 416.1 [M+H]$^+$. $^1$H NMR (400 MHz, DMSO-d$_6$) δ 12.23 (s, 1H), 8.21 (s, 1H), 7.69-7.36 (m, 6H), 6.71-6.42 (m, 1H), 4.89 (d, J=172.2 Hz, 1H), 4.00 (s, 1H), 3.76 (d, J=29.1 Hz, 3H), 3.16-2.82 (m, 1H), 2.41 (d, J=16.3 Hz, 1H), 2.00-1.32 (m, 6H).

Example 24: racemic-(1-Methyl-1H-pyrrolo[2,3-b]pyridin-3-yl)((5R,9S)-2-methyl-3-phenyl-4,5,6,7,8,9-hexahydro-2H-5,9-epiminocycloocta[c]pyrazol-10-yl)methanone

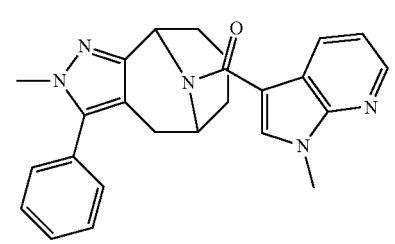 [SMILES: Cn1nc2c(c1-c1ccccc1)CC1CCCC2N1C(=O)c1cn(C)c2ncccc12]

The title compound was prepared in a manner analogous to Example 1, using 1-methyl-1H-pyrrolo[2,3-b] pyridine-3-carboxylic acid instead of quinoline-6-carboxylic acid. MS (ESI): mass calcd. for $C_{25}H_{25}N_5O$, 411.2; m/z found, 412.1 [M+H]$^+$. $^1$H NMR (500 MHz, DMSO-d$_6$) δ 8.34 (dd, J=4.6, 1.6 Hz, 1H), 8.16-7.91 (m, 2H), 7.48 (dd, J=38.4, 4.5 Hz, 5H), 7.21 (dd, J=7.9, 4.6 Hz, 1H), 4.78 (s, 1H), 3.87 (s, 3H), 3.76 (s, 3H), 3.27-3.07 (m, 2H), 2.49-2.39 (m, 1H), 2.05-1.36 (m, 6H).

Example 25: racemic-[1,2,4] Triazolo[1,5-a] pyridin-5-yl((5R,9S)-2-methyl-3-phenyl-4,5,6,7,8,9-hexahydro-2H-5,9-epiminocycloocta[c]pyrazol-10-yl)methanone

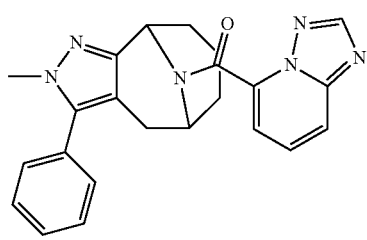 [SMILES: Cn1nc2c(c1-c1ccccc1)CC1CCCC2N1C(=O)c1cccc2ncnn12]

The title compound was prepared in a manner analogous to Example 1, using [1,2,4]triazolo[1,5-a] pyridine-5-carboxylic acid instead of quinoline-6-carboxylic acid. MS (ESI): mass calcd. for $C_{23}H_{22}N_6O$, 398.1; m/z found, 399.1 [M+H]$^+$. $^1$H NMR (400 MHz, DMSO-$d_6$) δ 8.66-8.42 (m, 1H), 8.00-7.63 (m, 2H), 7.58-7.06 (m, 6H), 5.85-5.09 (m, 1H), 3.76 (d, J=37.5 Hz, 4H), 3.06-2.79 (m, 1H), 2.36 (d, J=16.1 Hz, 1H), 2.08-1.33 (m, 6H).

Example 26: racemic-((5R,8S)-2-Methyl-3-phenyl-2,4,5,6,7,8-hexahydro-5,8-epiminocyclohepta[c]pyrazol-9-yl) (quinolin-6-yl) methanone

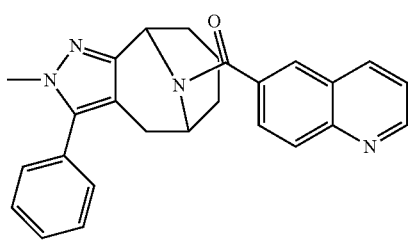 [SMILES: Cn1nc2c(c1-c1ccccc1)CC1CCCC2N1C(=O)c1ccc2ncccc2c1]

The title compound was prepared in a manner analogous to Example 1, using racemic-(5R,8S)-2-methyl-3-phenyl-2,4,5,6,7,8-hexahydro-5,8-epiminocyclohepta[c]pyrazole (Intermediate 34) instead of racemic-(5R,9S)-2-methyl-3-phenyl-4,5,6,7,8,9-hexahydro-2H-5,9-epiminocycloocta[c] pyrazole (Intermediate 1). MS (ESI): mass calcd. for $C_{25}H_{22}N_4O$, 394.1; m/z found, 395.1 [M+H]$^+$. $^1$H NMR (400 MHz, DMSO-$d_6$) δ 8.98 (s, 1H), 8.57-8.40 (m, 1H), 8.28-8.02 (m, 2H), 7.94-7.37 (m, 7H), 5.56-5.40 (m, 1H), 4.50-4.32 (m, 1H), 3.85-3.65 (m, 3H), 3.14-2.84 (m, 1H), 2.43-1.56 (m, 5H).

Example 27: racemic-(4-Chloroquinolin-6-yl) ((5R,9S)-2-methyl-3-phenyl-4,5,6,7,8,9-hexahydro-2H-5,9-epiminocycloocta[c]pyrazol-10-yl) methanone

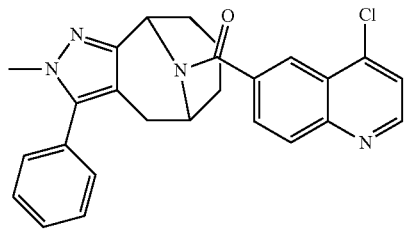 [SMILES: Cn1nc2c(c1-c1ccccc1)CC1CCCC2N1C(=O)c1ccc2nccc(Cl)c2c1]

The title compound was prepared in a manner analogous to Example 1, using 4-chloroquinoline-6-carboxylic acid instead of quinoline-6-carboxylic acid. MS (ESI): mass calcd. for $C_{26}H_{23}ClN_4O$, 442.1; m/z found, 443.1 [M+H]$^+$. $^1$H NMR (400 MHz, DMSO-$d_6$) δ 8.93 (dd, J=9.4, 4.7 Hz, 1H), 8.27-8.15 (m, 2H), 7.99-7.81 (m, 2H), 7.55-7.40 (m, 5H), 5.77 (d, J=8.5 Hz, 1H), 4.96 (d, J=96.1 Hz, 1H), 3.86-3.67 (m, 3H), 3.23-2.85 (m, 1H), 2.43 (d, J=16.2 Hz, 1H), 1.90-1.41 (m, 6H).

Example 28: racemic-(4-Hydroxyquinolin-6-yl) ((5R,9S)-2-methyl-3-phenyl-4,5,6,7,8,9-hexahydro-2H-5,9-epiminocycloocta[c]pyrazol-10-yl) methanone

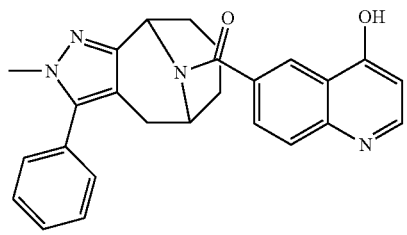 [SMILES: Cn1nc2c(c1-c1ccccc1)CC1CCCC2N1C(=O)c1ccc2nccc(O)c2c1]

The title compound was prepared in a manner analogous to Example 1, using 4-hydroxyquinoline-6-carboxylic acid instead of quinoline-6-carboxylic acid. MS (ESI): mass calcd. for $C_{26}H_{24}N_4O_2$, 424.2; m/z found, 425.2 [M+H]$^+$. $^1$H NMR (500 MHz, DMSO-$d_6$) δ 11.94 (s, 1H), 8.14-7.89 (m, 2H), 7.74-7.42 (m, 6H), 6.16-6.02 (m, 1H), 4.93 (d, J=74.9 Hz, 1H), 4.12 (s, 1H), 3.81-3.67 (m, 3H), 3.30-2.83 (m, 2H), 2.47-2.33 (m, 1H), 2.00-1.36 (m, 6H).

Example 29: racemic-((5R,9S)-2-Methyl-3-phenyl-4,5,6,7,8,9-hexahydro-2H-5,9-epiminocycloocta[c] pyrazol-10-yl) (quinoxalin-5-yl)methanone

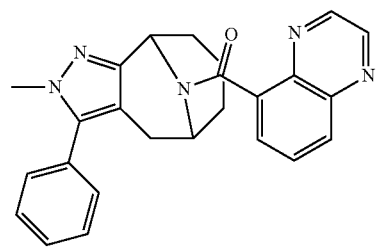 [SMILES: Cn1nc2c(c1-c1ccccc1)CC1CCCC2N1C(=O)c1cccc2nccnc12]

The title compound was prepared in a manner analogous to Example 1, using quinoxaline-5-carboxylic acid instead of quinoline-6-carboxylic acid. MS (ESI): mass calcd. for $C_{25}H_{23}N_5O$, 409.1; m/z found, 410.1 [M+H]+. 1H NMR (500 MHz, DMSO-$d_6$) δ 9.10-8.86 (m, 2H), 8.24-8.04 (m, 1H), 8.04-7.67 (m, 2H), 7.61-7.36 (m, 5H), 5.98-5.73 (m, 1H), 3.81 (d, J=3.8 Hz, 2H), 3.71-3.49 (m, 2H), 3.22-2.62 (m, 1H), 2.25 (dd, J=33.8, 15.9 Hz, 1H), 2.03-1.33 (m, 6H).

Example 30: racemic-((5R,9S)-2-Methyl-3-phenyl-4,5,6,7,8,9-hexahydro-2H-5,9-epiminocycloocta[c]pyrazol-10-yl) (quinoxalin-6-yl) methanone

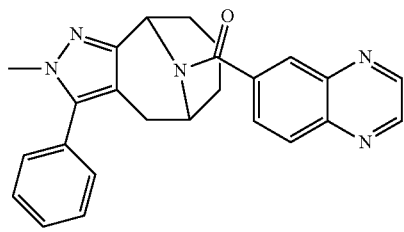 [SMILES: Cn1nc2c(c1-c1ccccc1)CC1CCCC2N1C(=O)c1ccc2nccnc2c1]

The title compound was prepared in a manner analogous to Example 1, using quinoxaline-6-carboxylic acid instead of quinoline-6-carboxylic acid. MS (ESI): mass calcd. for $C_{25}H_{23}N_5O$, 409.2; m/z found, 410.1 [M+H]+. 1H NMR (500 MHz, DMSO-$d_6$) δ 9.11-8.97 (m, 2H), 8.28-8.04 (m, 2H), 7.97-7.83 (m, 1H), 7.61-7.36 (m, 5H), 5.77 (d, J=13.7 Hz, 1H), 3.76 (d, J=44.7 Hz, 3H), 3.25-2.95 (m, 2H), 2.40 (d, J=16.2 Hz, 1H), 2.03-1.40 (m, 6H).

Example 31: racemic-((5R,9S)-2-Methyl-3-phenyl-4,5,6,7,8,9-hexahydro-2H-5,9-epiminocycloocta[c]pyrazol-10-yl) (quinazolin-6-yl) methanone

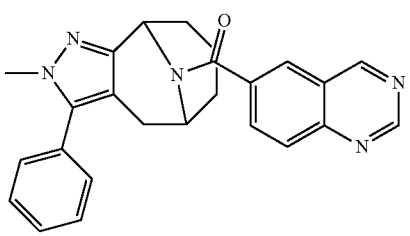 [SMILES: Cn1nc2c(c1-c1ccccc1)CC1CCCC2N1C(=O)c1ccc2ncncc2c1]

The title compound was prepared in a manner analogous to Example 1, using quinazoline-6-carboxylic acid instead of quinoline-6-carboxylic acid. MS (ESI): mass calcd. for $C_{25}H_{23}N_5O$, 409.2; m/z found, 410.1 [M+H]+. 1H NMR (500 MHz, DMSO-$d_6$) δ 9.71 (d, J=9.5 Hz, 1H), 9.37 (d, J=12.6 Hz, 1H), 8.31-8.22 (m, 1H), 8.19-7.95 (m, 2H), 7.57-7.41 (m, 5H), 5.77 (d, J=5.6 Hz, 1H), 3.76 (d, J=50.8 Hz, 3H), 3.20-3.01 (m, 2H), 2.47-2.34 (m, 1H), 2.04-1.41 (m, 6H).

Example 32: racemic-((5R,9S)-2-Methyl-3-phenyl-4,5,6,7,8,9-hexahydro-2H-5,9-epiminocycloocta[c]pyrazol-10-yl)(2-(trifluoromethyl)-1,8-naphthyridin-3-yl)methanone

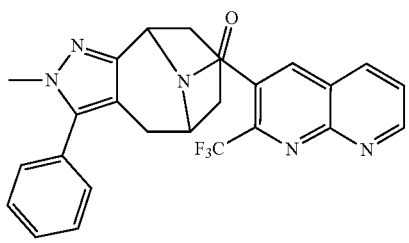

The title compound was prepared in a manner analogous to Example 1, using 2-(trifluoromethyl)-1,8-naphthyridine-3-carboxylic acid instead of quinoline-6-carboxylic acid. MS (ESI): mass calcd. for $C_{26}H_{12}F_3N_5O$. 477.2; m/z found, 478.2 [M+H]+. 1H NMR (500 MHz, DMSO-$d_6$) δ 9.40-8.60 (m, 3H), 7.94-7.81 (m, 1H), 7.65-7.38 (m, 5H), 5.83 (s, 1H), 4.10-3.92 (m, 1H), 3.92-3.68 (m, 3H), 3.30-3.04 (m, 1H), 2.45-2.26 (m, 1H), 2.07-1.34 (m, 6H).

Example 33: racemic-(2-Chloro-3-methoxyphenyl)((5R,9S)-3-(4-fluorophenyl)-2-methyl-4,5,6,7,8,9-hexahydro-2H-5,9-epiminocycloocta[c]pyrazol-10-yl) methanone

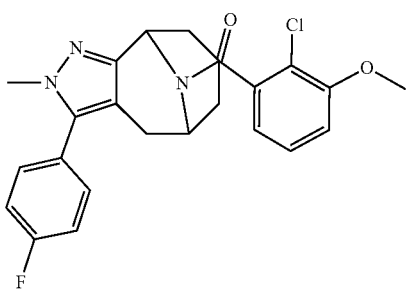

The title compound was prepared in a manner analogous to Example 1, using racemic-(5R,9S)-3-(4-fluorophenyl)-2-methyl-4,5,6,7,8,9-hexahydro-2H-5,9-epiminocycloocta[c]pyrazole (Intermediate 5) instead of racemic-(5R,9S)-2-methyl-3-phenyl-4,5,6,7,8,9-hexahydro-2H-5,9-epiminocycloocta[c]pyrazole (Intermediate 1) and 2-chloro-3-methoxybenzoic acid instead of quinoline-6-carboxylic acid. MS (ESI): mass calcd. for $C_{24}H_{23}ClFN_3O_2$, 439.1; m/z found, 440.1 [M+H]+. 1H NMR (400 MHz, DMSO-$d_6$) δ 7.69-7.30 (m, 5H), 7.26-6.59 (m, 2H), 5.90-5.55 (m, 1H), 5.17-4.37 (m, 1H), 3.96-3.86 (m, 3H), 3.81-3.65 (m, 3H), 3.15-2.73 (m, 1H), 2.36 (t, J=16.9 Hz, 1H), 1.98-1.26 (m, 6H).

Example 34: (2-(2H-1,2,3-Triazol-2-yl)phenyl)((5R,9S)-3-(4-fluorophenyl)-2-methyl-4,5,6,7,8,9-hexahydro-2H-5,9-epiminocycloocta[c]pyrazol-10-yl)methanone

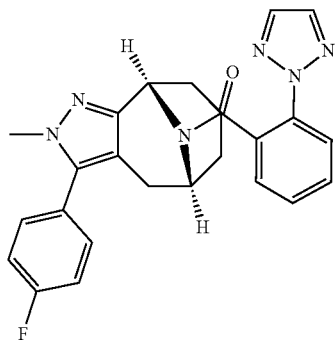

The title compound was prepared in a manner analogous to Example 1, using (5R,9S)-3-(4-fluorophenyl)-2-methyl-4,5,6,7,8,9-hexahydro-2H-5,9-epiminocycloocta[c]pyrazole (Intermediate 30) instead of racemic-(5R,9S)-2-methyl-3-phenyl-4,5,6,7,8,9-hexahydro-2H-5,9-epiminocycloocta[c]pyrazole (Intermediate 1) and 2-(2H-1,2,3-triazol-2-yl)benzoic acid (Intermediate 30) instead of quinoline-6-carboxylic acid. MS (ESI): mass calcd. for $C_{25}H_{23}FN_6O$, 442.1; m/z found, 443.1 [M+H]$^+$. $^1$H NMR (600 MHz, DMSO-$d_6$) δ 8.16 (d, J=12.8 Hz, 1H), 8.03-7.74 (m, 2H), 7.72-7.11 (m, 7H), 5.71-4.94 (m, 1H), 4.57-4.25 (m, 1H), 3.86-3.52 (m, 3H), 3.14-2.78 (m, 1H), 2.43-2.13 (m, 1H), 1.91-1.12 (m, 6H).

Example 35: racemic-(1,4-Dimethyl-1H-pyrazol-3-yl)((5R,9S)-3-(4-fluorophenyl)-2-methyl-4,5,6,7,8,9-hexahydro-2H-5,9-epiminocycloocta[c]pyrazol-10-yl)methanone

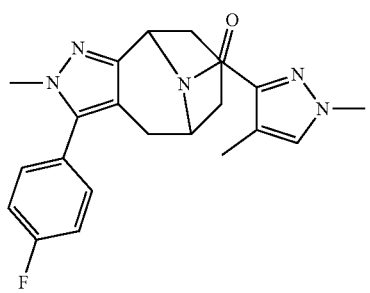

The title compound was prepared in a manner analogous to Example 1, using racemic-(5R,9S)-3-(4-fluorophenyl)-2-methyl-4,5,6,7,8,9-hexahydro-2H-5,9-epiminocycloocta[c]pyrazole (Intermediate 5) instead of racemic-(5R,9S)-2-methyl-3-phenyl-4,5,6,7,8,9-hexahydro-2H-5,9-epiminocycloocta[c]pyrazole (Intermediate 1) and 1,3-dimethyl-1H-pyrazole-4-carboxylic acid instead of quinoline-6-carboxylic acid. MS (ESI): mass calcd. for $C_{22}H_{24}FN_5O$, 393.2; m/z found, 394.2 [M+H]$^+$. $^1$H NMR (300 MHz, DMSO-$d_6$) δ 7.64-7.44 (m, 3H), 7.41-7.28 (m, 2H), 5.78-5.67 (m, 1H), 4.80-4.68 (m, 1H), 3.78 (s, 3H), 3.75 (s, 3H), 3.06-2.88 (m, 1H), 2.51-2.37 (m, 1H), 2.03 (s, 3H), 1.94-1.54 (m, 4H), 1.55-1.31 (m, 2H).

Example 36: ((5R,9S)-3-(4-Fluorophenyl)-2-methyl-4,5,6,7,8,9-hexahydro-2H-5,9-epiminocycloocta[c]pyrazol-10-yl)(1-methyl-1H-pyrazolo[3,4-b]pyridin-3-yl)methanone

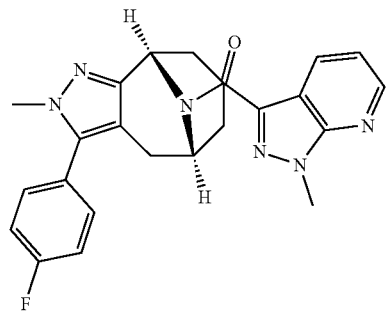

The title compound was prepared in a manner analogous to Example 1, using (5R,9S)-3-(4-fluorophenyl)-2-methyl-4,5,6,7,8,9-hexahydro-2H-5,9-epiminocycloocta[c]pyrazole (Intermediate 30) instead of racemic-(5R,9S)-2-methyl-3-phenyl-4,5,6,7,8,9-hexahydro-2H-5,9-epiminocycloocta[c]pyrazole (Intermediate 1) and 1-methyl-1H-pyrazolo[3,4-b]pyridine-3-carboxylic acid instead of quinoline-6-carboxylic acid. MS (ESI): mass calcd. for $C_{24}H_{23}FN_6O$, 430.1; m/z found, 431.1 [M+H]$^+$. $^1$H NMR (600 MHz, DMSO-$d_6$) δ 8.67-8.37 (m, 1H), 7.63-7.49 (m, 2H), 7.43-7.26 (m, 4H), 6.36-6.21 (m, 1H), 5.26-5.07 (m, 1H), 4.24-4.09 (m, 3H), 3.84-3.64 (m, 3H), 3.17-2.99 (m, 1H), 2.64-2.54 (m, 1H), 2.11-1.42 (m, 6H).

Example 37: racemic-((5R,9S)-3-(4-Fluorophenyl)-2-methyl-4,5,6,7,8,9-hexahydro-2H-5,9-epiminocycloocta[c]pyrazol-10-yl) (quinolin-6-yl) methanone

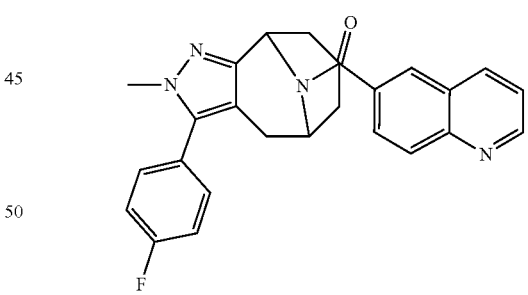

The title compound was prepared in a manner analogous to Example 1, using racemic-(5R,9S)-3-(4-fluorophenyl)-2-methyl-4,5,6,7,8,9-hexahydro-2H-5,9-epiminocycloocta[c]pyrazole (Intermediate 5) instead of racemic-(5R,9S)-2-methyl-3-phenyl-4,5,6,7,8,9-hexahydro-2H-5,9-epiminocycloocta[c]pyrazole (Intermediate 1). MS (ESI): mass calcd. for $C_{26}H_{23}FN_4O$, 426.2; m/z found, 427.1 [M+H]$^+$. $^1$H NMR (400 MHz, DMSO-$d_6$) δ 9.08-8.86 (m, 1H), 8.58-8.43 (m, 1H), 8.20-8.02 (m, 1H), 7.87-7.71 (m, 1H), 7.69-7.51 (m, 3H), 7.44-7.27 (m, 2H), 5.82-5.03 (m, 1H), 4.86-4.06 (m, 1H), 3.86-3.62 (m, 3H), 3.21-2.96 (m, 1H), 2.40 (d, J=16.2 Hz, 1H), 2.12-1.37 (m, 6H).

Example 38: ((5R,9S)-3-(4-Fluorophenyl)-2-methyl-4,5,6,7,8,9-hexahydro-2H-5,9-epiminocycloocta[c]pyrazol-10-yl) (quinolin-6-yl) methanone

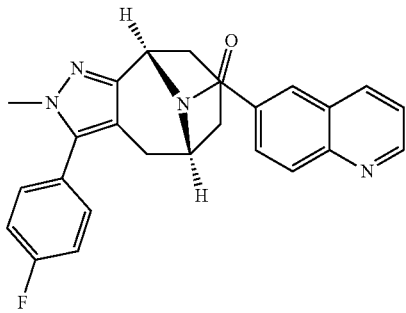

The title compound was prepared in a manner analogous to Example 1, using (5R,9S)-3-(4-fluorophenyl)-2-methyl-4,5,6,7,8,9-hexahydro-2H-5,9-epiminocycloocta[c]pyrazole (Intermediate 30) instead of racemic-(5R,9S)-2-methyl-3-phenyl-4,5,6,7,8,9-hexahydro-2H-5,9-epiminocycloocta[c]pyrazole (Intermediate 1). MS (ESI): mass calcd. for $C_{26}H_{23}FN_4O$, 426.1; m/z found, 427.1 [M+H]$^+$. $^1$H NMR (500 MHz, DMSO-$d_6$) δ 9.01-8.92 (m, 1H), 8.54-8.42 (m, 1H), 8.21-8.03 (m, 2H), 7.81-7.54 (m, 4H), 7.47-7.21 (m, 2H), 5.82-5.65 (m, 1H), 4.14-4.05 (m, 1H), 3.78-3.67 (m, 3H), 3.19-2.94 (m, 1H), 2.40 (d, J=16.2 Hz, 1H), 2.10-1.26 (m, 6H).

Example 39: racemic-(2-Chloro-3-methoxyphenyl) ((5R,9S)-3-(3-fluorophenyl)-2-methyl-4,5,6,7,8,9-hexahydro-2H-5,9-epiminocycloocta[c]pyrazol-10-yl) methanone

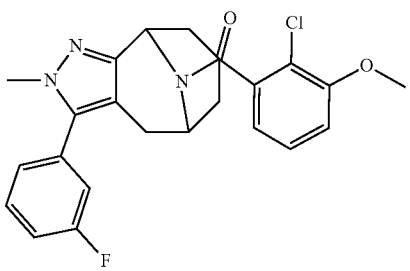

The title compound was prepared in a manner analogous to Example 1, using racemic-(5R,9S)-3-(3-fluorophenyl)-2-methyl-4,5,6,7,8,9-hexahydro-2H-5,9-epiminocycloocta[c]pyrazole (Intermediate 4) instead of racemic-(5R,9S)-2-methyl-3-phenyl-4,5,6,7,8,9-hexahydro-2H-5,9-epiminocycloocta[c]pyrazole (Intermediate 1) and 2-chloro-3-methoxybenzoic acid instead of quinoline-6-carboxylic acid. MS (ESI): mass calcd. for $C_{24}H_{23}ClFN_3O_2$, 439.1; m/z found, 440.1 [M+H]$^+$. $^1$H NMR (400 MHz, DMSO-$d_6$) δ 7.63-7.50 (m, 1H), 7.47-7.12 (m, 5H), 7.11-6.55 (m, 1H), 5.77 (d, J=8.5 Hz, 1H), 3.95-3.85 (m, 3H), 3.82-3.65 (m, 4H), 3.16-2.76 (m, 1H), 2.40 (dd, J=23.1, 16.1 Hz, 1H), 2.00-1.32 (m, 6H).

Example 40: racemic-((5R,9S)-3-(3-Fluorophenyl)-2-methyl-4,5,6,7,8,9-hexahydro-2H-5,9-epiminocycloocta[c]pyrazol-10-yl) (1-phenyl-1H-1,2,4-triazol-3-yl) methanone

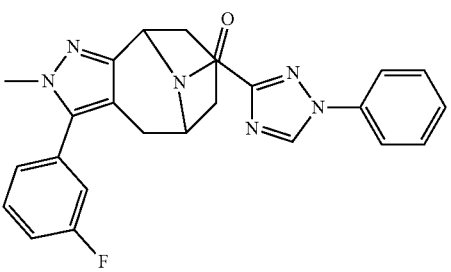

The title compound was prepared in a manner analogous to Example 1, using racemic-(5R,9S)-3-(3-fluorophenyl)-2-methyl-4,5,6,7,8,9-hexahydro-2H-5,9-epiminocycloocta[c]pyrazole (Intermediate 4) instead of racemic-(5R,9S)-2-methyl-3-phenyl-4,5,6,7,8,9-hexahydro-2H-5,9-epiminocycloocta[c]pyrazole (Intermediate 1) and 1-phenyl-1H-1,2,4-triazole-3-carboxylic acid instead of quinoline-6-carboxylic acid. MS (ESI): mass calcd. for $C_{25}H_{23}FN_6O$, 442.1; m/z found, 443.1 [M+H]$^+$. $^1$H NMR (400 MHz, DMSO-$d_6$) δ 9.41 (d, J=12.7 Hz, 1H), 7.95-7.83 (m, 2H), 7.66-7.24 (m, 7H), 5.57 (d, J=160.3 Hz, 1H), 5.12-4.55 (m, 1H), 3.78 (d, J=23.3 Hz, 3H), 3.20-2.97 (m, 1H), 2.61-2.55 (m, 1H), 2.15-1.38 (m, 6H).

Example 41: ((5R,9S)-3-(3-Fluorophenyl)-2-methyl-4,5,6,7,8,9-hexahydro-2H-5,9-epiminocycloocta[c]pyrazol-10-yl) (furo[3,2-b]pyridin-6-yl) methanone

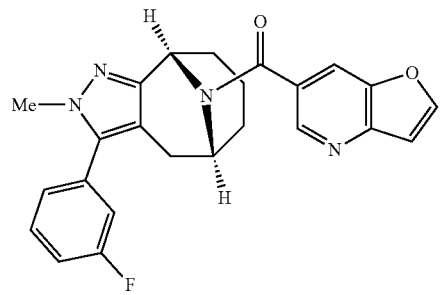 [SMILES: Cn1nc2c(c1-c1cccc(F)c1)C[C@H]1CCC[C@@H]2N1C(=O)c1cnc2ccoc2c1]

The title compound was prepared in a manner analogous to Example 1, using (5R,9S)-3-(3-fluorophenyl)-2-methyl-4,5,6,7,8,9-hexahydro-2H-5,9-epiminocycloocta[c]pyrazole (Intermediate 13) instead of racemic-(5R,9S)-2-methyl-3-phenyl-4,5,6,7,8,9-hexahydro-2H-5,9-epiminocycloocta[c]pyrazole (Intermediate 1) and furo[3,2-b]pyridine-6-carboxylic acid instead of quinoline-6-carboxylic acid. MS (ESI): mass calcd. for $C_{24}H_{21}FN_4O_2$, 416.1; m/z found, 417.1 [M+H]$^+$. $^1$H NMR (500 MHz, DMSO-$d_6$) δ 8.63-8.41 (m, 2H), 8.23-8.06 (m, 1H), 7.62-7.18 (m, 5H), 5.80-5.02 (m, 1H), 4.88-4.00 (m, 1H), 3.78 (d, J=39.0 Hz, 3H), 3.15-3.03 (m, 1H), 2.40 (d, J=16.2 Hz, 1H), 2.05-1.38 (m, 6H).

Example 42: racemic-((5R,9S)-3-(3-Fluorophenyl)-2-methyl-4,5,6,7,8,9-hexahydro-2H-5,9-epiminocycloocta[c]pyrazol-10-yl) (quinolin-6-yl)methanone

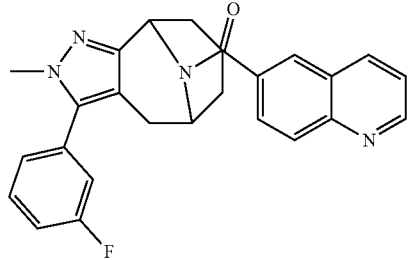

The title compound was prepared in a manner analogous to Example 1, using racemic-(5R,9S)-3-(3-fluorophenyl)-2-methyl-4,5,6,7,8,9-hexahydro-2H-5,9-epiminocycloocta[c]pyrazole (Intermediate 4) instead of racemic-(5R,9S)-2-methyl-3-phenyl-4,5,6,7,8,9-hexahydro-2H-5,9-epiminocycloocta[c]pyrazole (Intermediate 1). MS (ESI): mass calcd. for $C_{26}H_{23}FN_4O$, 426.1; m/z found, 427.1 [M+H]$^+$. $^1$H NMR (400 MHz, DMSO-d$_6$) δ 9.06-8.93 (m, 1H), 8.48 (d, J=8.3 Hz, 1H), 8.08 (dd, J=7.2, 3.8 Hz, 2H), 7.85-7.70 (m, 1H), 7.67-7.51 (m, 2H), 7.51-7.20 (m, 3H), 5.76 (d, J=5.9 Hz, 1H), 4.24-4.05 (m, 1H), 3.78 (d, J=40.8 Hz, 3H), 3.22-3.02 (m, 1H), 2.44 (d, J=16.1 Hz, 1H), 2.11-1.37 (m, 6H).

Example 43: ((5S,9R)-3-(3-Fluorophenyl)-2-methyl-4,5,6,7,8,9-hexahydro-2H-5,9-epiminocycloocta[c]pyrazol-10-yl) (quinolin-6-yl) methanone

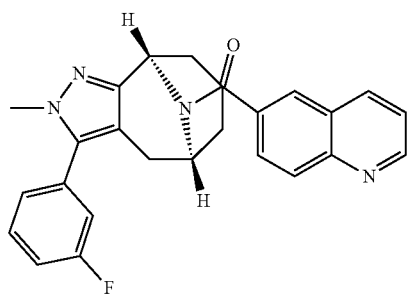

The title compound was prepared in a manner analogous to Example 1, using (5S,9R)-3-(3-fluorophenyl)-2-methyl-4,5,6,7,8,9-hexahydro-2H-5,9-epiminocycloocta[c] pyrazole (Intermediate 28) instead of racemic-(5R,9S)-2-methyl-3-phenyl-4,5,6,7,8,9-hexahydro-2H-5,9-epiminocycloocta[c]pyrazole (Intermediate 1). MS (ESI): mass calcd. for $C_{26}H_{23}FN_4O$, 426.2; m/z found, 427.2 [M+H]$^+$. $^1$H NMR (500 MHz, DMSO-d$_6$) δ 9.09-8.91 (m, 1H), 8.56-8.43 (m, 1H), 8.18-7.99 (m, 2H), 7.84-7.66 (m, 1H), 7.66-7.50 (m, 2H), 7.50-7.24 (m, 3H), 5.77 (s, 1H), 4.12 (d, J=6.5 Hz, 1H), 3.78 (d, J=51.1 Hz, 3H), 3.25-2.88 (m, 1H), 2.47-2.32 (m, 1H), 2.11-1.38 (m, 6H).

Example 44: ((5R,9S)-3-(3-Fluorophenyl)-2-methyl-4,5,6,7,8,9-hexahydro-2H-5,9-epiminocycloocta[c]pyrazol-10-yl) (quinolin-6-yl) methanone

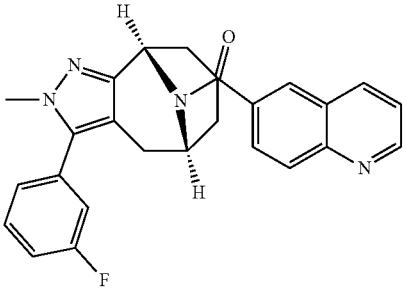

The title compound was prepared in a manner analogous to Example 1, using (5R,9S)-3-(3-fluorophenyl)-2-methyl-4,5,6,7,8,9-hexahydro-2H-5,9-epiminocycloocta[c]pyrazole (Intermediate 13) instead of racemic-(5R,9S)-2-methyl-3-phenyl-4,5,6,7,8,9-hexahydro-2H-5,9-epiminocycloocta[c] pyrazole (Intermediate 1). MS (ESI): mass calcd. for $C_{26}H_{23}FN_4O$, 426.2; m/z found, 427.2 [M+H]$^+$. $^1$H NMR (500 MHz, DMSO-d$_6$) δ 9.04-8.90 (m, 1H), 8.57-8.37 (m, 1H), 8.19-8.05 (m, 2H), 7.88-7.70 (m, 1H), 7.68-7.52 (m, 2H), 7.50-7.23 (m, 3H), 5.77 (s, 1H), 4.12 (s, 1H), 3.88-3.68 (m, 3H), 3.17-2.99 (m, 1H), 2.48-2.38 (m, 1H), 2.06-1.39 (m, 6H).

Example 45: racemic-((5R,9S)-2-Cyclopropyl-3-(3-fluorophenyl)-4,5,6,7,8,9-hexahydro-2H-5,9-epiminocycloocta[c]pyrazol-10-yl) (quinolin-6-yl)methanone

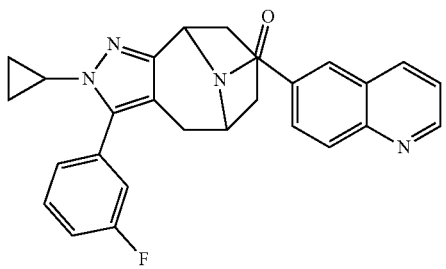

The title compound was prepared in a manner analogous to Example 1, using racemic-(5R,9S)-2-cyclopropyl-3-(3-fluorophenyl)-4,5,6,7,8,9-hexahydro-2H-5,9-epiminocycloocta[c]pyrazole (Intermediate 11) instead of racemic-(5R,9S)-2-methyl-3-phenyl-4,5,6,7,8,9-hexahydro-2H-5,9-epiminocycloocta[c]pyrazole (Intermediate 1). MS (ESI): mass calcd. for $C_{28}H_{25}FN_4O$, 452.2; m/z found, 453.2 [M+H]$^+$. $^1$H NMR (400 MHz, DMSO-d$_6$) δ 9.05-8.82 (m, 1H), 8.48 (d, J=8.5 Hz, 1H), 8.17-7.98 (m, 2H), 7.85-7.69 (m, 1H), 7.69-7.40 (m, 4H), 7.39-7.18 (m, 1H), 5.76-5.73 (m, 1H), 3.83-3.58 (m, 1H), 3.22-2.93 (m, 2H), 2.42 (d, J=16.4 Hz, 1H), 2.10-1.36 (m, 6H), 1.10-0.74 (m, 4H).

Example 46: (3-(1H-1,2,4-Triazol-1-yl)phenyl)((5R,9S)-3-(3-chlorophenyl)-2-methyl-4,5,6,7,8,9-hexahydro-2H-5,9-epiminocycloocta[c]pyrazol-10-yl)methanone

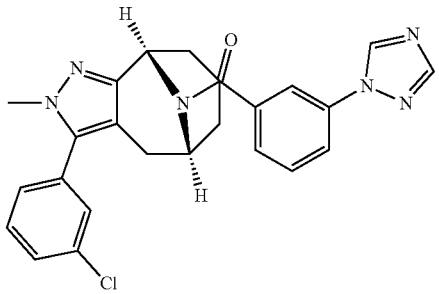

The title compound was prepared in a manner analogous to Example 1, using (5R,9S)-3-(3-chlorophenyl)-2-methyl-4,5,6,7,8,9-hexahydro-2H-5,9-epiminocycloocta[c]pyrazole (Intermediate 14) instead of racemic-(5R,9S)-2-methyl-3-phenyl-4,5,6,7,8,9-hexahydro-2H-5,9-epiminocycloocta[c]pyrazole (Intermediate 1) and 3-(1H-1,2,4-triazol-1-yl)benzoic acid instead of quinoline-6-carboxylic acid. MS (ESI): mass calcd. for $C_{25}H_{23}ClN_6O$, 458.2; m/z found, 459.2 [M+H]$^+$. $^1$H NMR (500 MHz, DMSO-d$_6$) δ 9.38 (s, 1H), 8.26 (s, 1H), 7.99-7.94 (m, 1H), 7.94-7.91 (m, 1H), 7.71-7.59 (m, 2H), 7.59-7.38 (m, 4H), 5.77-5.70 (m, 1H), 4.11-4.02 (m, 1H), 3.80 (s, 3H), 3.01 (dd, J=16.2, 7.4 Hz, 1H), 2.43 (d, J=16.2 Hz, 1H), 2.03-1.36 (m, 6H).

Example 47: (3-(1H-Pyrazol-4-yl)phenyl)((5R,9S)-3-(3-chlorophenyl)-2-methyl-4,5,6,7,8,9-hexahydro-2H-5,9-epiminocycloocta[c]pyrazol-10-yl)methanone

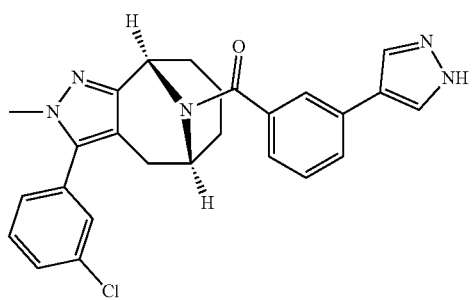 [SMILES: Cn1nc2c(c1-c1cccc(Cl)c1)C[C@H]1CCC[C@@H]2N1C(=O)c1cccc(-c2cn[nH]c2)c1]

The title compound was prepared in a manner analogous to Example 1, using (5R,9S)-3-(3-chlorophenyl)-2-methyl-4,5,6,7,8,9-hexahydro-2H-5,9-epiminocycloocta[c]pyrazole (Intermediate 14) instead of racemic-(5R,9S)-2-methyl-3-phenyl-4,5,6,7,8,9-hexahydro-2H-5,9-epiminocycloocta[c]pyrazole (Intermediate 1) and 3-(1H-pyrazol-4-yl)benzoic acid instead of quinoline-6-carboxylic acid. MS (ESI): mass calcd. for $C_{26}H_{24}ClN_5O$, 457.2; m/z found, 458.2 [M+H]$^+$. $^1$H NMR (500 MHz, Methanol-d$_4$) δ 8.15-7.84 (m, 2H), 7.76-7.69 (m, 1H), 7.67-7.58 (m, 1H), 7.57-7.45 (m, 4H), 7.45-7.39 (m, 1H), 7.30-7.24 (m, 1H), 5.94-5.88, 5.05-5.00 (m, 1H), 5.22-5.15, 4.30-4.22 (m, 1H), 3.84, 3.77 (s, 3H), 3.19, 3.01 (dd, J=16.4, 7.4 Hz, 1H), 2.60, 2.50 (d, J=16.3 Hz, 1H), 2.18-1.49 (m, 6H).

Example 48: (3-(1H-Pyrazol-1-yl)phenyl)((5R,9S)-3-(3-chlorophenyl)-2-methyl-4,5,6,7,8,9-hexahydro-2H-5,9-epiminocycloocta[c]pyrazol-10-yl)methanone

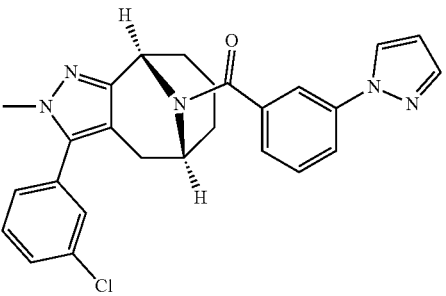 [SMILES: Cn1nc2c(c1-c1cccc(Cl)c1)C[C@H]1CCC[C@@H]2N1C(=O)c1cccc(-n2cccn2)c1]

The title compound was prepared in a manner analogous to Example 1, using (5R,9S)-3-(3-chlorophenyl)-2-methyl-4,5,6,7,8,9-hexahydro-2H-5,9-epiminocycloocta[c]pyrazole (Intermediate 14) instead of racemic-(5R,9S)-2-methyl-3-phenyl-4,5,6,7,8,9-hexahydro-2H-5,9-epiminocycloocta[c]pyrazole (Intermediate 1) and 3-(1H-pyrazol-1-yl)benzoic acid instead of quinoline-6-carboxylic acid. MS (ESI): mass calcd. for $C_{26}H_{24}ClN_5O$, 457.2; m/z found, 458.2 [M+H]$^+$. $^1$H NMR (300 MHz, DMSO-d$_6$) δ 8.69-8.52 (m, 1H), 8.03-7.92 (m, 1H), 7.91-7.82 (m, 1H), 7.81-7.74 (m, 1H), 7.68-7.44 (m, 5H), 7.39-7.24 (m, 1H), 6.63-6.50 (m, 1H), 5.81-5.66 (m, 1H), 4.15-4.00 (m, 1H), 3.80 (s, 3H), 2.99 (dd, J=16.2, 7.3 Hz, 1H), 2.43 (d, J=17.3 Hz, 1H), 2.08-1.35 (m, 6H).

Example 49 (3-(1H-Tetrazol-1-yl)phenyl)((5R,9S)-3-(3-chlorophenyl)-2-methyl-4,5,6,7,8,9-hexahydro-2H-5,9-epiminocycloocta[c]pyrazol-10-yl)methanone

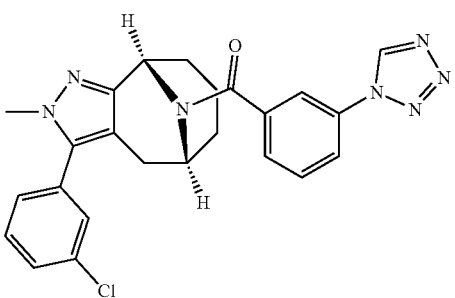 [SMILES: Cn1nc2c(c1-c1cccc(Cl)c1)C[C@H]1CCC[C@@H]2N1C(=O)c1cccc(-n2cnnn2)c1]

The title compound was prepared in a manner analogous to Example 1, using (5R,9S)-3-(3-chlorophenyl)-2-methyl-4,5,6,7,8,9-hexahydro-2H-5,9-epiminocycloocta[c]pyrazole (Intermediate 14) instead of racemic-(5R,9S)-2-methyl-3-phenyl-4,5,6,7,8,9-hexahydro-2H-5,9-epiminocycloocta[c]pyrazole (Intermediate 1) and 3-(1H-tetrazol-1-yl)benzoic acid instead of quinoline-6-carboxylic acid. MS (ESI): mass calcd. for $C_{24}H_{22}ClN_7O$, 459.2; m/z found, 460.2 [M+H]$^+$. $^1$H NMR (500 MHz, DMSO-d$_6$) δ 10.15 (s, 1H), 8.05-8.00 (m, 1H), 7.99-7.94 (m, 1H), 7.73 (t, J=7.9 Hz, 1H), 7.64-7.59 (m, 2H), 7.59-7.47 (m, 3H), 5.78-5.69 (m, 1H), 4.11-4.02 (m, 1H), 3.81 (s, 3H), 3.03 (dd, J=16.2, 7.4 Hz, 1H), 2.43 (d, J=16.2 Hz, 1H), 2.08-1.37 (m, 6H).

Example 50: (2-Chloro-5-(4H-1,2,4-triazol-4-ylphenyl)((5R,9S)-3-(3-chlorophenyl)-2-methyl-4,5,6,7,8,9-hexahydro-2H-5,9-epiminocycloocta[c]pyrazol-10-yl)methanone

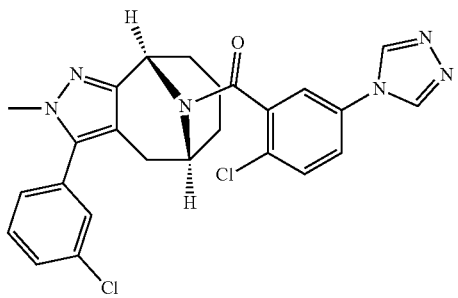

The title compound was prepared in a manner analogous to Example 1, using (5R,9S)-3-(3-chlorophenyl)-2-methyl-4,5,6,7,8,9-hexahydro-2H-5,9-epiminocycloocta[c]pyrazole (Intermediate 14) instead of racemic-(5R,9S)-2-methyl-3-phenyl-4,5,6,7,8,9-hexahydro-2H-5,9-epiminocycloocta[c]pyrazole (Intermediate 1) and 2-chloro-5-[1,2,4]triazol-4-yl-benzoic acid instead of quinoline-6-carboxylic acid. MS (ESI): mass calcd. for $C_{25}H_{22}Cl_2N_6O$, 492.1; m/z found, 493.1 [M+H]$^+$. $^1$H NMR (500 MHz, DMSO-d$_6$) δ 9.19 (s, 2H), 7.90-7.69 (m, 3H), 7.64-7.45 (m, 4H), 5.84-5.80 (m, 1H), 3.87-3.78 (m, 1H), 3.81 (s, 3H), 3.13-2.89 (m, 1H), 2.51-2.37 (m, 1H), 2.00-1.36 (m, 6H).

Example 51: (4-(4H-1,2,4-Triazol-4-yl)phenyl)((5R,9S)-3-(3-chlorophenyl)-2-methyl-4,5,6,7,8,9-hexahydro-2H-5,9-epiminocycloocta[c]pyrazol-10-yl)methanone

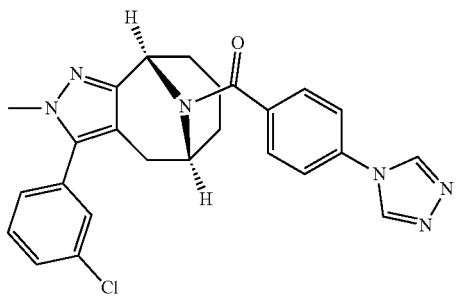 [SMILES: Cn1nc2c(c1-c1cccc(Cl)c1)C[C@H]1CCC[C@@H]2N1C(=O)c1ccc(-n2cnnc2)cc1]

The title compound was prepared in a manner analogous to Example 1, using (5R,9S)-3-(3-chlorophenyl)-2-methyl-4,5,6,7,8,9-hexahydro-2H-5,9-epiminocycloocta[c]pyrazole (Intermediate 14) instead of racemic-(5R,9S)-2-methyl-3-phenyl-4,5,6,7,8,9-hexahydro-2H-5,9-epiminocycloocta[c]pyrazole (Intermediate 1) and 4-(4H-1,2,4-triazol-4-yl)benzoic acid instead of quinoline-6-carboxylic acid. MS (ESI): mass calcd. for $C_{25}H_{23}ClN_6O$, 458.2; m/z found, 459.2 [M+H]$^+$. $^1$H NMR (500 MHz, DMSO-d$_6$) δ 9.20-9.15 (m, 2H), 7.80-7.75 (m, 2H), 7.66-7.60 (m, 2H), 7.60-7.47 (m, 4H), 5.76-5.67 (m, 1H), 4.08-3.99 (m, 1H), 3.80 (s, 3H), 3.04 (dd, J=16.0, 7.0 Hz, 1H), 2.42 (d, J=16.1 Hz, 1H), 2.07-1.31 (m, 6H).

Example 52 ((5R,9S)-3-(3-Chlorophenyl)-2-methyl-4,5,6,7,8,9-hexahydro-2H-5,9-epiminocycloocta[c]pyrazol-10-yl)(1-isopropyl-1H-1,2,4-triazol-3-yl)methanone

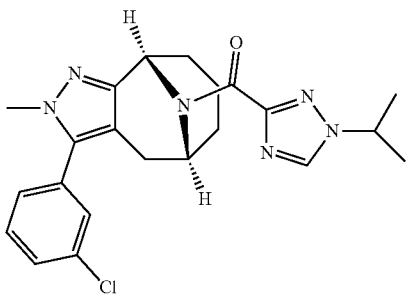 [SMILES: CC(C)n1cnc(C(=O)N2[C@@H]3CCC[C@H]2c2nn(C)c(-c4cccc(Cl)c4)c2C3)n1]

The title compound was prepared in a manner analogous to Example 1, using (5R,9S)-3-(3-chlorophenyl)-2-methyl-4,5,6,7,8,9-hexahydro-2H-5,9-epiminocycloocta[c]pyrazole (Intermediate 14) instead of racemic-(5R,9S)-2-methyl-3-phenyl-4,5,6,7,8,9-hexahydro-2H-5,9-epiminocycloocta[c]pyrazole (Intermediate 1) and 1-isopropyl-1H-1,2,4-triazole-3-carboxylic acid instead of quinoline-6-carboxylic acid. MS (ESI): mass calcd. for $C_{22}H_{25}ClN_6O$, 424.2; m/z found, 425.2 [M+H]$^+$. $^1$H NMR (500 MHz, DMSO-d$_6$) δ 8.64 (s, 1H), 7.63-7.57 (m, 1H), 7.57-7.43 (m, 3H), 5.76-5.69 (m, 1H), 4.71-4.60 (m, 1H), 4.54-4.48 (m, 1H), 3.78 (s, 3H), 2.99 (dd, J=15.8, 7.4 Hz, 1H), 2.57-2.46 (m, 1H), 2.07-1.54 (m, 4H), 1.54-1.38 (m, 2H), 1.45 (d, J=6.7 Hz, 6H).

Example 53: ((5R,9S)-3-(3-Chlorophenyl)-2-methyl-4,5,6,7,8,9-hexahydro-2H-5,9-epiminocycloocta[c]pyrazol-10-yl)(1-(2-fluorophenyl)-1H-1,2,4-triazol-3-yl)methanone

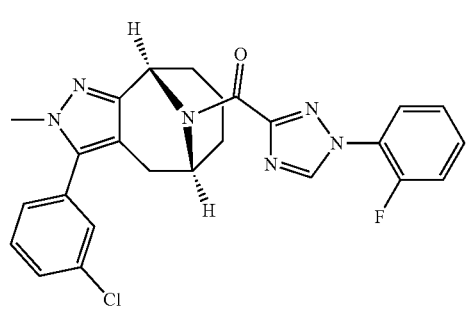 [SMILES: Cn1nc2c(c1-c1cccc(Cl)c1)C[C@H]1CCC[C@@H]2N1C(=O)c1ncn(-c2ccccc2F)n1]

The title compound was prepared in a manner analogous to Example 1, using (5R,9S)-3-(3-chlorophenyl)-2-methyl-4,5,6,7,8,9-hexahydro-2H-5,9-epiminocycloocta[c]pyrazole (Intermediate 14) instead of racemic-(5R,9S)-2-methyl-3-phenyl-4,5,6,7,8,9-hexahydro-2H-5,9-epiminocycloocta[c]pyrazole (Intermediate 1) and 1-(2-fluorophenyl)-1H-1,2,4-triazole-3-carboxylic acid (Intermediate 39) instead of quinoline-6-carboxylic acid. MS (ESI): mass calcd. for $C_{25}H_{22}ClFN_6O$, 476.2; m/z found, 477.2 [M+H]$^+$. $^1$H NMR (500 MHz, DMSO-d$_6$) δ 9.13 (d, J=2.2 Hz, 1H), 7.89-7.80 (m, 1H), 7.64-7.40 (m, 7H), 5.80-5.75 (m, 1H), 4.59-4.49 (m, 1H), 3.79 (s, 3H), 3.07-2.97 (m, 1H), 2.53 (d, J=16.4 Hz, 1H), 2.04-1.38 (m, 6H).

Example 54: ((5R,9S)-3-(3-Chlorophenyl)-2-methyl-4,5,6,7,8,9-hexahydro-2H-5,9-epiminocycloocta[c]pyrazol-10-yl)(1-(pyridin-2-yl)-1H-1,2,4-triazol-3-yl)methanone

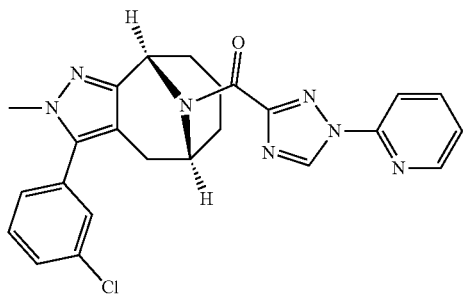 [SMILES: Cn1nc2c(c1-c1cccc(Cl)c1)C[C@H]1CCC[C@@H]2N1C(=O)c1ncn(-c2ccccn2)n1]

The title compound was prepared in a manner analogous to Example 1, using (5R,9S)-3-(3-chlorophenyl)-2-methyl-4,5,6,7,8,9-hexahydro-2H-5,9-epiminocycloocta[c]pyrazole (Intermediate 14) instead of racemic-(5R,9S)-2-methyl-3-phenyl-4,5,6,7,8,9-hexahydro-2H-5,9-epiminocycloocta[c]pyrazole (Intermediate 1) and 1-(pyridin-2-yl)-1H-1,2,4-triazole-3-carboxylic acid instead of quinoline-6-carboxylic acid. MS (ESI): mass calcd. for $C_{24}H_{22}ClN_7O$, 459.2; m/z found, 460.1 [M+H]$^+$. $^1$H NMR (500 MHz, DMSO-d$_6$) δ 9.47 (s, 1H), 8.64-8.53 (m, 1H), 8.15-8.06 (m, 1H), 7.92-7.85 (m, 1H), 7.64-7.59 (m, 1H), 7.58-7.45 (m, 4H), 5.81-5.75 (m, 1H), 4.60-4.53 (m, 1H), 3.80 (s, 3H), 3.13-3.00 (m, 1H), 2.55-2.49 (m, 1H), 2.06-1.40 (m, 6H).

Example 55: ((5R,9S)-3-(3-Chlorophenyl)-2-methyl-4,5, 6, 7, 8, 9-hexahydro-2H-5,9-epiminocycloocta[c]pyrazol-10-yl)(1-(3-fluorophenyl)-1H-1,2,4-triazol-3-yl)methanone

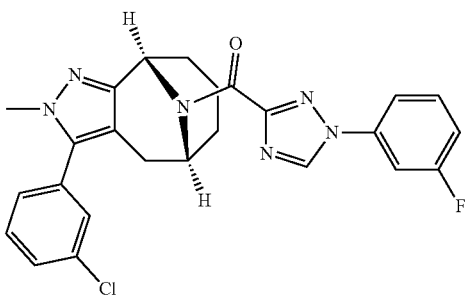 [SMILES: Cn1nc2c(c1-c1cccc(Cl)c1)C[C@H]1CCC[C@@H]2N1C(=O)c1ncn(-c2cccc(F)c2)n1]

The title compound was prepared in a manner analogous to Example 1, using (5R,9S)-3-(3-chlorophenyl)-2-methyl-4,5,6,7,8,9-hexahydro-2H-5,9-epiminocycloocta[c]pyrazole (Intermediate 14) instead of racemic-(5R,9S)-2-methyl-3-phenyl-4,5,6,7,8,9-hexahydro-2H-5,9-epiminocycloocta[c]pyrazole (Intermediate 1) and 1-(3-fluorophenyl)-1H-1,2,4-triazole-3-carboxylic acid instead of quinoline-6-carboxylic acid. MS (ESI): mass calcd. for $C_{25}H_{22}ClFN_6O$, 476.2; m/z found, 477.2 [M+H]$^+$. $^1$H NMR (500 MHz, DMSO-d$_6$) δ 9.43 (s, 1H), 7.86-7.79 (m, 1H), 7.79-7.72 (m, 1H), 7.69-7.58 (m, 2H), 7.58-7.46 (m, 3H), 7.36-7.28 (m, 1H), 5.80-5.73 (m, 1H), 4.58-4.48 (m, 1H), 3.79 (s, 3H), 3.12-2.97 (m, 1H), 2.56-2.48 (m, 1H), 1.93-1.39 (m, 6H).

Example 56: (1-(3-Chlorophenyl)-1H-1,2,4-triazol-3-yl)((5R,9S)-3-(3-chlorophenyl)-2-methyl-4,5,6,7,8,9-hexahydro-2H-5,9-epiminocycloocta[c]pyrazol-10-yl)methanone

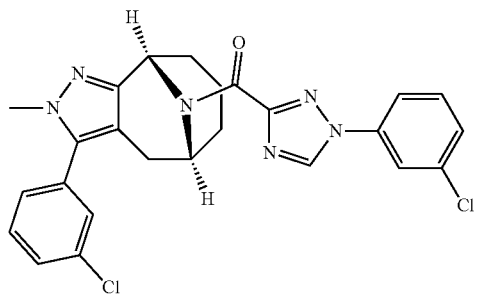 [SMILES: Cn1nc2c(c1-c1cccc(Cl)c1)C[C@H]1CCC[C@@H]2N1C(=O)c1ncn(-c2cccc(Cl)c2)n1]

The title compound was prepared in a manner analogous to Example 1, using (5R,9S)-3-(3-chlorophenyl)-2-methyl-4,5,6,7,8,9-hexahydro-2H-5,9-epiminocycloocta[c]pyrazole (Intermediate 14) instead of racemic-(5R,9S)-2-methyl-3-phenyl-4,5,6,7,8,9-hexahydro-2H-5,9-epiminocycloocta[c]pyrazole (Intermediate 1) and 1-(3-chlorophenyl)-1,2,4-triazole-3-carboxylic acid (Intermediate 37) instead of quinoline-6-carboxylic acid. MS (ESI): mass calcd. for $C_{25}H_{22}Cl_2N_6O$, 492.1; m/z found, 493.2 [M+H]$^+$. $^1$H NMR (500 MHz, DMSO-d$_6$) δ 9.44 (s, 1H), 8.08-8.00 (m, 1H), 7.91-7.83 (m, 1H), 7.63 (t, J=8.2 Hz, 1H), 7.63-7.59 (m, 1H), 7.58-7.46 (m, 4H), 5.80-5.74 (m, 1H), 4.58-4.50 (m, 1H), 3.79 (s, 3H), 3.11-2.99 (m, 1H), 2.55-2.50 (m, 1H), 2.07-1.35 (m, 6H).

Example 57: ((5R,9S)-3-(3-Chlorophenyl)-2-methyl-4,5, 6, 7, 8, 9-hexahydro-2H-5,9-epiminocycloocta[c]pyrazol-10-yl)(1-phenyl-5-(trifluoromethyl)-1H-pyrazol-4-yl)methanone

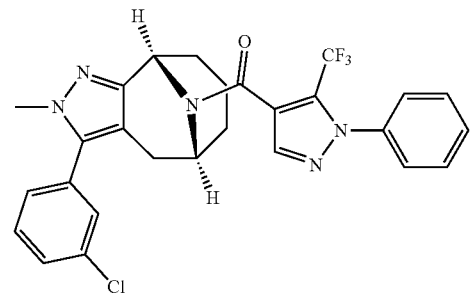 [SMILES: Cn1nc2c(c1-c1cccc(Cl)c1)C[C@H]1CCC[C@@H]2N1C(=O)c1cnn(-c2ccccc2)c1C(F)(F)F]

The title compound was prepared in a manner analogous to Example 1, using (5R,9S)-3-(3-chlorophenyl)-2-methyl-4,5,6,7,8,9-hexahydro-2H-5,9-epiminocycloocta[c]pyrazole (Intermediate 14) instead of racemic-(5R,9S)-2-methyl-3-phenyl-4,5,6,7,8,9-hexahydro-2H-5,9-epiminocycloocta[c]pyrazole (Intermediate 1) and 1-phenyl-5-(trifluoromethyl)-1H-pyrazole-4-carboxylic acid instead of quinoline-6-carboxylic acid. MS (ESI): mass calcd. for $C_{27}H_{23}ClF_3N_5O$, 525.2; m/z found, 526.1 [M+H]$^+$. $^1$H NMR (500 MHz, DMSO-d$_6$) δ 8.12 (s, 1H), 7.66-7.44 (m, 9H), 5.78-5.71 (m, 1H), 4.21-4.11 (m, 1H), 3.80 (s, 3H), 3.04 (dd, J=16.2, 7.4 Hz, 1H), 2.51-2.44 (m, 1H), 1.94-1.37 (m, 6H).

Example 58: ((5R,9S)-3-(3-Chlorophenyl)-2-methyl-4,5,6,7,8,9-hexahydro-2H-5,9-epiminocycloocta[c]pyrazol-10-yl)(5-methyl-1-(3-(trifluoromethyl)phenyl)-1H-1,2,4-triazol-3-yl)methanone

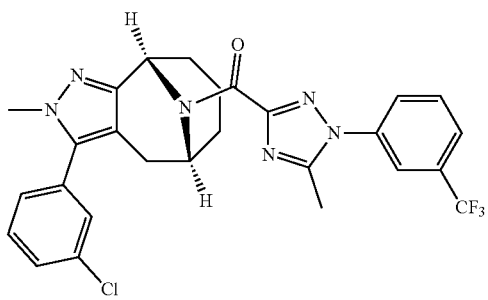 [SMILES: Cc1nc(C(=O)N2[C@@H]3CCC[C@H]2c2nn(C)c(-c4cccc(Cl)c4)c2C3)nn1-c1cccc(C(F)(F)F)c1]

The title compound was prepared in a manner analogous to Example 1, using (5R,9S)-3-(3-chlorophenyl)-2-methyl-4,5,6,7,8,9-hexahydro-2H-5,9-epiminocycloocta[c]pyrazole (Intermediate 14) instead of racemic-(5R,9S)-2-methyl-3-phenyl-4,5,6,7,8,9-hexahydro-2H-5,9-epiminocycloocta[c]pyrazole (Intermediate 1) and 5-methyl-1-(3-(trifluoromethyl)phenyl)-1H-1,2,4-triazole-3-carboxylic acid (Intermediate 40) instead of quinoline-6-carboxylic acid. MS (ESI): mass calcd. for $C_{27}H_{24}ClF_3N_6O$, 540.2; m/z found, 541.1 [M+H]$^+$. $^1$H NMR (500 MHz, DMSO-d$_6$) δ 8.05-8.02 (m, 1H), 8.00-7.96 (m, 1H), 7.95-7.90 (m, 1H), 7.88-7.84 (m, 1H), 7.61-7.58 (m, 1H), 7.57-7.45 (m, 3H), 5.78-5.72 (m, 1H), 4.67-4.59 (m, 1H), 3.79 (s, 3H), 3.09-2.97 (m, 1H), 2.60-2.42 (m, 1H), 2.53 (s, 3H), 1.98-1.59 (m, 4H), 1.58-1.41 (m, 2H).

Example 59: ((5R,9S)-3-(3-Chlorophenyl)-2-methyl-4,5,6,7,8,9-hexahydro-2H-5,9-epiminocycloocta[c]pyrazol-10-yl)(1-(3-(trifluoromethyl)phenyl)-1H-1,2,4-triazol-3-yl)methanone

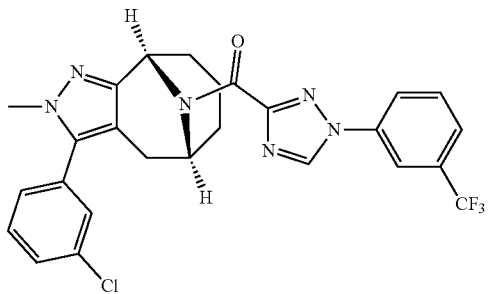 [SMILES: Cn1nc2c(c1-c1cccc(Cl)c1)C[C@H]1CCC[C@@H]2N1C(=O)c1ncn(-c2cccc(C(F)(F)F)c2)n1]

The title compound was prepared in a manner analogous to Example 1, using (5R,9S)-3-(3-chlorophenyl)-2-methyl-4,5,6,7,8,9-hexahydro-2H-5,9-epiminocycloocta[c]pyrazole (Intermediate 14) instead of racemic-(5R,9S)-2-methyl-3-phenyl-4,5,6,7,8,9-hexahydro-2H-5,9-epiminocycloocta[c]pyrazole (Intermediate 1) and 1-(3-(trifluoromethyl)phenyl)-1H-1,2,4-triazole-3-carboxylic acid (Intermediate 38) instead of quinoline-6-carboxylic acid. MS (ESI): mass calcd. for $C_{26}H_{22}ClF_3N_6O$, 526.2; m/z found, 527.2 [M+H]$^+$. $^1$H NMR (500 MHz, DMSO-d$_6$) δ 9.53 (s, 1H), 8.29-8.24 (m, 1H), 8.24-8.18 (m, 1H), 7.89-7.79 (m, 2H), 7.63-7.59 (m, 1H), 7.57-7.45 (m, 3H), 5.81-5.74 (m, 1H), 4.57-4.50 (m, 1H), 3.80 (s, 3H), 3.13-2.98 (m, 1H), 2.57-2.47 (m, 1H), 2.07-1.40 (m, 6H).

Example 60: (1-Benzyl-1H-1,2,4-triazol-3-yl)((5R,9S)-3-(3-chlorophenyl)-2-methyl-4,5,6,7,8,9-hexahydro-2H-5,9-epiminocycloocta[c]pyrazol-10-yl)methanone

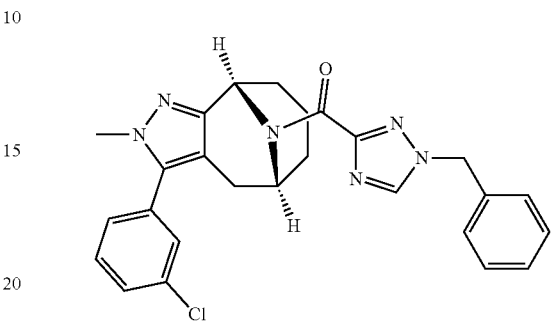

The title compound was prepared in a manner analogous to Example 1, using (5R,9S)-3-(3-chlorophenyl)-2-methyl-4,5,6,7,8,9-hexahydro-2H-5,9-epiminocycloocta[c]pyrazole (Intermediate 14) instead of racemic-(5R,9S)-2-methyl-3-phenyl-4,5,6,7,8,9-hexahydro-2H-5,9-epiminocycloocta[c]pyrazole (Intermediate 1) and 1-benzyl-1H-1,2,4-triazole-3-carboxylic acid instead of quinoline-6-carboxylic acid. MS (ESI): mass calcd. for $C_{26}H_{25}ClN_6O$, 472.2; m/z found, 473.2 [M+H]$^+$. $^1$H NMR (500 MHz, DMSO-d$_6$) δ 8.75 (s, 1H), 7.61-7.56 (m, 1H), 7.56-7.49 (m, 2H), 7.49-7.43 (m, 1H), 7.43-7.27 (m, 5H), 5.73-5.68 (m, 1H), 5.45 (s, 2H), 4.48-4.42 (m, 1H), 3.77 (s, 3H), 2.94 (dd, J=16.0, 7.4 Hz, 1H), 2.46 (d, J=16.2 Hz, 1H), 1.96-1.37 (m, 6H).

Example 61: Benzo[d]isoxazol-3-yl((5R,9S)-3-(3-chlorophenyl)-2-methyl-4,5,6,7,8,9-hexahydro-2H-5,9-epiminocycloocta[c]pyrazol-10-yl)methanone

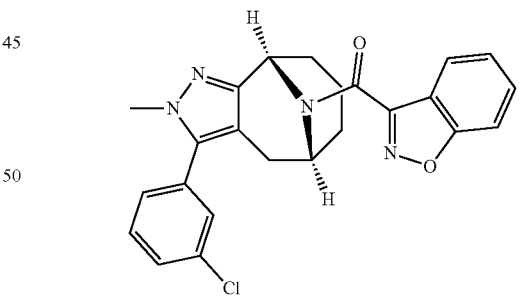

The title compound was prepared in a manner analogous to Example 1, using (5R,9S)-3-(3-chlorophenyl)-2-methyl-4,5,6,7,8,9-hexahydro-2H-5,9-epiminocycloocta[c]pyrazole (Intermediate 14) instead of racemic-(5R,9S)-2-methyl-3-phenyl-4,5,6,7,8,9-hexahydro-2H-5,9-epiminocycloocta[c]pyrazole (Intermediate 1) and benzo[d]isoxazole-3-carboxylic acid instead of quinoline-6-carboxylic acid. MS (ESI): mass calcd. for $C_{24}H_{21}ClN_4O_2$, 432.1; m/z found, 433.1 [M+H]$^+$. $^1$H NMR (500 MHz, DMSO-d$_6$) δ 7.93-7.90 (m, 1H), 7.88-7.85 (m, 1H), 7.78-7.72 (m, 1H), 7.62-7.59 (m, 1H), 7.58-7.45 (m, 4H), 5.93-5.80 (m, 1H), 4.65-4.51 (m, 1H), 3.80 (s, 3H), 3.01 (dd, J=16.2, 7.3 Hz, 1H), 2.54 (d, J=16.1 Hz, 1H), 2.02-1.68 (m, 4H), 1.59-1.41 (m, 2H).

Example 62: ((5R,9S)-3-(3-chlorophenyl)-2-methyl-4,5,6,7,8,9-hexahydro-2H-5,9-epiminocycloocta[c]pyrazol-10-yl)(1-methyl-1H-indazol-3-yl)methanone

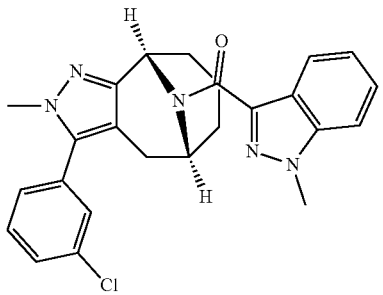 [SMILES: Cn1nc2c(c1-c1cccc(Cl)c1)C[C@@H]1CCC[C@H]2N1C(=O)c1nn(C)c2ccccc12]

The title compound was prepared in a manner analogous to Example 1, using (5R,9S)-3-(3-chlorophenyl)-2-methyl-4,5,6,7,8,9-hexahydro-2H-5,9-epiminocycloocta[c]pyrazole (Intermediate 14) instead of racemic-(5R,9S)-2-methyl-3-phenyl-4,5,6,7,8,9-hexahydro-2H-5,9-epiminocycloocta[c]pyrazole (Intermediate 1) and 1-methyl-1H-indazol-3-carboxylic acid instead of quinoline-6-carboxylic acid. MS (ESI): mass calcd. for $C_{25}H_{24}ClN_5O$, 445.2; m/z found, 446.1 [M+H]$^+$. $^1$H NMR (500 MHz, DMSO-d$_6$) δ 8.00-7.94 (m, 1H), 7.72 (dd, J=12.9, 8.5 Hz, 1H), 7.63-7.57 (m, 1H), 7.57-7.42 (m, 4H), 7.27-7.21 (m, 1H), 5.88-5.80 (m, 1H), 5.39-5.31 (m, 1H), 4.10 (s, 3H), 3.79 (s, 3H), 3.14-3.03 (m, 1H), 2.56 (dd, J=16.2, 11.7 Hz, 1H), 2.10-1.62 (m, 4H), 1.57-1.42 (m, 2H).

Example 63: racemic-((5R,9S)-3-(3-Chlorophenyl)-2-methyl-4,5,6,7,8,9-hexahydro-2H-5,9-epiminocycloocta[c]pyrazol-10-yl) (quinolin-6-yl) methanone

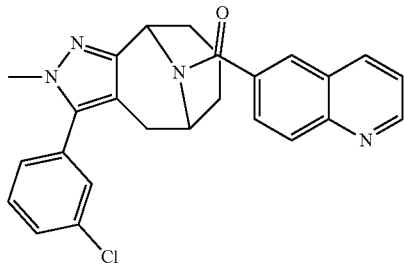 [SMILES: Cn1nc2c(c1-c1cccc(Cl)c1)CC1CCCC2N1C(=O)c1ccc2ncccc2c1]

The title compound was prepared in a manner analogous to Example 1, using racemic-(5R,9S)-3-(3-chlorophenyl)-2-methyl-4,5,6,7,8,9-hexahydro-2H-5,9-epiminocycloocta[c]pyrazole (Intermediate 6) instead of racemic-(5R,9S)-2-methyl-3-phenyl-4,5,6,7,8,9-hexahydro-2H-5,9-epiminocycloocta[c]pyrazole (Intermediate 1). MS (ESI): mass calcd. for $C_{26}H_{23}ClN_4O$, 442.1; m/z found, 443.1 [M+H]$^+$. $^1$H NMR (400 MHz, DMSO-d$_6$) δ 9.04-8.89 (m, 1H), 8.48 (d, J=8.3 Hz, 1H), 8.18-7.99 (m, 2H), 7.85-7.46 (m, 6H), 5.77 (s, 1H), 3.77 (s, 3H), 3.21-2.95 (m, 2H), 2.44 (d, J=16.2 Hz, 1H), 2.07-1.38 (m, 6H).

Example 64: ((5R,9S)-3-(3-Chlorophenyl)-2-methyl-4,5,6,7,8,9-hexahydro-2H-5,9-epiminocycloocta[c]pyrazol-10-yl) (quinoxalin-6-yl) methanone

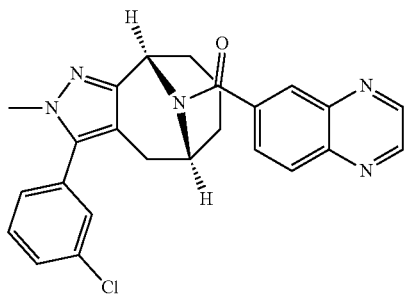 [SMILES: Cn1nc2c(c1-c1cccc(Cl)c1)C[C@@H]1CCC[C@H]2N1C(=O)c1ccc2nccnc2c1]

The title compound was prepared in a manner analogous to Example 1, using (5R,9S)-3-(3-chlorophenyl)-2-methyl-4,5,6,7,8,9-hexahydro-2H-5,9-epiminocycloocta[c]pyrazole (Intermediate 14) instead of racemic-(5R,9S)-2-methyl-3-phenyl-4,5,6,7,8,9-hexahydro-2H-5,9-epiminocycloocta[c]pyrazole (Intermediate 1) and quinoxaline-6-carboxylic acid instead of quinoline-6-carboxylic acid. MS (ESI): mass calcd. for $C_{25}H_{22}ClN_5O$, 443.1; m/z found, 444.1 [M+H]$^+$. $^1$H NMR (500 MHz, DMSO-d$_6$) δ 9.09-8.95 (m, 2H), 8.25-8.01 (m, 2H), 7.93-7.78 (m, 1H), 7.68-7.43 (m, 4H), 5.77 (d, J=14.8 Hz, 1H), 4.08 (d, J=5.7 Hz, 1H), 3.84-3.66 (m, 3H), 3.16-2.98 (m, 1H), 2.41 (d, J=16.2 Hz, 1H), 2.04-1.39 (m, 6H).

Example 65: ((5R,9S)-3-(3,5-Difluorophenyl)-2-methyl-4,5,6,7,8,9-hexahydro-2H-5,9-epiminocycloocta[c]pyrazol-10-yl)(4-(2-fluoroethoxy)quinolin-6-yl)methanone

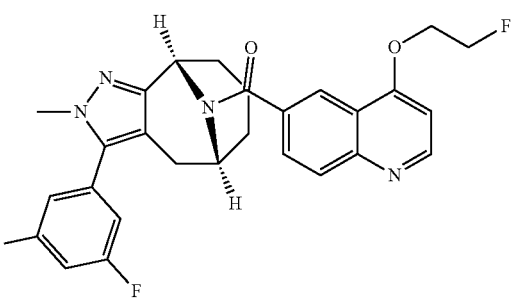

Step A: ((5R,9S)-3-(3,5-Difluorophenyl)-2-methyl-4,5,6,7,8,9-hexahydro-2H-5,9-epiminocycloocta[c]pyrazol-10-yl)(4-hydroxyquinolin-6-yl)methanone To a solution of 4-hydroxyquinoline-6-carboxylic acid (70 mg, 0.37 mmol), (5R,9S)-3-(3,5-difluorophenyl)-2-methyl-4,5,6,7,8,9-hexahydro-2H-5,9-epiminocycloocta[c]pyrazole (Intermediate 12), trifluoroacetic acid (100 mg, 0.25 mmol) and HATU (141 mg, 0.37 mmol) in DCM (1.6 ml), was added triethylamine (0.10 ml, 0.74 mmol). The mixture was stirred at rt for 16 hrs. The reaction was concentrated, and directly-loaded to a silica gel column (12 g) and eluted with a gradient of 0 to 20% MeOH/DCM to yield a yellow oil (80 mg, 70% yield). MS (ESI): mass calcd. for $C_{26}H_{22}F_2N_4O_2$, 460.2; m/z found, 461.1 [M+H]$^+$.

Step B: ((5R,9S)-3-(3,5-Difluorophenyl)-2-methyl-4,5,6,7,8,9-hexahydro-2H-5,9-epiminocycloocta[c]pyrazol-10-yl)(4-(2-fluoroethoxy)quinolin-6-yl)methanone. A solution of ((5R,9S)-3-(3,5-difluorophenyl)-2-methyl-4,5,6,7,8,9-hexahydro-2H-5,9-epiminocycloocta[c]pyrazol-10-yl)(4-hydroxyquinolin-6-yl)methanone (80 mg, 0.17 mmol) in dimethylformamide (DMF) (0.7 mL) was treated with 1-fluoro-2-iodoethane (45 mg, 0.26 mmol) and cesium carbonate (113 mg, 0.35 mmol). The reaction was stirred at rt for 16 h and then diluted with water. The solid precipitates were filtered and purified on a silica gel column (4 g) with methanol (MeOH) in dichloromethane (DCM) (1 to 5% gradient) to afford the title compound as a white solid (21 mg, 24% yield). MS (ESI): mass calcd. for $C_{28}H_{25}F_3N_4O_2$, 506.2; m/z found, 507.2 [M+H]$^+$. $^1$H NMR (CDCl$_3$) δ 8.81 (d, J=5.3, 1.1 Hz, 1H), 8.41 (dd, J=9.2, 1.9 Hz, 1H), 8.08 (dd, J=8.6, 4.2 Hz, 1H), 7.77 (td, J=8.9, 2.0 Hz, 1H), 6.98-6.84 (m, 3H), 6.78 (dd, J=5.2, 1.4 Hz, 1H), 6.06 and 5.12 (s, 1H), 5.30 and 4.28 (m, 1H), 4.95-4.86 (m, 2H), 4.49-4.41 (m, 2H), 3.89 and 3.80 (s, 3H), 3.31-3.28 and 3.10-3.04 (m, 1H), 2.54 and 2.44 (d, J=16.2 Hz, 1H), 2.13-1.99 (m, 1H), 1.94-1.73 (m, 3H), 1.68-1.51 (m, 2H).

Example 66: ((5R,9S)-3-(3,5-Difluorophenyl)-2-methyl-4,5,6,7,8,9-hexahydro-2H-5,9-epiminocycloocta[c]pyrazol-10-yl)(3-(2-fluoroethoxy)phenyl)methanone

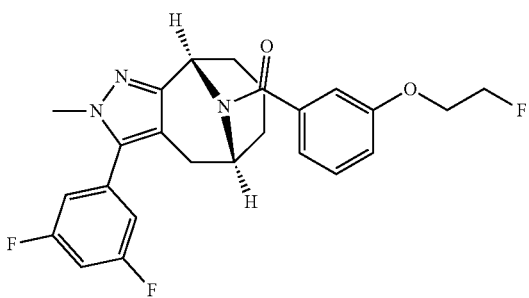 [SMILES: Cn1nc2c(c1-c1cc(F)cc(F)c1)C[C@@H]1CCC[C@H]2N1C(=O)c1cccc(OCCF)c1]

The title compound was prepared in a manner analogous to Example 65, using 3-hydroxybenzoic acid instead of 4-hydroxyquinoline-6-carboxylic acid in Step A. MS (ESI): mass calcd. for $C_{25}H_{24}F_3N_3O_2$, 455.2 m/z found, 456.2 [M+H]$^+$. $^1$H NMR (CDCl$_3$): δ 7.34-7.30 (m, 1H), 7.02-6.96 (m, 3H), 6.91-6.82 (m, 3H), 5.98 and 5.05 (m, 1H), 5.21 and 4.22 (m, 1H), 4.80-4.69 (m, 2H), 4.25-4.19 (m, 2H) 3.85 and 3.79 (s, 3H), 3.23-3.19 and 2.97-2.91 (m, 1H), 2.44 (dd, J=36.7, 16.3 Hz, 1H), 2.01-1.68 (m, 3H), 1.63-1.47 (3H).

Example 67: ((5R,9S)-3-(3,5-Difluorophenyl)-2-methyl-4,5,6,7,8,9-hexahydro-2H-5,9-epiminocycloocta[c]pyrazol-10-yl)(3-(2-(fluoro-18F)ethoxy)phenyl)methanone

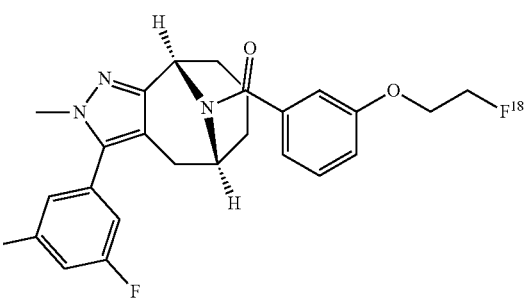

Step A: 2-(3-((5R,9S)-3-(3,5-Difluorophenyl)-2-methyl-4,5,6,7,8,9-hexahydro-2H-5,9-epiminocycloocta[c]pyrazole-10-carbonyl)phenoxy)ethyl 4-methylbenzenesulfonate. The title compound was prepared in a manner analogous to Example 65, Step B, using ethylene ditosylate instead of 1-fluoro-2-iodoethane. MS (ESI): mass calcd. for $C_{32}H_{31}F_2N_3SO_5$, 607.2 m/z found, 608.2 [M+H]$^+$.

Step B: ((5R,9S)-3-(3,5-Difluorophenyl)-2-methyl-4,5,6,7,8,9-hexahydro-2H-5,9-epiminocycloocta[c]pyrazol-10-yl)(3-(2-(fluoro-$^{18}$F)ethoxy)phenyl)methanone. [$^{18}$F]fluoride in a shipping vial from PETNET Solutions Inc. (San Diego, CA USA) is transferred onto and trapped on an ion exchange cartridge. It is then eluted into the reaction vessel (RV1) of the Synthra RNPlus® module with a solution of potassium carbonate (0.75 mg) and Kryptofix 222 (7.2 mg) in 0.8 mL of acetonitrile/water (6/2, v/v). After the solvent was evaporated under a stream of nitrogen at 85° C. under vacuum, anhydrous CH$_3$CN (0.5 mL) was added. This process was repeated and the temperature increased to 110° C. for 3.5 min. The reaction vial was then cooled to 70° C. before a solution of 3.0 mg of 2-(3-((5R,9S)-3-(3,5-difluorophenyl)-2-methyl-4,5,6,7,8,9-hexahydro-2H-5,9-epiminocycloocta[c]pyrazole-10-carbonyl)phenoxy)ethyl 4-methylbenzenesulfonate in 0.7 mL anhydrous acetonitrile (MeCN/ACN) was added to reaction vessel. The reaction mixture is heated at 110° C. for 10 min. The reactor is cooled to 40° C., diluted with water (4.3 mL), and the contents are transferred into the HPLC injector loop for purification. Purification is performed by HPLC using a semi-preparative Eclipse XDB-C18 column (5 μm, 9.4 mm×250 mm) with a mixture of 10 mM NH$_4$OAc and MeCN (45:55 v/v) at a flow rate of 4 mL/min with UV detection at 254 nm. The purified radiotracer solution was diluted with 30 mL of water and passed through a SepPak Light C-18 cartridge. The C-18 cartridge was further washed with 10 mL of water before 0.5 mL EtOH was used to elute the tracer. The tracer solution was further diluted with 4.5 mL of saline. The final formulation contains an ethanol concentration of 10%, suitable for intravenous injection (IV).

Example 68: racemic-(2-(2H-1,2,3-Triazol-2-yl) phenyl) ((5R,9S)-3-(3,5-difluorophenyl)-2-methyl-4,5,6,7,8,9-hexahydro-2H-5,9-epiminocycloocta[c]pyrazol-10-yl) methanone

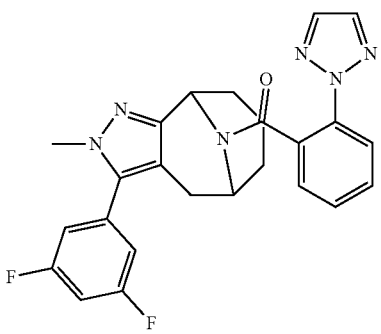 [SMILES: Cn1nc2c(c1-c1cc(F)cc(F)c1)CC1CCCC2N1C(=O)c1ccccc1-n1nccn1]

The title compound was prepared in a manner analogous to Example 1, using racemic-(5R,9S)-3-(3,5-difluorophenyl)-2-methyl-4,5,6,7,8,9-hexahydro-2H-5,9-epiminocycloocta[c]pyrazole (Intermediate 7) instead of racemic-(5R,9S)-2-methyl-3-phenyl-4,5,6,7,8,9-hexahydro-2H-5,9-epiminocycloocta[c]pyrazole (Intermediate 1) and 2-(2H-1,2,3-triazol-2-yl)benzoic acid (Intermediate 49) instead of quinoline-6-carboxylic acid. MS (ESI): mass calcd. for $C_{25}H_{22}F_2N_6O$, 460.1; m/z found, 461.1 [M+H]$^+$. $^1$H NMR (500 MHz, DMSO-d$_6$) δ 8.16 (d, J=11.4 Hz, 1H), 8.00-7.74 (m, 1H), 7.70-7.49 (m, 3H), 7.46-7.13 (m, 4H), 5.69 (d, J=3.2 Hz, 1H), 3.97-3.62 (m, 4H), 3.22-2.87 (m, 1H), 2.43-2.21 (m, 1H), 1.90-1.27 (m, 6H).

Example 69: (2-(1H-1,2,4-Triazol-5-yl) phenyl) ((5R,9S)-3-(3,5-difluorophenyl)-2-methyl-4,5,6,7,8,9-hexahydro-2H-5,9-epiminocycloocta[c]pyrazol-10-yl) methanone

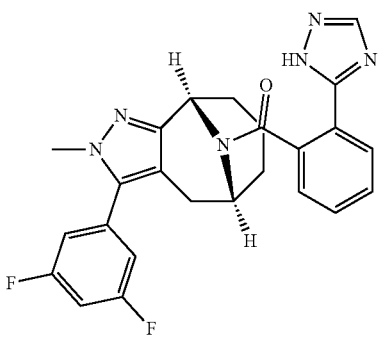 [SMILES: Cn1nc2c(c1-c1cc(F)cc(F)c1)C[C@@H]1CCC[C@H]2N1C(=O)c1ccccc1-c1ncn[nH]1]

The title compound was prepared in a manner analogous to Example 1, using (5R,9S)-3-(3,5-difluorophenyl)-2-methyl-4,5,6,7,8,9-hexahydro-2H-5,9-epiminocycloocta[c]pyrazole (Intermediate 12) instead of racemic-(5R,9S)-2-methyl-3-phenyl-4,5,6,7,8,9-hexahydro-2H-5,9-epiminocycloocta[c]pyrazol (Intermediate 1) and 2-(1H-1,2,4-triazol-5-yl)benzoic acid instead of quinoline-6-carboxylic acid. MS (ESI): mass calcd. for $C_{25}H_{22}F_2N_6O$, 460.1; m/z found, 461.1 [M+H]$^+$. $^1$H NMR (500 MHz, DMSO-d$_6$) δ 8.60-7.82 (m, 2H), 7.72-6.80 (m, 6H), 5.75 (d, J=3.3 Hz, 1H), 4.35 (d, J=82.0 Hz, 1H), 3.89-3.55 (m, 4H), 3.11-2.78 (m, 1H), 2.38 (dd, J=44.8, 15.9 Hz, 1H), 2.17-1.27 (m, 6H).

Example 70: (2-(5-Chloro-1H-1,2,4-triazol-3-yl) phenyl)((5R,9S)-3-(3,5-difluorophenyl)-2-methyl-4,5,6,7,8,9-hexahydro-2H-5,9-epiminocycloocta[c]pyrazol-10-yl)methanone

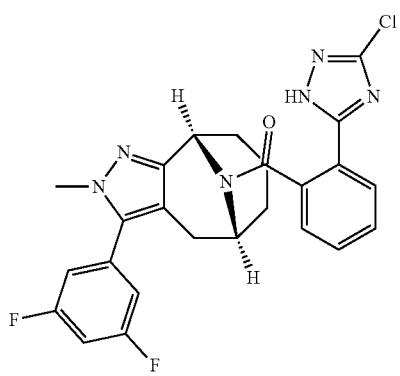 [SMILES: Cn1nc2c(c1-c1cc(F)cc(F)c1)C[C@@H]1CCC[C@H]2N1C(=O)c1ccccc1-c1nc(Cl)n[nH]1]

The title compound was prepared in a manner analogous to Example 1, using (5R,9S)-3-(3,5-difluorophenyl)-2-methyl-4,5,6,7,8,9-hexahydro-2H-5,9-epiminocycloocta[c]pyrazole (Intermediate 12) instead of racemic-(5R,9S)-2-methyl-3-phenyl-4,5,6,7,8,9-hexahydro-2H-5,9-epiminocycloocta[c]pyrazol (Intermediate 1) and 2-(3-chloro-1H-1,2,4-triazol-5-yl)benzoic acid instead of quinoline-6-carboxylic acid. MS (ESI): mass calcd. for $C_{25}H_{21}ClF_2N_6O$, 494.1; m/z found, 495.1 [M+H]$^+$. $^1$H NMR (500 MHz, DMSO-d$_6$) δ 15.00-14.33 (m, 1H), 7.90-7.00 (m, 7H), 5.76-5.63 (m, 1H), 3.79 (s, 3H), 3.79-3.68 (m, 1H), 3.00-2.86 (m, 1H), 2.58-2.42 (m, 1H), 2.25-1.16 (m, 6H).

Example 71: ((5R,9S)-3-(3,5-Difluorophenyl)-2-methyl-4,5,6,7,8,9-hexahydro-2H-5,9-epiminocycloocta[c]pyrazol-10-yl)(3-(1-methyl-1H-pyrazol-4-yl)phenyl)methanone

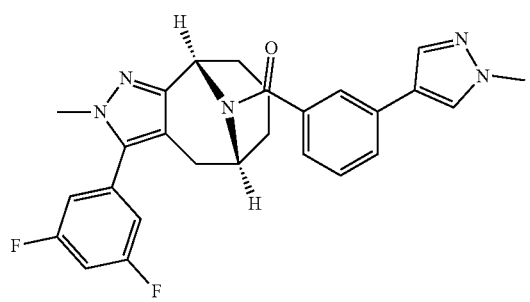 [SMILES: Cn1cc(-c2cccc(C(=O)N3[C@H]4CCC[C@@H]3c3nn(C)c(-c5cc(F)cc(F)c5)c3C4)c2)cn1]

The title compound was prepared in a manner analogous to Example 1, using (5R,9S)-3-(3,5-difluorophenyl)-2-methyl-4,5,6,7,8,9-hexahydro-2H-5,9-epiminocycloocta[c]pyrazole (Intermediate 12) instead of racemic-(5R,9S)-2-methyl-3-phenyl-4,5,6,7,8,9-hexahydro-2H-5,9-epiminocycloocta[c]pyrazol (Intermediate 1) and 3-(1-methyl-1H-pyrazol-4-yl)benzoic acid instead of quinoline- 6-carboxylic acid. MS (ESI): mass calcd. for $C_{27}H_{25}F_2N_5O$, 473.2; m/z found, 474.2 [M+H]⁺. ¹H NMR (300 MHz, DMSO-d₆) δ 8.23 (s, 1H), 7.93 (s, 1H), 7.72-7.61 (m, 1H), 7.61-7.56 (m, 1H), 7.49-7.27 (m, 4H), 7.26-7.17 (m, 1H), 5.81-5.64 (m, 1H), 4.16-3.99 (m, 1H), 3.86 (s, 3H), 3.83 (s, 3H), 3.06-2.94 (m, 1H), 2.51-2.36 (m, 1H), 2.06-1.30 (m, 6H).

Example 72: (3-(4H-1,2,4-Triazol-4-yl) phenyl) ((5R,9S)-3-(3,5-difluorophenyl)-2-methyl-4,5,6,7,8, 9-hexahydro-2H-5,9-epiminocycloocta[c]pyrazol-10-yl)methanone

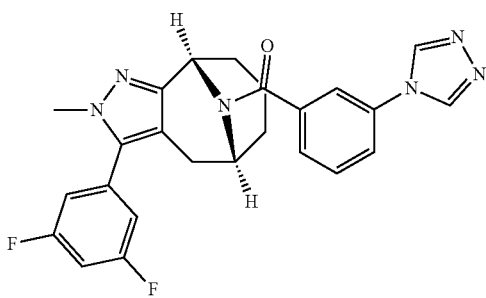 [SMILES: Cn1nc2c(c1-c1cc(F)cc(F)c1)C[C@@H]1CCC[C@H]2N1C(=O)c1cccc(-n2cnnc2)c1]

The title compound was prepared in a manner analogous to Example 1, using (5R,9S)-3-(3,5-difluorophenyl)-2-methyl-4,5,6,7,8,9-hexahydro-2H-5,9-epiminocycloocta[c]pyrazole (Intermediate 12) instead of racemic-(5R,9S)-2-methyl-3-phenyl-4,5,6,7,8,9-hexahydro-2H-5,9-epiminocycloocta[c]pyrazole (Intermediate 1) and 3-(4H-1,2,4-triazol-4-yl)benzoic acid instead of quinoline-6-carboxylic acid. MS (ESI): mass calcd. for $C_{25}H_{22}F_2N_6O$, 460.1; m/z found, 461.1 [M+H]⁺. ¹H NMR (500 MHz, DMSO-d₆) δ 9.20 (d, J=4.4 Hz, 2H), 7.91-7.74 (m, 2H), 7.73-7.58 (m, 1H), 7.51-7.28 (m, 4H), 5.73 (d, J=3.5 Hz, 1H), 4.05 (t, J=6.2 Hz, 1H), 3.85-3.69 (m, 3H), 3.15-2.98 (m, 1H), 2.44 (d, J=16.2 Hz, 1H), 2.08-1.37 (m, 6H).

Example 73: ((5R,9S)-3-(3,5-Difluorophenyl)-2-methyl-4,5,6,7,8,9-hexahydro-2H-5,9-epiminocycloocta[c]pyrazol-10-yl)(5-methyl-2-(2H-1,2,3-triazol-2-yl)phenyl)methanone

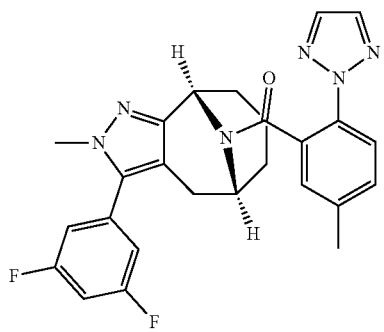 [SMILES: Cc1ccc(-n2nccn2)c(C(=O)N2[C@H]3CCC[C@@H]2c2nn(C)c(-c4cc(F)cc(F)c4)c2C3)c1]

The title compound was prepared in a manner analogous to Example 1, using (5R,9S)-3-(3,5-difluorophenyl)-2-methyl-4,5,6,7,8,9-hexahydro-2H-5,9-epiminocycloocta[c]pyrazole (Intermediate 12) instead of racemic-(5R,9S)-2-methyl-3-phenyl-4,5,6,7,8,9-hexahydro-2H-5,9-epiminocycloocta[c]pyrazole (Intermediate 1) and 5-methyl-2-(2H-1,2,3-triazol-2-yl)benzoic acid instead of quinoline-6-carboxylic acid. MS (ESI): mass calcd. for $C_{26}H_{24}F_2N_6O$, 474.2; m/z found, 475.2 [M+H]⁺. ¹H NMR (300 MHz, DMSO-d₆): 8.11 (s, 1H), 7.86-6.95 (m, 7H), 5.74-5.61 (m, 1H), 3.94-3.77 (m, 1H), 3.82 (s, 3H), 3.03-2.85 (m, 1H), 2.49-2.31 (m, 4H), 1.95-1.13 (m, 6H).

Example 74: ((5R,9S)-3-(3,5-Difluorophenyl)-2-methyl-4,5,6,7,8,9-hexahydro-2H-5,9-epiminocycloocta[c]pyrazol-10-yl) (3-fluoro-2-(2H-1,2,3-triazol-2-yl) phenyl) methanone

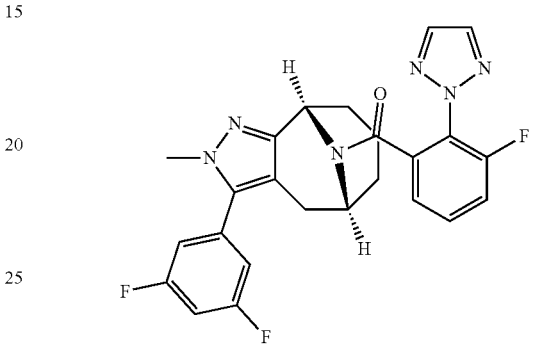

The title compound was prepared in a manner analogous to Example 1, using (5R,9S)-3-(3,5-difluorophenyl)-2-methyl-4,5,6,7,8,9-hexahydro-2H-5,9-epiminocycloocta[c]pyrazole (Intermediate 12) instead of racemic-(5R,9S)-2-methyl-3-phenyl-4,5,6,7,8,9-hexahydro-2H-5,9-epiminocycloocta[c]pyrazol (Intermediate 1) and 3-fluoro-2-(2H-1,2,3-triazol-2-yl)benzoic acid [WO2016040789] instead of quinoline-6-carboxylic acid. MS (ESI): mass calcd. for $C_{25}H_{21}F_3N_6O$, 478.1; m/z found, 479.1 [M+H]⁺. ¹H NMR (500 MHz, DMSO-d₆) δ 8.18 (d, J=8.2 Hz, 1H), 7.86-7.43 (m, 3H), 7.35 (t, J=9.0 Hz, 4H), 5.51 (s, 1H), 3.95 (s, 1H), 3.81 (s, 3H), 3.06 (dd, J=16.3, 7.5 Hz, 1H), 2.47-2.33 (m, 1H), 1.86-1.26 (m, 6H).

Example 75: ((5R,9S)-3-(3,5-Difluorophenyl)-2-methyl-4,5,6,7,8,9-hexahydro-2H-5,9-epiminocycloocta[c]pyrazol-10-yl)(3-fluoro-2-(oxazol-2-yl) phenyl)methanone

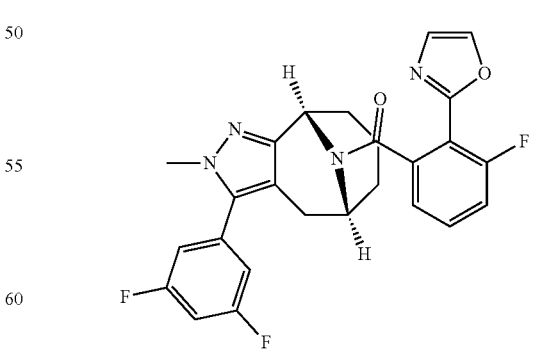

The title compound was prepared in a manner analogous to Example 1, using (5R,9S)-3-(3,5-difluorophenyl)-2-methyl-4,5,6,7,8,9-hexahydro-2H-5,9-epiminocycloocta[c]pyrazole (Intermediate 12) instead of racemic-(5R,9S)-2- methyl-3-phenyl-4,5,6,7,8,9-hexahydro-2H-5,9-epiminocycloocta[c]pyrazole (Intermediate 1) and 3-fluoro-2-(oxazol-2-yl)benzoic acid instead of quinoline-6-carboxylic acid. MS (ESI): mass calcd. for $C_{26}H_{21}F_3N_4O_2$, 471.2; m/z found, 472.2 [M+H]$^+$. $^1$H NMR (300 MHz, DMSO-d$_6$) δ 8.51-8.16 (m, 1H), 7.75-7.57 (m, 1H), 7.60-7.13 (m, 6H), 5.72-5.58 (m, 1H), 3.82 (s, 3H), 3.92-3.63 (m, 1H), 3.19-2.77 (m, 1H), 2.52-2.31 (m, 1H), 1.97-1.22 (m, 6H).

Example 76: racemic-((5R,9S)-3-(3,5-Difluorophenyl)-2-methyl-4,5,6,7,8,9-hexahydro-2H-5,9-epiminocycloocta[c]pyrazol-10-yl)(2-(pyrimidin-2-yl)phenyl)methanone

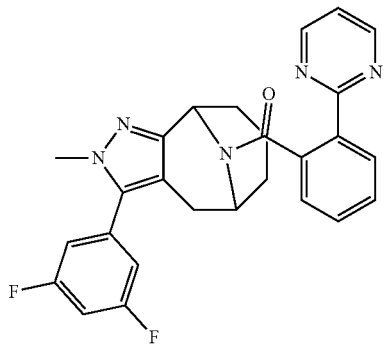 [SMILES: Cn1nc2c(c1-c1cc(F)cc(F)c1)CC1CCCC2N1C(=O)c1ccccc1-c1ncccn1]

The title compound was prepared in a manner analogous to Example 1, using racemic-(5R,9S)-3-(3,5-difluorophenyl)-2-methyl-4,5,6,7,8,9-hexahydro-2H-5,9-epiminocycloocta[c]pyrazole (Intermediate 7) instead of racemic-(5R,9S)-2-methyl-3-phenyl-4,5,6,7,8,9-hexahydro-2H-5,9-epiminocycloocta[c]pyrazole (Intermediate 1) and 2-(pyrimidin-2-yl)benzoic acid instead of quinoline-6-carboxylic acid. MS (ESI): mass calcd. for $C_{26}H_{21}F_3N_4O_2$, 478.2; m/z found, 479.2 [M+H]$^+$. $^1$H NMR (300 MHz, DMSO-d$_6$) δ 8.51-8.16 (m, 1H), 7.75-7.57 (m, 1H), 7.60-7.13 (m, 6H), 5.72-5.58 (m, 1H), 3.82 (s, 3H), 3.92-3.63 (m, 1H), 3.19-2.77 (m, 1H), 2.52-2.31 (m, 1H), 1.97-1.22 (m, 6H).

Example 77: racemic-((5R,9S)-3-(3,5-Difluorophenyl)-2-methyl-4,5,6,7,8,9-hexahydro-2H-5,9-epiminocycloocta[c]pyrazol-10-yl)(5-methoxy-1-methyl-1H-pyrazol-4-yl)methanone

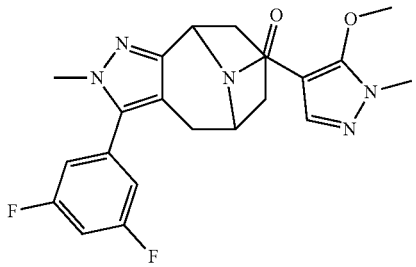

The title compound was prepared in a manner analogous to Example 1, using racemic-(5R,9S)-3-(3,5-difluorophenyl)-2-methyl-4,5,6,7,8,9-hexahydro-2H-5,9-epiminocycloocta[c]pyrazole (Intermediate 7) instead of racemic-(5R,9S)-2-methyl-3-phenyl-4,5,6,7,8,9-hexahydro-2H-5,9-epiminocycloocta[c]pyrazole (Intermediate 1) and 5-methoxy-1-methyl-1H-pyrazole-4-carboxylic acid instead of quinoline-6-carboxylic acid. MS (ESI): mass calcd. for $C_{22}H_{23}F_2N_5O_2$, 427.2; m/z found, 428.2 [M+H]$^+$. $^1$H NMR (300 MHz, DMSO-d$_6$) δ 7.47 (s, 1H), 7.41-7.18 (m, 3H), 5.73-5.53 (m, 1H), 4.51-4.31 (m, 1H), 3.93 (s, 3H), 3.81 (s, 3H), 3.59 (s, 3H), 3.26-3.10 (m, 1H), 2.51-2.35 (m, 1H), 2.05-1.23 (m, 6H).

Example 78: racemic-((5R,9S)-3-(3,5-Difluorophenyl)-2-methyl-4,5,6,7,8,9-hexahydro-2H-5,9-epiminocycloocta[c]pyrazol-10-yl)(1-ethyl-5-(trifluoromethyl)-1H-pyrazol-3-yl)methanone

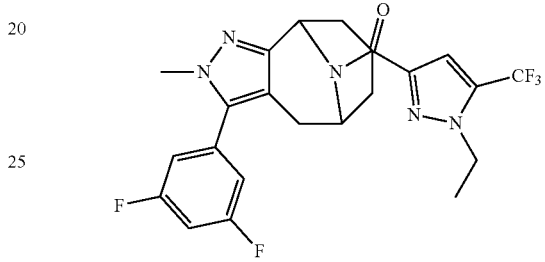

The title compound was prepared in a manner analogous to Example 1, using racemic-(5R,9S)-3-(3,5-difluorophenyl)-2-methyl-4,5,6,7,8,9-hexahydro-2H-5,9-epiminocycloocta[c]pyrazole (Intermediate 7) instead of racemic-(5R,9S)-2-methyl-3-phenyl-4,5,6,7,8,9-hexahydro-2H-5,9-epiminocycloocta[c]pyrazole (Intermediate 1) and 1-ethyl-5-(trifluoromethyl)-1H-pyrazole-3-carboxylic acid instead of quinoline-6-carboxylic acid. MS (ESI): mass calcd. for $C_{23}H_{22}F_5N_5O$, 479.2; m/z found, 480.2 [M+H]$^+$. $^1$H NMR (500 MHz, DMSO-d$_6$) δ 7.37-7.27 (m, 3H), 7.17-7.13 (m, 1H), 5.75-5.70 (m, 1H), 4.92-4.85 (m, 1H), 4.29 (q, J=7.2 Hz, 2H), 3.81 (s, 3H), 3.13-3.00 (m, 1H), 2.61-2.52 (m, 1H), 1.88-1.61 (m, 4H), 1.55-1.43 (m, 2H), 1.41 (t, J=7.2 Hz, 3H).

Example 79: racemic-(5-Cyclopropyl-1H-pyrazol-4-yl)((5R,9S)-3-(3,5-difluorophenyl)-2-methyl-4,5,6,7,8,9-hexahydro-2H-5,9-epiminocycloocta[c]pyrazol-10-yl)methanone

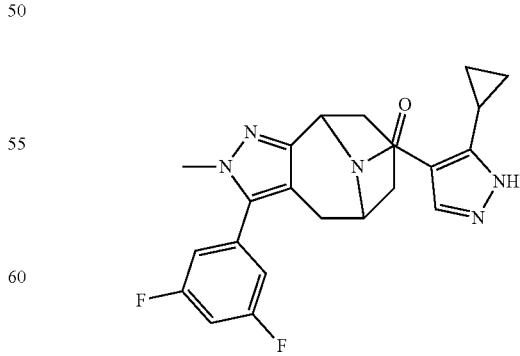

The title compound was prepared in a manner analogous to Example 1, using racemic-(5R,9S)-3-(3,5-difluorophenyl)-2-methyl-4,5,6,7,8,9-hexahydro-2H-5,9-epiminocycloocta[c]pyrazole (Intermediate 7) instead of racemic-(5R,9S)-2-methyl-3-phenyl-4,5,6,7,8,9-hexahydro-2H-5,9-epiminocycloocta[c]pyrazole (Intermediate 1) and 5-cyclopropyl-1H-pyrazole-4-carboxylic acid instead of quinoline-6-carboxylic acid. MS (ESI): mass calcd. for $C_{23}H_{23}F_2N_5O$, 423.2; m/z found, 424.2 [M+H]$^+$. $^1$H NMR (500 MHz, DMSO-d$_6$) δ 12.68-12.55 (m, 1H), 7.60-7.39 (m, 1H), 7.39-7.24 (m, 3H), 5.77-5.55 (m, 1H), 4.44-4.24 (m, 1H), 3.89-3.69 (m, 3H), 3.14-2.99 (m, 1H), 2.17-1.54 (m, 5H), 1.54-1.34 (m, 2H), 1.01-0.67 (m, 4H).

Example 80: racemic-(5-Cyclopropyl-1-(2-hydroxyethyl)-1H-pyrazol-4-yl)((5R,9S)-3-(3,5-difluorophenyl)-2-methyl-4,5,6,7,8,9-hexahydro-21H-5,9-epiminocycloocta[c]pyrazol-10-yl)methanone

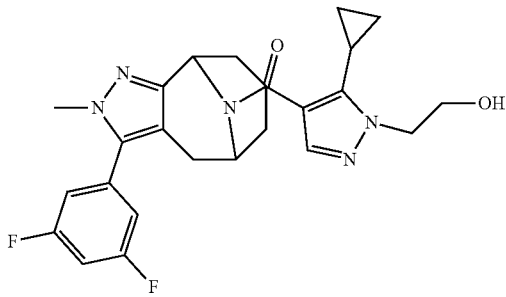

The title compound was prepared in a manner analogous to Example 1, using racemic-(5R,9S)-3-(3,5-difluorophenyl)-2-methyl-4,5,6,7,8,9-hexahydro-2H-5,9-epiminocycloocta[c]pyrazole (Intermediate 7) instead of racemic-(5R,9S)-2-methyl-3-phenyl-4,5,6,7,8,9-hexahydro-2H-5,9-epiminocycloocta[c]pyrazole (Intermediate 1) and 5-cyclopropyl-1-(2-hydroxyethyl)-1H-pyrazole-4-carboxylic acid instead of quinoline-6-carboxylic acid. MS (ESI): mass calcd. for $C_{25}H_{27}F_2N_5O_2$, 467.2; m/z found, 468.3 [M+H]$^+$. $^1$H NMR (500 MHz, DMSO-d$_6$) δ 7.45 (s, 1H), 7.37-7.25 (m, 3H), 5.72-5.66 (m, 1H), 4.91-4.85 (m, 1H), 4.25-4.14 (m, 3H), 3.85-3.73 (m, 5H), 3.08-2.96 (m, 1H), 2.47-2.40 (m, 1H), 1.96-1.30 (m, 7H), 0.96-0.81 (m, 2H), 0.71-0.57 (m, 2H).

Example 81: racemic-(3-Cyclopropyl-1-(2,2,2-trifluoroethyl)-1H-pyrazol-4-yl)((5R,9S)-3-(3,5-difluorophenyl)-2-methyl-4,5,6,7,8,9-hexahydro-2H-5,9-epiminocycloocta[c]pyrazol-10-yl)methanone

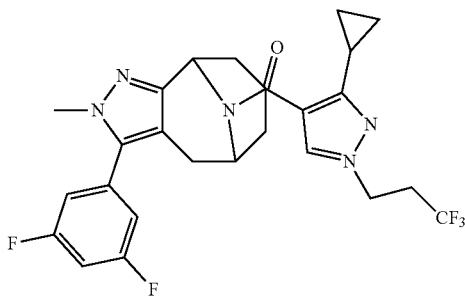

The title compound was prepared in a manner analogous to Example 1, using racemic-(5R,9S)-3-(3,5-difluorophenyl)-2-methyl-4,5,6,7,8,9-hexahydro-2H-5,9-epiminocycloocta[c]pyrazole (Intermediate 7) instead of racemic-(5R,9S)-2-methyl-3-phenyl-4,5,6,7,8,9-hexahydro-2H-5,9-epiminocycloocta[c]pyrazole (Intermediate 1) and 3-cyclopropyl-1-(3,3,3-trifluoropropyl)-1H-pyrazole-4-carboxylic acid instead of quinoline-6-carboxylic acid. MS (ESI): mass calcd. for $C_{25}H_{24}F_5N_5O$, 505.2; m/z found, 506.2 [M+H]$^+$. $^1$H NMR (500 MHz, DMSO-d$_6$) δ 7.62 (s, 1H), 7.37-7.25 (m, 3H), 5.75-5.66 (m, 1H), 5.14 (q, J=9.0 Hz, 2H), 4.11-4.02 (m, 1H), 3.82 (s, 3H), 3.08-2.98 (m, 1H), 2.49-2.42 (m, 1H), 1.95-1.33 (m, 7H), 1.03-0.85 (m, 2H), 0.76-0.63 (m, 2H).

Example 82: racemic-(5-Cyclopropyl-1-phenyl-1H-pyrazol-4-yl)((5R,9S)-3-(3,5-difluorophenyl)-2-methyl-4,5,6,7,8,9-hexahydro-2H-5,9-epiminocycloocta[c]pyrazol-10-yl)methanone

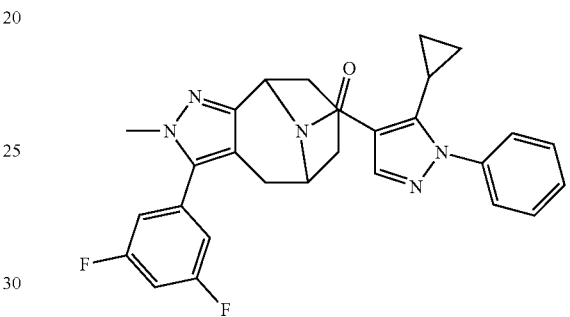

The title compound was prepared in a manner analogous to Example 1, using racemic-(5R,9S)-3-(3,5-difluorophenyl)-2-methyl-4,5,6,7,8,9-hexahydro-2H-5,9-epiminocycloocta[c]pyrazole (Intermediate 7) instead of racemic-(5R,9S)-2-methyl-3-phenyl-4,5,6,7,8,9-hexahydro-2H-5,9-epiminocycloocta[c]pyrazole (Intermediate 1) and 5-cyclopropyl-1-phenyl-1H-pyrazole-4-carboxylic acid instead of quinoline-6-carboxylic acid. MS (ESI): mass calcd. for $C_{29}H_{27}F_2N_5O$, 499.2; m/z found, 500.2 [M+H]$^+$. $^1$H NMR (300 MHz, DMSO-d$_6$) δ 7.74 (s, 1H), 7.71-7.60 (m, 2H), 7.59-7.50 (m, 2H), 7.49-7.41 (m, 1H), 7.41-7.24 (m, 3H), 5.82-5.65 (m, 1H), 4.40-4.18 (m, 1H), 3.83 (s, 3H), 3.22-2.99 (m, 1H), 2.51-2.35 (m, 1H), 2.11-1.27 (m, 7H), 0.92-0.67 (m, 2H), 0.65-0.42 (m, 2H).

Example 83: racemic-(5-Cyclopropyl-1-(3-(trifluoromethyl)phenyl)-1H-pyrazol-4-yl)((5R,9S)-3-(3,5-difluorophenyl)-2-methyl-4,5,6,7,8,9-hexahydro-2H-5,9-epiminocycloocta[c]pyrazol-10-yl)methanone

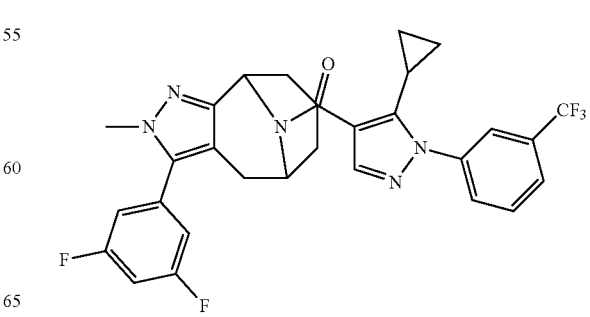

The title compound was prepared in a manner analogous to Example 1, using racemic-(5R,9S)-3-(3,5-difluorophenyl)-2-methyl-4,5,6,7,8,9-hexahydro-2H-5,9-epiminocycloocta[c]pyrazole (Intermediate 7) instead of racemic-(5R,9S)-2-methyl-3-phenyl-4,5,6,7,8,9-hexahydro-2H-5,9-epiminocycloocta[c]pyrazole (Intermediate 1) and 5-cyclopropyl-1-(3-(trifluoromethyl)phenyl)-1H-pyrazole-4-carboxylic acid instead of quinoline-6-carboxylic acid. MS (ESI): mass calcd. for $C_{30}H_{26}F_5N_5O$, 567.2; m/z found, 568.2 [M+H]$^+$. $^1$H NMR (500 MHz, DMSO-d$_6$) δ 8.09-7.99 (m, 2H), 7.86-7.75 (m, 3H), 7.41-7.24 (m, 3H), 5.78-5.71 (m, 1H), 4.38-4.29 (m, 1H), 3.83 (s, 3H), 3.15-3.03 (m, 1H), 2.51-2.43 (m, 1H), 2.15-2.03 (m, 1H), 1.88-1.57 (m, 4H), 1.55-1.37 (m, 2H), 0.90-0.74 (m, 2H), 0.62-0.45 (m, 2H).

Example 84: racemic-((5R,9S)-3-(3,5-Difluorophenyl)-2-methyl-4,5,6,7,8,9-hexahydro-2H-5,9-epiminocycloocta[c]pyrazol-10-yl)(5-methyl-1-phenyl-1H-1,2,4-triazol-3-yl)methanone

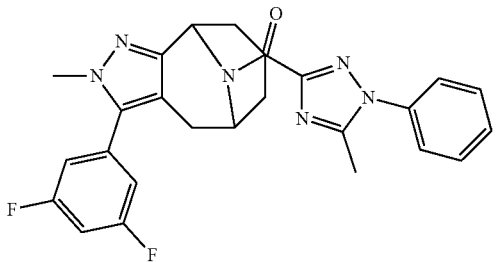

The title compound was prepared in a manner analogous to Example 1, using racemic-(5R,9S)-3-(3,5-difluorophenyl)-2-methyl-4,5,6,7,8,9-hexahydro-2H-5,9-epiminocycloocta[c]pyrazole (Intermediate 7) instead of racemic-(5R,9S)-2-methyl-3-phenyl-4,5,6,7,8,9-hexahydro-2H-5,9-epiminocycloocta[c]pyrazole (Intermediate 1) and 5-methyl-1-phenyl-1H-1,2,4-triazole-3-carboxylic acid instead of quinoline-6-carboxylic acid. MS (ESI): mass calcd. for $C_{26}H_{24}F_2N_6O$, 474.2; m/z found, 475.2 [M+H]$^+$. $^1$H NMR (500 MHz, DMSO-d$_6$) δ 7.69-7.49 (m, 5H), 7.37-7.27 (m, 3H), 5.77-5.73 (m, 1H), 4.71-4.64 (m, 1H), 3.81 (s, 3H), 3.10-2.98 (m, 1H), 2.62-2.54 (m, 1H), 2.52 (s, 3H), 1.89-1.67 (m, 4H), 1.57-1.40 (m, 2H).

Example 85: racemic-((5R,9S)-3-(3,5-Difluorophenyl)-2-methyl-4,5,6,7,8,9-hexahydro-2H-5,9-epiminocycloocta[c]pyrazol-10-yl)(1-(4-fluorophenyl)-5-methyl-1H-1,2,4-triazol-3-yl)methanone

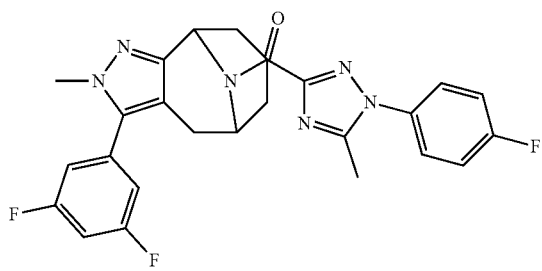

The title compound was prepared in a manner analogous to Example 1, using racemic-(5R,9S)-3-(3,5-difluorophenyl)-2-methyl-4,5,6,7,8,9-hexahydro-2H-5,9-epiminocycloocta[c]pyrazole (Intermediate 7) instead of racemic-(5R,9S)-2-methyl-3-phenyl-4,5,6,7,8,9-hexahydro-2H-5,9-epiminocycloocta[c]pyrazole (Intermediate 1) and 1-(4-fluorophenyl)-5-methyl-1H-1,2,4-triazole-3-carboxylic acid instead of quinoline-6-carboxylic acid. MS (ESI): mass calcd. for $C_{26}H_{23}F_3N_6O$, 492.2; m/z found, 493.2 [M+H]$^+$. $^1$H NMR (500 MHz, DMSO-d$_6$) δ 7.75-7.65 (m, 2H), 7.49-7.39 (m, 2H), 7.37-7.26 (m, 3H), 5.77-5.72 (m, 1H), 4.69-4.63 (m, 1H), 3.81 (s, 3H), 3.12-2.97 (m, 1H), 2.62-2.53 (m, 1H), 2.47 (s, 3H), 1.88-1.66 (m, 4H), 1.56-1.38 (m, 2H).

Example 86: racemic-((5R,9S)-3-(3,5-Difluorophenyl)-2-methyl-4,5,6,7,8,9-hexahydro-2H-5,9-epiminocycloocta[c]pyrazol-10-yl)(5-ethyl-1-phenyl-1H-1,2,4-triazol-3-yl)methanone

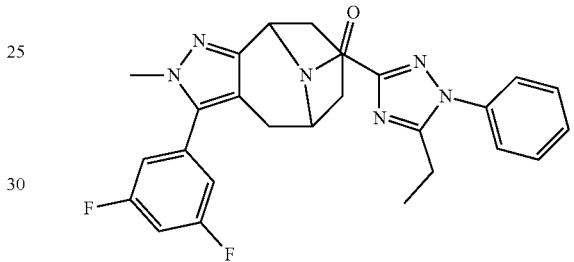

The title compound was prepared in a manner analogous to Example 1, using racemic-(5R,9S)-3-(3,5-difluorophenyl)-2-methyl-4,5,6,7,8,9-hexahydro-2H-5,9-epiminocycloocta[c]pyrazole (Intermediate 7) instead of racemic-(5R,9S)-2-methyl-3-phenyl-4,5,6,7,8,9-hexahydro-2H-5,9-epiminocycloocta[c]pyrazole (Intermediate 1) and 5-ethyl-1-phenyl-1H-1,2,4-triazole-3-carboxylic acid instead of quinoline-6-carboxylic acid. MS (ESI): mass calcd. for $C_{27}H_{26}F_2N_6O$, 488.2; m/z found, 489.2 [M+H]$^+$. $^1$H NMR (500 MHz, DMSO-d$_6$) δ 7.66-7.50 (m, 5H), 7.38-7.27 (m, 3H), 5.79-5.71 (m, 1H), 4.70-4.61 (m, 1H), 3.81 (s, 3H), 3.11-2.98 (m, 1H), 2.88-2.77 (m, 2H), 2.62-2.55 (m, 1H), 2.02-1.39 (m, 6H), 1.22 (t, J=7.6 Hz, 3H).

Example 87: ((5R,9S)-3-(3,5-Difluorophenyl)-2-methyl-4,5,6,7,8,9-hexahydro-2H-5,9-epiminocycloocta[c]pyrazol-10-yl)(2-fluoropyridin-4-yl)methanone

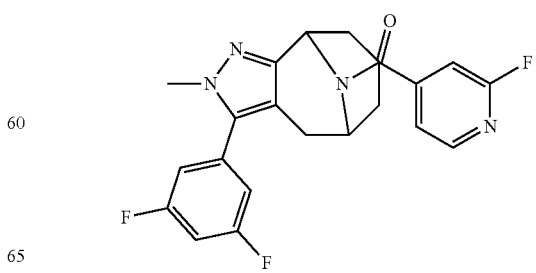

The title compound was prepared in a manner analogous to Example 1, using racemic-(5R,9S)-3-(3,5-difluorophenyl)-2-methyl-4,5,6,7,8,9-hexahydro-2H-5,9-epiminocycloocta[c]pyrazole (Intermediate 7) instead of racemic-(5R,9S)-2-methyl-3-phenyl-4,5,6,7,8,9-hexahydro-2H-5,9-epiminocycloocta[c]pyrazole (Intermediate 1) and 2-fluoroisonicotinic acid instead of quinoline-6-carboxylic acid. MS (ESI): mass calcd. for $C_{22}H_{19}F_3N_4O$, 412.2; m/z found, 413.2 [M+H]+. 1H NMR (CDCl3) δ 8.30 (d, J=5.0 Hz, 1H), 7.19 (m, 1H), 6.94 (m, 1H), 6.91-6.84 (m, 3H), 5.97 and 4.85 (m, 1H), 5.21 and 4.03 (m, 1H), 3.85 and 3.81 (s, 3H), 3.23-3.18 and 2.95-2.90 (m, 1H), 2.46 (dd, J=23.1, 16.3 Hz, 1H), 2.01-1.93 (m, 1H), 1.91-1.82 (m, 1H), 1.80-1.73 (m, 1H), 1.63-1.50 (3H).

Example 88: ((5R,9S)-3-(3,5-Difluorophenyl)-2-methyl-4,5,6,7,8,9-hexahydro-2H-5,9-epiminocycloocta[c]pyrazol-10-yl)(5-methoxypyridin-3-yl)methanone

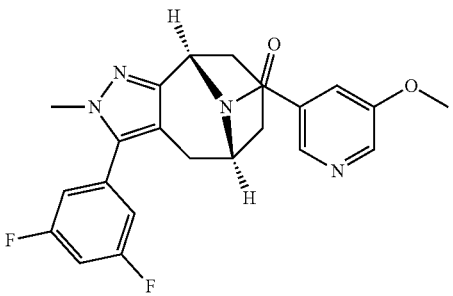

The title compound was prepared in a manner analogous to Example 1, using (5R,9S)-3-(3,5-difluorophenyl)-2-methyl-4,5,6,7,8,9-hexahydro-2H-5,9-epiminocycloocta[c]pyrazole (Intermediate 12) instead of racemic-(5R,9S)-2-methyl-3-phenyl-4,5,6,7,8,9-hexahydro-2H-5,9-epiminocycloocta[c]pyrazole (Intermediate 1) and 5-methoxynicotinic acid instead of quinoline-6-carboxylic acid. MS (ESI): mass calcd. for $C_{23}H_{22}F_2N_4O_2$, 424.2; m/z found, 425.2 [M+H]+. 1H NMR (300 MHz, DMSO-d6) δ 8.38 (d, J=2.9 Hz, 1H), 8.22 (d, J=1.6 Hz, 1H), 7.46-7.40 (m, 1H), 7.39-7.25 (m, 3H), 5.78-5.64 (m, 1H), 4.08-3.95 (m, 1H), 3.87 (s, 3H), 3.83 (s, 3H), 3.17-3.00 (m, 1H), 2.40 (d, J=16.4 Hz, 1H), 2.08-1.30 (m, 6H).

Example 89: (5-Aminopyridin-2-yl)((5R,9S)-3-(3,5-difluorophenyl)-2-methyl-4,5,6,7,8,9-hexahydro-2H-5,9-epiminocycloocta[c]pyrazol-10-yl)methanone

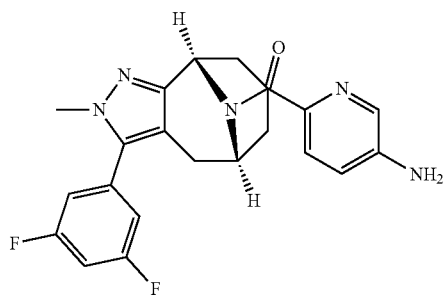

The title compound was prepared in a manner analogous to Example 1, using (5R,9S)-3-(3,5-difluorophenyl)-2-methyl-4,5,6,7,8,9-hexahydro-2H-5,9-epiminocycloocta[c]pyrazole (Intermediate 12) instead of racemic-(5R,9S)-2-methyl-3-phenyl-4,5,6,7,8,9-hexahydro-2H-5,9-epiminocycloocta[c]pyrazole (Intermediate 1) and 4-aminopicolinic acid instead of quinoline-6-carboxylic acid. MS (ESI): mass calcd. for $C_{22}H_{21}F_2N_5O$, 409.2; m/z found, 410.2 [M+H]+. 1H NMR (500 MHz, DMSO-d6) δ 7.86-7.78 (m, 1H), 7.39-7.21 (m, 4H), 6.94-6.88 (m, 1H), 5.72 (s, 2H), 5.67-5.60 (m, 1H), 4.76-4.67 (m, 1H), 3.78 (s, 3H), 3.10-2.89 (m, 1H), 2.67-2.31 (m, 1H), 2.14-1.31 (m, 6H).

Example 90: ((5R,9S)-3-(3,5-Difluorophenyl)-2-methyl-4,5,6,7,8,9-hexahydro-2H-5,9-epiminocycloocta[c]pyrazol-10-yl)(5-methoxybenzofuran-2-yl)methanone

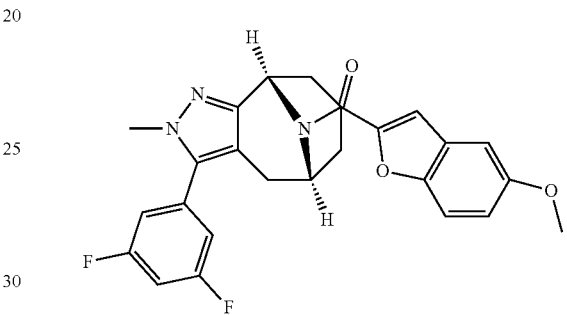

The title compound was prepared in a manner analogous to Example 1, using (5R,9S)-3-(3,5-difluorophenyl)-2-methyl-4,5,6,7,8,9-hexahydro-2H-5,9-epiminocycloocta[c]pyrazole (Intermediate 12) instead of racemic-(5R,9S)-2-methyl-3-phenyl-4,5,6,7,8,9-hexahydro-2H-5,9-epiminocycloocta[c]pyrazole (Intermediate 1) and 5-methoxybenzofuran-2-carboxylic acid instead of quinoline-6-carboxylic acid. MS (ESI): mass calcd. for $C_{26}H_{23}F_2N_3O_3$, 463.2; m/z found, 464.2 [M+H]+. 1H NMR (300 MHz, DMSO-d6) δ 7.59-7.53 (m, 1H), 7.43-7.28 (m, 4H), 7.24-7.17 (m, 1H), 7.09-7.02 (m, 1H), 5.76-5.60 (m, 1H), 4.88-4.69 (m, 1H), 3.89-3.68 (m, 6H), 3.32-3.02 (m, 1H), 2.60 (d, J=16.3 Hz, 1H), 1.95-1.61 (m, 4H), 1.61-1.35 (m, 2H).

Example 91: ((5R,9S)-3-(3,5-Difluorophenyl)-2-methyl-4,5,6,7,8,9-hexahydro-2H-5,9-epiminocycloocta[c]pyrazol-10-yl) (2-methylbenzo[d]oxazol-6-yl) methanone

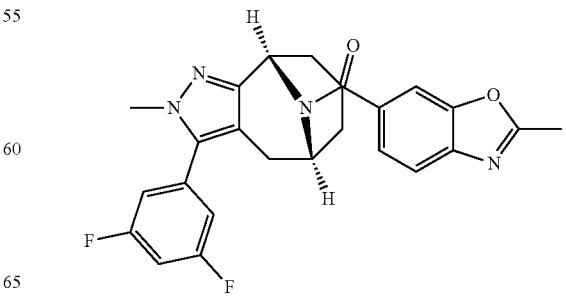

The title compound was prepared in a manner analogous to Example 1, using (5R,9S)-3-(3,5-difluorophenyl)-2-methyl-4,5,6,7,8,9-hexahydro-2H-5,9-epiminocycloocta[c]pyrazole (Intermediate 12) instead of racemic-(5R,9S)-2-methyl-3-phenyl-4,5,6,7,8,9-hexahydro-2H-5,9-epiminocycloocta[c]pyrazole (Intermediate 1) and 2-methylbenzo[d]oxazole-6-carboxylic acid instead of quinoline-6-carboxylic acid. MS (ESI): mass calcd. for $C_{25}H_{22}F_2N_4O_2$, 448.1; m/z found, 449.1 [M+H]$^+$. $^1$H NMR (500 MHz, DMSO-$d_6$) δ 7.81-7.69 (m, 2H), 7.45-7.29 (m, 4H), 5.72 (d, J=3.1 Hz, 1H), 4.16-4.01 (m, 1H), 3.87-3.73 (m, 3H), 3.17-3.02 (m, 1H), 2.66-2.57 (m, 3H), 2.48-2.37 (m, 1H), 1.99-1.38 (m, 6H).

Example 92: (2-Aminobenzo[d]oxazol-6-yl) ((5R,9S)-3-(3,5-difluorophenyl)-2-methyl-4,5,6,7,8,9-hexahydro-2H-5,9-epiminocycloocta[c]pyrazol-10-yl) methanone

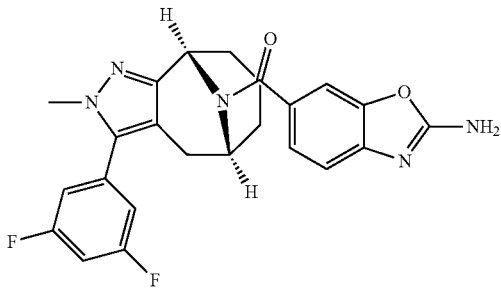

The title compound was prepared in a manner analogous to Example 1, using (5R,9S)-3-(3-fluorophenyl)-2-methyl-4,5,6,7,8,9-hexahydro-2H-5,9-epiminocycloocta[c]pyrazole (Intermediate 12) instead of racemic-(5R,9S)-2-methyl-3-phenyl-4,5,6,7,8,9-hexahydro-2H-5,9-epiminocycloocta[c]pyrazole (Intermediate 1) and 2-aminobenzo[d]oxazole-6-carboxylic acid instead of quinoline-6-carboxylic acid. MS (ESI): mass calcd. for $C_{24}H_{21}F_2N_5O_2$, 449.1; m/z found, 450.1 [M+H]$^+$. $^1$H NMR (500 MHz, DMSO-$d_6$) δ 9.28-9.08 (m, 1H), 8.75 (dd, J=16.4, 5.9 Hz, 1H), 8.40-8.24 (m, 1H), 8.08-7.90 (m, 1H), 7.81-7.63 (m, 1H), 7.41-7.24 (m, 3H), 5.97-5.09 (m, 1H), 3.95-3.66 (m, 4H), 2.99-2.63 (m, 1H), 2.45 (d, J=16.2 Hz, 1H), 2.08-1.40 (m, 6H).

Example 93: ((5R,9S)-3-(3,5-Difluorophenyl)-2-methyl-4,5,6,7,8,9-hexahydro-2H-5,9-epiminocycloocta[c]pyrazol-10-yl) (furo[3,2-b]pyridin-2-yl) methanone

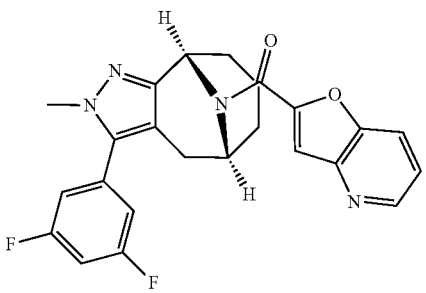

The title compound was prepared in a manner analogous to Example 1, using (5R,9S)-3-(3,5-difluorophenyl)-2-methyl-4,5,6,7,8,9-hexahydro-2H-5,9-epiminocycloocta[c]pyrazole (Intermediate 12) instead of racemic-(5R,9S)-2-methyl-3-phenyl-4,5,6,7,8,9-hexahydro-2H-5,9-epiminocycloocta[c]pyrazole (Intermediate 1) and furo[3,2-b]pyridine-2-carboxylic acid instead of quinoline-6-carboxylic acid. MS (ESI): mass calcd. for $C_{24}H_{20}F_2N_4O_2$, 434.1; m/z found, 435.1 [M+H]$^+$. $^1$H NMR (500 MHz, DMSO-$d_6$) δ 8.67-8.53 (m, 1H), 8.16 (t, J=8.7 Hz, 1H), 7.64-7.27 (m, 5H), 5.76-5.37 (m, 1H), 5.03-4.62 (m, 1H), 3.89-3.74 (m, 3H), 3.19-3.03 (m, 1H), 2.65-2.54 (m, 1H), 2.12-1.45 (m, 6H).

Example 94: ((5R,9S)-3-(3,5-Difluorophenyl)-2-methyl-4,5,6,7,8,9-hexahydro-2H-5,9-epiminocycloocta[c]pyrazol-10-yl)(furo[3,2-c]pyridin-4-yl) methanone

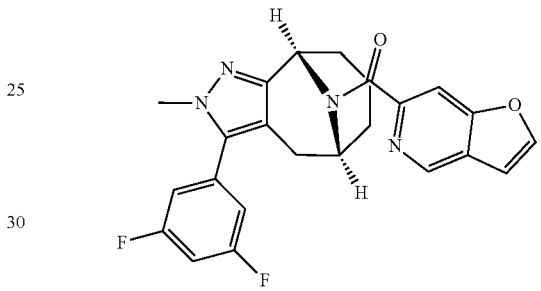

The title compound was prepared in a manner analogous to Example 1, using (5R,9S)-3-(3,5-difluorophenyl)-2-methyl-4,5,6,7,8,9-hexahydro-2H-5,9-epiminocycloocta[c]pyrazole (Intermediate 12) instead of racemic-(5R,9S)-2-methyl-3-phenyl-4,5,6,7,8,9-hexahydro-2H-5,9-epiminocycloocta[c]pyrazole (Intermediate 1) and furo[3,2-c]pyridine-6-carboxylic acid instead of quinoline-6-carboxylic acid. MS (ESI): mass calcd. for $C_{24}H_{20}F_2N_4O_2$, 434.2; m/z found, 435.2 [M+H]$^+$. $^1$H NMR (300 MHz, DMSO-$d_6$) δ 8.47 (d, J=5.7 Hz, 1H), 8.24-8.12 (m, 1H), 7.82-7.76 (m, 1H), 7.41-7.23 (m, 3H), 7.10-7.03 (m, 1H), 5.89-5.76 (m, 1H), 4.36-4.21 (m, 1H), 3.83 (s, 3H), 2.99 (dd, J=16.1, 7.4 Hz, 1H), 2.59-2.36 (m, 1H), 2.03-1.35 (m, 6H).

Example 95: ((5R,9S)-3-(3,5-Difluorophenyl)-2-methyl-4,5,6,7,8,9-hexahydro-2H-5,9-epiminocycloocta[c]pyrazol-10-yl) (1-methyl-1H-pyrazolo[3,4-b] pyridin-3-yl) methanone

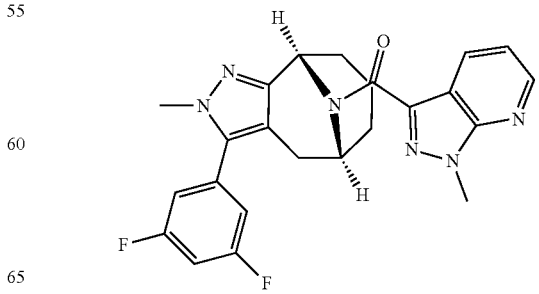

The title compound was prepared in a manner analogous to Example 1, using (5R,9S)-3-(3,5-difluorophenyl)-2-methyl-4,5,6,7,8,9-hexahydro-2H-5,9-epiminocycloocta[c]pyrazole (Intermediate 12) instead of racemic-(5R,9S)-2-methyl-3-phenyl-4,5,6,7,8,9-hexahydro-2H-5,9-epiminocycloocta[c]pyrazole (Intermediate 1) and 1-methyl-1H-pyrazolo[3,4-b]pyridine-3-carboxylic acid instead of quinoline-6-carboxylic acid. MS (ESI): mass calcd. for $C_{24}H_{22}F_2N_6O$, 448.1; m/z found, 449.1 [M+H]$^+$. $^1$H NMR (500 MHz, DMSO-d$_6$) δ 8.68-8.59 (m, 1H), 8.48-8.35 (m, 1H), 7.40-7.27 (m, 4H), 6.09 (d, J=247.3 Hz, 1H), 5.55-5.09 (m, 1H), 4.21-4.08 (m, 3H), 3.89-3.74 (m, 3H), 3.21-3.05 (m, 1H), 2.61 (dd, J=16.2, 7.8 Hz, 1H), 2.06-1.48 (m, 6H).

Example 96: racemic-((5R,9S)-3-(3,5-Difluorophenyl)-2-methyl-4,5,6,7,8,9-hexahydro-2H-5,9-epiminocycloocta[c]pyrazol-10-yl) (quinolin-6-yl) methanone

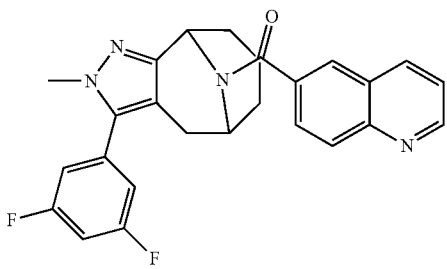 [SMILES: Cn1nc2c(c1-c1cc(F)cc(F)c1)CC1CCCC2N1C(=O)c1ccc2ncccc2c1]

The title compound was prepared in a manner analogous to Example 1, using racemic-(5R,9S)-3-(3,5-difluorophenyl)-2-methyl-4,5,6,7,8,9-hexahydro-2H-5,9-epiminocycloocta[c]pyrazole (Intermediate 7) instead of racemic-(5R,9S)-2-methyl-3-phenyl-4,5,6,7,8,9-hexahydro-2H-5,9-epiminocycloocta[c]pyrazole (Intermediate 1). MS (ESI): mass calcd. for $C_{26}H_{22}F_2N_4O$, 444.2; m/z found, 445.1 [M+H]$^+$. $^1$H NMR (400 MHz, DMSO-d$_6$) δ 9.08-8.78 (m, 1H), 8.48 (d, J=8.4 Hz, 1H), 8.18-8.00 (m, 2H), 7.88-7.55 (m, 2H), 7.45-7.25 (m, 3H), 5.76 (s, 1H), 3.87-3.66 (m, 3H), 3.29-2.87 (m, 2H), 2.46 (d, J=16.1 Hz, 1H), 2.12-1.34 (m, 6H).

Example 97: ((5R,9S)-3-(3,5-Difluorophenyl)-2-methyl-4,5,6,7,8,9-hexahydro-2H-5,9-epiminocycloocta[c]pyrazol-10-yl)(quinolin-6-yl)methanone

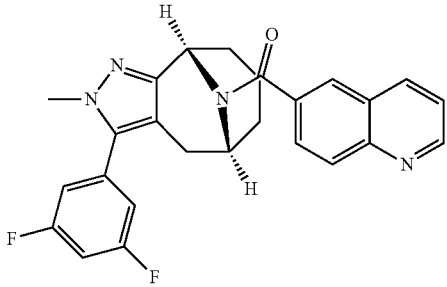

The title compound was prepared in a manner analogous to Example 1, using (5R,9S)-3-(3,5-difluorophenyl)-2-methyl-4,5,6,7,8,9-hexahydro-2H-5,9-epiminocycloocta[c]pyrazole (Intermediate 12) instead of racemic-(5R,9S)-2-methyl-3-phenyl-4,5,6,7,8,9-hexahydro-2H-5,9-epiminocycloocta[c]pyrazole (Intermediate 1). MS (ESI): mass calcd. for $C_{26}H_{22}F_2N_4O$, 444.2; m/z found, 445.1 [M+H]$^+$. $^1$H NMR (400 MHz, DMSO-d$_6$) δ 9.04-8.92 (m, 1H), 8.55-8.42 (m, 1H), 8.17-8.04 (m, 2H), 7.87-7.55 (m, 2H), 7.45-7.24 (m, 3H), 5.83-5.70 (m, 1H), 4.18-4.05 (m, 1H), 3.89-3.69 (m, 3H), 3.21-3.06 (m, 1H), 2.47 (d, J=16.3 Hz, 1H), 2.09-1.41 (m, 6H).

Example 98: ((5S,9R)-3-(3,5-Difluorophenyl)-2-methyl-4,5,6,7,8,9-hexahydro-2H-5,9-epiminocycloocta[c]pyrazol-10-yl) (quinolin-6-yl) methanone

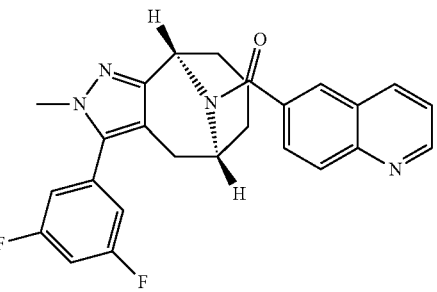

The title compound was prepared in a manner analogous to Example 1, using (5S,9R)-3-(3,5-difluorophenyl)-2-methyl-4,5,6,7,8,9-hexahydro-2H-5,9-epiminocycloocta[c]pyrazole (Intermediate 29) instead of racemic-(5R,9S)-2-methyl-3-phenyl-4,5,6,7,8,9-hexahydro-2H-5,9-epiminocycloocta[c]pyrazole (Intermediate 1). MS (ESI): mass calcd. for $C_{26}H_{22}F_2N_4O$, 444.2; m/z found, 445.1 [M+H]$^+$. $^1$H NMR (400 MHz, DMSO-d$_6$) δ 9.04-8.92 (m, 1H), 8.55-8.42 (m, 1H), 8.17-8.04 (m, 2H), 7.87-7.55 (m, 2H), 7.45-7.24 (m, 3H), 5.83-5.70 (m, 1H), 4.18-4.05 (m, 1H), 3.89-3.69 (m, 3H), 3.21-3.06 (m, 1H), 2.47 (d, J=16.3 Hz, 1H), 2.09-1.41 (m, 6H).

Example 99: ((5R,9S)-3-(3,5-Difluorophenyl)-2-methyl-4,5,6,7,8,9-hexahydro-2H-5,9-epiminocycloocta[c]pyrazol-10-yl) (isoquinolin-3-yl) methanone

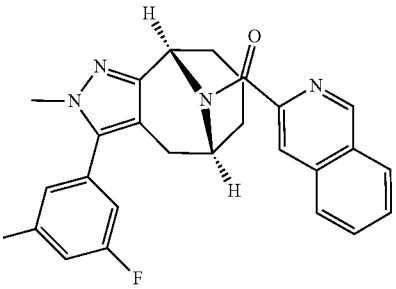

The title compound was prepared in a manner analogous to Example 1, using (5R,9S)-3-(3,5-difluorophenyl)-2-methyl-4,5,6,7,8,9-hexahydro-2H-5,9-epiminocycloocta[c]pyrazole (Intermediate 12) instead of racemic-(5R,9S)-2-methyl-3-phenyl-4,5,6,7,8,9-hexahydro-2H-5,9-epiminocycloocta[c]pyrazole (Intermediate 1) and isoquinoline-3-carboxylic acid instead of quinoline-6-carboxylic acid. MS (ESI): mass calcd. for $C_{26}H_{22}F_2N_4O$, 444.2; m/z found, 445.1 [M+H]⁺. ¹H NMR (500 MHz, DMSO-$d_6$) δ 9.44-9.28 (m, 1H), 8.27-8.05 (m, 3H), 7.92-7.71 (m, 2H), 7.40-7.27 (m, 3H), 5.80 (s, 1H), 4.36-4.04 (m, 1H), 3.88-3.72 (m, 3H), 3.15-2.97 (m, 1H), 2.49-2.31 (m, 1H), 2.08-1.43 (m, 6H).

Example 100: ((5R,9S)-3-(3,5-Difluorophenyl)-2-methyl-4,5,6,7,8,9-hexahydro-2H-5,9-epiminocycloocta[c]pyrazol-10-yl)(quinolin-7-yl)methanone

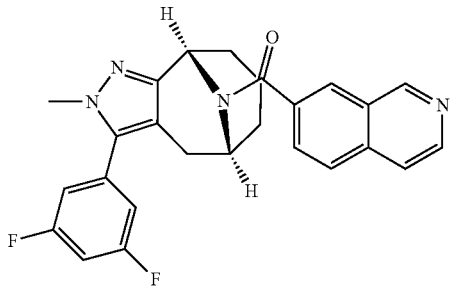

The title compound was prepared in a manner analogous to Example 1, using (5R,9S)-3-(3,5-difluorophenyl)-2-methyl-4,5,6,7,8,9-hexahydro-2H-5,9-epiminocycloocta[c]pyrazole (Intermediate 12) instead of racemic-(5R,9S)-2-methyl-3-phenyl-4,5,6,7,8,9-hexahydro-2H-5,9-epiminocycloocta[c]pyrazole (Intermediate 1) and isoquinoline-7-carboxylic acid instead of quinoline-6-carboxylic acid. MS (ESI): mass calcd. for $C_{26}H_{22}F_2N_4O$, 444.2; m/z found, 445.2 [M+H]⁺. ¹H NMR (500 MHz, DMSO-$d_6$) δ 9.02-8.93 (m, 1H), 8.49-8.41 (m, 1H), 8.08 (d, J=8.4 Hz, 1H), 8.04-8.00 (m, 1H), 7.67-7.54 (m, 2H), 7.40-7.26 (m, 3H), 5.82-5.73 (m, 1H), 4.15-4.03 (m, 1H), 3.84 (s, 3H), 3.06 (dd, J=16.2, 7.3 Hz, 1H), 2.44 (d, J=16.2 Hz, 1H), 2.07-1.36 (m, 6H).

Example 101: (4-Bromoquinolin-6-yl)((5R,9S)-3-(3,5-difluorophenyl)-2-methyl-4,5,6,7,8,9-hexahydro-2H-5,9-epiminocycloocta[c]pyrazol-10-yl)methanone

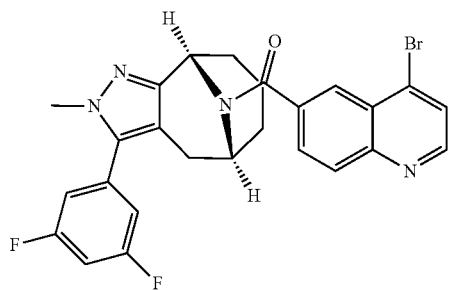

The title compound was prepared in a manner analogous to Example 1, using (5R,9S)-3-(3,5-difluorophenyl)-2-methyl-4,5,6,7,8,9-hexahydro-2H-5,9-epiminocycloocta[c]pyrazole (Intermediate 12) instead of racemic-(5R,9S)-2-methyl-3-phenyl-4,5,6,7,8,9-hexahydro-2H-5,9-epiminocycloocta[c]pyrazole (Intermediate 1) and 4-bromoquinoline-6-carboxylic acid instead of quinoline-6-carboxylic acid. MS (ESI): mass calcd. for $C_{26}H_{21}BrF_2N_4O$, 522.1; m/z found, 523.1 [M+H]⁺. ¹H NMR (500 MHz, DMSO-$d_6$) δ 8.81 (dd, J=9.0, 4.6 Hz, 1H), 8.21-7.98 (m, 3H), 7.95-7.80 (m, 1H), 7.43-7.23 (m, 3H), 5.77 (s, 1H), 4.10 (s, 1H), 3.92-3.71 (m, 3H), 3.22-2.98 (m, 1H), 2.46 (s, 1H), 2.03-1.43 (m, 6H).

Example 102: (3-Bromoquinolin-6-yl) (5R,9S)-3-(3,5-difluorophenyl)-2-methyl-4,5,6,7,8,9-hexahydro-2H-5,9-epiminocycloocta[c]pyrazol-10-yl)methanone

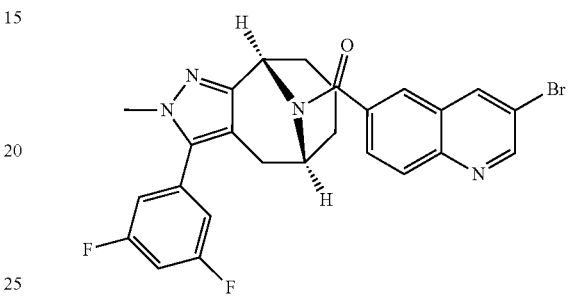

The title compound was prepared in a manner analogous to Example 1, using (5R,9S)-3-(3,5-difluorophenyl)-2-methyl-4,5,6,7,8,9-hexahydro-2H-5,9-epiminocycloocta[c]pyrazole (Intermediate 12) instead of racemic-(5R,9S)-2-methyl-3-phenyl-4,5,6,7,8,9-hexahydro-2H-5,9-epiminocycloocta[c]pyrazole (Intermediate 1) and 3-bromoquinoline-6-carboxylic acid instead of quinoline-6-carboxylic acid. MS (ESI): mass calcd. for $C_{26}H_{21}BrF_2N_4O$, 522.1; m/z found, 523.1 [M+H]⁺. ¹H NMR (500 MHz, DMSO-$d_6$) δ 9.01 (d, J=2.4 Hz, 1H), 8.84-8.82 (m, 1H), 8.10 (d, J=8.7 Hz, 1H), 8.07-8.04 (m, 1H), 7.84 (dd, J=8.6, 1.9 Hz, 1H), 7.40-7.28 (m, 3H), 5.81-5.69 (m, 1H), 4.13-4.05 (m, 1H), 3.84 (s, 3H), 3.09 (dd, J=16.3, 7.4 Hz, 1H), 2.50-2.43 (m, 1H), 2.12-1.33 (m, 6H).

Example 103: (8-Bromoquinolin-6-yl)(5R,9S)-3-(3,5-difluorophenyl)-2-methyl-4,5,6,7,8,9-hexahydro-2H-5,9-epiminocycloocta[c]pyrazol-10-yl)methanone

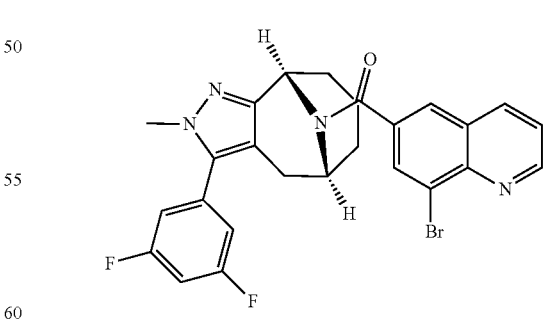

The title compound was prepared in a manner analogous to Example 1, using (5R,9S)-3-(3,5-difluorophenyl)-2-methyl-4,5,6,7,8,9-hexahydro-2H-5,9-epiminocycloocta[c]pyrazole (Intermediate 12) instead of racemic-(5R,9S)-2-methyl-3-phenyl-4,5,6,7,8,9-hexahydro-2H-5,9-epiminocycloocta[c]pyrazole (Intermediate 1) and 8-bromoquinoline-6-carboxylic acid (Intermediate 1) instead of quinoline-6-carboxylic acid. MS (ESI): mass calcd. for $C_{26}H_{21}BrF_2N_4O$, 522.1; m/z found, 523.1 [M+H]+. 1H NMR (300 MHz, DMSO-$d_6$) δ 9.16-8.99 (m, 1H), 8.60-8.48 (m, 1H), 8.21-8.03 (m, 2H), 7.81-7.62 (m, 1H), 7.44-7.23 (m, 3H), 5.83-5.68 (m, 1H), 4.25-4.07 (m, 1H), 3.85 (s, 3H), 3.22-2.97 (m, 1H), 2.66-2.37 (m, 1H), 2.13-1.30 (m, 6H).

Example 104: (2-Chloroquinolin-6-yl)((5R,9S)-3-(3,5-difluorophenyl)-2-methyl-4,5,6,7,8,9-hexahydro-2H-5,9-epiminocycloocta[c]pyrazol-10-yl)methanone

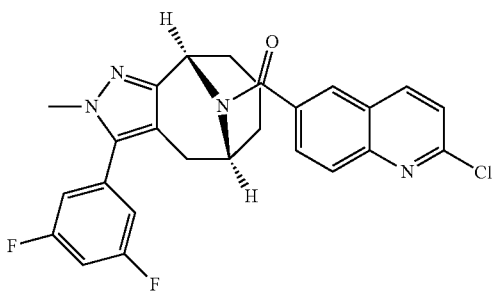

The title compound was prepared in a manner analogous to Example 1, using (5R,9S)-3-(3,5-difluorophenyl)-2-methyl-4,5,6,7,8,9-hexahydro-2H-5,9-epiminocycloocta[c]pyrazole (Intermediate 12) instead of racemic-(5R,9S)-2-methyl-3-phenyl-4,5,6,7,8,9-hexahydro-2H-5,9-epiminocycloocta[c]pyrazole (Intermediate 1) and 2-chloroquinoline-6-carboxylic acid instead of quinoline-6-carboxylic acid. MS (ESI): mass calcd. for $C_{26}H_{21}ClF_2N_4O$, 478.1; m/z found, 479.1 [M+H]+. 1H NMR (500 MHz, DMSO-$d_6$) δ 8.55 (d, J=8.7 Hz, 1H), 8.16 (d, J=1.9 Hz, 1H), 8.02 (d, J=8.7 Hz, 1H), 7.86 (dd, J=8.6, 1.9 Hz, 1H), 7.67 (d, J=8.6 Hz, 1H), 7.40-7.27 (m, 3H), 5.81-5.71 (m, 1H), 4.13-4.04 (m, 1H), 3.84 (s, 3H), 3.10 (dd, J=16.6, 7.4 Hz, 1H), 2.46 (d, J=16.0 Hz, 1H), 2.08-1.35 (m, 6H).

Example 105: ((5R,9S)-3-(3,5-Difluorophenyl)-2-methyl-4,5,6,7,8,9-hexahydro-2H-5,9-epiminocycloocta[c]pyrazol-10-yl)(8-fluoroquinolin-5-yl)methanone

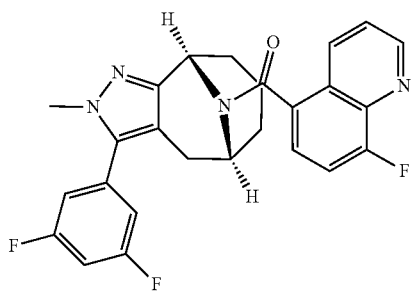

The title compound was prepared in a manner analogous to Example 1, using (5R,9S)-3-(3,5-difluorophenyl)-2-methyl-4,5,6,7,8,9-hexahydro-2H-5,9-epiminocycloocta[c]pyrazole (Intermediate 12) instead of racemic-(5R,9S)-2-methyl-3-phenyl-4,5,6,7,8,9-hexahydro-2H-5,9-epiminocycloocta[c]pyrazole (Intermediate 1) and 8-fluoroquinoline-5-carboxylic acid instead of quinoline-6-carboxylic acid. MS (ESI): mass calcd. for $C_{26}H_{21}F_3N_4O$, 462.2; m/z found, 463.2 [M+H]+. 1H NMR (500 MHz, DMSO-$d_6$) δ 9.12-8.98 (m, 1H), 8.46-8.36 (m, 1H), 7.83-7.47 (m, 3H), 7.42-7.26 (m, 3H), 5.96-5.84 (m, 1H), 3.84 (s, 3H), 3.80-3.63 (m, 1H), 3.10-2.95 (m, 1H), 2.66-2.35 (m, 1H), 2.13-1.66 (m, 2H), 1.64-1.30 (m, 4H).

Example 106: ((5R,9S)-3-(3,5-Difluorophenyl)-2-methyl-4,5,6,7,8,9-hexahydro-2H-5,9-epiminocycloocta[c]pyrazol-10-yl)(8-fluoroquinolin-6-yl)methanone

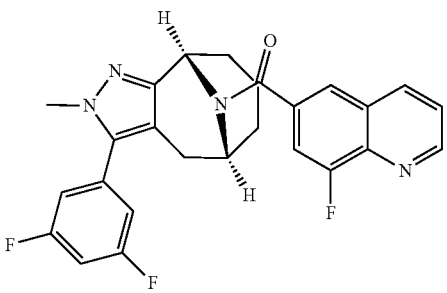

The title compound was prepared in a manner analogous to Example 1, using (5R,9S)-3-(3,5-difluorophenyl)-2-methyl-4,5,6,7,8,9-hexahydro-2H-5,9-epiminocycloocta[c]pyrazole (Intermediate 12) instead of racemic-(5R,9S)-2-methyl-3-phenyl-4,5,6,7,8,9-hexahydro-2H-5,9-epiminocycloocta[c]pyrazole (Intermediate 1) and 8-fluoroquinoline-6-carboxylic acid instead of quinoline-6-carboxylic acid. MS (ESI): mass calcd. for $C_{26}H_{21}F_3N_4O$, 462.2; m/z found, 463.1 [M+H]+. 1H NMR (500 MHz, DMSO-$d_6$) δ 9.02 (dd, J=4.2, 1.6 Hz, 1H), 8.57-8.52 (m, 1H), 7.95-7.92 (m, 1H), 7.70 (dd, J=8.3, 4.2 Hz, 1H), 7.67 (dd, J=10.9, 1.7 Hz, 1H), 7.39-7.30 (m, 3H), 5.79-5.70 (m, 1H), 4.18-4.09 (m, 1H), 3.84 (s, 3H), 3.10 (dd, J=16.1, 7.4 Hz, 1H), 2.45 (d, J=16.2 Hz, 1H), 1.98-1.67 (m, 3H), 1.64-1.37 (m, 3H).

Example 107: ((5R,9S)-3-(3,5-Difluorophenyl)-2-methyl-4,5,6,7,8,9-hexahydro-2H-5,9-epiminocycloocta[c]pyrazol-10-yl)(2-(trifluoromethyl)quinolin-6-yl)methanone

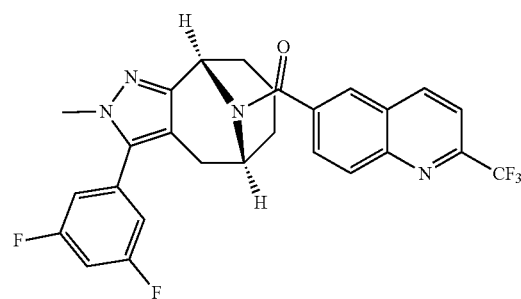 [SMILES: Cn1nc2c(c1-c1cc(F)cc(F)c1)C[C@H]1CCC[C@@H]2N1C(=O)c1ccc2nc(C(F)(F)F)ccc2c1]

The title compound was prepared in a manner analogous to Example 1, using (5R,9S)-3-(3,5-difluorophenyl)-2-methyl-4,5,6,7,8,9-hexahydro-2H-5,9-epiminocycloocta[c]

pyrazole (Intermediate 12) instead of racemic-(5R,9S)-2-methyl-3-phenyl-4,5,6,7,8,9-hexahydro-2H-5,9-epiminocycloocta[c]pyrazole (Intermediate 1) and 2-(trifluoromethyl)quinoline-6-carboxylic acid instead of quinoline-6-carboxylic acid. MS (ESI): mass calcd. for $C_{27}H_{21}F_5N_4O$, 512.2; m/z found, 513.1 $[M+H]^+$. $^1H$ NMR (500 MHz, DMSO-$d_6$) δ 8.87-8.79 (m, 1H), 8.29-8.24 (m, 1H), 8.24 (d, J=8.7 Hz, 1H), 8.06 (d, J=8.6 Hz, 1H), 7.95 (dd, J=8.7, 1.9 Hz, 1H), 7.41-7.29 (m, 3H), 5.84-5.72 (m, 1H), 4.14-4.03 (m, 1H), 3.85 (s, 3H), 3.10 (dd, J=16.4, 7.6 Hz, 1H), 2.50-2.42 (m, 1H), 2.09-1.34 (m, 6H).

Example 108: ((5R,9S)-3-(3,5-Difluorophenyl)-2-methyl-4,5,6,7,8,9-hexahydro-2H-5,9-epiminocycloocta[c]pyrazol-10-yl)(8-hydroxyquinolin-6-yl)methanone

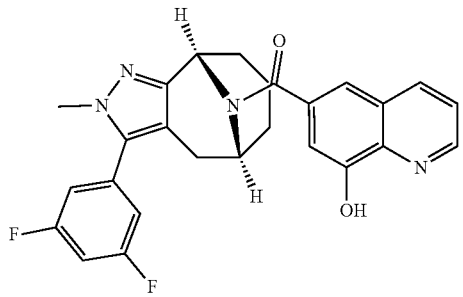 [SMILES: Cn1nc2c(c1-c1cc(F)cc(F)c1)C[C@H]1CCC[C@@H]2N1C(=O)c1cc(O)c2ncccc2c1]

The title compound was prepared in a manner analogous to Example 1, using (5R,9S)-3-(3,5-difluorophenyl)-2-methyl-4,5,6,7,8,9-hexahydro-2H-5,9-epiminocycloocta[c]pyrazole (Intermediate 12) instead of racemic-(5R,9S)-2-methyl-3-phenyl-4,5,6,7,8,9-hexahydro-2H-5,9-epiminocycloocta[c]pyrazole (Intermediate 1) and 8-hydroxyquinoline-6-carboxylic acid instead of quinoline-6-carboxylic acid. MS (ESI): mass calcd. for $C_{26}H_{22}F_2N_4O_2$, 460.2; m/z found, 461.2 $[M+H]^+$. $^1H$ NMR (300 MHz, DMSO-$d_6$) δ 10.37-10.05 (m, 1H), 9.01-8.81 (m, 1H), 8.47-8.34 (m, 1H), 7.69-7.55 (m, 1H), 7.50-7.41 (m, 1H), 7.39-7.27 (m, 3H), 7.12-7.01 (m, 1H), 5.84-5.65 (m, 1H), 4.24-4.00 (m, 1H), 3.84 (s, 3H), 3.23-2.94 (m, 1H), 2.56-2.39 (m, 1H), 2.09-1.26 (m, 6H).

Example 109: ((5R,9S)-3-(3,5-Difluorophenyl)-2-methyl-4,5,6,7,8,9-hexahydro-2H-5,9-epiminocycloocta[c]pyrazol-10-yl)(5-methoxyquinolin-3-yl)methanone

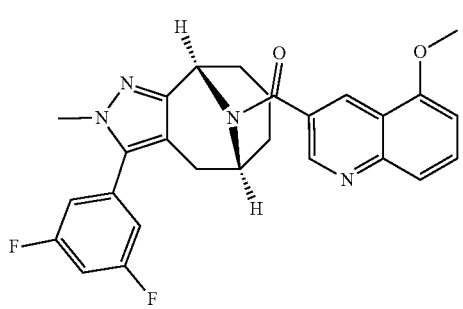 [SMILES: COc1cccc2ncc(C(=O)N3[C@@H]4CCC[C@H]3c3nn(C)c(-c5cc(F)cc(F)c5)c3C4)cc12]

The title compound was prepared in a manner analogous to Example 1, using (5R,9S)-3-(3,5-difluorophenyl)-2-methyl-4,5,6,7,8,9-hexahydro-2H-5,9-epiminocycloocta[c]pyrazole (Intermediate 12) instead of racemic-(5R,9S)-2-methyl-3-phenyl-4,5,6,7,8,9-hexahydro-2H-5,9-epiminocycloocta[c]pyrazole (Intermediate 1) and 5-methoxyquinoline-3-carboxylic acid instead of quinoline-6-carboxylic acid. MS (ESI): mass calcd. for $C_{27}H_{24}F_2N_4O_2$, 474.2; m/z found, 475.2 $[M+H]^+$. $^1H$ NMR (500 MHz, DMSO-$d_6$) δ 8.94 (d, J=2.2 Hz, 1H), 8.53 (d, J=2.2 Hz, 1H), 7.79-7.74 (m, 1H), 7.69-7.61 (m, 1H), 7.40-7.29 (m, 3H), 7.19-7.11 (m, 1H), 5.82-5.71 (m, 1H), 4.18-4.09 (m, 1H), 4.01 (s, 3H), 3.84 (s, 3H), 3.07 (dd, J=16.2, 7.4 Hz, 1H), 2.44 (d, J=16.4 Hz, 1H), 2.07-1.38 (m, 6H).

Example 110: ((5R,9S)-3-(3,5-Difluorophenyl)-2-methyl-4,5,6,7,8,9-hexahydro-2H-5,9-epiminocycloocta[c]pyrazol-10-yl)(8-nitroquinolin-6-yl)methanone

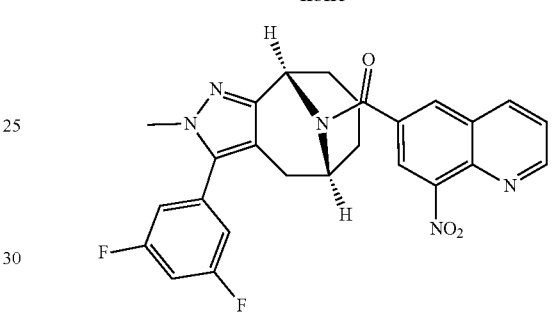

The title compound was prepared in a manner analogous to Example 1, using (5R,9S)-3-(3,5-difluorophenyl)-2-methyl-4,5,6,7,8,9-hexahydro-2H-5,9-epiminocycloocta[c]pyrazole (Intermediate 12) instead of racemic-(5R,9S)-2-methyl-3-phenyl-4,5,6,7,8,9-hexahydro-2H-5,9-epiminocycloocta[c]pyrazole (Intermediate 1) and 8-nitroquinoline-6-carboxylic acid instead of quinoline-6-carboxylic acid. MS (ESI): mass calcd. for $C_{26}H_{21}F_2N_5O_3$, 489.2; m/z found, 490.2 $[M+H]^+$. $^1H$ NMR (300 MHz, DMSO-$d_6$) δ 9.18-9.03 (m, 1H), 8.75-8.59 (m, 1H), 8.45-8.28 (m, 2H), 7.81 (dd, J=8.4, 4.3 Hz, 1H), 7.44-7.22 (m, 3H), 5.82-5.68 (m, 1H), 4.23-4.07 (m, 1H), 3.85 (s, 3H), 3.13 (dd, J=16.3, 7.3 Hz, 1H), 2.58-2.37 (m, 1H), 2.20-1.31 (m, 6H).

Example 111: (8-Aminoquinolin-6-yl)((5R,9S)-3-(3,5-difluorophenyl)-2-methyl-4,5,6,7,8,9-hexahydro-2H-5,9-epiminocycloocta[c]pyrazol-10-yl)methanone

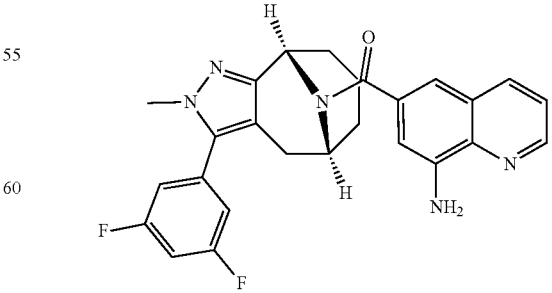

The title compound was prepared in a manner analogous to Example 1, using (5R,9S)-3-(3,5-difluorophenyl)-2- methyl-4,5,6,7,8,9-hexahydro-2H-5,9-epiminocyclooctal[c]pyrazole (Intermediate 12) instead of racemic-(5R,9S)-2-methyl-3-phenyl-4,5,6,7,8,9-hexahydro-2H-5,9-epiminocyclooctal[c]pyrazole (Intermediate 1) and 8-aminoquinoline-6-carboxylic acid instead of quinoline-6-carboxylic acid. MS (ESI): mass calcd. for $C_{26}H_{23}F_2N_5O$, 459.2; m/z found, 460.1 [M+H]$^+$. $^1$H NMR (500 MHz, DMSO-$d_6$) δ 8.77 (dd, J=4.2, 1.7 Hz, 1H), 8.30-8.23 (m, 1H), 7.51 (dd, J=8.3, 4.1 Hz, 1H), 7.39-7.29 (m, 3H), 7.11 (d, J=1.7 Hz, 1H), 6.82 (d, J=1.7 Hz, 1H), 6.10 (s, 2H), 5.76-5.68 (m, 1H), 4.24-4.15 (m, 1H), 3.84 (s, 3H), 3.02 (dd, J=16.2, 7.4 Hz, 1H), 2.55-2.44 (m, 1H), 2.02-1.31 (m, 6H).

Example 112: ((5R,9S)-3-(3,5-Difluorophenyl)-2-methyl-4,5,6,7,8,9-hexahydro-2H-5,9-epiminocyclooctal[c]pyrazol-10-yl) (quinazolin-7-yl) methanone

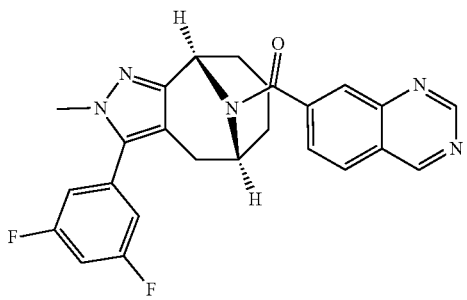 [SMILES: Cn1nc2c(c1-c1cc(F)cc(F)c1)C[C@H]1CCC[C@@H]2N1C(=O)c1ccc2cncnc2c1]

The title compound was prepared in a manner analogous to Example 1, using (5R,9S)-3-(3,5-difluorophenyl)-2-methyl-4,5,6,7,8,9-hexahydro-2H-5,9-epiminocyclooctal[c]pyrazole (Intermediate 12) instead of racemic-(5R,9S)-2-methyl-3-phenyl-4,5,6,7,8,9-hexahydro-2H-5,9-epiminocyclooctal[c]pyrazole (Intermediate 1) and quinazoline-7carboxylic acid instead of quinoline-6-carboxylic acid. MS (ESI): mass calcd. for $C_{25}H_{21}F_2N_5O$, 445.2; m/z found, 446.1 [M+H]$^+$. $^1$H NMR (500 MHz, DMSO-$d_6$) δ 9.70 (dd, J=6.2, 0.9 Hz, 1H), 9.37 (d, J=6.4 Hz, 1H), 8.36-8.22 (m, 1H), 8.10-7.67 (m, 2H), 7.43-7.27 (m, 3H), 5.78 (d, J=3.5 Hz, 1H), 4.13-3.92 (m, 1H), 3.88-3.73 (m, 3H), 3.16-3.01 (m, 1H), 2.42 (d, J=16.2 Hz, 1H), 2.06-1.38 (m, 6H).

Example 113: ((5R,9S)-3-(3,5-Difluorophenyl)-2-methyl-4,5,6,7,8,9-hexahydro-2H-5,9-epiminocyclooctal[c]pyrazol-10-yl) (quinoxalin-6-yl)methanone

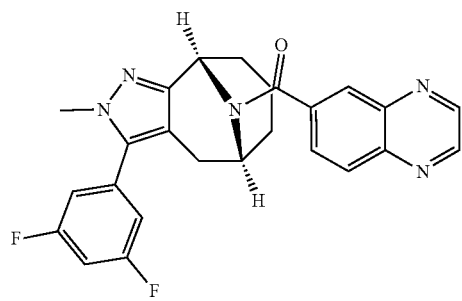 [SMILES: Cn1nc2c(c1-c1cc(F)cc(F)c1)C[C@H]1CCC[C@@H]2N1C(=O)c1ccc2nccnc2c1]

The title compound was prepared in a manner analogous to Example 1, using (5R,9S)-3-(3,5-difluorophenyl)-2-methyl-4,5,6,7,8,9-hexahydro-2H-5,9-epiminocyclooctal[c]pyrazole (Intermediate 12) instead of racemic-(5R,9S)-2-methyl-3-phenyl-4,5,6,7,8,9-hexahydro-2H-5,9-epiminocyclooctal[c]pyrazole (Intermediate 1) and quinoxaline-6-carboxylic acid instead of quinoline-6-carboxylic acid. MS (ESI): mass calcd. for $C_{25}H_{21}F_2N_5O$, 445.2; m/z found, 446.1 [M+H]$^+$. $^1$H NMR (500 MHz, DMSO-$d_6$) δ 9.03 (d, J=7.5 Hz, 2H), 8.24-8.05 (m, 2H), 7.95-7.77 (m, 1H), 7.46-7.30 (m, 3H), 5.80 (d, J=3.2 Hz, 1H), 4.09 (t, J=5.8 Hz, 1H), 3.90-3.71 (m, 3H), 3.22-3.00 (m, 1H), 2.44 (d, J=16.2 Hz, 1H), 2.00-1.35 (m, 6H).

Example 114: ((5R,9S)-3-(3,5-Difluorophenyl)-2-methyl-4,5,6,7,8,9-hexahydro-2H-5,9-epiminocyclooctal[c]pyrazol-10-yl)(quinazolin-6-yl)methanone

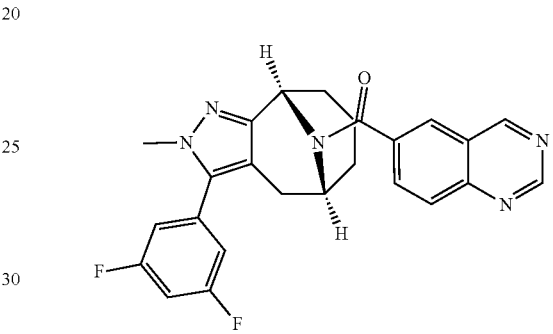

The title compound was prepared in a manner analogous to Example 1, using (5R,9S)-3-(3,5-difluorophenyl)-2-methyl-4,5,6,7,8,9-hexahydro-2H-5,9-epiminocyclooctal[c]pyrazole (Intermediate 12) instead of racemic-(5R,9S)-2-methyl-3-phenyl-4,5,6,7,8,9-hexahydro-2H-5,9-epiminocyclooctal[c]pyrazole (Intermediate 1) and quinoxaline-6-carboxylic acid instead of quinoline-6-carboxylic acid. MS (ESI): mass calcd. for $C_{25}H_{21}F_2N_5O$, 445.2; m/z found, 446.1 [M+H]$^+$. $^1$H NMR (500 MHz, DMSO-$d_6$) δ 9.70 (s, 1H), 9.36 (s, 1H), 8.28-8.22 (m, 1H), 8.14-8.04 (m, 2H), 7.41-7.28 (m, 3H), 5.82-5.72 (m, 1H), 4.14-4.06 (m, 1H), 3.85 (s, 3H), 3.10 (dd, J=16.5, 7.6 Hz, 1H), 2.50-2.43 (m, 1H), 2.11-1.35 (m, 6H).

Example 115: ((5R,9S)-3-(3,5-Difluorophenyl)-2-methyl-4,5,6,7,8,9-hexahydro-2H-5,9-epiminocyclooctal[c]pyrazol-10-yl)(2-methylquinoxalin-6-yl)methanone

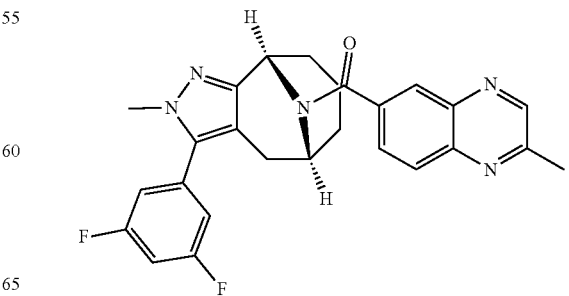

The title compound was prepared in a manner analogous to Example 1, using (5R,9S)-3-(3,5-difluorophenyl)-2-methyl-4,5,6,7,8,9-hexahydro-2H-5,9-epiminocycloocta[c]pyrazole (Intermediate 12) instead of racemic-(5R,9S)-2-methyl-3-phenyl-4,5,6,7,8,9-hexahydro-2H-5,9-epiminocycloocta[c]pyrazole (Intermediate 1) and 2-methylquinoxaline-6-carboxylic acid (Intermediate 33) instead of quinoline-6-carboxylic acid. MS (ESI): mass calcd. for $C_{26}H_{23}F_2N_5O$, 459.2; m/z found, 460.2 $[M+H]^+$. $^1$H NMR (300 MHz, DMSO-$d_6$) δ 8.92 (s, 1H), 8.20-7.90 (m, 2H), 7.88-7.70 (m, 1H), 7.46-7.23 (m, 3H), 5.86-5.66 (m, 1H), 4.16-3.96 (m, 1H), 3.84 (s, 3H), 3.25-2.99 (m, 1H), 2.73 (s, 3H), 2.53-2.34 (m, 1H), 2.06-1.31 (m, 6H).

Example 116: ((5R,9S)-3-(3,5-Difluorophenyl)-2-methyl-4,5,6,7,8,9-hexahydro-2H-5,9-epiminocycloocta[c]pyrazol-10-yl) (7-fluoroquinoxaline-6-yl) methanone

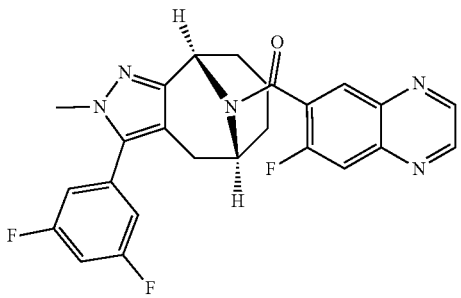 [SMILES: Cn1nc2c(c1-c1cc(F)cc(F)c1)C[C@H]1CCC[C@@H]2N1C(=O)c1cc2nccnc2cc1F]

The title compound was prepared in a manner analogous to Example 1, using (5R,9S)-3-(3,5-difluorophenyl)-2-methyl-4,5,6,7,8,9-hexahydro-2H-5,9-epiminocycloocta[c]pyrazole (Intermediate 12) instead of racemic-(5R,9S)-2-methyl-3-phenyl-4,5,6,7,8,9-hexahydro-2H-5,9-epiminocycloocta[c]pyrazol (Intermediate 1) and 7-fluoroquinoxaline-6-carboxylic acid instead of quinoline-6-carboxylic acid. MS (ESI): mass calcd. for $C_{25}H_{20}F_3N_5O$, 463.1; m/z found, 464.1 $[M+H]^+$. $^1$H NMR (500 MHz, DMSO-$d_6$) δ 9.10-8.88 (m, 2H), 8.41-7.85 (m, 2H), 7.43-7.24 (m, 3H), 5.83 (s, 1H), 3.97 (s, 1H), 3.88-3.72 (m, 3H), 3.16-2.84 (m, 1H), 2.47-2.32 (m, 1H), 1.99-1.34 (m, 6H).

Example 117: ((5R,9S)-3-(3,5-Difluorophenyl)-2-methyl-4,5,6,7,8,9-hexahydro-2H-5,9-epiminocycloocta[c]pyrazol-10-yl) (1,6-naphthyridin-5-yl) methanone

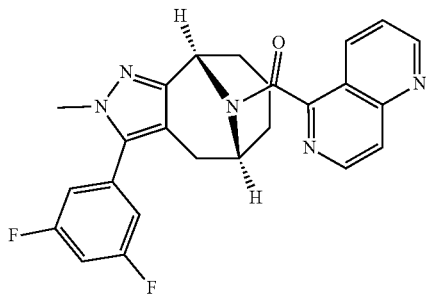 [SMILES: Cn1nc2c(c1-c1cc(F)cc(F)c1)C[C@H]1CCC[C@@H]2N1C(=O)c1nccc2ncccc12]

The title compound was prepared in a manner analogous to Example 1, using (5R,9S)-3-(3,5-difluorophenyl)-2-methyl-4,5,6,7,8,9-hexahydro-2H-5,9-epiminocycloocta[c]pyrazole (Intermediate 12) instead of racemic-(5R,9S)-2-methyl-3-phenyl-4,5,6,7,8,9-hexahydro-2H-5,9-epiminocycloocta[c]pyrazole (Intermediate 1) and 1,6-naphthyridine-5-carboxylic acid instead of quinoline-6-carboxylic acid. MS (ESI): mass calcd. for $C_{25}H_{21}F_2N_5O$, 445.2; m/z found, 446.1 $[M+H]^+$. $^1$H NMR (500 MHz, DMSO-$d_6$) δ 9.24-9.09 (m, 1H), 8.75 (dd, J=16.4, 5.9 Hz, 1H), 8.42-8.23 (m, 1H), 8.07-7.93 (m, 1H), 7.79-7.66 (m, 1H), 7.41-7.22 (m, 3H), 5.98-5.21 (m, 1H), 3.91-3.62 (m, 4H), 2.95-2.63 (m, 1H), 2.48-2.35 (m, 1H), 2.07-1.40 (m, 6H).

Example 118: ((5R,9S)-3-(3,5-Difluoropbenyl)-2-methyl-4,5,6,7,8,9-hexahydro-2H-5,9-epiminocycloocta[c]pyrazol-10-yl)(1,8-naphthyridin-3-yl) methanone

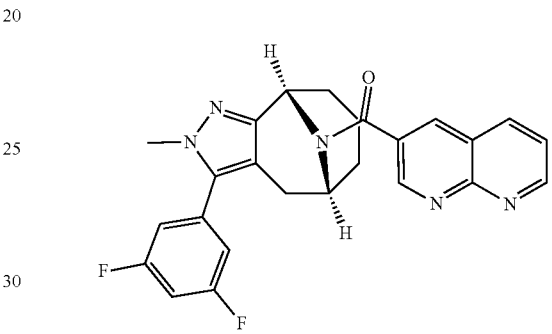

The title compound was prepared in a manner analogous to Example 1, using (5R,9S)-3-(3,5-difluorophenyl)-2-methyl-4,5,6,7,8,9-hexahydro-2H-5,9-epiminocycloocta[c]pyrazole (Intermediate 12) instead of racemic-(5R,9S)-2-methyl-3-phenyl-4,5,6,7,8,9-hexahydro-2H-5,9-epiminocycloocta[c]pyrazole (Intermediate 1) and 1,8-naphthyridine-3-carboxylic acid instead of quinoline-6-carboxylic acid. MS (ESI): mass calcd. for $C_{25}H_{21}F_2N_5O$, 445.2; m/z found, 446.1 $[M+H]^+$. $^1$H NMR (500 MHz, DMSO-$d_6$) δ 9.16 (dd, J=4.2, 2.0 Hz, 1H), 9.13 (d, J=2.4 Hz, 1H), 8.60 (d, J=2.4 Hz, 1H), 8.59-8.57 (m, 1H), 7.72 (dd, J=8.1, 4.2 Hz, 1H), 7.41-7.27 (m, 3H), 5.83-5.75 (m, 1H), 4.21-4.12 (m, 1H), 3.85 (s, 3H), 3.16 (dd, J=16.3, 7.4 Hz, 1H), 2.52-2.42 (m, 1H), 2.12-1.37 (m, 6H).

Example 119: ((5R,9S)-3-(3,5-Difluorophenyl)-2-methyl-4,5,6,7,8,9-hexahydro-2H-5,9-epiminocycloocta[c]pyrazol-10-yl)(1,8-naphthyridin-4-yl) methanone

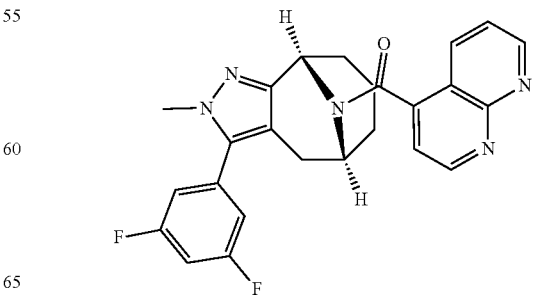

The title compound was prepared in a manner analogous to Example 1, using (5R,9S)-3-(3,5-difluorophenyl)-2-methyl-4,5,6,7,8,9-hexahydro-2H-5,9-epiminocycloocta[c]pyrazole (Intermediate 12) instead of racemic-(5R,9S)-2-methyl-3-phenyl-4,5,6,7,8,9-hexahydro-2H-5,9-epiminocycloocta[c]pyrazole (Intermediate 1) and 1,8-naphthyridine-4-carboxylic acid instead of quinoline-6-carboxylic acid. MS (ESI): mass calcd. for $C_{25}H_{21}F_2N_5O$, 445.2; m/z found, 446.2 [M+H]$^+$. $^1$H NMR (300 MHz, DMSO-d$_6$) δ 9.30-9.01 (m, 2H), 8.51-8.33 (m, 1H), 7.85-7.54 (m, 2H), 7.45-7.18 (m, 3H), 5.97-5.83 (m, 1H), 3.85 (s, 3H), 3.81-3.61 (m, 1H), 3.15-2.95 (m, 1H), 2.38 (d, J=16.3 Hz, 1H), 2.20-1.31 (m, 6H).

Example 120: ((5R,9S)-3-(3,5-Difluorophenyl)-2-methyl-4,5,6,7,8,9-hexahydro-2H-5,9-epiminocycloocta[c]pyrazol-10-yl)(17-naphthyridin-4-yl)methanone

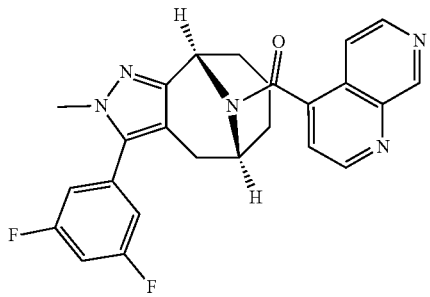 [SMILES: Cn1nc2c(c1-c1cc(F)cc(F)c1)C[C@H]1CCC[C@@H]2N1C(=O)c1ccnc2cnccc12]

The title compound was prepared in a manner analogous to Example 1, using (5R,9S)-3-(3,5-difluorophenyl)-2-methyl-4,5,6,7,8,9-hexahydro-2H-5,9-epiminocycloocta[c]pyrazole (Intermediate 12) instead of racemic-(5R,9S)-2-methyl-3-phenyl-4,5,6,7,8,9-hexahydro-2H-5,9-epiminocycloocta[c]pyrazole (Intermediate 1) and 1,7-naphthyridine-4-carboxylic acid instead of quinoline-6-carboxylic acid. MS (ESI): mass calcd. for $C_{25}H_{21}F_2N_5O$, 445.2; m/z found, 446.2 [M+H]$^+$. $^1$H NMR (500 MHz, DMSO-d$_6$) δ 9.56-9.41 (m, 1H), 9.16-9.05 (m, 1H), 8.79-8.61 (m, 1H), 8.02-7.71 (m, 1H), 7.48-7.17 (m, 4H), 5.96-5.84 (m, 1H), 3.85 (s, 3H), 3.84-3.60 (m, 1H), 3.25-2.94 (m, 1H), 2.44-2.29 (m, 1H), 2.18-1.35 (m, 6H).

Example 121: ((5R,9S)-3-(3,5-Difluorophenyl)-2-methyl-4,5,6,7,8,9-hexahydro-2H-5,9-epiminocycloocta[c]pyrazol-10-yl)(1,6-naphthyridin-4-yl)methanone

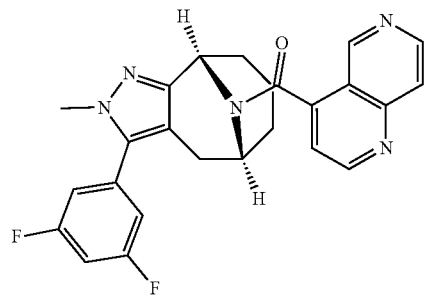 [SMILES: Cn1nc2c(c1-c1cc(F)cc(F)c1)C[C@H]1CCC[C@@H]2N1C(=O)c1ccnc2ccncc12]

The title compound was prepared in a manner analogous to Example 1, using (5R,9S)-3-(3,5-difluorophenyl)-2-methyl-4,5,6,7,8,9-hexahydro-2H-5,9-epiminocycloocta[c]pyrazole (Intermediate 12) instead of racemic-(5R,9S)-2-methyl-3-phenyl-4,5,6,7,8,9-hexahydro-2H-5,9-epiminocycloocta[c]pyrazole (Intermediate 1) and 1,6-naphthyridine-4-carboxylic acid instead of quinoline-6-carboxylic acid. MS (ESI): mass calcd. for $C_{25}H_{21}F_2N_5O$, 445.2; m/z found, 446.2 [M+H]$^+$. $^1$H NMR (500 MHz, DMSO-d$_6$) δ 9.45-8.70 (m, 3H), 8.10-7.94 (m, 1H), 7.73-7.60 (m, 1H), 7.42-7.29 (m, 3H), 5.99-5.84 (m, 1H), 3.85 (s, 3H), 3.83-3.61 (m, 1H), 3.27-3.01 (m, 1H), 2.41 (d, J=16.2 Hz, 1H), 2.17-1.34 (m, 6H).

Example 122: ((5R,9S)-3-(3,5-Difluorophenyl)-2-methyl-4,5,6,7,8,9-hexahydro-2H-5,9-epiminocycloocta[c]pyrazol-10-yl) (1,5-naphthyridin-2-yl)methanone

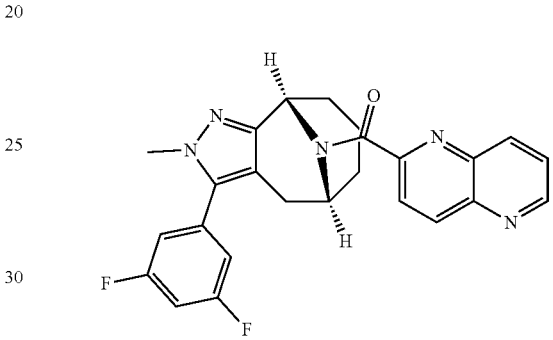

The title compound was prepared in a manner analogous to Example 1, using (5R,9S)-3-(3,5-difluorophenyl)-2-methyl-4,5,6,7,8,9-hexahydro-2H-5,9-epiminocycloocta[c]pyrazole (Intermediate 12) instead of racemic-(5R,9S)-2-methyl-3-phenyl-4,5,6,7,8,9-hexahydro-2H-5,9-epiminocycloocta[c]pyrazol (Intermediate 1) and 1,5-naphthyridine-2-carboxylic acid instead of quinoline-6-carboxylic acid. MS (ESI): mass calcd. for $C_{25}H_{21}F_2N_5O$, 445.2; m/z found, 446.1 [M+H]$^+$. $^1$H NMR (500 MHz, DMSO-d$_6$) δ 9.18-9.02 (m, 1H), 8.61-8.45 (m, 2H), 7.99-7.78 (m, 2H), 7.42-7.28 (m, 3H), 5.81 (s, 1H), 4.34-4.10 (m, 1H), 3.90-3.70 (m, 3H), 3.16-3.07 (m, 1H), 2.47 (d, J=5.7 Hz, 1H), 2.14-1.43 (m, 6H).

Example 123: 6-((5R,9S)-3-(3,5-Difluorophenyl-2-methyl-4,5,6,7,8,9-hexahydro-2H-5,9-epiminocycloocta[c]pyrazole-10-carbonyl)-1-(2-fluoroethyl)quinolin-4(1H)-one

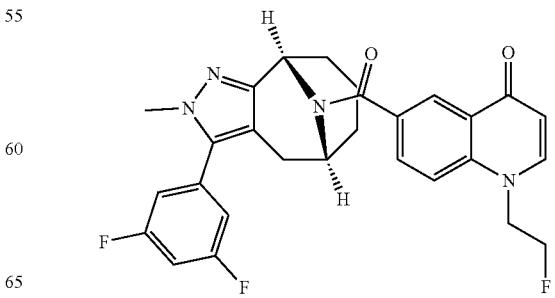

The title compound was obtained as a side product during the purification of Example 65, Step B. MS (ESI): mass calcd. for $C_{28}H_{25}F_3N_4O_2$, 506.2; m/z found, 507.2 [M+H]$^+$. $^1$H NMR (CDCl$_3$): δ 8.50 (dd, J=18.7, 2.1 Hz, 1H), 7.73 (ddd, J=30.2, 8.8, 2.1 Hz, 1H), 7.54 (dd, J=7.8, 0.7 Hz, 1H), 7.37 (dd, J=11.7, 8.8 Hz, 1H), 6.91-6.82 (m, 3H), 6.27 (d, J=7.8 Hz, 1H), 5.99 and 5.01 (s, 1H), 5.20 and 4.27 (m, 1H), 4.82-4.72 (m, 2H), 4.45-4.40 (m, 2H), 3.86 and 3.76 (s, 3H), 3.27-3.19 and 3.05-3.00 (m, 1H), 2.46 (dd, J=33.9, 16.3 Hz, 1H), 2.12-1.94 (m, 1H), 1.94-1.67 (m, 3H), 1.64-1.51 (m, 2H).

Example 124: 6-((5R,9S)-3-(3,5-Difluorophenyl)-2-methyl-4,5,6,7,8,9-hexahydro-2H-5,9-epiminocycloocta[c]pyrazole-10-carbonyl)-4-methyl-2H-benzo[b][1,4]oxazin-3(4H)-one

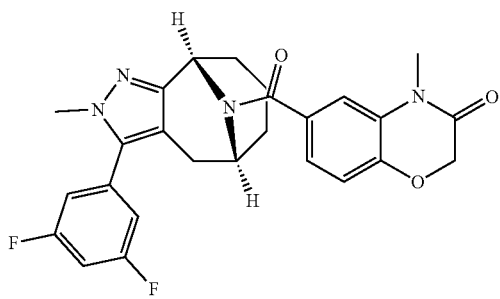 [SMILES: CN1C(=O)COc2ccc(C(=O)N3[C@@H]4CCC[C@H]3c3nn(C)c(-c5cc(F)cc(F)c5)c3C4)cc21]

The title compound was prepared in a manner analogous to Example 1, using (5R,9S)-3-(3,5-difluorophenyl)-2-methyl-4,5,6,7,8,9-hexahydro-2H-5,9-epiminocycloocta[c]pyrazole (Intermediate 12) instead of racemic-(5R,9S)-2-methyl-3-phenyl-4,5,6,7,8,9-hexahydro-2H-5,9-epiminocycloocta[c]pyrazol (Intermediate 1) and 4-methyl-3-oxo-3,4-dihydro-2H-benzo[b][1,4]oxazine-6-carboxylic acid instead of quinoline-6-carboxylic acid. MS (ESI): mass calcd. for $C_{26}H_{24}F_2N_4O_3$, 478.2; m/z found, 479.3 [M+H]$^+$. $^1$H NMR (500 MHz, DMSO-d$_6$) δ 7.40-7.27 (m, 3H), 7.22-7.15 (m, 1H), 7.11-6.99 (m, 2H), 5.73-5.60 (m, 1H), 4.70 (s, 2H), 4.21-4.08 (m, 1H), 3.82 (s, 3H), 3.30-3.25 (m, 3H), 3.03 (dd, J=16.0, 7.2 Hz, 1H), 2.45 (d, J=16.6 Hz, 1H), 2.08-1.31 (m, 6H).

Example 125: ((5R,9S)-3-(3,5-Difluorophenyl)-2-methyl-4,5,6,7,8,9-hexahydro-2H-5,9-epiminocycloocta[c]pyrazol-10-yl)(4-methyl-3,4-dihydro-2H-pyrido[3,2-b][1,4]oxazin-7-yl)methanone

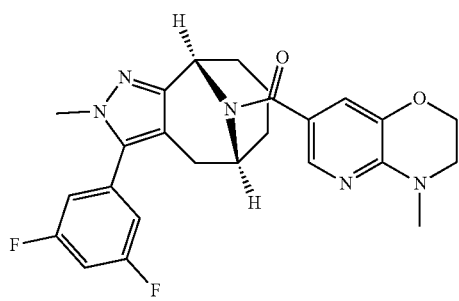 [SMILES: CN1CCOc2cc(C(=O)N3[C@@H]4CCC[C@H]3c3nn(C)c(-c5cc(F)cc(F)c5)c3C4)cnc21]

The title compound was prepared in a manner analogous to Example 1, using (5R,9S)-3-(3,5-difluorophenyl)-2-methyl-4,5,6,7,8,9-hexahydro-2H-5,9-epiminocycloocta[c]pyrazole (Intermediate 12) instead of racemic-(5R,9S)-2-methyl-3-phenyl-4,5,6,7,8,9-hexahydro-2H-5,9-epiminocycloocta[c]pyrazol (Intermediate 1) and 4-methyl-3,4-dihydro-2H-pyrido[3,2-b][1,4]oxazine-7-carboxylic acid instead of quinoline-6-carboxylic acid. MS (ESI): mass calcd. for $C_{25}H_{25}F_2N_5O_2$, 465.2; m/z found, 466.2 [M+H]$^+$. $^1$H NMR (500 MHz, DMSO-d$_6$) δ 7.85-7.71 (m, 1H), 7.41-7.26 (m, 3H), 7.01-6.89 (m, 1H), 5.67-5.50 (m, 1H), 4.34-4.22 (m, 1H), 4.24-4.19 (m, 2H), 3.88-3.71 (m, 3H), 3.54-3.44 (m, 2H), 3.18-2.99 (m, 1H), 3.07 (s, 3H), 2.55-2.38 (m, 1H), 2.01-1.32 (m, 6H).

Example 126: (2-(2H-1,2,3-Triazol-2-yl)phenyl)((5R,9S)-3-(3,4-difluorophenyl)-2-methyl-4,5,6,7,8,9-hexahydro-2H-5,9-epiminocycloocta[c]pyrazol-10-yl)methanone

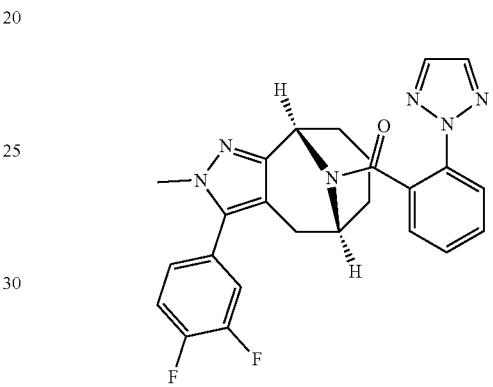

The title compound was prepared in a manner analogous to Example 1, using (5R,9S)-3-(3,4-difluorophenyl)-2-methyl-4,5,6,7,8,9-hexahydro-2H-5,9-epiminocycloocta[c]pyrazole (Intermediate 24) instead of racemic-(5R,9S)-2-methyl-3-phenyl-4,5,6,7,8,9-hexahydro-2H-5,9-epiminocycloocta[c]pyrazole (Intermediate 1) and 2-(2H-1,2,3-triazol-2-yl)benzoic acid (Intermediate 49) instead of quinoline-6-carboxylic acid. MS (ESI): mass calcd. for $C_{25}H_{22}F_2N_6O$, 460.1; m/z found, 461.1 [M+H]$^+$. $^1$H NMR (600 MHz, Chloroform-d) δ 12.91 (d, J=13.3 Hz, 1H), 12.75-12.58 (m, 1H), 12.58-11.63 (m, 7H), 10.60-10.28 (m, 1H), 9.36-8.96 (m, 1H), 8.65-8.35 (m, 3H), 7.87-7.61 (m, 1H), 7.19-6.84 (m, 1H), 6.68-5.89 (m, 6H).

Example 127: racemic-((5R,9S)-3-(3,4-Difluorophenyl)-2-methyl-4,5,6,7,8,9-hexahydro-2H-5,9-epiminocycloocta[c]pyrazol-10-yl) (quinolin-6-yl) methanone

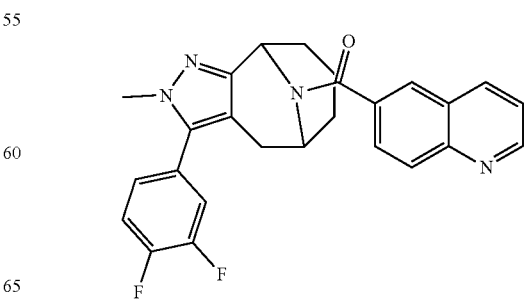

The title compound was prepared in a manner analogous to Example 1, using racemic-(5R,9S)-3-(3,4-difluorophenyl)-2-methyl-4,5,6,7,8,9-hexahydro-2H-5,9-epiminocyclooocta[c]pyrazole (Intermediate 8) instead of racemic-(5R,9S)-2-methyl-3-phenyl-4,5,6,7,8,9-hexahydro-2H-5,9-epiminocycloocta[c]pyrazole (Intermediate 1). MS (ESI): mass calcd. for $C_{26}H_{22}F_2N_4O$, 444.1; m/z found, 445.1 [M+H]$^+$. $^1$H NMR (500 MHz, DMSO-d$_6$) δ 9.03-8.91 (m, 1H), 8.56-8.40 (m, 1H), 8.19-8.00 (m, 2H), 7.86-7.56 (m, 4H), 7.42 (d, J=9.2 Hz, 1H), 5.76 (d, J=3.6 Hz, 1H), 4.11 (s, 1H), 3.87-3.66 (m, 3H), 3.09 (ddd, J=32.8, 16.2, 7.4 Hz, 1H), 2.48-2.34 (m, 1H), 2.10-1.40 (m, 6H).

Example 128: ((5R,9S)-3-(3,4-Difluorophenyl)-2-methyl-4,5,6,7,8,9-hexahydro-2H-5,9-epiminocyclooocta[c]pyrazol-10-yl)(quinolin-6-yl)methanone

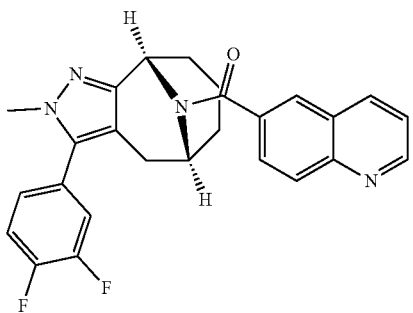 [SMILES: Cn1nc2c(c1-c1ccc(F)c(F)c1)C[C@H]1CCC[C@@H]2N1C(=O)c1ccc2ncccc2c1]

The title compound was prepared in a manner analogous to Example 1, using (5R,9S)-3-(3,4-difluorophenyl)-2-methyl-4,5,6,7,8,9-hexahydro-2H-5,9-epiminocycloocta[c]pyrazole (Intermediate 24) instead of racemic-(5R,9S)-2-methyl-3-phenyl-4,5,6,7,8,9-hexahydro-2H-5,9-epiminocycloocta[c]pyrazole (Intermediate 1). MS (ESI): mass calcd. for $C_{26}H_{22}F_2N_4O$, 444.1; m/z found, 445.1 [M+H]$^+$. $^1$H NMR (500 MHz, DMSO-d$_6$) δ 9.05-8.91 (m, 1H), 8.55-8.39 (m, 1H), 8.16-7.98 (m, 2H), 7.82-7.56 (m, 4H), 7.41 (s, 1H), 5.86-5.68 (m, 1H), 4.19-4.02 (m, 1H), 3.87-3.68 (m, 3H), 3.16-2.98 (m, 1H), 2.48-2.32 (m, 1H), 2.05-1.41 (m, 6H).

Example 129: racemic-((5R,9S)-3-(3,4-Difluorophenyl)-2-methyl-4,5,6,7,8,9-hexahydro-2H-5,9-epiminocycloocta[c]pyrazol-10-yl) (quinoxalin-6-yl)methanone

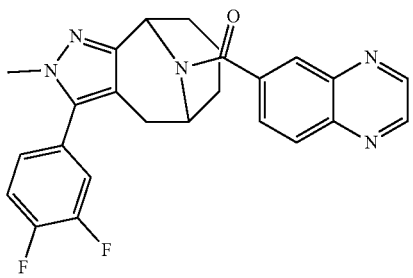 [SMILES: Cn1nc2c(c1-c1ccc(F)c(F)c1)CC1CCCC2N1C(=O)c1ccc2nccnc2c1]

The title compound was prepared in a manner analogous to Example 1, using racemic-(5R,9S)-3-(3,4-difluorophenyl)-2-methyl-4,5,6,7,8,9-hexahydro-2H-5,9-epiminocycloocta[c]pyrazole (Intermediate 8) instead of racemic-(5R,9S)-2-methyl-3-phenyl-4,5,6,7,8,9-hexahydro-2H-5,9-epiminocycloocta[c]pyrazole (Intermediate 1) and quinoxaline-6-carboxylic acid instead of quinoline-6-carboxylic acid. MS (ESI): mass calcd. for $C_{25}H_{21}F_2N_5O$, 445.1; m/z found, 446.1 [M+H]$^+$. $^1$H NMR (500 MHz, DMSO-d$_6$) δ 9.12-8.94 (m, 2H), 8.27-8.02 (m, 2H), 7.95-7.67 (m, 2H), 7.66-7.38 (m, 2H), 5.78 (s, 1H), 4.08 (s, 1H), 3.87-3.65 (m, 3H), 3.21-3.01 (m, 1H), 2.47-2.27 (m, 1H), 2.07-1.34 (m, 6H).

Example 130: ((5R,9S)-3-(3-Fluoro-5-methoxyphenyl)-2-methyl-4,5,6,7,8,9-hexahydro-2H-5,9-epiminocycloocta[c]pyrazol-10-yl) (quinoxalin-6-yl)methanone

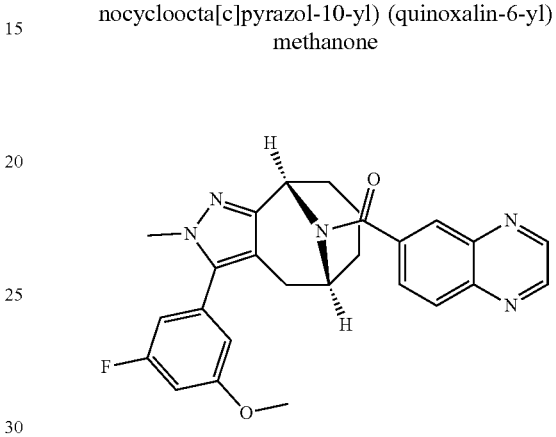

The title compound was prepared in a manner analogous to Example 1, using (5R,9S)-3-(3-fluoro-5-methoxyphenyl)-2-methyl-4,5,6,7,8,9-hexahydro-2H-5,9-epiminocycloocta[c]pyrazole (Intermediate 15) instead of racemic-(5R,9S)-2-methyl-3-phenyl-4,5,6,7,8,9-hexahydro-2H-5,9-epiminocycloocta[c]pyrazole (Intermediate 1) and quinoxaline-6-carboxylic acid instead of quinoline-6-carboxylic acid. MS (ESI): mass calcd. for $C_{26}H_{24}FN_5O_2$, 457.1; m/z found, 458.1 [M+H]$^+$. $^1$H NMR (400 MHz, DMSO-d$_6$) δ 9.03 (d, J=7.1 Hz, 2H), 8.28-7.80 (m, 3H), 7.08-6.80 (m, 3H), 5.88-5.71 (m, 1H), 4.16-3.97 (m, 1H), 3.93-3.64 (m, 6H), 3.19-3.00 (m, 1H), 2.47-2.33 (m, 1H), 2.05-1.36 (m, 6H).

Example 131: ((5R,9S)-3-(4-Chloro-3-fluorophenyl)-2-methyl-4,5,6,7,8,9-hexahydro-2H-5,9-epiminocycloocta[c]pyrazol-10-yl) (quinoxalin-6-yl)methanone

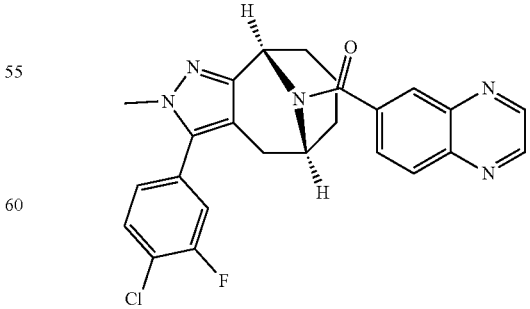

The title compound was prepared in a manner analogous to Example 1, using (5R,9S)-3-(4-chloro-3-fluorophenyl)-

2-methyl-4,5,6,7,8,9-hexahydro-2H-5,9-epiminocycloocta[c]pyrazole (Intermediate 20) instead of racemic-(5R,9S)-2-methyl-3-phenyl-4,5,6,7,8,9-hexahydro-2H-5,9-epiminocycloocta[c]pyrazole (Intermediate 1) and quinoxaline-6-carboxylic acid instead of quinoline-6-carboxylic acid. MS (ESI): mass calcd. for $C_{25}H_{21}ClFN_5O$, 461.1; m/z found, 462.1 [M+H]$^+$. $^1$H NMR (500 MHz, DMSO-d$_6$) δ 9.02 (d, J=12.1 Hz, 2H), 8.26-8.04 (m, 2H), 7.93-7.66 (m, 2H), 7.60-7.31 (m, 2H), 5.85-5.75 (m, 1H), 4.10-3.97 (m, 1H), 3.74-3.64 (m, 3H), 3.07-2.83 (m, 1H), 2.39-2.27 (m, 1H), 2.05-1.37 (m, 6H).

Example 132: ((5R,9S)-3-(3-Chloro-4-methoxyphenyl)-2-methyl-4,5,6,7,8,9-hexahydro-2H-5,9-epiminocycloocta[c]pyrazol-10-yl) (quinoxalin-6-yl)methanone

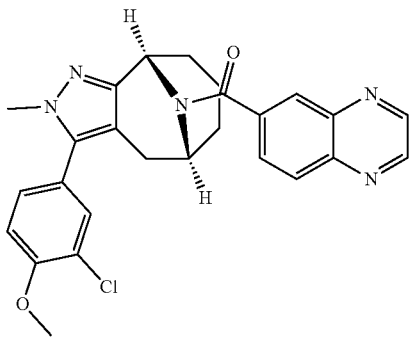

The title compound was prepared in a manner analogous to Example 1, using (5R,9S)-3-(3-chloro-4-methoxyphenyl)-2-methyl-4,5,6,7,8,9-hexahydro-2H-5,9-epiminocycloocta[c]pyrazole (Intermediate 18) instead of racemic-(5R,9S)-2-methyl-3-phenyl-4,5,6,7,8,9-hexahydro-2H-5,9-epiminocycloocta[c]pyrazole (Intermediate 1) and quinoxaline-6-carboxylic acid instead of quinoline-6-carboxylic acid. MS (ESI): mass calcd. for $C_{26}H_{24}ClN_5O_2$, 473.1; m/z found, 474.1 [M+H]$^+$. $^1$H NMR (500 MHz, DMSO-d$_6$) δ 9.11-8.95 (m, 2H), 8.26-7.97 (m, 2H), 7.95-7.78 (m, 1H), 7.50-7.21 (m, 2H), 7.16-7.01 (m, 1H), 5.79 (s, 1H), 4.21-3.97 (m, 1H), 3.96-3.86 (m, 3H), 3.65-3.54 (m, 3H), 2.98-2.71 (m, 1H), 2.40-2.17 (m, 1H), 2.06-1.40 (m, 6H).

Example 133: (2-(2H-1,2,3-Triazol-2-yl)phenyl) ((5R,9S)-3-(3-chloro-4-methoxyphenyl)-2-methyl-4,5,6,7,8,9-hexahydro-2H-5,9-epiminocycloocta[c]pyrazol-10-yl)methanone

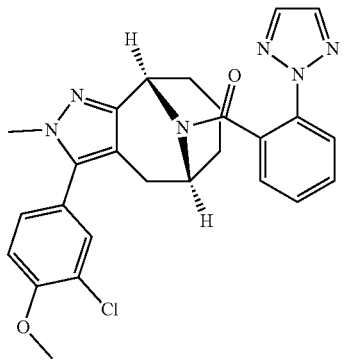 [SMILES: COc1ccc(-c2c3c(nn2C)[C@@H]2CCC[C@H](C3)N2C(=O)c2ccccc2-n2nccn2)cc1Cl]

The title compound was prepared in a manner analogous to Example 1, using (5R,9S)-3-(3-chloro-4-methoxyphenyl)-2-methyl-4,5,6,7,8,9-hexahydro-2H-5,9-epiminocycloocta[c]pyrazole (Intermediate 18) instead of racemic-(5R,9S)-2-methyl-3-phenyl-4,5,6,7,8,9-hexahydro-2H-5,9-epiminocycloocta[c]pyrazole (Intermediate 1) and 2-(2H-1,2,3-triazol-2-yl)benzoic acid (Intermediate 49) instead of quinoline-6-carboxylic acid. MS (ESI): mass calcd. for $C_{26}H_{25}ClN_6O_2$, 488.1; m/z found, 489.1 [M+H]$^+$. $^1$H NMR (600 MHz, DMSO-d$_6$) δ 8.36-7.69 (m, 3H), 7.71-6.77 (m, 6H), 5.77-5.52 (m, 1H), 4.60-4.26 (m, 1H), 3.96-3.84 (m, 3H), 3.79-3.58 (m, 3H), 3.07-2.85 (m, 1H), 2.43-2.30 (m, 1H), 1.94-1.11 (m, 6H).

Example 134: ((5R,9S)-3-(3-Chloro-4-methoxyphenyl)-2-methyl-4,5,6,7,8,9-hexahydro-2H-5,9-epiminocycloocta[c]pyrazol-10-yl) (1-methyl-1H-pyrazolo[3,4-b]pyridin-3-yl)methanone

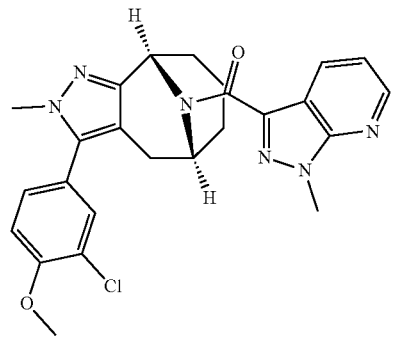 [SMILES: COc1ccc(-c2c3c(nn2C)[C@@H]2CCC[C@H](C3)N2C(=O)c2nn(C)c3ncccc23)cc1Cl]

The title compound was prepared in a manner analogous to Example 1, using (5R,9S)-3-(3-chloro-4-methoxyphenyl)-2-methyl-4,5,6,7,8,9-hexahydro-2H-5,9-epiminocycloocta[c]pyrazole (Intermediate 18) instead of racemic-(5R,9S)-2-methyl-3-phenyl-4,5,6,7,8,9-hexahydro-2H-5,9-epiminocycloocta[c]pyrazole (Intermediate 1) and 1-methyl-1H-pyrazolo[3,4-b]pyridine-3-carboxylic acid instead of quinoline-6-carboxylic acid. MS (ESI): mass calcd. for $C_{25}H_{25}ClN_6O_2$, 476.1; m/z found, 477.1 [M+H]$^+$. $^1$H NMR (600 MHz, DMSO-d$_6$) δ 8.71-8.59 (m, 1H), 8.50-8.26 (m, 1H), 7.62-7.48 (m, 1H), 7.46-7.37 (m, 1H), 7.38-7.31 (m, 1H), 7.26 (dd, J=8.6, 6.4 Hz, 1H), 6.36-5.77 (m, 1H), 5.49-5.02 (m, 1H), 4.21-4.07 (m, 3H), 3.96-3.88 (m, 3H), 3.79-3.69 (m, 3H), 3.15-2.99 (m, 1H), 2.57-2.52 (m, 1H), 2.05-1.46 (m, 6H).

Example 135: ((5R,9S)-3-(3-Chloro-4-methoxyphenyl)-2-methyl-4,5,6,7,8,9-hexahydro-2H-5,9-epiminocycloocta[c]pyrazol-10-yl)(quinolin-6-yl)methanone

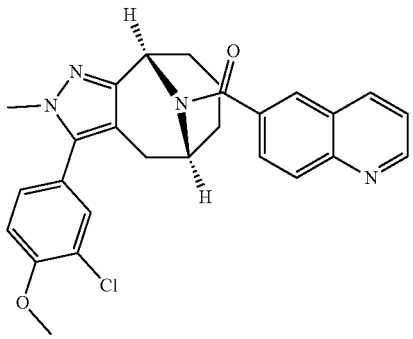 [SMILES: COc1ccc(-c2c3c(nn2C)[C@@H]2CCC[C@H](C3)N2C(=O)c2ccc3ncccc3c2)cc1Cl]

The title compound was prepared in a manner analogous to Example 1, using (5R,9S)-3-(3-chloro-4-methoxyphenyl)-2-methyl-4,5,6,7,8,9-hexahydro-2H-5,9-epiminocycloocta[c]pyrazole (Intermediate 18) instead of racemic-(5R,9S)-2-methyl-3-phenyl-4,5,6,7,8,9-hexahydro-2H-5,9-epiminocycloocta[c]pyrazole (Intermediate 1). MS (ESI): mass calcd. for $C_{27}H_{25}ClN_4O_2$, 472.1; m/z found, 473.1 [M+H]$^+$. $^1$H NMR (600 MHz, DMSO-d$_6$) δ 9.01-8.91 (m, 1H), 8.47 (d, J=8.3 Hz, 1H), 8.15-8.01 (m, 2H), 7.82-7.71 (m, 1H), 7.66-7.54 (m, 2H), 7.53-7.41 (m, 1H), 7.27 (t, J=9.6 Hz, 1H), 4.14-4.05 (m, 1H), 3.94-3.89 (m, 4H), 3.82-3.62 (m, 3H), 3.14-2.95 (m, 1H), 2.40 (d, J=15.9 Hz, 1H), 2.04-1.40 (m, 6H).

Example 136: ((5R,9S)-3-(3-Chloro-5-methoxyphenyl)-2-methyl-4,5,6,7,8,9-hexahydro-2H-5,9-epiminocycloocta[c]pyrazol-10-yl)(2-methylbenzo[d]oxazol-6-yl)methanone

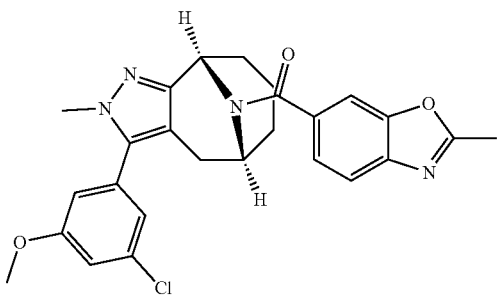

The title compound was prepared in a manner analogous to Example 1, using (5R,9S)-3-(3-chloro-5-methoxyphenyl)-2-methyl-4,5,6,7,8,9-hexahydro-2H-5,9-epiminocycloocta[c]pyrazole (Intermediate 17) instead of racemic-(5R,9S)-2-methyl-3-phenyl-4,5,6,7,8,9-hexahydro-2H-5,9-epiminocycloocta[c]pyrazole (Intermediate 1) and 2-methylbenzo[d]oxazole-6-carboxylic acid instead of quinoline-6-carboxylic acid. MS (ESI): mass calcd. for $C_{26}H_{25}ClN_4O_3$, 476.1; m/z found, 477.1 [M+H]$^+$. $^1$H NMR (600 MHz, DMSO-d$_6$) δ 7.86-7.66 (m, 2H), 7.46-7.27 (m, 1H), 7.22-6.96 (m, 3H), 5.79-5.61 (m, 1H), 4.15-3.95 (m, 1H), 3.92-3.60 (m, 6H), 3.15-2.94 (m, 1H), 2.64 (d, J=6.7 Hz, 3H), 2.38 (d, J=16.0 Hz, 1H), 2.00-1.33 (m, 6H).

Example 137: ((5R,9S)-3-(3-Chloro-5-methoxyphenyl)-2-methyl-4,5,6,7,8,9-hexahydro-2H-5,9-epiminocycloocta[c]pyrazol-10-yl)(quinolin-6-yl)methanone

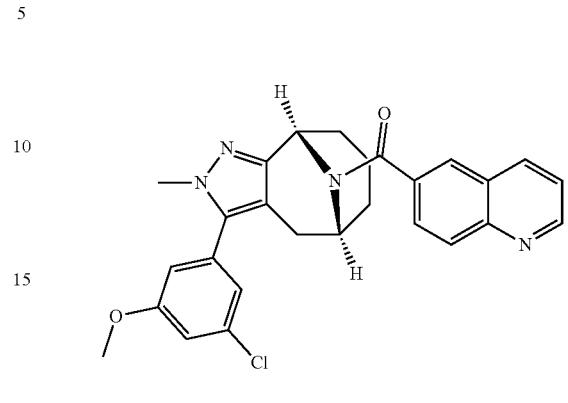

The title compound was prepared in a manner analogous to Example 1, using (5R,9S)-3-(3-chloro-5-methoxyphenyl)-2-methyl-4,5,6,7,8,9-hexahydro-2H-5,9-epiminocycloocta[c]pyrazole (Intermediate 17) instead of racemic-(5R,9S)-2-methyl-3-phenyl-4,5,6,7,8,9-hexahydro-2H-5,9-epiminocycloocta[c]pyrazole (Intermediate 1). MS (ESI): mass calcd. for $C_{27}H_{25}ClN_4O_2$, 472.1; m/z found, 473.1 [M+H]$^+$. $^1$H NMR (400 MHz, DMSO-d$_6$) δ 9.04-8.87 (m, 1H), 8.48 (d, J=8.4 Hz, 1H), 8.15-8.03 (m, 2H), 7.85-7.51 (m, 2H), 7.23-6.93 (m, 3H), 5.81-5.63 (m, 1H), 4.19-4.06 (m, 1H), 3.89-3.70 (m, 6H), 3.11-2.96 (m, 1H), 2.43 (d, J=16.2 Hz, 1H), 2.06-1.40 (m, 6H).

Example 138: ((5R,9S)-3-(3-Chloro-5-methoxyphenyl)-2-methyl-4,5,6,7,8,9-hexahydro-2H-5,9-epiminocycloocta[c]pyrazol-10-yl)(quinoxalin-6-yl)methanone

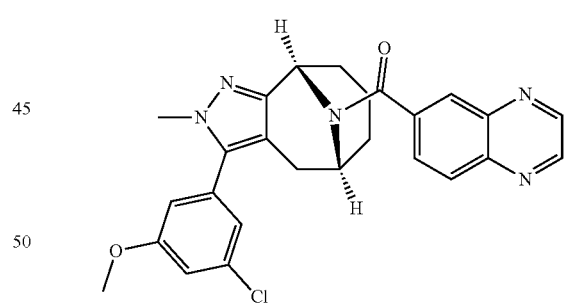

The title compound was prepared in a manner analogous to Example 1, using (5R,9S)-3-(3-chloro-5-methoxyphenyl)-2-methyl-4,5,6,7,8,9-hexahydro-2H-5,9-epiminocycloocta[c]pyrazole (Intermediate 17) instead of racemic-(5R,9S)-2-methyl-3-phenyl-4,5,6,7,8,9-hexahydro-2H-5,9-epiminocycloocta[c]pyrazole (Intermediate 1) and quinoxaline-6-carboxylic acid instead of quinoline-6-carboxylic acid. MS (ESI): mass calcd. for $C_{26}H_{24}ClN_5O_2$, 473.1; m/z found, 474.1 [M+H]$^+$. $^1$H NMR (600 MHz, DMSO-d$_6$) δ 9.09-8.99 (m, 2H), 8.26-8.01 (m, 2H), 7.97-7.77 (m, 1H), 7.24-6.96 (m, 3H), 5.86-5.70 (m, 1H), 4.16-3.95 (m, 1H), 3.91-3.64 (m, 6H), 3.20-2.94 (m, 1H), 2.41 (d, J=16.0 Hz, 1H), 2.04-1.37 (m, 6H).

Example 139: ((5R,9S)-3-(3,5-Dimethoxyphenyl)-2-methyl-4,5,6,7,8,9-hexahydro-2H-5,9-epiminocyclooctа[c]pyrazol-10-yl)(2-methylbenzo[d]oxazol-6-yl)methanone

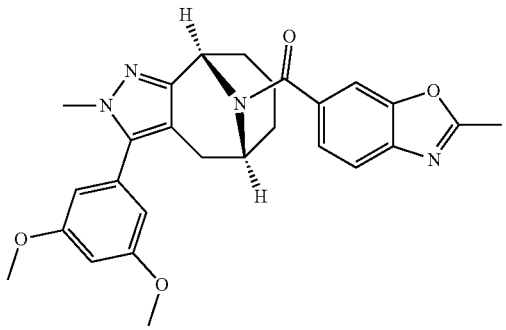

The title compound was prepared in a manner analogous to Example 1, using (5R,9S)-3-(3,5-dimethoxyphenyl)-2-methyl-4,5,6,7,8,9-hexahydro-2H-5,9-epiminocycloocta[c]pyrazole (Intermediate 23) instead of racemic-(5R,9S)-2-methyl-3-phenyl-4,5,6,7,8,9-hexahydro-2H-5,9-epiminocycloocta[c]pyrazole (Intermediate 1) and 2-methylbenzo[d]oxazole-6-carboxylic acid instead of quinoline-6-carboxylic acid. MS (ESI): mass calcd. for $C_{27}H_{28}N_4O_4$, 472.2; m/z found, 473.2 [M+H]$^+$. $^1$H NMR (600 MHz, DMSO-d$_6$) δ 7.81-7.65 (m, 2H), 7.45-7.27 (m, 1H), 6.70-6.52 (m, 3H), 5.82-5.52 (m, 1H), 4.09-3.98 (m, 1H), 3.90-3.66 (m, 9H), 3.15-2.93 (m, 1H), 2.64 (d, J=8.4 Hz, 3H), 2.37 (d, J=16.0 Hz, 1H), 1.98-1.37 (m, 6H).

Example 140: ((5R,9S)-3-(3,5-Dimethoxyphenyl)-2-methyl-4,5,6,7,8,9-hexahydro-2H-5,9-epiminocycloocta[c]pyrazol-10-yl)(quinoxalin-6-yl)methanone

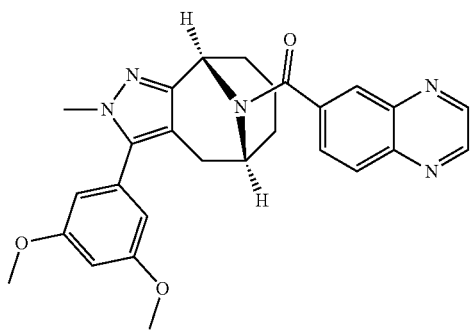 [SMILES: COc1cc(OC)cc(-c2c3c(nn2C)[C@@H]2CCC[C@H](C3)N2C(=O)c2ccc3nccnc3c2)c1]

The title compound was prepared in a manner analogous to Example 1, using (5R,9S)-3-(3,5-dimethoxyphenyl)-2-methyl-4,5,6,7,8,9-hexahydro-2H-5,9-epiminocycloocta[c]pyrazole (Intermediate 23) instead of racemic-(5R,9S)-2-methyl-3-phenyl-4,5,6,7,8,9-hexahydro-2H-5,9-epiminocycloocta[c]pyrazole (Intermediate 1) and quinoxaline-6-carboxylic acid instead of quinoline-6-carboxylic acid. MS (ESI): mass calcd. for $C_{27}H_{27}N_5O_3$, 469.2; m/z found, 470.2 [M+H]$^+$. $^1$H NMR (600 MHz, DMSO-d$_6$) δ 9.12-8.95 (m, 2H), 8.27-8.02 (m, 2H), 7.96-7.73 (m, 1H), 6.72-6.43 (m, 3H), 5.83-5.63 (m, 1H), 4.14-4.00 (m, 1H), 3.84-3.69 (m, 9H), 3.22-2.92 (m, 1H), 2.40 (d, J=15.9 Hz, 1H), 2.04-1.37 (m, 6H).

Example 141: (3-(4H-1,2,4Ttriazol-4-yl)phenyl)((5R,9S)-3-(3,5-dichlorophenyl)-2-methyl-4,5,6,7,8,9-hexahydro-2H-5,9-epiminocycloocta[c]pyrazol-10-yl)methanone

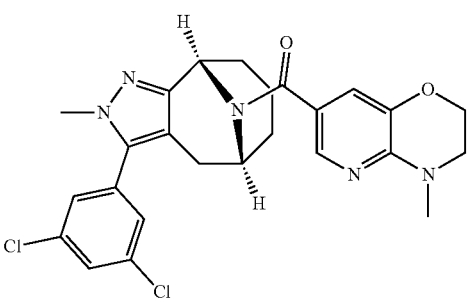 [SMILES: CN1CCOc2cc(C(=O)N3[C@@H]4CCC[C@H]3c3nn(C)c(-c5cc(Cl)cc(Cl)c5)c3C4)cnc21]

The title compound was prepared in a manner analogous to Example 1, using (5R,9S)-3-(3,5-dichlorophenyl)-2-methyl-4,5,6,7,8,9-hexahydro-2H-5,9-epiminocycloocta[c]pyrazole (Intermediate 19) instead of racemic-(5R,9S)-2-methyl-3-phenyl-4,5,6,7,8,9-hexahydro-2H-5,9-epiminocycloocta[c]pyrazole (Intermediate 1) and 3-(4H-1,2,4-triazol-4-yl) benzoic acid instead of quinoline-6-carboxylic acid. MS (ESI): mass calcd. for $C_{25}H_{22}Cl_2N_6O$, 492.1; m/z found, 493.1 [M+H]$^+$. $^1$H NMR (600 MHz, DMSO-d$_6$) δ 9.20 (d, J=6.2 Hz, 2H), 7.90-7.33 (m, 7H), 5.83-5.62 (m, 1H), 4.14-3.98 (m, 1H), 3.85-3.70 (m, 3H), 3.11-2.95 (m, 1H), 2.44 (d, J=16.1 Hz, 1H), 2.06-1.40 (m, 6H).

Example 142: ((5R,9S)-3-(3,5-Dichlorophenyl)-2-methyl-4,5,6,7,8,9-hexahydro-2H-5,9-epiminocycloocta[c]pyrazol-10-yl)(4-methyl-3,4-dihydro-2H-pyrido[3,2-b][1,4]oxazin-7-yl)methanone The title compound was prepared in a manner analogous to Example 1, using (5R,9S)-3-(3,5-dichlorophenyl)-2-methyl-4,5,6,7,8,9-hexahydro-2H-5,9-epiminocycloocta[c]pyrazole (Intermediate 19) instead of racemic-(5R,9S)-2-methyl-3-phenyl-4,5,6,7,8,9-hexahydro-2H-5,9-epiminocycloocta[c]pyrazole (Intermediate 1) and 4-methyl-3,4-dihydro-2H-pyrido[3,2-b] [1,4]oxazine-7-carboxylic acid instead of quinoline-6-carboxylic acid. MS (ESI): mass calcd. for $C_{25}H_{25}Cl_2N_5O_2$, 497.1; m/z found, 498.1 [M+H]$^+$. $^1$H NMR (600 MHz, DMSO-d$_6$) δ 7.87-7.55 (m, 4H), 6.94 (d, J=51.0 Hz, 1H), 5.72-5.49 (m, 1H), 4.27 (s, 1H), 4.22 (t, J=4.4 Hz, 2H), 3.85-3.69 (m, 3H), 3.49 (t, J=4.4 Hz, 2H), 3.18-2.95 (m, 4H), 2.41 (d, J=16.1 Hz, 1H), 2.02-1.34 (m, 6H).

Example 143: ((5R,9S)-3-(3,5-Dichlorophenyl)-2-methyl-4,5,6,7,8,9-hexahydro-2H-5,9-epiminocycloocta[c]pyrazol-10-yl)(5-methoxy-1-methyl-1H-pyrazol-4-yl)methanone

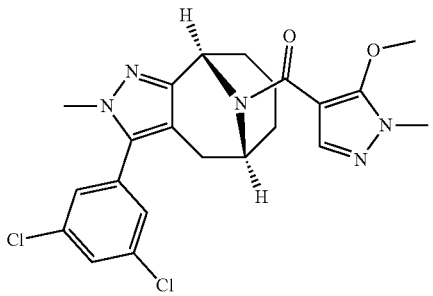 [SMILES: COc1c(C(=O)N2[C@@H]3CCC[C@H]2c2nn(C)c(-c4cc(Cl)cc(Cl)c4)c2C3)cnn1C]

The title compound was prepared in a manner analogous to Example 1, using (5R,9S)-3-(3,5-dichlorophenyl)-2-methyl-4,5,6,7,8,9-hexahydro-2H-5,9-epiminocycloocta[c]pyrazole (Intermediate 19) instead of racemic-(5R,9S)-2-methyl-3-phenyl-4,5,6,7,8,9-hexahydro-2H-5,9-epiminocycloocta[c]pyrazole (Intermediate 1) and 5-methoxy-1-methyl-1H-pyrazole-4-carboxylic acid instead of quinoline-6-carboxylic acid. MS (ESI): mass calcd. for $C_{22}H_{23}Cl_2N_5O_2$, 492.1; m/z found, 493.1 [M+H]$^+$. $^1$H NMR (600 MHz, DMSO-d$_6$) δ 7.76-7.59 (m, 3H), 7.42 (d, J=75.0 Hz, 1H), 5.70-5.56 (m, 1H), 4.54-4.31 (m, 1H), 4.00-3.71 (m, 6H), 3.64-3.57 (m, 3H), 3.20-2.96 (m, 1H), 2.50-2.35 (m, 1H), 1.96-1.36 (m, 6H).

Example 144: (5-Cyclopropyl-1-methyl-1H-pyrazol-4-yl)((5R,9S)-3-(3,5-dichlorophenyl)-2-methyl-4,5,6,7,8,9-hexahydro-2H-5,9-epiminocycloocta[c]pyrazol-10-yl)methanone

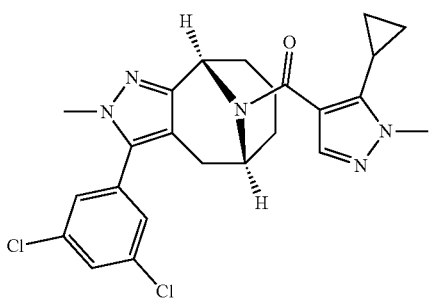 [SMILES: Cn1nc2c(c1-c1cc(Cl)cc(Cl)c1)C[C@H]1CCC[C@@H]2N1C(=O)c1cnn(C)c1C1CC1]

The title compound was prepared in a manner analogous to Example 1, using (5R,9S)-3-(3,5-dichlorophenyl)-2-methyl-4,5,6,7,8,9-hexahydro-2H-5,9-epiminocycloocta[c]pyrazole (Intermediate 19) instead of racemic-(5R,9S)-2-methyl-3-phenyl-4,5,6,7,8,9-hexahydro-2H-5,9-epiminocycloocta[c]pyrazole (Intermediate 1) and 5-cyclopropyl-1-methyl-1H-pyrazole-4-carboxylic acid instead of quinoline-6-carboxylic acid. MS (ESI): mass calcd. for $C_{24}H_{25}Cl_2N_5O$, 469.1; m/z found, 470.1 [M+H]$^+$. $^1$H NMR (600 MHz, DMSO-d$_6$) δ 7.80-7.56 (m, 3H), 7.37 (d, J=75.0 Hz, 1H), 5.73-5.58 (m, 1H), 4.28-4.04 (m, 1H), 3.88-3.73 (m, 6H), 3.06-2.94 (m, 1H), 2.42 (d, J=16.1 Hz, 1H), 1.92-1.37 (m, 7H), 0.95-0.42 (m, 4H).

Example 145: ((5R,9S)-3-(3,5-Dichlorophenyl)-2-methyl-4,5,6,7,8,9-hexahydro-2H-5,9-epiminocycloocta[c]pyrazol-10-yl)(1-phenyl-1H-1,2,4-triazol-3-yl)methanone

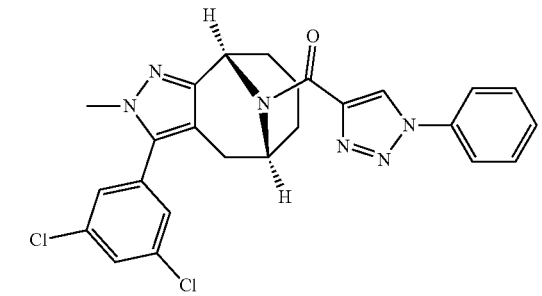 [SMILES: Cn1nc2c(c1-c1cc(Cl)cc(Cl)c1)C[C@H]1CCC[C@@H]2N1C(=O)c1cn(-c2ccccc2)nn1]

The title compound was prepared in a manner analogous to Example 1, using (5R,9S)-3-(3,5-dichlorophenyl)-2-methyl-4,5,6,7,8,9-hexahydro-2H-5,9-epiminocycloocta[c]pyrazole (Intermediate 19) instead of racemic-(5R,9S)-2-methyl-3-phenyl-4,5,6,7,8,9-hexahydro-2H-5,9-epiminocycloocta[c]pyrazole (Intermediate 1) and 1-phenyl-1H-1,2,4-triazole-3-carboxylic acid instead of quinoline-6-carboxylic acid. MS (ESI): mass calcd. for $C_{25}H_{22}Cl_2N_6O$, 492.1; m/z found, 493.1 [M+H]$^+$. $^1$H NMR (600 MHz, DMSO-d$_6$) δ 9.42 (d, J=15.2 Hz, 1H), 7.97-7.80 (m, 2H), 7.78-7.39 (m, 6H), 5.92-5.69 (m, 1H), 4.77-4.31 (m, 1H), 3.86-3.66 (m, 3H), 3.13-2.98 (m, 1H), 2.58 (dd, J=31.4, 16.1 Hz, 1H), 2.02-1.43 (m, 6H).

Example 146: ((5R,9S)-3-(3,5-Dichlorophenyl)-2-methyl-4,5,6,7,8,9-hexahydro-2H-5,9-epiminocycloocta[c]pyrazol-10-yl)(5-methoxypyridin-3-yl)methanone

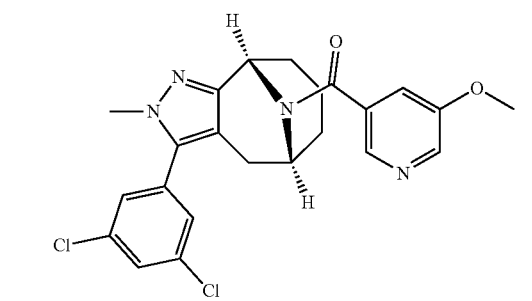 [SMILES: COc1cncc(C(=O)N2[C@@H]3CCC[C@H]2c2nn(C)c(-c4cc(Cl)cc(Cl)c4)c2C3)c1]

The title compound was prepared in a manner analogous to Example 1, using (5R,9S)-3-(3,5-dichlorophenyl)-2-methyl-4,5,6,7,8,9-hexahydro-2H-5,9-epiminocycloocta[c]pyrazole (Intermediate 19) instead of racemic-(5R,9S)-2-methyl-3-phenyl-4,5,6,7,8,9-hexahydro-2H-5,9-epiminocycloocta[c]pyrazole (Intermediate 1) and 5-methoxynicotinic acid instead of quinoline-6-carboxylic acid. MS (ESI): mass calcd. for $C_{23}H_{22}Cl_2N_4O_2$, 456.1; m/z found, 457.1 [M+H]$^+$. $^1$H NMR (600 MHz, DMSO-d$_6$) δ 8.46-8.32 (m, 1H), 8.27-8.10 (m, 1H), 7.77-7.58 (m, 3H), 7.47-7.30 (m, 1H), 5.80-5.62 (m, 1H), 4.04-3.98 (m, 1H), 3.88-3.69 (m, 6H), 3.13-2.96 (m, 1H), 2.42 (d, J=16.1 Hz, 1H), 2.01-1.36 (m, 6H).

Example 147: ((5R,9S)-3-(3,5-Dichlorophenyl)-2-methyl-4,5,6,7,8,9-hexahydro-2H-5,9-epiminocycloocta[c]pyrazol-10-yl)(6-methyl-3-(2H-1,2,3-triazol-2-yl)pyridin-2-yl)methanone

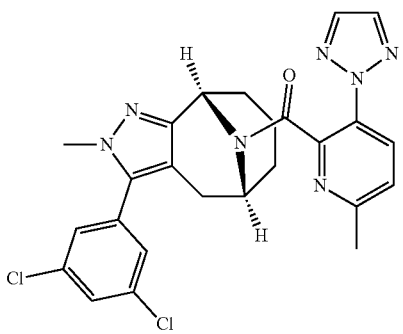 [SMILES: Cc1ccc(-n2nccn2)c(C(=O)N2[C@@H]3CCC[C@H]2c2nn(C)c(-c4cc(Cl)cc(Cl)c4)c2C3)n1]

The title compound was prepared in a manner analogous to Example 1, using (5R,9S)-3-(3,5-dichlorophenyl)-2-methyl-4,5,6,7,8,9-hexahydro-2H-5,9-epiminocycloocta[c]pyrazole (Intermediate 19) instead of racemic-(5R,9S)-2-methyl-3-phenyl-4,5,6,7,8,9-hexahydro-2H-5,9-epiminocycloocta[c]pyrazole (Intermediate 1) and 6-methyl-3-(2H-1,2,3-triazol-2-yl) picolinic acid [WO2016040789] instead of quinoline-6-carboxylic acid. MS (ESI): mass calcd. for $C_{25}H_{23}Cl_2N_7O$, 507.1; m/z found, 508.1 [M+H]$^+$. $^1$H NMR (500 MHz, DMSO-d$_6$) δ 8.23 (dd, J=9.6, 8.4 Hz, 1H), 8.04 (d, J=41.6 Hz, 2H), 7.72-7.47 (m, 4H), 5.73-5.52 (m, 1H), 3.91-3.84 (m, 1H), 3.83-3.66 (m, 3H), 2.90-2.67 (m, 1H), 2.59-2.52 (m, 3H), 2.46-2.35 (m, 1H), 1.94-1.30 (m, 6H).

Example 148: ((5R,9S)-3-(3,5-Dichlorophenyl)-2-methyl-4,5,6,7,8,9-hexahydro-2H-5,9-epiminocycloocta[c]pyrazol-10-yl)(2-methylbenzo[d]oxazol-6-yl)methanone

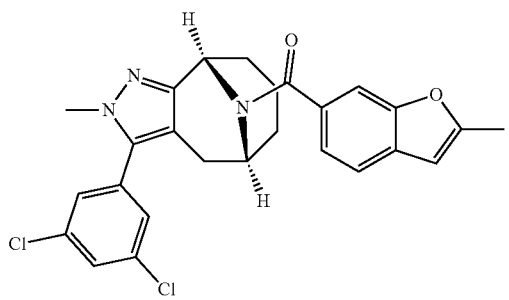 [SMILES: Cc1cc2ccc(C(=O)N3[C@@H]4CCC[C@H]3c3nn(C)c(-c5cc(Cl)cc(Cl)c5)c3C4)cc2o1]

The title compound was prepared in a manner analogous to Example 1, using (5R,9S)-3-(3,5-dichlorophenyl)-2-methyl-4,5,6,7,8,9-hexahydro-2H-5,9-epiminocycloocta[c]pyrazole (Intermediate 19) instead of racemic-(5R,9S)-2-methyl-3-phenyl-4,5,6,7,8,9-hexahydro-2H-5,9-epiminocycloocta[c]pyrazole (Intermediate 1) and 2-methylbenzo[d]oxazole-6-carboxylic acid instead of quinoline-6-carboxylic acid. MS (ESI): mass calcd. for $C_{25}H_{22}Cl_2N_4O_2$, 480.1; m/z found, 481.1 [M+H]$^+$. $^1$H NMR (600 MHz, DMSO-d$_6$) δ 7.83-7.60 (m, 5H), 7.45-7.27 (m, 1H), 5.75-5.57 (m, 1H), 4.11-3.96 (m, 1H), 3.84-3.67 (m, 3H), 3.15-2.99 (m, 1H), 2.64 (d, 3H), 2.40 (d, J=16.0 Hz, 1H), 2.03-1.39 (m, 6H).

Example 149: ((5R,9S)-3-(3,5-Dichlorophenyl)-2-methyl-4,5,6,7,8,9-hexahydro-2H-5,9-epiminocycloocta[c]pyrazol-10-yl)(furo[3,2-b]pyridin-2-yl)methanone

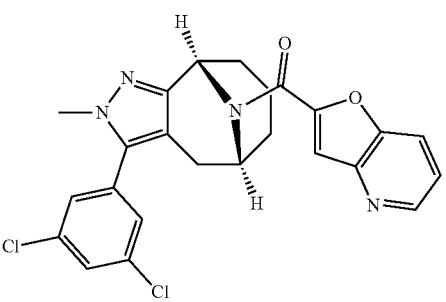 [SMILES: Cn1nc2c(c1-c1cc(Cl)cc(Cl)c1)C[C@H]1CCC[C@@H]2N1C(=O)c1cc2ncccc2o1]

The title compound was prepared in a manner analogous to Example 1, using (5R,9S)-3-(3,5-dichlorophenyl)-2-methyl-4,5,6,7,8,9-hexahydro-2H-5,9-epiminocycloocta[c]pyrazole (Intermediate 19) instead of racemic-(5R,9S)-2-methyl-3-phenyl-4,5,6,7,8,9-hexahydro-2H-5,9-epiminocycloocta[c]pyrazole (Intermediate 1) and furo[3,2-b] pyridine-2-carboxylic acid instead of quinoline-6-carboxylic acid. MS (ESI): mass calcd. for $C_{24}H_{20}Cl_2N_4O_2$, 466.1; m/z found, 467.1 [M+H]$^+$. $^1$H NMR (600 MHz, DMSO-d$_6$) δ 8.63 (dd, J=13.0, 4.6 Hz, 1H), 8.23-8.10 (m, 1H), 7.79-7.39 (m, 5H), 5.78-5.35 (m, 1H), 5.06-4.66 (m, 1H), 3.87-3.70 (m, 3H), 3.30-3.03 (m, 1H), 2.65-2.56 (m, 1H), 2.12-1.45 (m, 6H).

Example 150: ((5R,9S)-3-(3,5-Dichlorophenyl)-2-methyl-4,5,6,7,8,9-hexahydro-2H-5,9-epiminocycloocta[c]pyrazol-10-yl)(imidazo[1,5-a]pyridin-8-yl)methanone

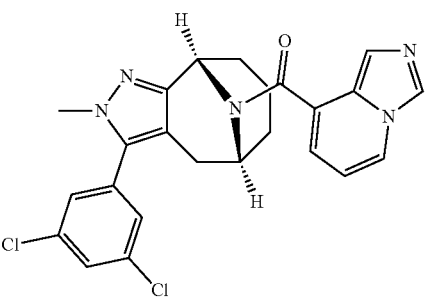 [SMILES: Cn1nc2c(c1-c1cc(Cl)cc(Cl)c1)C[C@H]1CCC[C@@H]2N1C(=O)c1cccn2cncc12]

The title compound was prepared in a manner analogous to Example 1, using (5R,9S)-3-(3,5-dichlorophenyl)-2-methyl-4,5,6,7,8,9-hexahydro-2H-5,9-epiminocycloocta[c]pyrazole (Intermediate 19) instead of racemic-(5R,9S)-2-methyl-3-phenyl-4,5,6,7,8,9-hexahydro-2H-5,9-epiminocycloocta[c]pyrazole (Intermediate 1) and imidazo[1,5-a] pyridine-8-carboxylic acid instead of quinoline-6-carboxylic acid. MS (ESI): mass calcd. for $C_{24}H_{21}Cl_2N_5O$, 465.1; m/z found, 466.1 [M+H]$^+$. $^1$H NMR (500 MHz, DMSO-d$_6$) δ 8.53-8.29 (m, 2H), 7.74-7.55 (m, 3H), 7.24 (d, J=54.5 Hz, 1H), 6.83-6.64 (m, 2H), 5.82-5.61 (m, 1H), 4.11-3.93 (m, 1H), 3.85-3.67 (m, 3H), 3.19-2.90 (m, 1H), 2.45-2.33 (m, 1H), 2.01-1.36 (m, 6H).

Example 151: ((5R,9S)-3-(3,5-Dichlorophenyl)-2-methyl-4,5,6,7,8,9-hexahydro-2H-5,9-epiminocycloocta[c]pyrazol-10-yl)(imidazo[1,2-a]pyridin-3-yl)methanone

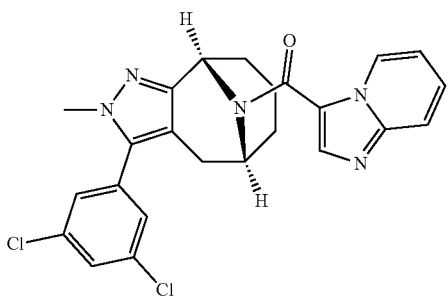 [SMILES: Cn1nc2c(c1-c1cc(Cl)cc(Cl)c1)C[C@H]1CCC[C@@H]2N1C(=O)c1cnc2ccccn12]

The title compound was prepared in a manner analogous to Example 1, using (5R,9S)-3-(3,5-dichlorophenyl)-2-methyl-4,5,6,7,8,9-hexahydro-2H-5,9-epiminocycloocta[c]pyrazole (Intermediate 19) instead of racemic-(5R,9S)-2-methyl-3-phenyl-4,5,6,7,8,9-hexahydro-2H-5,9-epiminocycloocta[c]pyrazole (Intermediate 1) and imidazo[1,2-a]pyridine-3-carboxylic acid instead of quinoline-6-carboxylic acid. MS (ESI): mass calcd. for $C_{24}H_{21}Cl_2N_5O$, 465.1; m/z found, 466.1 [M+H]$^+$. $^1$H NMR (500 MHz, DMSO-$d_6$) δ 9.00-8.81 (m, 1H), 8.06 (s, 1H), 7.77-7.59 (m, 4H), 7.49-7.40 (m, 1H), 7.17-6.98 (m, 1H), 5.68 (s, 1H), 4.92 (s, 1H), 3.80 (s, 3H), 3.28-3.05 (m, 1H), 2.55 (d, J=16.2 Hz, 1H), 2.07-1.44 (m, 6H).

Example 152: ((5R,9S)-3-(3,5-Dichlorophenyl)-2-methyl-4,5,6,7,8,9-hexahydro-2H-5,9-epiminocycloocta[c]pyrazol-10-yl)(quinolin-6-yl)methanone

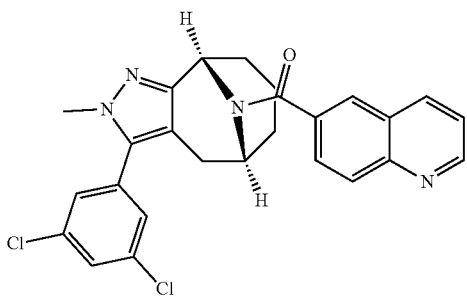 [SMILES: Cn1nc2c(c1-c1cc(Cl)cc(Cl)c1)C[C@H]1CCC[C@@H]2N1C(=O)c1ccc2ncccc2c1]

The title compound was prepared in a manner analogous to Example 1, using (5R,9S)-3-(3,5-dichlorophenyl)-2-methyl-4,5,6,7,8,9-hexahydro-2H-5,9-epiminocycloocta[c]pyrazole (Intermediate 19) instead of racemic-(5R,9S)-2-methyl-3-phenyl-4,5,6,7,8,9-hexahydro-2H-5,9-epiminocycloocta[c]pyrazole (Intermediate 1). MS (ESI): mass calcd. for $C_{26}H_{22}Cl_2N_4O$, 476.1; m/z found, 477.1 [M+H]$^+$. $^1$H NMR (600 MHz, DMSO-$d_6$) δ 9.04-8.86 (m, 1H), 8.52-8.34 (m, 1H), 8.13-7.99 (m, 2H), 7.83-7.48 (m, 5H), 5.83-5.59 (m, 1H), 4.18-3.98 (m, 1H), 3.84-3.71 (m, 3H), 3.12-2.97 (m, 1H), 2.45 (d, J=16.1 Hz, 1H), 2.04-1.40 (m, 6H).

Example 153: ((5R,9S)-3-(3,5-Dichlorophenyl)-2-methyl-4,5,6,7,8,9-hexahydro-2H-5,9-epiminocycloocta[c]pyrazol-10-yl)(quinoxalin-6-yl)methanone

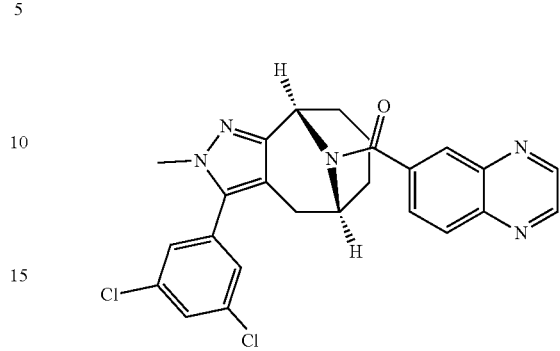

The title compound was prepared in a manner analogous to Example 1, using (5R,9S)-3-(3,5-dichlorophenyl)-2-methyl-4,5,6,7,8,9-hexahydro-2H-5,9-epiminocycloocta[c]pyrazole (Intermediate 19) instead of racemic-(5R,9S)-2-methyl-3-phenyl-4,5,6,7,8,9-hexahydro-2H-5,9-epiminocycloocta[c]pyrazole (Intermediate 1) and quinoxaline-6-carboxylic acid instead of quinoline-6-carboxylic acid. MS (ESI): mass calcd. for $C_{25}H_{21}Cl_2N_5O$, 477.1; m/z found, 478.1 [M+H]$^+$. $^1$H NMR (600 MHz, DMSO-$d_6$) δ 9.13-8.90 (m, 2H), 8.28-8.00 (m, 2H), 7.97-7.44 (m, 4H), 5.86-5.68 (m, 1H), 4.14-3.99 (m, 1H), 3.88-3.68 (m, 3H), 3.17-3.01 (m, 1H), 2.47-2.31 (m, 1H), 2.04-1.40 (m, 6H).

Example 154: racemic-((5R,9S)-3-(3-(Difluoromethyl)-4-fluorophenyl)-2-methyl-4,5,6,7,8,9-hexahydro-2H-5,9-epiminocycloocta[c]pyrazol-10-yl)(quinolin-6-yl) methanone

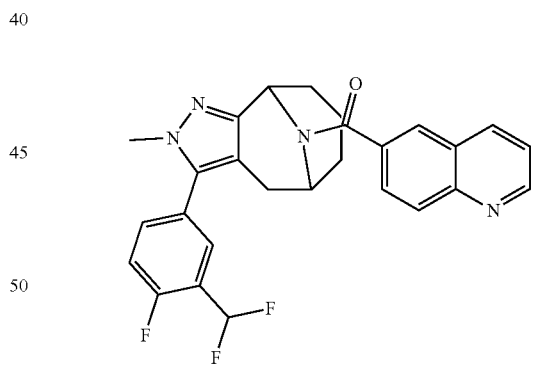

The title compound was prepared in a manner analogous to Example 1, using racemic-(5R,9S)-3-(3-(difluoromethyl)-4-fluorophenyl)-2-methyl-4,5,6,7,8,9-hexahydro-2H-5,9-epiminocycloocta[c]pyrazole (Intermediate 10) instead of racemic-(5R,9S)-2-methyl-3-phenyl-4,5,6,7,8,9-hexahydro-2H-5,9-epiminocycloocta[c]pyrazol (Intermediate 1). MS (ESI): mass calcd. for $C_{27}H_{23}F_3N_4O$, 476.1; m/z found, 477.1 [M+H]$^+$. $^1$H NMR (500 MHz, DMSO-$d_6$) δ 9.08-8.88 (m, 1H), 8.48 (t, J=7.9 Hz, 1H), 8.18-8.02 (m, 2H), 7.87-7.71 (m, 3H), 7.66-7.48 (m, 2H), 7.43-7.05 (m, 1H), 5.77 (s, 1H), 4.13 (s, 1H), 3.88-3.65 (m, 3H), 3.17-2.97 (m, 1H), 2.43 (d, J=16.1 Hz, 1H), 2.07-1.42 (m, 6H).

Example 155: racemic-((5R,9S)-3-(3-(Difluoromethyl)-4-fluorophenyl)-2-methyl-4,5,6,7,8,9-hexahydro-2H-5,9-epiminocycloocta[c]pyrazol-10-yl)(quinoxalin-6-yl) methanone

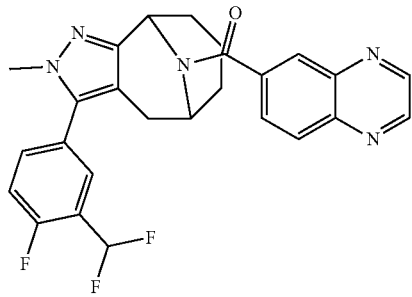 [SMILES: Cn1nc2c(c1-c1ccc(F)c(C(F)F)c1)CC1CCCC2N1C(=O)c1ccc2nccnc2c1]

The title compound was prepared in a manner analogous to Example 1, using racemic-(5R,9S)-3-(3-(difluoromethyl)-4-fluorophenyl)-2-methyl-4,5,6,7,8,9-hexahydro-2H-5,9-epiminocycloocta[c]pyrazole (Intermediate 10) instead of racemic-(5R,9S)-2-methyl-3-phenyl-4,5,6,7,8,9-hexahydro-2H-5,9-epiminocycloocta[c]pyrazole (Intermediate 1) and quinoxaline-6-carboxylic acid instead of quinoline-6-carboxylic acid. MS (ESI): mass calcd. for $C_{26}H_{22}F_3N_5O$, 477.1; m/z found, 478.1 [M+H]$^+$. $^1$H NMR (500 MHz, DMSO-$d_6$) δ 9.11-8.90 (m, 2H), 8.27-8.01 (m, 2H), 7.97-7.72 (m, 3H), 7.64-7.46 (m, 1H), 7.39-7.07 (m, 1H), 5.79 (s, 1H), 4.09 (t, J=5.7 Hz, 1H), 3.83-3.63 (m, 3H), 3.22-2.89 (m, 1H), 2.40 (d, J=16.1 Hz, 1H), 2.06-1.34 (m, 6H).

Example 156: ((5R,9S)-3-(3-Fluoro-5-(trifluoromethyl) phenyl)-2-methyl-4,5,6,7,8,9-hexahydro-2H-5,9-epiminocycloocta[c]pyrazol-10-yl) (quinoxalin-6-yl) methanone

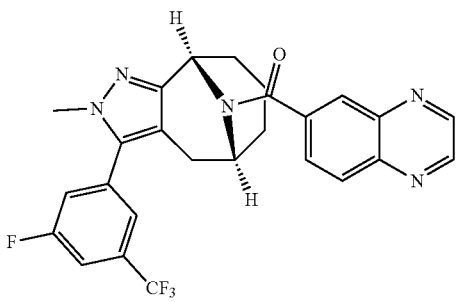

The title compound was prepared in a manner analogous to Example 1, using (5R,9S)-3-(3-fluoro-5-(trifluoromethyl) phenyl)-2-methyl-4,5,6,7,8,9-hexahydro-2H-5,9-epiminocycloocta[c]pyrazole (Intermediate 16) instead of racemic-(5R,9S)-2-methyl-3-phenyl-4,5,6,7,8,9-hexahydro-2H-5,9-epiminocycloocta[c]pyrazole (Intermediate 1) and quinoxaline-6-carboxylic acid instead of quinoline-6-carboxylic acid. MS (ESI): mass calcd. for $C_{26}H_{21}F_4N_5O$, 495.2; m/z found, 496.2 [M+H]$^+$. $^1$H NMR (500 MHz, DMSO-$d_6$) δ 9.11-8.88 (m, 2H), 8.26-8.00 (m, 2H), 7.94-7.67 (m, 4H), 5.79 (s, 1H), 4.09 (s, 1H), 3.89-3.71 (m, 3H), 3.14-3.03 (m, 1H), 2.49-2.37 (m, 1H), 2.02-1.31 (m, 6H).

Example 157: (3-Chloro-5-methoxyphenyl)((5R,9S)-2-methyl-3-(3,4,5-trifluorophenyl)-4,5,6,7,8,9-hexahydro-2H-5,9-epiminocycloocta[c]pyrazol-10-yl)methanone

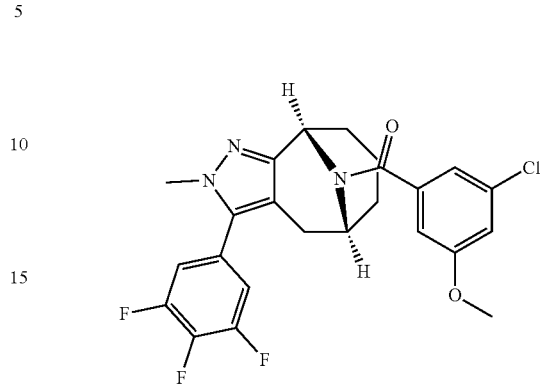

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 3-chloro-5-methoxybenzoic acid instead of quinoline-6-carboxylic acid. MS (ESI): mass calcd. for $C_{24}H_{21}ClF_3N_3O_2$, 475.1; m/z found, 476.1 [M+H]$^+$. $^1$H NMR (400 MHz, DMSO-$d_6$) δ 7.58 (t, J=7.8 Hz, 2H), 7.19-6.78 (m, 3H), 5.67 (s, 1H), 4.00 (s, 1H), 3.86-3.66 (m, 6H), 3.05-2.91 (m, 1H), 2.45-2.39 (m, 1H), 1.96-1.32 (m, 6H).

Example 158: N-(3-Methoxy-5-((5R,9S)-2-methyl-3-(3,4,5-trifluorophenyl)-4,5,6,7,8,9-hexahydro-2H-5,9-epiminocycloocta[c]pyrazole-10-carbonyl) phenyl)acetamide

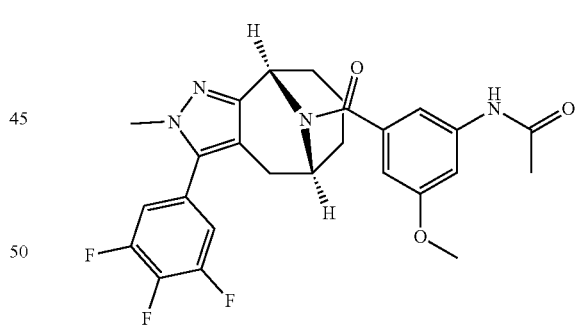

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 3-acetamido-5-methoxybenzoic acid instead of quinoline-6-carboxylic acid. MS (ESI): mass calcd. for $C_{26}H_{25}F_3N_4O_3$, 498.1; m/z found, 499.0 [M+H]$^+$. $^1$H NMR (500 MHz, DMSO-$d_6$) δ 10.12-9.96 (m, 1H), 7.66-7.43 (m, 2H), 7.39-7.14 (m, 2H), 6.64-6.47 (m, 1H), 5.83-5.55 (m, 1H), 4.15-3.96 (m, 1H), 3.86-3.64 (m, 6H), 3.12-2.90 (m, 1H), 2.48-2.30 (m, 1H), 2.04 (d, J=2.2 Hz, 3H), 1.96-1.35 (m, 6H).

Example 159: (3-(4H-1,2,4-Triazol-4-yl)phenyl)
((5R,9S)-2-methyl-3-(3,4,5-trifluorophenyl)-4,5,6,7,
8,9-hexahydro-2H-5,9-epiminocycloocta[c]pyrazol-
10-yl)methanone

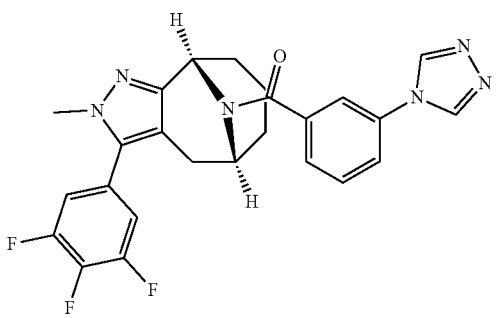 [SMILES: Cn1nc2c(c1-c1cc(F)c(F)c(F)c1)C[C@H]1CCC[C@@H]2N1C(=O)c1cccc(-n2cnnc2)c1]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 3-(4H-1,2,4-triazol-4-yl)benzoic acid instead of quinoline-6-carboxylic acid. MS (ESI): mass calcd. for $C_{25}H_{21}F_3N_6O$, 478.1; m/z found, 479.1 [M+H]$^+$. $^1$H NMR (600 MHz, DMSO-d$_6$) δ 9.20 (d, J=5.7 Hz, 2H), 7.93-7.74 (m, 2H), 7.74-7.58 (m, 3H), 7.54-7.35 (m, 1H), 5.79-5.64 (m, 1H), 4.08-3.94 (m, 1H), 3.87-3.70 (m, 3H), 3.11-2.97 (m, 1H), 2.47-2.34 (m, 1H), 2.05-1.35 (m, 6H).

Example 160: (2-(4H-1,2,4-Triazol-4-yl)phenyl)
((5R,9S)-2-methyl-3-(3,4,5-trifluorophenyl)-4,5,6,7,
8,9-hexahydro-2H-5,9-epiminocycloocta[c]pyrazol-
10-yl)methanone

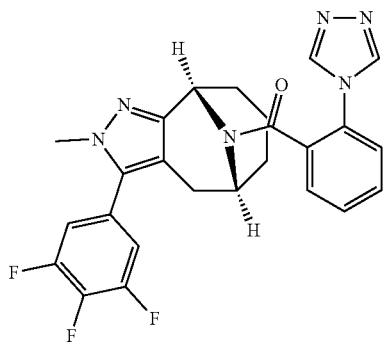 [SMILES: Cn1nc2c(c1-c1cc(F)c(F)c(F)c1)C[C@H]1CCC[C@@H]2N1C(=O)c1ccccc1-n1cnnc1]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 2-(4H-1,2,4-triazol-4-yl)benzoic acid instead of quinoline-6-carboxylic acid. MS (ESI): mass calcd. for $C_{25}H_{21}F_3N_6O$, 478.1; m/z found, 479.1 [M+H]$^+$. $^1$H NMR (500 MHz, DMF-d$_7$) δ 9.33-8.96 (m, 1H), 8.56 (s, 2H), 8.17-7.78 (m, 5H), 6.15-5.99 (m, 1H), 4.88-4.63 (m, 1H), 4.20-4.06 (m, 3H), 3.51-3.21 (m, 1H), 2.81-2.62 (m, 1H), 2.27-1.63 (m, 6H).

Example 161: (3-Fluoro-2-(1H-1,2,4-triazol-1-yl)
phenyl)((5R,9S)-2-methyl-3-(3,4,5-trifluorophenyl)-
4,5,6,7,8,9-hexahydro-2H-5,9-epiminocycloocta[c]
pyrazol-10-yl)methanone

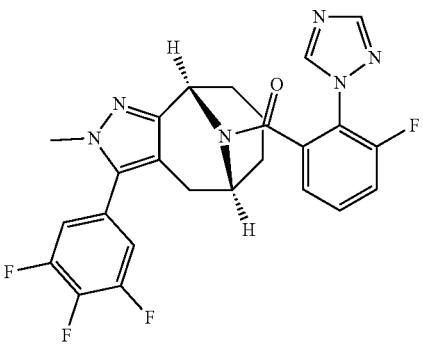 [SMILES: Cn1nc2c(c1-c1cc(F)c(F)c(F)c1)C[C@H]1CCC[C@@H]2N1C(=O)c1cccc(F)c1-n1cncn1]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 3-fluoro-2-(1H-1,2,4-triazol-1-yl)benzoic acid (Intermediate 54) instead of quinoline-6-carboxylic acid. MS (ESI): mass calcd. for $C_{25}H_{20}F_4N_6O$, 496.2; m/z found, 497.1 [M+H]$^+$. $^1$H NMR (300 MHz, DMSO-d$_6$) δ 9.01-8.90 (m, 1H), 8.38-8.25 (m, 1H), 7.77-7.29 (m, 5H), 5.58-5.49 (m, 1H), 3.95-3.84 (m, 1H), 3.79 (s, 3H), 3.13-2.95 (m, 1H), 2.40-2.24 (m, 1H), 1.96-1.18 (m, 6H).

Example 162: (4-Fluoro-2-(1H-1,2,4-triazol-1-yl)
phenyl)((5R,9S)-2-methyl-3-(3-(3,4,5-trifluorophe-
nyl)-4,5,6,7,8,9-hexahydro-2H-5,9-epiminocycloocta
[c]pyrazol-10-yl)methanone

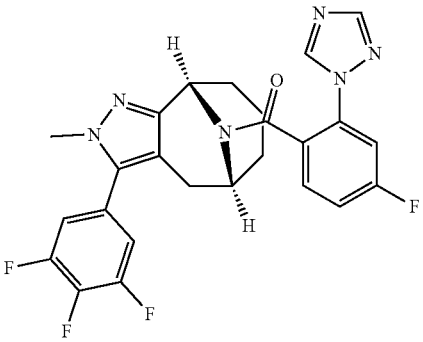 [SMILES: Cn1nc2c(c1-c1cc(F)c(F)c(F)c1)C[C@H]1CCC[C@@H]2N1C(=O)c1ccc(F)cc1-n1cncn1]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 4-fluoro-2-(1H-1,2,4-triazol-1-yl)benzoic acid (Intermediate 55)

instead of quinoline-6-carboxylic acid. MS (ESI): mass calcd. for $C_{25}H_{20}F_4N_6O$, 496.2; m/z found, 497.2 [M+H]$^+$. $^1$H NMR (300 MHz, DMSO-d$_6$) δ 9.02-8.94 (m, 1H), 8.32-8.24 (m, 1H), 7.89-7.33 (m, 5H), 5.68-5.57 (m, 1H), 3.87-3.65 (m, 1H), 3.80 (s, 3H), 2.97 (dd, J=16.3, 7.2 Hz, 1H), 2.42-2.33 (m, 1H), 1.80-1.16 (m, 6H).

Example 163: (5-Fluoro-2-(1H-1,2,4-triazol-1-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone

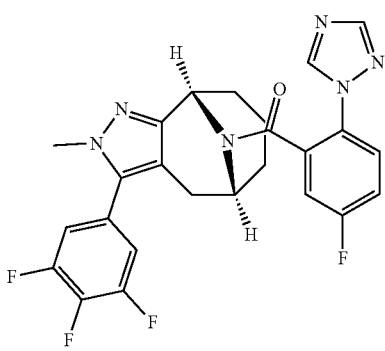

The title compound was prepared in a manner analogous to Example 1, using (5R,9S)-2-methyl-3-(3,4,5-trifluoro-phenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 5-fluoro-2-(1H-1,2,4-triazol-1-yl)benzoic acid (Intermediate 56) instead of quinoline-6-carboxylic acid. MS (ESI): mass calcd. for $C_{25}H_{20}F_4N_6O$, 496.2; m/z found, 497.1 [M+H]$^+$. $^1$H NMR (500 MHz, DMSO-d$_6$) δ 8.91-8.85 (m, 1H), 8.30-8.22 (m, 1H), 7.81-7.75 (m, 1H), 7.65-7.39 (m, 4H), 5.63-5.56 (m, 1H), 3.86-3.76 (m, 1H), 3.80 (s, 3H), 3.04 (dd, J=16.0, 7.4 Hz, 1H), 2.42-2.25 (m, 1H), 1.83-1.18 (m, 6H).

Example 164: (4-Methyl-2-(1H-1,2,4-triazol-1-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone

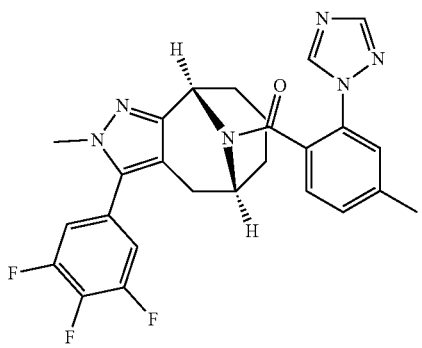 [SMILES: Cc1ccc(C(=O)N2[C@@H]3CCC[C@H]2c2nn(C)c(-c4cc(F)c(F)c(F)c4)c2C3)c(-n2cncn2)c1]

The title compound was prepared in a manner analogous to Example 1, using (5R,9S)-2-methyl-3-(3,4,5-trifluoro-phenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 4-methyl-2-(1H-1,2,4-triazol-1-yl)benzoic acid (Intermediate 57) instead of quinoline-6-carboxylic acid. MS (ESI): mass calcd. for $C_{26}H_{23}F_3N_6O$, 492.2; m/z found, 493.2 [M+H]$^+$. $^1$H NMR (300 MHz, DMSO-d$_6$) δ 8.96-8.83 (m, 1H), 8.29-8.20 (m, 1H), 7.68-7.29 (m, 5H), 5.67-5.57 (m, 1H), 3.86-3.77 (m, 1H), 3.79 (s, 3H), 2.95 (dd, J=16.0, 7.0 Hz, 1H), 2.42 (s, 3H), 2.45-2.24 (m, 1H), 1.77-0.97 (m, 6H).

Example 165: (5-Methyl-2-(1H-1,2,4-triazol-1-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone

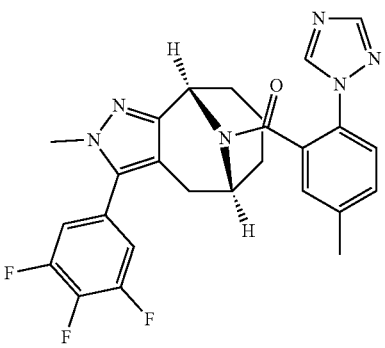 [SMILES: Cc1ccc(-n2cncn2)c(C(=O)N2[C@@H]3CCC[C@H]2c2nn(C)c(-c4cc(F)c(F)c(F)c4)c2C3)c1]

The title compound was prepared in a manner analogous to Example 1, using (5R,9S)-2-methyl-3-(3,4,5-trifluoro-phenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 5-methyl-2-(1H-1,2,4-triazol-1-yl)benzoic acid (Intermediate 58) instead of quinoline-6-carboxylic acid. MS (ESI): mass calcd. for $C_{26}H_{23}F_3N_6O$, 492.2; m/z found, 493.2 [M+H]$^+$. $^1$H NMR (300 MHz, DMSO-d$_6$) δ 8.85 (s, 1H), 8.23 (s, 1H), 7.68-7.52 (m, 3H), 7.48-7.36 (m, 2H), 5.66-5.59 (m, 1H), 3.80 (s, 3H), 3.70-3.63 (m, 1H), 2.99-2.86 (m, 1H), 2.39 (s, 3H), 2.46-2.22 (m, 1H), 1.92-1.17 (m, 6H).

Example 166: (2-(1H-1,2,4-Triazol-1-yl)-5-(trifluoromethyl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone

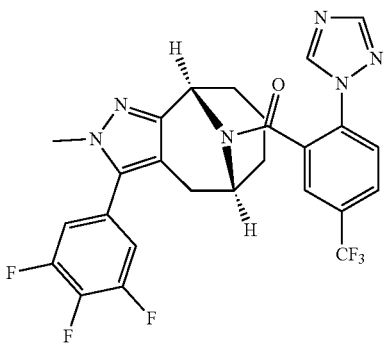 [SMILES: Cn1nc2c(c1-c1cc(F)c(F)c(F)c1)C[C@H]1CCC[C@@H]2N1C(=O)c1cc(C(F)(F)F)ccc1-n1cncn1]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 2-(1H-1,2,4-triazol-1-yl)-5-(trifluoromethyl)benzoic acid (Intermediate 52) instead of quinoline-6-carboxylic acid. MS (ESI): mass calcd. for $C_{26}H_{20}F_6N_6O$, 546.2; m/z found, 547.1 [M+H]$^+$. $^1$H NMR (300 MHz, DMSO-d$_6$) δ 9.09-9.04 (m, 1H), 8.39-8.30 (m, 1H), 8.12-7.81 (m, 3H), 7.66-7.52 (m, 1H), 7.54-7.36 (m, 1H), 5.71-5.62 (m, 1H), 3.80 (s, 3H), 3.84-3.70 (m, 1H), 2.97-2.79 (m, 1H), 2.45-2.21 (m, 1H), 1.88-1.19 (m, 6H).

Example 167: ((5R,9S)-2-Methyl-3-(3,4,5-trifluorophenyl)-4,5,6,7,8,9-hexahydro-2H-5,9-epiminocycloocta[c]pyrazol-10-yl)(2-(3-(trifluoromethyl)-1H-1,2,4-triazol-1-yl)phenyl methanone

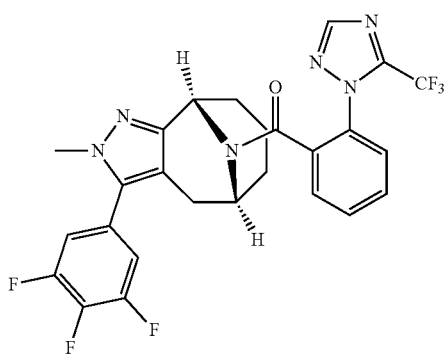 [SMILES: Cn1nc2c(c1-c1cc(F)c(F)c(F)c1)C[C@H]1CCC[C@@H]2N1C(=O)c1ccccc1-n1ncnc1C(F)(F)F]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 2-(3-(trifluoromethyl)-1H-1,2,4-triazol-1-yl)benzoic acid (Intermediate 53) instead of quinoline-6-carboxylic acid. MS (ESI): mass calcd. for $C_{26}H_{20}F_6N_6O$, 546.2; m/z found, 547.1 [M+H]$^+$. $^1$H NMR (500 MHz, DMSO-d$_6$) δ 9.34-9.30 (m, 1H), 7.87-7.82 (m, 1H), 7.77-7.57 (m, 3H), 7.56-7.51 (m, 1H), 7.41-7.31 (m, 1H), 5.60-5.55 (m, 1H), 4.01-3.92 (m, 1H), 3.80 (s, 3H), 3.11 (dd, J=16.3, 7.5 Hz, 1H), 2.46-2.40 (m, 1H), 1.95-1.29 (m, 6H).

Example 168: (2-(1H-Imidazol-1-yl)phenyl)((5R 9S)-2-methyl-3-(3,4,5-trifluorophenyl)-4,5,6,7,8,9-hexahydro-2H-5,9-epiminocycloocta[c]pyrazol-10-yl)methanone

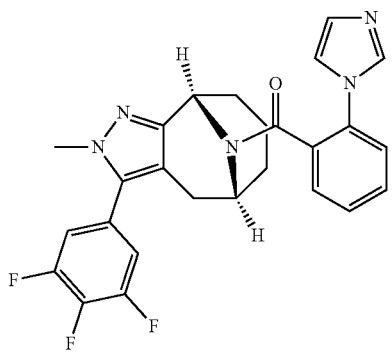 [SMILES: Cn1nc2c(c1-c1cc(F)c(F)c(F)c1)C[C@H]1CCC[C@@H]2N1C(=O)c1ccccc1-n1ccnc1]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 2-(1H-imidazol-1-yl)benzoic acid (Intermediate 43) instead of quinoline-6-carboxylic acid. MS (ESI): mass calcd. for $C_{26}H_{22}F_3N_5O$, 477.2; m/z found, 478.2 [M+H]$^+$. $^1$H NMR (300 MHz, DMSO-d$_6$) δ 8.15-6.58 (m, 9H), 5.75-5.63 (m, 1H), 3.78 (s, 3H), 3.66-3.53 (m, 1H), 2.86-2.69 (m, 1H), 2.39-2.23 (m, 1H), 1.93-1.03 (m, 6H).

Example 169: (5-Fluoro-2-(1H-pyrazol-1-yl)phenyl) ((5R,9S)-2-methyl-3-(3,4,5-trifluorophenyl)-4,5,6,7,8,9-hexahydro-2H-5,9-epiminocycloocta[c]pyrazol-10-yl)methanone

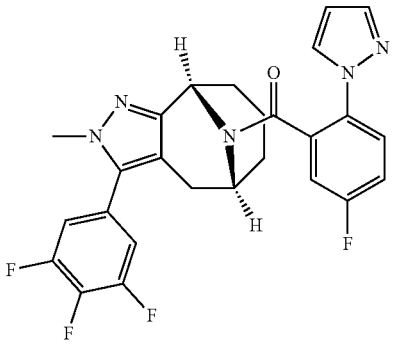 [SMILES: Cn1nc2c(c1-c1cc(F)c(F)c(F)c1)C[C@H]1CCC[C@@H]2N1C(=O)c1cc(F)ccc1-n1cccn1]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 5-fluoro-2-(1H-pyrazol-1-yl)benzoic acid instead of quinoline-6-carboxylic acid. MS (ESI): mass calcd. for $C_{26}H_{21}F_4N_5O$, 495.1; m/z found, 496.1 [M+H]$^+$. $^1$H NMR (600 MHz, DMSO-d$_6$) δ 8.18-7.82 (m, 1H), 7.73-7.28 (m, 6H), 6.65-

6.48 (m, 1H), 5.74-5.55 (m, 1H), 3.86-3.72 (m, 4H), 3.01-2.82 (m, 1H), 2.38-2.22 (m, 1H), 1.70-1.15 (m, 6H).

Example 170: (3-(1-Methyl-1H-pyrazol-4-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone

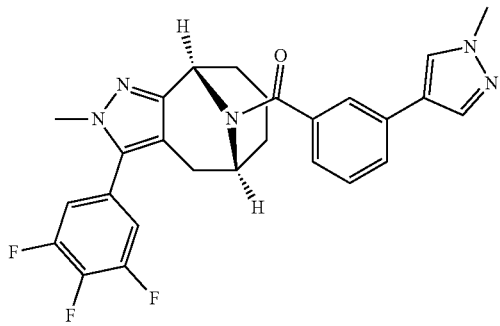 [SMILES: Cn1cc(-c2cccc(C(=O)N3[C@@H]4CCC[C@H]3c3nn(C)c(-c5cc(F)c(F)c(F)c5)c3C4)c2)cn1]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 3-(1-methyl-1H-pyrazol-4-yl)benzoic acid instead of quinoline-6-carboxylic acid. MS (ESI): mass calcd. for $C_{27}H_{24}F_3N_5O$, 491.1; m/z found, 492.1 [M+H]$^+$. $^1$H NMR (600 MHz, DMSO-d$_6$) δ 8.23 (d, J=7.4 Hz, 1H), 7.93 (dd, J=12.6, 0.8 Hz, 1H), 7.74-7.53 (m, 4H), 7.49-7.38 (m, 1H), 7.22-7.09 (m, 1H), 5.80-5.65 (m, 1H), 4.12-4.00 (m, 1H), 3.88-3.71 (m, 6H), 3.13-2.95 (m, 1H), 2.47-2.36 (m, 1H), 2.01-1.39 (m, 6H).

Example 171: (3-(4-Fluoro-1H-pyrazol-1-yl)phenyl)(5R,9S)-2-methyl-3-(3,4,5-trifluorophenyl)-4,5,6,7,8,9-hexahydro-2H-5,9-epiminocycloocta[c]pyrazol-10-yl)methanone

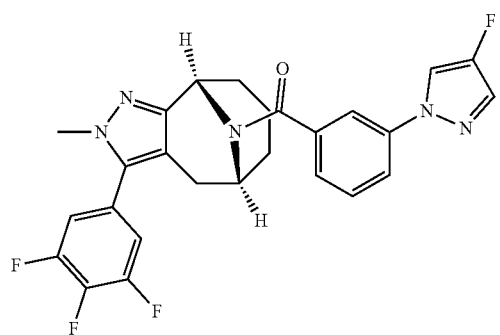 [SMILES: Cn1nc2c(c1-c1cc(F)c(F)c(F)c1)C[C@H]1CCC[C@@H]2N1C(=O)c1cccc(-n2cc(F)cn2)c1]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 3-(4-fluoro-1H-pyrazol-1-yl)benzoic acid (Intermediate 60) instead of quinoline-6-carboxylic acid. MS (ESI): mass calcd. for $C_{26}H_{21}F_4N_5O$, 495.2; m/z found, 496.2 [M+H]$^+$. $^1$H NMR (500 MHz, DMSO-d$_6$) δ 8.79 (d, J=4.4 Hz, 1H), 7.95-7.89 (m, 1H), 7.89-7.84 (m, 1H), 7.83-7.77 (m, 1H), 7.64-7.53 (m, 3H), 7.38-7.32 (m, 1H), 5.76-5.70 (m, 1H), 4.10-4.03 (m, 1H), 3.81 (s, 3H), 2.99 (dd, J=16.2, 7.3 Hz, 1H), 2.44 (d, J=16.3 Hz, 1H), 2.00-1.65 (m, 3H), 1.60 (d, J=13.2 Hz, 1H), 1.56-1.38 (m, 2H).

Example 172: ((5R,9S)-2-Methyl-3-(3,4,5-trifluorophenyl)-4,5,6,7,8,9-hexahydro-2H-5,9-epiminocycloocta[c]pyrazol-10-yl)(3-(4-(trifluoromethyl)-1H-pyrazol-1-yl)phenyl)methanone

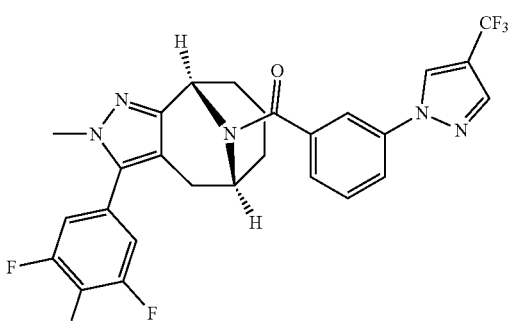

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 3-[4-(trifluoromethyl)pyrazol-1-yl]benzoic acid (Intermediate 59) instead of quinoline-6-carboxylic acid. MS (ESI): mass calcd. for $C_{27}H_{21}F_6N_5O$, 545.2; m/z found, 546.1 [M+H]$^+$. $^1$H NMR (500 MHz, DMSO-d$_6$) δ 9.31-9.26 (m, 1H), 8.26-8.22 (m, 1H), 8.04-8.00 (m, 1H), 7.96-7.94 (m, 1H), 7.68-7.54 (m, 3H), 7.46-7.41 (m, 1H), 5.76-5.71 (m, 1H), 4.09-4.02 (m, 1H), 3.82 (s, 3H), 3.01 (dd, J=16.2, 7.4 Hz, 1H), 2.46-2.40 (m, 1H), 2.03-1.38 (m, 6H).

Example 173: (3-(4-Methoxy-1H-pyrazol-1-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone

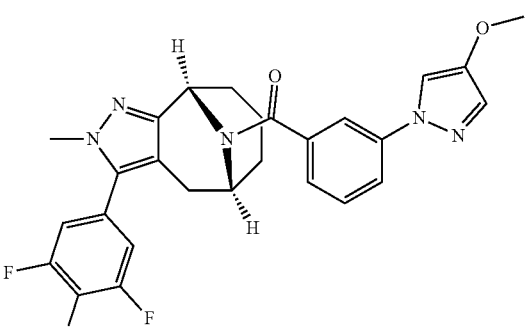

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 3-(4-methoxy-1H-pyrazol-1-yl)benzoic acid (Intermediate 61) instead of quinoline-6-carboxylic acid. MS (ESI): mass calcd. for $C_{27}H_{24}F_3N_5O_2$, 507.2; m/z found, 508.2 [M+H]$^+$. $^1$H NMR (500 MHz, DMSO-d$_6$) δ 8.40 (s, 1H), 7.92-7.86 (m, 1H), 7.82-7.78 (m, 1H), 7.64-7.51 (m, 3H), 7.57 (s, 1H), 7.31-7.25 (m, 1H), 5.76-5.70 (m, 1H), 4.09-4.04 (m, 1H), 3.82 (s, 3H), 3.77 (s, 3H), 3.01 (dd, J=16.2, 7.3 Hz, 1H), 2.44 (d, J=16.2 Hz, 1H), 1.99-1.37 (m, 6H).

Example 174: (5R,9S)-2-Methyl-3-(3,4,5-trifluorophenyl)-4,5,6,7,8,9-hexahydro-2H-5,9-epiminocycloocta[c]pyrazol-10-yl)(3-(3-(trifluoromethyl)-1H-pyrazol-1-yl)phenyl)methanone

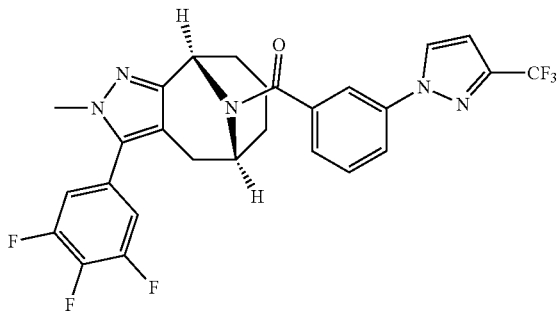 [SMILES: Cn1nc2c(c1-c1cc(F)c(F)c(F)c1)C[C@H]1CCC[C@@H]2N1C(=O)c1cccc(-n2ccc(C(F)(F)F)n2)c1]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 3-[3-(trifluoromethyl)pyrazol-1-yl]benzoic acid (Intermediate 44) instead of quinoline-6-carboxylic acid. MS (ESI): mass calcd. for $C_{27}H_{21}F_6N_5O$, 545.2; m/z found, 546.1 [M+H]$^+$. $^1$H NMR (300 MHz, DMSO-d$_6$) δ 8.88-8.78 (m, 1H), 8.07-7.97 (m, 1H), 7.95-7.83 (m, 1H), 7.72-7.53 (m, 3H), 7.50-7.42 (m, 1H), 7.12-7.03 (m, 1H), 5.78-5.68 (m, 1H), 4.15-4.01 (m, 1H), 3.82 (s, 3H), 3.03 (dd, J=16.1, 7.3 Hz, 1H), 2.59-2.36 (m, 1H), 2.05-1.38 (m, 6H).

Example 175: (3-(2H-1,2,3-Triazol-2-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone

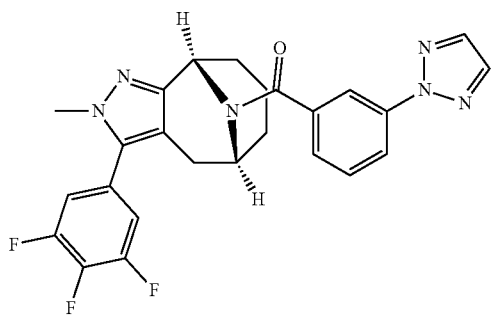 [SMILES: Cn1nc2c(c1-c1cc(F)c(F)c(F)c1)C[C@H]1CCC[C@@H]2N1C(=O)c1cccc(-n2nccn2)c1]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 3-(2H-1,2,3-triazol-2-yl)benzoic acid (Intermediate 51) instead of quinoline-6-carboxylic acid. MS (ESI): mass calcd. for $C_{25}H_{21}F_3N_6O$, 478.2; m/z found, 479.2 [M+H]$^+$. $^1$H NMR (500 MHz, DMSO-d$_6$) δ 8.15 (s, 2H), 8.13-8.09 (m, 1H), 8.02-7.98 (m, 1H), 7.70-7.55 (m, 3H), 7.49-7.44 (m, 1H), 5.73-5.69 (m, 1H), 4.12-4.06 (m, 1H), 3.80 (s, 3H), 2.99 (dd, J=16.3, 7.4 Hz, 1H), 2.44 (d, J=16.3 Hz, 1H), 1.98-1.35 (m, 6H).

Example 176: (5-Fluoro-2-(2H-1,2,3-triazol-2-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone

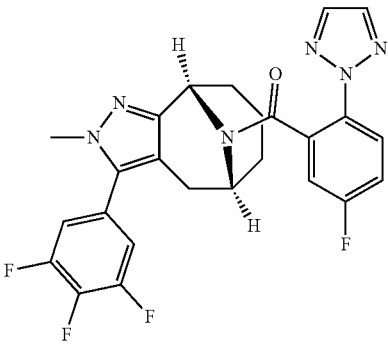 [SMILES: Cn1nc2c(c1-c1cc(F)c(F)c(F)c1)C[C@H]1CCC[C@@H]2N1C(=O)c1cc(F)ccc1-n1nccn1]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 5-fluoro-2-(2H-1,2,3-triazol-2-yl)benzoic acid [prepared according to procedure as described in PCT. Patent Pub. WO2016040789] instead of quinoline-6-carboxylic acid. MS (ESI): mass calcd. for $C_{25}H_{20}F_4N_6O$, 496.1; m/z found, 497.1 [M+H]$^+$. $^1$H NMR (600 MHz, DMSO-d$_6$) δ 8.17 (d, J=15.0 Hz, 1H), 8.03-7.86 (m, 1H), 7.79-6.98 (m, 5H), 5.65 (s, 1H), 4.41 (d, J=132.8 Hz, 1H), 3.93-3.60 (m, 3H), 3.11-2.94 (m, 1H), 2.43-2.29 (m, 1H), 1.94-1.23 (m, 6H).

Example 177: (3-Methyl-2-(2H-1,2,3-triazol-2-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone

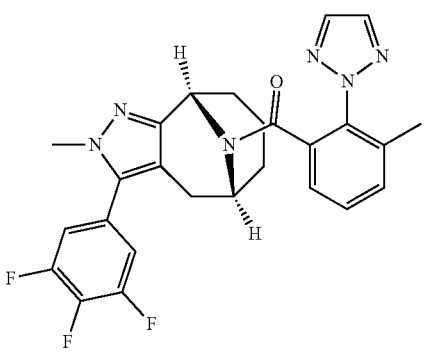 [SMILES: Cc1cccc(C(=O)N2[C@@H]3CCC[C@H]2c2nn(C)c(-c4cc(F)c(F)c(F)c4)c2C3)c1-n1nccn1]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 3-methyl-2-(2H-1,2,3-triazol-2-yl)benzoic acid [WO2016040789] instead of quinoline-6-carboxylic acid. MS (ESI): mass calcd. for $C_{26}H_{23}F_3N_6O$, 492.1; m/z found, 493.1 [M+H]$^+$. $^1$H NMR (600 MHz, DMSO-d$_6$) δ 8.11 (d, J=7.4 Hz, 1H), 7.79-7.36 (m, 5H), 7.35-6.89 (m, 1H), 5.53-5.43 (m, 1H), 3.98-3.86 (m, 1H), 3.82-3.69 (m, 3H), 3.08-2.97 (m, 1H), 2.39 (d, J=16.0 Hz, 1H), 2.19-2.05 (m, 3H), 1.96-1.26 (m, 6H).

Example 178: (3-Methoxy-2-(2H-1,2,3-triazol-2-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone

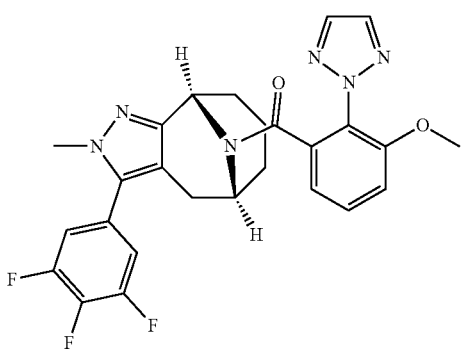 [SMILES: COc1cccc(C(=O)N2[C@@H]3CCC[C@H]2c2nn(C)c(-c4cc(F)c(F)c(F)c4)c2C3)c1-n1nccn1]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 3-methoxy-2-(2H-1,2,3-triazol-2-yl)benzoic acid (Intermediate 47) instead of quinoline-6-carboxylic acid. MS (ESI): mass calcd. for $C_{26}H_{23}F_3N_6O_2$, 508.2; m/z found, 509.2 [M+H]$^+$. $^1$H NMR (500 MHz, DMSO-d$_6$) δ 8.01 (s, 2H), 7.65-7.53 (m, 3H), 7.38-7.28 (m, 1H), 7.03-6.96 (m, 1H), 5.42 (s, 1H), 3.95-3.88 (m, 1H), 3.78 (s, 3H), 3.76 (s, 3H), 2.99 (dd, J=16.1, 7.3 Hz, 1H), 2.38 (d, J=16.0 Hz, 1H), 1.97-1.21 (m, 6H).

Example 179: (4-Methoxy-2-(2H-1,2,3-triazol-2-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone

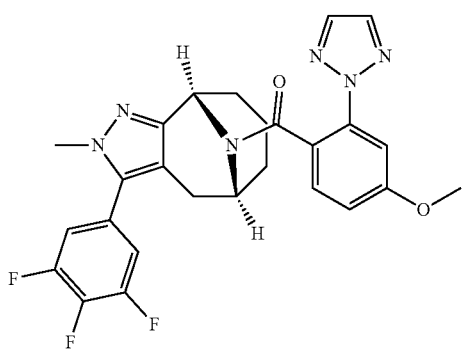 [SMILES: COc1ccc(C(=O)N2[C@@H]3CCC[C@H]2c2nn(C)c(-c4cc(F)c(F)c(F)c4)c2C3)c(-n2nccn2)c1]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 4-methoxy-2-(2H-1,2,3-triazol-2-yl)benzoic acid [WO2016040789] instead of quinoline-6-carboxylic acid. MS (ESI): mass calcd. for $C_{26}H_{23}F_3N_6O_2$, 508.2; m/z found, 509.1 [M+H]$^+$. $^1$H NMR (600 MHz, DMSO-d$_6$) δ 8.16 (d, J=14.0 Hz, 1H), 7.89-6.79 (m, 6H), 5.65 (s, 1H), 4.57-4.24 (m, 1H), 3.94-3.51 (m, 6H), 3.13-2.91 (m, 1H), 2.43-2.25 (m, 1H), 1.91-1.17 (m, 6H).

Example 180: (5-Methoxy-2-(2H-1,2,3-triazol-2-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone

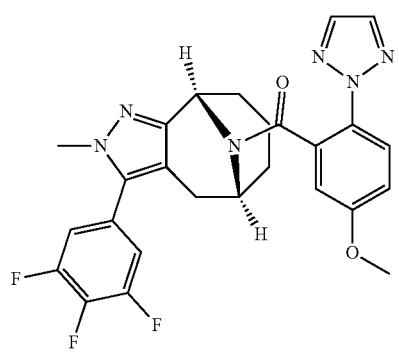 [SMILES: COc1ccc(-n2nccn2)c(C(=O)N2[C@@H]3CCC[C@H]2c2nn(C)c(-c4cc(F)c(F)c(F)c4)c2C3)c1]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2- methyl-3-phenyl-4,5,6,7,8,9-hexahydro-2H-5,9-epiminocycloocta[c]pyrazole (Intermediate 1) and 5-methoxy-2-(2H-1,2,3-triazol-2-yl)benzoic acid (Intermediate 46) instead of quinoline-6-carboxylic acid. MS (ESI): mass calcd. for $C_{26}H_{23}F_3N_6O_2$, 508.2; m/z found, 509.2 [M+H]$^+$. $^1$H NMR (300 MHz, DMSO-d$_6$) δ 8.10 (d, J=5.0 Hz, 1H), 7.88-7.72 (m, 1H), 7.71-7.37 (m, 3H), 7.25-7.13 (m, 1H), 6.91 (d, J=2.8 Hz, 1H), 5.70-5.60 (m, 1H), 3.89 (s, 1H), 3.83 (s, 3H), 3.80 (s, 3H), 3.02-2.90 (m, 1H), 2.40-2.22 (m, 1H), 1.98-1.20 (m, 6H).

Example 181:(2-(2H-1,2,3-Triazol-2-yl)-3-(trifluoromethyl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone

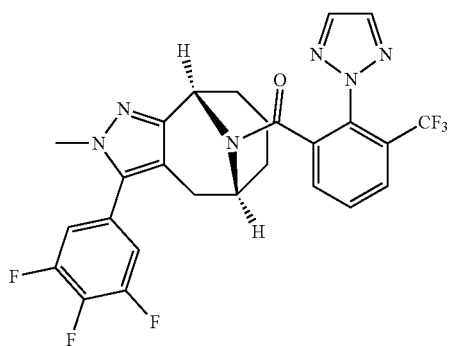 [SMILES: Cn1nc2c(c1-c1cc(F)c(F)c(F)c1)C[C@H]1CCC[C@@H]2N1C(=O)c1cccc(C(F)(F)F)c1-n1nccn1]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 2-(2H-1,2,3-triazol-2-yl)-3-(trifluoromethyl)benzoic acid (Intermediate 77) instead of quinoline-6-carboxylic acid. MS (ESI): mass calcd. for $C_{26}H_{20}F_6N_6O$, 546.2; m/z found, 547.1 [M+H]$^+$. $^1$H NMR (500 MHz, DMSO-d$_6$) δ 8.29-8.15 (m, 1H), 8.24-8.23 (m, 1H), 7.97-7.79 (m, 1H), 7.86-7.84 (m, 1H), 7.69-7.53 (m, 3H), 5.73-5.67 (m, 1H), 3.91-3.71 (m, 1H), 3.81 (s, 3H), 3.05-2.93 (m, 1H), 2.42-2.34 (m, 1H), 1.98-1.60 (m, 2H), 1.59-1.17 (m, 4H).

Example 182: (2-(2H-1,2,3-Triazol-2-yl)-5-(trifluoromethyl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone

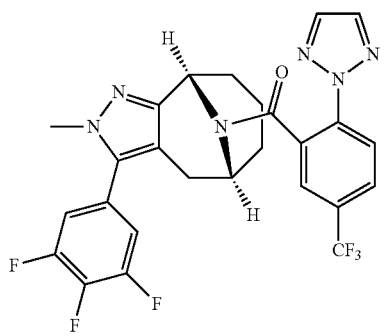

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 2-(2H-1,2,3-triazol-2-yl)-5-(trifluoromethyl)benzoic acid (Intermediate 45) instead of quinoline-6-carboxylic acid. MS (ESI): mass calcd. for $C_{26}H_{20}F_6N_6O$, 546.2; m/z found, 547.1 [M+H]$^+$. $^1$H NMR (300 MHz, DMSO-d$_6$) δ 8.27-8.25 (m, 1H), 8.23-8.10 (m, 1H), 8.08-7.96 (m, 1H), 7.89-7.85 (m, 1H), 7.79-7.74 (m, 1H), 7.65-7.51 (m, 2H), 5.76-5.65 (m, 1H), 3.86-3.72 (m, 1H), 3.81 (s, 3H), 2.96-2.83 (m, 1H), 2.46-2.29 (m, 1H), 2.11-1.20 (m, 6H).

Example 183: (2-(1H-1,2,3-Triazol-1-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone

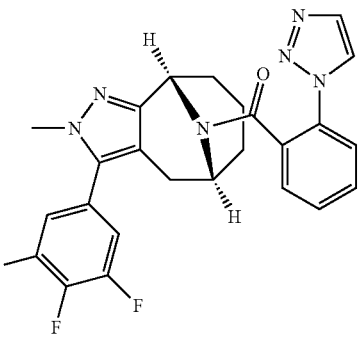

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 2-(1H-1,2,3-triazol-1-yl)benzoic acid (Intermediate 50) instead of quinoline-6-carboxylic acid. MS (ESI): mass calcd. for $C_{25}H_{21}F_3N_6O$, 478.2; m/z found, 479.2 [M+H]$^+$. $^1$H NMR (500 MHz, DMSO-d$_6$) δ 8.51-8.46 (m, 1H), 7.99-7.94 (m, 1H), 7.74-7.55 (m, 5H), 7.54-7.42 (m, 1H), 5.63-5.58 (m, 1H), 3.87-3.73 (m, 1H), 3.79 (s, 3H), 2.97 (dd, J=16.1, 7.3 Hz, 1H), 2.42-2.31 (m, 1H), 1.81-1.20 (m, 6H).

Example 184: (3-Methoxy-2-(1H-1,2,3-triazol-1-yl)phenyl)((5R,9S)-2-methyl-3-(3,4,5-trifluorophenyl)-4,5,6,7,89-hexahydro-2H-5,9-epiminocycloocta[c]pyrazol-10-yl)methanone

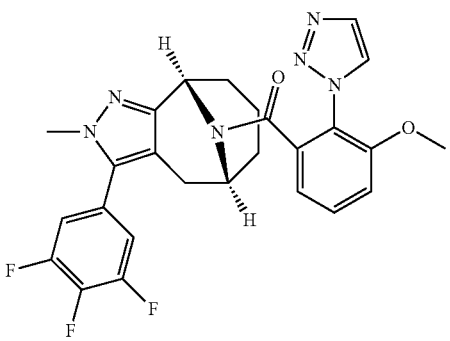

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 3-methoxy-2-(1H-1,2,3-triazol-1-yl)benzoic acid (Intermediate 48) instead of quinoline-6-carboxylic acid. MS (ESI): mass calcd. for $C_{26}H_{23}F_3N_6O_2$, 508.2; m/z found, 509.2 [M+H]$^+$. $^1$H NMR (500 MHz, DMSO-d$_6$) δ 8.32-8.27 (m, 1H), 7.90-7.85 (m, 1H), 7.65-7.44 (m, 3H), 7.40-7.31 (m, 1H), 7.07-7.01 (m, 1H), 5.47-5.40 (m, 1H), 3.99-3.93 (m, 1H), 3.81 (s, 3H), 3.77 (s, 3H), 3.02 (dd, J=16.2, 7.3 Hz, 1H), 2.39 (d, J=16.0 Hz, 1H), 1.92-1.19 (m, 6H).

Example 185: ((5R,9S)-2-Methyl-3-(3,4,5-trifluorophenyl)-4,5,6,7,8,9-hexahydro-2H-5,9-epiminocycloocta[c]pyrazol-10-yl)(4,5,6,7-tetrahydropyrazolo[1,5-a]pyridin-3-yl)methanone

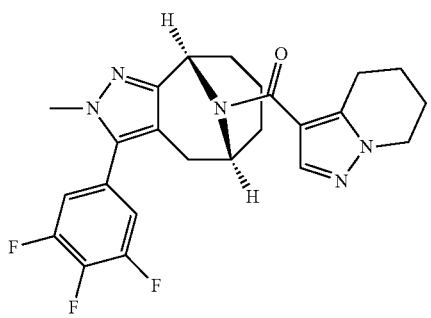

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 4,5,6,7-tetrahydropyrazolo[1,5-a]pyridine-3-carboxylic acid instead of quinoline-6-carboxylic acid. MS (ESI): mass calcd. for $C_{24}H_{24}F_3N_5O$, 455.2; m/z found, 456.0 [M+H]$^+$. $^1$H NMR (500 MHz, DMSO-d$_6$) δ 7.73-7.39 (m, 3H), 5.69-5.10 (m, 1H), 4.99-4.36 (m, 1H), 4.17-3.95 (m, 2H), 3.79 (s, 3H), 3.22-3.04 (m, 1H), 2.92-2.69 (m, 2H), 2.46-2.36 (m, 1H), 2.03-1.90 (m, 2H), 1.83-1.33 (m, 8H).

Example 186: (3,4-Dihydro-2H-pyrano[3,2-b]pyridin-7-yl)((5R,9S)-2-methyl-3-(3,4,5-trifluorophenyl)-4,5,6,7,8,9-hexahydro-2H-5,9-epiminocycloocta[c]pyrazol-10-yl)methanone

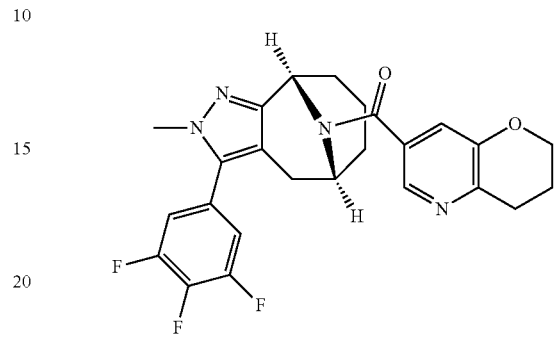

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 3,4-dihydro-2H-pyrano[3,2-b]pyridine-7-carboxylic acid instead of quinoline-6-carboxylic acid. MS (ESI): mass calcd. for $C_{25}H_{23}F_3N_4O_2$, 468.1; m/z found, 469.0 [M+H]$^+$. $^1$H NMR (500 MHz, DMSO-d$_6$) δ 8.18-7.97 (m, 1H), 7.65-7.41 (m, 2H), 7.24-6.72 (m, 1H), 5.81-5.63 (m, 1H), 4.33-3.99 (m, 2H), 3.88-3.67 (m, 4H), 3.09-2.95 (m, 1H), 2.93-2.81 (m, 2H), 2.43-2.27 (m, 1H), 2.12-1.90 (m, 2H), 1.85-1.27 (m, 6H).

Example 187: (6,7-Dihydro-5H-pyrazolo[5,1-b][1,3]oxazin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone

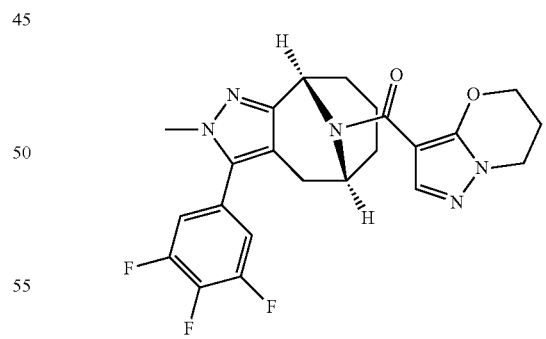

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and (6,7-dihydro-5H-pyrazolo[5,1-b][1,3]oxazine-3-carboxylic acid instead of quinoline-6-carboxylic acid. MS (ESI): mass calcd. for $C_{23}H_{22}F_3N_5O_2$, 457.1; m/z found, 458.1 [M+H]$^+$.

¹H NMR (600 MHz, DMSO-d₆) δ 7.61-7.35 (m, 3H), 5.54 (s, 1H), 5.15-4.73 (m, 1H), 4.38 (s, 2H), 4.09 (s, 2H), 3.85-3.65 (m, 3H), 3.02 (s, 1H), 2.48-2.35 (m, 1H), 2.19 (s, 2H), 2.00-1.36 (m, 6H).

Example 188: ((5R,9S)-2-Methyl-3-(3,4,5-trifluorophenyl)-4,5,6,7,8,9-hexahydro-2H-5,9-epiminocycloocta[c]pyrazol-10-yl)(6-methyl-6,7-dihydro-5H-pyrazolo[5,1-b][1,3]oxazin-3-yl)methanone

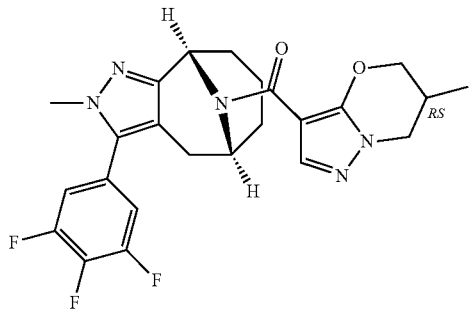

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and (R/S)6-methyl-6,7-dihydro-5H-pyrazolo[5,1-b][1,3]oxazine-3-carboxylic acid instead of quinoline-6-carboxylic acid. MS (ESI): mass calcd. for $C_{24}H_{24}F_3N_5O_2$, 471.1; m/z found, 472.1 [M+H]⁺. ¹H NMR (500 MHz, DMSO-d₆) δ 7.63-7.40 (m, 3H), 5.53 (s, 1H), 5.13-4.73 (m, 1H), 4.46-3.94 (m, 4H), 3.86-3.65 (m, 4H), 3.15-2.91 (m, 1H), 2.44-2.30 (m, 1H), 2.03-1.37 (m, 6H), 1.02 (s, 3H).

Example 189: (6,7-Dihydro-5H-pyrazolo[5,1-b][1,3]oxazin-2-yl)((5R,9S)-2-methyl-3-(3,4,5-trifluorophenyl)-4,5,6,7,8,9-hexahydro-2H-5,9-epiminocycloocta[c]pyrazol-10-yl)methanone

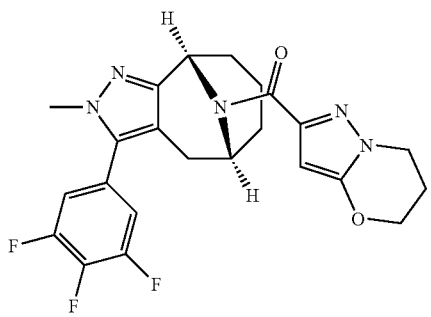

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 6,7-dihydro-5H-pyrazolo[5,1-b][1,3]oxazine-2-carboxylic acid instead of quinoline-6-carboxylic acid. MS (ESI): mass calcd. for $C_{23}H_{22}F_3N_5O_2$, 457.1; m/z found, 458.1 [M+H]⁺. ¹H NMR (500 MHz, DMSO-d₆) δ 7.64-7.45 (m, 2H), 5.75 (d, J=9.3 Hz, 1H), 5.71-5.57 (m, 1H), 5.07-4.91 (m, 1H), 4.37-4.25 (m, 2H), 4.19-4.03 (m, 2H), 3.82-3.71 (m, 3H), 3.08-2.91 (m, 1H), 2.63-2.52 (m, 1H), 2.26-2.13 (m, 2H), 1.93-1.39 (m, 6H).

Example 190: ((5R,9S)-2-Methyl-3-(3,4,5-trifluorophenyl)-4,5,6,7,8,9-hexahydro-2H-5,9-epiminocycloocta[c]pyrazol-10-yl)(1-methyl-5-(trifluoromethyl)-1H-pyrazol-4-yl)methanone

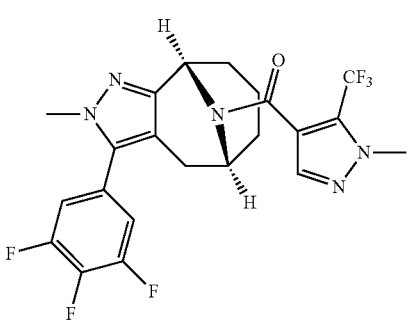

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 1-methyl-5-(trifluoromethyl)-1H-pyrazole-4-carboxylic acid instead of quinoline-6-carboxylic acid. MS (ESI): mass calcd. for $C_{22}H_{19}F_6N_5O$, 483.1; m/z found, 484.1 [M+H]⁺. ¹H NMR (300 MHz, DMSO-d₆) δ 7.80 (s, 1H), 7.65-7.51 (m, 2H), 5.76-5.66 (m, 1H), 4.09-3.94 (m, 1H), 4.00 (s, 3H), 3.80 (s, 3H), 2.97 (dd, J=15.8, 7.3 Hz, 1H), 2.61-2.33 (m, 1H), 1.85-1.31 (m, 6H).

Example 191: (1-(tert-Butyl)-5-(trifluoromethyl)-1H-pyrazol-4-yl)((5R,9S)-2-methyl-3-(3,4,5-trifluorophenyl)-4,5,6,7,8,9-hexahydro-2H-5,9-epiminocycloocta[c]pyrazol-10-yl)methanone

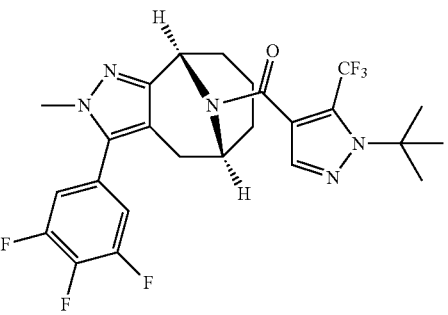

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 1-(tert-butyl)-5-(trifluoromethyl)-1H-pyrazole-4-carboxylic acid instead of quinoline-6-carboxylic acid. MS (ESI): mass calcd. for $C_{25}H_{25}F_6N_5O$, 525.2; m/z found, 526.0 [M+H]$^+$. $^1$H NMR (400 MHz, DMSO-d$_6$) δ 7.78 (s, 1H), 7.63-7.54 (m, 2H), 5.81-5.55 (m, 1H), 4.01-3.87 (m, 1H), 3.81-3.76 (m, 3H), 3.07-2.89 (m, 1H), 2.46-2.40 (m, 1H), 1.79-1.67 (m, 3H), 1.63 (s, 9H), 1.45 (t, J=19.0 Hz, 3H).

Example 192: (5-Ethyl-1-phenyl-1H-1,2,4-triazol-3-yl)((5R,9S)-2-methyl-3-(3,4,5-trifluorophenyl)-4,5,6,7,8,9-hexahydro-2H-5,9-epiminocycloocta[c]pyrazol-10-yl)methanone

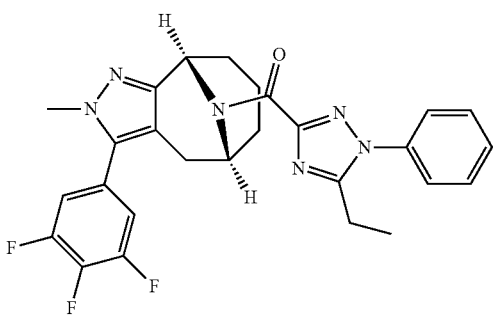

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 1-phenyl-1H-1,2,4-triazole-3-carboxylic acid instead of quinoline-6-carboxylic acid. MS (ESI): mass calcd. for $C_{27}H_{25}F_3N_6O$, 506.2; m/z found, 507.2 [M+H]$^+$. $^1$H NMR (600 MHz, DMSO-d$_6$) δ 7.66-7.50 (m, 7H), 5.80-5.40 (m, 1H), 5.10-4.62 (m, 1H), 3.83-3.70 (m, 3H), 3.12-2.94 (m, 1H), 2.90-2.75 (m, 2H), 2.62-2.53 (m, 1H), 1.99-1.42 (m, 6H), 1.29-1.14 (m, 3H).

Example 193: ((5R,9S)-2-Methyl-3-(3,4,5-trifluorophenyl)-4,5,6,7,8,9-hexahydro-2H-5,9-epiminocycloocta[c]pyrazol-10-yl)(1-phenyl-5-(trifluoromethyl)-1H-pyrazol-3-yl)methanone

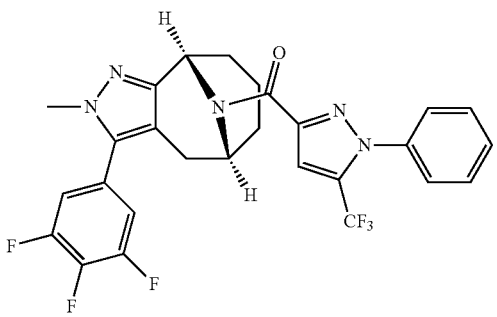

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 1-phenyl-5-(trifluoromethyl)-1H-pyrazole-3-carboxylic acid instead of quinoline-6-carboxylic acid. MS (ESI): mass calcd. for $C_{27}H_{21}F_6N_5O$, 545.2; m/z found, 546.1 [M+H]$^+$. $^1$H NMR (500 MHz, DMSO-d$_6$) δ 7.66-7.52 (m, 7H), 7.42 (s, 1H), 5.78-5.73 (m, 1H), 5.01-4.94 (m, 1H), 3.79 (s, 3H), 3.09-2.99 (m, 1H), 2.61-2.53 (m, 1H), 1.99-1.39 (m, 6H).

Example 194: ((5R,9S)-2-Methyl-3-(3,4,5-trifluorophenyl)-4,5,6,7,8,9-hexahydro-2H-5,9-epiminocycloocta[c]pyrazol-10-yl)(1-phenyl-5-(trifluoromethyl)-1H-1,2,4-triazol-3-yl)methanone

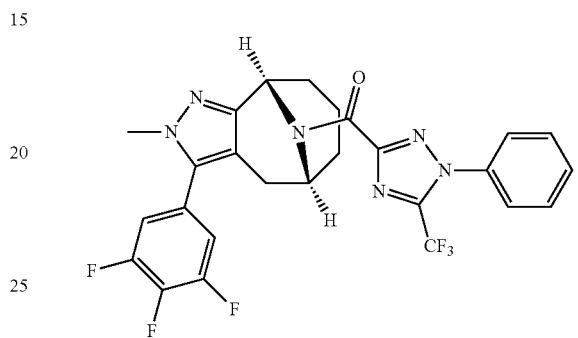

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 1-phenyl-5-(trifluoromethyl)-1H-1,2,4-triazole-3-carboxylic acid instead of quinoline-6-carboxylic acid. MS (ESI): mass calcd. for $C_{26}H_{20}F_6N_6O$, 546.2; m/z found, 547.1 [M+H]$^+$. $^1$H NMR (500 MHz, DMSO-d$_6$) δ 7.70-7.62 (m, 7H), 5.77-5.73 (m, 1H), 4.69-4.63 (m, 1H), 3.80 (s, 3H), 2.99 (dd, J=16.1, 7.4 Hz, 1H), 2.60 (d, J=16.1 Hz, 1H), 1.89-1.69 (m, 4H), 1.56-1.39 (m, 2H).

Example 195: (5-Methoxy-1-phenyl-1H-1,2,4-triazol-3-yl)((5R,9S)-2-methyl-3-(3,4,5-trifluorophenyl)-4,5,6,7,8,9-hexahydro-2H-5,9-epiminocycloocta[c]pyrazol-10-yl)methanone

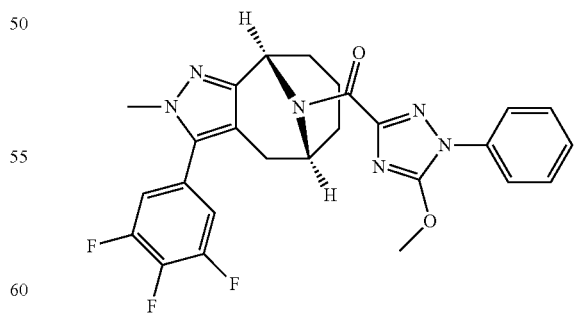

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9- epiminocycloocta[c]pyrazole (Intermediate 1) and 5-methoxy-1-phenyl-1,2,4-triazole-3-carboxylic acid (Intermediate 1) instead of quinoline-6-carboxylic acid. MS (ESI): mass calcd. for $C_{26}H_{23}F_3N_6O_2$, 508.2; m/z found, 509.2 [M+H]$^+$. $^1$H NMR (500 MHz, DMSO-d$_6$) δ 7.72-7.65 (m, 2H), 7.63-7.49 (m, 4H), 7.44-7.37 (m, 1H), 5.72-5.69 (m, 1H), 4.75-4.69 (m, 1H), 4.13 (s, 3H), 3.78 (s, 3H), 3.05-2.99 (m, 1H), 2.56 (d, J=16.2 Hz, 1H), 1.86-1.38 (m, 6H).

Example 196: (1-(3-Fluorophenyl)-1H-1,2,4-triazol-3-yl)((5R,9S)-2-methyl-3-(3,4,5-trifluorophenyl)-4,5,6,7,8,9-hexahydro-2H-5,9-epiminocycloocta[c]pyrazol-10-yl)methanone

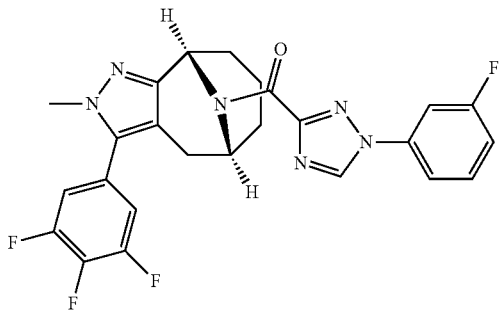

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 1-(3-fluorophenyl)-1H-1,2,4-triazole-3-carboxylic acid instead of quinoline-6-carboxylic acid. MS (ESI): mass calcd. for $C_{25}H_{20}F_4N_6O$, 496.2; m/z found, 497.1 [M+H]$^+$. $^1$H NMR (300 MHz, DMSO-d$_6$) δ 9.45 (s, 1H), 7.83-7.72 (m, 2H), 7.71-7.51 (m, 3H), 7.39-7.26 (m, 1H), 5.80-5.72 (m, 1H), 4.61-4.50 (m, 1H), 3.81 (s, 3H), 3.09-2.98 (m, 1H), 2.60-2.43 (m, 1H), 2.04-1.58 (m, 4H), 1.56-1.38 (m, 2H).

Example 197: (1-(4-Fluorophenyl)-5-methyl-1H-1,2,4-triazol-3-yl)((5R,9S)-2-methyl-3-(3,4,5-trifluorophenyl)-4,5,6,7,8,9-hexahydro-2H-5,9-epiminocycloocta[c]pyrazol-10-yl)methanone

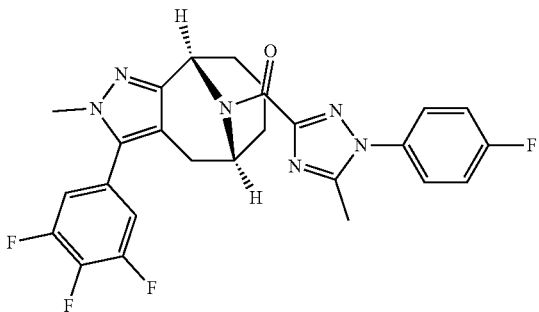 [SMILES: Cc1nc(C(=O)N2[C@@H]3CCC[C@H]2c2nn(C)c(-c4cc(F)c(F)c(F)c4)c2C3)nn1-c1ccc(F)cc1]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 1-(4-fluorophenyl)-5-methyl-1H-1,2,4-triazole-3-carboxylic acid instead of quinoline-6-carboxylic acid. MS (ESI): mass calcd. for $C_{26}H_{22}F_4N_6O$, 510.1; m/z found, 511.1 [M+H]$^+$. $^1$H NMR (600 MHz, DMSO-d$_6$) δ 7.75-7.67 (m, 2H), 7.64-7.55 (m, 2H), 7.52-7.37 (m, 2H), 5.79-5.39 (m, 1H), 5.11-4.57 (m, 1H), 3.84-3.73 (m, 3H), 3.09-2.97 (m, 1H), 2.65-2.53 (m, 1H), 2.50-2.46 (m, 3H), 1.98-1.37 (m, 6H).

Example 198: (1-(2-Methoxyphenyl)-1H-1,2,4-triazol-3-yl)((5R,9S)-2-methyl-3-(3,4,5-trifluorophenyl)-4,5,6,7,8,9-hexahydro-2H-5,9-epiminocycloocta[c]pyrazol-10-yl)methanone

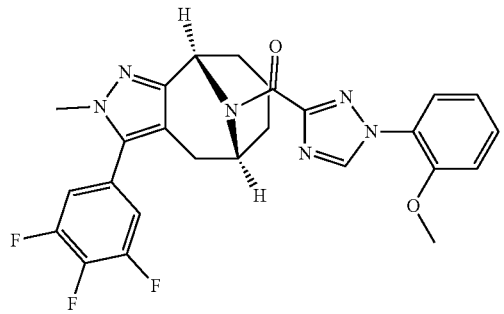 [SMILES: COc1ccccc1-n1cnc(C(=O)N2[C@@H]3CCC[C@H]2c2nn(C)c(-c4cc(F)c(F)c(F)c4)c2C3)n1]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 1-(2-methoxyphenyl)-1,2,4-triazole-3-carboxylic acid (Intermediate 1) instead of quinoline-6-carboxylic acid. MS (ESI): mass calcd. for $C_{26}H_{23}F_3N_6O_2$, 508.2; m/z found, 509.2 [M+H]$^+$. $^1$H NMR (300 MHz, DMSO-d$_6$) δ 9.04 (s, 1H), 7.66 (dd, J=7.9, 1.6 Hz, 1H), 7.63-7.55 (m, 2H), 7.54-7.44 (m, 1H), 7.38-7.31 (m, 1H), 7.20-7.09 (m, 1H), 5.80-5.72 (m, 1H), 4.64-4.52 (m, 1H), 3.89 (s, 3H), 3.80 (s, 3H), 3.08-2.96 (m, 1H), 2.64-2.42 (m, 1H), 2.02-1.57 (m, 4H), 1.57-1.38 (m, 2H).

Example 199: (1-(3-Methoxyphenyl)-1H-1,2,4-triazol-3-yl)((5R,9S)-2-methyl-3-(3,4,5-trifluorophenyl)-4,5,6,7,8,9-hexahydro-2H-5,9-epiminocycloocta[c]pyrazol-10-yl)methanone

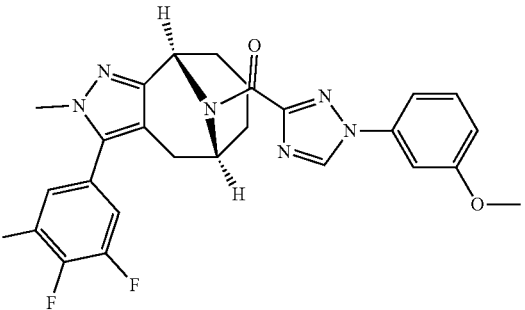

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 1-(3-methoxyphenyl)-1,2,4-triazole-3-carboxylic acid (Intermediate 41) instead of quinoline-6-carboxylic acid. MS (ESI): mass calcd. for $C_{26}H_{23}F_3N_6O_2$, 508.2; m/z found, 509.2 [M+H]$^+$. $^1$H NMR (300 MHz, DMSO-d$_6$) δ 9.41 (s, 1H), 7.68-7.55 (m, 2H), 7.54-7.41 (m, 3H), 7.08-6.99 (m, 1H), 5.80-5.72 (m, 1H), 4.61-4.51 (m, 1H), 3.85 (s, 3H), 3.80 (s, 3H), 3.10-2.98 (m, 1H), 2.60-2.43 (m, 1H), 2.08-1.37 (m, 6H).

Example 200: (4-Methoxypyridin-3-yl) (5R,9S)-2-methyl-3-(3,4,5-trifluorophenyl)-4,5,6,7,8,9-hexahydro-2H-5,9-epiminocycloocta[c]pyrazol-10-yl) methanone

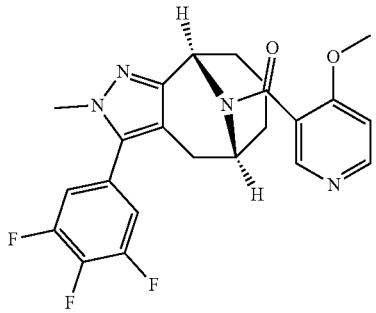 [SMILES: COc1ccncc1C(=O)N1[C@@H]2CCC[C@H]1c1nn(C)c(-c3cc(F)c(F)c(F)c3)c1C2]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 4-methoxynicotinic acid instead of quinoline-6-carboxylic acid. MS (ESI): mass calcd. for $C_{23}H_{21}F_3N_4O_2$, 442.2; m/z found, 443.2 [M+H]$^+$. $^1$H NMR (500 MHz, DMSO-d$_6$) δ 8.58-8.46 (m, 1H), 8.25-8.17 (m, 1H), 7.65-7.50 (m, 2H), 7.27-7.08 (m, 1H), 5.80-5.71 (m, 1H), 4.01-3.92 (m, 1H), 3.92 (s, 3H), 3.80 (s, 3H), 2.93-2.79 (m, 1H), 2.42-2.30 (m, 1H), 1.96-1.31 (m, 6H).

Example 201: (6-Methoxypyridin-2-yl) ((5R,9S)-2-methyl-3-(3,4,5-trifluorophenyl)-4,5,6,7,8,9-hexahydro-2H-5,9-epiminocycloocta[c]pyrazol-10-yl) methanone

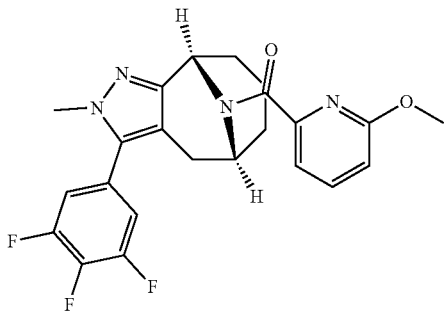 [SMILES: COc1cccc(C(=O)N2[C@@H]3CCC[C@H]2c2nn(C)c(-c4cc(F)c(F)c(F)c4)c2C3)n1]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 6-methoxypicolinic acid instead of quinoline-6-carboxylic acid. MS (ESI): mass calcd. for $C_{23}H_{21}F_3N_4O_2$, 442.2; m/z found, 443.1 [M+H]$^+$. $^1$H NMR (600 MHz, DMSO-d$_6$) δ 7.88-7.70 (m, 1H), 7.63-7.46 (m, 2H), 7.16 (d, J=7.2 Hz, 1H), 7.00-6.85 (m, 1H), 5.81-5.58 (m, 1H), 4.35-4.20 (m, 1H), 3.91-3.70 (m, 6H), 3.12-2.91 (m, 1H), 2.65-2.51 (m, 1H), 2.10-1.38 (m, 6H).

Example 202: (4-Methoxypyridin-2-yl)((5R,9S)-2-methyl-3-(3,4,5-trifluorophenyl)-4,5,6,7,8,9-hexahydro-2H-5,9-epiminocycloocta[c]pyrazol-10-yl) methanone

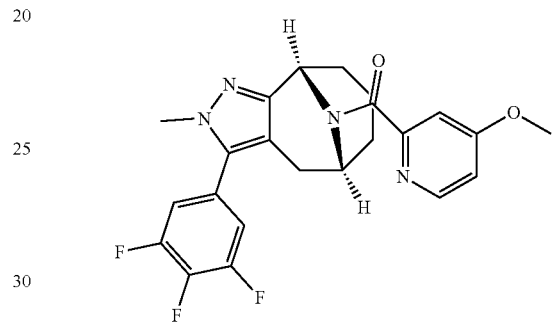

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 4-methoxypicolinic acid instead of quinoline-6-carboxylic acid. MS (ESI): mass calcd. for $C_{23}H_{21}F_3N_4O_2$, 442.2; m/z found, 443.2 [M+H]$^+$. $^1$H NMR (500 MHz, DMSO-d$_6$) δ 8.38 (d, J=5.7 Hz, 1H), 7.62-7.52 (m, 2H), 7.12-7.09 (m, 1H), 7.04 (dd, J=5.8, 2.6 Hz, 1H), 5.74-5.70 (m, 1H), 4.20-4.15 (m, 1H), 3.86 (s, 3H), 3.80 (s, 3H), 2.98 (dd, J=16.0, 7.3 Hz, 1H), 2.45 (d, J=16.0 Hz, 1H), 1.90-1.37 (m, 6H).

Example 203: (5-Methoxypyridin-2-yl)((5R,9S)-2-methyl-3-(3,4,5-trifluorophenyl)-4,5,6,7,8,9-hexahydro-2H-5,9-epiminocycloocta[c]pyrazol-10-yl) methanone

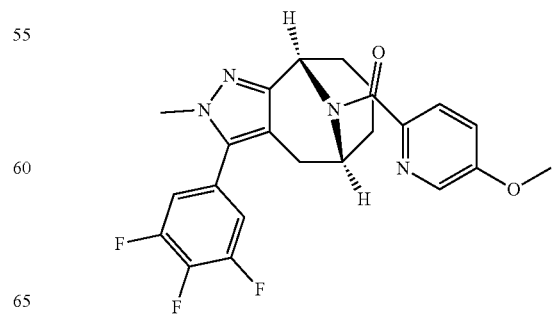

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 5-methoxypicolinic acid instead of quinoline-6-carboxylic acid. MS (ESI): mass calcd. for $C_{23}H_{21}F_3N_4O_2$, 442.2; m/z found, 443.2 $[M+H]^+$. $^1$H NMR (500 MHz, DMSO-$d_6$) δ 8.26 (d, J=2.7 Hz, 1H), 7.62-7.52 (m, 3H), 7.50-7.44 (m, 1H), 5.73-5.67 (m, 1H), 4.43-4.38 (m, 1H), 3.85 (s, 3H), 3.78 (s, 3H), 3.08-2.96 (m, 1H), 2.57-2.41 (m, 1H), 2.03-1.35 (m, 6H).

Example 204: (6-Methoxypyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone

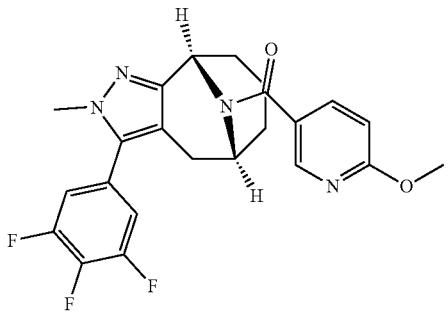 [SMILES: COc1ccc(C(=O)N2[C@@H]3CCC[C@H]2c2nn(C)c(-c4cc(F)c(F)c(F)c4)c2C3)cn1]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 6-methoxynicotinic acid instead of quinoline-6-carboxylic acid. MS (ESI): mass calcd. for $C_{23}H_{21}F_3N_4O_2$, 442.2; m/z found, 443.2 $[M+H]^+$. $^1$H NMR (500 MHz, DMSO-$d_6$) δ 8.28 (s, 1H), 7.81-7.74 (m, 1H), 7.65-7.52 (m, 2H), 6.92-6.83 (m, 1H), 5.70-5.60 (m, 1H), 4.15-4.08 (m, 1H), 3.88 (s, 3H), 3.79 (s, 3H), 3.10 (dd, J=16.4, 7.4 Hz, 1H), 2.40 (d, J=16.2 Hz, 1H), 2.00-1.35 (m, 6H).

Example 205: (5-Isopropoxypyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone

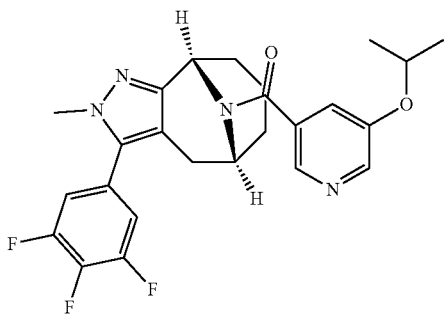 [SMILES: CC(C)Oc1cncc(C(=O)N2[C@@H]3CCC[C@H]2c2nn(C)c(-c4cc(F)c(F)c(F)c4)c2C3)c1]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 5-isopropoxynicotinic acid instead of quinoline-6-carboxylic acid. MS (ESI): mass calcd. for $C_{25}H_{25}F_3N_4O_2$, 470.1; m/z found, 471.1 $[M+H]^+$. $^1$H NMR (600 MHz, DMSO-$d_6$) δ 8.34 (dd, J=13.5, 2.8 Hz, 1H), 8.13 (dd, J=50.4, 1.7 Hz, 1H), 7.69-7.58 (m, 2H), 7.48-7.28 (m, 1H), 5.81-5.60 (m, 1H), 4.83-4.68 (m, 1H), 4.04-3.95 (m, 1H), 3.85-3.72 (m, 3H), 3.14-2.93 (m, 1H), 2.47-2.35 (m, 1H), 2.00-1.40 (m, 6H), 1.29 (dd, J=5.9, 1.3 Hz, 6H).

Example 206: ((5R,9S)-2-Methyl-3-(3,4,5-trifluorophenyl)-4,5,6,7,8,9-hexahydro-2H-5,9-epiminocycloocta[c]pyrazol-10-yl)(6-(trifluoromethoxy)pyridin-2-yl)methanone

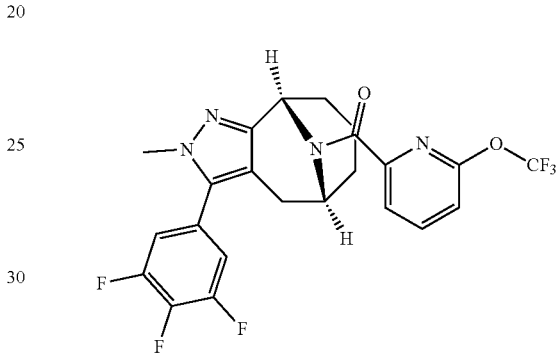

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 6-(trifluoromethoxy)picolinic acid instead of quinoline-6-carboxylic acid. MS (ESI): mass calcd. for $C_{23}H_{18}F_6N_4O_2$, 496.1; m/z found, 497.1 $[M+H]^+$. $^1$H NMR (500 MHz, DMSO-$d_6$) δ 8.25-8.10 (m, 1H), 7.71-7.37 (m, 4H), 5.75-5.60 (m, 1H), 4.26-4.09 (m, 1H), 3.83-3.67 (m, 3H), 3.15-2.88 (m, 1H), 2.68-2.52 (m, 1H), 2.09-1.38 (m, 6H).

Example 207: ((5R,9S)-2-Methyl-3-(3,4,5-trifluorophenyl)-4,5,6,7,8,9-hexahydro-2H-5,9-epiminocycloocta[c]pyrazol-10-yl)(5-(trifluoromethoxy)pyridin-2-yl)methanone

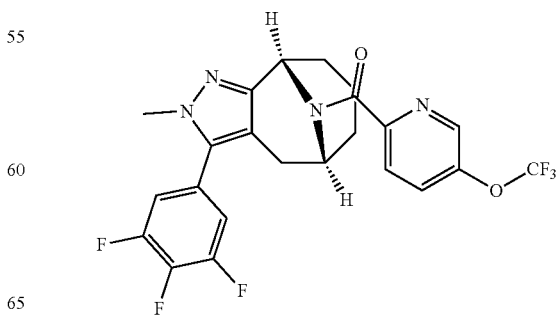

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 5-(trifluoromethoxy)picolinic acid instead of quinoline-6-carboxylic acid. MS (ESI): mass calcd. for $C_{23}H_{18}F_6N_4O_2$, 496.1; m/z found, 497.1 [M+H]$^+$. $^1$H NMR (500 MHz, DMSO-$d_6$) δ 8.80-8.51 (m, 1H), 8.10-7.99 (m, 1H), 7.86-7.69 (m, 1H), 7.66-7.47 (m, 2H), 5.88-5.59 (m, 1H), 4.27-4.04 (m, 1H), 3.85-3.66 (m, 3H), 3.12-2.95 (m, 1H), 2.68-2.52 (m, 1H), 2.08-1.34 (m, 6H).

Example 208: 6-((5R,9S)-2-Methyl-3-(3,4,5-trifluorophenyl)-4,5,6,7,8,9-hexahydro-2H-5,9-epiminocycloocta[c]pyrazole-10-carbonyl) picolinonitrile

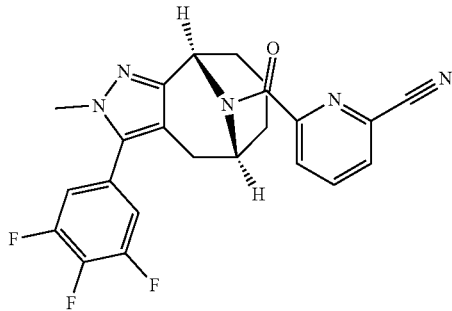 [SMILES: Cn1nc2c(c1-c1cc(F)c(F)c(F)c1)C[C@H]1CCC[C@@H]2N1C(=O)c1cccc(C#N)n1]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 6-cyanopicolinic acid instead of quinoline-6-carboxylic acid. MS (ESI): mass calcd. for $C_{23}H_{18}F_3N_5O$, 437.1; m/z found, 438.1 [M+H]$^+$. $^1$H NMR (600 MHz, DMSO-$d_6$) δ 9.13-8.86 (m, 1H), 8.54-8.23 (m, 1H), 7.86-7.70 (m, 1H), 7.69-7.50 (m, 2H), 5.89-5.50 (m, 1H), 4.15-3.96 (m, 1H), 3.89-3.69 (m, 3H), 3.13-2.91 (m, 1H), 2.48-2.37 (m, 1H), 1.95-1.42 (m, 6H).

Example 209: ((5R,9S)-2-Methyl-3-(3,4,5-trifluorophenyl)-4,5,6,7,8,9-hexahydro-2H-5,9-epiminocycloocta[c]pyrazol-10-yl)(pyrazin-2-yl)methanone

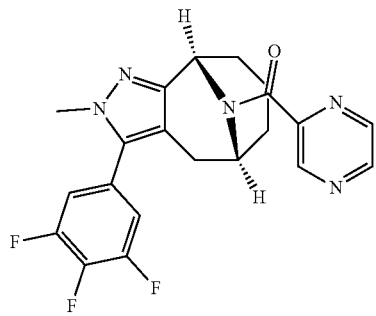 [SMILES: Cn1nc2c(c1-c1cc(F)c(F)c(F)c1)C[C@H]1CCC[C@@H]2N1C(=O)c1cnccn1]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and pyrazine-2-carboxylic acid instead of quinoline-6-carboxylic acid. MS (ESI): mass calcd. for $C_{21}H_{18}F_3N_5O$, 413.1; m/z found, 414.1 [M+H]$^+$. $^1$H NMR (300 MHz, DMSO-$d_6$) δ 8.86 (d, J=1.5 Hz, 1H), 8.77 (dd, J=7.5, 2.6 Hz, 1H), 8.73-8.65 (m, 1H), 7.67-7.52 (m, 2H), 5.80-5.70 (m, 1H), 4.27-4.16 (m, 1H), 3.81 (s, 3H), 3.04 (dd, J=15.9, 7.3 Hz, 1H), 2.60-2.38 (m, 1H), 2.09-1.31 (m, 6H).

Example 210: ((5R,9S)-2-Methyl-3-(3,4,5-trifluorophenyl)-4,5,6,7,8,9-hexahydro-2H-5,9-epiminocycloocta[c]pyrazol-10-yl)(pyrimidin-4-yl)methanone

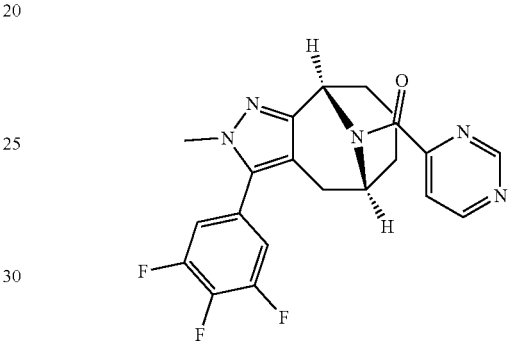

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and pyrimidine-4-carboxylic acid instead of quinoline-6-carboxylic acid. MS (ESI): mass calcd. for $C_{21}H_{18}F_3N_5O$, 413.1; m/z found, 414.1 [M+H]$^+$. $^1$H NMR (500 MHz, DMSO-$d_6$) δ 9.24 (d, J=1.4 Hz, 1H), 8.97 (d, J=5.1 Hz, 1H), 7.69 (dd, J=5.1, 1.5 Hz, 1H), 7.62-7.55 (m, 2H), 5.74-5.69 (m, 1H), 4.11-4.05 (m, 1H), 3.80 (s, 3H), 2.99 (dd, J=16.1, 7.4 Hz, 1H), 2.56-2.38 (m, 1H), 1.91-1.42 (m, 6H).

Example 211: ((5R,9S)-2-Methyl-3-(3,4,5-trifluorophenyl)-4,5,6,7,8,9-hexahydro-2H-5,9-epiminocycloocta[c]pyrazol-10-yl)(pyridazin-4-yl)methanone

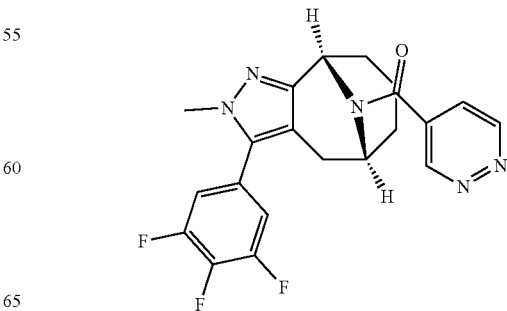

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and pyridazine-4-carboxylic acid instead of quinoline-6-carboxylic acid. MS (ESI): mass calcd. for $C_{21}H_{18}F_3N_5O$, 413.1; m/z found, 414.1 [M+H]$^+$. $^1$H NMR (300 MHz, DMSO-d$_6$) δ 9.41-9.31 (m, 1H), 9.34-9.31 (m, 1H), 7.77 (dd, J=5.2, 2.3 Hz, 1H), 7.66-7.53 (m, 2H), 5.77-5.67 (m, 1H), 3.97-3.88 (m, 1H), 3.81 (s, 3H), 3.10 (dd, J=16.4, 7.4 Hz, 1H), 2.42 (d, J=16.5 Hz, 1H), 2.07-1.31 (m, 6H).

Example 212: ((5R,9S)-2-Methyl-3-(3,4,5-trifluorophenyl)-4,5,6,7,8,9-hexahydro-2H-5,9-epiminocycloocta[c]pyrazol-10-yl)(pyrimidin-5-yl)methanone

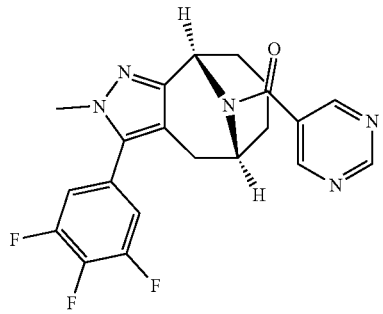 [SMILES: Cn1nc2c(c1-c1cc(F)c(F)c(F)c1)C[C@H]1CCC[C@@H]2N1C(=O)c1cncnc1]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and pyrimidine-5-carboxylic acid instead of quinoline-6-carboxylic acid. MS (ESI): mass calcd. for $C_{21}H_{18}F_3N_5O$, 413.1; m/z found, 414.1 [M+H]$^+$. $^1$H NMR (300 MHz, DMSO-d$_6$) δ 9.30 (s, 1H), 8.93 (s, 2H), 7.68-7.51 (m, 2H), 5.77-5.66 (m, 1H), 4.04 (d, J=6.5 Hz, 1H), 3.82 (s, 3H), 3.16 (dd, J=16.3, 7.3 Hz, 1H), 2.42 (d, J=16.5 Hz, 1H), 2.09-1.34 (m, 6H).

Example 213: (5-(1H-Pyrazol-1-yl)pyridin-3-yl) ((5R,9S)-2-methyl-3-(3,4,5-trifluorophenyl)-4,5,6,7,8,9-hexahydro-2H-5,9-epiminocycloocta[c]pyrazol-10-yl)methanone

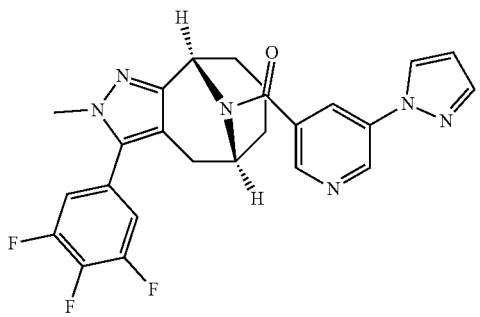 [SMILES: Cn1nc2c(c1-c1cc(F)c(F)c(F)c1)C[C@H]1CCC[C@@H]2N1C(=O)c1cncc(-n2cccn2)c1]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 5-(1H-pyrazol-1-yl)nicotinic acid instead of quinoline-6-carboxylic acid. MS (ESI): mass calcd. for $C_{25}H_{21}F_3N_6O$, 478.2; m/z found, 479.2 [M+H]$^+$. $^1$H NMR (300 MHz, DMSO-d$_6$) δ 9.23 (d, J=2.8 Hz, 1H), 8.70 (d, J=2.5 Hz, 1H), 8.61-8.54 (m, 1H), 8.32-8.26 (m, 1H), 7.90-7.80 (m, 1H), 7.68-7.51 (m, 2H), 6.68-6.55 (m, 1H), 5.81-5.68 (m, 1H), 4.14-4.03 (m, 1H), 3.82 (s, 3H), 3.17-3.00 (m, 1H), 2.49-2.37 (m, 1H), 2.07-1.38 (m, 6H).

Example 214: (6-(1H-Pyrazol-1-yl)pyridin-3-yl) ((5R,9S)-2-methyl-3-(3,4,5-trifluorophenyl)-4,5,6,7,8,9-hexahydro-2H-5,9-epiminocycloocta[c]pyrazol-10-yl)methanone

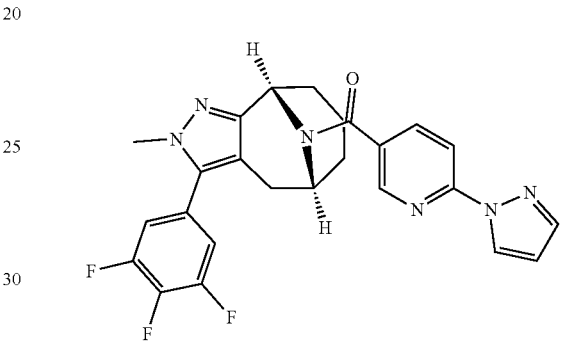

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 6-(1H-pyrazol-1-yl)nicotinic acid instead of quinoline-6-carboxylic acid. MS (ESI): mass calcd. for $C_{25}H_{21}F_3N_6O$, 478.2; m/z found, 479.1 [M+H]$^+$. $^1$H NMR (500 MHz, DMSO-d$_6$) δ 8.79-8.32 (m, 2H), 8.19-7.83 (m, 4H), 7.78-7.28 (m, 2H), 6.67-6.49 (m, 1H), 4.25-4.11 (m, 1H), 3.83-3.73 (m, 3H), 3.19-3.03 (m, 1H), 2.44 (d, J=16.3 Hz, 1H), 2.11-1.28 (m, 6H).

Example 215: (6-(1H-Pyrrol-1-yl) pyridin-3-yl) ((5R,9S)-2-methyl-3-(3,4,5-trifluorophenyl)-4,5,6,7,8,9-hexahydro-2H-5,9-epiminocycloocta[c]pyrazol-10-yl)methanone

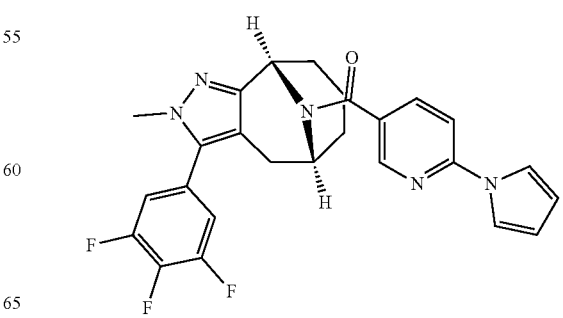

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 6-(1H-pyrrol-1-yl)nicotinic acid instead of quinoline-6-carboxylic acid. MS (ESI): mass calcd. for $C_{26}H_{22}F_3N_5O$, 477.1; m/z found, 478.1 [M+H]$^+$. $^1$H NMR (500 MHz, DMSO-$d_6$) δ 8.71-8.42 (m, 2H), 8.24-7.76 (m, 3H), 7.72-7.42 (m, 2H), 7.16 (d, J=1.3 Hz, 1H), 5.80-5.61 (m, 1H), 4.19-4.01 (m, 1H), 3.86-3.71 (m, 4H), 3.20-3.04 (m, 1H), 2.42 (d, J=16.2 Hz, 1H), 2.06-1.36 (m, 6H).

Example 216: (6-(1H-Imidazol-1-yl) pyridin-3-yl) ((5R,9S)-2-methyl-3-(3,4,5-trifluorophenyl)-4,5,6,7,8,9-hexahydro-2H-5,9-epiminocycloocta[c]pyrazol-10-yl)methanone

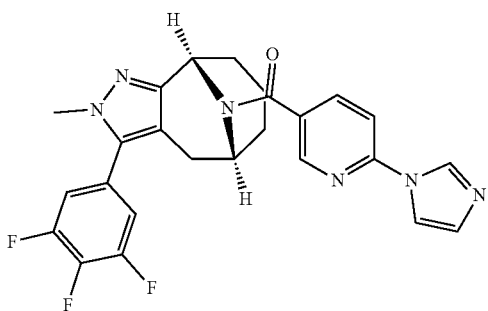 [SMILES: Cn1nc2c(c1-c1cc(F)c(F)c(F)c1)C[C@H]1CCC[C@@H]2N1C(=O)c1ccc(-n2ccnc2)nc1]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 6-(1H-imidazol-1-yl)nicotinic acid instead of quinoline-6-carboxylic acid. MS (ESI): mass calcd. for $C_{25}H_{21}F_3N_6O$, 478.1; m/z found, 479.1 [M+H]$^+$. $^1$H NMR (500 MHz, DMSO-$d_6$) δ 8.63-8.46 (m, 2H), 8.12-7.87 (m, 3H), 7.61 (td, J=10.4, 9.6, 6.5 Hz, 2H), 7.16 (d, J=1.2 Hz, 1H), 5.85-5.63 (m, 1H), 4.17-3.99 (m, 1H), 3.88-3.53 (m, 3H), 3.17-3.06 (m, 1H), 2.43 (d, J=16.2 Hz, 1H), 2.07-1.37 (m, 6H).

Example 217: (6-Methyl-3-(2H-1,2,3-triazol-2-yl) pyridin-2-yl)((5R,9S)-2-methyl-3-(3,4,5-trifluorophenyl)-4,5,6,7,8,9-hexahydro-2H-5,9-epiminocycloocta[c]pyrazol-10-yl)methanone

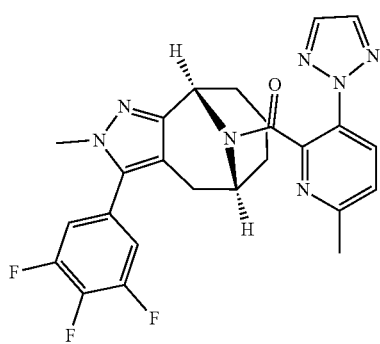 [SMILES: Cc1ccc(-n2nccn2)c(C(=O)N2[C@@H]3CCC[C@H]2c2nn(C)c(-c4cc(F)c(F)c(F)c4)c2C3)n1]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 6-methyl-3-(2H-1,2,3-triazol-2-yl)picolinic acid [WO2016040789] instead of quinoline-6-carboxylic acid. MS (ESI): mass calcd. for $C_{25}H_{22}F_3N_7O$, 493.1; m/z found, 494.1 [M+H]$^+$. $^1$H NMR (500 MHz, DMSO-$d_6$) δ 8.23 (dd, J=9.3, 8.4 Hz, 1H), 8.12-7.93 (m, 2H), 7.65-7.47 (m, 3H), 5.75-5.58 (m, 1H), 3.89-3.84 (m, 1H), 3.82-3.69 (m, 3H), 3.11-2.75 (m, 1H), 2.57-2.53 (m, 3H), 2.47-2.42 (m, 1H), 2.02-1.34 (m, 6H).

Example 218: ((5R,9S)-2-Methyl-3-(3,4,5-trifluorophenyl)-4,5,6,7,8,9-hexahydro-2H-5,9-epiminocycloocta[c]pyrazol-10-yl)(5-(pyrrolidin-1-yl)pyridin-3-yl)methanone

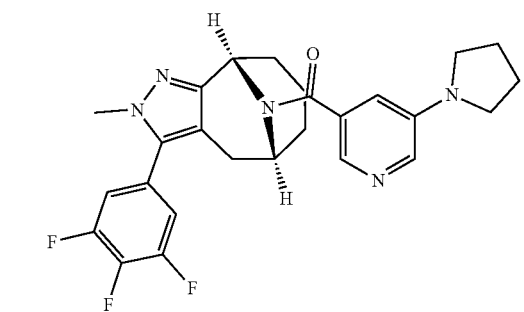 [SMILES: Cn1nc2c(c1-c1cc(F)c(F)c(F)c1)C[C@H]1CCC[C@@H]2N1C(=O)c1cncc(N2CCCC2)c1]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 5-(pyrrolidin-1-yl)nicotinic acid instead of quinoline-6-carboxylic acid. MS (ESI): mass calcd. for $C_{26}H_{26}F_3N_5O$, 481.2; m/z found, 482.1 [M+H]$^+$. $^1$H NMR (600 MHz, DMSO-$d_6$) δ 8.01 (dd, J=11.6, 2.8 Hz, 1H), 7.89-7.71 (m, 1H), 7.68-7.52 (m, 2H), 6.89-6.74 (m, 1H), 5.73-5.60 (m, 1H), 4.10-4.00 (m, 1H), 3.85-3.69 (m, 3H), 3.31-3.22 (m, 4H), 3.11-2.94 (m, 1H), 2.46-2.34 (m, 1H), 1.99-1.90 (m, 4H), 1.92-1.35 (m, 6H).

Example 219: 1-(5-((5R,9S)-2-Methyl-3-(3,4,5-trifluorophenyl)-4,5,6,7,8,9-hexahydro-2H-5,9-epiminocycloocta[c]pyrazole-10-carbonyl) pyridin-3-yl) pyrrolidin-2-one

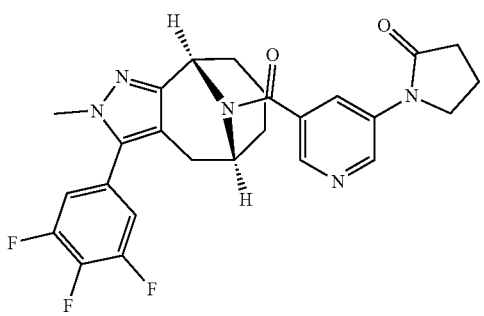 [SMILES: Cn1nc2c(c1-c1cc(F)c(F)c(F)c1)C[C@H]1CCC[C@@H]2N1C(=O)c1cncc(N2CCCC2=O)c1]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 5-(2-oxopyrrolidin-1-yl)nicotinic acid instead of quinoline-6-carboxylic acid. MS (ESI): mass calcd. for $C_{26}H_{24}F_3N_5O_2$, 495.1; m/z found, 496.1 [M+H]$^+$. $^1$H NMR (400 MHz, DMSO-d$_6$) δ 8.95-8.80 (m, 1H), 8.44-8.15 (m, 2H), 7.64-7.44 (m, 2H), 5.72 (s, 1H), 4.05 (s, 1H), 3.91 (t, J=7.0 Hz, 2H), 3.85-3.72 (m, 3H), 3.27-3.00 (m, 2H), 2.57 (d, J=20.3 Hz, 1H), 2.49-2.40 (m, 1H), 2.16-2.03 (m, 2H), 1.99-1.35 (m, 6H).

Example 220: ((5R,9S)-2-Methyl-3-(3,4,5-trifluorophenyl)-4,5,6,7,8,9-hexahydro-2H-5,9-epiminocycloocta[c]pyrazol-10-yl)(5-morpholinopyridin-3-yl)methanone

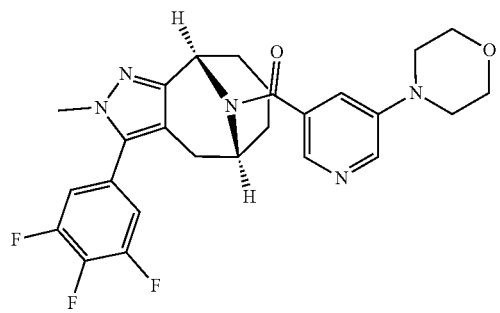 [SMILES: Cn1nc2c(c1-c1cc(F)c(F)c(F)c1)C[C@H]1CCC[C@@H]2N1C(=O)c1cncc(N2CCOCC2)c1]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 5-morpholinonicotinic acid instead of quinoline-6-carboxylic acid. MS (ESI): mass calcd. for $C_{26}H_{26}F_3N_5O_2$, 497.2; m/z found, 498.2 [M+H]$^+$. $^1$H NMR (400 MHz, DMSO-d$_6$) δ 8.46-8.34 (m, 1H), 8.07-7.90 (m, 1H), 7.69-7.55 (m, 2H), 7.41-7.16 (m, 1H), 5.76-5.61 (m, 1H), 4.12-3.96 (m, 1H), 3.83-3.71 (m, 6H), 3.27-3.15 (m, 5H), 3.14-2.89 (m, 1H), 2.47-2.32 (m, 1H), 2.02-1.38 (m, 6H).

Example 221: ((5R,9S)-2-Methyl-3-(3,4,5-trifluorophenyl)-4,5,6,7,8,9-hexahydro-2H-5,9-epiminocycloocta[c]pyrazol-10-yl)(2-methylindolizin-6-yl)methanone

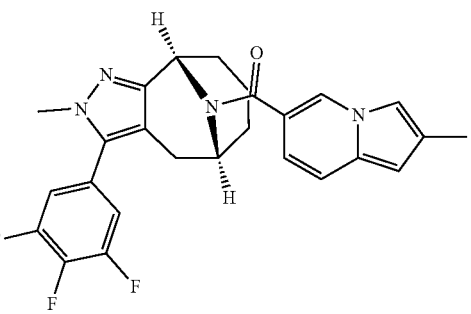

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 2-methylindolizine-6-carboxylic acid instead of quinoline-6-carboxylic acid. MS (ESI): mass calcd. for $C_{26}H_{23}F_3N_4O$, 464.1; m/z found, 465.1 [M+H]$^+$. $^1$H NMR (500 MHz, DMSO-d$_6$) δ 8.45-8.12 (m, 1H), 7.67-7.27 (m, 4H), 6.65 (s, 1H), 6.29 (s, 1H), 5.73-5.53 (m, 1H), 4.43-4.13 (m, 1H), 3.87-3.70 (m, 3H), 3.15-2.98 (m, 1H), 2.26 (s, 3H), 2.64-2.53 (m, 1H), 2.11-1.36 (m, 6H).

Example 222: ((5R,9S)-2-Methyl-3-(3,4,5-trifluorophenyl)-4,5,6,7,8,9-hexahydro-2H-5,9-epiminocycloocta[c]pyrazol-10-yl) (2-methylbenzo[d]oxazol-6-yl) methanone

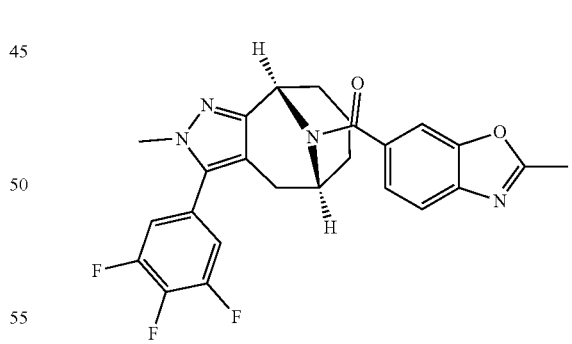

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 2-methylbenzo[d]oxazole-6-carboxylic acid instead of quinoline-6-carboxylic acid. MS (ESI): mass calcd. for $C_{25}H_{21}F_3N_4O_2$, 466.1; m/z found, 467.1 [M+H]$^+$. $^1$H NMR (500 MHz, DMSO-d$_6$) δ 7.79-7.68 (m, 2H), 7.61 (t, J=7.8

Hz, 2H), 7.47-7.29 (m, 1H), 5.78-5.57 (m, 1H), 4.19-4.00 (m, 1H), 3.84-3.70 (m, 3H), 3.14-2.99 (m, 1H), 2.64 (d, J=3.0 Hz, 3H), 2.39 (d, J=16.2 Hz, 1H), 2.02-1.36 (m, 6H).

Example 223: ((5R,9S)-2-Methyl-3-(3,4,5-trifluorophenyl)-4,5,6,7,8,9-hexahydro-2H-5,9-epiminocycloocta[c]pyrazol-10-yl)(pyrazolo[1,5-a]pyridin-3-yl)methanone

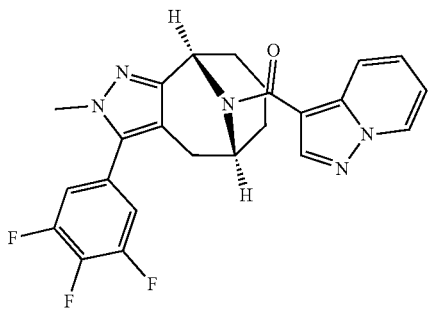 [SMILES: Cn1nc2c(c1-c1cc(F)c(F)c(F)c1)C[C@H]1CCC[C@@H]2N1C(=O)c1cnn2ccccc12]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and pyrazolo[1,5-a]pyridine-3-carboxylic acid instead of quinoline-6-carboxylic acid. MS (ESI): mass calcd. for $C_{24}H_{20}F_3N_5O$, 451.1; m/z found, 452.1 [M+H]$^+$. $^1$H NMR (500 MHz, DMSO-d$_6$) δ 8.90-8.71 (m, 1H), 8.29 (s, 1H), 7.88 (s, 1H), 7.61 (t, J=7.5 Hz, 2H), 7.50-7.39 (m, 1H), 7.12-6.92 (m, 1H), 5.75-5.33 (m, 1H), 5.04-4.62 (m, 1H), 3.89-3.68 (m, 3H), 3.25-3.01 (m, 1H), 2.67-2.52 (m, 1H), 2.07-1.39 (m, 6H).

Example 224: ((5R,9S)-2-Methyl-3-(3,4,5-trifluorophenyl)-4,5,6,7,8,9-hexahydro-2H-5,9-epiminocycloocta[c]pyrazol-10-yl)(5-methylpyrazolo[1,5-a]pyridin-3-yl)methanone

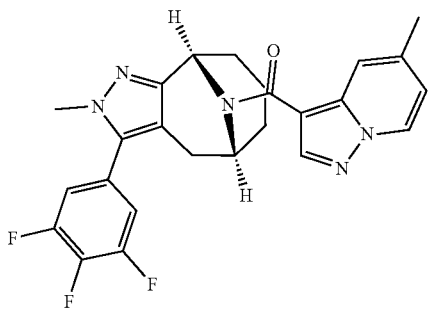 [SMILES: Cc1ccn2ncc(C(=O)N3[C@@H]4CCC[C@H]3c3nn(C)c(-c5cc(F)c(F)c(F)c5)c3C4)c2c1]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 5-methylpyrazolo[1,5-a]pyridine-3-carboxylic acid instead of quinoline-6-carboxylic acid. MS (ESI): mass calcd. for $C_{25}H_{22}F_3N_5O$, 465.1; m/z found, 466.0 [M+H]$^+$. $^1$H NMR (600 MHz, DMSO-d$_6$) δ 8.66 (d, J=7.0 Hz, 1H), 8.21 (s, 1H), 7.72-7.54 (m, 3H), 6.89 (dd, J=7.1, 1.9 Hz, 1H), 5.75-5.30 (m, 1H), 5.06-4.62 (m, 1H), 3.89-3.69 (m, 3H), 3.25-3.10 (m, 1H), 2.59-2.52 (m, 1H), 2.45-2.31 (m, 3H), 2.01-1.38 (m, 6H).

Example 225: ((5R,9S)-2-Methyl-3-(3,4,5-trifluorophenyl)-4,5,6,7,8,9-hexahydro-2H-5,9-epiminocycloocta[c]pyrazol-10-yl)(pyrazolo[1,5-a]pyridin-5-yl)methanone

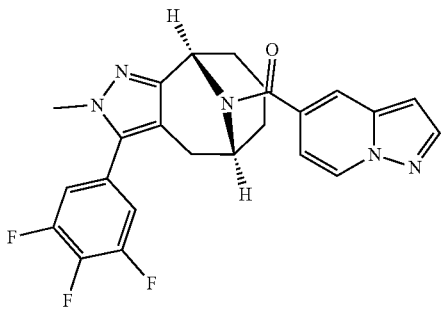 [SMILES: Cn1nc2c(c1-c1cc(F)c(F)c(F)c1)C[C@H]1CCC[C@@H]2N1C(=O)c1ccn2nccc2c1]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and pyrazolo[1,5-a]pyridine-5-carboxylic acid instead of quinoline-6-carboxylic acid. MS (ESI): mass calcd. for $C_{24}H_{20}F_3N_5O$, 451.2; m/z found, 452.1 [M+H]$^+$. $^1$H NMR (500 MHz, DMSO-d$_6$) δ 8.74 (dd, J=14.5, 7.2 Hz, 1H), 8.12-7.99 (m, 1H), 7.78 (d, J=16.6 Hz, 1H), 7.67-7.56 (m, 2H), 6.94-6.62 (m, 2H), 5.76-5.55 (m, 1H), 4.25-4.08 (m, 1H), 3.85-3.71 (m, 3H), 3.13-3.01 (m, 1H), 2.49-2.40 (m, 1H), 2.03-1.38 (m, 6H).

Example 226: ((5R,9S)-2-Methyl-3-(3,4,5-trifluorophenyl)-4,5,6,7,8,9-hexahydro-2H-5,9-epiminocycloocta[c]pyrazol-10-yl)(pyrazolo[1,5-a]pyridin-6-yl)methanone

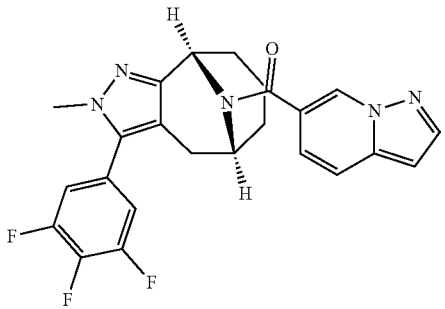 [SMILES: Cn1nc2c(c1-c1cc(F)c(F)c(F)c1)C[C@H]1CCC[C@@H]2N1C(=O)c1ccc2ccnn2c1]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9- epiminocycloocta[c]pyrazole (Intermediate 1) and pyrazolo[1,5-a]pyridine-6-carboxylic acid instead of quinoline-6-carboxylic acid. MS (ESI): mass calcd. for $C_{24}H_{20}F_3N_5O$, 451.2; m/z found, 452.0 [M+H]$^+$. $^1$H NMR (500 MHz, DMSO-$d_6$) δ 8.20-7.90 (m, 1H), 7.85-7.72 (m, 1H), 7.65-7.44 (m, 2H), 7.37-6.64 (m, 3H), 5.85-5.75 (m, 1H), 3.86-3.55 (m, 4H), 3.16-2.74 (m, 1H), 2.47-2.29 (m, 1H), 2.03-1.27 (m, 6H).

Example 227: ((5R,9S)-2-Methyl-3-(3,4,5-trifluorophenyl)-4,5,6,7,8,9-hexahydro-2H-5,9-epiminocycloocta[c]pyrazol-10-yl)(pyrazolo[1,5-a]pyridin-2-yl)methanone

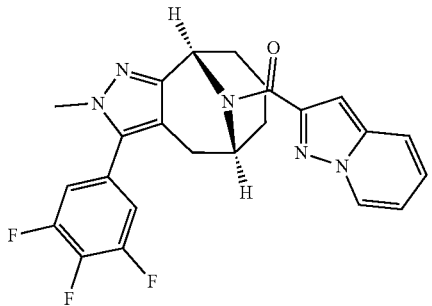 [SMILES: Cn1nc2c(c1-c1cc(F)c(F)c(F)c1)C[C@H]1CCC[C@@H]2N1C(=O)c1cc2ccccn2n1]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and pyrazolo[1,5-a]pyridine-2-carboxylic acid instead of quinoline-6-carboxylic acid. MS (ESI): mass calcd. for $C_{24}H_{20}F_3N_5O$, 451.2; m/z found, 452.1 [M+H]$^+$. $^1$H NMR (600 MHz, DMSO-$d_6$) δ 8.79-8.62 (m, 1H), 7.81-7.64 (m, 1H), 7.58 (dd, J=8.7, 6.6 Hz, 2H), 7.34-7.24 (m, 1H), 7.04-6.93 (m, 1H), 6.86 (dd, J=5.2, 0.9 Hz, 1H), 5.84-5.66 (m, 1H), 5.12-4.86 (m, 1H), 3.83-3.68 (m, 3H), 3.13-3.01 (m, 1H), 2.64-2.53 (m, 1H), 1.99-1.42 (m, 6H).

Example 228: Imidazo[1,2-a]pyridin-5-yl((5R,9S)-2-methyl-3-(3,4,5-trifluorophenyl)-4,5,6,7,8,9-hexahydro-2H-5,9-epiminocycloocta[c]pyrazol-10-yl)methanone

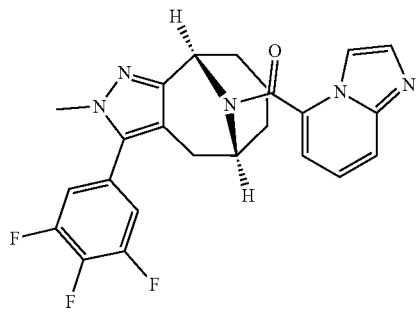 [SMILES: Cn1nc2c(c1-c1cc(F)c(F)c(F)c1)C[C@H]1CCC[C@@H]2N1C(=O)c1cccc2nccn12]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and imidazo[1,2-a]pyridine-5-carboxylic acid instead of quinoline-6-carboxylic acid. MS (ESI): mass calcd. for $C_{24}H_{20}F_3N_5O$, 451.2; m/z found, 452.1 [M+H]$^+$. $^1$H NMR (500 MHz, DMSO-$d_6$) δ 7.93-7.45 (m, 5H), 7.39-7.16 (m, 1H), 7.09-6.88 (m, 1H), 5.87-5.64 (m, 1H), 4.12-3.98 (m, 1H), 3.86-3.68 (m, 3H), 3.17-2.98 (m, 1H), 2.47-2.37 (m, 1H), 2.13-1.34 (m, 6H).

Example 229: Imidazo[1,5-a]pyridin-5-yl((5R,9S)-2-methyl-3-(3,4,5-trifluorophenyl)-4,5,6,7,8,9-hexahydro-2H-5,9-epiminocycloocta[c]pyrazol-10-yl)methanone

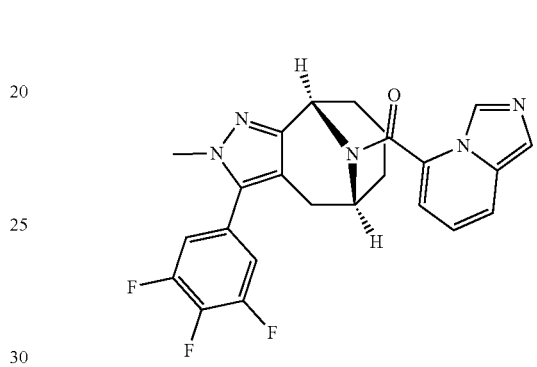

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and imidazo[1,5-a]pyridine-5-carboxylic acid instead of quinoline-6-carboxylic acid. MS (ESI): mass calcd. for $C_{24}H_{20}F_3N_5O$, 451.2; m/z found, 452.1 [M+H]$^+$. $^1$H NMR (400 MHz, DMSO-$d_6$) δ 8.35-8.05 (m, 1H), 7.74-7.43 (m, 4H), 6.91-6.62 (m, 2H), 5.88-5.63 (m, 1H), 4.30-4.06 (m, 1H), 3.87-3.65 (m, 3H), 3.18-2.98 (m, 1H), 2.76-2.52 (m, 1H), 2.15-1.34 (m, 6H).

Example 230: Imidazo[1,5-a]pyridin-6-yl((5R,9S)-2-methyl-3-(3,4,5-trifluorophenyl)-4,5,6,7,8,9-hexahydro-2H-5,9-epiminocycloocta[c]pyrazol-10-yl)methanone

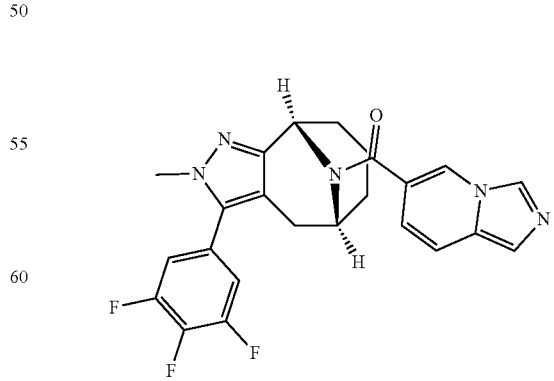

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and imidazo[1,5-a]pyridine-6-carboxylic acid instead of quinoline-6-carboxylic acid. MS (ESI): mass calcd. for $C_{24}H_{20}F_3N_5O$, 451.2; m/z found, 452.1 [M+H]$^+$. $^1$H NMR (500 MHz, DMSO-d$_6$) δ 8.59-8.48 (m, 1H), 8.46-8.36 (m, 1H), 7.67-7.52 (m, 3H), 7.45-7.36 (m, 1H), 6.83-6.74 (m, 1H), 5.70-5.57 (m, 1H), 4.34-4.20 (m, 1H), 3.80 (s, 3H), 3.12-3.02 (m, 1H), 2.60-2.40 (m, 1H), 1.92-1.32 (m, 6H).

Example 231: Imidazo[1,2-a]pyridin-6-yl((5R,9S)-2-methyl-3-(3,4,5-trifluorophenyl)-4,5,6,7,8,9-hexahydro-2H-5,9-epiminocycloocta[c]pyrazol-10-yl)methanone

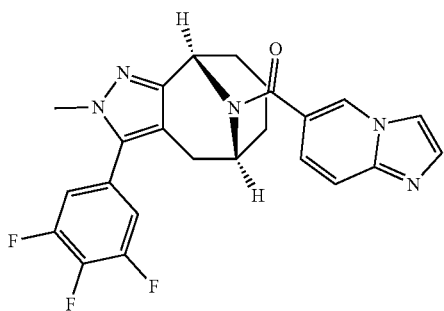 [SMILES: Cn1nc2c(c1-c1cc(F)c(F)c(F)c1)C[C@H]1CCC[C@@H]2N1C(=O)c1ccc2nccn2c1]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and imidazo[1,2-a]pyridine-6-carboxylic acid instead of quinoline-6-carboxylic acid. MS (ESI): mass calcd. for $C_{24}H_{20}F_3N_5O$, 451.2; m/z found, 452.2 [M+H]$^+$. $^1$H NMR (300 MHz, DMSO-d$_6$) δ 8.85-8.71 (m, 1H), 8.06-7.90 (m, 1H), 7.72-7.53 (m, 4H), 7.35-7.12 (m, 1H), 5.74-5.57 (m, 1H), 4.38-4.17 (m, 1H), 3.82 (s, 3H), 3.10 (dd, J=16.3, 7.4 Hz, 1H), 2.65-2.36 (m, 1H), 2.13-1.32 (m, 6H).

Example 232: ((5R,9S)-2-Methyl-3-(3,4,5-trifluorophenyl)-4,5,6,7,8,9-hexahydro-2H-5,9-epiminocycloocta[c]pyrazol-10-yl)(7-methylimidazo[1,2-a]pyridin-3-yl)methanone

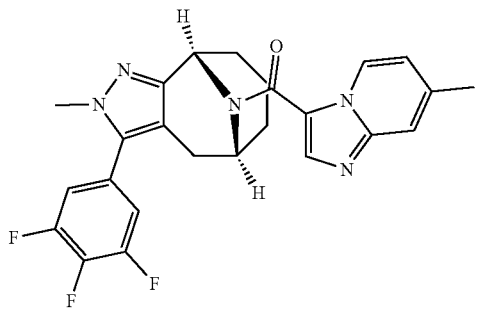 [SMILES: Cc1ccn2c(C(=O)N3[C@@H]4CCC[C@H]3c3nn(C)c(-c5cc(F)c(F)c(F)c5)c3C4)cnc2c1]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 7-methylimidazo[1,2-a]pyridine-3-carboxylic acid instead of quinoline-6-carboxylic acid. MS (ESI): mass calcd. for $C_{25}H_{22}F_3N_5O$, 465.1; m/z found, 466.1 [M+H]$^+$. $^1$H NMR (400 MHz, DMSO-d$_6$) δ 8.79 (dd, J=7.0, 0.9 Hz, 1H), 7.97 (s, 1H), 7.62 (dd, J=8.8, 6.7 Hz, 2H), 7.50-7.42 (m, 1H), 6.93 (dd, J=7.2, 1.7 Hz, 1H), 5.66 (s, 1H), 4.92 (s, 1H), 3.80 (s, 3H), 3.17 (s, 1H), 2.60-2.53 (m, 1H), 2.44-2.31 (m, 3H), 2.03-1.42 (m, 6H).

Example 233: (1-Methyl-1H-pyrrolo[2,3-b]pyridin-4-yl)((5R,9S)-2-methyl-3-(3,4,5-trifluorophenyl)-4,5,6,7,8,9-hexahydro-2H-5,9-epiminocycloocta[c]pyrazol-10-yl)methanone

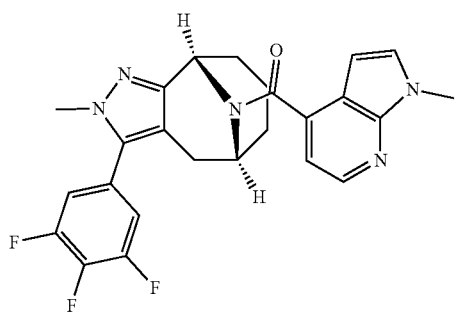 [SMILES: Cn1nc2c(c1-c1cc(F)c(F)c(F)c1)C[C@H]1CCC[C@@H]2N1C(=O)c1ccnc2c1ccn2C]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 1-methyl-1H-pyrrolo[2,3-b]pyridine-4-carboxylic acid instead of quinoline-6-carboxylic acid. MS (ESI): mass calcd. for $C_{25}H_{22}F_3N_5O$, 465.1; m/z found, 466.1 [M+H]$^+$. $^1$H NMR (600 MHz, DMSO-d$_6$) δ 8.33 (dd, J=13.1, 4.7 Hz, 1H), 7.68-7.49 (m, 3H), 7.09-6.92 (m, 1H), 6.47-6.29 (m, 1H), 5.88-5.77 (m, 1H), 4.61-4.49 (m, 1H), 3.88-3.76 (m, 6H), 3.22-2.80 (m, 1H), 2.37 (d, J=16.1 Hz, 1H), 2.03-1.34 (m, 6H).

Example 234: (1-Methyl-1H-pyrrolo[2,3-b]pyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone

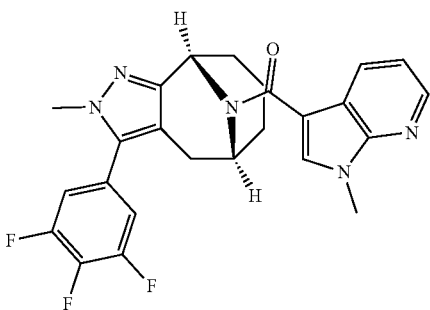 [SMILES: Cn1nc2c(c1-c1cc(F)c(F)c(F)c1)C[C@H]1CCC[C@@H]2N1C(=O)c1cn(C)c2ncccc12]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 1-methyl-1H-pyrrolo[2,3-b]pyridine-3-carboxylic acid instead of quinoline-6-carboxylic acid. MS (ESI): mass calcd. for $C_{25}H_{22}F_3N_5O$, 465.1; m/z found, 466.1 [M+H]$^+$. $^1$H NMR (600 MHz, DMSO-$d_6$) δ 8.34 (dd, J=4.6, 1.6 Hz, 1H), 7.95 (s, 2H), 7.61 (t, J=7.6 Hz, 2H), 7.20 (dd, J=7.9, 4.6 Hz, 1H), 5.79-5.43 (m, 1H), 4.95-4.64 (m, 1H), 3.90-3.71 (m, 6H), 3.21-3.06 (m, 1H), 2.58-2.51 (m, 1H), 2.03-1.37 (m, 6H).

Example 235: ((5R,9S)-2-Methyl-3-(3,4,5-trifluorophenyl)-4,5,6,7,8,9-hexahydro-2H-5,9-epiminocycloocta[c]pyrazol-10-yl)(pyrrolo[1,2-b]pyridazin-5-yl)methanone

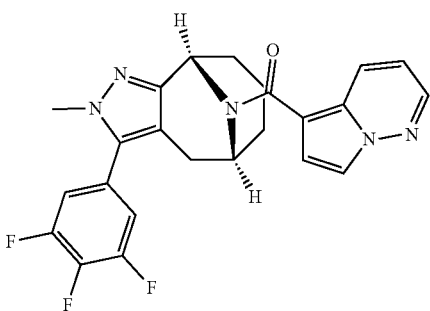 [SMILES: Cn1nc2c(c1-c1cc(F)c(F)c(F)c1)C[C@H]1CCC[C@@H]2N1C(=O)c1ccn2ncccc12]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and (pyrrolo[1,2-b]pyridazine-5-carboxylic acid instead of quinoline-6-carboxylic acid. MS (ESI): mass calcd. for $C_{24}H_{20}F_3N_5O$, 451.2; m/z found, 452.1 [M+H]$^+$. $^1$H NMR (400 MHz, DMSO-$d_6$) δ 8.39-8.26 (m, 1H), 8.15 (d, J=9.2 Hz, 1H), 7.89 (d, J=2.9 Hz, 1H), 7.68-7.49 (m, 2H), 7.08 (s, 1H), 6.97-6.81 (m, 1H), 5.71-5.34 (m, 1H), 4.91-4.62 (m, 1H), 3.84-3.68 (m, 3H), 3.26-3.03 (m, 1H), 2.67 (s, 1H), 2.07-1.39 (m, 6H).

Example 236: ((5R,9S)-2-Methyl-3-(3,4,5-trifluorophenyl)-4,5,6,7,8,9-hexahydro-2H-5,9-epiminocycloocta[c]pyrazol-10-yl)(pyrrolo[1,2-a]pyrazin-8-yl)methanone

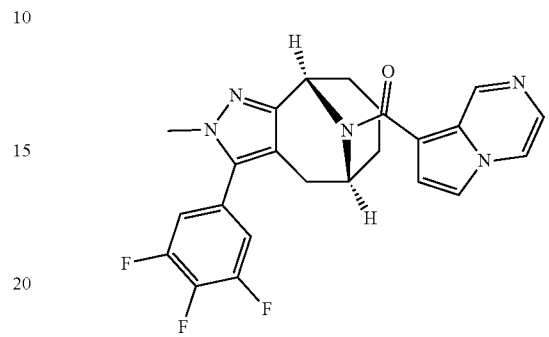

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and pyrrolo[1,2-a]pyrazine-8-carboxylic acid instead of quinoline-6-carboxylic acid. MS (ESI): mass calcd. for $C_{24}H_{20}F_3N_5O$, 466.1; m/z found, 467.1 [M+H]$^+$. $^1$H NMR (400 MHz, DMSO-$d_6$) δ 9.01 (s, 1H), 8.37 (dd, J=4.8, 1.5 Hz, 1H), 7.79 (d, J=2.7 Hz, 1H), 7.71-7.57 (m, 3H), 7.11 (s, 1H), 5.79-5.22 (m, 1H), 5.09-4.42 (m, 1H), 3.79 (s, 3H), 3.25-3.09 (m, 1H), 2.64-2.51 (m, 1H), 2.06-1.35 (m, 6H).

Example 237: (4-Methoxy-1-methyl-1H-indazol-3-yl)((5R,9S)-2-methyl-3-(3,4,5-trifluorophenyl)-4,5,6,7,8,9-hexahydro-2H-5,9-epiminocycloocta[c]pyrazol-10-yl)methanone

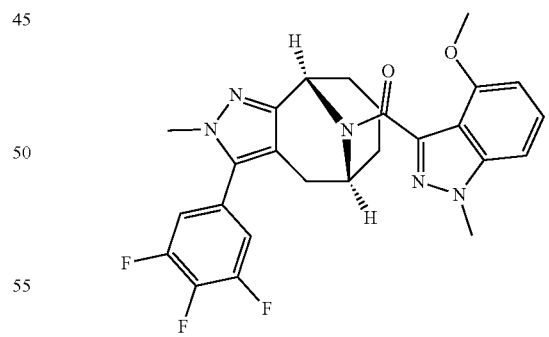

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 4-methoxy-1-methyl-1H-indazole-3-carboxylic acid instead of quinoline-6-carboxylic acid. MS (ESI): mass calcd. for $C_{26}H_{24}F_3N_5O_2$, 495.2; m/z found, 496.2 [M+H]$^+$. $^1$H NMR (500 MHz, DMSO-d$_6$) δ 7.67-7.51 (m, 2H), 7.42-7.29 (m, 1H), 7.20 (dd, J=11.3, 8.4 Hz, 1H), 6.57 (dd, J=12.5, 7.7 Hz, 1H), 5.87-5.68 (m, 1H), 4.61-4.42 (m, 1H), 4.06-3.93 (m, 3H), 3.83-3.59 (m, 6H), 3.13-2.68 (m, 1H), 2.47-2.37 (m, 1H), 1.99-1.28 (m, 6H).

Example 238: (1-Methyl-1H-pyrazolo[3,4-b]pyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone

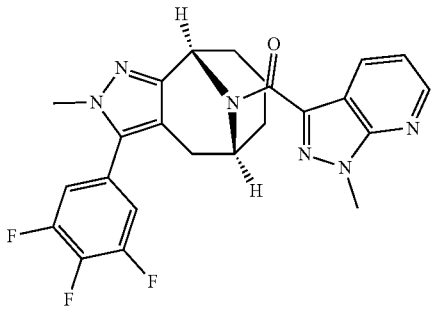 [SMILES: Cn1nc2c(c1-c1cc(F)c(F)c(F)c1)C[C@H]1CCC[C@@H]2N1C(=O)c1nn(C)c2ncccc12]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 1-methyl-1H-pyrazolo[3,4-b]pyridine-3-carboxylic acid instead of quinoline-6-carboxylic acid. MS (ESI): mass calcd. for C$_{24}$H$_{21}$F$_3$N$_6$O, 466.1; m/z found, 467.1 [M+H]$^+$. $^1$H NMR (400 MHz, DMSO-d$_6$) δ 8.74-8.61 (m, 1H), 8.49-8.33 (m, 1H), 7.66-7.52 (m, 2H), 7.35 (dd, J=8.1, 4.5 Hz, 1H), 6.41-5.78 (m, 1H), 5.54-5.08 (m, 1H), 4.14 (d, J=17.8 Hz, 3H), 3.78 (d, J=20.9 Hz, 3H), 3.21-3.04 (m, 1H), 2.64-2.55 (m, 1H), 2.03-1.45 (m, 6H).

Example 239: ((5R,9S)-2-Methyl-3-(3,4,5-trifluorophenyl)-4,5,6,7,8,9-hexahydro-2H-5,9-epiminocycloocta[c]pyrazol-10-yl)(pyrazolo[1,5-b]pyridazin-3-yl)methanone

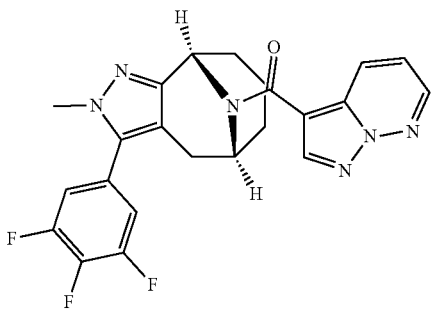 [SMILES: Cn1nc2c(c1-c1cc(F)c(F)c(F)c1)C[C@H]1CCC[C@@H]2N1C(=O)c1cnn2ncccc12]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and pyrazolo[1,5-b]pyridazine-3-carboxylic acid instead of quinoline-6-carboxylic acid. MS (ESI): mass calcd. for C$_{23}$H$_{19}$F$_3$N$_6$O, 452.1; m/z found, 453.1 [M+H]$^+$. $^1$H NMR (600 MHz, DMSO-d$_6$) δ 8.67-8.26 (m, 3H), 7.63 (s, 2H), 7.39 (dd, J=9.1, 4.4 Hz, 1H), 5.78-5.29 (m, 1H), 5.04-4.55 (m, 1H), 3.90-3.62 (m, 3H), 3.30-3.03 (m, 1H), 2.66-2.52 (m, 1H), 2.14-1.37 (m, 6H).

Example 240: ((5R,9S)-2-Methyl-3-(3,4,5-trifluorophenyl)-4,5,6,7,8,9-hexahydro-2H-5,9-epiminocycloocta[c]pyrazol-10-yl) (pyrazolo[1,5-a]pyrimidin-2-yl)methanone

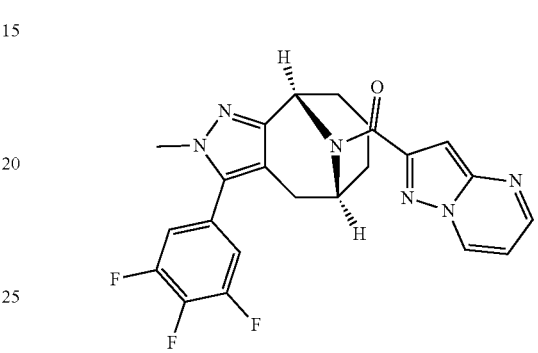

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and pyrazolo[1,5-a]pyrimidine-2-carboxylic acid instead of quinoline-6-carboxylic acid. MS (ESI): mass calcd. for C$_{23}$H$_{19}$F$_3$N$_6$O, 452.1; m/z found, 453.1 [M+H]$^+$. $^1$H NMR (500 MHz, DMSO-d$_6$) δ 9.25-9.07 (m, 1H), 8.70-8.53 (m, 1H), 7.67-7.54 (m, 2H), 7.20-7.10 (m, 1H), 7.02-6.85 (m, 1H), 5.83-5.58 (m, 1H), 5.12-4.66 (m, 1H), 3.85-3.70 (m, 3H), 3.14-3.02 (m, 1H), 2.60 (d, J=16.3 Hz, 1H), 2.03-1.31 (m, 6H).

Example 241: ((5R,9S)-2-Methyl-3-(3,4,5-trifluorophenyl)-4,5,6,7,8,9-hexahydro-2H-5,9-epiminocycloocta[c]pyrazol-10-yl)(pyrazolo[1,5-a]pyrimidin-3-yl)methanone

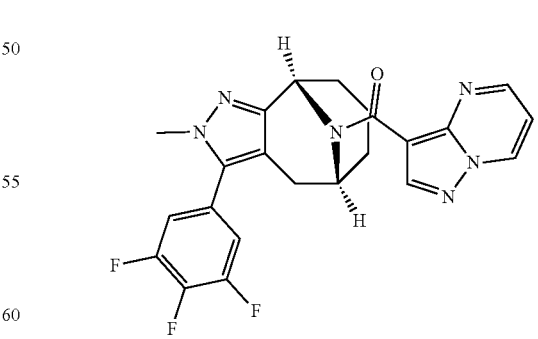

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9- epiminocycloocta[c]pyrazole (Intermediate 1) and pyrazolo[1,5-a]pyrimidine-3-carboxylic acid instead of quinoline-6-carboxylic acid. MS (ESI): mass calcd. for $C_{23}H_{19}F_3N_6O$, 452.1; m/z found, 453.1 [M+H]$^+$. $^1$H NMR (600 MHz, DMSO-$d_6$) δ 9.30-9.03 (m, 1H), 8.82-8.62 (m, 1H), 8.41 (d, J=16.9 Hz, 1H), 7.57 (dd, J=8.6, 6.6 Hz, 2H), 7.27-6.96 (m, 1H), 5.82-5.57 (m, 1H), 4.52-4.00 (m, 1H), 3.88-3.64 (m, 3H), 3.16-3.02 (m, 1H), 2.42-2.25 (m, 1H), 1.97-1.41 (m, 6H).

Example 242: ((5R,9S)-2-Methyl-3-(3,4,5-trifluorophenyl)-4,5,6,7,8,9-hexahydro-2H-5,9-epiminocycloocta[c]pyrazol-10-yl)(6-methylpyrazolo[1,5-a]pyrimidin-3-yl)methanone

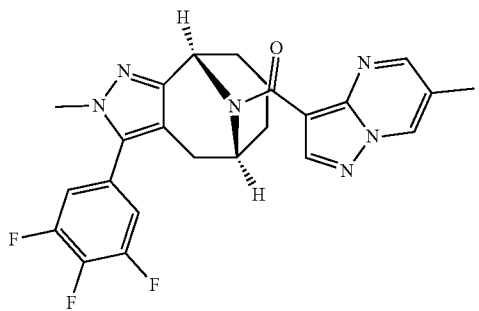 [SMILES: Cc1cnc2c(C(=O)N3[C@@H]4CCC[C@H]3c3nn(C)c(-c5cc(F)c(F)c(F)c5)c3C4)cnn2c1]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 6-methylpyrazolo[1,5-a]pyrimidine-3-carboxylic acid instead of quinoline-6-carboxylic acid. MS (ESI): mass calcd. for $C_{24}H_{21}F_3N_6O$, 466.1; m/z found, 467.1 [M+H]$^+$. $^1$H NMR (600 MHz, DMSO-$d_6$) δ 9.06 (d, J=20.2 Hz, 1H), 8.69-8.56 (m, 1H), 8.32 (d, J=17.3 Hz, 1H), 7.57 (dd, J=8.7, 6.6 Hz, 2H), 5.78-5.61 (m, 1H), 4.53-4.29 (m, 1H), 3.86-3.63 (m, 3H), 3.20-3.03 (m, 1H), 2.47-2.40 (m, 1H), 2.38-2.27 (m, 3H), 1.93-1.39 (m, 6H).

Example 243: ((5R,9S)-2-Methyl-3-(3,4,5-trifluorophenyl)-4,5,6,7,8,9-hexahydro-2H-5,9-epiminocycloocta[c]pyrazol-10-yl)(pyrazolo[1,5-a]pyrimidin-5-yl)methanone

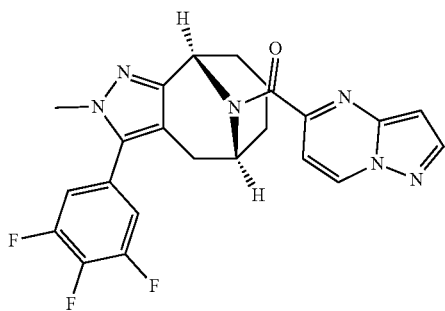 [SMILES: Cn1nc2c(c1-c1cc(F)c(F)c(F)c1)C[C@H]1CCC[C@@H]2N1C(=O)c1ccn2nccc2n1]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and pyrazolo[1,5-a]pyrimidine-5-carboxylic acid instead of quinoline-6-carboxylic acid. MS (ESI): mass calcd. for $C_{23}H_{19}F_3N_6O$, 452.1; m/z found, 453.1 [M+H]$^+$. $^1$H NMR (600 MHz, DMSO-$d_6$) δ 9.32-9.09 (m, 1H), 8.32 (dd, J=19.6, 2.3 Hz, 1H), 7.66-7.44 (m, 2H), 7.15 (dd, J=13.8, 7.1 Hz, 1H), 6.89-6.73 (m, 1H), 5.98-5.60 (m, 1H), 4.44-3.96 (m, 1H), 3.87-3.71 (m, 3H), 3.16-2.98 (m, 1H), 2.66-2.52 (m, 1H), 2.04-1.43 (m, 6H).

Example 244: ((5R,9S)-2-Methyl-3-(3,4,5-trifluorophenyl)-4,5,6,7,8,9-hexahydro-2H-5,9-epiminocycloocta[c]pyrazol-10-yl)(pyrazolo[1,5-a]pyrazin-3-yl)methanone

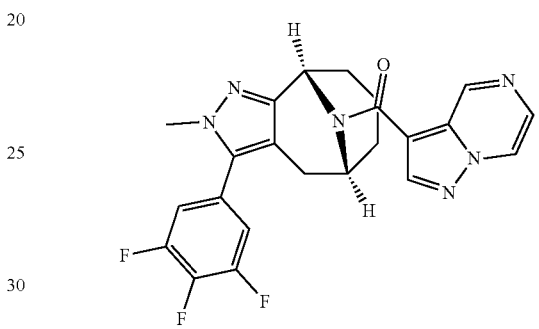

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and pyrazolo[1,5-a]pyrazine-3-carboxylic acid instead of quinoline-6-carboxylic acid. MS (ESI): mass calcd. for $C_{23}H_{19}F_3N_6O$, 452.1; m/z found, 453.1 [M+H]$^+$. $^1$H NMR (500 MHz, DMSO-$d_6$) δ 9.40-9.17 (m, 1H), 8.90 (dd, J=4.8, 1.5 Hz, 1H), 8.47 (s, 1H), 8.14-8.00 (m, 1H), 7.62 (s, 2H), 5.79-5.29 (m, 1H), 5.12-4.59 (m, 1H), 3.92-3.71 (m, 3H), 3.21-2.94 (m, 1H), 2.70-2.51 (m, 1H), 2.04-1.39 (m, 6H).

Example 245: Imidazo[1,2-b]pyridazin-6-yl((5R,9S)-2-methyl-3-(3,4,5-trifluorophenyl)-4,5,6,7,8,9-hexahydro-2H-5,9-epiminocycloocta[c]pyrazol-10-yl)methanone

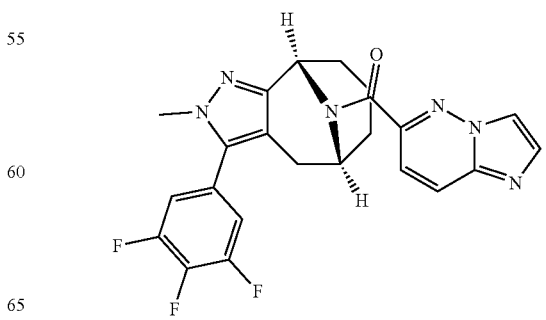

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and imidazo[1,2-b]pyridazine-6-carboxylic acid instead of quinoline-6-carboxylic acid. MS (ESI): mass calcd. for $C_{23}H_{19}F_3N_6O$, 452.1; m/z found, 453.0 [M+H]$^+$. $^1$H NMR (400 MHz, DMSO-d$_6$) δ 8.44-8.33 (m, 1H), 8.30-8.18 (m, 1H), 7.90 (dd, J=12.9, 1.3 Hz, 1H), 7.68-7.55 (m, 2H), 7.34 (dd, J=15.1, 9.4 Hz, 1H), 5.82-5.63 (m, 1H), 4.43-4.20 (m, 1H), 3.86-3.70 (m, 3H), 3.14-3.02 (m, 1H), 2.77-2.54 (m, 1H), 2.04-1.42 (m, 6H).

Example 246: Imidazo[1,2-b]pyridazin-3-yl((5R,9S)-2-methyl-3-(3,4,5-trifluorophenyl)-4,5,6,7,8,9-hexahydro-2H-5,9-epiminocycloocta[c]pyrazol-10-yl)methanone

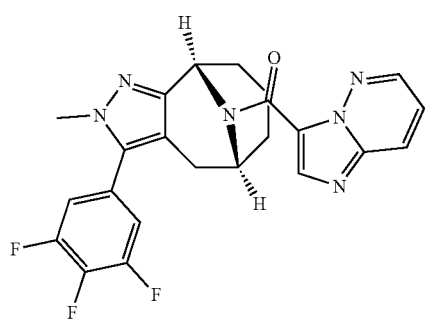 [SMILES: Cn1nc2c(c1-c1cc(F)c(F)c(F)c1)C[C@H]1CCC[C@@H]2N1C(=O)c1cnc2cccnn12]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and imidazo[1,2-b]pyridazine-3-carboxylic acid instead of quinoline-6-carboxylic acid. MS (ESI): mass calcd. for $C_{23}H_{19}F_3N_6O$, 452.1; m/z found, 453.1 [M+H]$^+$. $^1$H NMR (600 MHz, DMSO-d$_6$) δ 8.62 (dd, J=4.4, 1.6 Hz, 1H), 8.22 (d, J=9.4 Hz, 1H), 8.00 (d, J=36.2 Hz, 1H), 7.64-7.51 (m, 2H), 7.41-7.22 (m, 1H), 5.90-5.62 (m, 1H), 4.24-4.02 (m, 1H), 3.89-3.58 (m, 3H), 3.16-3.03 (m, 1H), 2.49-2.37 (m, 1H), 1.96-1.37 (m, 6H).

Example 247: [1,2,4]Triazolo[1,5-a]pyridin-7-yl((5R,9S)-2-methyl-3-(3,4,5-trifluorophenyl)-4,5,6,7,8,9-hexahydro-2H-5,9-epiminocycloocta[c]pyrazol-10-yl)methanone

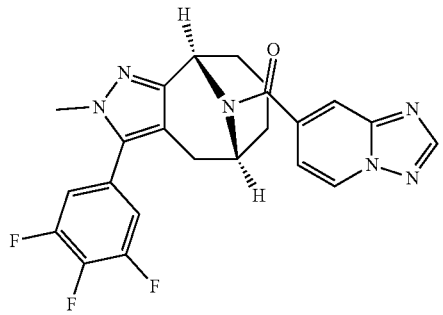 [SMILES: Cn1nc2c(c1-c1cc(F)c(F)c(F)c1)C[C@H]1CCC[C@@H]2N1C(=O)c1ccn2ncnc2c1]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and [1,2,4]triazolo[1,5-a]pyridine-7-carboxylic acid instead of quinoline-6-carboxylic acid. MS (ESI): mass calcd. for $C_{23}H_{19}F_3N_6O$, 452.2; m/z found, 453.1 [M+H]$^+$. $^1$H NMR (500 MHz, DMSO-d$_6$) δ 9.05-8.99 (m, 1H), 8.59-8.56 (m, 1H), 7.94-7.88 (m, 1H), 7.65-7.55 (m, 2H), 7.28-7.17 (m, 1H), 5.74-5.66 (m, 1H), 4.11-4.03 (m, 1H), 3.80 (s, 3H), 3.14-3.02 (m, 1H), 2.39 (d, J=16.3 Hz, 1H), 2.04-1.32 (m, 6H).

Example 248: ((5R,9S)-2-Methyl-3-(3,4,5-trifluorophenyl)-4,5,6,7,8,9-hexahydro-2H-5,9-epiminocycloocta[c]pyrazol-10-yl)(5-methyl-5H-pyrrolo[2,3-b]pyrazin-7-yl)methanone

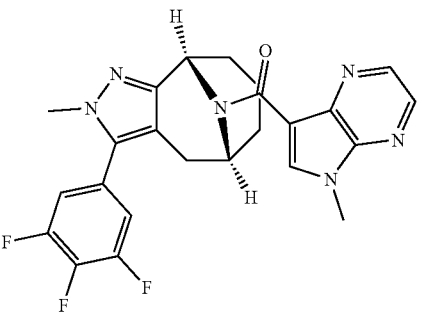 [SMILES: Cn1nc2c(c1-c1cc(F)c(F)c(F)c1)C[C@H]1CCC[C@@H]2N1C(=O)c1cn(C)c2nccnc12]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 5-methyl-5H-pyrrolo[2,3-b]pyrazine-7-carboxylic acid instead of quinoline-6-carboxylic acid. MS (ESI): mass calcd. for $C_{24}H_{21}F_3N_6O$, 466.1; m/z found, 467.1 [M+H]$^+$. $^1$H NMR (600 MHz, DMSO-d$_6$) δ 8.62-8.18 (m, 3H), 7.61-7.39 (m, 2H), 5.86-5.54 (m, 1H), 4.72-4.35 (m, 1H), 3.96-3.65 (m, 6H), 3.14-3.03 (m, 1H), 2.48-2.27 (m, 1H), 1.95-1.36 (m, 6H).

Example 249: Imidazo[1,2-a]pyrimidin-3-yl((5R,9S)-2-methyl-3-(3,4,5-trifluorophenyl)-4,5,6,7,8,9-hexahydro-2H-5,9-epiminocycloocta[c]pyrazol-10-yl)methanone

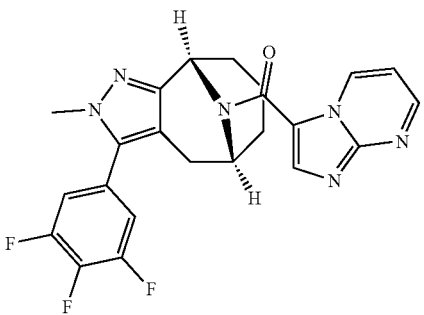

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and imidazo[1,2-a]pyrimidine-3-carboxylic acid instead of quinoline-6-carboxylic acid. MS (ESI): mass calcd. for $C_{23}H_{19}F_3N_6O$, 452.1; m/z found, 453.0 [M+H]$^+$. $^1$H NMR (500 MHz, DMSO-d$_6$) δ 9.26 (dd, J=6.9, 2.0 Hz, 1H), 8.70 (dd, J=4.1, 2.0 Hz, 1H), 8.32-8.03 (m, 1H), 7.76-7.53 (m, 2H), 7.23 (dd, J=6.9, 4.1 Hz, 1H), 5.80-5.58 (m, 1H), 5.04-4.82 (m, 1H), 3.86-3.70 (m, 3H), 3.21-3.08 (m, 1H), 2.70-2.54 (m, 1H), 1.90-1.18 (m, 6H).

Example 250: ((5R,9S)-2-Methyl-3-(3,4,5-trifluorophenyl)-4,5,6,7,8,9-hexahydro-2H-5,9-epiminocycloocta[c]pyrazol-10-yl)(quinolin-4-yl)methanone

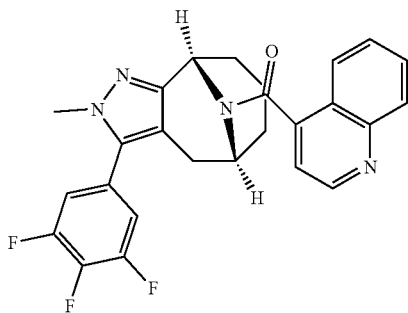 [SMILES: Cn1nc2c(c1-c1cc(F)c(F)c(F)c1)C[C@H]1CCC[C@@H]2N1C(=O)c1ccnc2ccccc12]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and quinoline-4-carboxylic acid instead of quinoline-6-carboxylic acid. MS (ESI): mass calcd. for $C_{26}H_{21}F_3N_4O$, 462.1; m/z found, 463.1 [M+H]$^+$. $^1$H NMR (500 MHz, DMSO-d$_6$) δ 9.06-8.83 (m, 1H), 8.17-7.05 (m, 7H), 6.02-5.78 (m, 1H), 4.45-4.02 (m, 1H), 3.85-3.68 (m, 3H), 3.08-2.60 (m, 1H), 2.37 (d, J=16.1 Hz, 1H), 2.10-1.32 (m, 6H).

Example 251: Isoquinolin-1-yl((5R,9S)-2-methyl-3-(3,4,5-trifluorophenyl)-4,5,6,7,8,9-hexahydro-2H-5,9-epiminocycloocta[c]pyrazol-10-yl)methanone

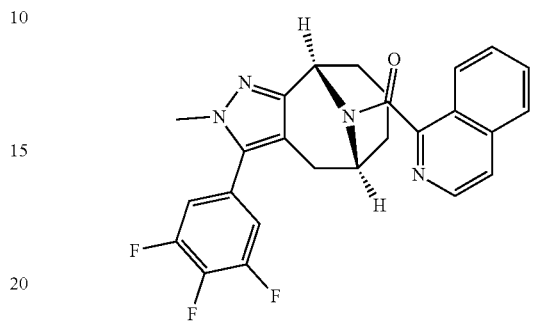

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and isoquinoline-1-carboxylic acid instead of quinoline-6-carboxylic acid. MS (ESI): mass calcd. for $C_{26}H_{21}F_3N_4O$, 462.1; m/z found, 463.1 [M+H]$^+$. $^1$H NMR (500 MHz, DMSO-d$_6$) δ 8.51 (dd, J=15.5, 5.6 Hz, 1H), 8.17-8.02 (m, 1H), 7.99-7.49 (m, 6H), 5.99-5.73 (m, 1H), 3.87-3.70 (m, 3H), 3.69-3.56 (m, 1H), 2.86-2.75 (m, 1H), 2.47-2.37 (m, 1H), 2.09-1.37 (m, 6H).

Example 252: ((5R,9S)-2-Methyl-3-(3,4,5-trifluorophenyl)-4,5,6,7,8,9-hexahydro-2H-5,9-epiminocycloocta[c]pyrazol-10-yl) (quinolin-6-yl) methanone

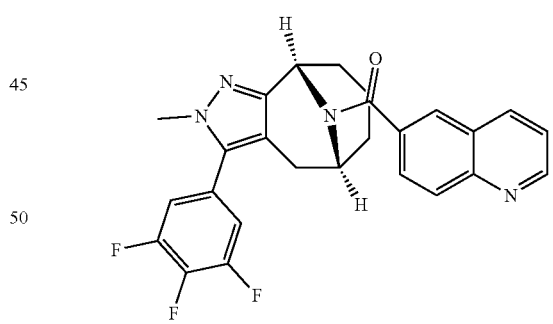

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1). MS (ESI): mass calcd. for $C_{26}H_{21}F_3N_4O$, 462.1; m/z found, 463.1 [M+H]$^+$. $^1$H NMR (400 MHz, DMSO-d$_6$) δ 8.97 (dd, J=4.2, 1.7 Hz, 1H), 8.48 (d, J=8.4 Hz, 1H), 8.14-8.00 (m, 2H), 7.82-7.51 (m, 4H), 5.87-5.69 (m, 1H), 4.22-4.04 (m, 1H), 3.87-3.70 (m, 3H), 3.15-3.03 (m, 1H), 2.47-2.40 (m, 1H), 2.00-1.37 (m, 6H).

Example 253: ((5R,9S)-2-Methyl-3-(3,4,5-trifluorophenyl)-4,5,6,7,8,9-hexahydro-2H-5,9-epiminocycloocta[c]pyrazol-10-yl)(quinolin-7-yl)methanone

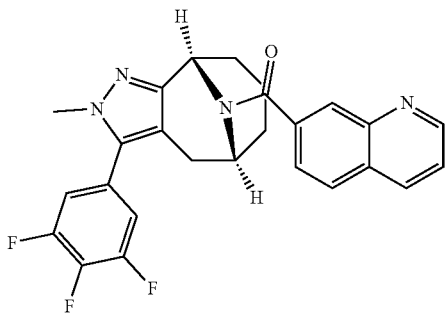 [SMILES: Cn1nc2c(c1-c1cc(F)c(F)c(F)c1)C[C@H]1CCC[C@@H]2N1C(=O)c1ccc2cccnc2c1]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and quinoline-7-carboxylic acid instead of quinoline-6-carboxylic acid. MS (ESI): mass calcd. for $C_{26}H_{21}F_3N_4O$, 462.1; m/z found, 463.1 [M+H]$^+$. $^1$H NMR (500 MHz, DMSO-d$_6$) δ 9.05-8.86 (m, 1H), 8.53-8.40 (m, 1H), 8.16-7.88 (m, 2H), 7.74-7.52 (m, 4H), 5.83-5.66 (m, 1H), 4.18-4.01 (m, 1H), 3.86-3.69 (m, 3H), 3.14-2.96 (m, 1H), 2.46-2.30 (m, 1H), 2.03-1.38 (m, 6H).

Example 254: ((5R,9S)-2-Methyl-3-(3,4,5-trifluorophenyl)-4,5,6,7,8,9-hexahydro-2H-5,9-epiminocycloocta[c]pyrazol-10-yl)(quinazolin-4-yl)methanone

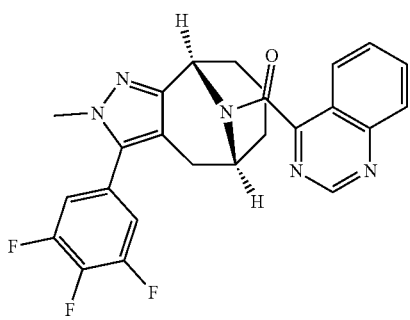 [SMILES: Cn1nc2c(c1-c1cc(F)c(F)c(F)c1)C[C@H]1CCC[C@@H]2N1C(=O)c1ncnc2ccccc12]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and quinazoline-4-carboxylic acid instead of quinoline-6-carboxylic acid. MS (ESI): mass calcd. for $C_{25}H_{20}F_3N_5O$, 463.1; m/z found, 464.0 [M+H]$^+$. $^1$H NMR (500 MHz, DMSO-d$_6$) δ 9.33 (d, J=18.1 Hz, 1H), 8.33-7.38 (m, 6H), 5.99-5.78 (m, 1H), 4.19-4.02 (m, 1H), 3.86-3.65 (m, 3H), 2.93-2.79 (m, 1H), 2.45-2.37 (m, 1H), 2.05-1.46 (m, 6H).

Example 255: ((5R,9S)-2-Methyl-3-(3,4,5-trifluorophenyl)-4,5,6,7,8,9-hexahydro-2H-5,9-epiminocycloocta[c]pyrazol-10-yl) (quinoxalin-6-yl) methanone

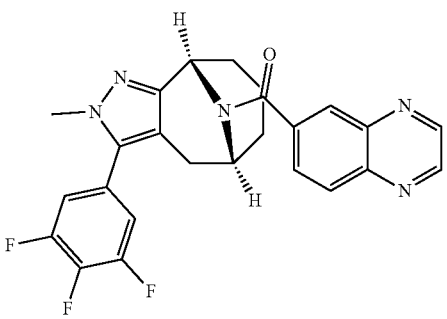 [SMILES: Cn1nc2c(c1-c1cc(F)c(F)c(F)c1)C[C@H]1CCC[C@@H]2N1C(=O)c1ccc2nccnc2c1]

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and quinoxaline-6-carboxylic acid instead of quinoline-6-carboxylic acid. MS (ESI): mass calcd. for $C_{25}H_{20}F_3N_5O$, 463.1; m/z found, 464.1 [M+H]$^+$. $^1$H NMR (500 MHz, DMSO-d$_6$) δ 9.07-8.96 (m, 2H), 8.25-7.99 (m, 2H), 7.93-7.79 (m, 1H), 7.64-7.52 (m, 2H), 5.81-5.74 (m, 1H), 4.08 (s, 1H), 3.86-3.70 (m, 3H), 3.19-2.99 (m, 1H), 2.41 (d, J=16.1 Hz, 1H), 2.05-1.38 (m, 6H).

Example 256: ((5R,9S)-2-Methyl-3-(3,4,5-trifluorophenyl)-4,5,6,7,8,9-hexahydro-2H-5,9-epiminocycloocta[c]pyrazol-10-yl)(2-methylquinoxalin-6-yl) methanone

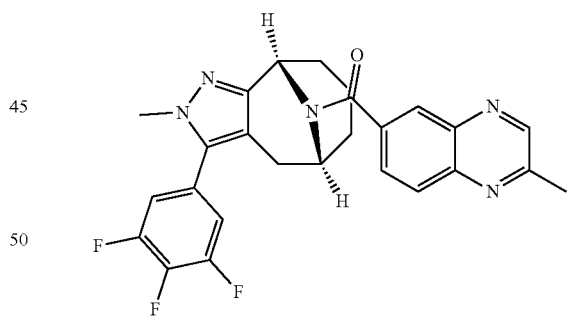

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 2-methylquinoxaline-6-carboxylic acid (Intermediate 33) instead of quinoline-6-carboxylic acid. MS (ESI): mass calcd. for $C_{26}H_{22}F_3N_5O$, 477.1; m/z found, 478.0 [M+H]$^+$. $^1$H NMR (600 MHz, DMSO-d$_6$) δ 8.98-8.87 (m, 1H), 8.14-7.59 (m, 5H), 5.83-5.69 (m, 1H), 4.17-4.02 (m, 1H), 3.84-3.68 (m, 3H), 3.16-3.02 (m, 1H), 2.81-2.69 (m, 3H), 2.47-2.38 (m, 1H), 1.99-1.42 (m, 6H).

Example 257: ((5R,9S)-2-Methyl-3-(3,4,5-trifluorophenyl)-4,5,6,7,8,9-hexahydro-2H-5,9-epiminocyclooctal[c]pyrazol-10-yl)(quinoxalin-2-yl)methanone

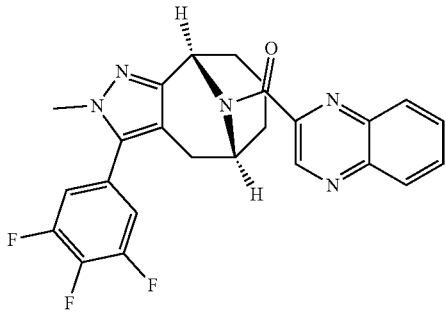

The title compound was prepared in a manner analogous to Example 1, using (5R,9S)-2-methyl-3-(3,4,5-trifluorophenyl)-4,5,6,7,8,9-hexahydro-2H-5,9-epiminocyclooctal[c]pyrazole (Intermediate 25) instead of racemic-(5R,9S)-2-methyl-3-phenyl-4,5,6,7,8,9-hexahydro-2H-5,9-epiminocyclooctal[c]pyrazole (Intermediate 1) and quinoxaline-2-carboxylic acid instead of quinoline-6-carboxylic acid. MS (ESI): mass calcd. for $C_{25}H_{20}F_3N_5O$, 463.1; m/z found, 464.1 [M+H]$^+$. $^1$H NMR (500 MHz, DMSO-$d_6$) δ 9.12 (d, J=4.4 Hz, 1H), 8.22-8.04 (m, 2H), 8.04-7.88 (m, 2H), 7.69-7.43 (m, 2H), 5.89-5.57 (m, 1H), 4.52-4.30 (m, 1H), 3.89-3.65 (m, 3H), 3.24-3.04 (m, 1H), 2.65 (d, J=16.3 Hz, 1H), 2.17-1.46 (m, 6H).

Example 258: Cinnolin-3-yl((5R,9S)-2-methyl-3-(3,4,5-trifluorophenyl)-4,5,6,7,8,9-hexahydro-2H-5,9-epiminocyclooctal[c]pyrazol-10-yl)methanone

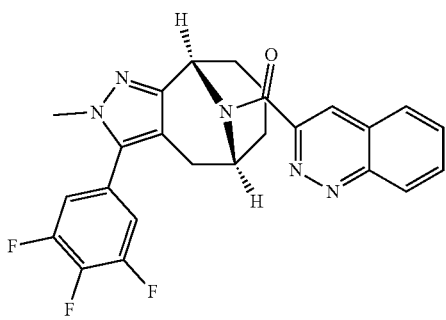 [SMILES: Cn1nc2c(c1-c1cc(F)c(F)c(F)c1)C[C@H]1CCC[C@@H]2N1C(=O)c1cc2ccccc2nn1]

The title compound was prepared in a manner analogous to Example 1, using (5R,9S)-2-methyl-3-(3,4,5-trifluorophenyl)-4,5,6,7,8,9-hexahydro-2H-5,9-epiminocyclooctal[c]pyrazole (Intermediate 25) instead of racemic-(5R,9S)-2-methyl-3-phenyl-4,5,6,7,8,9-hexahydro-2H-5,9-epiminocyclooctal[c]pyrazole (Intermediate 1) and cinnoline-3-carboxylic acid instead of quinoline-6-carboxylic acid. MS (ESI): mass calcd. for $C_{25}H_{20}F_3N_5O$, 463.1; m/z found, 464.1 [M+H]$^+$. $^1$H NMR (600 MHz, DMSO-$d_6$) δ 8.61-8.42 (m, 2H), 8.24-8.11 (m, 1H), 8.10-7.90 (m, 2H), 7.68-7.45 (m, 2H), 5.91-5.78 (m, 1H), 4.32-4.11 (m, 1H), 3.85-3.70 (m, 3H), 3.19-3.02 (m, 1H), 2.49-2.39 (m, 1H), 2.09-1.44 (m, 6H).

Example 259: Cinnolin-6-yl((5R,9S)-2-methyl-3-(3,4,5-trifluorophenyl)-4,5,6,7,8,9-hexahydro-2H-5,9-epiminocyclooctal[c]pyrazol-10-yl) methanone

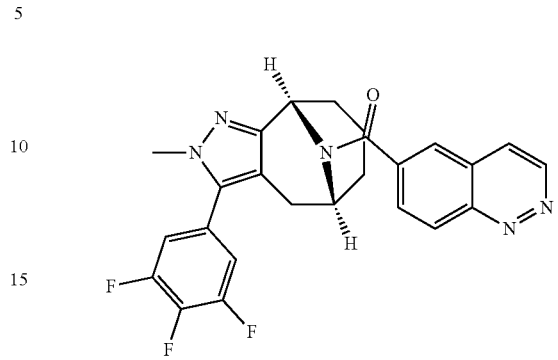

The title compound was prepared in a manner analogous to Example 1, using (5R,9S)-2-methyl-3-(3,4,5-trifluorophenyl)-4,5,6,7,8,9-hexahydro-2H-5,9-epiminocyclooctal[c]pyrazole (Intermediate 25) instead of racemic-(5R,9S)-2-methyl-3-phenyl-4,5,6,7,8,9-hexahydro-2H-5,9-epiminocyclooctal[c]pyrazole (Intermediate 1) and cinnoline-6-carboxylic acid instead of quinoline-6-carboxylic acid. MS (ESI): mass calcd. for $C_{25}H_{20}F_3N_5O$, 463.1; m/z found, 464.1 [M+H]$^+$. $^1$H NMR (600 MHz, DMSO-$d_6$) δ 9.46 (dd, J=8.8, 5.8 Hz, 1H), 8.60-8.48 (m, 1H), 8.38-8.27 (m, 1H), 8.21-8.08 (m, 1H), 8.00-7.85 (m, 1H), 7.65-7.54 (m, 2H), 5.82-5.64 (m, 1H), 4.14-3.96 (m, 1H), 3.86-3.69 (m, 3H), 3.16-2.99 (m, 1H), 2.46-2.40 (m, 1H), 2.05-1.43 (m, 6H).

Example 260: ((5R,9S)-2-Methyl-3-(3,4,5-trifluorophenyl)-4,5,6,7,8,9-hexahydro-2H-5,9-epiminocyclooctal[c]pyrazol-10-yl)(1,5-naphthyridin-2-yl)methanone

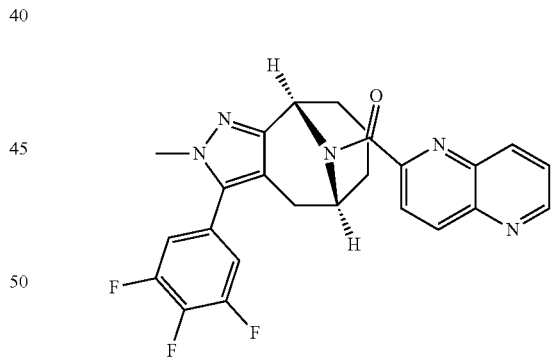

The title compound was prepared in a manner analogous to Example 1, using (5R,9S)-2-methyl-3-(3,4,5-trifluorophenyl)-4,5,6,7,8,9-hexahydro-2H-5,9-epiminocyclooctal[c]pyrazole (Intermediate 25) instead of racemic-(5R,9S)-2-methyl-3-phenyl-4,5,6,7,8,9-hexahydro-2H-5,9-epiminocyclooctal[c]pyrazole (Intermediate 1) and 1,5-naphthyridine-2-carboxylic acid instead of quinoline-6-carboxylic acid. MS (ESI): mass calcd. for $C_{25}H_{20}F_3N_5O$, 463.1; m/z found, 464.1 [M+H]$^+$. $^1$H NMR (600 MHz, DMSO-$d_6$) δ 9.16-9.04 (m, 1H), 8.61-8.43 (m, 2H), 8.02-7.80 (m, 2H), 7.70-7.52 (m, 2H), 5.85-5.76 (m, 1H), 4.32-4.13 (m, 1H), 3.86-3.70 (m, 3H), 3.16-3.07 (m, 1H), 2.75-2.56 (m, 1H), 2.16-1.42 (m, 6H).

Example 261: ((5R,9S)-2-Methyl-3-(3,4,5-trifluorophenyl)-4,5,6,7,8,9-hexahydro-2H-5,9-epiminocycloocta[c]pyrazol-10-yl)(1,5-naphthyridin-3-yl)methanone

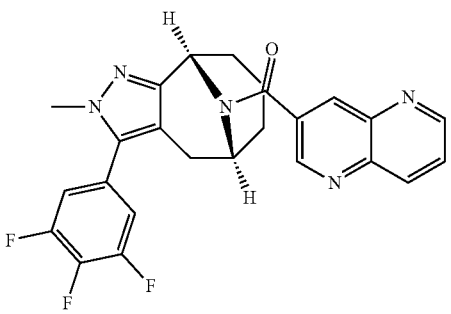

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 1,5-naphthyridine-3-carboxylic acid instead of quinoline-6-carboxylic acid. MS (ESI): mass calcd. for $C_{25}H_{20}F_3N_5O$, 463.1; m/z found, 464.1 [M+H]$^+$. $^1$H NMR (600 MHz, DMSO-d$_6$) δ 9.16-8.94 (m, 2H), 8.54-8.28 (m, 2H), 7.96-7.79 (m, 1H), 7.71-7.50 (m, 2H), 5.84-5.73 (m, 1H), 4.23-4.08 (m, 1H), 3.88-3.73 (m, 3H), 3.20-3.06 (m, 1H), 2.46-2.31 (m, 1H), 2.06-1.37 (m, 6H).

Example 262: ((5R,9S)-2-Methyl-3-(3,4,5-trifluorophenyl)-4,5,6,7,8,9-hexahydro-2H-5,9-epiminocycloocta[c]pyrazol-10-yl)(1,6-naphthyridin-8-yl)methanone

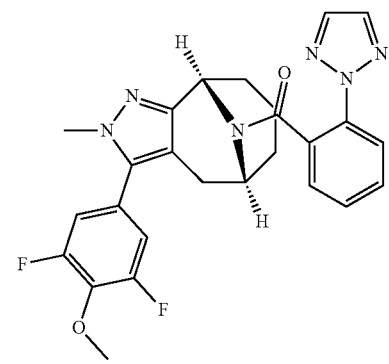

The title compound was prepared in a manner analogous to Example 1, using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 1,6-naphthyridine-8-carboxylic acid instead of quinoline-6-carboxylic acid. MS (ESI): mass calcd. for $C_{25}H_{20}F_3N_5O$, 463.1; m/z found, 464.1 [M+H]$^+$. $^1$H NMR (500 MHz, DMSO-d$_6$) δ 9.54-9.39 (m, 1H), 9.27-8.37 (m, 3H), 7.88-7.44 (m, 3H), 6.02-5.77 (m, 1H), 4.38-3.98 (m, 1H), 3.88-3.69 (m, 3H), 3.18-2.89 (m, 1H), 2.45-2.22 (m, 1H), 2.06-1.32 (m, 6H).

Example 263: (2-(2H-1,2,3-Triazol-2-yl)phenyl)((5R,9S)-3-(3,5-difluoro-4-methoxyphenyl)-2-methyl-4,5,6,7,8,9-hexahydro-2H-5,9-epiminocycloocta[c]pyrazol-10-yl)methanone

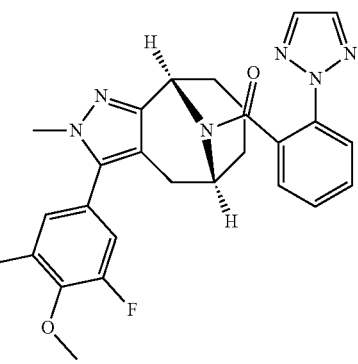

The title compound was prepared in a manner analogous to Example 1, using (5R,9S)-3-(3,5-difluoro-4-methoxyphenyl)-2-methyl-4,5,6,7,8,9-hexahydro-2H-5,9-epiminocycloocta[c]pyrazole (Intermediate 22) instead of racemic-(5R,9S)-2-methyl-3-phenyl-4,5,6,7,8,9-hexahydro-2H-5,9-epiminocycloocta[c]pyrazole (Intermediate 1) and 2-(2H-1,2,3-triazol-2-yl)benzoic acid (Intermediate 49) instead of quinoline-6-carboxylic acid. MS (ESI): mass calcd. for $C_{26}H_{24}F_2N_6O_2$, 490.1; m/z found, 491.1 [M+H]$^+$. $^1$H NMR (600 MHz, DMSO-d$_6$) δ 8.16 (d, J=13.2 Hz, 1H), 8.03-7.72 (m, 2H), 7.70-7.39 (m, 3H), 7.31-6.89 (m, 2H), 5.74-5.61 (m, 1H), 4.56-4.26 (m, 1H), 4.00-3.85 (m, 3H), 3.85-3.60 (m, 3H), 3.15-2.88 (m, 1H), 2.46-2.35 (m, 1H), 1.90-1.19 (m, 6H).

Example 264: ((5R,9S)-3-(3,5-Difluoro-4-methoxyphenyl)-2-methyl-4,5,6,7,8,9-hexahydro-2H-5,9-epiminocycloocta[c]pyrazol-10-yl)(1-methyl-1H-pyrazolo[3,4-b]pyridin-3-yl)methanone

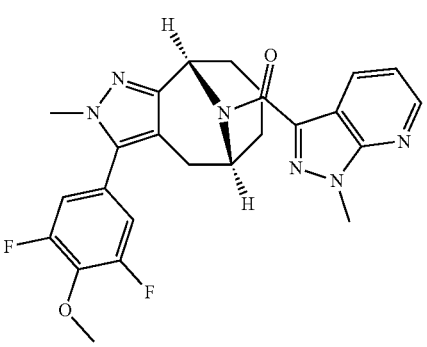

The title compound was prepared in a manner analogous to Example 1, using (5R,9S)-3-(3,5-difluoro-4-methoxyphenyl)-2-methyl-4,5,6,7,8,9-hexahydro-2H-5,9-epiminocycloocta[c]pyrazole (Intermediate 22) instead of racemic-(5R,9S)-2-methyl-3-phenyl-4,5,6,7,8,9-hexahydro-2H-5,9-epiminocycloocta[c]pyrazole (Intermediate 1) and 1-methyl-1H-pyrazolo[3,4-b]pyridine-3-carboxylic acid instead of quinoline-6-carboxylic acid. MS (ESI): mass calcd. for $C_{25}H_{24}F_2N_6O_2$, 478.1; m/z found, 479.1 [M+H]$^+$.

$^1$H NMR (600 MHz, DMSO-d$_6$) δ 8.69-8.54 (m, 1H), 8.47-8.32 (m, 1H), 7.42-7.29 (m, 3H), 6.36-6.25 (m, 1H), 5.17-5.08 (m, 1H), 4.19-4.10 (m, 3H), 4.01-3.96 (m, 3H), 3.82-3.73 (m, 3H), 3.15-3.08 (m, 1H), 2.63-2.55 (m, 1H), 2.02-1.41 (m, 6H).

Example 265: ((5R,9S)-3-(3,5-Difluoro-4-methoxyphenyl)-2-methyl-4,5,6,7,8,9-hexahydro-2H-5,9-epiminocycloocta[c]pyrazol-10-yl)(quinolin-6-yl)methanone

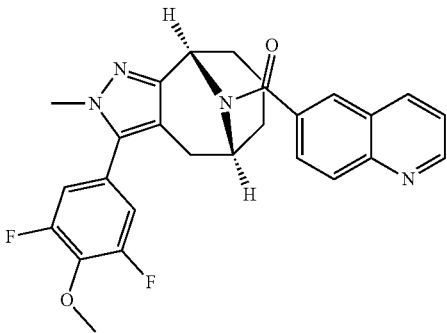

The title compound was prepared in a manner analogous to Example 1, using (5R,9S)-3-(3,5-difluoro-4-methoxyphenyl)-2-methyl-4,5,6,7,8,9-hexahydro-2H-5,9-epiminocycloocta[c]pyrazole (Intermediate 22) instead of racemic-(5R,9S)-2-methyl-3-phenyl-4,5,6,7,8,9-hexahydro-2H-5,9-epiminocycloocta[c]pyrazole (Intermediate 1). MS (ESI): mass calcd. for C$_{27}$H$_{24}$F$_2$N$_4$O$_2$, 474.2; m/z found, 475.0 [M+H]$^+$. $^1$H NMR (400 MHz, DMSO-d$_6$) δ 8.96 (d, J=4.5 Hz, 1H), 8.48 (d, J=8.3 Hz, 1H), 8.19-8.04 (m, 2H), 7.85-7.56 (m, 2H), 7.39 (t, J=8.6 Hz, 2H), 5.87-5.69 (m, 1H), 4.16-4.09 (m, 1H), 4.01-3.96 (m, 3H), 3.84-3.79 (m, 3H), 2.49-2.40 (m, 1H), 1.94-1.40 (m, 7H).

Example 266: (2-(2H-1,2,3-Triazol-2-yl)phenyl)((5R,9S)-3-(3,4-difluoro-5-methoxyphenyl)-2-methyl-4,5,6,7,8,9-hexahydro-2H-5,9-epiminocycloocta[c]pyrazol-10-yl)methanone

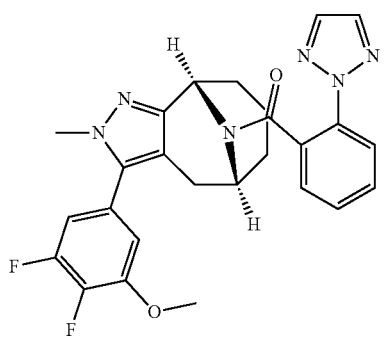

The title compound was prepared in a manner analogous to Example 1, using (5R,9S)-3-(3,4-difluoro-5-methoxyphenyl)-2-methyl-4,5,6,7,8,9-hexahydro-2H-5,9-epiminocycloocta[c]pyrazole (Intermediate 21) instead of racemic-(5R,9S)-2-methyl-3-phenyl-4,5,6,7,8,9-hexahydro-2H-5,9-epiminocycloocta[c]pyrazole (Intermediate 1) and 2-(2H-1,2,3-triazol-2-yl)benzoic acid (Intermediate 49) instead of quinoline-6-carboxylic acid. MS (ESI): mass calcd. for C$_{26}$H$_{24}$F$_2$N$_6$O$_2$, 490.1; m/z found, 491.1 [M+H]$^+$. $^1$H NMR (600 MHz, DMSO-d$_6$) δ 8.16 (d, J=13.2 Hz, 1H), 8.03-7.72 (m, 2H), 7.70-7.39 (m, 3H), 7.31-6.89 (m, 2H), 5.74-5.61 (m, 1H), 4.56-4.26 (m, 1H), 4.00-3.85 (m, 3H), 3.85-3.60 (m, 3H), 3.15-2.88 (m, 1H), 2.46-2.35 (m, 1H), 1.90-1.19 (m, 6H).

Example 267: ((5R,9S)-3-(3,4-Difluoro-5-methoxyphenyl)-2-methyl-4,5,6,7,8,9-hexahydro-2H-5,9-epiminocycloocta[c]pyrazol-10-yl) (1-methyl-1H-pyrazolo[3,4-b] pyridin-3-yl) methanone

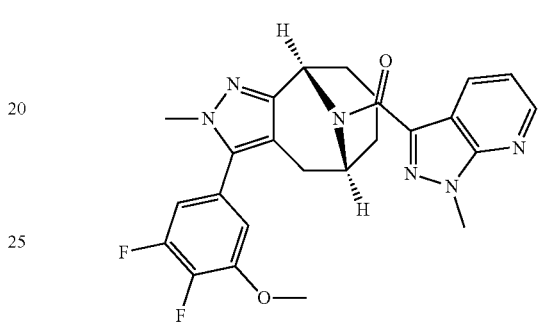

The title compound was prepared in a manner analogous to Example 1, using (5R,9S)-3-(3,4-difluoro-5-methoxyphenyl)-2-methyl-4,5,6,7,8,9-hexahydro-2H-5,9-epiminocycloocta[c]pyrazole (Intermediate 21) instead of racemic-(5R,9S)-2-methyl-3-phenyl-4,5,6,7,8,9-hexahydro-2H-5,9-epiminocycloocta[c]pyrazole (Intermediate 1) and 1-methyl-1H-pyrazolo[3,4-b]pyridine-3-carboxylic acid instead of quinoline-6-carboxylic acid. MS (ESI): mass calcd. for C$_{25}$H$_{24}$F$_2$N$_6$O$_2$, 478.1; m/z found, 479.1 [M+H]$^+$. $^1$H NMR (500 MHz, DMSO-d$_6$) δ 8.69-8.58 (m, 1H), 8.47-8.37 (m, 1H), 7.39-7.32 (m, 1H), 7.25-7.07 (m, 2H), 6.37-6.23 (m, 1H), 5.26-5.06 (m, 1H), 4.20-4.10 (m, 3H), 3.96-3.90 (m, 3H), 3.83-3.74 (m, 3H), 3.18-3.07 (m, 1H), 2.65-2.55 (m, 1H), 2.08-1.35 (m, 6H).

Example 268: ((5R,9S)-3-(3,4-Difluoro-5-methoxyphenyl)-2-methyl-4,5,6,7,8,9-hexahydro-2H-5,9-epiminocycloocta[c]pyrazol-10-yl)(quinolin-6-yl)methanone

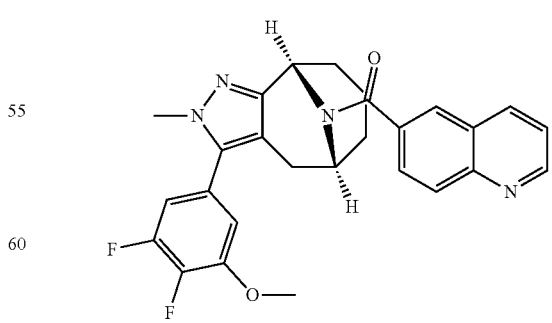

The title compound was prepared in a manner analogous to Example 1, using (5R,9S)-3-(3,4-difluoro-5-methoxyphenyl)-2-methyl-4,5,6,7,8,9-hexahydro-2H-5,9-epiminocycloocta[c]pyrazole (Intermediate 21) instead of racemic-(5R,9S)-2-methyl-3-phenyl-4,5,6,7,8,9-hexahydro-2H-5,9-epiminocycloocta[c]pyrazole (Intermediate 1). MS (ESI): mass calcd. for $C_{27}H_{24}F_2N_4O_2$, 474.1; m/z found, 475.1 [M+H]$^+$. $^1$H NMR (600 MHz, DMSO-d$_6$) δ 9.05-8.93 (m, 1H), 8.47 (t, J=7.8 Hz, 1H), 8.15-8.01 (m, 2H), 7.86-7.56 (m, 2H), 7.32-7.07 (m, 2H), 5.76 (s, 1H), 4.12 (s, 1H), 3.97-3.93 (m, 3H), 3.84-3.73 (m, 3H), 3.22-3.02 (m, 1H), 2.43 (d, J=16.1 Hz, 1H), 2.05-1.42 (m, 6H).

Example 269: ((5R,9S)-2-Methyl-3-(1-methyl-1H-indol-2-yl)-4,5,6,7,8,9-hexahydro-2H-5,9-epiminocycloocta[c]pyrazol-10-yl) (quinolin-6-yl) methanone

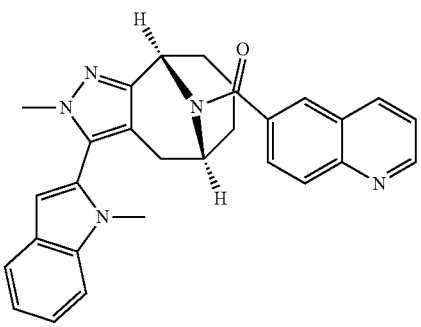

The title compound was prepared in a manner analogous to Example 1, using (5R,9S)-2-methyl-3-(1-methyl-1H-indol-2-yl)-4,5,6,7,8,9-hexahydro-2H-5,9-epiminocycloocta[c]pyrazole (Intermediate 32) instead of racemic-(5R,9S)-2-methyl-3-phenyl-4,5,6,7,8,9-hexahydro-2H-5,9-epiminocycloocta[c]pyrazole (Intermediate 1). MS (ESI): mass calcd. for $C_{29}H_{27}N_5O$, 461.2; m/z found, 462.1 [M+H]$^+$. $^1$H NMR (500 MHz, DMSO-d$_6$) δ 9.06-8.89 (m, 1H), 8.48 (dd, J=17.5, 8.2 Hz, 1H), 8.16-8.03 (m, 2H), 7.82-7.71 (m, 1H), 7.68-7.47 (m, 3H), 7.29-7.05 (m, 2H), 6.70 (s, 1H), 5.88-5.68 (m, 1H), 4.16-4.06 (m, 1H), 3.81-3.56 (m, 6H), 2.98-2.82 (m, 1H), 2.40-2.30 (m, 1H), 2.00-1.46 (m, 6H).

Example 270: racemic-((5R,9S)-2-Methyl-3-(5-(trifluoromethyl)thiophen-2-yl)-4,5,6,7,8,9-hexahydro-2H-5,9-epiminocycloocta[c]pyrazol-10-yl) (quinolin-6-yl)methanone

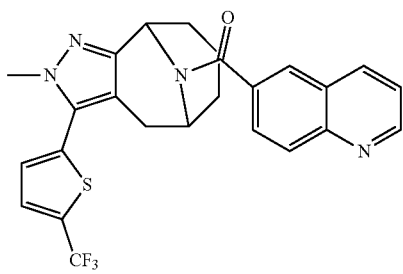 [SMILES: Cn1nc2c(c1-c1ccc(C(F)(F)F)s1)CC1CCCC2N1C(=O)c1ccc2ncccc2c1]

The title compound was prepared in a manner analogous to Example 1, using racemic-(5R,9S)-2-methyl-3-(5-(trifluoromethyl) thiophen-2-yl)-4,5,6,7,8,9-hexahydro-2H-5,9-epiminocycloocta[c]pyrazole (Intermediate 9) instead of racemic-(5R,9S)-2-methyl-3-phenyl-4,5,6,7,8,9-hexahydro-2H-5,9-epiminocycloocta[c]pyrazole (Intermediate 1). MS (ESI): mass calcd. for $C_{25}H_{21}F_3N_4OS$, 482.1; m/z found, 483.1 [M+H]$^+$. $^1$H NMR (500 MHz, DMSO-d$_6$) δ 9.03-8.91 (m, 1H), 8.55-8.37 (m, 1H), 8.15-8.02 (m, 2H), 7.90-7.45 (m, 4H), 5.77 (s, 1H), 4.17 (s, 1H), 3.99-3.80 (m, 3H), 3.26-2.98 (m, 1H), 2.65 (dd, J=69.0, 16.4 Hz, 1H), 2.11-1.33 (m, 6H).

Example 271: (4-Methoxyphenyl)((5R,9S)-2-methyl-3-(3,4,5-trifluorophenyl)-4,5,6,7,8,9-hexahydro-2H-5,9-epiminocycloocta[c]pyrazol-10-yl) methanone

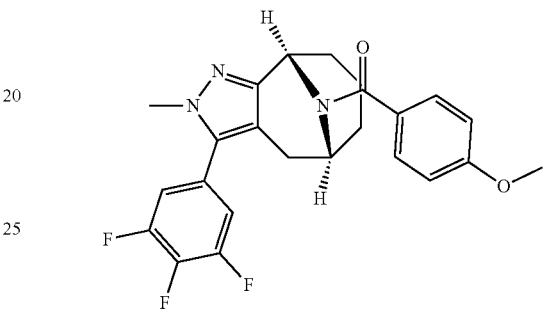

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 4-methoxybenzoic acid instead of quinoline-6-carboxylic acid. MS (ESI): mass calcd. for $C_{24}H_{22}F_3N_3O_2$, 441.2; m/z found, 442.2 [M+H]$^+$. $^1$H NMR (500 MHz, DMSO-d$_6$): 7.65-7.54 (m, 2H), 7.43-7.37 (m, 2H), 7.04-6.94 (m, 2H), 5.71-5.59 (m, 1H), 4.22-4.06 (m, 1H), 3.80 (s, 3H), 3.79 (s, 3H), 3.12-2.96 (m, 1H), 2.42 (d, J=16.2 Hz, 1H), 1.99-1.32 (m, 6H).

Example 272: (2-Fluoro-4-methylphenyl)((5R,9S)-2-methyl-3-(3,4,5-trifluorophenyl)-4,5,6,7,8,9-hexahydro-2H-5,9-epiminocycloocta[c]pyrazol-10-yl) methanone

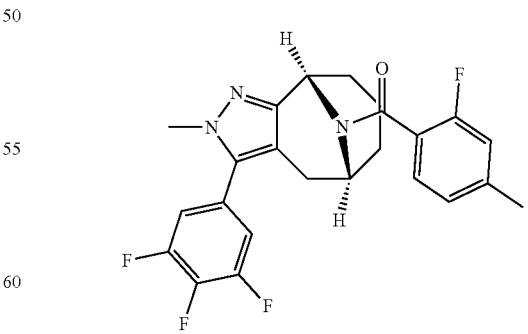

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2- methyl-3-phenyl-4,5,6,7,8,9-hexahydro-2H-5,9-epiminocycloocta[c]pyrazole (Intermediate 1) and 2-fluoro-4-methylbenzoic acid instead of quinoline-6-carboxylic acid. MS (ESI): mass calcd. for $C_{24}H_{21}F_4N_3O$, 443.2; m/z found, 444.2 [M+H]$^+$. $^1$H NMR (500 MHz, DMSO-d$_6$): 7.62-7.50 (m, 2H), 7.37-7.09 (m, 1H), 7.14-7.08 (m, 1H), 7.08-7.04 (m, 1H), 5.78-5.64 (m, 1H), 3.92-3.81 (m, 1H), 3.77 (s, 3H), 2.83 (dd, J=16.1, 7.4 Hz, 1H), 2.51-2.43 (m, 1H), 2.32 (s, 3H), 1.90-1.29 (m, 6H).

Example 273: (2-Fluoro-4-methoxyphenyl)((5R,9S)-2-methyl-3-(3,4,5-trifluorophenyl)-4,5,6,7,8,9-hexahydro-2H-5,9-epiminocycloocta[c]pyrazol-10-yl)methanone

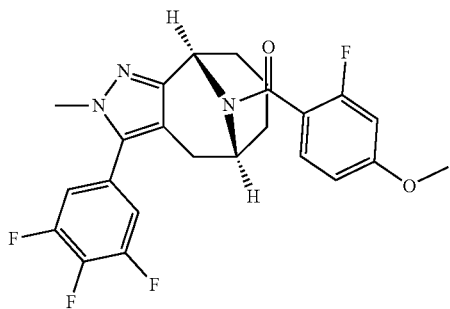

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 2-fluoro-4-methoxybenzoic acid instead of quinoline-6-carboxylic acid. MS (ESI): mass calcd. for $C_{24}H_{21}F_4N_3O_2$, 459.2; m/z found, 460.1 [M+H]$^+$. $^1$H NMR (400 MHz, DMSO-d$_6$) δ 7.67-7.48 (m, 2H), 7.31 (s, 1H), 7.02-6.74 (m, 2H), 5.83-5.59 (m, 1H), 5.08-4.57 (m, 1H), 3.85-3.70 (m, 6H), 3.22-2.80 (m, 1H), 2.49-2.42 (m, 1H), 1.88-1.31 (m, 6H).

Example 274: (3-Fluoro-5-(1H-pyrazol-1-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone

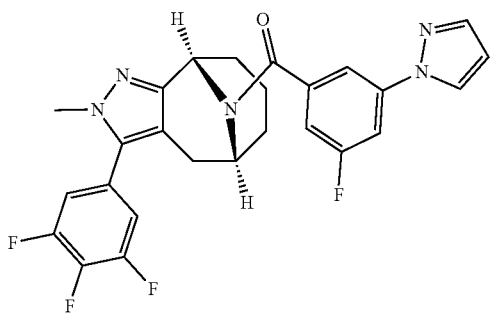 [SMILES: Cn1nc2c(c1-c1cc(F)c(F)c(F)c1)C[C@H]1CCC[C@@H]2N1C(=O)c1cc(F)cc(-n2cccn2)c1]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 3-fluoro-5-pyrazol-1-yl-benzoic acid (Intermediate 64) instead of quinoline-6-carboxylic acid. MS (ESI): mass calcd. for $C_{26}H_{21}F_4N_5O$, 495.2; m/z found, 496.2 [M+H]$^+$. $^1$H NMR (500 MHz, DMSO-d$_6$): 8.64 (d, J=2.6 Hz, 1H), 7.84-7.80 (m, 1H), 7.77 (d, J=1.7 Hz, 1H), 7.74-7.71 (m, 1H), 7.61-7.53 (m, 2H), 7.21-7.16 (m, 1H), 6.59-6.55 (m, 1H), 5.70-5.67 (m, 1H), 4.06-4.00 (m, 1H), 3.79 (s, 3H), 2.99 (dd, J=16.2, 7.4 Hz, 1H), 2.41 (d, J=16.1 Hz, 1H), 1.98-1.35 (m, 6H).

Example 275: (3-Fluoro-5-(4H-1,2,4-triazol-4-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone

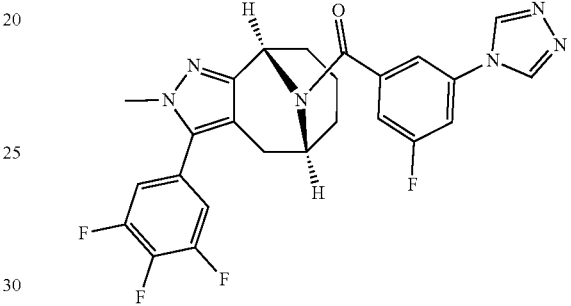

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 3-fluoro-5-(4H-1,2,4-triazol-4-yl)benzoic acid (Intermediate 68) instead of quinoline-6-carboxylic acid. MS (ESI): mass calcd. for $C_{25}H_{20}F_4N_6O$, 496.2; m/z found, 497.2 [M+H]$^+$. $^1$H NMR (300 MHz, DMSO-d$_6$): 9.25 (s, 2H), 7.91-7.82 (m, 1H), 7.72-7.65 (m, 1H), 7.63-7.53 (m, 2H), 7.42-7.33 (m, 1H), 5.74-5.67 (m, 1H), 4.06-3.97 (m, 1H), 3.82 (s, 3H), 3.05 (dd, J=16.4, 7.2 Hz, 1H), 2.42 (d, J=16.5 Hz, 1H), 2.09-1.35 (m, 6H).

Example 276: (4-Fluoro-3-(4H-1,2,4-triazol-4-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone

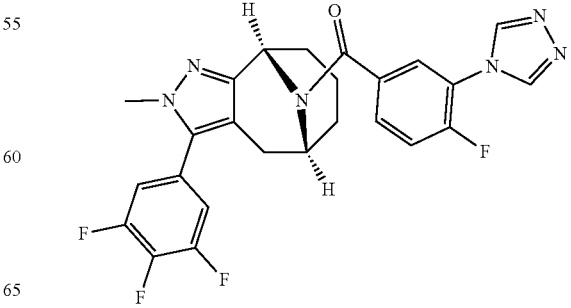

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 4-fluoro-3-(4H-1,2,4-triazol-4-yl)benzoic acid (Intermediate 69) instead of quinoline-6-carboxylic acid. MS (ESI): mass calcd. for $C_{25}H_{20}F_4N_6O$, 496.2; m/z found, 497.2 [M+H]$^+$. $^1$H NMR (300 MHz, DMSO-d$_6$): 8.98 (s, 2H), 7.89-7.72 (m, 1H), 7.69-7.45 (m, 4H), 5.70 (s, 1H), 4.10 (d, J=6.7 Hz, 1H), 3.81 (s, 3H), 3.12-2.97 (m, 1H), 2.59-2.37 (m, 1H), 2.07-1.35 (m, 6H).

Example 277: ((5R,9S)-2-Methyl-3-(3,4,5-trifluorophenyl)-4,5,6,7,8,9-hexahydro-2H-5,9-epiminocycloocta[c]pyrazol-10-yl)(4-methyl-3-(4H-1,2,4-triazol-4-yl)phenyl)methanone

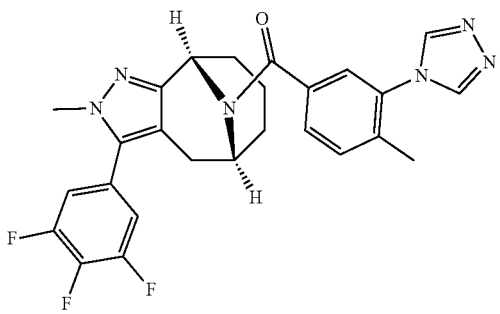 [SMILES: Cc1ccc(C(=O)N2[C@@H]3CCC[C@H]2c2nn(C)c(-c4cc(F)c(F)c(F)c4)c2C3)cc1-n1cnnc1]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 4-methyl-3-(4H-1,2,4-triazol-4-yl)benzoic acid (Intermediate 72) instead of quinoline-6-carboxylic acid. MS (ESI): mass calcd. for $C_{26}H_{23}F_3N_6O$, 492.2; m/z found, 493.2 [M+H]$^+$. $^1$H NMR (500 MHz, DMSO-d$_6$): 8.84 (s, 2H), 7.63-7.38 (m, 5H), 5.73-5.64 (m, 1H), 4.15-4.08 (m, 1H), 3.80 (s, 3H), 3.03 (dd, J=16.5, 7.4 Hz, 1H), 2.44 (d, J=16.3 Hz, 1H), 2.18 (s, 3H), 1.91-1.38 (m, 6H).

Example 278: ((5R,9S)-2-Methyl-3-(3,4,5-trifluorophenyl)-4,5,6,7,8,9-hexahydro-2H-5,9-epiminocycloocta[c]pyrazol-10-yl)(3-methyl-5-(4H-1,2,4-triazol-4-yl)phenyl)methanone

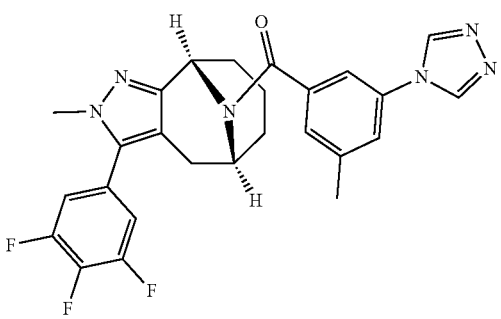 [SMILES: Cc1cc(C(=O)N2[C@@H]3CCC[C@H]2c2nn(C)c(-c4cc(F)c(F)c(F)c4)c2C3)cc(-n2cnnc2)c1]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 3-methyl-5-(4H-1,2,4-triazol-4-yl)benzoic acid (Intermediate 70) instead of quinoline-6-carboxylic acid. MS (ESI): mass calcd. for $C_{26}H_{23}F_3N_6O$, 492.2; m/z found, 493.2 [M+H]$^+$. $^1$H NMR (300 MHz, DMSO-d$_6$): 9.17 (s, 2H), 7.73-7.65 (m, 1H), 7.64-7.49 (m, 3H), 7.32-7.25 (m, 1H), 5.77-5.64 (m, 1H), 4.11-3.99 (m, 1H), 3.82 (s, 3H), 3.01 (dd, J=15.5, 7.1 Hz, 1H), 2.66-2.36 (m, 1H), 2.43 (s, 3H), 2.07-1.33 (m, 6H).

Example 279: ((5R,9S)-2-Methyl-3-(3,4,5-trifluorophenyl)-4,5,6,7,8,9-hexahydro-2H-5,9-epiminocycloocta[c]pyrazol-10-yl)(2-methyl-3-(4H-1,2,4-triazol-4-yl)phenyl)methanone

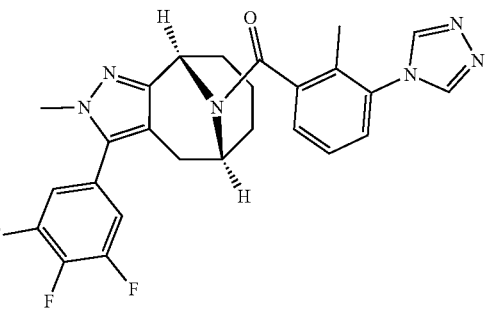

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 2-methyl-3-(4H-1,2,4-triazol-4-yl)benzoic acid (Intermediate 71) instead of quinoline-6-carboxylic acid. MS (ESI): mass calcd. for $C_{26}H_{23}F_3N_6O$, 492.2; m/z found, 493.2 [M+H]$^+$. $^1$H NMR (300 MHz, DMSO-d$_6$): 8.83 (s, 2H), 7.68-7.30 (m, 5H), 5.85-5.75 (m, 1H), 3.81 (s, 3H), 3.78-3.70 (m, 1H), 3.43-3.22 (m, 1H), 3.03-2.81 (m, 1H), 2.10 (s, 3H), 1.95-1.31 (m, 6H).

Example 280: (2-(2H-1,2,3-Triazol-2-yl)phenyl)
((5R,9S)-2-methyl-3-(3,4,5-trifluorophenyl)-4,5,6,7,
8,9-hexahydro-2H-5,9-epiminocycloocta[c]pyrazol-
10-yl)methanone

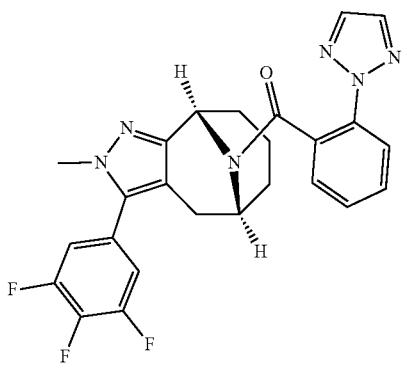 [SMILES: Cn1nc2c(c1-c1cc(F)c(F)c(F)c1)C[C@H]1CCC[C@@H]2N1C(=O)c1ccccc1-n1nccn1]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 2-(2H-1,2,3-triazol-2-yl)benzoic acid (Intermediate 49) instead of quinoline-6-carboxylic acid. MS (ESI): mass calcd. for $C_{25}H_{21}F_3N_6O$, 478.2; m/z found, 479.2 [M+H]$^+$. $^1$H NMR (500 MHz, DMSO-d$_6$): 8.12 (s, 2H), 7.90-7.86 (m, 1H), 7.66-7.36 (m, 5H), 5.67-5.63 (m, 1H), 3.88-3.81 (m, 1H), 3.78 (s, 3H), 2.95 (dd, J=16.3, 7.6 Hz, 1H), 2.35 (d, J=16.1 Hz, 1H), 1.88-1.19 (m, 6H).

Example 281: (4-Fluoro-2-(2H-1,2,3-triazol-2-yl)
phenyl)((5R,9S)-2-methyl-3-(3,4,5-trifluorophenyl)-
4,5,6,7,8,9-hexahydro-2H-5,9-epiminocycloocta[c]
pyrazol-10-yl)methanone

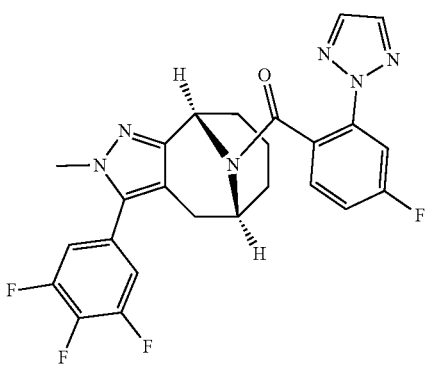 [SMILES: Cn1nc2c(c1-c1cc(F)c(F)c(F)c1)C[C@H]1CCC[C@@H]2N1C(=O)c1ccc(F)cc1-n1nccn1]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 4-fluoro-2-(2H-1,2,3-triazol-2-yl)benzoic acid (Intermediate 74) instead of quinoline-6-carboxylic acid. MS (ESI): mass calcd. for $C_{25}H_{20}F_4N_6O$, 496.2; m/z found, 497.2 [M+H]$^+$. $^1$H NMR (300 MHz, DMSO-d$_6$): 8.25-8.14 (m, 1H), 7.89-7.28 (m, 6H), 5.73-5.62 (m, 1H), 3.92-3.76 (m, 1H), 3.81 (s, 3H), 3.03-2.91 (m, 1H), 2.42-2.34 (m, 1H), 1.94-1.17 (m, 6H).

Example 282: (3-Fluoro-2-(2H-1,2,3-triazol-2-yl)
phenyl)((5R,9S)-2-methyl-3-(3,4,5-trifluorophenyl)-
4,5,6,7,8,9-hexahydro-2H-5,9-epiminocycloocta[c]
pyrazol-10-yl)methanone

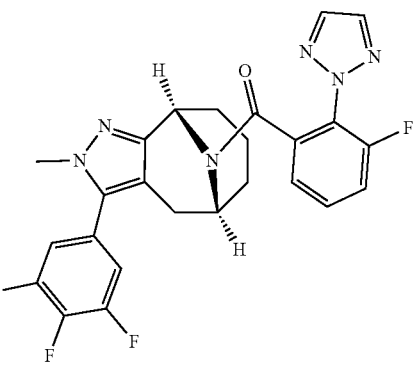

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 3-fluoro-2-(2H-1,2,3-triazol-2-yl)benzoic acid (Intermediate 75) instead of quinoline-6-carboxylic acid. MS (ESI): mass calcd. for $C_{25}H_{20}F_4N_6O$, 496.2; m/z found, 497.2 [M+H]$^+$. $^1$H NMR (500 MHz, DMSO-d$_6$): 8.17 (s, 1H), 7.75-7.31 (m, 6H), 5.55-5.47 (m, 1H), 3.98-3.91 (m, 1H), 3.79 (s, 3H), 3.04 (dd, J=16.2, 7.2 Hz, 1H), 2.41 (d, J=16.2 Hz, 1H), 1.89-1.27 (m, 6H).

Example 283: (5-Fluoro-2-(2H-1,2,3-triazol-2-yl)
phenyl)((5R,9S)-2-methyl-3-(3,4,5-trifluorophenyl)-
4,5,6,7,8,9-hexahydro-2H-5,9-epiminocycloocta[c]
pyrazol-10-yl)methanone

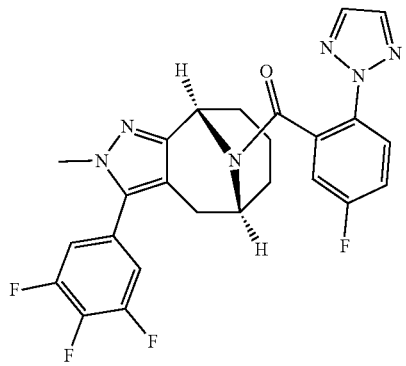 [SMILES: Cn1nc2c(c1-c1cc(F)c(F)c(F)c1)C[C@H]1CCC[C@@H]2N1C(=O)c1cc(F)ccc1-n1nccn1]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2- methyl-3-phenyl-4,5,6,7,8,9-hexahydro-2H-5,9-epiminocycloocta[c]pyrazole (Intermediate 1) and 5-fluoro-2-(2H-1,2,3-triazol-2-yl)benzoic acid (Intermediate 112) instead of quinoline-6-carboxylic acid. MS (ESI): mass calcd. for $C_{25}H_{20}F_4N_6O$, 496.2; m/z found, 497.2 [M+H]$^+$. $^1$H NMR (500 MHz, DMSO-$d_6$): 8.12 (s, 2H), 7.91 (dd, J=9.0, 4.9 Hz, 1H), 7.61-7.55 (m, 1H), 7.55-7.30 (m, 3H), 5.65-5.60 (m, 1H), 3.88-3.83 (m, 1H), 3.78 (s, 3H), 3.02 (dd, J=16.1, 7.2 Hz, 1H), 2.33 (d, J=16.0 Hz, 1H), 1.82-1.19 (m, 6H).

Example 284: (5-Methyl-2-(2H-1,2,3-triazol-2-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone

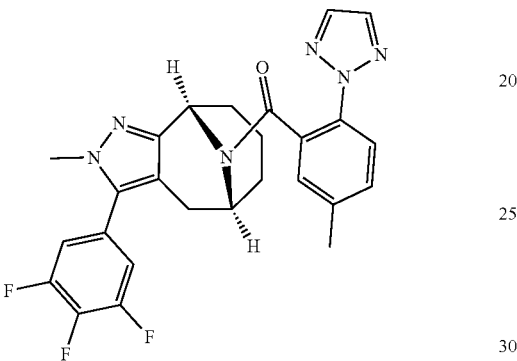

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 5-methyl-2-(2H-1,2,3-triazol-2-yl)benzoic acid (Intermediate 76) instead of quinoline-6-carboxylic acid. MS (ESI): mass calcd. for $C_{26}H_{23}F_3N_6O$, 492.2; m/z found, 493.2 [M+H]$^+$. $^1$H NMR (300 MHz, DMSO-$d_6$): 8.11 (s, 2H), 7.84-7.31 (m, 5H), 5.73-5.58 (m, 1H), 3.92-3.81 (m, 1H), 3.81 (s, 3H), 2.99-2.87 (m, 1H), 2.39 (s, 3H), 2.45-2.22 (m, 1H), 1.91-1.10 (m, 6H).

Example 285: (2-(2H-1,2,3-Triazol-2-yl)-3-(trifluoromethyl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone

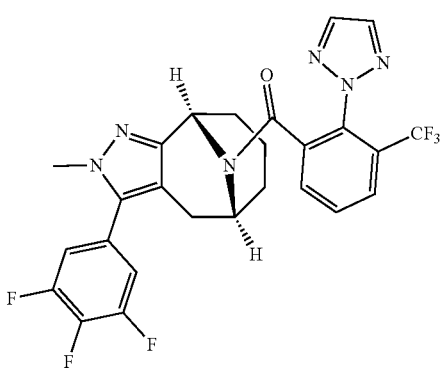 [SMILES: Cn1nc2c(c1-c1cc(F)c(F)c(F)c1)C[C@H]1CCC[C@@H]2N1C(=O)c1cccc(C(F)(F)F)c1-n1nccn1]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 2-(2H-1,2,3-triazol-2-yl)-3-(trifluoromethyl)benzoic acid (Intermediate 77) instead of quinoline-6-carboxylic acid. MS (ESI): mass calcd. for $C_{26}H_{20}F_6N_6O$, 546.2; m/z found, 547.2 [M+H]$^+$. $^1$H NMR (300 MHz, DMSO-$d_6$): 8.17 (s, 2H), 8.12-7.39 (m, 5H), 5.51-5.38 (m, 1H), 3.95-3.84 (m, 1H), 3.79 (s, 3H), 3.14-2.98 (m, 1H), 2.63-2.33 (m, 1H), 2.05-1.20 (m, 6H).

Example 286: (2-(4-Methyl-2H-1,2,3-triazol-2-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone

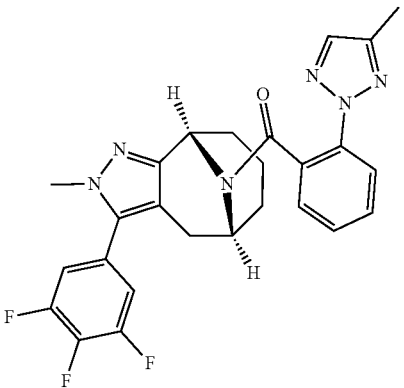 [SMILES: Cc1cnn(-c2ccccc2C(=O)N2[C@@H]3CCC[C@H]2c2nn(C)c(-c4cc(F)c(F)c(F)c4)c2C3)n1]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 2-(4-methyl-2H-1,2,3-triazol-2-yl)benzoic acid (Intermediate 73) instead of quinoline-6-carboxylic acid. MS (ESI): mass calcd. for $C_{26}H_{23}F_3N_6O$, 492.2; m/z found, 493.2 [M+H]$^+$. $^1$H NMR (500 MHz, DMSO-$d_6$): 7.88 (s, 1H), 7.90-7.77 (m, 1H), 7.62-7.55 (m, 2H), 7.46-7.41 (m, 1H), 7.62-7.32 (m, 2H), 5.70-5.64 (m, 1H), 3.90-3.84 (m, 1H), 3.78 (s, 3H), 3.00-2.93 (m, 1H), 2.50-2.42 (m, 1H), 2.33 (s, 3H), 1.91-1.18 (m, 6H).

Example 287: ((5R,9S)-2-Methyl-3-(3,4,5-trifluorophenyl)-4,5,6,7,8,9-hexahydro-2H-5,9-epiminocycloocta[c]pyrazol-10-yl)(2-(4-(trifluoromethyl)-2H-1,2,3-triazol-2-yl)phenyl)methanone

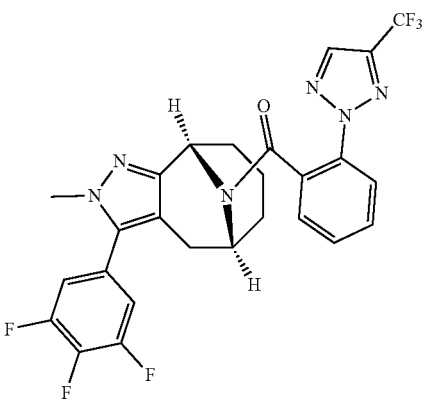 [SMILES: Cn1nc2c(c1-c1cc(F)c(F)c(F)c1)C[C@H]1CCC[C@@H]2N1C(=O)c1ccccc1-n1ncc(C(F)(F)F)n1]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 2-[4-(trifluoromethyl)triazol-2-yl]benzoic acid (Intermediate 66) instead of quinoline-6-carboxylic acid. MS (ESI): mass calcd. for $C_{26}H_{20}F_6N_6O$, 546.2; m/z found, 547.2 [M+H]$^+$. $^1$H NMR (500 MHz, DMSO-d$_6$): 8.79 (s, 1H), 7.95-7.91 (m, 1H), 7.73-7.65 (m, 2H), 7.64-7.56 (m, 2H), 7.51-7.46 (m, 1H), 5.62-5.57 (m, 1H), 4.02-3.94 (m, 1H), 3.78 (s, 3H), 3.14-3.01 (m, 1H), 2.42 (d, J=16.3 Hz, 1H), 1.90-1.30 (m, 6H).

Example 288: (5-Methoxy-2-(1H-1,2,4-triazol-1-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone

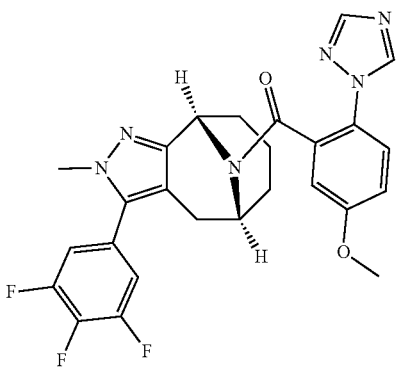 [SMILES: COc1ccc(-n2cncn2)c(C(=O)N2[C@@H]3CCC[C@H]2c2nn(C)c(-c4cc(F)c(F)c(F)c4)c2C3)c1]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 5-methoxy-2-(1H-1,2,4-triazol-1-yl)benzoic acid (Intermediate 65) instead of quinoline-6-carboxylic acid. MS (ESI): mass calcd. for $C_{26}H_{23}F_3N_6O_2$, 508.2; m/z found, 509.2 [M+H]$^+$. $^1$H NMR (500 MHz, DMSO-d$_6$): 8.75 (s, 1H), 8.18 (s, 1H), 7.59 (d, J=8.7 Hz, 1H), 7.59-7.53 (m, 2H), 7.15 (dd, J=8.9, 2.8 Hz, 1H), 6.95 (d, J=2.8 Hz, 1H), 5.60-5.55 (m, 1H), 3.81 (s, 3H), 3.76 (s, 3H), 3.81-3.74 (m, 1H), 2.94 (dd, J=16.1, 7.2 Hz, 1H), 2.34 (d, J=16.1 Hz, 1H), 1.77-1.19 (m, 6H).

Example 289: ((5R,9S)-2-Methyl-3-(3,4,5-trifluorophenyl)-4,5,6,7,8,9-hexahydro-2H-5,9-epiminocycloocta[c]pyrazol-10-yl)(2-(4-(trifluoromethyl)-1H-1,2,3-triazol-1-yl)phenyl)methanone

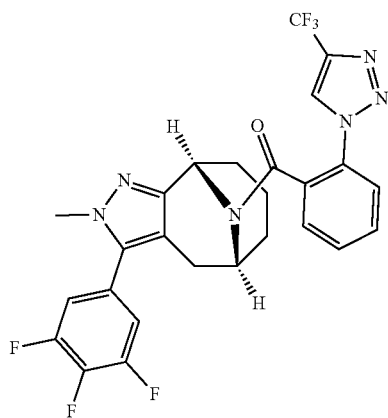 [SMILES: Cn1nc2c(c1-c1cc(F)c(F)c(F)c1)C[C@H]1CCC[C@@H]2N1C(=O)c1ccccc1-n1cc(C(F)(F)F)nn1]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 2-[4-(trifluoromethyl)triazol-1-yl]benzoic acid (Intermediate 67) instead of quinoline-6-carboxylic acid. MS (ESI): mass calcd. for $C_{26}H_{20}F_6N_6O$, 546.2; m/z found, 547.3 [M+H]$^+$. $^1$H NMR (500 MHz, DMSO-d$_6$): 9.35 (s, 1H), 7.83-7.77 (m, 1H), 7.75-7.68 (m, 2H), 7.63-7.54 (m, 2H), 7.45-7.28 (m, 1H), 5.62-5.46 (m, 1H), 3.77 (s, 3H), 3.75-3.68 (m, 1H), 3.12-2.97 (m, 1H), 2.40 (d, J=16.3 Hz, 1H), 1.90-1.21 (m, 6H).

Example 290: (6-Isopropylpyrimidin-4-yl)((5R,9S)-2-methyl-3-(3,4,5-trifluorophenyl)-4,5,6,7,8,9-hexahydro-2H-5,9-epiminocycloocta[c]pyrazol-10-yl)methanone

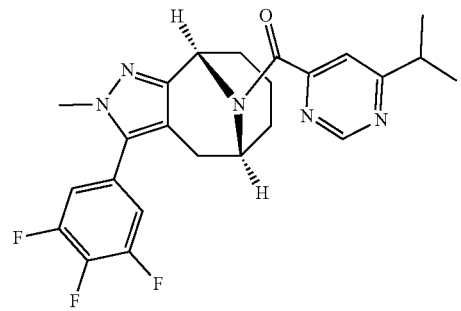 [SMILES: CC(C)c1cc(C(=O)N2[C@@H]3CCC[C@H]2c2nn(C)c(-c4cc(F)c(F)c(F)c4)c2C3)ncn1]

Step A: 6-Isopropylpyrimidine-4-carboxylic acid. To a solution of methyl 6-(propan-2-yl)pyrimidine-4-carboxylate (135 mg, 0.749 mmol) in 1,4-dioxane (500 µL) and water (500 µL) was added sodium hydroxide (60 mg, 1.50 mmol). The reaction mixture was stirred at room temperature for 16 h. The reaction mixture was acidified to pH 3 with 6 M hydrochloric acid (0.25 mL), diluted with ethyl acetate (1 mL) and water (1 mL) and the layers were separated. The aqueous layer was extracted with ethyl acetate (3×2 mL). The combined organic layers were dried over sodium sulfate, filtered and evaporated to afford the title compound (82 mg, 0.493 mmol, 65%) as a white powder. MS (ESI): mass calcd. for $C_8H_{10}N_2O_2$, 166.1; m/z found, 167.1 [M+H]$^+$. $^1$H NMR (500 MHz, DMSO-d$_6$) δ 13.84 (br s, 1H), 9.24 (s, 1H), 7.90 (s, 1H), 3.20-3.04 (m, 1H), 1.26 (d, J=6.8 Hz, 6H).

Step B: (6-Isopropylpyrimidin-4-yl)((5R,9S)-2-methyl-3-(3,4,5-trifluorophenyl)-4,5,6,7,8,9-hexahydro-2H-5,9-epiminocycloocta[c]pyrazol-10-yl)methanone. The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 6-isopropylpyrimidine-4-carboxylic acid instead of quinoline-6-carboxylic acid. MS (ESI): mass calcd. for $C_{24}H_{24}F_3N_5O$, 455.2; m/z found, 456.2 [M+H]$^+$. $^1$H NMR (500 MHz, DMSO-d$_6$): 9.09 (d, J=1.3 Hz, 1H), 7.59-7.53 (m, 2H), 7.56 (s, 1H), 5.74-5.62 (m, 1H), 4.09-3.99 (m, 1H), 3.78 (s, 3H), 3.08-3.00 (m, 1H), 2.95 (dd, J=16.1, 7.3 Hz, 1H), 2.51-2.41 (m, 1H), 1.87-1.36 (m, 6H), 1.23 (d, J=6.9 Hz, 6H).

Example 291: (6-Methoxypyrimidin-4-yl)((5R,9S)-2-methyl-3-(3,4,5-trifluorophenyl)-4,5,6,7,8,9-hexahydro-2H-5,9-epiminocycloocta[c]pyrazol-10-yl)methanone

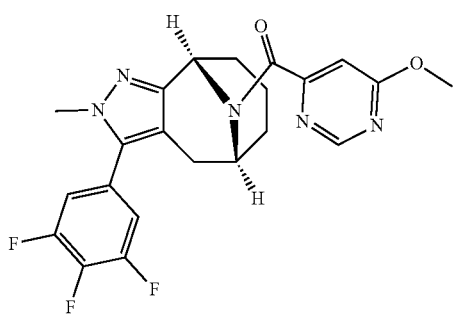 [SMILES: COc1cc(C(=O)N2[C@@H]3CCC[C@H]2c2nn(C)c(-c4cc(F)c(F)c(F)c4)c2C3)ncn1]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 6-methoxypyrimidine-4-carboxylic acid instead of quinoline-6-carboxylic acid. MS (ESI): mass calcd. for $C_{22}H_{20}F_3N_5O_2$, 443.2; m/z found, 444.2 [M+H]$^+$. $^1$H NMR (300 MHz, DMSO-d$_6$): 8.84-8.79 (m, 1H), 7.70-7.47 (m, 2H), 7.14-7.07 (m, 1H), 5.76-5.63 (m, 1H), 4.11-4.02 (m, 1H), 3.97 (s, 3H), 3.80 (s, 3H), 3.15-2.89 (m, 1H), 2.65-2.34 (m, 1H), 2.01-1.33 (m, 6H).

Example 292: (6-(Dimethylamino)pyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone

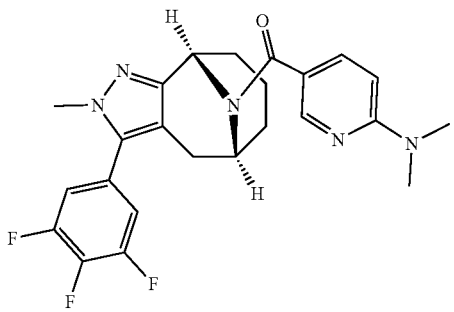 [SMILES: CN(C)c1ccc(C(=O)N2[C@@H]3CCC[C@H]2c2nn(C)c(-c4cc(F)c(F)c(F)c4)c2C3)cn1]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 6-(dimethylamino)nicotinic acid instead of quinoline-6-carboxylic acid. MS (ESI): mass calcd. for $C_{24}H_{24}F_3N_5O$, 455.2; m/z found, 456.3 [M+H]$^+$. $^1$H NMR (500 MHz, DMSO-d$_6$): 8.22-8.16 (m, 1H), 7.65-7.45 (m, 3H), 6.62 (d, J=8.8 Hz, 1H), 5.67-5.46 (m, 1H), 4.32-4.14 (m, 1H), 3.77 (s, 3H), 3.15-2.98 (m, 1H), 3.04 (s, 6H), 2.40 (d, J=16.3 Hz, 1H), 1.99-1.29 (m, 6H).

Example 293: (5-Methoxy-4-methylpyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone

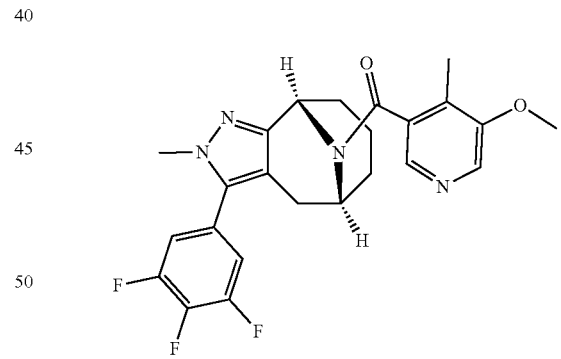

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 5-methoxy-4-methylnicotinic acid hydrochloride instead of quinoline-6-carboxylic acid. MS (ESI): mass calcd. for $C_{24}H_{23}F_3N_4O_2$, 456.2; m/z found, 457.2 [M+H]$^+$. $^1$H NMR (300 MHz, DMSO-d$_6$): 8.40-8.26 (m, 2H), 7.71-7.48 (m, 2H), 5.89-5.69 (m, 1H), 3.94 (s, 3H), 3.81 (s, 3H), 3.85-3.63 (m, 1H), 3.18-2.94 (m, 1H), 2.41-2.32 (m, 1H), 2.18 (s, 3H), 2.02-1.29 (m, 6H).

Example 294: (6-Methoxy-5-methylpyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone

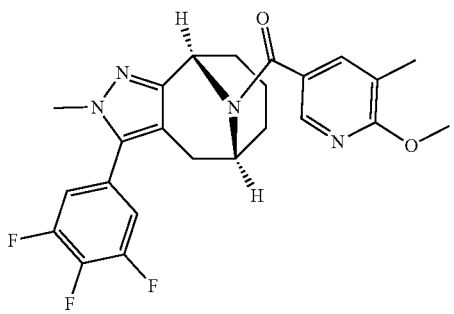 [SMILES: COc1ncc(C(=O)N2[C@@H]3CCC[C@H]2c2nn(C)c(-c4cc(F)c(F)c(F)c4)c2C3)cc1C]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 6-methoxy-5-methylnicotinic acid instead of quinoline-6-carboxylic acid. MS (ESI): mass calcd. for $C_{24}H_{23}F_3N_4O_2$, 456.2; m/z found, 457.2 [M+H]$^+$. $^1$H NMR (500 MHz, DMSO-d$_6$): 8.11-8.07 (m, 1H), 7.64-7.52 (m, 3H), 5.66-5.60 (m, 1H), 4.16-4.09 (m, 1H), 3.89 (s, 3H), 3.78 (s, 3H), 3.08 (dd, J=16.1, 7.3 Hz, 1H), 2.39 (d, J=16.3 Hz, 1H), 2.15 (s, 3H), 1.87-1.32 (m, 6H).

Example 295: (5-Fluoro-6-methoxypyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone

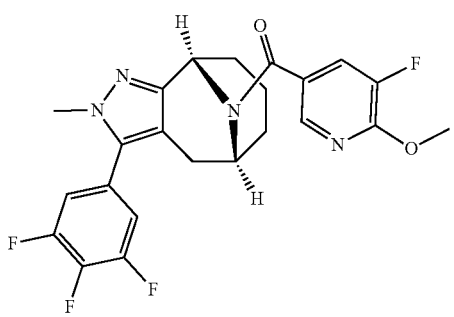 [SMILES: COc1ncc(C(=O)N2[C@@H]3CCC[C@H]2c2nn(C)c(-c4cc(F)c(F)c(F)c4)c2C3)cc1F]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 5-fluoro-6-methoxynicotinic acid instead of quinoline-6-carboxylic acid. MS (ESI): mass calcd. for $C_{23}H_{20}F_4N_4O_2$, 460.2; m/z found, 461.3 [M+H]$^+$. $^1$H NMR (500 MHz, DMSO-d$_6$): 8.08 (d, J=1.9 Hz, 1H), 7.77 (dd, J=10.7, 1.9 Hz, 1H), 7.63-7.52 (m, 2H), 5.66-5.59 (m, 1H), 4.15-4.06 (m, 1H), 3.96 (s, 3H), 3.78 (s, 3H), 3.10 (dd, J=16.3, 7.4 Hz, 1H), 2.38 (d, J=16.3 Hz, 1H), 1.88-1.30 (m, 6H).

Example 296: (5-Fluoro-2-methoxypyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone

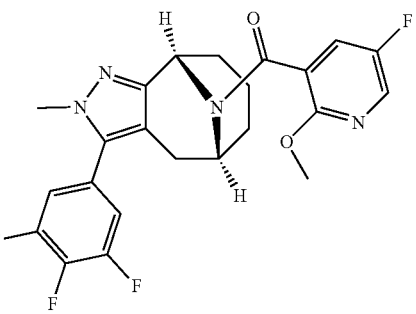

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 5-fluoro-2-methoxynicotinic acid instead of quinoline-6-carboxylic acid. MS (ESI): mass calcd. for $C_{23}H_{20}F_4N_4O_2$, 460.2; m/z found, 461.2 [M+H]$^+$. $^1$H NMR (500 MHz, DMSO-d$_6$): 8.28-8.17 (m, 2H), 7.61-7.46 (m, 2H), 5.75-5.64 (m, 1H), 3.77 (s, 3H), 3.80-3.69 (m, 4H), 2.91-2.79 (m, 1H), 2.51-2.42 (m, 1H), 1.95-1.29 (m, 6H).

Example 297: (5,6-Dimethoxypyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone

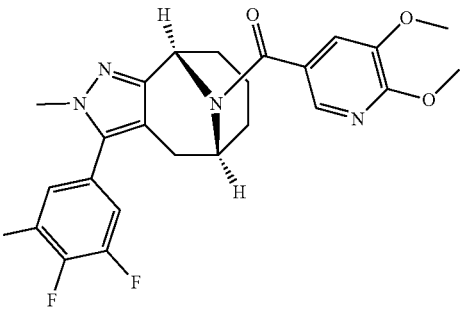

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 5,6-dimethoxynicotinic acid instead of quinoline-6-carboxylic acid. MS (ESI): mass calcd. for $C_{24}H_{23}F_3N_4O_3$, 472.2; m/z found, 473.2 [M+H]$^+$. $^1$H NMR (500 MHz, DMSO-d$_6$): 7.80-7.76 (m, 1H), 7.62-7.53 (m, 2H), 7.30-7.26 (m, 1H), 5.67-5.61 (m, 1H), 4.19-4.12 (m, 1H), 3.88 (s, 3H), 3.79 (s, 3H), 3.78 (s, 3H), 3.06 (dd, J=16.0, 7.4 Hz, 1H), 2.39 (d, J=16.2 Hz, 1H), 2.00-1.34 (m, 6H).

Example 298: (5,6-Dimethoxypyridin-2-yl)((5R,9S)-2-methyl-3-(3,4,5-trifluorophenyl)-4,5,6,7,8,9-hexahydro-2H-5,9-epiminocycloocta[c]pyrazol-10-yl)methanone

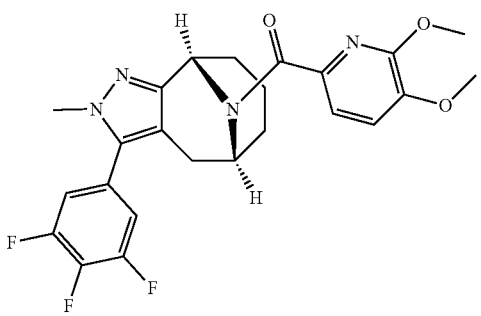 [SMILES: COc1ccc(C(=O)N2[C@@H]3CCC[C@H]2c2nn(C)c(-c4cc(F)c(F)c(F)c4)c2C3)nc1OC]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 5,6-dimethoxypicolinic acid instead of quinoline-6-carboxylic acid. MS (ESI): mass calcd. for $C_{24}H_{23}F_3N_4O_3$, 472.2; m/z found, 473.2 [M+H]$^+$. $^1$H NMR (500 MHz, DMSO-$d_6$): 7.61-7.48 (m, 2H), 7.34 (d, J=8.0 Hz, 1H), 7.21 (d, J=7.9 Hz, 1H), 5.69-5.63 (m, 1H), 4.63-4.55 (m, 1H), 3.84 (s, 3H), 3.80 (s, 3H), 3.76 (s, 3H), 3.03-2.94 (m, 1H), 2.58-2.44 (m, 1H), 1.86-1.70 (m, 2H), 1.68-1.52 (m, 2H), 1.52-1.35 (m, 2H).

Example 299: (3-Chloro-2-methoxypyridin-4-yl)((5R,9S)-2-methyl-3-(3,4,5-trifluorophenyl)-4,5,6,7,8,9-hexahydro-2H-5,9-epiminocycloocta[c]pyrazol-10-yl)methanone

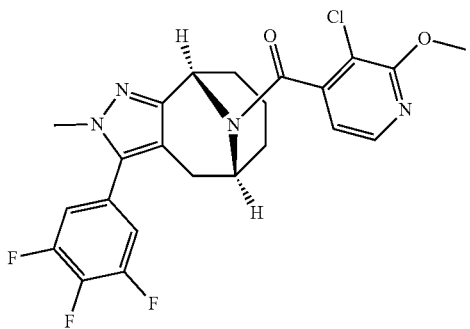 [SMILES: COc1nccc(C(=O)N2[C@@H]3CCC[C@H]2c2nn(C)c(-c4cc(F)c(F)c(F)c4)c2C3)c1Cl]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 3-chloro-2-methoxyisonicotinic acid instead of quinoline-6-carboxylic acid. MS (ESI): mass calcd. for $C_{23}H_{20}ClF_3N_4O_2$, 476.1; m/z found, 477.2 [M+H]$^+$. $^1$H NMR (300 MHz, DMSO-$d_6$): 8.17 (d, J=5.1 Hz, 1H), 7.72-7.43 (m, 2H), 6.99 (d, J=5.0 Hz, 1H), 5.81-5.65 (m, 1H), 3.98 (s, 3H), 3.81 (s, 3H), 3.85-3.69 (m, 1H), 2.99-2.81 (m, 1H), 2.63-2.33 (m, 1H), 1.98-1.31 (m, 6H).

Example 300: (5-Chloro-6-methoxypyridin-2-yl)((5R,9S)-2-methyl-3-(3,4,5-trifluorophenyl)-4,5,6,7,8,9-hexahydro-2H-5,9-epiminocycloocta[c]pyrazol-10-yl)methanone

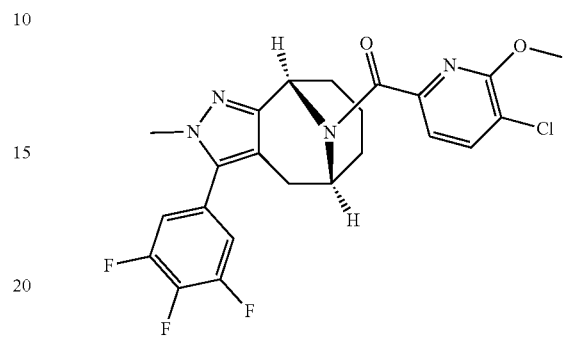

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 5-chloro-6-methoxypicolinic acid instead of quinoline-6-carboxylic acid. MS (ESI): mass calcd. for $C_{23}H_{20}ClF_3N_4O_2$, 476.1; m/z found, 477.2 [M+H]$^+$. $^1$H NMR (300 MHz, DMSO-$d_6$): 8.05-7.95 (m, 1H), 7.67-7.46 (m, 2H), 7.22 (d, J=7.8 Hz, 1H), 5.77-5.61 (m, 1H), 4.45-4.26 (m, 1H), 3.94 (s, 3H), 3.80 (s, 3H), 3.13-2.92 (m, 1H), 2.65-2.35 (m, 1H), 1.95-1.27 (m, 6H).

Example 301: (4-Chloro-2-methylpyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone

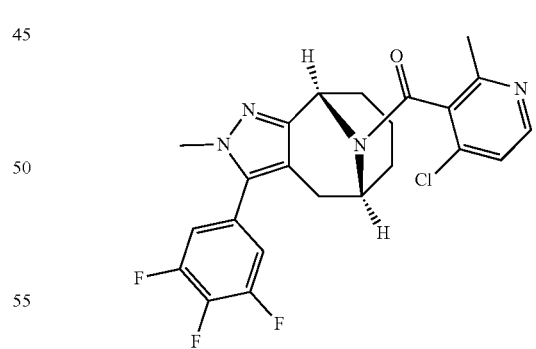

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 4-chloro-2-methylnicotinic acid instead of quinoline-6-carboxylic acid. MS (ESI): mass calcd. for $C_{23}H_{20}ClF_3N_4O$, 460.1; m/z found, 461.2 [M+H]$^+$. $^1$H NMR (500 MHz, DMSO-$d_6$):

8.48) 8.5-7.44 (m, 1H), 7.6742 (m, 3H), 5.85-5.82 (m, 1H), 3.80 (s, 3H), 3.82-3.75 (m, 1H), 2.95 (dd, J=16.2, 7.5 Hz, 1H), 2.56-2.46 (m, 1H), 2.26 (s, 3H), 1.92-1.35 (m, 6H).

Example 302: (4-Chloro-5-methylpyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone

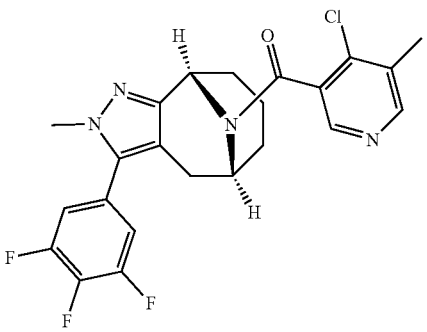 [SMILES: Cc1cncc(C(=O)N2[C@@H]3CCC[C@H]2c2nn(C)c(-c4cc(F)c(F)c(F)c4)c2C3)c1Cl]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 4-chloro-5-methylnicotinic acid instead of quinoline-6-carboxylic acid. MS (ESI): mass calcd. for $C_{23}H_{20}ClF_3N_4O$, 460.1; m/z found, 461.2 [M+H]$^+$. $^1$H NMR (500 MHz, DMSO-d$_6$): 8.57-8.55 (m, 1H), 8.34-8.29 (m, 1H), 7.63-7.55 (m, 2H), 5.79-5.75 (m, 1H), 3.78 (s, 3H), 3.75-3.69 (m, 1H), 3.00-2.93 (m, 1H), 2.36 (s, 3H), 2.40-2.29 (m, 1H), 1.96-1.27 (m, 6H).

Example 303: (3-Chloro-5-fluoropyridin-4-yl)((5R,9S)-2-methyl-3-(3,4,5-trifluorophenyl)-4,5,6,7,8,9-hexahydro-2H-5,9-epiminocycloocta[c]pyrazol-10-yl)methanone

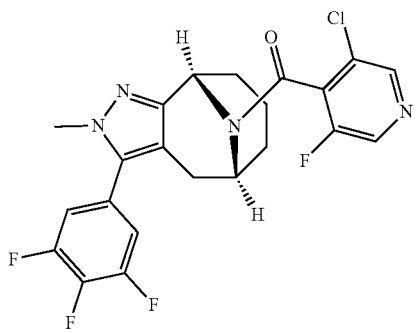 [SMILES: Cn1nc2c(c1-c1cc(F)c(F)c(F)c1)C[C@H]1CCC[C@@H]2N1C(=O)c1c(F)cncc1Cl]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 3-chloro-5-fluoroisonicotinic acid instead of quinoline-6-carboxylic acid. MS (ESI): mass calcd. for $C_{22}H_{17}ClF_4N_4O$, 464.1; m/z found, 465.1 [M+H]$^+$. $^1$H NMR (500 MHz, DMSO-d$_6$): 8.70-8.69 (m, 1H), 8.69-8.68 (m, 1H), 7.63-7.52 (m, 2H), 5.80-5.75 (m, 1H), 3.94-3.86 (m, 1H), 3.80 (s, 3H), 2.79 (dd, J=16.3, 7.3 Hz, 1H), 2.58-2.45 (m, 1H), 1.89-1.61 (m, 4H), 1.56-1.36 (m, 2H).

Example 304: (6-Cyclopropyl-2-methylpyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone

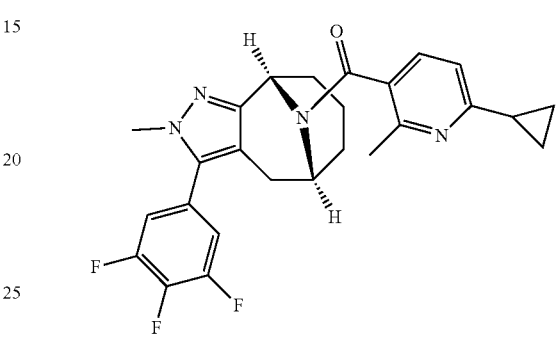

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 6-cyclopropyl-2-methylnicotinic acid instead of quinoline-6-carboxylic acid. MS (ESI): mass calcd. for $C_{26}H_{25}F_3N_4O$, 466.2; m/z found, 467.3 [M+H]$^+$. $^1$H NMR (500 MHz, DMSO-d$_6$): 7.64-7.49 (m, 3H), 7.14-7.01 (m, 1H), 5.77-5.71 (m, 1H), 3.78 (s, 3H), 3.81-3.70 (m, 1H), 2.96-2.75 (m, 1H), 2.53 (d, J=16.3 Hz, 1H), 2.41-2.36 (m, 3H), 2.10-2.03 (m, 1H), 1.86-1.28 (m, 6H), 0.98-0.82 (m, 4H).

Example 305: 1-(5-((5R,9S)-2-Methyl-3-(3,4,5-trifluorophenyl)-4,5,6,7,8,9-hexahydro-2H-5,9-epiminocycloocta[c]pyrazole-10-carbonyl)pyridin-2-yl)cyclopropane-1-carbonitrile

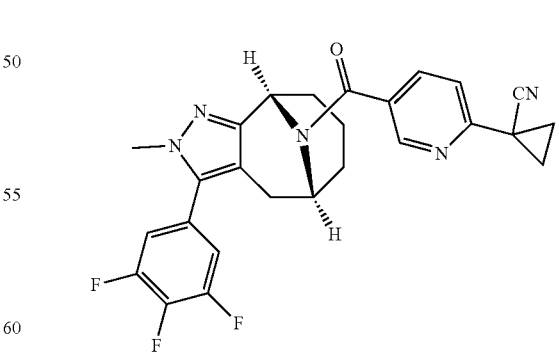

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9- epiminocycloocta[c]pyrazole (Intermediate 1) and 6-(1-cyanocyclopropyl)nicotinic acid instead of quinoline-6-carboxylic acid. MS (ESI): mass calcd. for $C_{26}H_{22}F_3N_5O$, 477.2; m/z found, 478.2 [M+H]$^+$. $^1$H NMR (500 MHz, DMSO-d$_6$): 8.56 (d, J=2.1 Hz, 1H), 7.89 (dd, J=8.1, 2.3 Hz, 1H), 7.65-7.53 (m, 3H), 5.72-5.61 (m, 1H), 4.03-3.95 (m, 1H), 3.78 (s, 3H), 3.11-3.01 (m, 1H), 2.38 (d, J=16.3 Hz, 1H), 1.89-1.78 (m, 4H), 1.77-1.32 (m, 6H).

Example 306: (2-(1H-Pyrazol-1-yl)pyridin-4-yl)((5R,9S)-2-methyl-3-(3,4,5-trifluorophenyl)-4,5,6,7,8,9-hexahydro-2H-5,9-epiminocycloocta[c]pyrazol-10-yl)methanone

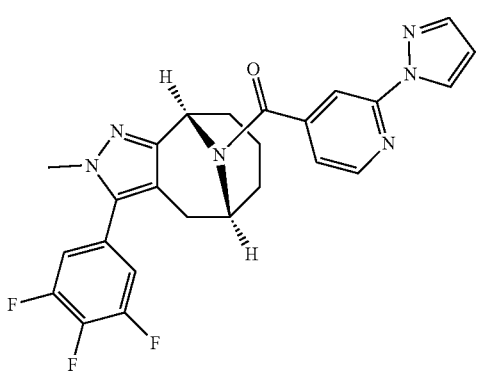 [SMILES: Cn1nc2c(c1-c1cc(F)c(F)c(F)c1)C[C@H]1CCC[C@@H]2N1CC(=O)c1ccnc(-n2cccn2)c1]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 2-(1H-pyrazol-1-yl)isonicotinic acid instead of quinoline-6-carboxylic acid. MS (ESI): mass calcd. for $C_{25}H_{21}F_3N_6O$, 478.2; m/z found, 479.2 [M+H]$^+$. $^1$H NMR (500 MHz, DMSO-d$_6$): 8.63-8.61 (m, 1H), 8.53 (d, J=5.0 Hz, 1H), 7.85-7.81 (m, 2H), 7.63-7.54 (m, 2H), 7.36 (dd, J=5.1, 1.4 Hz, 1H), 6.60-6.57 (m, 1H), 5.73-5.68 (m, 1H), 4.01-3.96 (m, 1H), 3.79 (s, 3H), 2.97 (dd, J=16.3, 7.4 Hz, 1H), 2.43 (d, J=16.3 Hz, 1H), 1.95-1.33 (m, 6H).

Example 307: (4-(1H-Pyrazol-1-yl)pyridin-2-yl)((5R,9S)-2-methyl-3-(3,4,5-trifluorophenyl)-4,5,6,7,8,9-hexahydro-2H-5,9-epiminocycloocta[c]pyrazol-10-yl)methanone

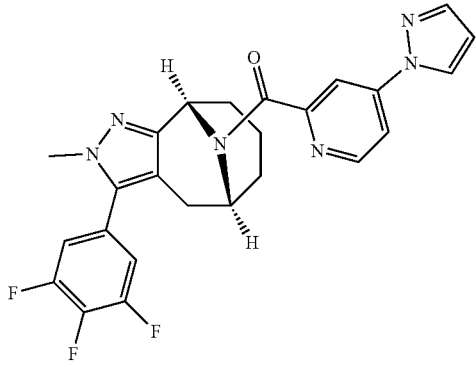 [SMILES: Cn1nc2c(c1-c1cc(F)c(F)c(F)c1)C[C@H]1CCC[C@@H]2N1CC(=O)c1cc(-n2cccn2)ccn1]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 4-(1H-pyrazol-1-yl)picolinic acid (Intermediate 78) instead of quinoline-6-carboxylic acid. MS (ESI): mass calcd. for $C_{25}H_{21}F_3N_6O$, 478.2; m/z found, 479.2 [M+H]$^+$. $^1$H NMR (300 MHz, DMSO-d$_6$): 8.88-8.74 (m, 1H), 8.64 (d, J=5.6 Hz, 1H), 8.07-8.02 (m, 1H), 8.02-7.94 (m, 1H), 7.93-7.83 (m, 1H), 7.68-7.45 (m, 2H), 6.74-6.57 (m, 1H), 5.82-5.69 (m, 1H), 4.30-4.16 (m, 1H), 3.81 (s, 3H), 3.14-2.91 (m, 1H), 2.67-2.36 (m, 1H), 2.06-1.30 (m, 6H).

Example 308: (4-(1H-Pyrazol-1-yl)pyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone

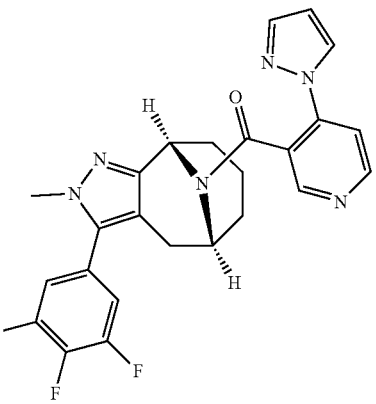

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 4-(1H-pyrazol-1-yl)nicotinic acid (Intermediate 82) instead of quinoline-6-carboxylic acid. MS (ESI): mass calcd. for $C_{25}H_{21}F_3N_6O$, 478.2; m/z found, 479.3 [M+H]$^+$. $^1$H NMR (500 MHz, DMSO-d$_6$): 8.70 (d, J=5.6 Hz, 1H), 8.50-8.46 (m, 1H), 8.42 (d, J=2.6 Hz, 1H), 7.86 (d, J=1.6 Hz, 1H), 7.79 (d, J=5.5 Hz, 1H), 7.63-7.54 (m, 2H), 6.65-6.62 (m, 1H), 5.76-5.70 (m, 1H), 3.78 (s, 3H), 3.75-3.67 (m, 1H), 2.97 (dd, J=16.3, 7.4 Hz, 1H), 2.29 (d, J=16.1 Hz, 1H), 1.93-1.17 (m, 6H).

Example 309: (6-(1H-Pyrazol-1-yl)pyridin-2-yl)((5R,9S)-2-methyl-3-(3,4,5-trifluorophenyl)-4,5,6,7,8,9-hexahydro-2H-5,9-epiminocycloocta[c]pyrazol-10-yl)methanone

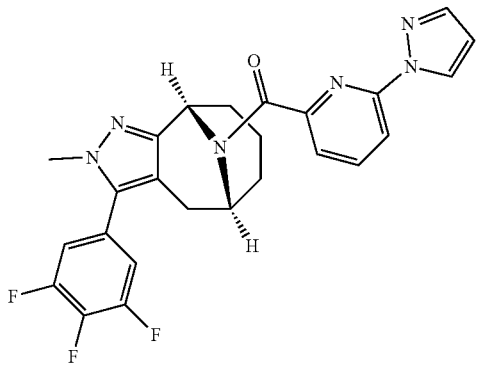 [SMILES: Cn1nc2c(c1-c1cc(F)c(F)c(F)c1)C[C@H]1CCC[C@@H]2N1CC(=O)c1cccc(-n2cccn2)n1]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 6-(1H-pyrazol-1-yl)picolinic acid instead of quinoline-6-carboxylic acid. MS (ESI): mass calcd. for $C_{25}H_{21}F_3N_6O$, 478.2; m/z found, 479.1 [M+H]$^+$. $^1$H NMR (300 MHz, DMSO-d$_6$): 8.59-8.56 (m, 1H), 8.17-8.07 (m, 1H), 8.06-7.97 (m, 1H), 7.87-7.83 (m, 1H), 7.68-7.46 (m, 3H), 6.61-6.54 (m, 1H), 5.80-5.71 (m, 1H), 4.32-4.21 (m, 1H), 3.81 (s, 3H), 3.09-2.97 (m, 1H), 2.56-2.38 (m, 1H), 1.96-1.37 (m, 6H).

Example 310: (6-Methyl-3-(1H-pyrazol-1-yl)pyridin-2-yl)((5R,9S)-2-methyl-3-(3,4,5-trifluorophenyl)-4,5,6,7,8,9-hexahydro-2H-5,9-epiminocycloocta[c]pyrazol-10-yl)methanone

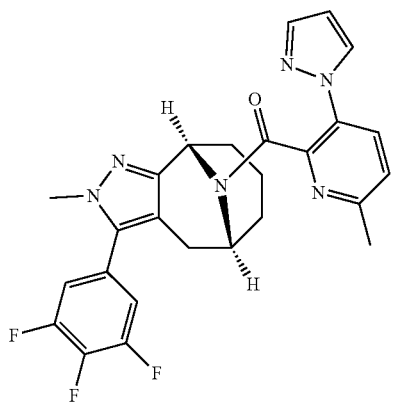 [SMILES: Cc1ccc(-n2cccn2)c(C(=O)CN2[C@@H]3CCC[C@H]2c2nn(C)c(-c4cc(F)c(F)c(F)c4)c2C3)n1]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 6-methyl-3-(1H-pyrazol-1-yl)picolinic acid (Intermediate 84) instead of quinoline-6-carboxylic acid. MS (ESI): mass calcd. for $C_{26}H_{23}F_3N_6O$, 492.2; m/z found, 493.3 [M+H]$^+$. $^1$H NMR (500 MHz, Chloroform-d): 7.98 (d, J=2.5 Hz, 1H), 7.93-7.88 (m, 1H), 7.72-7.67 (m, 1H), 7.34-7.32 (m, 1H), 7.00-6.90 (m, 2H), 6.39-6.35 (m, 1H), 6.02-5.97 (m, 1H), 3.81 (s, 3H), 3.87-3.65 (m, 1H), 2.63 (s, 3H), 2.65-2.57 (m, 1H), 2.17 (d, J=16.1 Hz, 1H), 2.00-1.31 (m, 6H).

Example 311: (4-Methoxy-5-(1H-pyrazol-1-yl)pyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone

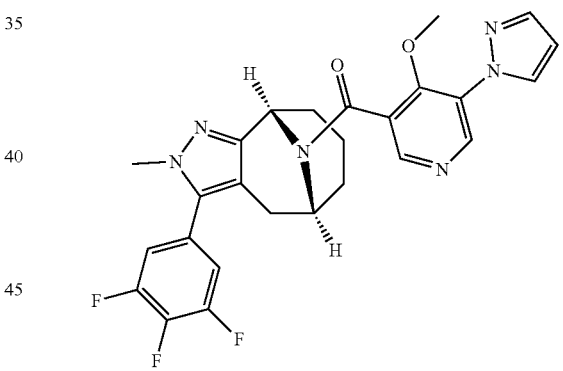

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 4-methoxy-5-(1H-pyrazol-1-yl)nicotinic acid (Intermediate 81) instead of quinoline-6-carboxylic acid. MS (ESI): mass calcd. for $C_{26}H_{23}F_3N_6O_2$, 508.2; m/z found, 509.2 [M+H]$^+$. $^1$H NMR (500 MHz, DMSO-d$_6$): 8.73 (d, J=2.3 Hz, 1H), 8.41 (d, J=2.3 Hz, 1H), 7.91-7.87 (m, 1H), 7.69-7.66 (m, 1H), 7.59-7.51 (m, 2H), 6.46-6.43 (m, 1H), 5.74-5.70 (m, 1H), 4.07-4.01 (m, 1H), 3.80 (s, 6H), 2.98 (dd, J=16.2, 7.4 Hz, 1H), 2.48-2.43 (m, 1H), 1.85-1.57 (m, 3H), 1.51-1.32 (m, 3H).

Example 312: (6-Methyl-3-(1H-1,2,4-triazol-1-yl)pyridin-2-yl)((5R,9S)-2-methyl-3-(3,4,5-trifluorophenyl)-4,5,6,7,8,9-hexahydro-2H-5,9-epiminocycloocta[c]pyrazol-10-yl)methanone

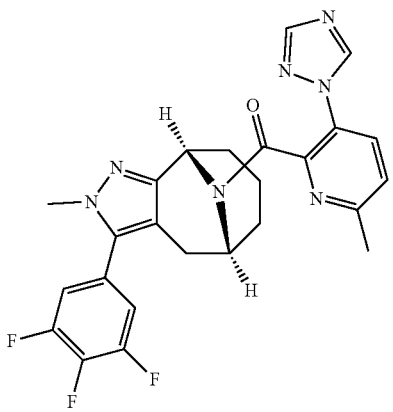 [SMILES: Cc1ccc(-n2cncn2)c(C(=O)CN2[C@@H]3CCC[C@H]2c2nn(C)c(-c4cc(F)c(F)c(F)c4)c2C3)n1]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 6-methyl-3-(1H-1,2,4-triazol-1-yl)picolinic acid (Intermediate 83) instead of quinoline-6-carboxylic acid. MS (ESI): mass calcd. for $C_{25}H_{22}F_3N_7O$, 493.2; m/z found, 494.2 [M+H]$^+$. $^1$H NMR (500 MHz, Chloroform-d): 8.61 (s, 1H), 8.07 (s, 1H), 7.89 (d, J=8.3 Hz, 1H), 7.38 (d, J=8.3 Hz, 1H), 7.00-6.91 (m, 2H), 6.00-5.95 (m, 1H), 3.82 (s, 3H), 3.80-3.73 (m, 1H), 2.71 (dd, J=16.3, 7.2 Hz, 1H), 2.66 (s, 3H), 2.25 (d, J=16.0 Hz, 1H), 2.01-1.35 (m, 6H).

Example 313: (5-(4H-1,2,4-Triazol-4-yl)pyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone

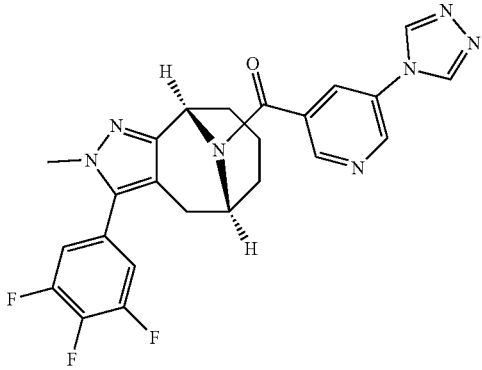 [SMILES: Cn1nc2c(c1-c1cc(F)c(F)c(F)c1)C[C@H]1CCC[C@@H]2N1CC(=O)c1cncc(-n2cnnc2)c1]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 5-(4H-1,2,4-triazol-4-yl)nicotinic acid (Intermediate 88) instead of quinoline-6-carboxylic acid. MS (ESI): mass calcd. for $C_{24}H_{20}F_3N_7O$, 479.2; m/z found, 480.1 [M+H]$^+$. $^1$H NMR (500 MHz, DMSO-d$_6$): 9.25 (s, 2H), 9.10 (d, J=2.6 Hz, 1H), 8.69 (d, J=1.7 Hz, 1H), 8.27 (s, 1H), 7.65-7.54 (m, 2H), 5.77-5.72 (m, 1H), 4.11-4.00 (m, 1H), 3.82 (s, 3H), 3.15-3.04 (m, 1H), 2.44 (d, J=16.3 Hz, 1H), 2.11-1.37 (m, 6H).

Example 314: (4-(4H-1,2,4-Triazol-4-yl)pyridin-2-yl)((5R,9S)-2-methyl-3-(3,4,5-trifluorophenyl)-4,5,6,7,8,9-hexahydro-2H-5,9-epiminocycloocta[c]pyrazol-10-yl)methanone

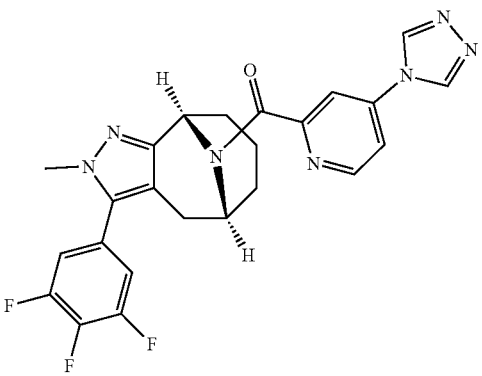 [SMILES: Cn1nc2c(c1-c1cc(F)c(F)c(F)c1)C[C@H]1CCC[C@@H]2N1CC(=O)c1cc(-n2cnnc2)ccn1]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 4-(4H-1,2,4-triazol-4-yl)picolinic acid (Intermediate 87) instead of quinoline-6-carboxylic acid. MS (ESI): mass calcd. for $C_{24}H_{20}F_3N_7O$, 479.2; m/z found, 480.2 [M+H]$^+$. $^1$H NMR (500 MHz, DMSO-d$_6$): 9.41 (s, 2H), 8.74 (d, J=5.5 Hz, 1H), 8.06 (d, J=2.2 Hz, 1H), 7.93 (dd, J=5.5, 2.3 Hz, 1H), 7.62-7.53 (m, 2H), 5.81-5.73 (m, 1H), 4.19-4.10 (m, 1H), 3.81 (s, 3H), 3.01 (dd, J=15.8, 7.2 Hz, 1H), 2.53-2.44 (m, 1H), 1.94-1.40 (m, 6H).

Example 315: ((5R,9S)-2-Methyl-3-(3,4,5-trifluorophenyl)-4,5,6,7,8,9-hexahydro-2H-5,9-epiminocycloocta[c]pyrazol-10-yl)(6-methyl-4-(4H-1,2,4-triazol-4-yl)pyridin-2-yl)methanone

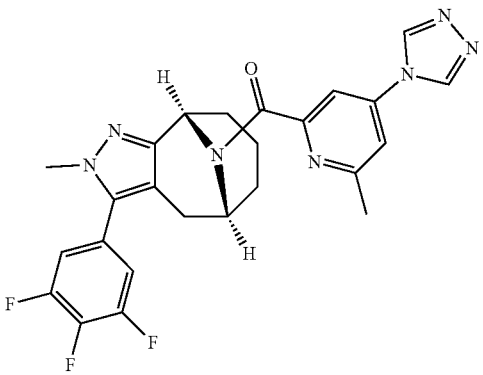 [SMILES: Cc1cc(-n2cnnc2)cc(C(=O)CN2[C@@H]3CCC[C@H]2c2nn(C)c(-c4cc(F)c(F)c(F)c4)c2C3)n1]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 6-methyl-4-(4H-1,2,4-triazol-4-yl)picolinic acid (Intermediate 89) instead of quinoline-6-carboxylic acid. MS (ESI): mass calcd. for $C_{25}H_{22}F_3N_7O$, 493.2; m/z found, 494.2 $[M+H]^+$. $^1H$ NMR (300 MHz, DMSO-$d_6$): 9.38 (s, 2H), 7.95-7.77 (m, 2H), 7.66-7.48 (m, 2H), 5.80-5.68 (m, 1H), 4.20-4.08 (m, 1H), 3.81 (s, 3H), 3.11-2.95 (m, 1H), 2.72-2.58 (m, 1H), 2.56 (s, 3H), 2.12-1.33 (m, 6H).

Example 316: (5-(2H-1,2,3-Triazol-2-yl)pyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone

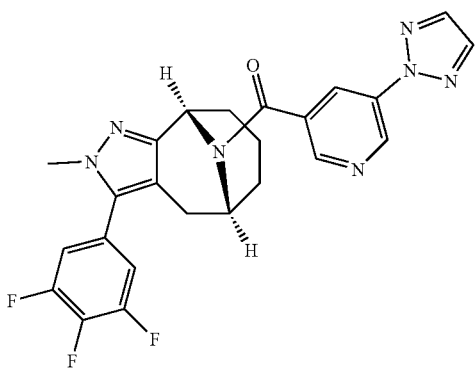 [SMILES: Cn1nc2c(c1-c1cc(F)c(F)c(F)c1)C[C@H]1CCC[C@@H]2N1CC(=O)c1cncc(-n2nccn2)c1]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 5-(triazol-2-yl)pyridine-3-carboxylic acid (Intermediate 90) instead of quinoline-6-carboxylic acid. MS (ESI): mass calcd. for $C_{24}H_{20}F_3N_7O$, 479.2; m/z found, 480.2 $[M+H]^+$. $^1H$ NMR (500 MHz, DMSO-$d_6$): 9.30 (d, J=2.5 Hz, 1H), 8.68 (d, J=1.9 Hz, 1H), 8.38-8.33 (m, 1H), 8.23 (s, 2H), 7.63-7.54 (m, 2H), 5.75-5.69 (m, 1H), 4.12-4.04 (m, 1H), 3.79 (s, 3H), 3.06 (dd, J=16.3, 7.5 Hz, 1H), 2.41 (d, J=16.2 Hz, 1H), 2.01-1.32 (m, 6H).

Example 317: (3-(2H-1,2,3-Triazol-2-yl)pyridin-2-yl)((5R,9S)-2-methyl-3-(3,4,5-trifluorophenyl)-4,5,6,7,8,9-hexahydro-2H-5,9-epiminocycloocta[c]pyrazol-10-yl)methanone

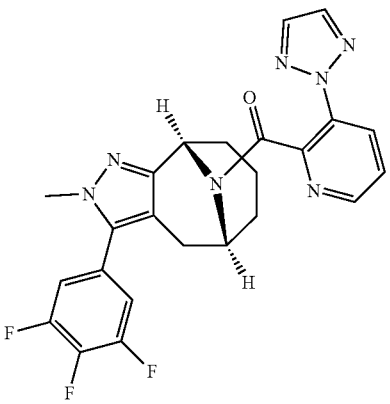 [SMILES: Cn1nc2c(c1-c1cc(F)c(F)c(F)c1)C[C@H]1CCC[C@@H]2N1CC(=O)c1ncccc1-n1nccn1]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 3-(2H-1,2,3-triazol-2-yl)picolinic acid (Intermediate 85) instead of quinoline-6-carboxylic acid. MS (ESI): mass calcd. for $C_{24}H_{20}F_3N_7O$, 479.2; m/z found, 480.2 $[M+H]^+$. $^1H$ NMR (500 MHz, DMSO-$d_6$): 8.65 (dd, J=4.7, 1.4 Hz, 1H), 8.36 (dd, J=8.3, 1.5 Hz, 1H), 8.12 (s, 2H), 7.69 (dd, J=8.3, 4.7 Hz, 1H), 7.56-7.52 (m, 2H), 5.69-5.65 (m, 1H), 3.89-3.84 (m, 1H), 3.81 (s, 3H), 2.80 (dd, J=15.9, 7.2 Hz, 1H), 2.44 (d, J=15.9 Hz, 1H), 1.96-1.34 (m, 6H).

Example 318: ((5R,9S)-2-Methyl-3-(3,4,5-trifluorophenyl)-4,5,6,7,8,9-hexahydro-2H-5,9-epiminocycloocta[c]pyrazol-10-yl)(6-methyl-4-(2H-1,2,3-triazol-2-yl)pyridin-2-yl)methanone

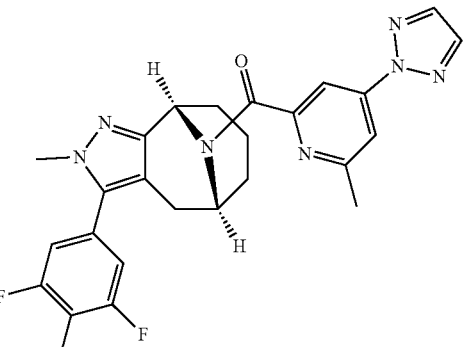

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 6-methyl-4-(2H-1,2,3-triazol-2-yl)picolinic acid (Intermediate 86) instead of quinoline-6-carboxylic acid. MS (ESI): mass calcd. for $C_{25}H_{22}F_3N_7O$, 493.2; m/z found, 494.2 [M+H]$^+$. $^1$H NMR (500 MHz, DMSO-d$_6$): 8.25 (s, 2H), 7.94 (d, J=1.9 Hz, 1H), 7.88 (d, J=1.9 Hz, 1H), 7.63-7.50 (m, 2H), 5.75-5.67 (m, 1H), 4.31-4.22 (m, 1H), 3.78 (s, 3H), 3.00 (dd, J=16.0, 7.3 Hz, 1H), 2.57 (s, 3H), 2.49-2.41 (m, 1H), 1.92-1.36 (m, 6H).

Example 319: (1,5-Dimethyl-1H-pyrazol-4-yl)((5R,9S)-2-methyl-3-(3,4,5-trifluorophenyl)-4,5,6,7,8,9-hexahydro-2H-5,9-epiminocycloocta[c]pyrazol-10-yl)methanone

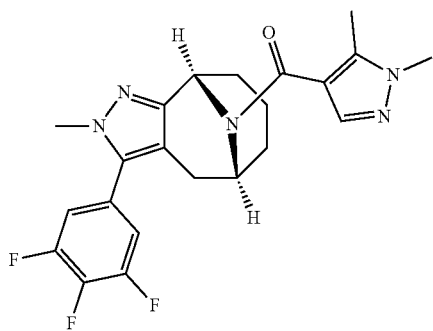 [SMILES: Cc1c(C(=O)N2[C@@H]3CCC[C@H]2c2nn(C)c(-c4cc(F)c(F)c(F)c4)c2C3)cnn1C]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 1,5-dimethyl-1H-pyrazole-4-carboxylic acid instead of quinoline-6-carboxylic acid. MS (ESI): mass calcd. for $C_{22}H_{22}F_3N_5O$, 429.2; m/z found, 430.1 [M+H]$^+$. $^1$H NMR (500 MHz, Chloroform-d) δ 7.55-7.39 (m, 1H), 7.03-6.96 (m, 2H), 5.91 (brs, 0.33H), 5.34 (brs, 0.55H), 5.15 (brs, 0.57H), 4.58 (brs, 0.36H), 3.85-3.74 (m, 6H), 3.23-2.91 (m, 1H), 2.51-2.31 (m, 4H), 2.06-1.44 (m, 6H).

Example 320: (5-Ethyl-1-methyl-1H-pyrazol-4-yl)((5R,9S)-2-methyl-3-(3,4,5-trifluorophenyl)-4,5,6,7,8,9-hexahydro-2H-5,9-epiminocycloocta[c]pyrazol-10-yl)methanone

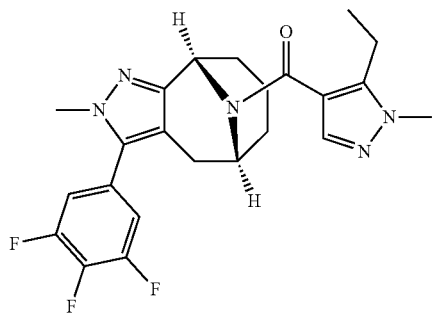 [SMILES: CCc1c(C(=O)N2[C@@H]3CCC[C@H]2c2nn(C)c(-c4cc(F)c(F)c(F)c4)c2C3)cnn1C]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 5-ethyl-1-methyl-1H-pyrazole-4-carboxylic acid instead of quinoline-6-carboxylic acid. MS (ESI): mass calcd. for $C_{23}H_{24}F_3N_5O$, 443.2; m/z found, 444.3 [M+H]$^+$. $^1$H NMR (500 MHz, DMSO-d$_6$): 7.78 (s, 1H), 7.63-7.47 (m, 2H), 5.70-5.52 (m, 1H), 4.44-4.26 (m, 1H), 3.76 (s, 3H), 3.75-3.70 (m, 3H), 3.10-2.93 (m, 1H), 2.64-2.38 (m, 3H), 1.89-1.51 (m, 4H), 1.47-1.29 (m, 2H), 1.14-0.98 (m, 3H).

Example 321: ((5R,9S)-2-Methyl-3-(3,4,5-trifluorophenyl)-4,5,6,7,8,9-hexahydro-2H-5,9-epiminocycloocta[c]pyrazol-10-yl)(1,3,5-trimethyl-1H-pyrazol-4-yl)methanone

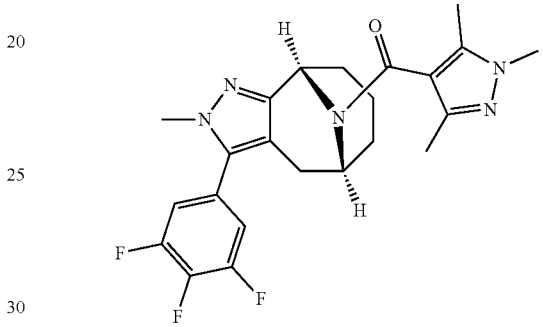

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 1,3,5-trimethyl-1H-pyrazole-4-carboxylic acid instead of quinoline-6-carboxylic acid. MS (ESI): mass calcd. for $C_{23}H_{24}F_3N_5O$, 443.2; m/z found, 444.1 [M+H]$^+$. $^1$H NMR (500 MHz, Chloroform-d) δ 6.99 (br s, 2H), 5.93 (br s, 0.31H), 5.20 (br s, 0.60H), 4.97 (br s, 0.57H), 4.22 (br s, 0.33H), 3.80 (s, 3H), 3.70 (s, 3H), 3.22-3.10 (m, 0.58H), 2.86 (br s, 0.36H), 2.49-2.35 (m, 1.34H), 2.31-2.09 (m, 5.45H), 2.02-1.39 (m, 6.35H).

Example 322: (5-Methoxy-1-methyl-1H-pyrazol-4-yl)((5R,9S)-2-methyl-3-(3,4,5-trifluorophenyl)-4,5,6,7,8,9-hexahydro-2H-5,9-epiminocycloocta[c]pyrazol-10-yl)methanone

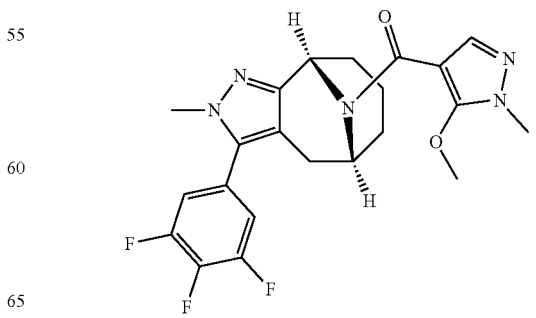

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 5-methoxy-1-methyl-1H-pyrazole-4-carboxylic acid instead of quinoline-6-carboxylic acid. MS (ESI): mass calcd. for $C_{22}H_{22}F_3N_5O_2$, 445.2; m/z found, 446.2 [M+H]$^+$. $^1$H NMR (500 MHz, DMSO-d$_6$): 7.63-7.56 (m, 2H), 7.44 (s, 1H), 5.65-5.56 (m, 1H), 4.43-4.36 (m, 1H), 3.90 (s, 3H), 3.77 (s, 3H), 3.56 (s, 3H), 3.14 (dd, J=16.3, 7.5 Hz, 1H), 2.42 (d, J=16.4 Hz, 1H), 1.80-1.33 (m, 6H).

Example 323: (3-Methoxy-1-methyl-1H-pyrazol-4-yl)((5R,9S)-2-methyl-3-(3,4,5-trifluorophenyl)-4,5,6,7,8,9-hexahydro-2H-5,9-epiminocycloocta[c]pyrazol-10-yl)methanone Example 324: (3-Fluoro-1,5-dimethyl-1H-pyrazol-4-yl)((5R,9S)-2-methyl-3-(3,4,5-trifluorophenyl)-4,5,6,7,8,9-hexahydro-2H-5,9-epiminocycloocta[c]pyrazol-10-yl)methanone

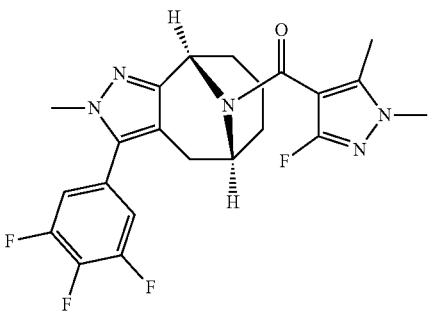

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 3-fluoro-1,5-dimethyl-1H-pyrazole-4-carboxylic acid (Intermediate 91) instead of quinoline-6-carboxylic acid. MS (ESI): mass calcd. for $C_{22}H_{21}F_4N_5O$, 447.2; m/z found, 448.1 [M+H]$^+$. $^1$H NMR (500 MHz, Chloroform-d) δ 7.03-6.96 (m, 2H), 5.91 (brs, 0.32H), 5.18-5.01 (m, 1.20H), 4.30 (brs, 0.32H), 3.81 (brs, 3H), 3.68 (s, 3H), 3.24-2.92 (m, 1H), 2.49-2.37 (m, 1H), 2.33-2.20 (m, 3H), 2.01-1.76 (m, 3.20H), 1.76-1.41 (m, 3H).

Example 325: (5-(Difluoromethyl)-1-methyl-1H-pyrazol-4-yl)((5R,9S)-2-methyl-3-(3,4,5-trifluorophenyl)-4,5,6,7,8,9-hexahydro-2H-5,9-epiminocycloocta[c]pyrazol-10-yl)methanone

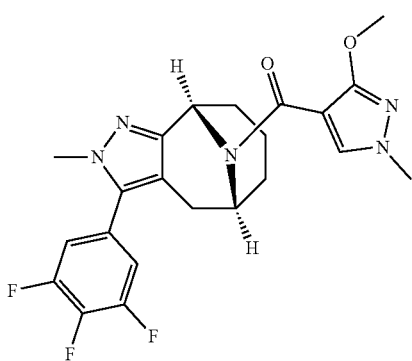 [SMILES: COc1nn(C)cc1C(=O)N1[C@@H]2CCC[C@H]1c1nn(C)c(-c3cc(F)c(F)c(F)c3)c1C2]

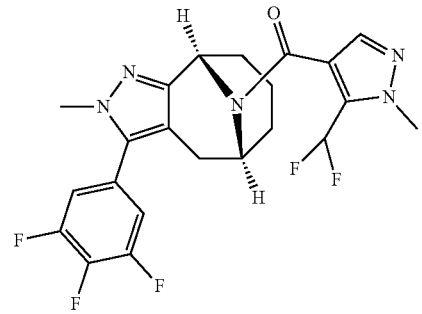 [SMILES: Cn1nc2c(c1-c1cc(F)c(F)c(F)c1)C[C@H]1CCC[C@@H]2N1C(=O)c1cnn(C)c1C(F)F]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 3-methoxy-1-methyl-1H-pyrazole-4-carboxylic acid instead of quinoline-6-carboxylic acid. MS (ESI): mass calcd. for $C_{22}H_{22}F_3N_5O_2$, 445.2; m/z found, 446.2 [M+H]$^+$. $^1$H NMR (500 MHz, DMSO-d$_6$): 7.76 (s, 1H), 7.60-7.46 (m, 2H), 5.60-5.46 (m, 1H), 4.34-4.21 (m, 1H), 3.79 (s, 3H), 3.75 (s, 3H), 3.67 (s, 3H), 3.02-2.87 (m, 1H), 2.54-2.41 (m, 1H), 1.79-1.52 (m, 4H), 1.50-1.29 (m, 2H).

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 5-(difluoromethyl)-1-methyl-1H-pyrazole-4-carboxylic acid instead of quinoline-6-carboxylic acid. MS (ESI): mass calcd. for $C_{22}H_{20}F_5N_5O$, 465.2; m/z found, 466.2 [M+H]$^+$. $^1$H NMR (300 MHz, DMSO-d$_6$): 7.76 (s, 1H), 7.69-7.51 (m, 2H), 7.27 (t, J=52.6 Hz, 1H), 5.76-5.57 (m, 1H), 4.36-4.20

(m, 1H), 3.98 (s, 3H), 3.80 (s, 3H), 3.14 (dd, J=16.3, 7.2 Hz, 1H), 2.69-2.32 (m, 1H), 2.01-1.30 (m, 6H).

Example 326: (1-Cyclopropyl-5-methyl-1H-pyrazol-4-yl)((5R,9S)-2-methyl-3-(3,4,5-trifluorophenyl)-4,5,6,7,8,9-hexahydro-2H-5,9-epiminocycloocta[c]pyrazol-10-yl)methanone

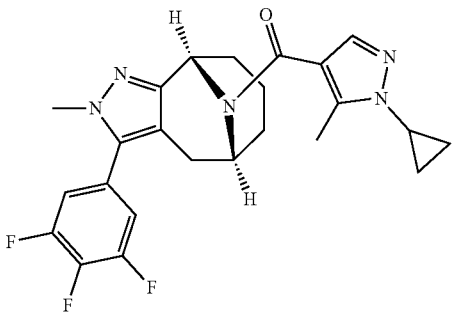 [SMILES: Cc1c(C(=O)N2[C@@H]3CCC[C@H]2c2nn(C)c(-c4cc(F)c(F)c(F)c4)c2C3)cnn1C1CC1]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 1-cyclopropyl-5-methyl-pyrazole-4-carboxylic acid (Intermediate 92) instead of quinoline-6-carboxylic acid. MS (ESI): mass calcd. for $C_{24}H_{24}F_3N_5O$, 455.2; m/z found, 456.4 [M+H]$^+$. $^1$H NMR (500 MHz, DMSO-d$_6$): 7.63-7.52 (m, 2H), 7.46 (s, 1H), 5.66-5.51 (m, 1H), 4.46-4.27 (m, 1H), 3.77 (s, 3H), 3.55-3.46 (m, 1H), 3.14-2.96 (m, 1H), 2.45-2.27 (m, 1H), 2.36 (s, 3H), 1.94-1.52 (m, 4H), 1.50-1.30 (m, 2H), 1.09-0.94 (m, 4H).

Example 327: (1-Cyclopropyl-3-methyl-1H-pyrazol-4-yl)((5R,9S)-2-methyl-3-(3,4,5-trifluorophenyl)-4,5,6,7,8,9-hexahydro-2H-5,9-epiminocycloocta[c]pyrazol-10-yl)methanone

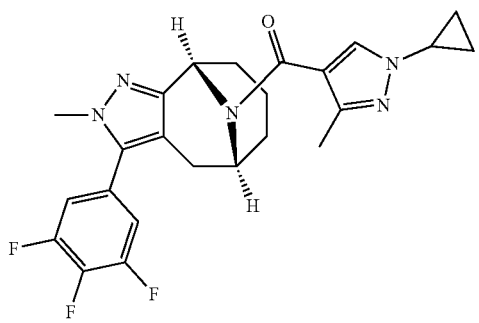 [SMILES: Cc1nn(C2CC2)cc1C(=O)N1[C@@H]2CCC[C@H]1c1nn(C)c(-c3cc(F)c(F)c(F)c3)c1C2]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 1-cyclopropyl-3-methyl-1H-pyrazole-4-carboxylic acid (Intermediate 93) instead of quinoline-6-carboxylic acid. MS (ESI): mass calcd. for $C_{24}H_{24}F_3N_5O$, 455.2; m/z found, 456.3 [M+H]$^+$. $^1$H NMR (500 MHz, DMSO-d$_6$): 7.86 (s, 1H), 7.61-7.48 (m, 2H), 5.68-5.53 (m, 1H), 4.42-4.22 (m, 1H), 3.77 (s, 3H), 3.70-3.58 (m, 1H), 3.11-2.94 (m, 1H), 2.57-2.38 (m, 1H), 2.13 (s, 3H), 1.93-1.53 (m, 4H), 1.49-1.30 (m, 2H), 1.07-0.97 (m, 2H), 0.94-0.85 (m, 2H).

Example 328: (3-Cyclopropyl-1-methyl-1H-pyrazol-4-yl)((5R,9S)-2-methyl-3-(3,4,5-trifluorophenyl)-4,5,6,7,8,9-hexahydro-2H-5,9-epiminocycloocta[c]pyrazol-10-yl)methanone

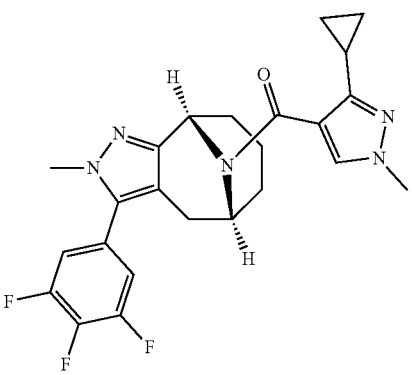 [SMILES: Cn1cc(C(=O)N2[C@@H]3CCC[C@H]2c2nn(C)c(-c4cc(F)c(F)c(F)c4)c2C3)c(C2CC2)n1]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 3-cyclopropyl-1-methyl-1H-pyrazole-4-carboxylic acid instead of quinoline-6-carboxylic acid. MS (ESI): mass calcd. for $C_{24}H_{24}F_3N_5O$, 455.2; m/z found, 456.2 [M+H]$^+$. $^1$H NMR (500 MHz, DMSO-d$_6$): 7.75 (s, 1H), 7.61-7.47 (m, 2H), 5.70-5.56 (m, 1H), 4.44-4.26 (m, 1H), 3.76 (s, 3H), 3.70 (s, 3H), 3.07-2.93 (m, 1H), 2.65-2.30 (m, 1H), 2.00-1.54 (m, 5H), 1.50-1.29 (m, 2H), 0.84-0.64 (m, 4H).

Example 329: Indolizin-7-yl((5R,9S)-2-methyl-3-(3,4,5-trifluorophenyl)-4,5,6,7,8,9-hexahydro-2H-5,9-epiminocycloocta[c]pyrazol-10-yl)methanone

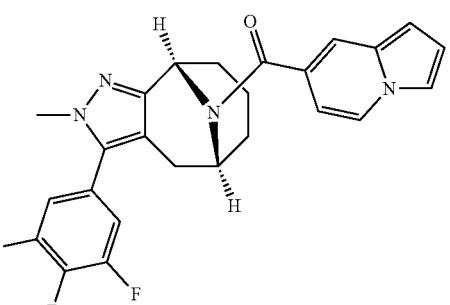

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and indolizine-7-carboxylic acid (Intermediate 79) instead of quinoline-6-carboxylic acid. MS (ESI): mass calcd. for $C_{25}H_{21}F_3N_4O$, 450.2; m/z found, 451.1 [M+H]$^+$. $^1$H NMR (300 MHz, DMSO-d$_6$): 8.29 (d, J=7.1 Hz, 1H), 7.73-7.45 (m, 4H), 6.90-6.74 (m, 1H), 6.66-6.42 (m, 2H), 5.74-5.51 (m, 1H), 4.46-4.20 (m, 1H), 3.80 (s, 3H), 3.10 (dd, J=16.6, 7.4 Hz, 1H), 2.63-2.33 (m, 1H), 2.06-1.33 (m, 6H).

Example 330: (4-Fluoropyrazolo[1,5-a]pyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone

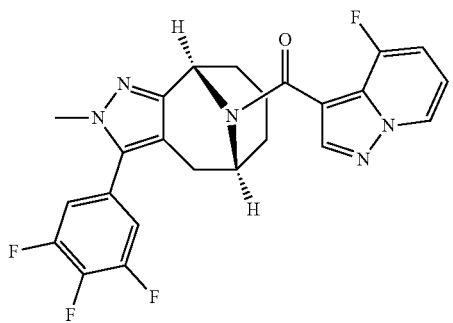 [SMILES: Cn1nc2c(c1-c1cc(F)c(F)c(F)c1)C[C@H]1CCC[C@@H]2N1C(=O)c1cnn2cccc(F)c12]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 4-fluoropyrazolo[1,5-a] pyridine-3-carboxylic acid instead of quinoline-6-carboxylic acid. MS (ESI): mass calcd. for $C_{24}H_{19}F_4N_5O$, 469.2; m/z found, 470.1 [M+H]$^+$. $^1$H NMR (500 MHz, DMSO-d$_6$) δ 8.68 (d, J=7.0 Hz, 1H), 8.20 (d, J=47.2 Hz, 1H), 7.60 (t, J=7.8 Hz, 2H), 7.26 (dd, J=10.6, 7.7 Hz, 1H), 7.01 (d, J=6.3 Hz, 1H), 5.81-5.65 (m, 1H), 5.15-4.16 (m, 1H), 3.84-3.65 (m, 3H), 3.13-3.01 (m, 1H), 2.46-2.22 (m, 1H), 1.99-1.36 (m, 6H).

Example 331: (6-Fluoropyrazolo[1,5-a]pyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone

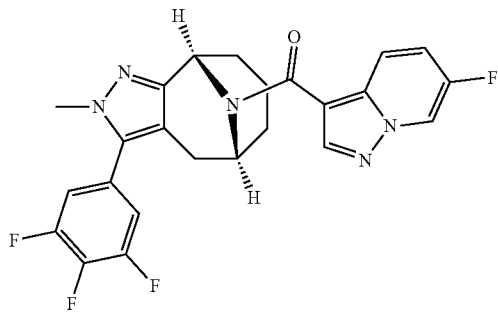 [SMILES: Cn1nc2c(c1-c1cc(F)c(F)c(F)c1)C[C@H]1CCC[C@@H]2N1C(=O)c1cnn2cc(F)ccc12]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 6-fluoropyrazolo[1,5-a] pyridine-3-carboxylic acid instead of quinoline-6-carboxylic acid. MS (ESI): mass calcd. for $C_{24}H_{19}F_4N_5O$, 469.1; m/z found, 470.0 [M+H]$^+$. $^1$H NMR (400 MHz, DMSO-d$_6$) δ 9.18-9.08 (m, 1H), 8.32 (s, 1H), 7.92 (s, 1H), 7.67-7.47 (m, 3H), 5.75-5.34 (m, 1H), 5.04-4.62 (m, 1H), 3.79 (s, 3H), 3.23-3.02 (m, 1H), 2.61-2.52 (m, 1H), 2.01-1.37 (m, 6H).

Example 332: ((5R,9S)-2-Methyl-3-(3,4,5-trifluorophenyl)-4,5,6,7,8,9-hexahydro-2H-5,9-epiminocycloocta[c]pyrazol-10-yl)(7-methylpyrazolo[1,5-a]pyridin-3-yl)methanone

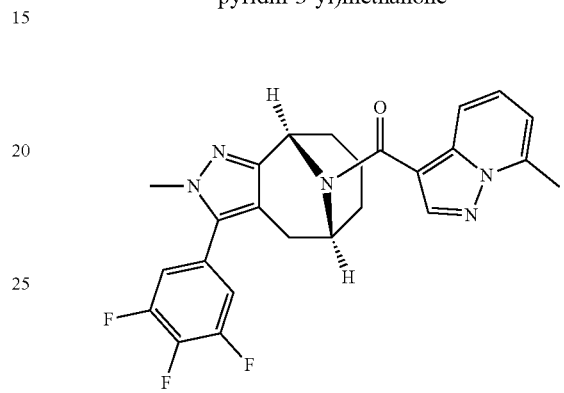

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 7-methylpyrazolo[1,5-a] pyridine-3-carboxylic acid instead of quinoline-6-carboxylic acid. MS (ESI): mass calcd. for $C_{25}H_{22}F_3N_5O$, 465.2; m/z found, 466.2 [M+H]$^+$. $^1$H NMR (500 MHz, DMSO-d$_6$) δ 8.30 (s, 1H), 7.77 (s, 1H), 7.60 (t, J=7.7 Hz, 2H), 7.38 (dd, J=8.9, 6.9 Hz, 1H), 7.04-6.93 (m, 1H), 5.77-5.33 (m, 1H), 5.04-4.51 (m, 1H), 3.79 (s, 3H), 3.25-3.12 (m, 1H), 2.72 (s, 3H), 2.59-2.51 (m, 1H), 2.05-1.36 (m, 6H).

Example 333: (4-Methoxypyrazolo[1,5-a]pyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone

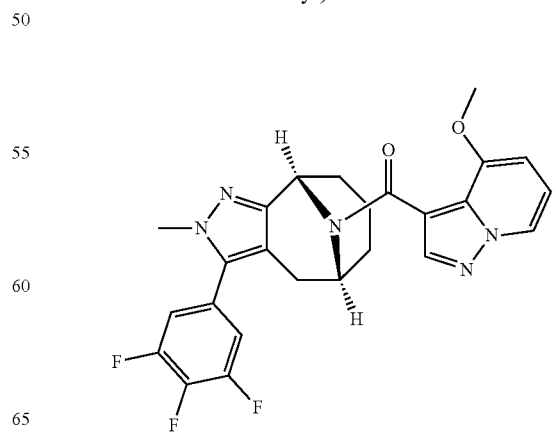

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 4-methoxypyrazolo[1,5-a] pyridine-3-carboxylic acid instead of quinoline-6-carboxylic acid. MS (ESI): mass calcd. for $C_{25}H_{22}F_3N_5O_2$, 481.2; m/z found, 482.1 [M+H]$^+$. $^1$H NMR (500 MHz, DMSO-d$_6$) δ 8.34 (dd, J=9.4, 6.8 Hz, 1H), 7.98 (s, 1H), 7.65-7.51 (m, 2H), 6.93-6.84 (m, 1H), 6.67 (dd, J=26.1, 7.7 Hz, 1H), 5.80-5.10 (m, 1H), 4.64-3.91 (m, 1H), 3.83-3.42 (m, 6H), 3.14-2.72 (m, 1H), 2.37 (d, J=16.0 Hz, 1H), 1.91-1.34 (m, 6H).

Example 334: (6-Methoxypyrazolo[1,5-a] pyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone

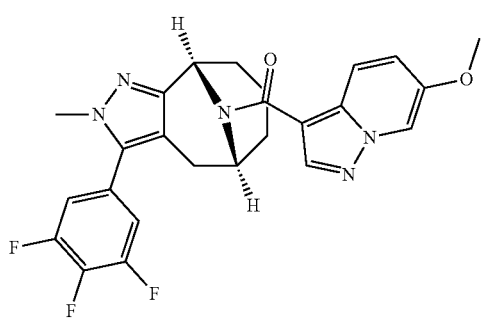 [SMILES: COc1ccc2c(C(=O)N3[C@H]4CCC[C@@H]3c3nn(C)c(-c5cc(F)c(F)c(F)c5)c3C4)cnn2c1]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 6-methoxypyrazolo[1,5-a] pyridine-3-carboxylic acid instead of quinoline-6-carboxylic acid. MS (ESI): mass calcd. for $C_{25}H_{22}F_3N_5O_2$, 481.1; m/z found, 482.1 [M+H]$^+$. $^1$H NMR (400 MHz, DMSO-d$_6$) δ 8.51 (dd, J=2.3, 0.8 Hz, 1H), 8.19 (s, 1H), 7.79 (d, J=9.8 Hz, 1H), 7.61 (t, J=7.9 Hz, 2H), 7.23 (dd, J=9.6, 2.2 Hz, 1H), 5.77-5.35 (m, 1H), 5.04-4.59 (m, 1H), 3.85 (s, 3H), 3.81-3.73 (m, 3H), 3.28-3.12 (m, 2H), 2.00-1.38 (m, 6H).

Example 335: Imidazo[1,5-a]pyridin-7-yl((5R,9S)-2-methyl-3-(3,4,5-trifluorophenyl)-4,5,6,7,8,9-hexahydro-2H-5,9-epiminocycloocta[c]pyrazol-10-yl)methanone

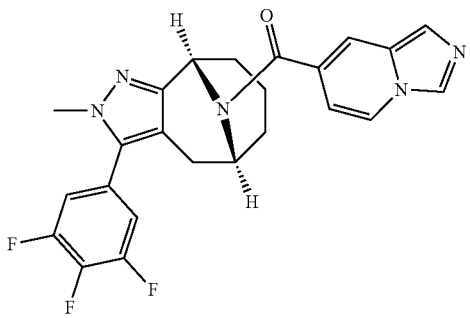 [SMILES: Cn1nc2c(c1-c1cc(F)c(F)c(F)c1)C[C@@H]1CCC[C@H]2N1C(=O)c1ccn2cncc2c1]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and imidazo[1,5-a]pyridine-7-carboxylic acid instead of quinoline-6-carboxylic acid. MS (ESI): mass calcd. for $C_{24}H_{20}F_3N_5O$, 451.2; m/z found, 452.1 [M+H]$^+$. $^1$H NMR (300 MHz, DMSO-d$_6$): 8.51-8.43 (m, 1H), 8.42-8.31 (m, 1H), 7.72-7.54 (m, 3H), 7.53-7.42 (m, 1H), 6.74-6.55 (m, 1H), 5.73-5.55 (m, 1H), 4.43-4.13 (m, 1H), 3.81 (s, 3H), 3.16-3.02 (m, 1H), 2.64-2.33 (m, 1H), 2.05-1.34 (m, 6H).

Example 336: ((5R,9S)-2-Methyl-3-(3,4,5-trifluorophenyl)-4,5,6,7,8,9-hexahydro-2H-5,9-epiminocycloocta[c]pyrazol-10-yl)(5-methylimidazo[1,5-a]pyridin-6-yl)methanone

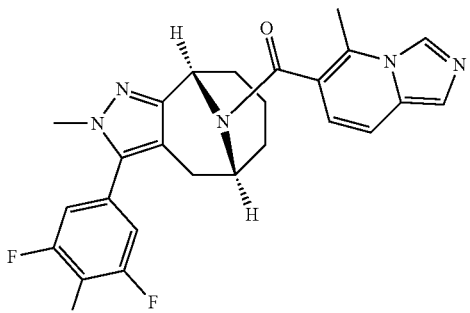

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 5-methylimidazo[1,5-a]pyridine-6-carboxylic acid instead of quinoline-6-carboxylic acid. MS (ESI): mass calcd. for $C_{25}H_{22}F_3N_5O$, 465.2; m/z found, 466.4 [M+H]$^+$. $^1$H NMR (500 MHz, DMSO-d$_6$): 8.38 (s, 1H), 7.63-7.53 (m, 2H), 7.51 (d, J=9.1 Hz, 1H), 7.47 (s, 1H), 6.62 (d, J=9.2 Hz, 1H), 5.77-5.72 (m, 1H), 3.98-3.93 (m, 1H), 3.79 (s, 3H), 2.95 (dd, J=16.1, 7.3 Hz, 1H), 2.59 (s, 3H), 2.54 (dd, J=16.3, 6.9 Hz, 1H), 1.90-1.32 (m, 6H).

Example 337: ((5R,9S)-2-Methyl-3-(3,4,5-trifluorophenyl)-4,5,6,7,8,9-hexahydro-2H-5,9-epiminocycloocta[c]pyrazol-10-yl)(3-methylimidazo[1,5-a]pyridin-6-yl)methanone

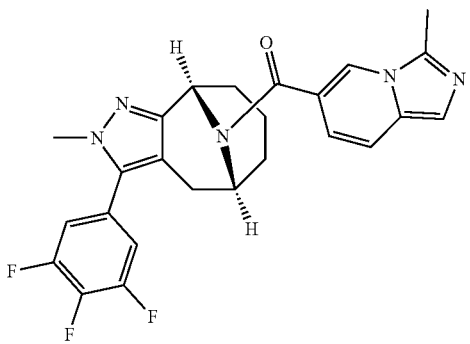 [SMILES: Cc1ncc2ccc(C(=O)N3[C@H]4CCC[C@@H]3c3nn(C)c(-c5cc(F)c(F)c(F)c5)c3C4)cn12]

The title compound was prepare in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 3-methylimidazo[1,5-a]pyridine-6-carboxylic acid instead of quinoline-6-carboxylic acid. MS (ESI): mass calcd. for $C_{25}H_{22}F_3N_5O$, 465.2; m/z found, 466.4 [M+H]$^+$. $^1$H NMR (500 MHz, DMSO-d$_6$): 8.46-8.37 (m, 1H), 7.78-7.55 (m, 4H), 7.00-6.93 (m, 1H), 5.72-5.66 (m, 1H), 4.25-4.17 (m, 1H), 3.82 (s, 3H), 3.11-3.04 (m, 1H), 2.74 (s, 3H), 2.57-2.40 (m, 1H), 1.93-1.37 (m, 6H).

Example 338: ((5R,9S)-2-Methyl-3-(3,4,5-trifluorophenyl)-4,5,6,7,8,9-hexahydro-2H-5,9-epiminocycloocta[c]pyrazol-10-yl)(5-methylimidazo[1,2-a]pyridin-6-yl)methanone

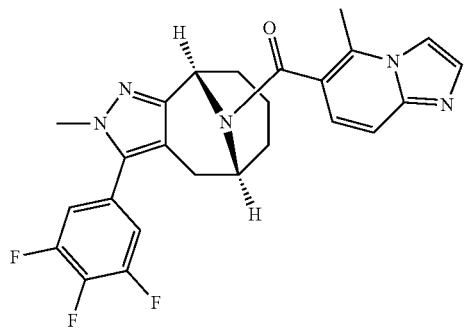 [SMILES: Cc1c(C(=O)N2[C@H]3CCC[C@@H]2c2nn(C)c(-c4cc(F)c(F)c(F)c4)c2C3)ccc2nccn12]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 5-methylimidazo[1,2-a]pyridine-6-carboxylic acid instead of quinoline-6-carboxylic acid. MS (ESI): mass calcd. for $C_{25}H_{22}F_3N_5O$, 465.2; m/z found, 466.4 [M+H]$^+$. $^1$H NMR (500 MHz, DMSO-d$_6$): 7.93-7.91 (m, 1H), 7.69-7.67 (m, 1H), 7.63-7.57 (m, 2H), 7.57-7.45 (m, 1H), 7.07 (d, J=9.1 Hz, 1H), 5.80-5.72 (m, 1H), 3.96-3.88 (m, 1H), 3.79 (s, 3H), 2.96 (dd, J=16.2, 7.3 Hz, 1H), 2.61 (s, 3H), 2.44-2.35 (m, 1H), 1.94-1.52 (m, 4H), 1.51-1.33 (m, 2H).

Example 339: ((5R,9S)-2-Methyl-3-(3,4,5-trifluorophenyl)-4,5,6,7,8,9-hexahydro-2H-5,9-epiminocycloocta[c]pyrazol-10-yl)(7-methylimidazo[1,2-a]pyridin-5-yl)methanone

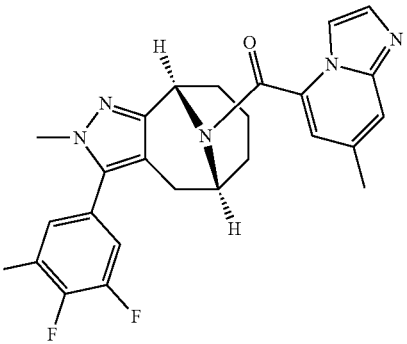

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 7-methylimidazo[1,2-a]pyridine-5-carboxylic acid (Intermediate 95) instead of quinoline-6-carboxylic acid. MS (ESI): mass calcd. for $C_{25}H_{22}F_3N_5O$, 465.2; m/z found, 466.3 [M+H]$^+$. $^1$H NMR (500 MHz, DMSO-d$_6$): 7.70-7.50 (m, 3H), 7.58-7.53 (m, 1H), 7.47-7.44 (m, 1H), 6.89-6.86 (m, 1H), 5.83-5.74 (m, 1H), 4.09-3.99 (m, 1H), 3.83 (s, 3H), 3.07-2.93 (m, 1H), 2.61-2.44 (m, 1H), 2.38 (s, 3H), 2.10-1.34 (m, 6H).

Example 340: ((5R,9S)-2-Methyl-3-(3,4,5-trifluorophenyl)-4,5,6,7,8,9-hexahydro-2H-5,9-epiminocycloocta[c]pyrazol-10-yl)(3-methylimidazo[1,2-a]pyridin-5-yl)methanone

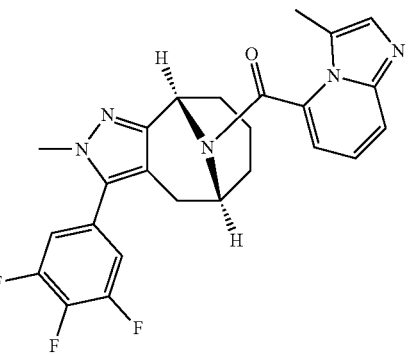

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 3-methylimidazo[1,2-a]pyridine-5-carboxylic acid instead of quinoline-6-carboxylic acid. MS (ESI): mass calcd. for $C_{25}H_{22}F_3N_5O$, 465.2; m/z found, 466.4 [M+H]$^+$. $^1$H NMR (500 MHz, DMSO-d$_6$): 7.71-7.61 (m, 2H), 7.61-7.52 (m, 1H), 7.47 (s, 1H), 7.20 (dd, J=9.0, 6.8 Hz, 1H), 6.95 (dd, J=6.9, 1.2 Hz, 1H), 5.90-5.78 (m, 1H), 4.27-4.11 (m, 1H), 3.83 (s, 3H), 3.21 (dd, J=16.1, 7.4 Hz, 1H), 2.55-2.39 (m, 1H), 2.13-1.37 (m, 6H), 1.92 (s, 3H).

Example 341: ((5R,9S)-2-Methyl-3-(3,4,5-trifluorophenyl)-4,5,6,7,8,9-hexahydro-2H-5,9-epiminocycloocta[c]pyrazol-10-yl)(3-methylimidazo[1,2-a]pyridin-6-yl)methanone

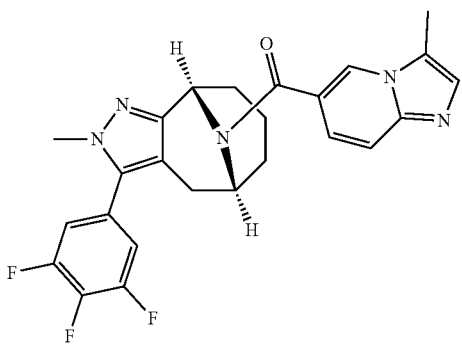 [SMILES: Cc1cnc2ccc(C(=O)N3[C@H]4CCC[C@@H]3c3nn(C)c(-c5cc(F)c(F)c(F)c5)c3C4)cn12]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 3-methylimidazo[1,2-a]pyridine-6-carboxylic acid instead of quinoline-6-carboxylic acid. MS (ESI): mass calcd. for $C_{25}H_{22}F_3N_5O$, 465.2; m/z found, 466.4 [M+H]$^+$. $^1$H NMR (300 MHz, DMSO-d$_6$): 8.45-8.36 (m, 1H), 7.70-7.53 (m, 3H), 7.49-7.43 (m, 1H), 7.30-7.10 (m, 1H), 5.78-5.65 & 5.09-4.92 (m, 1H), 4.31-4.19 & 3.86-3.73 (m, 1H), 3.84 (s, 3H), 3.18-3.03 (m, 1H), 2.62-2.35 (m, 4H), 2.15-1.31 (m, 6H).

Example 342: ((5R,9S)-2-Methyl-3-(3,4,5-trifluorophenyl)-4,5,6,7,8,9-hexahydro-2H-5,9-epiminocycloocta[c]pyrazol-10-yl)(2-methylimidazo[1,2-a]pyridin-6-yl)methanone

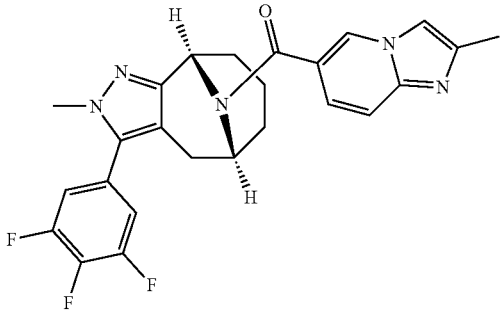 [SMILES: Cc1cn2cc(C(=O)N3[C@H]4CCC[C@@H]3c3nn(C)c(-c5cc(F)c(F)c(F)c5)c3C4)ccc2n1]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 2-methylimidazo[1,2-a]pyridine-6-carboxylic acid instead of quinoline-6-carboxylic acid. MS (ESI): mass calcd. for $C_{25}H_{22}F_3N_5O$, 465.2; m/z found, 466.2 [M+H]$^+$. $^1$H NMR (500 MHz, DMSO-d$_6$): 8.66 (s, 1H), 7.78-7.69 (m, 1H), 7.64-7.56 (m, 3H), 7.52-7.42 (m, 1H), 5.71-5.61 (m, 1H), 4.30-4.19 (m, 1H), 3.81 (s, 3H), 3.09 (dd, J=16.3, 7.4 Hz, 1H), 2.54-2.42 (m, 1H), 2.34 (s, 3H), 1.93-1.37 (m, 6H).

Example 343: ((5R,9S)-2-Methyl-3-(3,4,5-trifluorophenyl)-4,5,6,7,8,9-hexahydro-2H-5,9-epiminocycloocta[c]pyrazol-10-yl)(2-methylimidazo[1,2-a]pyridin-5-yl)methanone

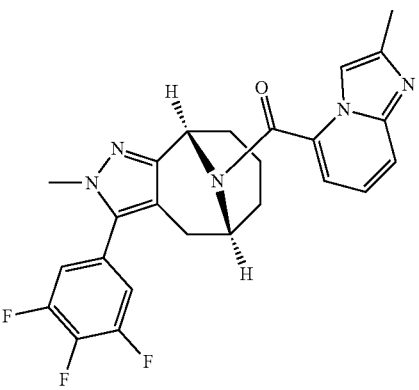 [SMILES: Cc1cn2c(C(=O)N3[C@H]4CCC[C@@H]3c3nn(C)c(-c5cc(F)c(F)c(F)c5)c3C4)cccc2n1]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 2-methylimidazo[1,2-a]pyridine-5-carboxylic acid instead of quinoline-6-carboxylic acid. MS (ESI): mass calcd. for $C_{25}H_{22}F_3N_5O$, 465.2; m/z found, 466.2 [M+H]$^+$. $^1$H NMR (500 MHz, DMSO-d$_6$): 7.64-7.49 (m, 4H), 7.22-7.17 (m, 1H), 6.96-6.91 (m, 1H), 5.79-5.72 (m, 1H), 4.07-4.00 (m, 1H), 3.80 (s, 3H), 3.07-2.93 (m, 1H), 2.46-2.39 (m, 1H), 2.32 (s, 3H), 2.05-1.34 (m, 6H).

Example 344: Imidazo[1,2-a]pyridin-3-yl((5R,9S)-2-methyl-3-(3,4,5-trifluorophenyl)-4,5,6,7,8,9-hexahydro-2H-5,9-epiminocycloocta[c]pyrazol-10-yl)methanone

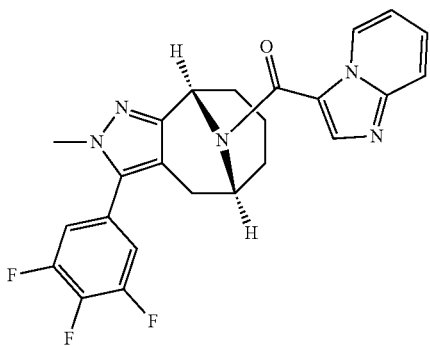 [SMILES: Cn1nc2c(c1-c1cc(F)c(F)c(F)c1)C[C@@H]1CCC[C@H]2N1C(=O)c1cnc2ccccn12]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and imidazo[1,2-a]pyridine-3-carboxylic acid instead of quinoline-6-carboxylic acid. MS (ESI): mass calcd. for $C_{24}H_{20}F_3N_5O$, 451.2; m/z found, 452.1 [M+H]$^+$. $^1$H NMR (400 MHz, DMSO-$d_6$) δ 8.92-8.85 (m, 1H), 8.05 (s, 1H), 7.77-7.69 (m, 1H), 7.62 (dd, J=8.8, 6.7 Hz, 2H), 7.50-7.37 (m, 1H), 7.12-7.05 (m, 1H), 5.74-5.60 (m, 1H), 5.03-4.80 (m, 1H), 3.80 (s, 3H), 3.30-3.14 (m, 1H), 2.59-2.52 (m, 1H), 2.05-1.43 (m, 6H).

Example 345: (7-Fluoroimidazo[1,2-a]pyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone

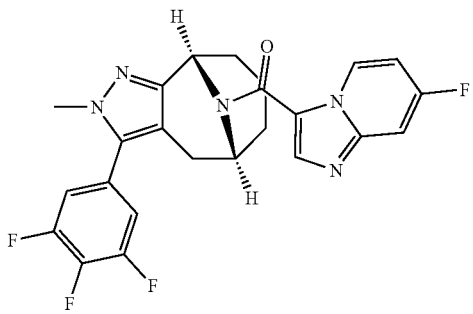 [SMILES: Cn1nc2c(c1-c1cc(F)c(F)c(F)c1)C[C@@H]1CCC[C@H]2N1C(=O)c1cnc2cc(F)ccn12]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and potassium 7-fluoroimidazo[1,2-a]pyridine-3-carboxylate (Intermediate 96) instead of quinoline-6-carboxylic acid. MS (ESI): mass calcd. for $C_{24}H_{19}F_4N_5O$, 469.2; m/z found, 470.1 [M+H]$^+$. $^1$H NMR (500 MHz, DMSO-$d_6$) δ 8.93 (dd, J=7.7, 5.9 Hz, 1H), 8.05 (s, 1H), 7.70-7.53 (m, 3H), 7.21-6.99 (m, 1H), 5.81-5.48 (m, 1H), 5.07-4.81 (m, 1H), 3.80 (s, 3H), 2.65-2.51 (m, 2H), 2.06-1.41 (m, 6H).

Example 346: (7-Chloroimidazo[1,2-a]pyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone

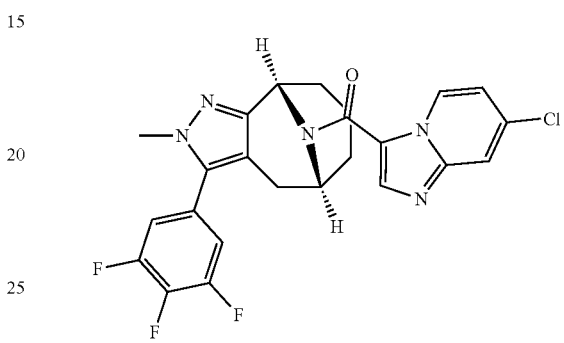

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 7-chloroimidazo[1,2-a]pyridine-3-carboxylic acid instead of quinoline-6-carboxylic acid. MS (ESI): mass calcd. for $C_{24}H_{19}ClF_3N_5O$, 485.1; m/z found, 486.0 [M+H]$^+$. $^1$H NMR (400 MHz, DMSO-$d_6$) δ 8.65-8.54 (m, 1H), 8.35 (dd, J=3.1, 0.8 Hz, 1H), 7.91-7.77 (m, 1H), 7.63-7.50 (m, 2H), 7.15-7.01 (m, 1H), 5.81-5.57 (m, 1H), 3.82-3.70 (m, 3H), 3.25-2.95 (m, 2H), 2.60-2.52 (m, 1H), 2.03-1.40 (m, 6H).

Example 347: ((5R,9S)-2-Methyl-3-(3,4,5-trifluorophenyl)-4,5,6,7,8,9-hexahydro-2H-5,9-epiminocycloocta[c]pyrazol-10-yl)(2-methylimidazo[1,2-a]pyridin-3-yl) methanone

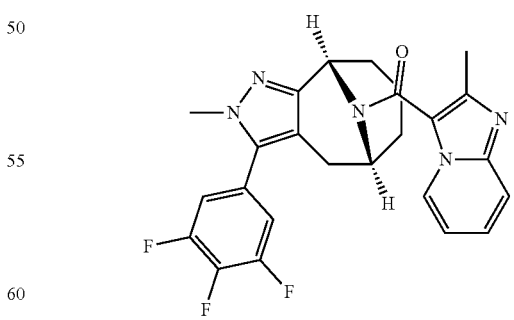

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9- epiminocycloocta[c]pyrazole (Intermediate 1) and 2-methylimidazo[1,2-a]pyridine-3-carboxylic acid instead of quinoline-6-carboxylic acid. MS (ESI): mass calcd. for $C_{25}H_{22}F_3N_5O$, 465.5; m/z found, 467.0 [M+H]$^+$. $^1$H NMR (400 MHz, DMSO-d$_6$) δ 8.39 (s, 1H), 7.67-7.51 (m, 3H), 7.41-7.27 (m, 1H), 6.96 (t, J=6.9 Hz, 1H), 5.62-5.12 (m, 1H), 3.80 (s, 3H), 3.22-2.99 (m, 2H), 2.37 (s, 3H), 2.01-1.35 (m, 7H).

Example 348: (2,7-Dimethylimidazo[1,2-a]pyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone

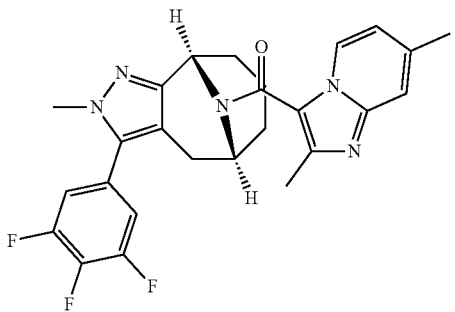 [SMILES: Cc1ccn2c(C(=O)N3[C@H]4CCC[C@@H]3c3nn(C)c(-c5cc(F)c(F)c(F)c5)c3C4)c(C)nc2c1]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 2,7-dimethylimidazo[1,2-a] pyridine-3-carboxylic acid instead of quinoline-6-carboxylic acid. MS (ESI): mass calcd. for $C_{26}H_{24}F_3N_5O$, 479.2; m/z found, 480.1 [M+H]$^+$. $^1$H NMR (500 MHz, DMSO-d$_6$) δ 8.28 (s, 1H), 7.59 (dd, J=8.7, 6.6 Hz, 2H), 7.40-7.27 (m, 1H), 6.86-6.73 (m, 1H), 5.52-5.06 (m, 1H), 4.77-4.32 (m, 1H), 3.79 (s, 3H), 3.18-3.01 (m, 1H), 2.55 (s, 1H), 2.40-2.29 (m, 6H), 1.99-1.37 (m, 6H).

Example 349: ((5R,9S)-3-(3-Fluoro-5-methylphenyl)-2-methyl-4,5,6,7,8,9-hexahydro-2H-5,9-epiminocycloocta[c]pyrazol-10-yl)(2-methylimidazo[1,2-a]pyridin-3-yl)methanone

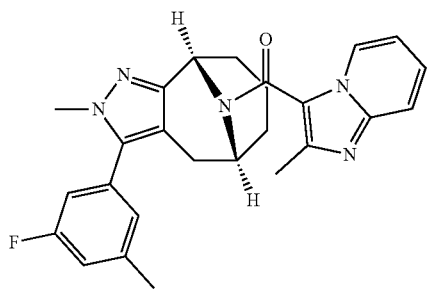 [SMILES: Cc1cc(F)cc(-c2c3c(nn2C)[C@@H]2CCC[C@H](C3)N2C(=O)c2c(C)nc3ccccn23)c1]

The title compound was prepared in a manner analogous to Example 1 using (5R,9S)-3-(3-fluoro-5-methylphenyl)-2-methyl-4,5,6,7,8,9-hexahydro-2H-5,9-epiminocycloocta[c]pyrazole (Intermediate 63) instead of racemic-(5R,9S)-2-methyl-3-phenyl-4,5,6,7,8,9-hexahydro-2H-5,9-epiminocycloocta[c]pyrazole (Intermediate 1) and 2-methylimidazo[1,2-a]pyridine-3-carboxylic acid instead of quinoline-6-carboxylic acid. MS (ESI): mass calcd. for $C_{26}H_{26}FN_5O$, 443.2; m/z found, 444.1 [M+H]$^+$. $^1$H NMR (500 MHz, DMSO-d$_6$) δ 8.39 (s, 1H), 7.61-7.51 (m, 1H), 7.40-7.30 (m, 1H), 7.18 (d, J=10.3 Hz, 2H), 7.11 (d, J=9.8 Hz, 1H), 6.96 (t, J=6.8 Hz, 1H), 5.49-4.80 (m, 1H) 3.78 (s, 3H), 3.22-2.91 (m, 2H), 2.63-2.52 (m, 1H), 2.41-2.30 (m, 6H), 1.95-1.37 (m, 6H).

Example 350: ((5R,9S)-2-Methyl-3-(3,4,5-trifluorophenyl)-4,5,6,7,8,9-hexahydro-2H-5,9-epiminocycloocta[c]pyrazol-10-yl)(5-methylimidazo[1,2-a]pyridin-3-yl)methanone

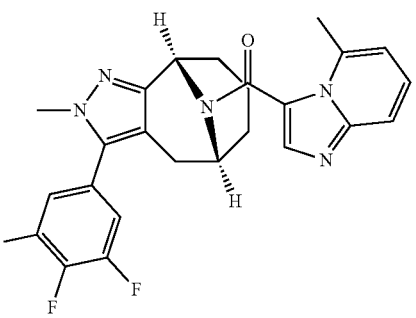

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and lithium 5-methylimidazo[1,2-a] pyridine-3-carboxylate instead of quinoline-6-carboxylic acid. MS (ESI): mass calcd. for $C_{25}H_{22}F_3N_5O$, 465.2; m/z found, 466.1 [M+H]$^+$. $^1$H NMR (400 MHz, DMSO-d$_6$) δ 7.95 (s, 1H), 7.72-7.53 (m, 3H), 7.37 (dd, J=9.0, 6.8 Hz, 1H), 6.90 (d, J=6.9 Hz, 1H), 5.83-5.69 (m, 1H), 5.13-4.52 (m, 1H), 3.88-3.69 (m, 3H), 3.23-3.01 (m, 1H), 2.65-2.56 (m, 1H), 2.53-2.48 (m, 3H), 1.93-1.37 (m, 6H).

Example 351: ((5R,9S)-2-Methyl-3-(3,4,5-trifluorophenyl)-4,5,6,7,8,9-hexahydro-2H-5,9-epiminocycloocta[c]pyrazol-10-yl)(7-(trifluoromethyl)imidazo[1,2-a]pyridin-3-yl)methanone

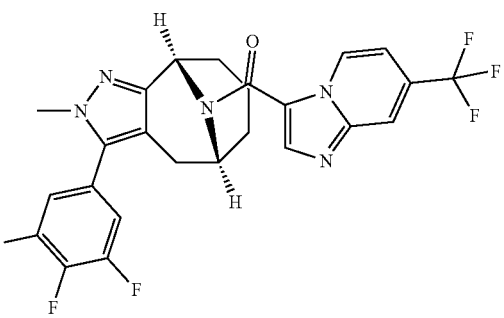

The title compound was prepared in a manner analogous to Example 1 using (5R,9S)-2-methyl-3-(3,4,5-trifluorophenyl)-4,5,6,7,8,9-hexahydro-2H-5,9-epiminocyclooctal[c]pyrazole (Intermediate 25) instead of racemic-(5R,9S)-2-methyl-3-phenyl-4,5,6,7,8,9-hexahydro-2H-5,9-epiminocyclooctal[c]pyrazole (Intermediate 1) and 7-(trifluoromethyl) imidazo[1,2-a] pyridine-3-carboxylic acid instead of quinoline-6-carboxylic acid. MS (ESI): mass calcd. for $C_{25}H_{19}F_6N_5O$, 519.5; m/z found, 520.1 [M+H]$^+$. $^1$H NMR (400 MHz, DMSO-d$_6$) δ 9.03 (d, J=7.3 Hz, 1H), 8.29-8.16 (m, 2H), 7.63 (t, J=7.7 Hz, 2H), 7.35 (dd, J=7.4, 2.0 Hz, 1H), 5.81-5.48 (m, 1H), 5.07-4.72 (m, 1H), 3.81 (s, 3H), 2.63-2.54 (m, 1H), 2.07-1.92 (m, 1H), 1.91-1.41 (m, 6H).

Example 352: (2-(Difluoromethyl)imidazo[1,2-a]pyridin-3-yl)((5R,9S)-2-methyl-3-(3,4,5-trifluorophenyl)-4,5,6,7,8,9-hexahydro-2H-5,9-epiminocyclooctal[c]pyrazol-10-yl)methanone

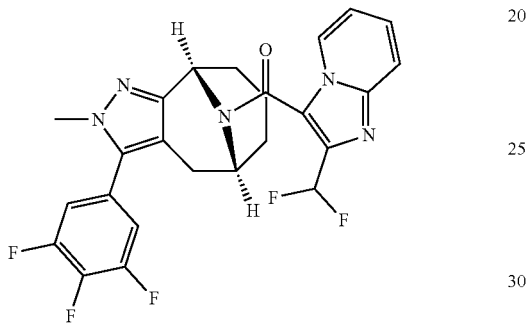

The title compound was prepared in a manner analogous to Example 1 using (5R,9S)-2-methyl-3-(3,4,5-trifluorophenyl)-4,5,6,7,8,9-hexahydro-2H-5,9-epiminocyclooctal[c]pyrazole (Intermediate 25) instead of racemic-(5R,9S)-2-methyl-3-phenyl-4,5,6,7,8,9-hexahydro-2H-5,9-epiminocyclooctal[c]pyrazole (Intermediate 1) and 2-(difluoromethyl)imidazo[1,2-a]pyridine-3-carboxylic acid instead of quinoline-6-carboxylic acid. MS (ESI): mass calcd. for $C_{25}H_{20}F_5N_5O$, 501.2; m/z found, 502.1 [M+H]$^+$. $^1$H NMR (400 MHz, DMSO-d$_6$) δ 8.28 (d, J=174.0 Hz, 1H), 7.81-7.68 (m, 1H), 7.62-7.42 (m, 3H), 7.36-6.89 (m, 2H), 5.75 (s, 1H), 5.35-4.45 (m, 1H), 3.79 (s, 3H), 3.27-2.75 (m, 2H), 2.11-1.31 (m, 6H).

Example 353: (2-Methyl-2H-indazol-3-yl)((5R,9S)-2-methyl-3-(3,4,5-trifluorophenyl)-4,5,6,7,8,9-hexahydro-2H-5,9-epiminocyclooctal[c]pyrazol-10-yl)methanone

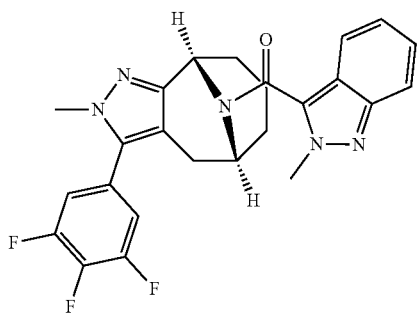 [SMILES: Cn1nc2c(c1-c1cc(F)c(F)c(F)c1)C[C@H]1CCC[C@@H]2N1C(=O)c1c2ccccc2nn1C]

The title compound was prepared in a manner analogous to Example 1 using (5R,9S)-2-methyl-3-(3,4,5-trifluorophenyl)-4,5,6,7,8,9-hexahydro-2H-5,9-epiminocyclooctal[c]pyrazole (Intermediate 25) instead of racemic-(5R,9S)-2-methyl-3-phenyl-4,5,6,7,8,9-hexahydro-2H-5,9-epiminocyclooctal[c]pyrazole (Intermediate 1) and 2-methyl-2H-indazole-3-carboxylic acid instead of quinoline-6-carboxylic acid. MS (ESI): mass calcd. for $C_{25}H_{22}F_3N_5O$, 465.2; m/z found, 466.1 [M+H]$^+$. $^1$H NMR (400 MHz, DMSO-d$_6$) δ 7.73-7.55 (m, 3H), 7.35-7.13 (m, 2H), 5.78 (s, 1H), 5.23-4.71 (m, 1H), 4.22-4.00 (m, 3H), 3.87-3.72 (m, 3H), 3.24-2.57 (m, 2H), 2.33-2.02 (m, 1H), 2.11-1.33 (m, 6H).

Example 354: (2,7-Dimethylpyrazolo[1,5-a]pyrimidin-5-yl)((5R,9S)-2-methyl-3-(3,4,5-trifluorophenyl)-4,5,6,7,8,9-hexahydro-2H-5,9-epiminocycloocta[c]pyrazol-10-yl)methanone

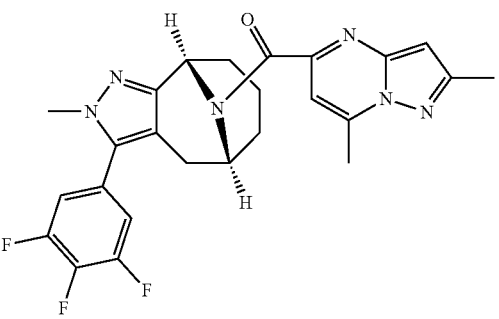 [SMILES: Cc1cc2nc(C(=O)N3[C@@H]4CCC[C@H]3c3nn(C)c(-c5cc(F)c(F)c(F)c5)c3C4)cc(C)n2n1]

The title compound was prepare in a manner analogous to Example 1 using (5R,9S)-2-methyl-3-(3,4,5-trifluorophenyl)-4,5,6,7,8,9-hexahydro-2H-5,9-epiminocyclooctal[c]pyrazole (Intermediate 25) instead of racemic-(5R,9S)-2-methyl-3-phenyl-4,5,6,7,8,9-hexahydro-2H-5,9-epiminocyclooctal[c]pyrazole (Intermediate 1) and 2,7-dimethylpyrazolo[1,5-a]pyrimidine-5-carboxylic acid instead of quinoline-6-carboxylic acid. MS (ESI): mass calcd. for $C_{25}H_{23}F_3N_6O$, 480.2; m/z found, 481.2 [M+H]$^+$. $^1$H NMR (500 MHz, DMSO-d$_6$): 7.61-7.53 (m, 2H), 7.03-7.01 (m, 1H), 6.56 (s, 1H), 5.71-5.67 (m, 1H), 4.31-4.25 (m, 1H), 3.78 (s, 3H), 2.98 (dd, J=16.1, 7.3 Hz, 1H), 2.70 (s, 3H), 2.51-2.45 (m, 1H), 2.43 (s, 3H), 1.90-1.33 (m, 6H).

Example 355: ((5R,9S)-2-Methyl-3-(3,4,5-trifluorophenyl)-4,5,6,7,8,9-hexahydro-2H-5,9-epiminocycloocta[c]pyrazol-10-yl)(7-methylpyrazolo[1,5-a]pyrimidin-6-yl)methanone

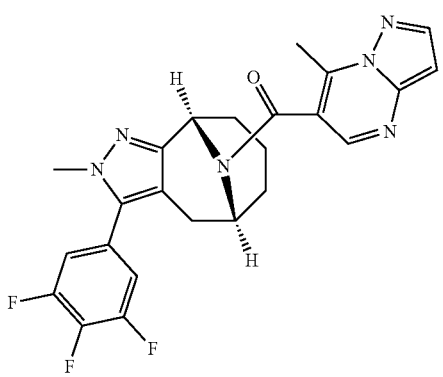 [SMILES: Cc1c(C(=O)N2[C@@H]3CCC[C@H]2c2nn(C)c(-c4cc(F)c(F)c(F)c4)c2C3)cnc2ccnn12]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 7-methylpyrazolo[1,5-a]pyrimidine-6-carboxylic acid instead of quinoline-6-carboxylic acid. MS (ESI): mass calcd. for $C_{24}H_{21}F_3N_6O$, 466.2; m/z found, 467.2 [M+H]$^+$. $^1$H NMR (500 MHz, DMSO-d$_6$): 8.43-8.34 (m, 1H), 8.30 (d, J=2.2 Hz, 1H), 7.67-7.52 (m, 2H), 6.80 (d, J=2.3 Hz, 1H), 5.79-5.74 (m, 1H), 4.10-4.04 (m, 1H), 3.80 (s, 3H), 3.21-3.02 (m, 1H), 2.82-2.71 (m, 3H), 2.57 (d, J=16.3 Hz, 1H), 2.01-1.30 (m, 6H).

Example 356: (5-Isopropyl-3-methylpyrazolo[1,5-a]pyrimidin-7-yl)((5R,9S)-2-methyl-3-(3,4,5-trifluorophenyl)-4,5,6,7,8,9-hexahydro-2H-5,9-epiminocycloocta[c]pyrazol-10-yl)methanone

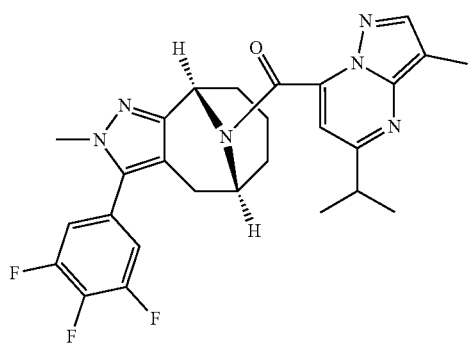 [SMILES: Cc1cnn2c(C(=O)N3[C@@H]4CCC[C@H]3c3nn(C)c(-c5cc(F)c(F)c(F)c5)c3C4)cc(C(C)C)nc12]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 5-isopropyl-3-methylpyrazolo[1,5-a]pyrimidine-7-carboxylic acid instead of quinoline-6-carboxylic acid. MS (ESI): mass calcd. for $C_{27}H_{27}F_3N_6O$, 508.2; m/z found, 509.2 [M+H]$^+$. $^1$H NMR (500 MHz, DMSO-d$_6$): 8.15 (s, 1H), 7.61-7.50 (m, 2H), 6.98 (s, 1H), 5.75-5.70 (m, 1H), 4.42-4.36 (m, 1H), 3.78 (s, 3H), 3.76-3.67 (m, 1H), 3.12-3.01 (m, 1H), 2.52-2.42 (m, 1H), 2.26 (s, 3H), 1.93-1.41 (m, 6H), 1.36 (d, J=7.1 Hz, 6H).

Example 357: ((5R,9S)-2-Methyl-3-(3,4,5-trifluorophenyl)-4,5,6,7,8,9-hexahydro-2H-5,9-epiminocycloocta[c]pyrazol-10-yl)(2,3,5-trimethylpyrazolo[1,5-a]pyrimidin-7-yl)methanone

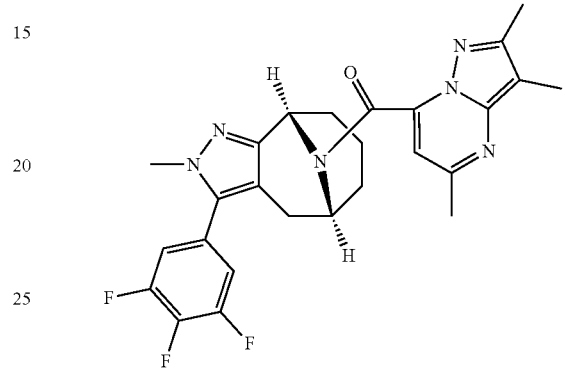

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 2,3,5-trimethylpyrazolo[1,5-a]pyrimidine-7-carboxylic acid instead of quinoline-6-carboxylic acid. MS (ESI): mass calcd. for $C_{26}H_{25}F_3N_6O$, 494.2; m/z found, 495.3 [M+H]$^+$. $^1$H NMR (500 MHz, DMSO-d$_6$): 7.63-7.54 (m, 2H), 6.73 (s, 1H), 5.77-5.69 (m, 1H), 3.79 (s, 3H), 3.68-3.62 (m, 1H), 2.90 (dd, J=16.3, 7.3 Hz, 1H), 2.55-2.45 (m, 3H), 2.40 (d, J=16.2 Hz, 1H), 2.33 (s, 3H), 2.16 (s, 3H), 1.97-1.67 (m, 3H), 1.59-1.30 (m, 3H).

Example 358: (7-Cyclopropyl-2-methylpyrazolo[1,5-a]pyrimidin-5-yl)((5R,9S)-2-methyl-3-(3,4,5-trifluorophenyl)-4,5,6,7,8,9-hexahydro-2H-5,9-epiminocycloocta[c]pyrazol-10-yl)methanone

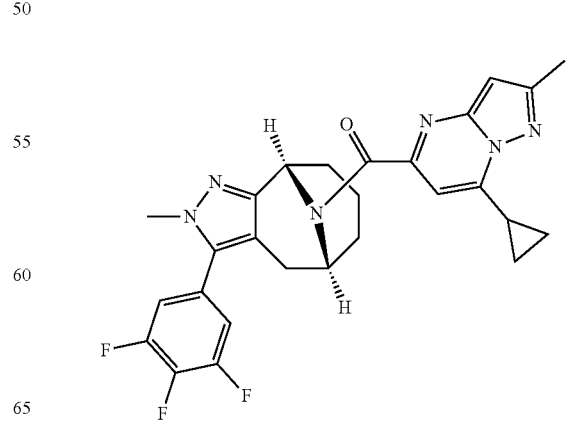

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 7-cyclopropyl-2-methylpyrazolo[1,5-a]pyrimidine-5-carboxylic acid instead of quinoline-6-carboxylic acid. MS (ESI): mass calcd. for $C_{27}H_{25}F_3N_6O$, 506.2; m/z found, 507.2 [M+H]$^+$. $^1$H NMR (500 MHz, DMSO-d$_6$): 7.62-7.52 (m, 2H), 6.89 (s, 1H), 6.34 (s, 1H), 5.77-5.72 (m, 1H), 3.79 (s, 3H), 3.78-3.65 (m, 1H), 2.92 (dd, J=16.7, 7.4 Hz, 1H), 2.46-2.35 (m, 1H), 2.36 (s, 3H), 2.21-2.01 (m, 1H), 1.96-1.33 (m, 6H), 1.09-0.97 (m, 4H).

Example 359: ((5R,9S)-2-Methyl-3-(3,4,5-trifluorophenyl)-4,5,6,7,8,9-hexahydro-2H-5,9-epiminocycloocta[c]pyrazol-10-yl)(2-methylpyrazolo[1,5-a]pyrimidin-3-yl)methanone

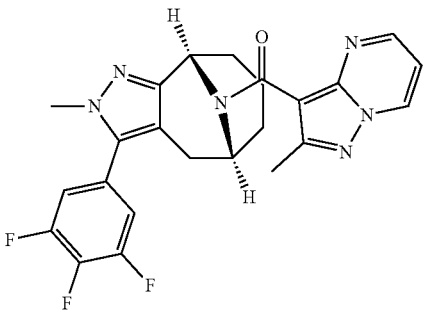 [SMILES: Cc1nn2cccnc2c1C(=O)N1[C@@H]2CCC[C@H]1c1nn(C)c(-c3cc(F)c(F)c(F)c3)c1C2]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 2-methylpyrazolo[1,5-a]pyrimidine-3-carboxylic acid instead of quinoline-6-carboxylic acid. MS (ESI): mass calcd. for $C_{24}H_{21}F_3N_6O$, 466.2; m/z found, 467.1 [M+H]$^+$. $^1$H NMR (400 MHz, DMSO-d$_6$) δ 9.18-9.00 (m, 1H), 8.66-8.50 (m, 1H), 7.68-7.49 (m, 2H), 7.19-6.91 (m, 1H), 5.88-5.00 (m, 1H), 4.94-4.13 (m, 1H), 3.91-3.67 (m, 3H), 3.15-2.94 (m, 1H), 2.47-2.30 (m, 4H), 1.92-1.34 (m, 6H).

Example 360: ((5R,9S)-2-Methyl-3-(3,4,5-trifluorophenyl)-4,5,6,7,8,9-hexahydro-2H-5,9-epiminocycloocta[c]pyrazol-10-yl)(2-methylpyrazolo[1,5-b]pyridazin-3-yl)methanone

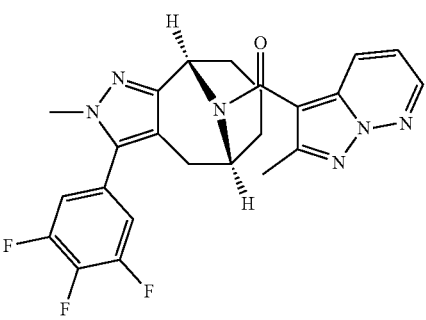 [SMILES: Cc1nn2ncccc2c1C(=O)N1[C@@H]2CCC[C@H]1c1nn(C)c(-c3cc(F)c(F)c(F)c3)c1C2]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 2-methylpyrazolo[1,5-b]pyridazine-3-carboxylic acid instead of quinoline-6-carboxylic acid. MS (ESI): mass calcd. for $C_{24}H_{21}F_3N_6O$, 466.2; m/z found, 467.1 [M+H]$^+$. $^1$H NMR (400 MHz, DMSO-d$_6$) δ 8.46 (dd, J=4.5, 1.9 Hz, 1H), 8.06 (s, 1H), 7.59 (dd, J=8.7, 6.6 Hz, 2H), 7.29 (dd, J=9.0, 4.5 Hz, 1H), 5.79-4.85 (m, 1H), 4.28-3.94 (m, 1H), 3.80 (s, 3H), 3.21-2.66 (m, 2H), 2.42 (s, 3H), 2.00-1.35 (m, 6H).

Example 361: ((5R,9S)-2-Methyl-3-(3,4,5-trifluorophenyl)-4,5,6,7,8,9-hexahydro-2H-5,9-epiminocycloocta[c]pyrazol-10-yl)(2-methylimidazo[1,2-a]pyrazin-8-yl)methanone

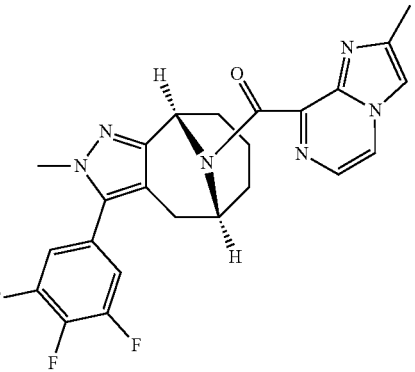

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 2-methylimidazo[1,2-a]pyrazine-8-carboxylic acid instead of quinoline-6-carboxylic acid. MS (ESI): mass calcd. for $C_{24}H_{21}F_3N_6O$, 466.2; m/z found, 467.2 [M+H]$^+$. $^1$H NMR (500 MHz, DMSO-d$_6$): 8.53 (d, J=4.5 Hz, 1H), 7.96-7.92 (m, 1H), 7.79 (d, J=4.5 Hz, 1H), 7.55-7.46 (m, 2H), 5.80-5.72 (m, 1H), 3.79 (s, 3H), 3.81-3.75 (m, 1H), 2.85 (dd, J=16.0, 7.4 Hz, 1H), 2.41-2.38 (m, 1H), 2.37 (s, 3H), 1.92-1.68 (m, 3H), 1.56-1.35 (m, 3H).

Example 362: ((5R,9S)-2-Methyl-3-(3,4,5-trifluoro-phenyl)-4,5,6,7,8,9-hexahydro-2H-5,9-epiminocycloocta[c]pyrazol-10-yl)(2,5,8-trimethylimidazo[1,2-a]pyrazin-3-yl)methanone

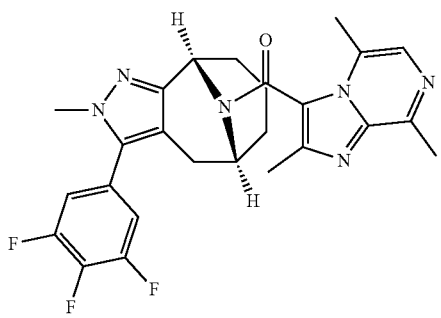 [SMILES: Cc1nc2c(C)ncc(C)n2c1C(=O)N1[C@@H]2CCC[C@H]1c1nn(C)c(-c3cc(F)c(F)c(F)c3)c1C2]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and potassium 2,5,8-trimethylimidazo[1,2-a]pyrazine-3-carboxylate (Intermediate 98) instead of quinoline-6-carboxylic acid. MS (ESI): mass calcd. for $C_{26}H_{25}F_3N_6O$, 494.2; m/z found, 495.1 [M+H]$^+$. $^1$H NMR (400 MHz, DMSO-d$_6$) δ 7.71-7.48 (m, 3H), 5.89-5.74 (m, 0.5H), 5.25-4.65 (m, 1H), 4.26-4.09 (m, 0.5H), 3.88-3.64 (m, 3H), 3.27-2.78 (m, 2H), 2.73-2.54 (m, 5H), 2.48-2.38 (m, 1H), 2.36-2.20 (m, 1H), 2.14-2.05 (m, 1H), 2.03-1.97 (m, 1H), 1.92-1.40 (m, 6H).

Example 363: ((5R,9S)-2-Methyl-3-(3,4,5-trifluoro-phenyl)-4,5,6,7,8,9-hexahydro-2H-5,9-epiminocycloocta[c]pyrazol-10-yl)(2-methylimidazo[1,2-b]pyridazin-3-yl)methanone

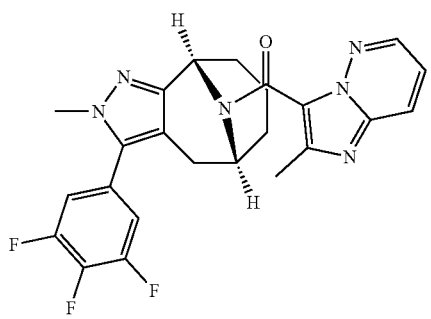 [SMILES: Cc1nc2cccnn2c1C(=O)N1[C@@H]2CCC[C@H]1c1nn(C)c(-c3cc(F)c(F)c(F)c3)c1C2]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 2-methylimidazo[1,2-b] pyridazine-3-carboxylic acid instead of quinoline-6-carboxylic acid. MS (ESI): mass calcd. for $C_{24}H_{21}F_3N_6O$, 466.2; m/z found, 467.1 [M+H]$^+$. $^1$H NMR (500 MHz, DMSO-d$_6$) δ 8.52 (d, J=4.4 Hz, 1H), 8.14-8.03 (m, 1H), 7.66-7.52 (m, 2H), 7.33-7.20 (m, 1H), 5.82-5.07 (m, 1H), 4.60-3.99 (m, 1H), 3.85-3.70 (m, 3H), 2.97-2.84 (m, 1H), 2.48-2.22 (m, 4H), 1.96-1.39 (m, 6H).

Example 364: (2,7-Dimethylimidazo[1,2-b]pyridazin-3-yl)((5R,9S)-2-methyl-3-(3,4,5-trifluoro-phenyl)-4,5,6,7,8,9-hexahydro-2H-5,9-epiminocycloocta[c]pyrazol-10-yl)methanone

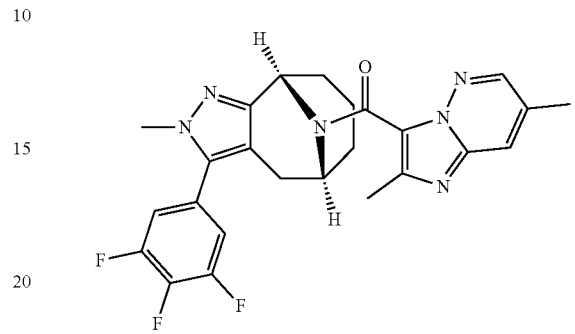

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and potassium 2,7-dimethylimidazo[1,2-b]pyridazine-3-carboxylate (Intermediate 97) instead of quinoline-6-carboxylic acid. MS (ESI): mass calcd. for $C_{25}H_{23}F_3N_6O$, 480.2; m/z found, 481.2 [M+H]$^+$. $^1$H NMR (400 MHz, DMSO-d$_6$) δ 8.41 (d, J=2.0 Hz, 1H), 7.87 (d, J=10.7 Hz, 1H), 7.65-7.50 (m, 2H), 5.85-5.70 (m, 1H), 5.16-4.49 (m, 1H), 3.82 (s, 3H), 3.74 (s, 1H), 3.20-3.13 (m, 1H), 2.42-2.33 (m, 5H), 2.31-2.21 (m, 1H), 1.95-1.39 (m, 6H).

Example 365: ((5R,9S)-2-Methyl-3-(3,4,5-trifluoro-phenyl)-4,5,6,7,8,9-hexahydro-2H-5,9-epiminocycloocta[c]pyrazol-10-yl)(3-methyl-3H-imidazo[4,5-b]pyridin-7-yl)methanone

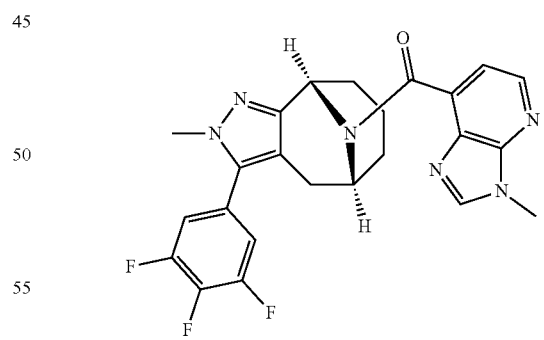

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 3-methyl-3H-imidazo[4,5-b]pyridine-7-carboxylic acid instead of quinoline-6-carboxylic acid. MS (ESI): mass calcd. for $C_{24}H_{21}F_3N_6O$, 466.2; m/z found, 467.2 [M+H]$^+$.

$^1$H NMR (500 MHz, DMSO-d$_6$): 8.45 (s, 1H), 8.43-8.37 (m, 1H), 7.55-7.49 (m, 2H), 7.21 (d, J=4.8 Hz, 1H), 5.84-5.76 (m, 1H), 3.84 (s, 3H), 3.79 (s, 3H), 3.77-3.72 (m, 1H), 2.88 (dd, J=16.1, 7.3 Hz, 1H), 2.34 (d, J=15.9 Hz, 1H), 1.95-1.65 (m, 3H), 1.55-1.29 (m, 3H).

Example 366: ((5R,9S)-2-Methyl-3-(3,4,5-trifluorophenyl)-4,5,6,7,8,9-hexahydro-2H-5,9-epiminocycloocta[c]pyrazol-10-yl)(3-methyl-3H-imidazo[4,5-b]pyridin-6-yl)methanone

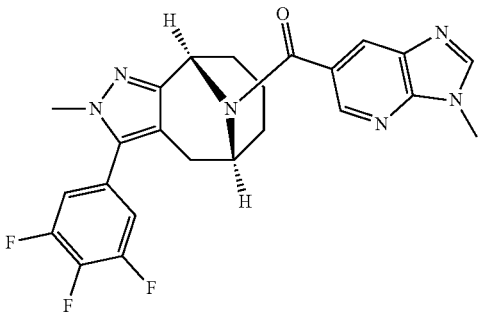 [SMILES: Cn1nc2c(c1-c1cc(F)c(F)c(F)c1)C[C@H]1CCC[C@@H]2N1C(=O)c1cnc2c(c1)ncn2C]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 3-methyl-3H-imidazo[4,5-b]pyridine-6-carboxylic acid instead of quinoline-6-carboxylic acid. MS (ESI): mass calcd. for C$_{24}$H$_{21}$F$_3$N$_6$O, 466.2; m/z found, 467.2 [M+H]$^+$. $^1$H NMR (500 MHz, DMSO-d$_6$): 8.51 (s, 1H), 8.44 (d, J=1.9 Hz, 1H), 8.13 (d, J=1.9 Hz, 1H), 7.65-7.54 (m, 2H), 5.74-5.67 (m, 1H), 4.11-4.03 (m, 1H), 3.85 (s, 3H), 3.79 (s, 3H), 3.09 (dd, J=16.2, 7.4 Hz, 1H), 2.39-2.32 (m, 1H), 2.01-1.32 (m, 6H).

Example 367: ((5R,9S)-2-Methyl-3-(3,4,5-trifluorophenyl)-4,5,6,7,8,9-hexahydro-2H-5,9-epiminocycloocta[c]pyrazol-10-yl)(7-methyl-7H-pyrrolo[2,3-d]pyrimidin-4-yl)methanone

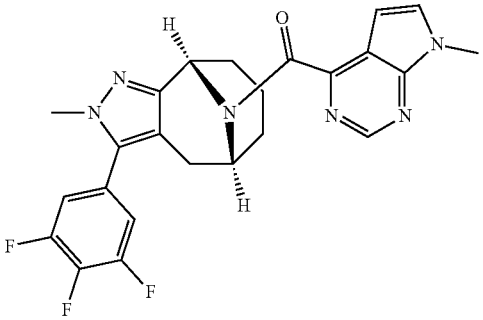 [SMILES: Cn1nc2c(c1-c1cc(F)c(F)c(F)c1)C[C@H]1CCC[C@@H]2N1C(=O)c1ncnc2c1ccn2C]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 7-methyl-7H-pyrrolo[2,3-d]pyrimidine-4-carboxylic acid instead of quinoline-6-carboxylic acid. MS (ESI): mass calcd. for C$_{24}$H$_{21}$F$_3$N$_6$O, 466.2; m/z found, 467.3 [M+H]$^+$. $^1$H NMR (500 MHz, DMSO-d$_6$): 8.79 (s, 1H), 7.67 (d, J=3.5 Hz, 1H), 7.56-7.52 (m, 2H), 6.54 (d, J=3.5 Hz, 1H), 5.80-5.76 (m, 1H), 4.06-4.00 (m, 1H), 3.82 (s, 3H), 3.79 (s, 3H), 2.87 (dd, J=16.1, 7.3 Hz, 1H), 2.43 (d, J=16.1 Hz, 1H), 1.95-1.35 (m, 6H).

Example 368: (1-Methyl-1H-pyrazolo[3,4-b]pyridin-4-yl)((5R,9S)-2-methyl-3-(3,4,5-trifluorophenyl)-4,5,6,7,8,9-hexahydro-2H-5,9-epiminocycloocta[c]pyrazol-10-yl)methanone

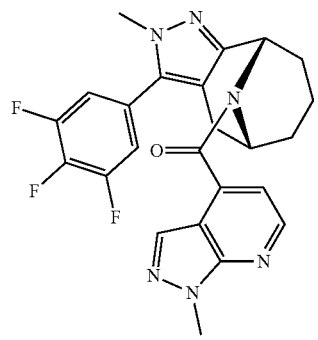 [SMILES: Cn1nc2c(c1-c1cc(F)c(F)c(F)c1)C[C@H]1CCC[C@@H]2N1C(=O)c1ccnc2c1cnn2C]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 1-methyl-1H-pyrazolo[3,4-b]pyridine-4-carboxylic acid (Intermediate 94) instead of quinoline-6-carboxylic acid. MS (ESI): mass calcd. for C$_{24}$H$_{21}$F$_3$N$_6$O, 466.2; m/z found, 467.2 [M+H]$^+$. $^1$H NMR (300 MHz, DMSO-d$_6$): 8.64 (d, J=4.8 Hz, 1H), 8.16 (s, 1H), 7.71-7.50 (m, 2H), 7.23 (d, J=4.6 Hz, 1H), 5.86-5.75 (m, 1H), 4.10 (s, 3H), 3.89-3.77 (m, 1H), 3.82 (s, 3H), 2.92 (dd, J=16.3, 7.3 Hz, 1H), 2.39 (d, J=17.0 Hz, 1H), 2.09-1.28 (m, 6H).

Example 369: (1-Methyl-1H-pyrazolo[3,4-d]pyrimidin-4-yl)((5R,9S)-2-methyl-3-(3,4,5-trifluorophenyl)-4,5,6,7,8,9-hexahydro-2H-5,9-epiminocycloocta[c]pyrazol-10-yl)methanone

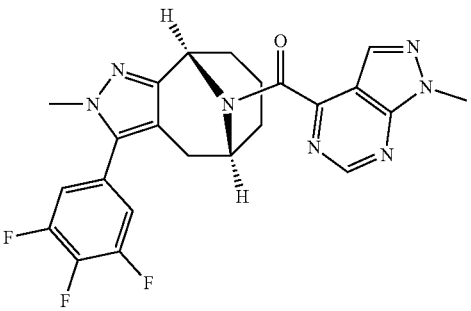 [SMILES: Cn1nc2c(c1-c1cc(F)c(F)c(F)c1)C[C@H]1CCC[C@@H]2N1C(=O)c1ncnc2c1cnn2C]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 1-methyl-1H-pyrazolo[3,4-d] pyrimidine-4-carboxylic acid instead of quinoline-6-carboxylic acid. MS (ESI): mass calcd. for $C_{23}H_{20}F_3N_7O$, 467.2; m/z found, 468.1 [M+H]$^+$. $^1$H NMR (400 MHz, DMSO-d$_6$) δ 9.08 (d, J=16.1 Hz, 1H), 8.35 (d, J=32.4 Hz, 1H), 7.69-7.49 (m, 2H), 5.81 (s, 1H), 5.22-4.96 (m, 1H), 4.14-4.05 (m, 3H), 3.77 (d, J=33.1 Hz, 3H), 3.23-3.09 (m, 1H), 3.03-2.89 (m, 1H), 2.00-1.41 (m, 6H).

Example 370: [1,2,4]Triazolo[4,3-a]pyridin-7-yl ((5R,9S)-2-methyl-3-(3,4,5-trifluorophenyl)-4,5,6,7,8,9-hexahydro-2H-5,9-epiminocycloocta[c]pyrazol-10-yl)methanone

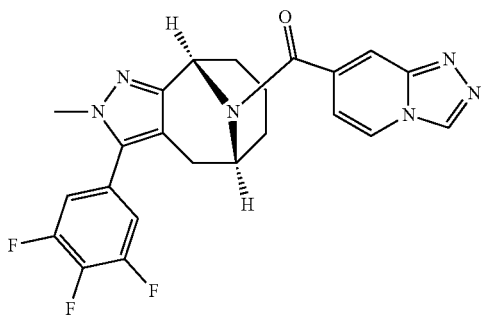 [SMILES: Cn1nc2c(c1-c1cc(F)c(F)c(F)c1)C[C@H]1CCC[C@@H]2N1C(=O)c1ccn2cnnc2c1]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and [1,2,4]triazolo[4,3-a]pyridine-7-carboxylic acid instead of quinoline-6-carboxylic acid. MS (ESI): mass calcd. for $C_{23}H_{19}F_3N_6O$, 452.2; m/z found, 453.1 [M+H]$^+$. $^1$H NMR (300 MHz, DMSO-d$_6$): 9.32 (s, 1H), 8.68-8.59 (m, 1H), 7.89-7.81 (m, 1H), 7.68-7.54 (m, 2H), 7.04-6.96 (m, 1H), 5.75-5.65 (m, 1H), 4.19-4.07 (m, 1H), 3.82 (s, 3H), 3.11 (dd, J=16.2, 7.4 Hz, 1H), 2.42 (d, J=16.9 Hz, 1H), 2.06-1.36 (m, 6H).

Example 371: ((5R,9S)-2-Methyl-3-(3,4,5-trifluorophenyl)-4,5,6,7,8,9-hexahydro-2H-5,9-epiminocycloocta[c]pyrazol-10-yl)(3-methylimidazo[1,5-a]pyrazin-1-yl)methanone

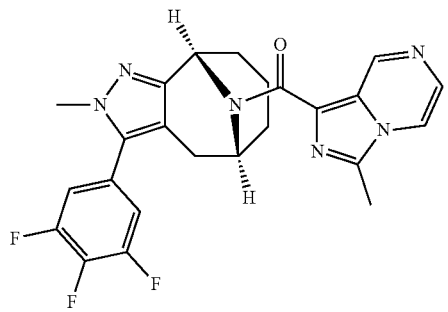 [SMILES: Cc1nc(C(=O)N2[C@@H]3CCC[C@H]2c2nn(C)c(-c4cc(F)c(F)c(F)c4)c2C3)c2cnccn12]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and sodium 3-methylimidazo[1,5-a]pyrazine-1-carboxylate (Intermediate 99) instead of quinoline-6-carboxylic acid. MS (ESI): mass calcd. for $C_{24}H_{21}F_3N_6O$, 466.2; m/z found, 467.1 [M+H]$^+$. $^1$H NMR (400 MHz, Methanol-d$_4$) δ 9.38 (s, 1H), 8.14 (s, 1H), 7.70 (d, J=5.1 Hz, 1H), 7.33 (t, J=7.3 Hz, 2H), 5.94 (s, 1H), 3.89-3.76 (m, 3H), 2.74 (d, J=12.1 Hz, 3H), 2.61 (t, J=15.8 Hz, 1H), 2.30-1.51 (m, 8H).

Example 372: ((5R,9S)-3-(3-Fluoro-5-methylphenyl)-2-methyl-4,5,6,7,8,9-hexahydro-2H-5,9-epiminocycloocta[c]pyrazol-10-yl)(quinolin-6-yl)methanone The title compound was prepared in a manner analogous to Example 1 using (5R,9S)-3-(3-fluoro-5-methylphenyl)-2-methyl-4,5,6,7,8,9-hexahydro-2H-5,9-epiminocycloocta[c]pyrazole (Intermediate 63) instead of racemic-(5R,9S)-2-methyl-3-phenyl-4,5,6,7,8,9-hexahydro-2H-5,9-epiminocycloocta[c]pyrazole (Intermediate 1) and quinoline-6-carboxylic acid instead of quinoline-6-carboxylic acid. MS (ESI): mass calcd. for $C_{27}H_{25}FN_4O$, 440.2; m/z found, 441.1 [M+H]$^+$. $^1$H NMR (500 MHz, DMSO-d$_6$) δ 9.02-8.93 (m, 1H), 8.48 (d, J=8.3 Hz, 1H), 8.15-8.04 (m, 2H), 7.83-7.68 (m, 1H), 7.65-7.52 (m, 1H), 7.25-7.04 (m, 3H), 5.82-5.01 (m, 1H), 4.91-3.99 (m, 1H), 3.86-3.66 (m, 3H), 3.14-3.00 (m, 1H), 2.48-2.31 (m, 4H), 2.07-1.36 (m, 6H).

Example 373: ((5R,9S)-2-Methyl-3-(3,4,5-trifluorophenyl)-4,5,6,7,8,9-hexahydro-2H-5,9-epiminocycloocta[c]pyrazol-10-yl)(4-methylquinolin-6-yl)methanone

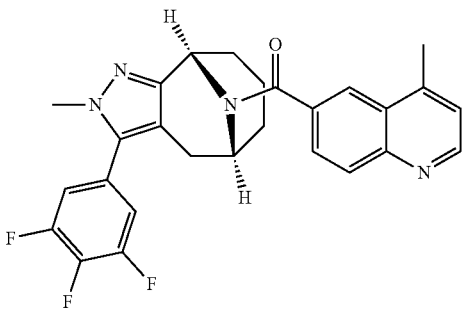 [SMILES: Cc1ccnc2ccc(C(=O)N3[C@@H]4CCC[C@H]3c3nn(C)c(-c5cc(F)c(F)c(F)c5)c3C4)cc12]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 4-methylquinoline-6-carboxylic acid instead of quinoline-6-carboxylic acid. MS (ESI): mass calcd. for $C_{27}H_{23}F_3N_4O$, 476.2; m/z found, 477.0 [M+H]$^+$. $^1$H NMR (400 MHz, DMSO-$d_6$) δ 8.82 (dd, J=8.0, 4.4 Hz, 1H), 8.16-8.02 (m, 2H), 7.82-7.66 (m, 1H), 7.66-7.39 (m, 3H), 5.83-4.82 (m, 1H), 4.17-4.01 (m, 1H), 3.88-3.63 (m, 3H), 3.15-2.98 (m, 1H), 2.76-2.65 (m, 3H), 2.47-2.37 (m, 1H), 2.06-1.42 (m, 6H).

Example 374: ((5R,9S)-3-(3,5-Difluorophenyl)-2-methyl-4,5,6,7,8,9-hexahydro-2H-5,9-epiminocycloocta[c]pyrazol-10-yl)(2-hydroxyquinolin-6-yl)methanone

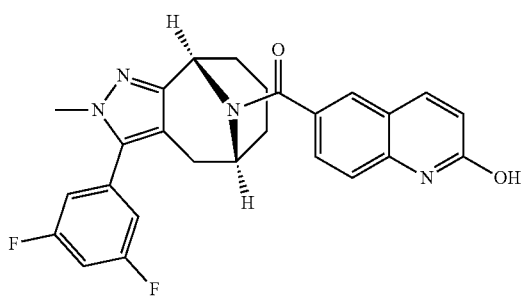 [SMILES: Cn1nc2c(c1-c1cc(F)cc(F)c1)C[C@H]1CCC[C@@H]2N1C(=O)c1ccc2nc(O)ccc2c1]

The title compound was prepared in a manner analogous to Example 1 using (5R,9S)-3-(3,5-difluorophenyl)-2-methyl-4,5,6,7,8,9-hexahydro-2H-5,9-epiminocycloocta[c]pyrazole (Intermediate 12) instead of racemic-(5R,9S)-2-methyl-3-phenyl-4,5,6,7,8,9-hexahydro-2H-5,9-epiminocycloocta[c]pyrazole (Intermediate 1) and 2-hydroxyquinoline-6-carboxylic acid instead of quinoline-6-carboxylic acid. MS (ESI): mass calcd. for $C_{26}H_{22}F_2N_4O_2$, 460.5; m/z found, 461.1 [M+H]$^+$. $^1$H NMR (500 MHz, DMSO-$d_6$) δ 11.99-11.80 (m, 1H), 8.01-7.93 (m, 1H), 7.77 (d, J=10.0 Hz, 1H), 7.54 (dd, J=25.0, 8.5 Hz, 1H), 7.39-7.27 (m, 4H), 6.55 (d, J=9.5 Hz, 1H), 5.75-5.61 (m, 1H), 5.05-4.78 (m, 1H), 3.89-3.70 (m, 3H), 3.19-3.04 (m, 1H), 2.49-2.43 (m, 1H), 2.04-1.40 (m, 6H).

Example 375: 6-((5R,9S)-3-(3,5-Difluorophenyl)-2-methyl-4,5,6,7,8,9-hexahydro-2H-5,9-epiminocycloocta[c]pyrazole-10-carbonyl) quinoline 1-oxide

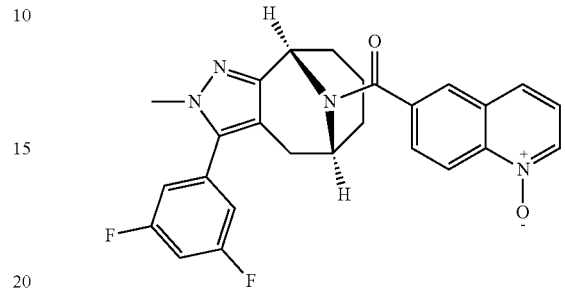

To an ice-cold solution of ((5R,9S)-3-(3,5-difluorophenyl)-2-methyl-4,5,6,7,8,9-hexahydro-2H-5,9-epiminocycloocta[c]pyrazol-10-yl)(quinolin-6-yl)methanone (Example 97, 150 mg, 0.34 mmol) in DCM (6.0 mL) was added meta-chloroperoxybenzoic acid (mCPBA or mCPBA) (87.4 mg, 0.51 mmol) portion wise, at 0° C. over a period of 10 minutes and the mixture was slowly warmed to rt. After stirring for 1 h, quenched the reaction mixture with saturated aqueous solution of NaHCO$_3$ and extracted with DCM (2×). The combined organics were washed with brine, dried over Na$_2$SO$_4$, filtered, and concentrated in vacuo. The crude product was purified by reverse-phase HPLC using a XBridge C18 column (5 μm, 100×4.6 mm), mobile phase of 10-100% ACN in 20 mM NH$_4$OH, to afford the title compound as white solid (111 mg, 71% yield). MS (ESI): mass calcd. for $C_{26}H_{22}F_2N_4O_2$, 460.5; m/z found, 461.1 [M+H]$^+$. $^1$H NMR (500 MHz, DMSO-$d_6$) δ 8.68-8.52 (m, 2H), 8.18 (dd, J=11.0, 1.7 Hz, 1H), 8.03 (dd, J=8.6, 4.5 Hz, 1H), 7.89-7.71 (m, 1H), 7.59-7.49 (m, 1H), 7.41-7.25 (m, 3H), 5.84-4.72 (m, 2H), 3.80 (d, J=48.8 Hz, 3H), 3.20-3.03 (m, 1H), 2.46 (d, J=16.2 Hz, 1H), 2.06-1.37 (m, 6H).

Example 376: ((5R,9S)-3-(3,5-Difluorophenyl)-2-methyl-4,5,6,7,8,9-hexahydro-2H-5,9-epiminocycloocta[c]pyrazol-10-yl)(quinolin-6-yl-4-t)methanone

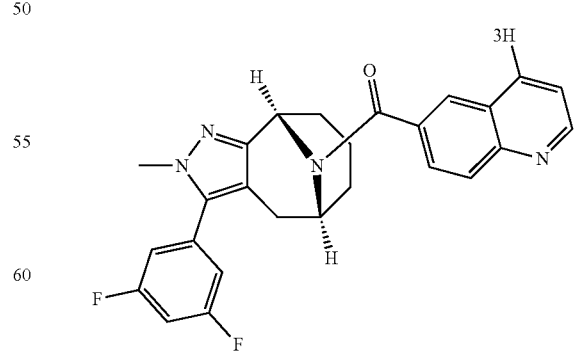

A 5 mL round bottom flask was charged with (4-bromoquinolin-6-yl)((5R,9S)-3-(3,5-difluorophenyl)-2-methyl-4,5,6,7,8,9-hexahydro-2H-5,9-epiminocycloocta[c]pyrazol- 10-yl)methanone (Example 101, 10 mg, 0.02 mmol), methanol (1.5 mL), and Pd/C (8 mg, 0.008 mmol). The mixture was stirred at rt for 2 h under 1 atm of tritium gas. The solvent was removed in vacuo and the residue was dissolved in ethanol and filtered. The labile tritium was removed by rotovap (3×), and the crude material was purified on an HPLC-C-18 column using (gradient A=water and B=ACN: A->100% B in 60 min, UV=254 nM, flow=6 mL/min). Product was assayed to have a specific activity=10.8 Ci/mmol and was packaged in EtOH (1 mCi/mL). MS (ESI): mass calcd. for $C_{26}H_{21}TF_2N_4O$, 446.2; m/z found, 446.9 [M+H]$^+$.

Example 377: ((5R,9S)-2-Methyl-3-(3,4,5-trifluorophenyl)-4,5,6,7,8,9-hexahydro-2H-5,9-epiminocycloocta[c]pyrazol-10-yl)(6-methylquinazolin-4-yl)methanone

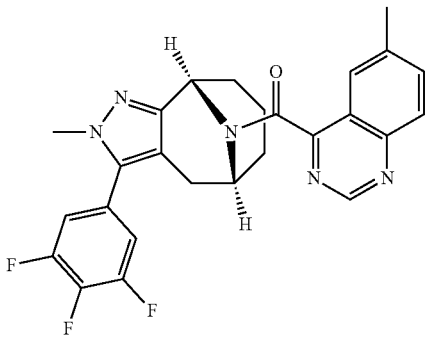 [SMILES: Cc1ccc2ncnc(C(=O)N3[C@@H]4CCC[C@H]3c3nn(C)c(-c5cc(F)c(F)c(F)c5)c3C4)c2c1]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 6-methylquinazoline-4-carboxylic acid instead of quinoline-6-carboxylic acid. MS (ESI): mass calcd. for $C_{26}H_{22}F_3N_5O$, 477.2; m/z found, 478.2 [M+H]$^+$. $^1$H NMR (500 MHz, DMSO-d$_6$) δ 9.26 (d, J=18.2 Hz, 1H), 8.04-7.90 (m, 2H), 7.70-7.54 (m, 3H), 5.97-4.30 (m, 3H), 3.77 (m, 2H), 2.87-2.60 (m, 1H), 2.52 (d, J=1.0 Hz, 2H), 2.48-2.44 (m, 2H), 2.09-1.40 (m, 6H).

Example 378: ((5R,9S)-2-Methyl-3-(3,4,5-trifluorophenyl)-4,5,6,7,8,9-hexahydro-2H-5,9-epiminocycloocta[c]pyrazol-10-yl)(quinoxalin-6-yl-2-d)methanone

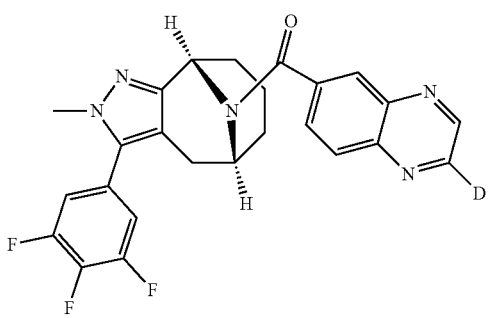 [SMILES: [2H]c1cnc2cc(C(=O)N3[C@@H]4CCC[C@H]3c3nn(C)c(-c5cc(F)c(F)c(F)c5)c3C4)ccc2n1]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and lithium quinoxaline-6-carboxylic-2-d acid (Intermediate 102) instead of quinoline-6-carboxylic acid. MS (ESI): mass calcd. for $C_{25}H_{19}DF_3N_5O$, 464.2; m/z found, 465.1 [M+H]$^+$. $^1$H NMR (500 MHz, DMSO-d$_6$) δ 9.09-8.99 (m, 1H), 8.20 (dd, J=14.5, 8.5 Hz, 1H), 8.09 (dd, J=42.7, 1.9 Hz, 1H), 7.94-7.74 (m, 1H), 7.66-7.55 (m, 2H), 5.83-4.74 (m, 1H), 4.16-4.03 (m, 1H), 3.86-3.66 (m, 3H), 3.18-3.04 (m, 1H), 2.45-2.36 (m, 1H), 2.01-1.35 (m, 6H).

Example 379: ((5R,9S)-2-Methyl-3-(3,4,5-trifluorophenyl)-4,5,6,7,8,9-hexahydro-2H-5,9-epiminocycloocta[c]pyrazol-10-yl)(quinoxalin-6-yl-2,3-d$_2$)methanone

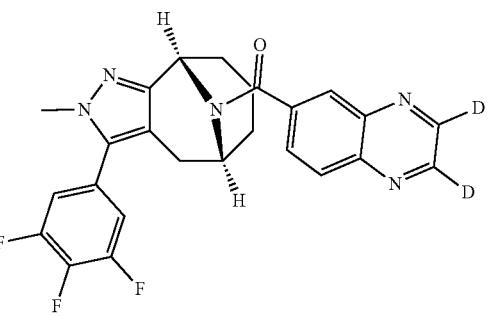

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and lithium quinoxaline-6-carboxylic-2,3-d$_2$ acid (Intermediate 101) instead of quinoline-6-carboxylic acid. MS (ESI): mass calcd. for $C_{25}H_{18}D_2F_3N_5O$, 465.2; m/z found, 466.0 [M+H]$^+$. $^1$H NMR (500 MHz, DMSO-d$_6$) δ 8.20 (dd, J=14.4, 8.5 Hz, 1H), 8.09 (dd, J=42.7, 1.9 Hz, 1H), 7.95-7.77 (m, 1H), 7.67-7.55 (m, 2H), 5.81-5.75 & 5.16-4.79 (m, 1H), 4.14-4.04 (m, 1H), 3.85-3.72 (m, 3H), 3.15-3.00 (m, 1H), 2.48-2.33 (m, 1H), 2.06-1.36 (m, 6H).

Example 380: ((5R,9S)-2-Methyl-3-(3,4,5-trifluoro-phenyl)-4,5,6,7,8,9-hexahydro-2H-5,9-epiminocycloocta[c]pyrazol-10-yl)(5-methyl-5,6,7,8-tetrahydroimidazo[1,2-a]pyridin-3-yl)methanone

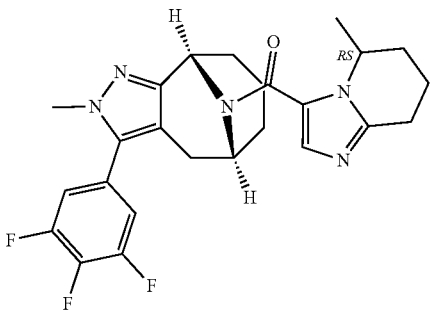 [SMILES: CC1CCCc2ncc(C(=O)N3[C@@H]4CCC[C@H]3c3nn(C)c(-c5cc(F)c(F)c(F)c5)c3C4)n21]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 5-methyl-5,6,7,8-tetrahydroimidazo[1,2-a]pyridine-3-carboxylic acid instead of quinoline-6-carboxylic acid. MS (ESI): mass calcd. for $C_{25}H_{26}F_3N_5O$, 469.2; m/z found, 470.1 [M+H]$^+$. $^1$H NMR (500 MHz, DMSO-d$_6$) δ 7.61 (d, J=54.4 Hz, 2H), 7.22 (s, 1H), 5.71-5.34 (m, 1H), 4.89-4.52 (m, 2H), 3.80 (s, 3H), 2.87-2.52 (m, 3H), 2.18-1.55 (m, 8H), 1.54-0.76 (m, 6H).

Example 381: ((5R,9S)-2-Methyl-3-(3,4,5-trifluoro-phenyl)-4,5,6,7,8,9-hexahydro-2H-5,9-epiminocycloocta[c]pyrazol-10-yl)(5,6,7,8-tetrahydroimidazo[1,2-a]pyridin-3-yl)methanone

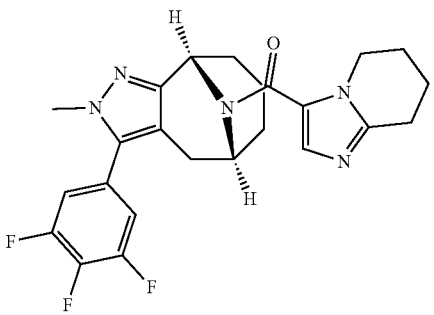 [SMILES: Cn1nc2c(c1-c1cc(F)c(F)c(F)c1)C[C@H]1CCC[C@@H]2N1C(=O)c1cnc2n1CCCC2]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and 5,6,7,8-tetrahydroimidazo[1,2-a] pyridine-3-carboxylic acid instead of quinoline-6-carboxylic acid. MS (ESI): mass calcd. for $C_{24}H_{24}F_3N_5O$, 455.2; m/z found, 456.1 [M+H]$^+$. $^1$H NMR (500 MHz, DMSO-d$_6$) δ 7.70-7.53 (m, 2H), 7.20 (s, 1H), 5.72-5.36 (m, 1H), 4.98-4.48 (m, 1H), 4.06 (dd, J=13.1, 6.9 Hz, 1H), 3.93 (s, 1H), 3.79 (s, 3H), 3.29-2.93 (m, 2H), 2.84-2.71 (m, 2H), 1.94-1.69 (m, 6H), 1.69-1.59 (m, 2H), 1.54-1.37 (m, 2H).

Example 382: ((5R,9S)-2-Methyl-3-(3,4,5-trifluoro-phenyl)-4,5,6,7,8,9-hexahydro-2H-5,9-epiminocycloocta[c]pyrazol-10-yl)(2,6,6-trimethyl-6,7-dihydro-4H-pyrazolo[5,1-c][1,4]oxazin-3-yl)methanone

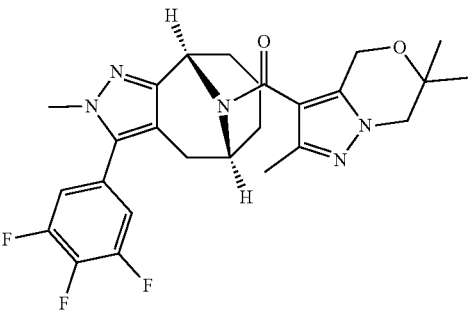 [SMILES: Cc1nn2c(c1C(=O)N1[C@@H]3CCC[C@H]1c1nn(C)c(-c4cc(F)c(F)c(F)c4)c1C3)COC(C)(C)C2]

The title compound was prepared in a manner analogous to Example 1 using (5R,9S)-2-methyl-3-(3,4,5-trifluorophenyl)-4,5,6,7,8,9-hexahydro-2H-5,9-epiminocycloocta[c]pyrazole (Intermediate 25) instead of racemic-(5R,9S)-2-methyl-3-phenyl-4,5,6,7,8,9-hexahydro-2H-5,9-epiminocycloocta[c]pyrazole (Intermediate 1) and potassium 2,6,6-trimethyl-6,7-dihydro-4H-pyrazolo[5,1-c][1,4]oxazine-3-carboxylate (Intermediate 103) instead of quinoline-6-carboxylic acid. MS (ESI): mass calcd. for $C_{26}H_{28}F_3N_5O_2$, 499.2; m/z found, 500.1 [M+H]$^+$. $^1$H NMR (400 MHz, DMSO-d$_6$) δ 7.64-7.48 (m, 2H), 5.78-5.16 (m, 1H), 4.67 (t, J=15.9 Hz, 2H), 3.88 (s, 2H), 3.79 (s, 3H), 3.26-2.62 (m, 2H), 2.47 (s, 1H), 2.12 (s, 3H), 1.74 (d, J=33.5 Hz, 3H), 1.63-1.31 (m, 3H), 1.26 (d, J=2.6 Hz, 6H).

Example 383: (3-Chlorophenyl)((5R,8S)-2-methyl-3-(3,4,5-trifluorophenyl)-2,4,5,6,7,8-hexahydro-5,8-epiminocyclohepta[c]pyrazol-9-yl)methanone

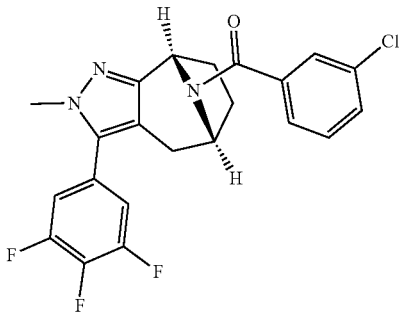 [SMILES: Cn1nc2c(c1-c1cc(F)c(F)c(F)c1)C[C@@H]1CC[C@H]2N1C(=O)c1cccc(Cl)c1]

The title compound was prepared in a manner analogous to Example 1, using (5R,8S)-2-methyl-3-(3,4,5-trifluorophenyl)-2,4,5,6,7,8-hexahydro-5,8-epiminocyclohepta[c]pyrazole 2,2,2-trifluoroacetate (Intermediate 105) instead of racemic-(5R,9S)-2-methyl-3-phenyl-4,5,6,7,8,9-hexahydro-2H-5,9-epiminocycloocta[c]pyrazole (Intermediate 1) and 3-chlorobenzoic acid instead of quinoline-6-carboxylic acid. MS (ESI): mass calcd. for $C_{22}H_{17}ClF_3N_3O$, 431.1; m/z found, 432.0 [M+H]⁺. ¹H NMR (400 MHz, CDCl₃) δ 7.49-7.27 (m, 4H), 7.02-6.88 (m, 2H), 5.84-3.96 (m, 2H), 3.78 (d, J=21.8 Hz, 3H), 3.39-3.23 (m, 1H), 2.44-2.14 (m, 3H), 2.14-1.91 (m, 1H), 1.76-1.59 (m, 1H).

Example 384: (3-Methoxyphenyl)((5R,8S)-2-methyl-3-(3,4,5-trifluorophenyl)-2,4,5,6,7,8-hexahydro-5,8-epiminocyclohepta[c]pyrazol-9-yl)methanone

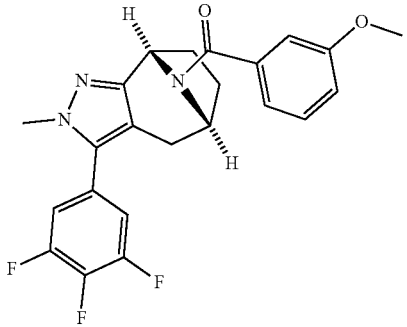 [SMILES: COc1cccc(C(=O)N2[C@@H]3CC[C@@H]2c2nn(C)c(-c4cc(F)c(F)c(F)c4)c2C3)c1]

The title compound was prepared in a manner analogous to Example 1, using (5R,8S)-2-methyl-3-(3,4,5-trifluorophenyl)-2,4,5,6,7,8-hexahydro-5,8-epiminocyclohepta[c]pyrazole 2,2,2-trifluoroacetate (Intermediate 105) instead of racemic-(5R,9S)-2-methyl-3-phenyl-4,5,6,7,8,9-hexahydro-2H-5,9-epiminocycloocta[c]pyrazole (Intermediate 1) and 3-methoxybenzoic acid instead of quinoline-6-carboxylic acid. MS (ESI): mass calcd. for C₂₃H₂₀F₃N₃O₂, 427.2; m/z found, 428.1 [M+H]⁺. ¹H NMR (400 MHz, CDCl₃) δ 7.39-7.27 (m, 1H), 7.15-6.91 (m, 5H), 5.80-5.13 (m, 1H), 5.13-4.35 (m, 1H), 3.88-3.74 (m, 6H), 3.36-2.84 (m, 1H), 2.45-2.11 (m, 3H), 2.11-1.93 (m, 1H), 1.74-1.59 (m, 1H).

Example 385: ((5R,8S)-3-(2,5-Difluorophenyl)-2-methyl-2,4,5,6,7,8-hexahydro-5,8-epiminocyclohepta[c]pyrazol-9-yl)(3-methoxyphenyl)methanone

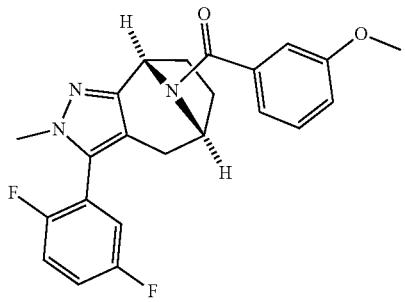 [SMILES: COc1cccc(C(=O)N2[C@@H]3CC[C@@H]2c2nn(C)c(-c4cc(F)ccc4F)c2C3)c1]

A microwave vial with (5R,8S)-9-(3-methoxybenzoyl)-2-methyl-2,4,5,6,7,8-hexahydro-5,8-epiminocyclohepta[c]pyrazol-3-yl trifluoromethanesulfonate (Intermediate 108) (20 mg, 0.045 mmol), 2,5-difluorophenylboronic acid (9 mg, 0.054 mmol), sodium carbonate (14 mg, 0.135 mmol) and XPhos Pd G2 (4 mg, 0.005 mmol) in 1,4-dioxane (2 mL) and water (0.5 mL) was purged with N₂ for 5 min. The resulting mixture was heated in a microwave reactor for 30 min at 110° C. The completed reaction was diluted with water and extracted into DCM (×3). The combined organics were dried over Na₂SO₄, filtered, concentrated under reduced pressure.

Purification (reverse-phase HPLC using a XBridge C18 column (5 mm, 100×4.6 mm), mobile phase of 10-100% ACN in 20 mM NH₄OH) afforded the title product (4.3 mg, 23%). MS (ESI): mass calcd. for C₂₃H₂₁F₂N₃O₂, 409.2; m/z found, 410.0 [M+H]⁺. ¹H NMR (500 MHz, CDCl₃) δ 7.36-7.28 (m, 1H), 7.23-6.90 (m, 6H), 5.87-5.11 (m, 1H), 5.10-4.30 (m, 1H), 3.81 (s, 3H), 3.79-3.67 (m, 3H), 3.31-2.83 (m, 1H), 2.45-2.11 (m, 2H), 2.11-1.96 (m, 1H), 1.78-1.64 (m, 1H), 1.36-1.25 (m, 1H).

Example 386: (3-Methoxyphenyl)((5R,8S)-2-methyl-3-(2,4,5-trifluorophenyl)-2,4,5,6,7,8-hexahydro-5,8-epiminocyclohepta[c]pyrazol-9-yl)methanone

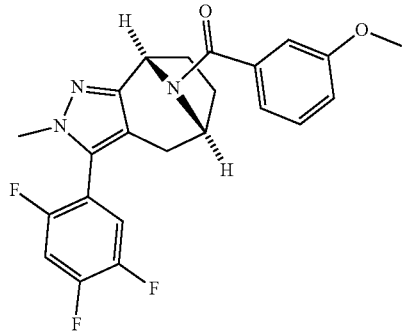 [SMILES: COc1cccc(C(=O)N2[C@@H]3CC[C@@H]2c2nn(C)c(-c4cc(F)c(F)cc4F)c2C3)c1]

The title compound was prepared in a manner analogous to Example 385 using 2,4,5-trifluorophenylbronic acid instead of 2,5-difluorophenylboronic acid. MS (ESI): mass calcd. for C₂₃H₂₀F₃N₃O₂, 427.2; m/z found, 428.1 [M+H]⁺. ¹H NMR (500 MHz, CDCl₃) δ 7.34-7.27 (m, 2H), 7.20-7.04 (m, 2H), 7.04-6.93 (m, 2H), 5.77-5.11 (m, 1H), 5.09-4.34 (m, 1H), 3.81 (s, 3H), 3.77-3.67 (m, 4H), 3.26-2.83 (m, 1H), 2.38-1.96 (m, 2H), 1.77-1.60 (m, 1H), 1.36-1.21 (m, 1H).

Example 387: ((5R,8S)-3-(2,3-Difluorophenyl)-2-methyl-2,4,5,6,7,8-hexahydro-5,8-epiminocyclohepta[c]pyrazol-9-yl)(3-methoxyphenyl)methanone

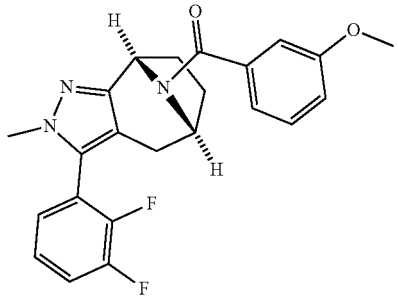

The title compound was prepared in a manner analogous to Example 385 using 2,3-difluorophenylbronic acid instead of 2,5-difluorophenylboronic acid. MS (ESI): mass calcd. for C₂₃H₂₁F₂N₃O₂, 409.2; m/z found, 410.1 [M+H]⁺. ¹H NMR (500 MHz, CDCl₃) δ 7.33-7.27 (m, 2H), 7.23-7.14 (m, 1H), 7.12-6.99 (m, 3H), 6.99-6.94 (m, 1H), 5.79-5.12 (m, 1H), 5.10-4.32 (m, 1H), 3.81 (s, 3H), 3.79-3.69 (m, 3H), 3.26-2.86 (m, 1H), 2.39-2.12 (m, 3H), 2.11-1.80 (m, 1H), 1.77-1.66 (m, 1H).

Example 388: (2,3-Dimethoxyphenyl)((5R,8S)-2-methyl-3-(3,4,5-trifluorophenyl)-2,4,5,6,7,8-hexahydro-5,8-epiminocyclohepta[c]pyrazol-9-yl)methanone

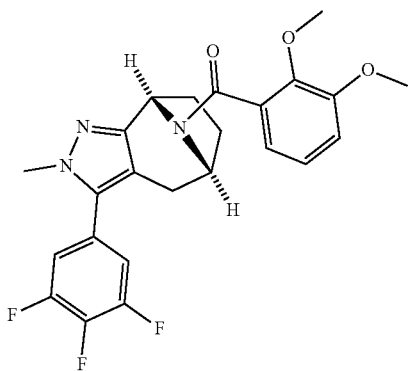 [SMILES: COc1cccc(C(=O)N2[C@@H]3CC[C@@H]2c2nn(C)c(-c4cc(F)c(F)c(F)c4)c2C3)c1OC]

The title compound was prepared in a manner analogous to Example 1, using (5R,8S)-2-methyl-3-(3,4,5-trifluorophenyl)-2,4,5,6,7,8-hexahydro-5,8-epiminocyclohepta[c]pyrazole 2,2,2-trifluoroacetate (Intermediate 105) instead of racemic-(5R,9S)-2-methyl-3-phenyl-4,5,6,7,8,9-hexahydro-2H-5,9-epiminocycloocta[c]pyrazole (Intermediate 1) and 2,3-dimethoxybenzoic acid instead of quinoline-6-carboxylic acid. MS (ESI): mass calcd. for $C_{24}H_{22}F_3N_3O_3$, 457.2; m/z found, 458.1 [M+H]$^+$. $^1$H NMR (600 MHz, CDCl$_3$) δ 7.11-7.01 (m, 1H), 6.99-6.85 (m, 3H), 6.77 (s, 1H), 5.80-5.13 (m, 1H), 4.73-4.09 (m, 1H), 3.94-3.82 (m, 6H), 3.82-3.71 (m, 3H), 3.33-3.23 (m, 1H), 2.39-2.13 (m, 3H), 2.09-1.89 (m, 1H), 1.70-1.60 (m, 1H).

Example 389: (2-Fluoro-3-methoxyphenyl)((5R,8S)-2-methyl-3-(3,4,5-trifluorophenyl)-2,4,5,6,7,8-hexahydro-5,8-epiminocyclohepta[c]pyrazol-9-yl)methanone

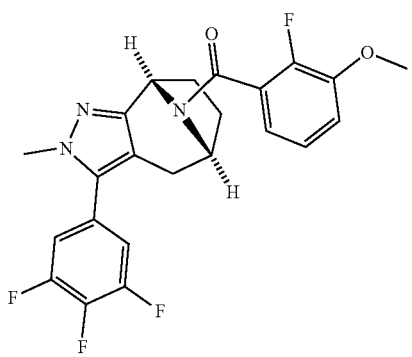 [SMILES: COc1cccc(C(=O)N2[C@@H]3CC[C@@H]2c2nn(C)c(-c4cc(F)c(F)c(F)c4)c2C3)c1F]

The title compound was prepared in a manner analogous to Example 1, using (5R,8S)-2-methyl-3-(3,4,5-trifluorophenyl)-2,4,5,6,7,8-hexahydro-5,8-epiminocyclohepta[c]pyrazole 2,2,2-trifluoroacetate (Intermediate 105) instead of racemic-(5R,9S)-2-methyl-3-phenyl-4,5,6,7,8,9-hexahydro-2H-5,9-epiminocycloocta[c]pyrazole (Intermediate 1) and 2-fluoro-3-methoxybenzoic acid instead of quinoline-6-carboxylic acid. MS (ESI): mass calcd. for $C_{23}H_{19}F_4N_3O_2$, 445.1; m/z found, 446.0 [M+H]$^+$. $^1$H NMR (600 MHz, CDCl$_3$) δ 7.15-7.06 (m, 1H), 7.04-6.86 (m, 4H), 5.80-5.07 (m, 1H), 4.82-4.17 (m, 1H), 3.95-3.87 (m, 3H), 3.83-3.70 (m, 3H), 3.34-2.80 (m, 1H), 2.40-2.21 (m, 3H), 2.08-1.95 (m, 1H), 1.69-1.60 (m, 1H).

Example 390: (2-Chloro-3-methoxyphenyl)((5R,8S)-2-methyl-3-(3,4,5-trifluorophenyl)-2,4,5,6,7,8-hexahydro-5,8-epiminocyclohepta[c]pyrazol-9-yl)methanone

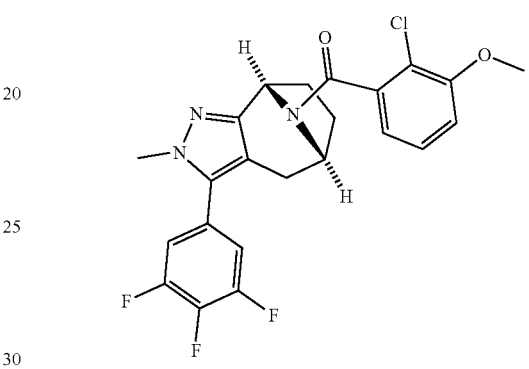

The title compound was prepared in a manner analogous to Example 1, using (5R,8S)-2-methyl-3-(3,4,5-trifluorophenyl)-2,4,5,6,7,8-hexahydro-5,8-epiminocyclohepta[c]pyrazole 2,2,2-trifluoroacetate (Intermediate 105) instead of racemic-(5R,9S)-2-methyl-3-phenyl-4,5,6,7,8,9-hexahydro-2H-5,9-epiminocycloocta[c]pyrazole (Intermediate 1) and 2-chloro-3-methoxybenzoic acid instead of quinoline-6-carboxylic acid. MS (ESI): mass calcd. for $C_{23}H_{19}ClF_3N_3O_2$, 461.1; m/z found, 462.0 [M+H]$^+$. $^1$H NMR (400 MHz, CDCl$_3$) δ 7.37-6.67 (m, 5H), 5.85-5.06 (m, 1H), 4.67-3.84 (m, 4H), 3.77 (d, J=23.6 Hz, 3H), 3.43-2.60 (m, 1H), 2.45-2.12 (m, 1H), 2.12-1.90 (m, 1H), 1.60 (s, 3H).

Example 391: (6-Methoxypyridin-2-yl)((5R,8S)-2-methyl-3-(3,4,5-trifluorophenyl)-2,4,5,6,7,8-hexahydro-5,8-epiminocyclohepta[c]pyrazol-9-yl)methanone

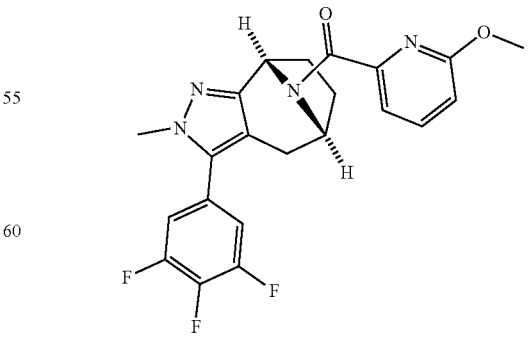

The title compound was prepared in a manner analogous to Example 1, using (5R,8S)-2-methyl-3-(3,4,5-trifluorophenyl)-2,4,5,6,7,8-hexahydro-5,8-epiminocyclohepta[c]pyrazole 2,2,2-trifluoroacetate (Intermediate 105) instead of racemic-(5R,9S)-2-methyl-3-phenyl-4,5,6,7,8,9-hexahydro-2H-5,9-epiminocycloocta[c]pyrazole (Intermediate 1) and 6-methoxypyridine-2-carboxylic acid instead of quinoline-6-carboxylic acid. MS (ESI): mass calcd. for $C_{22}H_{19}F_3N_4O_2$, 428.1; m/z found, 429.1 $[M+H]^+$. $^1$H NMR (600 MHz, $CDCl_3$) δ 7.70-7.63 (m, 1H), 7.56-7.45 (m, 1H), 7.00-6.91 (m, 2H), 6.86-6.80 (m, 1H), 6.16-5.73 (m, 1H), 5.42-5.14 (m, 1H), 4.03-3.92 (m, 3H), 3.83-3.71 (m, 3H), 3.36-3.22 (m, 1H), 2.44-2.28 (m, 3H), 2.28-1.96 (m, 1H), 1.79-1.61 (m, 1H).

Example 392: (1,5-Dimethyl-1H-pyrazol-4-yl)((5R,8S)-2-methyl-3-(3,4,5-trifluorophenyl)-2,4,5,6,7,8-hexahydro-5,8-epiminocyclohepta[c]pyrazol-9-yl)methanone

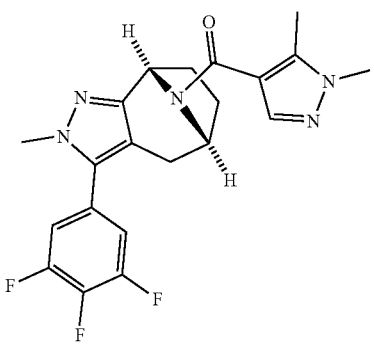 [SMILES: Cc1c(C(=O)N2[C@@H]3CC[C@@H]2c2nn(C)c(-c4cc(F)c(F)c(F)c4)c2C3)cnn1C]

The title compound was prepared in a manner analogous to Example 1, using (5R,8S)-2-methyl-3-(3,4,5-trifluorophenyl)-2,4,5,6,7,8-hexahydro-5,8-epiminocyclohepta[c]pyrazole 2,2,2-trifluoroacetate (Intermediate 105) instead of racemic-(5R,9S)-2-methyl-3-phenyl-4,5,6,7,8,9-hexahydro-2H-5,9-epiminocycloocta[c]pyrazole (Intermediate 1) and 1,5-dimethyl-1H-pyrazole-4-carboxylic acid instead of quinoline-6-carboxylic acid. MS (ESI): mass calcd. for $C_{21}H_{20}F_3N_5O$, 415.2; m/z found, 416.1 $[M+H]^+$. $^1$H NMR (400 MHz, $CDCl_3$) δ 7.54 (s, 1H), 6.97 (dd, J=7.7, 6.3 Hz, 2H), 5.18 (d, J=55.1 Hz, 2H), 3.79 (s, 3H), 3.78 (s, 3H), 3.17 (s, 1H), 2.42 (s, 3H), 2.38-2.12 (m, 3H), 2.03 (t, J=10.6 Hz, 1H), 1.67 (d, J=13.4 Hz, 1H).

Example 393: (5-Cyclopropyl-1-methyl-1H-pyrazol-4-yl)((5R,8S)-3-(3-fluoro-5-methylphenyl)-2-methyl-2,4,5,6,7,8-hexahydro-5,8-epiminocyclohepta[c]pyrazol-9-yl)methanone

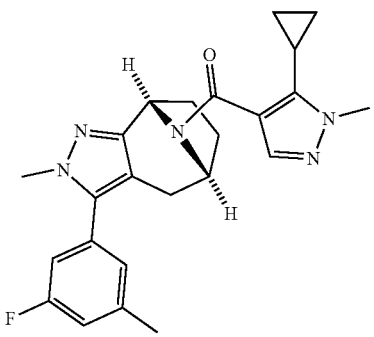 [SMILES: Cc1cc(F)cc(-c2c3c(nn2C)[C@H]2CC[C@H](C3)N2C(=O)c2cnn(C)c2C2CC2)c1]

The title compound was prepared in a manner analogous to Example 385 using (5R,8S)-9-(5-cyclopropyl-1-methyl-1H-pyrazole-4-carbonyl)-2-methyl-2,4,5,6,7,8-hexahydro-5,8-epiminocyclohepta[c]pyrazol-3-yl trifluoromethanesulfonate (Intermediate 109) instead of (5R,8S)-9-(3-methoxybenzoyl)-2-methyl-2,4,5,6,7,8-hexahydro-5,8-epiminocyclohepta[c]pyrazol-3-yl trifluoromethanesulfonate (Intermediate 108) and (3-fluoro-5-methylphenyl)boronic acid instead of 2,5-difluorophenylboronic acid. MS (ESI): mass calcd. for $C_{24}H_{26}FN_5O$, 419.2; m/z found, 420.1 $[M+H]^+$. $^1$H NMR (400 MHz, $CDCl_3$) δ 7.45 (s, 1H), 6.97-6.87 (m, 2H), 6.83 (d, J=9.2 Hz, 1H), 5.75-5.04 (m, 1H), 5.04-4.34 (m, 1H), 3.88 (s, 3H), 3.76 (s, 3H), 3.31 (d, J=15.7 Hz, 1H), 2.41 (s, 3H), 2.38-1.93 (m, 4H), 1.83-1.60 (m, 2H), 0.94 (d, J=38.0 Hz, 1H), 0.69 (s, 1H), 0.52 (s, 2H).

Example 394: (5-Cyclopropyl-1-methyl-1H-pyrazol-4-yl)((5R,8S)-2-methyl-3-phenyl-2,4,5,6,7,8-hexahydro-5,8-epiminocyclohepta[c]pyrazol-9-yl)methanone

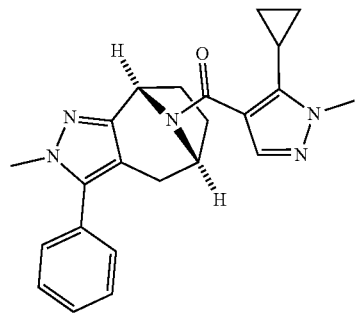

The title compound was prepared in a manner analogous to Example 1, using (5R,8S)-2-methyl-3-phenyl-2,4,5,6,7,8-hexahydro-5,8-epiminocyclohepta[c]pyrazole 2,2,2-trifluoroacetate (Intermediate 106) instead of racemic-(5R,9S)-2-methyl-3-phenyl-4,5,6,7,8,9-hexahydro-2H-5,9-epiminocycloocta[c]pyrazole (Intermediate 1) and 5-cyclopropyl-1-methyl-1H-pyrazole-4-carboxylic acid instead of quinoline-6-carboxylic acid. MS (ESI): mass calcd. for $C_{23}H_{25}N_5O$, 387.2; m/z found, 388.2 $[M+H]^+$. $^1$H NMR (400 MHz, $CDCl_3$) δ 7.57-7.38 (m, 4H), 7.32 (d, J=7.1 Hz, 2H), 5.08 (s, 1H), 5.03-4.36 (m, 1H), 3.98-3.82 (m, 3H), 3.77 (d, J=5.3 Hz, 3H), 3.45-2.83 (m, 1H), 2.47-1.93 (m, 3H), 1.50-1.14 (m, 3H), 1.05-0.43 (m, 4H).

Example 395: (5-Cyclopropyl-1-methyl-1H-pyrazol-4-yl)((5R,8S)-3-(3,4-difluorophenyl)-2-methyl-2,4,5,6,7,8-hexahydro-5,8-epiminocyclohepta[c]pyrazol-9-yl)methanone

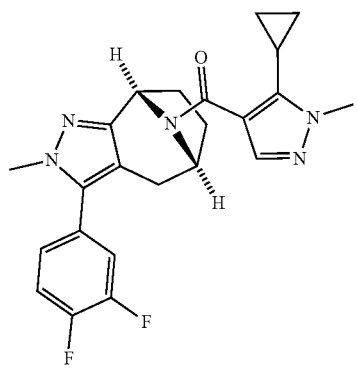

The title compound was prepared in a manner analogous to Example 385 using (5R,8S)-9-(5-cyclopropyl-1-methyl-1H-pyrazole-4-carbonyl)-2-methyl-2,4,5,6,7,8-hexahydro-5,8-epiminocyclohepta[c]pyrazol-3-yl trifluoromethanesulfonate (Intermediate 109) instead of (5R,8S)-9-(3-methoxybenzoyl)-2-methyl-2,4,5,6,7,8-hexahydro-5,8-epiminocyclohepta[c]pyrazol-3-yl trifluoromethanesulfonate (Intermediate 108) and 3,4-difluorophenylboronic acid instead of 2,5-difluorophenylboronic acid. MS (ESI): mass calcd. for $C_{23}H_{23}F_2N_5O$, 423.2; m/z found, 424.0 [M+H]$^+$. $^1$H NMR (400 MHz, CDCl$_3$) δ 7.45 (s, 1H), 7.32-7.21 (m, 1H), 7.13 (d, J=9.5 Hz, 1H), 7.06 (s, 1H), 5.08 (s, 1H), 4.71 (d, J=222.4 Hz, 1H), 3.88 (s, 3H), 3.76 (d, J=10.9 Hz, 3H), 3.42-2.79 (m, 1H), 2.43-1.91 (m, 5H), 1.87-1.62 (m, 1H), 0.90 (s, 1H), 0.71 (s, 1H), 0.52 (s, 2H).

Example 396: (5-Cyclopropyl-1-methyl-1H-pyrazol-4-yl)((5R,8S)-3-(2,4-difluorophenyl)-2-methyl-2,4,5,6,7,8-hexahydro-5,8-epiminocyclohepta[c]pyrazol-9-yl)methanone

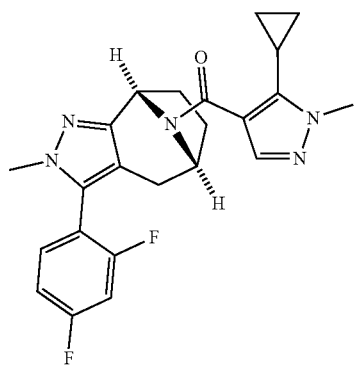

The title compound was prepared in a manner analogous to Example 385 using (5R,8S)-9-(5-cyclopropyl-1-methyl-1H-pyrazole-4-carbonyl)-2-methyl-2,4,5,6,7,8-hexahydro-5,8-epiminocyclohepta[c]pyrazol-3-yl trifluoromethanesulfonate (Intermediate 109) instead of (5R,8S)-9-(3-methoxybenzoyl)-2-methyl-2,4,5,6,7,8-hexahydro-5,8-epiminocyclohepta[c]pyrazol-3-yl trifluoromethanesulfonate (Intermediate 108) and 2,4-difluorophenylboronic acid instead of 2,5-difluorophenylboronic acid. MS (ESI): mass calcd. for $C_{23}H_{23}F_2N_5O$, 423.2; m/z found, 424.0 [M+H]$^+$. $^1$H NMR (400 MHz, CDCl$_3$) δ 7.45 (s, 1H), 7.26-7.20 (m, 1H), 6.98 (q, J=10.9, 9.9 Hz, 2H), 5.07 (s, 1H), 4.98 (s, 1H), 3.87 (s, 3H), 3.67 (s, 3H), 3.32-1.93 (m, 5H), 1.80-1.63 (m, 2H), 1.08-0.36 (m, 4H).

Example 397: (5-Cyclopropyl-1-methyl-1H-pyrazol-4-yl)((5R,8S)-3-(3,5-difluorophenyl)-2-methyl-2,4,5,6,7,8-hexahydro-5,8-epiminocyclohepta[c]pyrazol-9-yl)methanone

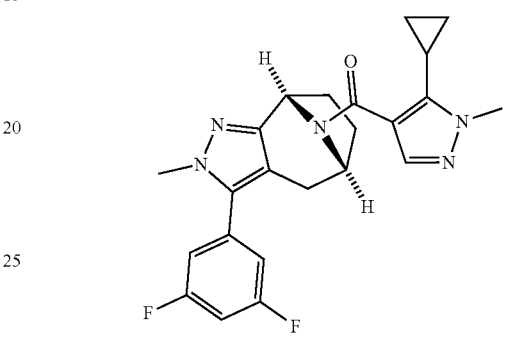

The title compound was prepared in a manner analogous to Example 385 using (5R,8S)-9-(5-cyclopropyl-1-methyl-1H-pyrazole-4-carbonyl)-2-methyl-2,4,5,6,7,8-hexahydro-5,8-epiminocyclohepta[c]pyrazol-3-yl trifluoromethanesulfonate (Intermediate 109) instead of (5R,8S)-9-(3-methoxybenzoyl)-2-methyl-2,4,5,6,7,8-hexahydro-5,8-epiminocyclohepta[c]pyrazol-3-yl trifluoromethanesulfonate (Intermediate 108) and 3,5-difluorophenylboronic acid instead of 2,5-difluorophenylboronic acid. MS (ESI): mass calcd. for $C_{23}H_{23}F_2N_5O$, 423.2; m/z found, 424.0 [M+H]$^+$. $^1$H NMR (400 MHz, CDCl$_3$) δ 7.45 (s, 1H), 6.85 (d, J=7.7 Hz, 3H), 5.04 (d, J=35.4 Hz, 1H), 3.88 (s, 3H), 3.78 (s, 3H), 3.31 (d, J=16.1 Hz, 1H), 2.42-2.11 (m, 2H), 2.04 (d, J=23.5 Hz, 1H), 1.81-1.60 (m, 2H), 1.54 (s, 2H), 0.88 (d, J=18.0 Hz, 1H), 0.70 (s, 1H), 0.52 (s, 2H).

Example 398: (5-Cyclopropyl-1-methyl-1H-pyrazol-4-yl)((5R,8S)-2-methyl-3-(2,3,4-trifluorophenyl)-2,4,5,6,7,8-hexahydro-5,8-epiminocyclohepta[c]pyrazol-9-yl)methanone

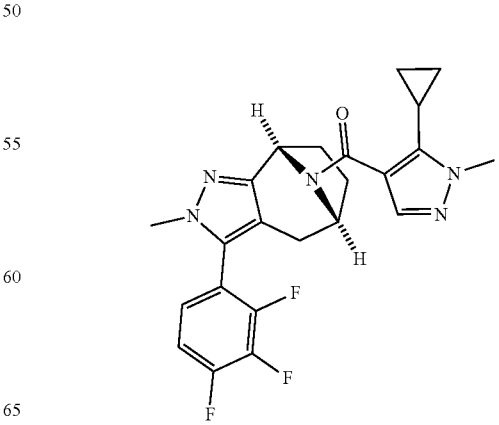

The title compound was prepared in a manner analogous to Example 385 using (5R,8S)-9-(5-cyclopropyl-1-methyl-1H-pyrazole-4-carbonyl)-2-methyl-2,4,5,6,7,8-hexahydro-5,8-epiminocyclohepta[c]pyrazol-3-yl trifluoromethanesulfonate (Intermediate 109) instead of (5R,8S)-9-(3-methoxybenzoyl)-2-methyl-2,4,5,6,7,8-hexahydro-5,8-epiminocyclohepta[c]pyrazol-3-yl trifluoromethanesulfonate (Intermediate 108) and 2,3,4-trifluorophenylboronic acid instead of 2,5-difluorophenylboronic acid. MS (ESI): mass calcd. for $C_{23}H_{22}F_3N_5O$, 441.2; m/z found, 442.0 [M+H]$^+$. $^1$H NMR (400 MHz, CDCl$_3$) δ 7.45 (s, 1H), 7.08 (t, J=8.1 Hz, 1H), 7.05-6.96 (m, 1H), 5.38 (d, J=243.7 Hz, 1H), 5.05-4.35 (m, 1H), 3.88 (s, 3H), 3.69 (s, 3H), 3.21 (d, J=15.8 Hz, 1H), 2.41-2.11 (m, 3H), 2.04 (d, J=11.4 Hz, 1H), 1.80-1.61 (m, 2H), 0.93 (d, J=37.3 Hz, 1H), 0.65 (s, 1H), 0.49 (d, J=20.4 Hz, 2H).

Example 399: (5-Cyclopropyl-1-methyl-1H-pyrazol-4-yl)((5R,8S)-2-methyl-3-(3,4,5-trifluorophenyl)-2,4,5,6,7,8-hexahydro-5,8-epiminocyclohepta[c]pyrazol-9-yl)methanone

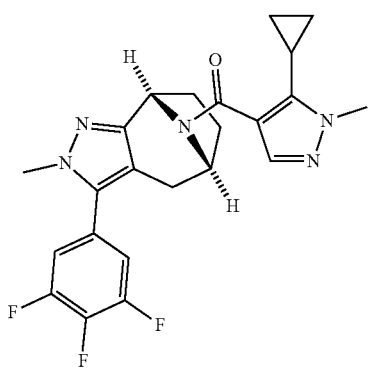

The title compound was prepared in a manner analogous to Example 1, using (5R,8S)-2-methyl-3-(3,4,5-trifluorophenyl)-2,4,5,6,7,8-hexahydro-5,8-epiminocyclohepta[c]pyrazole 2,2,2-trifluoroacetate (Intermediate 105) instead of racemic-(5R,9S)-2-methyl-3-phenyl-4,5,6,7,8,9-hexahydro-2H-5,9-epiminocycloocta[c]pyrazole (Intermediate 1) and 5-cyclopropyl-1-methyl-1H-pyrazole-4-carboxylic acid instead of quinoline-6-carboxylic acid. MS (ESI): mass calcd. for $C_{23}H_{22}F_3N_5O$, 441.2; m/z found, 442.2 [M+H]$^+$. $^1$H NMR (600 MHz, CDCl$_3$) δ 7.74-7.50 (m, 1H), 7.49-7.41 (m, 2H), 7.00-6.90 (m, 3H), 5.04 (d, J=50.6 Hz, 1H), 4.28-4.13 (m, 1H), 3.88 (s, 3H), 3.76 (s, 3H), 3.28 (d, J=15.3 Hz, 1H), 2.32 (d, J=16.9 Hz, 2H), 2.24-2.13 (m, 1H), 2.01 (d, J=11.9 Hz, 1H), 1.80-1.63 (m, 3H).

Example 400: ((5R,8S)-2-Methyl-3-(3,4,5-trifluorophenyl)-2,4,5,6,7,8-hexahydro-5,8-epiminocyclohepta[c]pyrazol-9-yl)(2-methyl-4-(trifluoromethyl)-1H-imidazol-5-yl)methanone

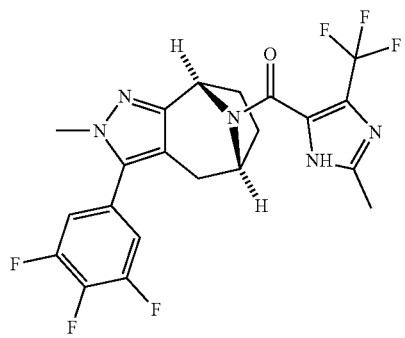 [SMILES: Cc1nc(C(F)(F)F)c(C(=O)N2[C@@H]3CC[C@H]2c2nn(C)c(-c4cc(F)c(F)c(F)c4)c2C3)[nH]1]

The title compound was prepared in a manner analogous to Example 1, using (5R,8S)-2-methyl-3-(3,4,5-trifluorophenyl)-2,4,5,6,7,8-hexahydro-5,8-epiminocyclohepta[c]pyrazole 2,2,2-trifluoroacetate (Intermediate 105) instead of racemic-(5R,9S)-2-methyl-3-phenyl-4,5,6,7,8,9-hexahydro-2H-5,9-epiminocycloocta[c]pyrazole (Intermediate 1) and 2-methyl-4-(trifluoromethyl)-1H-imidazole-5-carboxylic acid instead of quinoline-6-carboxylic acid. MS (ESI): mass calcd. for $C_{21}H_{17}F_6N_5O$, 469.1; m/z found, 470.0 [M+H]$^+$. $^1$H NMR (500 MHz, CDCl$_3$) δ 6.99-6.87 (m, 2H), 5.76-5.03 (m, 1H), 4.70-4.09 (m, 1H), 3.88-3.68 (m, 3H), 3.54-3.25 (m, 1H), 2.47-1.93 (m, 7H), 1.76-1.62 (m, 1H).

Example 401: (1H-Indol-7-yl)((5R,8S)-2-methyl-3-(3,4,5-trifluorophenyl)-2,4,5,6,7,8-hexahydro-5,8-epiminocyclohepta[c]pyrazol-9-yl)methanone

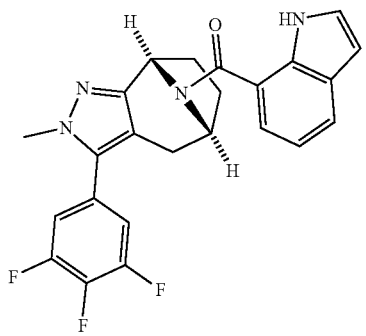 [SMILES: Cn1nc2c(c1-c1cc(F)c(F)c(F)c1)C[C@H]1CC[C@@H]2N1C(=O)c1cccc2cc[nH]c12]

The title compound was prepared in a manner analogous to Example 1, using (5R,8S)-2-methyl-3-(3,4,5-trifluorophenyl)-2,4,5,6,7,8-hexahydro-5,8-epiminocyclohepta[c]pyrazole 2,2,2-trifluoroacetate (Intermediate 105) instead of racemic-(5R,9S)-2-methyl-3-phenyl-4,5,6,7,8,9-hexahydro-2H-5,9-epiminocycloocta[c]pyrazole (Intermediate 1) and indole-7-carboxylic acid instead of quinoline-6-carboxylic acid. MS (ESI): mass calcd. for $C_{24}H_{19}F_3N_4O$, 436.2; m/z found, 437.0 [M+H]$^+$. $^1$H NMR (400 MHz, CDCl$_3$) δ 9.43 (s, 1H), 7.74 (d, J=7.9 Hz, 1H), 7.35 (d, J=7.3 Hz, 1H), 7.11 (t, J=7.7 Hz, 1H), 7.07-6.94 (m, 2H), 6.62-6.53 (m, 1H), 5.60 (s, 1H), 3.81 (s, 3H), 3.21 (s, 1H), 2.48-2.38 (m, 1H), 2.38-2.13 (m, 2H), 2.05 (t, J=10.1 Hz, 1H), 1.76-1.62 (m, 1H), 1.54 (s, 1H).

Example 402: (6-Fluoro-1H-indol-7-yl)((5R,8S)-2-methyl-3-(3,4,5-trifluorophenyl)-2,4,5,6,7,8-hexahydro-5,8-epiminocyclohepta[c]pyrazol-9-yl)methanone

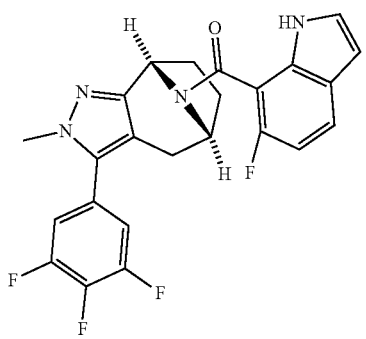 [SMILES: Cn1nc2c(c1-c1cc(F)c(F)c(F)c1)C[C@H]1CC[C@@H]2N1C(=O)c1c(F)ccc2cc[nH]c12]

The title compound was prepared in a manner analogous to Example 1, using (5R,8S)-2-methyl-3-(3,4,5-trifluorophenyl)-2,4,5,6,7,8-hexahydro-5,8-epiminocyclohepta[c]pyrazole 2,2,2-trifluoroacetate (Intermediate 105) instead of racemic-(5R,9S)-2-methyl-3-phenyl-4,5,6,7,8,9-hexahydro-2H-5,9-epiminocycloocta[c]pyrazole (Intermediate 1) and 6-fluoro-1H-indole-7-carboxylic acid instead of quinoline-6-carboxylic acid. MS (ESI): mass calcd. for $C_{24}H_{18}F_4N_4O$, 454.1; m/z found, 455.0 [M+H]$^+$. $^1$H NMR (600 MHz, CDCl$_3$) δ 8.46-8.30 (m, 1H), 7.49-7.39 (m, 1H), 7.35-7.28 (m, 2H), 7.03-6.90 (m, 2H), 6.56-6.49 (m, 1H), 5.82-5.12 (m, 1H), 4.93-4.23 (m, 1H), 3.86-3.68 (m, 3H), 3.36-2.80 (m, 1H), 2.43-2.18 (m, 3H), 2.11-1.92 (m, 1H), 1.72-1.60 (m, 1H).

Example 403: (2,3-Dimethyl-1H-indol-7-yl)((5R,8S)-2-methyl-3-(3,4,5-trifluorophenyl)-2,4,5,6,7,8-hexahydro-5,8-epiminocyclohepta[c]pyrazol-9-yl)methanone

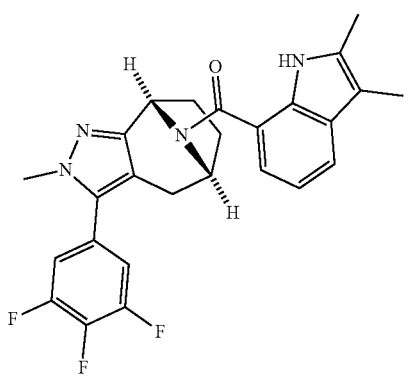 [SMILES: Cc1[nH]c2c(C(=O)N3[C@@H]4CC[C@H]3c3nn(C)c(-c5cc(F)c(F)c(F)c5)c3C4)cccc2c1C]

The title compound was prepared in a manner analogous to Example 1, using (5R,8S)-2-methyl-3-(3,4,5-trifluorophenyl)-2,4,5,6,7,8-hexahydro-5,8-epiminocyclohepta[c]pyrazole 2,2,2-trifluoroacetate (Intermediate 105) instead of racemic-(5R,9S)-2-methyl-3-phenyl-4,5,6,7,8,9-hexahydro-2H-5,9-epiminocycloocta[c]pyrazole (Intermediate 1) and 2,3-dimethyl-1H-Indole-7-carboxylic acid instead of quinoline-6-carboxylic acid. MS (ESI): mass calcd. for $C_{26}H_{23}F_3N_4O$, 464.2; m/z found, 465.1 [M+H]$^+$. $^1$H NMR (600 MHz, CDCl$_3$) δ 8.96 (s, 1H), 7.56 (d, J=7.8 Hz, 1H), 7.26 (s, 2H), 7.10-7.02 (m, 1H), 6.99 (t, J=6.9 Hz, 2H), 5.88-5.43 (m, 1H), 3.87-3.73 (m, 3H), 3.34-3.03 (m, 1H), 2.40 (d, J=15.3 Hz, 1H), 2.35 (s, 3H), 2.33-2.25 (m, 1H), 2.25-2.21 (m, 3H), 2.18 (s, 1H), 2.03 (t, J=10.4 Hz, 1H), 1.74-1.60 (m, 1H).

Example 404: (1H-Indazol-7-yl)((5R,8S)-2-methyl-3-(3,4,5-trifluorophenyl)-2,4,5,6,7,8-hexahydro-5,8-epiminocyclohepta[c]pyrazol-9-yl)methanone

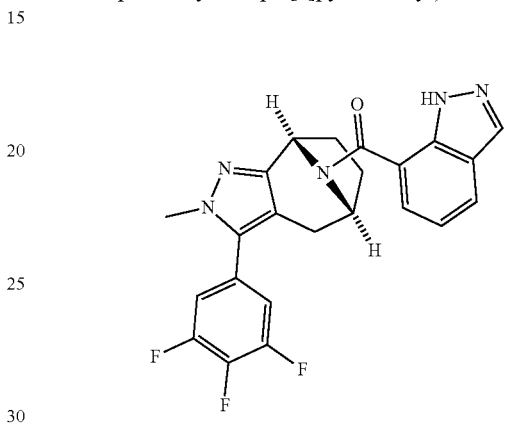

The title compound was prepared in a manner analogous to Example 1, using (5R,8S)-2-methyl-3-(3,4,5-trifluorophenyl)-2,4,5,6,7,8-hexahydro-5,8-epiminocyclohepta[c]pyrazole 2,2,2-trifluoroacetate (Intermediate 105) instead of racemic-(5R,9S)-2-methyl-3-phenyl-4,5,6,7,8,9-hexahydro-2H-5,9-epiminocycloocta[c]pyrazole (Intermediate 1) and 1H-indazole-7-carboxylic acid instead of quinoline-6-carboxylic acid. MS (ESI): mass calcd. for $C_{23}H_{18}F_3N_5O$, 437.1; m/z found, 438.0 [M+H]$^+$. $^1$H NMR (400 MHz, CDCl$_3$) δ 11.03 (s, 1H), 8.11 (s, 1H), 7.94-7.82 (m, 1H), 7.62-7.49 (m, 1H), 7.23-7.14 (m, 1H), 7.07-6.89 (m, 2H), 5.53 (s, 1H), 5.38-4.96 (m, 1H), 3.81 (s, 3H), 3.32-3.12 (m, 1H), 2.50-2.39 (m, 1H), 2.39-2.16 (m, 2H), 2.14-2.02 (m, 1H), 1.80-1.66 (m, 1H).

Example 405: (1H-Benzo[d]imidazol-7-yl)((5R,8S)-2-methyl-3-(3,4,5-trifluorophenyl)-2,4,5,6,7,8-hexahydro-5,8-epiminocyclohepta[c]pyrazol-9-yl)methanone

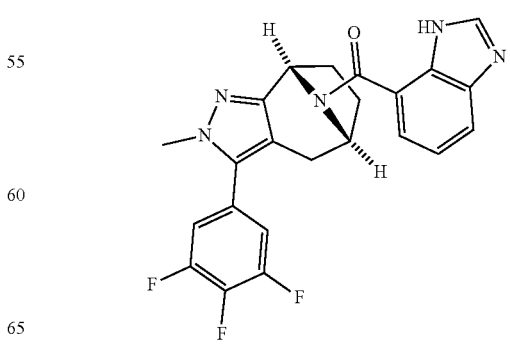

The title compound was prepared in a manner analogous to Example 1, using (5R,8S)-2-methyl-3-(3,4,5-trifluorophenyl)-2,4,5,6,7,8-hexahydro-5,8-epiminocyclohepta[c]pyrazole 2,2,2-trifluoroacetate (Intermediate 105) instead of racemic-(5R,9S)-2-methyl-3-phenyl-4,5,6,7,8,9-hexahydro-2H-5,9-epiminocycloocta[c]pyrazole (Intermediate 1) and 1H-benzimidazole-7-carboxylic acid instead of quinoline-6-carboxylic acid. MS (ESI): mass calcd. for $C_{23}H_{18}F_3N_5O$, 437.1; m/z found, 438.0 [M+H]$^+$. $^1$H NMR (400 MHz, CDCl$_3$) δ 10.29 (s, 1H), 8.09 (s, 1H), 7.94 (d, J=8.0 Hz, 1H), 7.50 (d, J=15.8 Hz, 1H), 7.30 (t, J=7.8 Hz, 1H), 7.07-6.92 (m, 2H), 5.74-5.48 (m, 1H), 5.39-5.08 (m, 1H), 3.82 (s, 3H), 3.32-3.12 (m, 1H), 2.50-2.40 (m, 1H), 2.40-2.15 (m, 2H), 2.15-2.01 (m, 1H), 1.81-1.64 (m, 1H).

Example 406: ((5R,8S)-2-Methyl-3-(3,4,5-trifluorophenyl)-2,4,5,6,7,8-hexahydro-5,8-epiminocyclohepta[c]pyrazol-9-yl)(2-methylbenzo[d]oxazol-6-yl)methanone

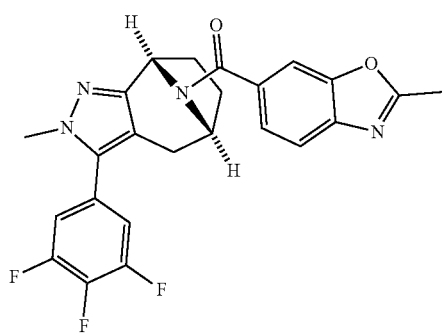 [SMILES: Cc1nc2ccc(C(=O)N3[C@@H]4CC[C@H]3c3nn(C)c(-c5cc(F)c(F)c(F)c5)c3C4)cc2o1]

The title compound was prepared in a manner analogous to Example 1, using (5R,8S)-2-methyl-3-(3,4,5-trifluorophenyl)-2,4,5,6,7,8-hexahydro-5,8-epiminocyclohepta[c]pyrazole 2,2,2-trifluoroacetate (Intermediate 105) instead of racemic-(5R,9S)-2-methyl-3-phenyl-4,5,6,7,8,9-hexahydro-2H-5,9-epiminocycloocta[c]pyrazole (Intermediate 1) and 2-methyl-1,3-benzoxazole-6-carboxylic acid instead of quinoline-6-carboxylic acid. MS (ESI): mass calcd. for $C_{24}H_{19}F_3N_4O_2$, 452.1; m/z found, 453.0 [M+H]$^+$. $^1$H NMR (600 MHz, CDCl$_3$) δ 7.72-7.59 (m, 2H), 7.43 (s, 1H), 6.99 (s, 2H), 5.19 (s, 1H), 5.10-4.37 (m, 1H), 3.79 (s, 3H), 3.54-3.19 (m, 1H), 2.67 (s, 3H), 2.46-1.92 (m, 4H), 1.75-1.63 (m, 1H).

Example 407: Furo[3,2-c]pyridin-4-yl((5R,8S)-2-methyl-3-(3,4,5-trifluorophenyl)-2,4,5,6,7,8-hexahydro-5,8-epiminocyclohepta[c]pyrazol-9-yl)methanone

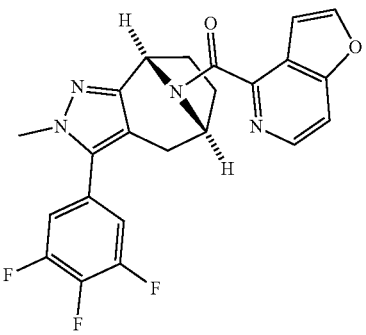 [SMILES: Cn1nc2c(c1-c1cc(F)c(F)c(F)c1)C[C@H]1CC[C@@H]2N1C(=O)c1nccc2occc12]

The title compound was prepared in a manner analogous to Example 1, using (5R,8S)-2-methyl-3-(3,4,5-trifluorophenyl)-2,4,5,6,7,8-hexahydro-5,8-epiminocyclohepta[c]pyrazole 2,2,2-trifluoroacetate (Intermediate 105) instead of racemic-(5R,9S)-2-methyl-3-phenyl-4,5,6,7,8,9-hexahydro-2H-5,9-epiminocycloocta[c]pyrazole (Intermediate 1) and furo[3,2-c]pyridine-4-carboxylic acid instead of quinoline-6-carboxylic acid. MS (ESI): mass calcd. for $C_{23}H_{17}F_3N_4O_2$, 438.1; m/z found, 439.2 [M+H]$^+$. $^1$H NMR (600 MHz, CDCl$_3$) δ 8.53-8.47 (m, 1H), 7.72-7.67 (m, 1H), 7.55-7.48 (m, 1H), 7.32-7.30 (m, 1H), 7.01-6.92 (m, 2H), 6.20-5.81 (m, 1H), 5.38-5.22 (m, 1H), 3.85-3.71 (m, 3H), 3.40-3.27 (m, 1H), 2.46-2.19 (m, 3H), 2.12-1.99 (m, 1H), 1.78-1.64 (m, 1H).

Example 408: (1-Methyl-1H-pyrrolo[2,3-b]pyridin-3-yl)((5R,8S)-2-methyl-3-phenyl-2,4,5,6,7,8-hexahydro-5,8-epiminocyclohepta[c]pyrazol-9-yl)methanone

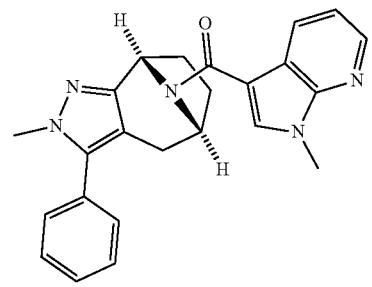 [SMILES: Cn1nc2c(c1-c1ccccc1)C[C@H]1CC[C@@H]2N1C(=O)c1cn(C)c2ncccc12]

The title compound was prepared in a manner analogous to Example 1, using (5R,8S)-2-methyl-3-phenyl-2,4,5,6,7,8-hexahydro-5,8-epiminocyclohepta[c]pyrazole 2,2,2-trifluoroacetate (Intermediate 106) instead of racemic-(5R,9S)-2-methyl-3-phenyl-4,5,6,7,8,9-hexahydro-2H-5,9-epiminocycloocta[c]pyrazole (Intermediate 1) and 1-methyl-1H-pyrolo[2,3-b]pyridine-3-carboxylic acid instead of quinoline-6-carboxylic acid. MS (ESI): mass calcd. for $C_{24}H_{23}N_5O$, 397.2; m/z found, 398.1 [M+H]$^+$. $^1$H NMR (400 MHz, CDCl$_3$) δ 8.40-8.36 (m, 1H), 8.29-8.23 (m, 1H), 7.58 (s, 1H), 7.50-7.44 (m, 2H), 7.44-7.37 (m, 1H), 7.36 (d, J=1.7 Hz, 1H), 7.35-7.32 (m, 1H), 7.20-7.14 (m, 1H), 5.48 (s, 1H), 5.15 (s, 1H), 3.91 (s, 3H), 3.82 (s, 3H), 3.25 (s, 1H), 2.45-2.36 (m, 1H), 2.36-2.17 (m, 2H), 2.14-2.03 (m, 1H), 1.77-1.64 (m, 1H).

Example 409: (1-Methyl-1H-pyrrolo[2,3-b]pyridin-3-yl)((5R,8S)-2-methyl-3-(3,4,5-trifluorophenyl)-2,4,5,6,7,8-hexahydro-5,8-epiminocyclohepta[c]pyrazol-9-yl)methanone

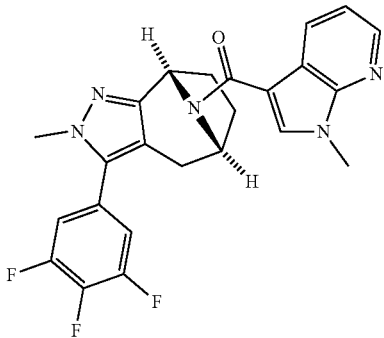

The title compound was prepared in a manner analogous to Example 1, using (5R,8S)-2-methyl-3-(3,4,5-trifluorophenyl)-2,4,5,6,7,8-hexahydro-5,8-epiminocyclohepta[c]pyrazole 2,2,2-trifluoroacetate (Intermediate 105) instead of racemic-(5R,9S)-2-methyl-3-phenyl-4,5,6,7,8,9-hexahydro-2H-5,9-epiminocycloocta[c]pyrazole (Intermediate 1) and 1-methyl-1H-pyrrolo[2,3-b]pyridine-3-carboxylic acid instead of quinoline-6-carboxylic acid. MS (ESI): mass calcd. for $C_{24}H_{20}F_3N_5O$, 451.2; m/z found, 452.0 [M+H]$^+$. $^1$H NMR (600 MHz, CDCl$_3$) δ 8.40-8.37 (m, 1H), 8.25-8.21 (m, 1H), 7.56 (s, 1H), 7.20-7.15 (m, 1H), 7.02-6.93 (m, 2H), 5.46 (s, 1H), 5.13 (s, 1H), 3.92 (s, 3H), 3.80 (s, 3H), 3.22 (s, 1H), 2.42-2.22 (m, 3H), 2.12-2.03 (m, 1H), 1.74-1.63 (m, 1H).

Example 410: Imidazo[1,2-a]pyridin-5-yl((5R,8S)-2-methyl-3-(3,4,5-trifluorophenyl)-2,4,5,6,7,8-hexahydro-5,8-epiminocyclohepta[c]pyrazol-9-yl)methanone

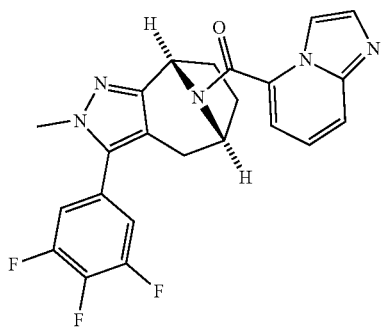

The title compound was prepared in a manner analogous to Example 1, using (5R,8S)-2-methyl-3-(3,4,5-trifluorophenyl)-2,4,5,6,7,8-hexahydro-5,8-epiminocyclohepta[c]pyrazole 2,2,2-trifluoroacetate (Intermediate 105) instead of racemic-(5R,9S)-2-methyl-3-phenyl-4,5,6,7,8,9-hexahydro-2H-5,9-epiminocycloocta[c]pyrazole (Intermediate 1) and imidazo[1,2-a]pyridine-5-carboxylic acid instead of quinoline-6-carboxylic acid. MS (ESI): mass calcd. for $C_{23}H_{18}F_3N_5O$, 437.1; m/z found, 438.0 [M+H]$^+$. $^1$H NMR (600 MHz, CDCl$_3$) δ 8.43 (s, 1H), 7.70 (d, J=1.3 Hz, 1H), 7.66-7.60 (m, 2H), 7.29 (d, J=6.9 Hz, 1H), 6.99 (t, J=6.9 Hz, 2H), 5.15 (s, 2H), 3.80 (s, 3H), 3.55-3.16 (m, 1H), 2.44-2.30 (m, 2H), 2.30-2.17 (m, 1H), 2.13-2.02 (m, 1H), 1.78-1.66 (m, 1H).

Example 411: Imidazo[1,2-a]pyridin-3-yl((5R,8S)-2-methyl-3-(3,4,5-trifluorophenyl)-2,4,5,6,7,8-hexahydro-5,8-epiminocyclohepta[c]pyrazol-9-yl)methanone

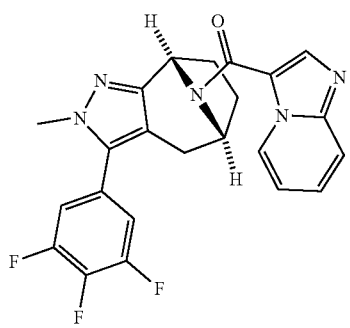

The title compound was prepared in a manner analogous to Example 1, using (5R,8S)-2-methyl-3-(3,4,5-trifluorophenyl)-2,4,5,6,7,8-hexahydro-5,8-epiminocyclohepta[c]pyrazole 2,2,2-trifluoroacetate (Intermediate 105) instead of racemic-(5R,9S)-2-methyl-3-phenyl-4,5,6,7,8,9-hexahydro-2H-5,9-epiminocycloocta[c]pyrazole (Intermediate 1) and imidazo[1,2-a]pyridine-3-carboxylic acid instead of quinoline-6-carboxylic acid. MS (ESI): mass calcd. for $C_{23}H_{18}F_3N_5O$, 437.1; m/z found, 438.1 [M+H]$^+$. $^1$H NMR (600 MHz, CDCl$_3$) δ 9.19 (d, J=7.0 Hz, 1H), 8.02 (s, 1H), 7.72-7.64 (m, 1H), 7.38-7.30 (m, 1H), 7.02-6.90 (m, 3H), 5.65 (s, 1H), 5.18 (s, 1H), 3.81 (s, 3H), 3.28-3.17 (m, 1H), 2.43 (d, J=15.3 Hz, 1H), 2.39-2.30 (m, 1H), 2.31-2.19 (m, 1H), 2.16-2.05 (m, 1H), 1.79-1.68 (m, 1H).

Example 412: (2-Chloroimidazo[1,2-a]pyridin-3-yl)((5R,8S)-2-methyl-3-(3,4,5-trifluorophenyl)-2,4,5,6,7,8-hexahydro-5,8-epiminocyclohepta[c]pyrazol-9-yl)methanone

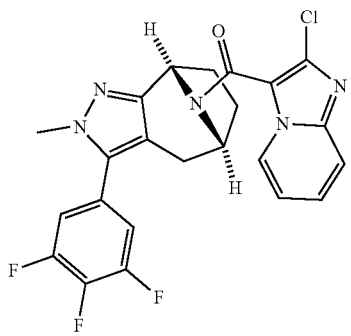

The title compound was prepared in a manner analogous to Example 1, using (5R,8S)-2-methyl-3-(3,4,5-trifluorophenyl)-2,4,5,6,7,8-hexahydro-5,8-epiminocyclohepta[c]pyrazole 2,2,2-trifluoroacetate (Intermediate 105) instead of racemic-(5R,9S)-2-methyl-3-phenyl-4,5,6,7,8,9-hexahydro-2H-5,9-epiminocycloocta[c]pyrazole (Intermediate 1) and 2-chloroimidazo[1,2-a]pyridine-3-carboxylic acid instead of quinoline-6-carboxylic acid. MS (ESI): mass calcd. for $C_{23}H_{17}ClF_3N_5O$, 471.1; m/z found, 472.0 [M+H]$^+$. $^1$H NMR (400 MHz, CDCl$_3$) δ 8.63-8.57 (m, 1H), 7.60-7.54 (m, 1H), 7.38-7.30 (m, 1H), 7.02-6.93 (m, 2H), 6.93-6.86 (m, 1H), 5.37 (s, 1H), 4.96 (s, 1H), 3.76 (s, 3H), 2.53-2.34 (m, 3H), 2.09 (t, J=9.4 Hz, 1H), 1.73 (t, J=7.6 Hz, 1H), 1.62-1.42 (m, 1H).

Example 413: (7-Methoxyimidazo[1,2-a]pyridin-3-yl)((5R,8S)-2-methyl-3-(3,4,5-trifluorophenyl)-2,4,5,6,7,8-hexahydro-5,8-epiminocyclohepta[c]pyrazol-9-yl)methanone

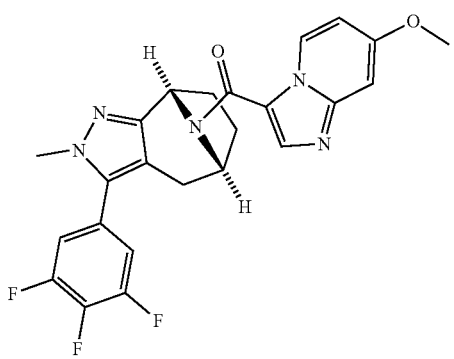

The title compound was prepared in a manner analogous to Example 1, using (5R,8S)-2-methyl-3-(3,4,5-trifluorophenyl)-2,4,5,6,7,8-hexahydro-5,8-epiminocyclohepta[c]pyrazole 2,2,2-trifluoroacetate (Intermediate 105) instead of racemic-(5R,9S)-2-methyl-3-phenyl-4,5,6,7,8,9-hexahydro-2H-5,9-epiminocycloocta[c]pyrazole (Intermediate 1) and 7-methyoxyimidazo[1,2-A]pyridine-3-carboxylic acid instead of quinoline-6-carboxylic acid. MS (ESI): mass calcd. for $C_{24}H_{20}F_3N_5O_2$, 467.2; m/z found, 468.0 [M+H]$^+$. $^1$H NMR (600 MHz, CDCl$_3$) δ 9.04 (d, J=7.7 Hz, 1H), 7.91 (s, 1H), 7.00-6.95 (m, 2H), 6.93 (d, J=2.5 Hz, 1H), 6.66-6.61 (m, 1H), 5.63 (s, 1H), 5.16 (s, 1H), 3.88 (s, 3H), 3.81 (s, 3H), 3.49 (d, J=5.5 Hz, 1H), 3.26-3.16 (m, 1H), 2.48-2.04 (m, 3H), 1.77-1.66 (m, 1H).

Example 414: ((5R,8S)-2-Methyl-3-(3,4,5-trifluorophenyl)-2,4,5,6,7,8-hexahydro-5,8-epiminocyclohepta[c]pyrazol-9-yl)(2-methylimidazo[1,2-a]pyridin-3-yl)methanone

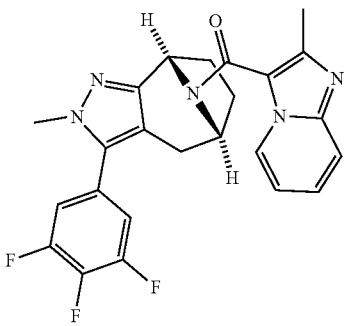

The title compound was prepared in a manner analogous to Example 1, using (5R,8S)-2-methyl-3-(3,4,5-trifluorophenyl)-2,4,5,6,7,8-hexahydro-5,8-epiminocyclohepta[c]pyrazole 2,2,2-trifluoroacetate (Intermediate 105) instead of racemic-(5R,9S)-2-methyl-3-phenyl-4,5,6,7,8,9-hexahydro-2H-5,9-epiminocycloocta[c]pyrazole (Intermediate 1) and 2-methylimidazo[1,2-a]pyridine-3-carboxylic acid instead of quinoline-6-carboxylic acid. MS (ESI): mass calcd. for $C_{24}H_{20}F_3N_5O$, 451.2; m/z found, 452.1 [M+H]$^+$. $^1$H NMR (500 MHz, CDCl$_3$) δ 8.58-8.52 (m, 1H), 7.58-7.51 (m, 1H), 7.30-7.21 (m, 1H), 7.01-6.91 (m, 2H), 6.84-6.77 (m, 1H), 5.19 (s, 1H), 4.95 (s, 1H), 3.78 (s, 3H), 3.36-3.11 (m, 1H), 2.52 (s, 3H), 2.45-2.32 (m, 2H), 2.32-2.18 (m, 1H), 2.12-2.05 (m, 1H), 1.84-1.61 (m, 1H).

Example 415: (2,5-Dimethylimidazo[1,2-a]pyridin-3-yl)((5R,8S)-2-methyl-3-(3,4,5-trifluorophenyl)-2,4,5,6,7,8-hexahydro-5,8-epiminocyclohepta[c]pyrazol-9-yl)methanone

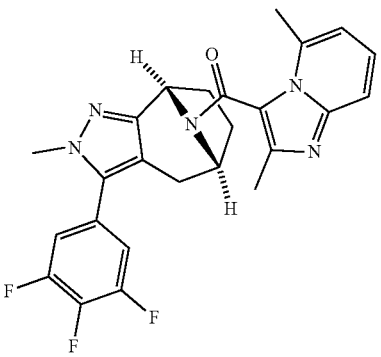 [SMILES: Cc1nc2cccc(C)n2c1C(=O)N1[C@@H]2CC[C@H]1c1nn(C)c(-c3cc(F)c(F)c(F)c3)c1C2]

The title compound was prepared in a manner analogous to Example 1, using (5R,8S)-2-methyl-3-(3,4,5-trifluorophenyl)-2,4,5,6,7,8-hexahydro-5,8-epiminocyclohepta[c]pyrazole 2,2,2-trifluoroacetate (Intermediate 105) instead of racemic-(5R,9S)-2-methyl-3-phenyl-4,5,6,7,8,9-hexahydro-2H-5,9-epiminocycloocta[c]pyrazole (Intermediate 1) and 2,5-dimethylimidazo[1,2-a]pyridine-3-carboxylic acid instead of quinoline-6-carboxylic acid. MS (ESI): mass calcd. for $C_{25}H_{22}F_3N_5O$, 465.2; m/z found, 466.0 [M+H]$^+$. $^1$H NMR (400 MHz, CDCl$_3$) δ 8.39 (d, J=6.9 Hz, 1H), 7.08-7.03 (m, 1H), 7.02-6.91 (m, 2H), 6.72 (t, J=6.9 Hz, 1H), 5.19 (s, 1H), 4.92 (s, 1H), 3.77 (s, 3H), 3.19 (s, 1H), 2.65-2.58 (m, 3H), 2.54 (s, 3H), 2.46-2.18 (m, 3H), 2.13-1.99 (m, 1H), 1.79-1.65 (m, 1H).

Example 416: (2,6-Dimethylimidazo[1,2-a]pyridin-3-yl)((5R,8S)-2-methyl-3-(3,4,5-trifluorophenyl)-2,4,5,6,7,8-hexahydro-5,8-epiminocyclohepta[c]pyrazol-9-yl)methanone

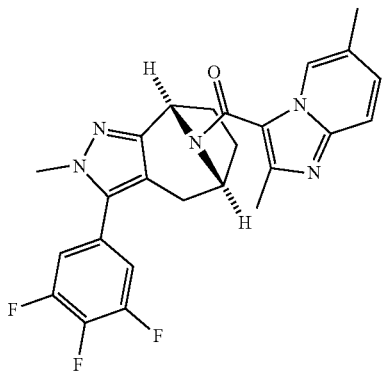

The title compound was prepared in a manner analogous to Example 1, using (5R,8S)-2-methyl-3-(3,4,5-trifluorophenyl)-2,4,5,6,7,8-hexahydro-5,8-epiminocyclohepta[c]pyrazole 2,2,2-trifluoroacetate (Intermediate 105) instead of racemic-(5R,9S)-2-methyl-3-phenyl-4,5,6,7,8,9-hexahydro-2H-5,9-epiminocycloocta[c]pyrazole (Intermediate 1) and 2,6-dimethylimidazo[1,2-a]pyridine-3-carboxylic acid instead of quinoline-6-carboxylic acid. MS (ESI): mass calcd. for $C_{25}H_{22}F_3N_5O$, 465.2; m/z found, 466.0 [M+H]$^+$. $^1$H NMR (400 MHz, CDCl$_3$) δ 8.38-8.32 (m, 1H), 7.49-7.40 (m, 1H), 7.14-7.07 (m, 1H), 7.03-6.90 (m, 2H), 5.20 (s, 1H), 4.95 (s, 1H), 3.79 (s, 3H), 3.30-3.10 (m, 1H), 2.50 (s, 3H), 2.44-2.18 (m, 5H), 2.15-2.01 (m, 1H), 1.79-1.63 (m, 1H), 1.55-1.38 (m, 1H).

Example 417: ((5R,8S)-2-Methyl-3-(3,4,5-trifluorophenyl)-2,4,5,6,7,8-hexahydro-5,8-epiminocyclohepta[c]pyrazol-9-yl)(2-methylimidazo[1,2-a]pyridin-3-yl)methanone

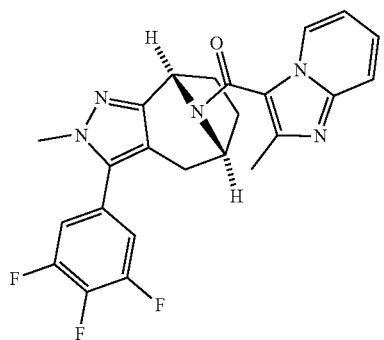

The title compound was prepared in a manner analogous to Example 1, using (5R,8S)-2-methyl-3-(3,4,5-trifluorophenyl)-2,4,5,6,7,8-hexahydro-5,8-epiminocyclohepta[c]pyrazole 2,2,2-trifluoroacetate (Intermediate 105) instead of racemic-(5R,9S)-2-methyl-3-phenyl-4,5,6,7,8,9-hexahydro-2H-5,9-epiminocycloocta[c]pyrazole (Intermediate 1) and 2-methylimidazo[1,2-a]pyridine-3-carboxylic acid instead of quinoline-6-carboxylic acid. MS (ESI): mass calcd. for $C_{25}H_{22}F_3N_5O$, 465.2; m/z found, 466.2 [M+H]$^+$. $^1$H NMR (500 MHz, CDCl$_3$) δ 8.48-8.41 (m, 1H), 7.32-7.28 (m, 1H), 7.01-6.90 (m, 2H), 6.68-6.61 (m, 1H), 5.19 (s, 1H), 4.93 (s, 1H), 3.78 (s, 3H), 3.16 (d, J=27.4 Hz, 1H), 2.49 (s, 3H), 2.44-2.32 (m, 5H), 2.32-2.18 (m, 1H), 2.14-2.01 (m, 1H), 1.70 (d, J=13.3 Hz, 1H).

Example 418: (5-Chloro-2-methylimidazo[1,2-a]pyridin-3-yl)((5R,8S)-2-methyl-3-(3,4,5-trifluorophenyl)-2,4,5,6,7,8-hexahydro-5,8-epiminocyclohepta[c]pyrazol-9-yl)methanone

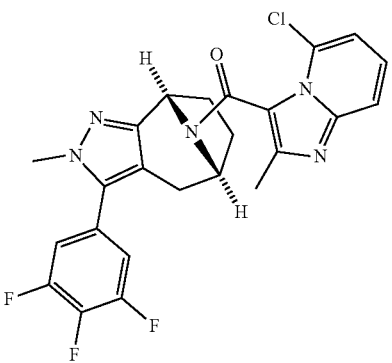

The title compound was prepared in a manner analogous to Example 1, using (5R,8S)-2-methyl-3-(3,4,5-trifluorophenyl)-2,4,5,6,7,8-hexahydro-5,8-epiminocyclohepta[c]pyrazole 2,2,2-trifluoroacetate (Intermediate 105) instead of racemic-(5R,9S)-2-methyl-3-phenyl-4,5,6,7,8,9-hexahydro-2H-5,9-epiminocycloocta[c]pyrazole (Intermediate 1) and 5-chloro-2-methylimidazo[1,2-a]pyridine-3-carboxylic acid instead of quinoline-6-carboxylic acid. MS (ESI): mass calcd. for $C_{24}H_{19}ClF_3N_5O$, 485.1; m/z found, 486.0 [M+H]$^+$. $^1$H NMR (400 MHz, CDCl$_3$) δ 8.63-8.57 (m, 1H), 7.52-7.45 (m, 1H), 7.25-7.19 (m, 1H), 7.04-6.92 (m, 2H), 5.15 (s, 1H), 4.96 (s, 1H), 3.79 (s, 3H), 3.23 (s, 1H), 2.51 (s, 3H), 2.49-2.33 (m, 2H), 2.33-2.19 (m, 2H), 2.15-2.03 (m, 1H), 1.81-1.65 (m, 1H).

Example 419: (2-(Difluoromethyl)imidazo[1,2-a]pyridin-3-yl)((5R,8S)-2-methyl-3-(3,4,5-trifluorophenyl)-2,4,5,6,7,8-hexahydro-5,8-epiminocyclohepta[c]pyrazol-9-yl)methanone

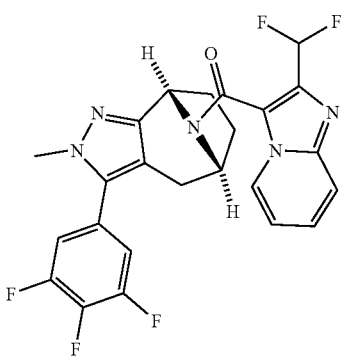

The title compound was prepared in a manner analogous to Example 1, using (5R,8S)-2-methyl-3-(3,4,5-trifluorophenyl)-2,4,5,6,7,8-hexahydro-5,8-epiminocyclohepta[c]pyrazole 2,2,2-trifluoroacetate (Intermediate 105) instead of racemic-(5R,9S)-2-methyl-3-phenyl-4,5,6,7,8,9-hexahydro-2H-5,9-epiminocycloocta[c]pyrazole (Intermediate 1) and 2-(difluoromethyl)imidazo[1,2-a]pyridine-3-carboxylic acid instead of quinoline-6-carboxylic acid. MS (ESI): mass calcd. for $C_{24}H_{18}F_5N_5O$, 487.1; m/z found, 488.0 [M+H]$^+$. $^1$H NMR (400 MHz, CDCl$_3$) δ 8.29 (d, J=7.0 Hz, 1H), 7.73-7.67 (m, 1H), 7.39-7.31 (m, 1H), 7.05-6.73 (m, 4H), 5.29 (d, J=7.7 Hz, 1H), 4.88 (s, 1H), 3.77 (s, 3H), 3.08 (d, J=48.6 Hz, 1H), 2.49-2.25 (m, 3H), 2.17-2.04 (m, 1H), 1.79-1.67 (m, 1H).

Example 420: ((5R,8S)-2-Methyl-3-(3,4,5-trifluorophenyl)-2,4,5,6,7,8-hexahydro-5,8-epiminocyclohepta[c]pyrazol-9-yl)(2-(trifluoromethyl)imidazo[1,2-a]pyridin-3-yl)methanone

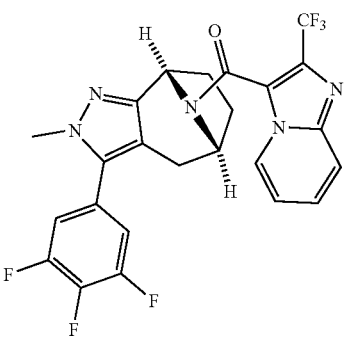

The title compound was prepared in a manner analogous to Example 1, using (5R,8S)-2-methyl-3-(3,4,5-trifluorophenyl)-2,4,5,6,7,8-hexahydro-5,8-epiminocyclohepta[c]pyrazole 2,2,2-trifluoroacetate (Intermediate 105) instead of racemic-(5R,9S)-2-methyl-3-phenyl-4,5,6,7,8,9-hexahydro-2H-5,9-epiminocycloocta[c]pyrazole (Intermediate 1) and 2-(trifluoromethyl)imidazo[1,2-a]pyridine-3-carboxylic acid instead of quinoline-6-carboxylic acid. MS (ESI): mass calcd. for $C_{24}H_{17}F_6N_5O$, 505.1; m/z found, 506.0 [M+H]$^+$. $^1$H NMR (400 MHz, CDCl$_3$) δ 8.14 (s, 1H), 7.72 (d, J=9.2 Hz, 1H), 7.37 (t, J=8.0 Hz, 1H), 6.94 (s, 3H), 5.03 (s, 1H), 3.76 (s, 3H), 3.41 (s, OH), 2.39 (s, 3H), 2.06 (d, J=14.3 Hz, 1H), 1.72 (s, 1H), 1.57 (s, 2H).

Example 421: (5-Methyl-2-(trifluoromethyl)imidazo[1,2-a]pyridin-3-yl)((5R,8S)-2-methyl-3-(3,4,5-trifluorophenyl)-2,4,5,6,7,8-hexahydro-5,8-epiminocyclohepta[c]pyrazol-9-yl)methanone

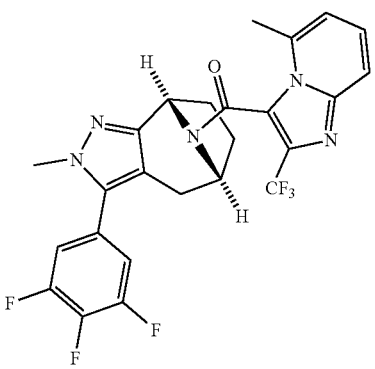

The title compound was prepared in a manner analogous to Example 1, using (5R,8S)-2-methyl-3-(3,4,5-trifluorophenyl)-2,4,5,6,7,8-hexahydro-5,8-epiminocyclohepta[c]pyrazole 2,2,2-trifluoroacetate (Intermediate 105) instead of racemic-(5R,9S)-2-methyl-3-phenyl-4,5,6,7,8,9-hexahydro-2H-5,9-epiminocycloocta[c]pyrazole (Intermediate 1) and 5-methyl-2-(trifluoromethyl)imidazo[1,2-a]pyridine-3-carboxylic acid instead of quinoline-6-carboxylic acid. MS (ESI): mass calcd. for $C_{25}H_{19}F_6N_5O$, 519.1; m/z found, 520.0 [M+H]$^+$. $^1$H NMR (600 MHz, CDCl$_3$) δ 7.99 (s, 1H), 7.14 (s, 1H), 7.02-6.83 (m, 3H), 5.68-4.69 (m, 1H), 3.78 (d, J=2.6 Hz, 3H), 3.22-3.00 (m, 1H), 2.65 (s, 3H), 2.52-1.98 (m, 4H), 1.84-1.66 (m, 1H), 1.42 (dd, J=30.7, 7.0 Hz, 1H).

Example 422: ((5R,8S)-2-Methyl-3-(3,4,5-trifluorophenyl)-2,4,5,6,7,8-hexahydro-5,8-epiminocyclohepta[c]pyrazol-9-yl)(pyrazolo[1,5-a]pyridin-3-yl)methanone

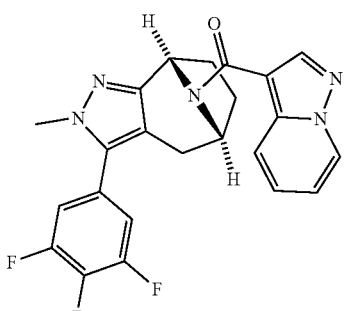

The title compound was prepared in a manner analogous to Example 1, using (5R,8S)-2-methyl-3-(3,4,5-trifluorophenyl)-2,4,5,6,7,8-hexahydro-5,8-epiminocyclohepta[c]pyrazole 2,2,2-trifluoroacetate (Intermediate 105) instead of racemic-(5R,9S)-2-methyl-3-phenyl-4,5,6,7,8,9-hexahydro-2H-5,9-epiminocycloocta[c]pyrazole (Intermediate 1) and pyrazolo[1,5-a]pyridine-3-carboxylic acid instead of quinoline-6-carboxylic acid. MS (ESI): mass calcd. for C₂₃H₁₈F₃N₅O, 437.1; m/z found, 438.1 [M+H]⁺. ¹H NMR (600 MHz, CDCl₃) δ 8.51-8.47 (m, 1H), 8.18 (s, 1H), 8.11 (d, J=8.9 Hz, 1H), 7.35-7.30 (m, 1H), 7.02-6.94 (m, 2H), 6.94-6.88 (m, 1H), 5.52 (s, 1H), 5.16 (s, 1H), 3.80 (s, 3H), 3.22 (s, 1H), 2.45-2.29 (m, 2H), 2.30-2.19 (m, 1H), 2.16-2.04 (m, 1H), 1.77-1.65 (m, 1H).

Example 423: ((5R,8S)-2-Methyl-3-(3,4,5-trifluorophenyl)-2,4,5,6,7,8-hexahydro-5,8-epiminocyclohepta[c]pyrazol-9-yl)(2-methylpyrazolo[1,5-a]pyridin-3-yl)methanone

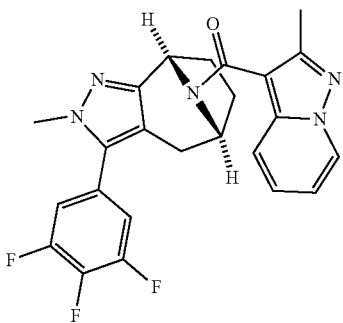

The title compound was prepared in a manner analogous to Example 1, using (5R,8S)-2-methyl-3-(3,4,5-trifluorophenyl)-2,4,5,6,7,8-hexahydro-5,8-epiminocyclohepta[c]pyrazole 2,2,2-trifluoroacetate (Intermediate 105) instead of racemic-(5R,9S)-2-methyl-3-phenyl-4,5,6,7,8,9-hexahydro-2H-5,9-epiminocycloocta[c]pyrazole (Intermediate 1) and 2-methylpyrazolo[1,5-a]pyridine-3-carboxylic acid instead of quinoline-6-carboxylic acid. MS (ESI): mass calcd. for C₂₄H₂₀F₃N₅O, 451.2; m/z found, 452.0 [M+H]⁺. ¹H NMR (400 MHz, CDCl₃) δ 8.39 (dt, J=6.9, 1.1 Hz, 1H), 7.47 (d, J=8.8 Hz, 1H), 7.21 (ddd, J=8.9, 6.8, 1.1 Hz, 1H), 7.04-6.90 (m, 2H), 6.79 (td, J=6.9, 1.4 Hz, 1H), 3.78 (s, 3H), 3.76-3.67 (m, 1H), 3.23-3.14 (m, 2H), 2.80 (s, 1H), 2.50 (s, 3H), 2.45-2.16 (m, 2H), 2.13-1.97 (m, 1H), 1.77-1.62 (m, 1H).

Example 424: (6-Methoxypyrazolo[1,5-a]pyridin-3-yl)((5R,8S)-2-methyl-3-(3,4,5-trifluorophenyl)-2,4,5,6,7,8-hexahydro-5,8-epiminocyclohepta[c]pyrazol-9-yl)methanone

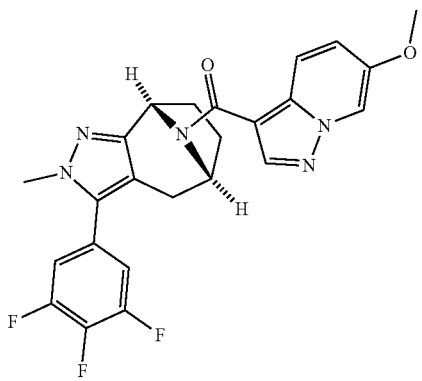 [SMILES: COc1ccc2c(C(=O)N3[C@@H]4CC[C@H]3c3nn(C)c(-c5cc(F)c(F)c(F)c5)c3C4)cnn2c1]

The title compound was prepared in a manner analogous to Example 1, using (5R,8S)-2-methyl-3-(3,4,5-trifluorophenyl)-2,4,5,6,7,8-hexahydro-5,8-epiminocyclohepta[c]pyrazole 2,2,2-trifluoroacetate (Intermediate 105) instead of racemic-(5R,9S)-2-methyl-3-phenyl-4,5,6,7,8,9-hexahydro-2H-5,9-epiminocycloocta[c]pyrazole (Intermediate 1) and 6-methoxy-pyrazolo[1,5-a]pyridine-3-carboxylic acid instead of quinoline-6-carboxylic acid. MS (ESI): mass calcd. for C₂₄H₂₀F₃N₅O₂, 467.2; m/z found, 468.0 [M+H]⁺. ¹H NMR (600 MHz, CDCl₃) δ 8.09 (s, 1H), 8.08-8.05 (m, 1H), 8.02 (d, J=9.6 Hz, 1H), 7.14-7.09 (m, 1H), 7.01-6.93 (m, 2H), 5.53 (s, 1H), 5.15 (s, 1H), 3.85 (s, 3H), 3.80 (s, 3H), 3.21 (d, J=15.3 Hz, 1H), 2.45-2.29 (m, 2H), 2.29-2.19 (m, 1H), 2.08 (t, J=10.6 Hz, 1H), 1.78-1.62 (m, 1H).

Example 425: ((5R,8S)-2-Methyl-3-(3,4,5-trifluorophenyl)-2,4,5,6,7,8-hexahydro-5,8-epiminocyclohepta[c]pyrazol-9-yl)(2-(trifluoromethyl)pyrazolo[1,5-a]pyridin-3-yl)methanone

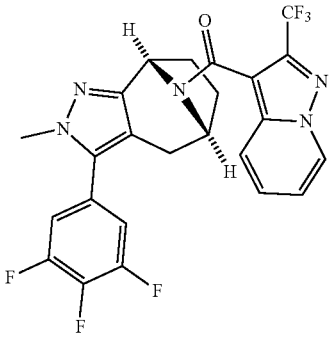

The title compound was prepared in a manner analogous to Example 1, using (5R,8S)-2-methyl-3-(3,4,5-trifluorophenyl)-2,4,5,6,7,8-hexahydro-5,8-epiminocyclohepta[c]pyrazole 2,2,2-trifluoroacetate (Intermediate 105) instead of racemic-(5R,9S)-2-methyl-3-phenyl-4,5,6,7,8,9-hexahydro-2H-5,9-epiminocycloocta[c]pyrazole (Intermediate 1) and 2-(trifluoromethyl)pyrazolo[1,5-a]pyridine-3-carboxylic acid (Intermediate 100) instead of quinoline-6-carboxylic acid. MS (ESI): mass calcd₂₄H₁₇F₆N₅O, 505.1; m/z found, 506.0 [M+H]⁺. ¹H NMR (400 MHz, CDCl₃) δ 8.51 (d, J=7.1 Hz, 1H), 7.34 (s, 2H), 7.08-6.86 (m, 3H), 6.23-4.60 (m, 2H), 3.90-3.61 (m, 2H), 3.29-3.12 (m, 2H), 2.81 (s, 3H), 2.33 (d, J=36.2 Hz, 1H), 2.15-1.63 (m, 1H).

Example 426: ((5R,8S)-2-Methyl-3-(3,4,5-trifluorophenyl)-2,4,5,6,7,8-hexahydro-5,8-epiminocyclohepta[c]pyrazol-9-yl)(pyrazolo[1,5-a]pyrazin-3-yl)methanone

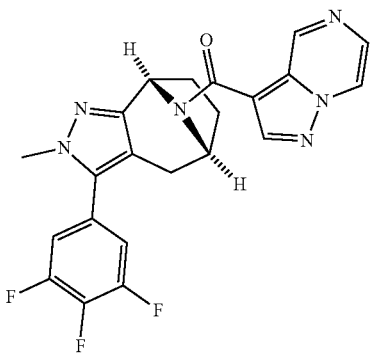 [SMILES: Cn1nc2c(c1-c1cc(F)c(F)c(F)c1)C[C@H]1CC[C@@H]2N1C(=O)c1cnn2ccncc12]

The title compound was prepared in a manner analogous to Example 1, using (5R,8S)-2-methyl-3-(3,4,5-trifluorophenyl)-2,4,5,6,7,8-hexahydro-5,8-epiminocyclohepta[c]pyrazole 2,2,2-trifluoroacetate (Intermediate 105) instead of racemic-(5R,9S)-2-methyl-3-phenyl-4,5,6,7,8,9-hexahydro-2H-5,9-epiminocycloocta[c]pyrazole (Intermediate 1) and pyrazolo[1,5-a]pyrazine-3-carboxylic acid instead of quinoline-6-carboxylic acid. MS (ESI): mass calcd. for $C_{22}H_{17}F_3N_6O$, 438.1; m/z found, 439.0 [M+H]$^+$. $^1$H NMR (500 MHz, CDCl$_3$) δ 9.54 (s, 1H), 8.40 (dd, J=4.7, 1.5 Hz, 1H), 8.24 (s, 1H), 8.03 (d, J=4.7 Hz, 1H), 6.98 (dd, J=7.7, 6.2 Hz, 2H), 5.57-5.10 (m, 2H), 3.81 (s, 3H), 3.55-3.14 (m, 1H), 2.49-2.21 (m, 3H), 2.12 (t, J=10.5 Hz, 1H), 1.81-1.67 (m, 1H).

Example 427: ((5R,8S)-2-Methyl-3-(3,4,5-trifluorophenyl)-2,4,5,6,7,8-hexahydro-5,8-epiminocyclohepta[c]pyrazol-9-yl)(pyrazolo[1,5-a]pyrimidin-3-yl)methanone

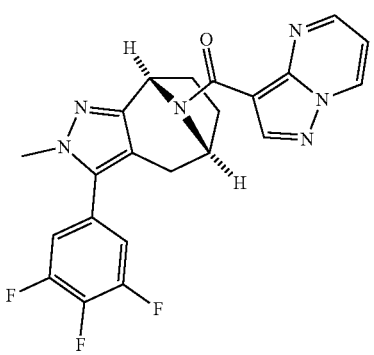 [SMILES: Cn1nc2c(c1-c1cc(F)c(F)c(F)c1)C[C@H]1CC[C@@H]2N1C(=O)c1cnn2cccnc12]

The title compound was prepared in a manner analogous to Example 1, using (5R,8S)-2-methyl-3-(3,4,5-trifluorophenyl)-2,4,5,6,7,8-hexahydro-5,8-epiminocyclohepta[c]pyrazole 2,2,2-trifluoroacetate (Intermediate 105) instead of racemic-(5R,9S)-2-methyl-3-phenyl-4,5,6,7,8,9-hexahydro-2H-5,9-epiminocycloocta[c]pyrazole (Intermediate 1) and pyrazolo[1,5-a]pyrimidine-3-carboxylic acid instead of quinoline-6-carboxylic acid. MS (ESI): mass calcd. for $C_{22}H_{17}F_3N_6O$, 438.1; m/z found, 439.0 [M+H]$^+$. $^1$H NMR (400 MHz, CDCl$_3$) δ 8.72 (d, J=6.9 Hz, 1H), 8.65 (dd, J=4.1, 1.8 Hz, 1H), 8.42 (s, 1H), 7.05-6.91 (m, 3H), 5.44 (s, 1H), 5.10 (s, 1H), 3.75 (d, J=17.4 Hz, 3H), 3.56-3.31 (m, 1H), 2.62-2.23 (m, 3H), 2.05 (t, J=9.7 Hz, 1H), 1.71 (dd, J=13.4, 7.6 Hz, 1H).

Example 428: ((5R,8S)-2-Methyl-3-(3,4,5-trifluorophenyl)-2,4,5,6,7,8-hexahydro-5,8-epiminocyclohepta[c]pyrazol-9-yl)(2-methylimidazo[1,2-b]pyridazin-3-yl)methanone

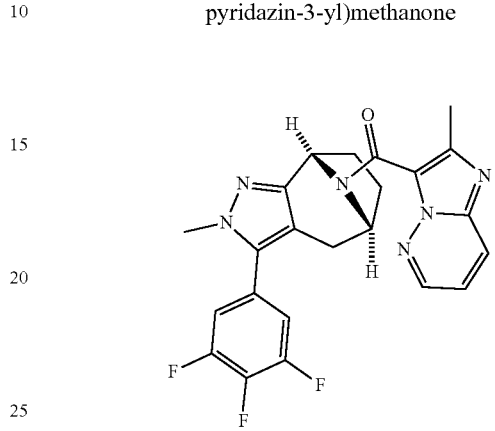

The title compound was prepared in a manner analogous to Example 1, using (5R,8S)-2-methyl-3-(3,4,5-trifluorophenyl)-2,4,5,6,7,8-hexahydro-5,8-epiminocyclohepta[c]pyrazole 2,2,2-trifluoroacetate (Intermediate 105) instead of racemic-(5R,9S)-2-methyl-3-phenyl-4,5,6,7,8,9-hexahydro-2H-5,9-epiminocycloocta[c]pyrazole (Intermediate 1) and 2-methylimidazo[1,2-b]pyridazine-3-carboxylic acid hydrochloride instead of quinoline-6-carboxylic acid. MS (ESI): mass calcd. for $C_{23}H_{19}F_3N_6O$, 452.2; m/z found, 453.0 [M+H]$^+$. $^1$H NMR (500 MHz, CDCl$_3$) δ 8.37-8.31 (m, 1H), 7.92-7.88 (m, 1H), 7.12-7.06 (m, 1H), 6.98 (s, 2H), 5.26-4.70 (m, 1H), 3.86-3.67 (m, 3H), 3.53-3.36 (m, 3H), 2.64-2.44 (m, 2H), 2.44-2.31 (m, 3H), 2.15-1.62 (m, 2H).

Example 429: ((5R,8S)-2-Methyl-3-(3,4,5-trifluorophenyl)-2,4,5,6,7,8-hexahydro-5,8-epiminocyclohepta[c]pyrazol-9-yl)(2-methylpyrazolo[1,5-a]pyrimidin-3-yl)methanone

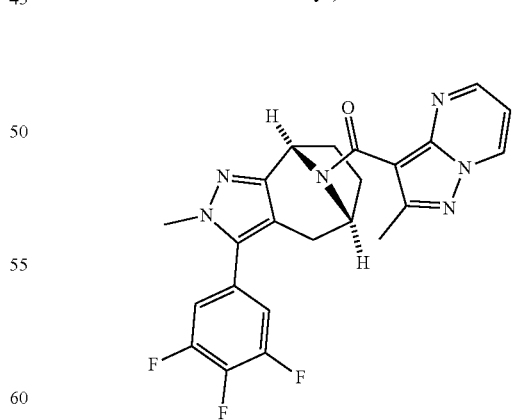

The title compound was prepared in a manner analogous to Example 1, using (5R,8S)-2-methyl-3-(3,4,5-trifluorophenyl)-2,4,5,6,7,8-hexahydro-5,8-epiminocyclohepta[c]pyrazole 2,2,2-trifluoroacetate (Intermediate 105) instead of racemic-(5R,9S)-2-methyl-3-phenyl-4,5,6,7,8,9-hexahydro- 2H-5,9-epiminocycloocta[c]pyrazole (Intermediate 1) and 2-methylpyrazolo[1,5-a]pyrimidine-3-carboxylic acid instead of quinoline-6-carboxylic acid. MS (ESI): mass calcd. for $C_{23}H_{19}F_3N_6O$, 452.2; m/z found, 453.0 [M+H]$^+$. $^1$H NMR (400 MHz, CDCl$_3$) δ 8.59 (d, J=7.0 Hz, 1H), 8.57-8.51 (m, 1H), 6.99 (d, J=6.4 Hz, 2H), 6.89-6.81 (m, 1H), 5.12 (s, 2H), 3.89-3.31 (m, 6H), 2.54 (s, 3H), 2.35 (d, J=15.4 Hz, 1H), 2.02 (s, 1H), 1.68 (s, 1H).

Example 430: (1-Methyl-1H-pyrazolo[3,4-b]pyridin-3-yl)((5R,8S)-2-methyl-3-(3,4,5-trifluorophenyl)-2,4,5,6,7,8-hexahydro-5,8-epiminocyclohepta[c]pyrazol-9-yl)methanone

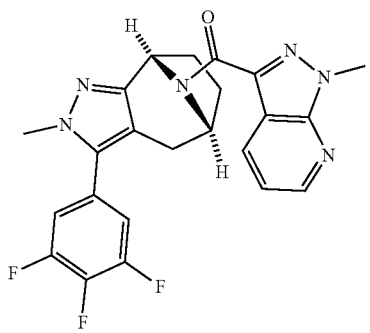 [SMILES: Cn1nc2c(c1-c1cc(F)c(F)c(F)c1)C[C@H]1CC[C@@H]2N1C(=O)c1nn(C)c2ncccc12]

The title compound was prepared in a manner analogous to Example 1, using (5R,8S)-2-methyl-3-(3,4,5-trifluorophenyl)-2,4,5,6,7,8-hexahydro-5,8-epiminocyclohepta[c]pyrazole 2,2,2-trifluoroacetate (Intermediate 105) instead of racemic-(5R,9S)-2-methyl-3-phenyl-4,5,6,7,8,9-hexahydro-2H-5,9-epiminocycloocta[c]pyrazole (Intermediate 1) and 1-methyl-1H-pyrazolo[3,4-b]pyridine-3-carboxylic acid instead of quinoline-6-carboxylic acid. MS (ESI): mass calcd. for $C_{23}H_{19}F_3N_6O$, 452.2; m/z found, 453.1 [M+H]$^+$. $^1$H NMR (600 MHz, CDCl$_3$) δ 8.71-8.59 (m, 1H), 8.60-8.52 (m, 1H), 7.24-7.19 (m, 1H), 7.00-6.89 (m, 2H), 6.72 (d, J=5.3 Hz, 1H), 5.88 (s, 1H), 4.26-4.17 (m, 3H), 3.82-3.71 (m, 3H), 3.38-3.20 (m, 1H), 2.49-1.99 (m, 4H), 1.85-1.63 (m, 1H).

Example 431: ((5R,8S)-2-Methyl-3-phenyl-2,4,5,6,7,8-hexahydro-5,8-epiminocyclohepta[c]pyrazol-9-yl)(quinolin-6-yl)methanone

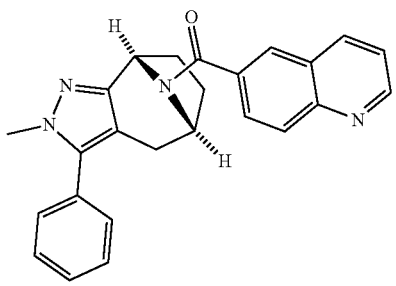 [SMILES: Cn1nc2c(c1-c1ccccc1)C[C@H]1CC[C@@H]2N1C(=O)c1ccc2ncccc2c1]

The title compound was prepared in a manner analogous to Example 1, using (5R,8S)-2-methyl-3-phenyl-2,4,5,6,7,8-hexahydro-5,8-epiminocyclohepta[c]pyrazole 2,2,2-trifluoroacetate (Intermediate 106) instead of racemic-(5R,9S)-

2-methyl-3-phenyl-4,5,6,7,8,9-hexahydro-2H-5,9-epiminocycloocta[c]pyrazole (Intermediate 1. MS (ESI): mass calcd. for $C_{25}H_{22}N_4O$, 394.2; m/z found, 395.1 [M+H]$^+$. $^1$H NMR (400 MHz, CDCl$_3$) δ 9.01-8.94 (m, 1H), 8.20 (d, J=8.3 Hz, 1H), 8.14 (d, J=8.7 Hz, 1H), 8.00 (s, 1H), 7.82 (d, J=8.8 Hz, 1H), 7.54-7.29 (m, 6H), 5.23 (s, 1H), 5.16-4.33 (m, 1H), 3.81 (s, 3H), 3.44-2.92 (m, 1H), 2.53-2.14 (m, 3H), 2.16-1.95 (m, 1H), 1.74 (d, J=10.4 Hz, 1H).

Example 432: ((5R,8S)-2-Methyl-3-(3,4,5-trifluorophenyl)-2,4,5,6,7,8-hexahydro-5,8-epiminocyclohepta[c]pyrazol-9-yl)(quinolin-8-yl)methanone

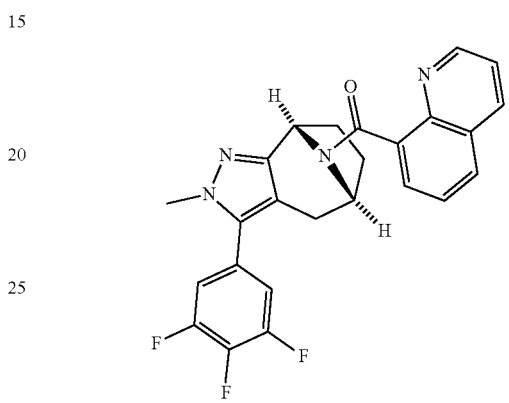

The title compound was prepared in a manner analogous to Example 1, using (5R,8S)-2-methyl-3-(3,4,5-trifluorophenyl)-2,4,5,6,7,8-hexahydro-5,8-epiminocyclohepta[c]pyrazole 2,2,2-trifluoroacetate (Intermediate 105) instead of racemic-(5R,9S)-2-methyl-3-phenyl-4,5,6,7,8,9-hexahydro-2H-5,9-epiminocycloocta[c]pyrazole (Intermediate 1) and 8-quinolinecarboxylic acid instead of quinoline-6-carboxylic acid. MS (ESI): mass calcd. for $C_{25}H_{19}F_3N_4O$, 448.2; m/z found, 449.1 [M+H]$^+$. $^1$H NMR (400 MHz, CDCl$_3$) δ 8.95 (d, J=17.9 Hz, 1H), 8.22-8.11 (m, 1H), 7.91-7.81 (m, 1H), 7.73-7.37 (m, 2H), 7.06-6.88 (m, 2H), 5.68 (d, J=237.4 Hz, 1H), 4.42 (d, J=5.6 Hz, 1H), 3.82 (s, 1H), 3.71 (s, 3H), 3.47-2.71 (m, 1H), 2.60-1.96 (m, 3H), 1.86 (t, J=10.4 Hz, 1H), 1.77-1.64 (m, 1H).

Example 433: ((5S,8R)-2-Methyl-3-(3,4,5-trifluorophenyl)-2,4,5,6,7,8-hexahydro-5,8-epiminocyclohepta[c]pyrazol-9-yl)(quinolin-6-yl)methanone

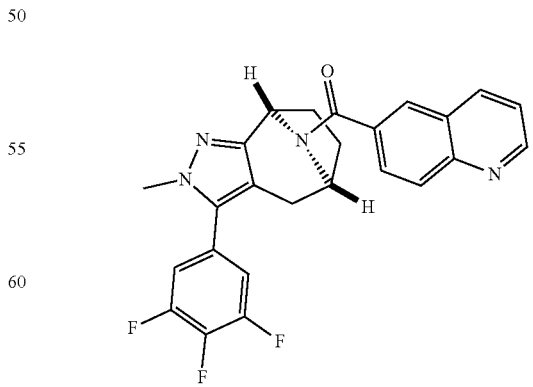

The title compound was prepared in a manner analogous to Example 1, using (5S,8R)-2-methyl-3-(3,4,5-trifluorophenyl)-2,4,5,6,7,8-hexahydro-5,8-epiminocyclohepta[c] pyrazole 2,2,2-trifluoroacetate (Intermediate 111) instead of (5R,9S)-2-methyl-3-phenyl-4,5,6,7,8,9-hexahydro-2H-5,9-epiminocycloocta[c]pyrazole (Intermediate 1). MS (ESI): mass calcd. for $C_{25}H_{19}F_3N_4O$, 448.2; m/z found, 449.1 [M+H]$^+$. $^1$H NMR (500 MHz, CDCl$_3$) δ 9.04-8.92 (m, 1H), 8.19 (d, J=8.3 Hz, 1H), 8.14 (d, J=8.5 Hz, 1H), 7.98 (s, 1H), 7.88-7.74 (m, 1H), 7.50-7.41 (m, 1H), 7.08-6.90 (m, 2H), 5.86-5.14 (m, 1H), 5.17-4.38 (m, 1H), 3.80 (s, 3H), 3.41-2.84 (m, 1H), 2.51-2.14 (m, 3H), 2.15-1.97 (m, 1H), 1.71 (d, J=11.2 Hz, 1H).

Example 434: ((5R,8S)-2-Methyl-3-(3,4,5-trifluorophenyl)-2,4,5,6,7,8-hexahydro-5,8-epiminocyclohepta[c]pyrazol-9-yl)(quinolin-6-yl)methanone

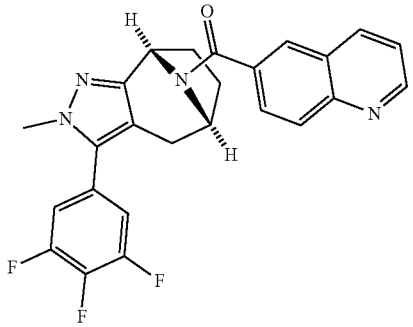

The title compound was prepared in a manner analogous to Example 1, using (5R,8S)-2-methyl-3-(3,4,5-trifluorophenyl)-2,4,5,6,7,8-hexahydro-5,8-epiminocyclohepta[c] pyrazole 2,2,2-trifluoroacetate (Intermediate 105) instead of racemic-(5R,9S)-2-methyl-3-phenyl-4,5,6,7,8,9-hexahydro-2H-5,9-epiminocycloocta[c]pyrazole (Intermediate 1). MS (ESI): mass calcd. for $C_{25}H_{19}F_3N_4O$, 448.2; m/z found, 449.1 [M+H]$^+$. $^1$H NMR (500 MHz, CDCl$_3$) δ 9.02-8.94 (m, 1H), 8.19 (d, J=8.4 Hz, 1H), 8.14 (d, J=8.5 Hz, 1H), 7.98 (s, 1H), 7.79 (d, J=8.7 Hz, 1H), 7.51-7.42 (m, 1H), 7.08-6.93 (m, 2H), 5.23 (s, 1H), 5.09 (d, J=5.2 Hz, 1H), 3.80 (s, 3H), 3.41-2.86 (m, 1H), 2.47-2.15 (m, 3H), 2.04 (t, J=10.3 Hz, 1H), 1.71 (d, J=11.3 Hz, 1H).

Example 435: (2,4-Dimethylquinolin-7-yl)((5R,8S)-2-methyl-3-(3,4,5-trifluorophenyl)-2,4,5,6,7,8-hexahydro-5,8-epiminocyclohepta[c]pyrazol-9-yl)methanone

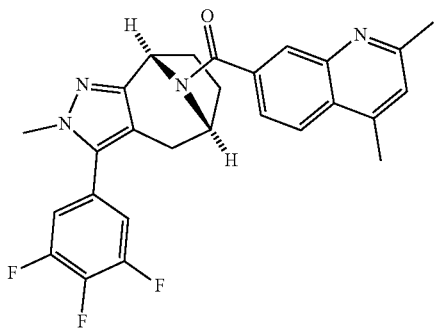

The title compound was prepared in a manner analogous to Example 1, using (5R,8S)-2-methyl-3-(3,4,5-trifluorophenyl)-2,4,5,6,7,8-hexahydro-5,8-epiminocyclohepta[c] pyrazole 2,2,2-trifluoroacetate (Intermediate 105) instead of racemic-(5R,9S)-2-methyl-3-phenyl-4,5,6,7,8,9-hexahydro-2H-5,9-epiminocycloocta[c]pyrazole (Intermediate 1) and 2,4-dimethylquinoline-7-carboxylic acid instead of quinoline-6-carboxylic acid. MS (ESI): mass calcd. for $C_{27}H_{23}F_3N_4O$, 476.2; m/z found, 477.1 [M+H]$^+$. $^1$H NMR (600 MHz, CDCl$_3$) δ 8.16-7.52 (m, 3H), 7.19 (s, 1H), 7.02-6.94 (m, 2H), 5.86-5.16 (m, 1H), 5.12-4.47 (m, 1H), 3.90-3.70 (m, 3H), 3.43-2.91 (m, 1H), 2.70 (s, 3H), 2.68 (s, 3H), 2.42-2.20 (m, 3H), 2.11-1.95 (m, 1H), 1.75-1.62 (m, 1H).

Example 436: ((5R,8S)-2-Methyl-3-(3,4,5-trifluorophenyl)-2,4,5,6,7,8-hexahydro-5,8-epiminocyclohepta[c]pyrazol-9-yl)(6-methylquinolin-8-yl)methanone

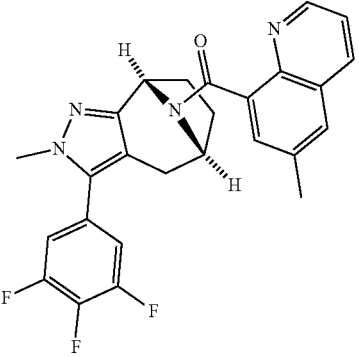 [SMILES: Cc1cc(C(=O)N2[C@@H]3CC[C@H]2c2nn(C)c(-c4cc(F)c(F)c(F)c4)c2C3)c2ncccc2c1]

The title compound was prepared in a manner analogous to Example 1, using (5R,8S)-2-methyl-3-(3,4,5-trifluorophenyl)-2,4,5,6,7,8-hexahydro-5,8-epiminocyclohepta[c] pyrazole 2,2,2-trifluoroacetate (Intermediate 105) instead of racemic-(5R,9S)-2-methyl-3-phenyl-4,5,6,7,8,9-hexahydro-2H-5,9-epiminocycloocta[c]pyrazole (Intermediate 1) and 6-methylquinoline-8-carboxylic acid instead of quinoline-6-carboxylic acid. MS (ESI): mass calcd. for $C_{26}H_{21}F_3N_4O$, 462.2; m/z found, 463.2 [M+H]$^+$. $^1$H NMR (500 MHz, CDCl$_3$) δ 8.86 (d, J=21.3 Hz, 1H), 8.15-7.97 (m, 1H), 7.66-7.33 (m, 3H), 7.07-6.88 (m, 2H), 6.04-5.28 (m, 1H), 4.48-4.36 (m, 1H), 3.87-3.61 (m, 3H), 3.46-3.26 (m, 1H), 2.62-2.34 (m, 5H), 2.28-2.01 (m, 1H), 1.94-1.79 (m, 1H), 1.78-1.62 (m, 1H).

Example 437: ((5R,8S)-2-Methyl-3-(3,4,5-trifluorophenyl)-2,4,5,6,7,8-hexahydro-5,8-epiminocyclohepta[c]pyrazol-9-yl)(quinoxalin-6-yl)methanone

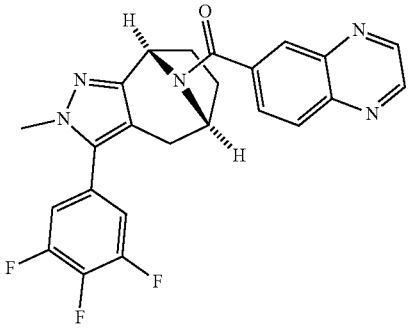 [SMILES: Cn1nc2c(c1-c1cc(F)c(F)c(F)c1)C[C@H]1CC[C@@H]2N1C(=O)c1ccc2nccnc2c1]

The title compound was prepared in a manner analogous to Example 1, using (5R,8S)-2-methyl-3-(3,4,5-trifluorophenyl)-2,4,5,6,7,8-hexahydro-5,8-epiminocyclohepta[c]pyrazole 2,2,2-trifluoroacetate (Intermediate 105) instead of racemic-(5R,9S)-2-methyl-3-phenyl-4,5,6,7,8,9-hexahydro-2H-5,9-epiminocycloocta[c]pyrazole (Intermediate 1) and quinoxaline-6-carboxylic acid instead of quinoline-6-carboxylic acid. MS (ESI): mass calcd. for $C_{24}H_{18}F_3N_5O$, 449.1; m/z found, 450.0 [M+H]$^+$. $^1$H NMR (400 MHz, CDCl$_3$) δ 8.91 (s, 2H), 8.17 (d, J=12.7 Hz, 2H), 7.99-7.81 (m, 1H), 7.08-6.92 (m, 2H), 5.51 (d, J=230.9 Hz, 1H), 4.75 (d, J=231.1 Hz, 1H), 3.93-3.25 (m, 3H), 2.49-2.20 (m, 3H), 2.20-1.98 (m, 1H), 1.72 (s, 1H), 1.55 (s, 1H).

Example 438: (2,3-Dimethylquinoxalin-6-yl)((5R,8S)-2-methyl-3-(3,4,5-trifluorophenyl)-2,4,5,6,7,8-hexahydro-5,8-epiminocyclohepta[c]pyrazol-9-yl)methanone

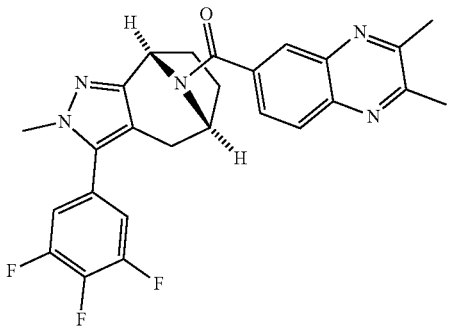 [SMILES: Cc1nc2ccc(C(=O)N3[C@@H]4CC[C@H]3c3nn(C)c(-c5cc(F)c(F)c(F)c5)c3C4)cc2nc1C]

The title compound was prepared in a manner analogous to Example 1, using (5R,8S)-2-methyl-3-(3,4,5-trifluorophenyl)-2,4,5,6,7,8-hexahydro-5,8-epiminocyclohepta[c]pyrazole 2,2,2-trifluoroacetate (Intermediate 105) instead of racemic-(5R,9S)-2-methyl-3-phenyl-4,5,6,7,8,9-hexahydro-2H-5,9-epiminocycloocta[c]pyrazole (Intermediate 1) and 2,3-dimethylquinoxaline-6-carboxylic acid instead of quinoline-6-carboxylic acid. MS (ESI): mass calcd. for $C_{26}H_{22}F_3N_5O$, 477.2; m/z found, 478.1 [M+H]$^+$. $^1$H NMR (600 MHz, CDCl$_3$) δ 8.13-7.98 (m, 2H), 7.85-7.71 (m, 1H), 7.03-6.94 (m, 2H), 5.49 (d, J=341.1 Hz, 1H), 5.12-4.39 (m, 1H), 3.89-3.68 (m, 3H), 3.34 (d, J=15.3 Hz, 1H), 2.85-2.68 (m, 6H), 2.48-2.21 (m, 3H), 2.15-1.96 (m, 1H), 1.79-1.65 (m, 1H).

Example 439: ((5R,8S)-2-Methyl-3-phenyl-2,4,5,6,7,8-hexahydro-5,8-epiminocyclohepta[c]pyrazol-9-yl)(quinoxalin-5-yl)methanone

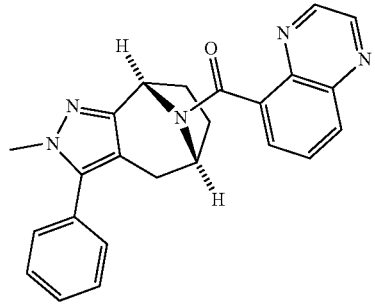 [SMILES: Cn1nc2c(c1-c1ccccc1)C[C@H]1CC[C@@H]2N1C(=O)c1cccc2nccnc12]

The title compound was prepared in a manner analogous to Example 1, using (5R,8S)-2-methyl-3-phenyl-2,4,5,6,7,8-hexahydro-5,8-epiminocyclohepta[c]pyrazole 2,2,2-trifluoroacetate (Intermediate 106) instead of racemic-(5R,9S)-2-methyl-3-phenyl-4,5,6,7,8,9-hexahydro-2H-5,9-epiminocycloocta[c]pyrazole (Intermediate 1 and quinoxaline-5-carboxylic acid instead of quinoline-6-carboxylic acid. MS (ESI): mass calcd. for $C_{24}H_{21}N_5O$, 395.2; m/z found, 396.1 [M+H]$^+$. $^1$H NMR (400 MHz, CDCl$_3$) δ 8.95-8.81 (m, 2H), 8.20-8.10 (m, 1H), 7.93-7.61 (m, 2H), 7.54-7.28 (m, 5H), 6.03-5.25 (m, 2H), 4.43 (d, J=5.6 Hz, 1H), 3.83 (s, 3H), 3.52-2.70 (m, 1H), 2.52-2.31 (m, 1H), 2.33-2.07 (m, 1H), 2.01-1.86 (m, 1H), 1.80-1.66 (m, 1H).

Example 440: ((5R,8S)-2-Methyl-3-(3,4,5-trifluorophenyl)-2,4,5,6,7,8-hexahydro-5,8-epiminocyclohepta[c]pyrazol-9-yl)(1,5-naphthyridin-3-yl)methanone

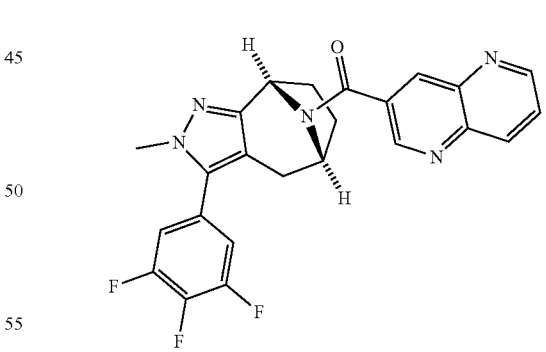

The title compound was prepared in a manner analogous to Example 1, using (5R,8S)-2-methyl-3-(3,4,5-trifluorophenyl)-2,4,5,6,7,8-hexahydro-5,8-epiminocyclohepta[c]pyrazole 2,2,2-trifluoroacetate (Intermediate 105) instead of racemic-(5R,9S)-2-methyl-3-phenyl-4,5,6,7,8,9-hexahydro-2H-5,9-epiminocycloocta[c]pyrazole (Intermediate 1) and 1,5-naphthyridine-3-carboxylic acid instead of quinoline-6-carboxylic acid. MS (ESI): mass calcd. for $C_{24}H_{18}F_3N_5O$, 449.1; m/z found, 450.1 [M+H]$^+$. $^1$H NMR (600 MHz, CDCl$_3$) δ 9.11-9.02 (m, 2H), 8.44 (s, 2H), 7.72 (s, 1H), 7.00

(s, 2H), 5.22 (s, 1H), 5.04 (s, 1H), 3.77 (s, 4H), 3.35 (s, 1H), 2.50-2.24 (m, 2H), 2.16-2.02 (m, 1H), 1.74 (s, 1H).

Example 441: ((5R,8S)-2-Methyl-3-(3,4,5-trifluorophenyl)-2,4,5,6,7,8-hexahydro-5,8-epiminocyclohepta[c]pyrazol-9-yl)(5-methyl-5,6,7,8-tetrahydroimidazo[1,2-a]pyridin-3-yl)methanone

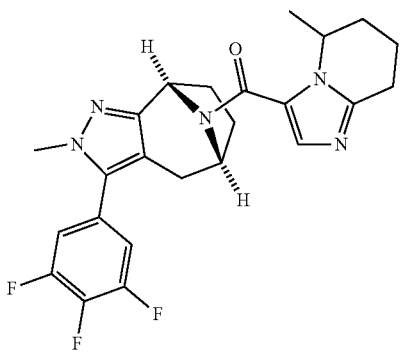 [SMILES: CC1CCCc2ncc(C(=O)N3[C@@H]4CC[C@H]3c3nn(C)c(-c5cc(F)c(F)c(F)c5)c3C4)n21]

The title compound was prepared in a manner analogous to Example 1, using (5R,8S)-2-methyl-3-(3,4,5-trifluorophenyl)-2,4,5,6,7,8-hexahydro-5,8-epiminocyclohepta[c]pyrazole 2,2,2-trifluoroacetate (Intermediate 105) instead of racemic-(5R,9S)-2-methyl-3-phenyl-4,5,6,7,8,9-hexahydro-2H-5,9-epiminocycloocta[c]pyrazole (Intermediate 1) and 5-methyl-5H,6H,7H,8H-imidazo[1,2-a]pyridine-3-carboxylic acid Hydrochloride instead of quinoline-6-carboxylic acid. MS (ESI): mass calcd. for $C_{24}H_{24}F_3N_5O$, 455.2; m/z found, 456.0 [M+H]$^+$. $^1$H NMR (500 MHz, CDCl$_3$) δ 7.24 (s, 1H), 7.00-6.90 (m, 2H), 5.70-4.59 (m, 2H), 3.85-3.70 (m, 3H), 3.41-3.00 (m, 1H), 3.00-2.86 (m, 1H), 2.86-2.72 (m, 1H), 2.53-2.20 (m, 1H), 2.19-1.61 (m, 5H), 1.56 (s, 3H), 1.41-0.96 (m, 4H).

Example 442: ((5R,8S)-2-Methyl-3-(3,4,5-trifluorophenyl)-2,4,5,6,7,8-hexahydro-5,8-epiminocyclohepta[c]pyrazol-9-yl)(5,6,7,8-tetrahydroimidazo[1,2-a]pyridin-3-yl)methanone

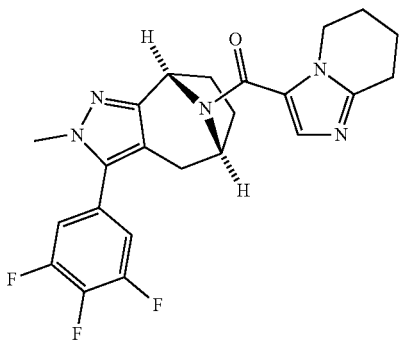 [SMILES: Cn1nc2c(c1-c1cc(F)c(F)c(F)c1)C[C@H]1CC[C@@H]2N1C(=O)c1cnc2n1CCCC2]

The title compound was prepared in a manner analogous to Example 1, using (5R,8S)-2-methyl-3-(3,4,5-trifluorophenyl)-2,4,5,6,7,8-hexahydro-5,8-epiminocyclohepta[c]pyrazole 2,2,2-trifluoroacetate (Intermediate 105) instead of racemic-(5R,9S)-2-methyl-3-phenyl-4,5,6,7,8,9-hexahydro-2H-5,9-epiminocycloocta[c]pyrazole (Intermediate 1) and 5H,6H,7H,8H-imidazo[1,2-a]pyridine-3-carboxylic acid hydrochloride instead of quinoline-6-carboxylic acid. MS (ESI): mass calcd. for $C_{23}H_{22}F_3N_5O$, 441.2; m/z found, 442.1 [M+H]$^+$. $^1$H NMR (600 MHz, CDCl$_3$) δ 7.29 (s, 1H), 6.99-6.93 (m, 2H), 5.64-5.38 (m, 1H), 5.20-4.90 (m, 1H), 4.43-4.02 (m, 2H), 3.80 (s, 3H), 3.15 (d, J=15.3 Hz, 1H), 2.90 (t, J=6.4 Hz, 2H), 2.43-2.33 (m, 1H), 2.29 (q, J=11.0 Hz, 1H), 2.20 (s, 1H), 2.11-2.02 (m, 1H), 2.04-1.83 (m, 4H), 1.70-1.62 (m, 1H).

Example 443: Isochroman-7-yl((5R,8S)-2-methyl-3-(3,4,5-trifluorophenyl)-2,4,5,6,7,8-hexahydro-5,8-epiminocyclohepta[c]pyrazol-9-yl)methanone

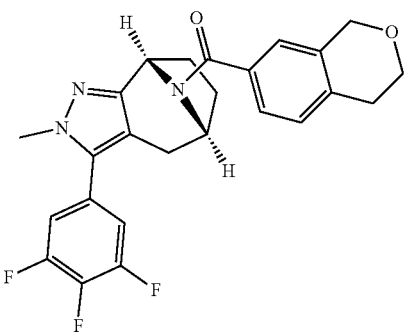

The title compound was prepared in a manner analogous to Example 1, using (5R,8S)-2-methyl-3-(3,4,5-trifluorophenyl)-2,4,5,6,7,8-hexahydro-5,8-epiminocyclohepta[c]pyrazole 2,2,2-trifluoroacetate (Intermediate 105) instead of racemic-(5R,9S)-2-methyl-3-phenyl-4,5,6,7,8,9-hexahydro-2H-5,9-epiminocycloocta[c]pyrazole (Intermediate 1) and 3,4-dihydro-1H-2-benzopyran-7-carboxylic acid instead of quinoline-6-carboxylic acid. MS (ESI): mass calcd. for $C_{25}H_{22}F_3N_3O_2$, 453.2; m/z found, 454.0 [M+H]$^+$. $^1$H NMR (400 MHz, CDCl$_3$) δ 7.26-7.20 (m, 1H), 7.19-7.08 (m, 2H), 7.04-6.91 (m, 2H), 5.22-5.10 (m, 1H), 5.08-4.98 (m, 1H), 4.77 (s, 2H), 3.98 (t, J=5.7 Hz, 2H), 3.79 (s, 3H), 3.34-3.18 (m, 1H), 2.88 (t, J=5.7 Hz, 2H), 2.43-2.07 (m, 3H), 2.06-1.94 (m, 1H), 1.74-1.61 (m, 1H).

Example 444: (2,3-Dihydrobenzo[b][1,4]dioxin-6-yl)((5R,8S)-2-methyl-3-(3,4,5-trifluorophenyl)-2,4,5,6,7,8-hexahydro-5,8-epiminocyclohepta[c]pyrazol-9-yl)methanone

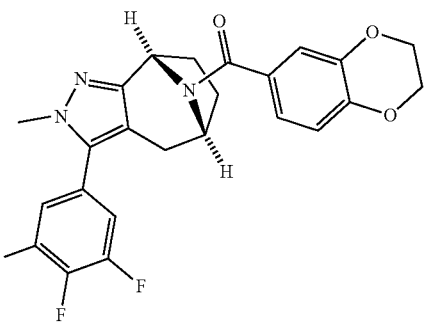

The title compound was prepared in a manner analogous to Example 1, using (5R,8S)-2-methyl-3-(3,4,5-trifluorophenyl)-2,4,5,6,7,8-hexahydro-5,8-epiminocyclohepta[c]pyrazole 2,2,2-trifluoroacetate (Intermediate 105) instead of racemic-(5R,9S)-2-methyl-3-phenyl-4,5,6,7,8,9-hexahydro-2H-5,9-epiminocycloocta[c]pyrazole (Intermediate 1) and 2,3-dihydrobenzo[b][1,4]dioxine-6-carboxylic acid instead of quinoline-6-carboxylic acid. MS (ESI): mass calcd. for $C_{24}H_{20}F_3N_3O_3$, 455.1; m/z found, 456.0 [M+H]$^+$. $^1$H NMR (400 MHz, CDCl$_3$) δ 7.10-6.68 (m, 5H), 5.81-4.66 (m, 2H), 4.33-4.02 (m, 5H), 3.85-3.72 (m, 3H), 3.56-2.73 (m, 1H), 2.37-2.12 (m, 2H), 2.12-1.88 (m, 1H), 1.73-1.59 (m, 1H).

Biological Data

The assay used to measure the in vitro activity of MGL is adapted from the assay used for another serine hydrolase (FAAH) described in Wilson et al., 2003 (A high-throughput-compatible assay for determining the activity of fatty acid amide hydrolase. Wilson S J, Lovenberg T W, Barbier A J. Anal Biochem. 2003 Jul. 15; 318(2):270-5). The assay consists of combining endogenously expressed MGL from HeLa cells with test compounds, adding [glycerol-1,3-$^3$H]-oleoyl glycerol, incubating for one hour, and then measuring the amount of cleaved [1,3-$^3$H]-glycerol that passes through an activated carbon filter. The amount of cleaved, tritiated glycerol passing through the carbon filter is proportional to the activity of the MGL enzyme in a particular well/test condition.

Standard conditions for this assay combine 300 nM [Glycerol-1,3-$^3$H]-oleoyl glycerol with human MGL from HeLa cells and test compounds for one hour, after which the reaction is filtered through activated carbon and tritium is measured in the flow through. The test compound concentration in screening mode is 10 uM, while the highest compound concentration in IC$_{50}$ assays is determined empirically. MGL is the predominant hydrolase in HeLa cells/cell homogenates.

NT means not tested.

TABLE 4

| Ex # | Compound Name | MGL IC$_{50}$ (nM) |
|---|---|---|
| 1 | racemic-((5R,9S)-2-Methyl-3-phenyl-4,5,6,7,8,9-hexahydro-2H-5,9-epiminocycloocta[c]pyrazol-10-yl)(quinolin-6-yl)methanone; | 4.94 |
| 2 | ((5R,9S)-3-Cyclopropyl-2-methyl-4,5,6,7,8,9-hexahydro-2H-5,9-epiminocycloocta[c]pyrazol-10-yl)(quinolin-6-yl)methanone; | 1625.92 |
| 3 | racemic-(2-Chloro-3-methoxyphenyl)((5R,9S)-2-methyl-3-phenyl-4,5,6,7,8,9-hexahydro-2H-5,9-epiminocycloocta[c]pyrazol-10-yl)methanone; | 0.78 |
| 4 | (2-Chloro-3-methoxyphenyl)((5R,9S)-2-methyl-3-phenyl-4,5,6,7,8,9-hexahydro-2H-5,9-epiminocycloocta[c]pyrazol-10-yl)methanone; | 0.26 |
| 5 | (2-Chloro-3-methoxyphenyl)((5S,9R)-2-methyl-3-phenyl-4,5,6,7,8,9-hexahydro-2H-5,9-epiminocycloocta[c]pyrazol-10-yl)methanone; | 515.70 |
| 6 | racemic-(2-(1H-1,2,4-Triazol-1-yl)phenyl)((5R,9S)-2-methyl-3-phenyl-4,5,6,7,8,9-hexahydro-2H-5,9-epiminocycloocta[c]pyrazol-10-yl)methanone; | 2.49 |
| 7 | racemic-(3-(4H-1,2,4-Triazol-4-yl)phenyl)((5R,9S)-2-methyl-3-phenyl-4,5,6,7,8,9-hexahydro-2H-5,9-epiminocycloocta[c]pyrazol-10-yl)methanone; | 20.36 |
| 8 | racemic-(4-(1H-1,2,4-Triazol-1-yl)phenyl)((5R,9S)-2-methyl-3-phenyl-4,5,6,7,8,9-hexahydro-2H-5,9-epiminocycloocta[c]pyrazol-10-yl)methanone; | 4.92 |
| 9 | racemic-(3-(1H-Imidazol-1-yl)phenyl)((5R,9S)-2-methyl-3-phenyl-4,5,6,7,8,9-hexahydro-2H-5,9-epiminocycloocta[c]pyrazol-10-yl)methanone; | 12.22 |
| 10 | racemic-(1-Methyl-1H-1,2,4-triazol-3-yl)((5R,9S)-2-methyl-3-phenyl-4,5,6,7,8,9-hexahydro-2H-5,9-epiminocycloocta[c]pyrazol-10-yl)methanone; | 5999.29 |
| 11 | racemic-(5-Chloro-1-methyl-1H-pyrazol-4-yl)((5R,9S)-2-methyl-3-phenyl-4,5,6,7,8,9-hexahydro-2H-5,9-epiminocycloocta[c]pyrazol-10-yl)methanone; | 101.51 |
| 12 | racemic-(5-Methoxy-1-methyl-1H-pyrazol-4-yl)((5R,9S)-2-methyl-3-phenyl-4,5,6,7,8,9-hexahydro-2H-5,9-epiminocycloocta[c]pyrazol-10-yl)methanone; | 92.17 |
| 13 | racemic-(4-Bromo-1-methyl-3-(trifluoromethyl)-1H-pyrazol-5-yl)((5R,9S)-2-methyl-3-phenyl-4,5,6,7,8,9-hexahydro-2H-5,9-epiminocycloocta[c]pyrazol-10-yl)methanone; | 543.63 |
| 14 | racemic-(5-Cyclopropyl-1-methyl-1H-pyrazol-4-yl)((5R,9S)-2-methyl-3-phenyl-4,5,6,7,8,9-hexahydro-2H-5,9-epiminocycloocta[c]pyrazol-10-yl)methanone; | 4.00 |
| 15 | racemic-((5R,9S)-2-Methyl-3-phenyl-4,5,6,7,8,9-hexahydro-2H-5,9-epiminocycloocta[c]pyrazol-10-yl)(1-phenyl-1H-1,2,4-triazol-3-yl)methanone; | 16.82 |
| 16 | racemic-((5R,9S)-2-Methyl-3-phenyl-4,5,6,7,8,9-hexahydro-2H-5,9-epiminocycloocta[c]pyrazol-10-yl)(1-phenyl-1H-pyrazol-3-yl)methanone; | 8.75 |
| 17 | racemic-(5-Methoxy-1-phenyl-1H-pyrazol-3-yl)((5R,9S)-2-methyl-3-phenyl-4,5,6,7,8,9-hexahydro-2H-5,9-epiminocycloocta[c]pyrazol-10-yl)methanone; | 6.61 |
| 18 | racemic-(1-Methyl-1H-indol-4-yl)((5R,9S)-2-methyl-3-phenyl-4,5,6,7,8,9-hexahydro-2H-5,9-epiminocycloocta[c]pyrazol-10-yl)methanone; | 0.26 |

TABLE 4-continued

| Ex # | Compound Name | MGL IC$_{50}$ (nM) |
|---|---|---|
| 19 | racemic-(5-Chloro-1H-indol-6-yl)((5R,9S)-2-methyl-3-phenyl-4,5,6,7,8,9-hexahydro-2H-5,9-epiminocycloocta[c]pyrazol-10-yl)methanone; | 24.73 |
| 20 | racemic-(7-Methyl-1H-indazol-5-yl)((5R,9S)-2-methyl-3-phenyl-4,5,6,7,8,9-hexahydro-2H-5,9-epiminocycloocta[c]pyrazol-10-yl)methanone; | 1.10 |
| 21 | racemic-(1-Methyl-1H-pyrrolo[2,3-b]pyridin-4-yl)((5R,9S)-2-methyl-3-phenyl-4,5,6,7,8,9-hexahydro-2H-5,9-epiminocycloocta[c]pyrazol-10-yl)methanone; | 0.29 |
| 22 | racemic-(4-Chloro-1H-pyrrolo[2,3-b]pyridin-5-yl)((5R,9S)-2-methyl-3-phenyl-4,5,6,7,8,9-hexahydro-2H-5,9-epiminocycloocta[c]pyrazol-10-yl)methanone; | 1.30 |
| 23 | racemic-(4-Fluoro-1H-pyrrolo[2,3-b]pyridin-5-yl)((5R,9S)-2-methyl-3-phenyl-4,5,6,7,8,9-hexahydro-2H-5,9-epiminocycloocta[c]pyrazol-10-yl)methanone; | 2.14 |
| 24 | racemic-(1-Methyl-1H-pyrrolo[2,3-b]pyridin-3-yl)((5R,9S)-2-methyl-3-phenyl-4,5,6,7,8,9-hexahydro-2H-5,9-epiminocycloocta[c]pyrazol-10-yl)methanone; | 15.65 |
| 25 | racemic-[1,2,4]Triazolo[1,5-a]pyridin-5-yl((5R,9S)-2-methyl-3-phenyl-4,5,6,7,8,9-hexahydro-2H-5,9-epiminocycloocta[c]pyrazol-10-yl)methanone; | 95.52 |
| 26 | racemic-((5R,8S)-2-Methyl-3-phenyl-2,4,5,6,7,8-hexahydro-5,8-epiminocyclohepta[c]pyrazol-9-yl)(quinolin-6-yl)methanone; | 47.72 |
| 27 | racemic-(4-Chloroquinolin-6-yl)((5R,9S)-2-methyl-3-phenyl-4,5,6,7,8,9-hexahydro-2H-5,9-epiminocycloocta[c]pyrazol-10-yl)methanone; | 1.62 |
| 28 | racemic-(4-Hydroxyquinolin-6-yl)((5R,9S)-2-methyl-3-phenyl-4,5,6,7,8,9-hexahydro-2H-5,9-epiminocycloocta[c]pyrazol-10-yl)methanone; | 223.98 |
| 29 | racemic-((5R,9S)-2-Methyl-3-phenyl-4,5,6,7,8,9-hexahydro-2H-5,9-epiminocycloocta[c]pyrazol-10-yl)(quinoxalin-5-yl)methanone; | 9.36 |
| 30 | racemic-((5R,9S)-2-Methyl-3-phenyl-4,5,6,7,8,9-hexahydro-2H-5,9-epiminocycloocta[c]pyrazol-10-yl)(quinoxalin-6-yl)methanone; | 16.58 |
| 31 | racemic-((5R,9S)-2-Methyl-3-phenyl-4,5,6,7,8,9-hexahydro-2H-5,9-epiminocycloocta[c]pyrazol-10-yl)(quinazolin-6-yl)methanone; | 132.10 |
| 32 | racemic-((5R,9S)-2-Methyl-3-phenyl-4,5,6,7,8,9-hexahydro-2H-5,9-epiminocycloocta[c]pyrazol-10-yl)(2-(trifluoromethyl)-1,8-naphthyridin-3-yl)methanone; | 1919.11 |
| 33 | racemic-(2-Chloro-3-methoxyphenyl)((5R,9S)-3-(4-fluorophenyl)-2-methyl-4,5,6,7,8,9-hexahydro-2H-5,9-epiminocycloocta[c]pyrazol-10-yl)methanone; | 7.85 |
| 34 | (2-(2H-1,2,3-Triazol-2-yl)phenyl)((5R,9S)-3-(4-fluorophenyl)-2-methyl-4,5,6,7,8,9-hexahydro-2H-5,9-epiminocycloocta[c]pyrazol-10-yl)methanone; | 11.66 |
| 35 | racemic-(1,4-Dimethyl-1H-pyrazol-3-yl)((5R,9S)-3-(4-fluorophenyl)-2-methyl-4,5,6,7,8,9-hexahydro-2H-5,9-epiminocycloocta[c]pyrazol-10-yl)methanone; | 3585.09 |
| 36 | ((5R,9S)-3-(4-Fluorophenyl)-2-methyl-4,5,6,7,8,9-hexahydro-2H-5,9-epiminocycloocta[c]pyrazol-10-yl)(1-methyl-1H-pyrazolo[3,4-b]pyridin-3-yl)methanone; | 18.68 |
| 37 | racemic-((5R,9S)-3-(4-Fluorophenyl)-2-methyl-4,5,6,7,8,9-hexahydro-2H-5,9-epiminocycloocta[c]pyrazol-10-yl)(quinolin-6-yl)methanone; | 22.61 |
| 38 | ((5R,9S)-3-(4-Fluorophenyl)-2-methyl-4,5,6,7,8,9-hexahydro-2H-5,9-epiminocycloocta[c]pyrazol-10-yl)(quinolin-6-yl)methanone; | 8.63 |
| 39 | racemic-(2-Chloro-3-methoxyphenyl)((5R,9S)-3-(3-fluorophenyl)-2-methyl-4,5,6,7,8,9-hexahydro-2H-5,9-epiminocycloocta[c]pyrazol-10-yl)methanone; | 1.87 |
| 40 | racemic-((5R,9S)-3-(3-Fluorophenyl)-2-methyl-4,5,6,7,8,9-hexahydro-2H-5,9-epiminocycloocta[c]pyrazol-10-yl)(1-phenyl-1H-1,2,4-triazol-3-yl)methanone; | 10.44 |
| 41 | ((5R,9S)-3-(3-Fluorophenyl)-2-methyl-4,5,6,7,8,9-hexahydro-2H-5,9-epiminocycloocta[c]pyrazol-10-yl)(furo[3,2-b]pyridin-6-yl)methanone; | 14.98 |
| 42 | racemic-((5R,9S)-3-(3-Fluorophenyl)-2-methyl-4,5,6,7,8,9-hexahydro-2H-5,9-epiminocycloocta[c]pyrazol-10-yl)(quinolin-6-yl)methanone; | 2.30 |
| 43 | ((5S,9R)-3-(3-Fluorophenyl)-2-methyl-4,5,6,7,8,9-hexahydro-2H-5,9-epiminocycloocta[c]pyrazol-10-yl)(quinolin-6-yl)methanone; | 1004.39 |
| 44 | ((5R,9S)-3-(3-Fluorophenyl)-2-methyl-4,5,6,7,8,9-hexahydro-2H-5,9-epiminocycloocta[c]pyrazol-10-yl)(quinolin-6-yl)methanone; | 1.63 |
| 45 | racemic-((5R,9S)-2-Cyclopropyl-3-(3-fluorophenyl)-4,5,6,7,8,9-hexahydro-2H-5,9-epiminocycloocta[c]pyrazol-10-yl)(quinolin-6-yl)methanone; | 11.84 |

TABLE 4-continued

| Ex # | Compound Name | MGL IC$_{50}$ (nM) |
|---|---|---|
| 46 | (3-(1H-1,2,4-Triazol-1-yl)phenyl)((5R,9S)-3-(3-chlorophenyl)-2-methyl-4,5,6,7,8,9-hexahydro-2H-5,9-epiminocycloocta[c]pyrazol-10-yl)methanone; | 1.50 |
| 47 | (3-(1H-Pyrazol-4-yl)phenyl)((5R,9S)-3-(3-chlorophenyl)-2-methyl-4,5,6,7,8,9-hexahydro-2H-5,9-epiminocycloocta[c]pyrazol-10-yl)methanone; | 2.46 |
| 48 | (3-(1H-Pyrazol-1-yl)phenyl)((5R,9S)-3-(3-chlorophenyl)-2-methyl-4,5,6,7,8,9-hexahydro-2H-5,9-epiminocycloocta[c]pyrazol-10-yl)methanone; | 4.27 |
| 49 | (3-(1H-Tetrazol-1-yl)phenyl)((5R,9S)-3-(3-chlorophenyl)-2-methyl-4,5,6,7,8,9-hexahydro-2H-5,9-epiminocycloocta[c]pyrazol-10-yl)methanone; | 5.10 |
| 50 | (2-Chloro-5-(4H-1,2,4-triazol-4-yl)phenyl)((5R,9S)-3-(3-chlorophenyl)-2-methyl-4,5,6,7,8,9-hexahydro-2H-5,9-epiminocycloocta[c]pyrazol-10-yl)methanone; | 44.32 |
| 51 | (4-(4H-1,2,4-Triazol-4-yl)phenyl)((5R,9S)-3-(3-chlorophenyl)-2-methyl-4,5,6,7,8,9-hexahydro-2H-5,9-epiminocycloocta[c]pyrazol-10-yl)methanone; | 2220.75 |
| 52 | ((5R,9S)-3-(3-Chlorophenyl)-2-methyl-4,5,6,7,8,9-hexahydro-2H-5,9-epiminocycloocta[c]pyrazol-10-yl)(1-isopropyl-1H-1,2,4-triazol-3-yl)methanone; | 240.10 |
| 53 | ((5R,9S)-3-(3-Chlorophenyl)-2-methyl-4,5,6,7,8,9-hexahydro-2H-5,9-epiminocycloocta[c]pyrazol-10-yl)(1-(2-fluorophenyl)-1H-1,2,4-triazol-3-yl)methanone; | 6.87 |
| 54 | ((5R,9S)-3-(3-Chlorophenyl)-2-methyl-4,5,6,7,8,9-hexahydro-2H-5,9-epiminocycloocta[c]pyrazol-10-yl)(1-(pyridin-2-yl)-1H-1,2,4-triazol-3-yl)methanone; | 12.75 |
| 55 | ((5R,9S)-3-(3-Chlorophenyl)-2-methyl-4,5,6,7,8,9-hexahydro-2H-5,9-epiminocycloocta[c]pyrazol-10-yl)(1-(3-fluorophenyl)-1H-1,2,4-triazol-3-yl)methanone; | 21.36 |
| 56 | (1-(3-Chlorophenyl)-1H-1,2,4-triazol-3-yl)((5R,9S)-3-(3-chlorophenyl)-2-methyl-4,5,6,7,8,9-hexahydro-2H-5,9-epiminocycloocta[c]pyrazol-10-yl)methanone; | 50.48 |
| 57 | ((5R,9S)-3-(3-Chlorophenyl)-2-methyl-4,5,6,7,8,9-hexahydro-2H-5,9-epiminocycloocta[c]pyrazol-10-yl)(1-phenyl-5-(trifluoromethyl)-1H-pyrazol-4-yl)methanone; | 87.70 |
| 58 | ((5R,9S)-3-(3-Chlorophenyl)-2-methyl-4,5,6,7,8,9-hexahydro-2H-5,9-epiminocycloocta[c]pyrazol-10-yl)(5-methyl-1-(3-(trifluoromethyl)phenyl)-1H-1,2,4-triazol-3-yl)methanone; | 272.58 |
| 59 | ((5R,9S)-3-(3-Chlorophenyl)-2-methyl-4,5,6,7,8,9-hexahydro-2H-5,9-epiminocycloocta[c]pyrazol-10-yl)(1-(3-(trifluoromethyl)phenyl)-1H-1,2,4-triazol-3-yl)methanone; | 531.74 |
| 60 | (1-Benzyl-1H-1,2,4-triazol-3-yl)((5R,9S)-3-(3-chlorophenyl)-2-methyl-4,5,6,7,8,9-hexahydro-2H-5,9-epiminocycloocta[c]pyrazol-10-yl)methanone; | 643.73 |
| 61 | Benzo[d]isoxazol-3-yl((5R,9S)-3-(3-chlorophenyl)-2-methyl-4,5,6,7,8,9-hexahydro-2H-5,9-epiminocycloocta[c]pyrazol-10-yl)methanone; | 0.43 |
| 62 | ((5R,9S)-3-(3-chlorophenyl)-2-methyl-4,5,6,7,8,9-hexahydro-2H-5,9-epiminocycloocta[c]pyrazol-10-yl)(1-methyl-1H-indazol-3-yl)methanone; | 2.10 |
| 63 | racemic-((5R,9S)-3-(3-Chlorophenyl)-2-methyl-4,5,6,7,8,9-hexahydro-2H-5,9-epiminocycloocta[c]pyrazol-10-yl)(quinolin-6-yl)methanone; | 0.54 |
| 64 | ((5R,9S)-3-(3-Chlorophenyl)-2-methyl-4,5,6,7,8,9-hexahydro-2H-5,9-epiminocycloocta[c]pyrazol-10-yl)(quinoxalin-6-yl)methanone; | 3.77 |
| 65 | ((5R,9S)-3-(3,5-Difluorophenyl)-2-methyl-4,5,6,7,8,9-hexahydro-2H-5,9-epiminocycloocta[c]pyrazol-10-yl)(4-(2-fluoroethoxy)quinolin-6-yl)methanone; | 0.24 |
| 66 | ((5R,9S)-3-(3,5-Difluorophenyl)-2-methyl-4,5,6,7,8,9-hexahydro-2H-5,9-epiminocycloocta[c]pyrazol-10-yl)(3-(2-fluoroethoxy)phenyl)methanone; | 2.24 |
| 68 | racemic-(2-(2H-1,2,3-Triazol-2-yl)phenyl)((5R,9S)-3-(3,5-difluorophenyl)-2-methyl-4,5,6,7,8,9-hexahydro-2H-5,9-epiminocycloocta[c]pyrazol-10-yl)methanone; | 6.51 |
| 69 | (2-(1H-1,2,4-Triazol-5-yl)phenyl)((5R,9S)-3-(3,5-difluorophenyl)-2-methyl-4,5,6,7,8,9-hexahydro-2H-5,9-epiminocycloocta[c]pyrazol-10-yl)methanone; | 10.00 |
| 70 | (2-(5-Chloro-1H-1,2,4-triazol-3-yl)phenyl)((5R,9S)-3-(3,5-difluorophenyl)-2-methyl-4,5,6,7,8,9-hexahydro-2H-5,9-epiminocycloocta[c]pyrazol-10-yl)methanone; | 3599.98 |
| 71 | ((5R,9S)-3-(3,5-Difluorophenyl)-2-methyl-4,5,6,7,8,9-hexahydro-2H-5,9-epiminocycloocta[c]pyrazol-10-yl)(3-(1-methyl-1H-pyrazol-4-yl)phenyl)methanone; | 17.44 |

TABLE 4-continued

| Ex # | Compound Name | MGL IC$_{50}$ (nM) |
|---|---|---|
| 72 | (3-(4H-1,2,4-Triazol-4-yl)phenyl)((5R,9S)-3-(3,5-difluorophenyl)-2-methyl-4,5,6,7,8,9-hexahydro-2H-5,9-epiminocycloocta[c]pyrazol-10-yl)methanone; | 23.90 |
| 73 | ((5R,9S)-3-(3,5-Difluorophenyl)-2-methyl-4,5,6,7,8,9-hexahydro-2H-5,9-epiminocycloocta[c]pyrazol-10-yl)(5-methyl-2-(2H-1,2,3-triazol-2-yl)phenyl)methanone; | 7.43 |
| 74 | ((5R,9S)-3-(3,5-Difluorophenyl)-2-methyl-4,5,6,7,8,9-hexahydro-2H-5,9-epiminocycloocta[c]pyrazol-10-yl)(3-fluoro-2-(2H-1,2,3-triazol-2-yl)phenyl)methanone; | 26.10 |
| 75 | ((5R,9S)-3-(3,5-Difluorophenyl)-2-methyl-4,5,6,7,8,9-hexahydro-2H-5,9-epiminocycloocta[c]pyrazol-10-yl)(3-fluoro-2-(oxazol-2-yl)phenyl)methanone; | 18.97 |
| 76 | racemic-((5R,9S)-3-(3,5-Difluorophenyl)-2-methyl-4,5,6,7,8,9-hexahydro-2H-5,9-epiminocycloocta[c]pyrazol-10-yl)(2-(pyrimidin-2-yl)phenyl)methanone; | 568.59 |
| 77 | racemic-((5R,9S)-3-(3,5-Difluorophenyl)-2-methyl-4,5,6,7,8,9-hexahydro-2H-5,9-epiminocycloocta[c]pyrazol-10-yl)(5-methoxy-1-methyl-1H-pyrazol-4-yl)methanone; | 65.10 |
| 78 | racemic-((5R,9S)-3-(3,5-Difluorophenyl)-2-methyl-4,5,6,7,8,9-hexahydro-2H-5,9-epiminocycloocta[c]pyrazol-10-yl)(1-ethyl-5-(trifluoromethyl)-1H-pyrazol-3-yl)methanone; | 178.61 |
| 79 | racemic-(5-Cyclopropyl-1H-pyrazol-4-yl)((5R,9S)-3-(3,5-difluorophenyl)-2-methyl-4,5,6,7,8,9-hexahydro-2H-5,9-epiminocycloocta[c]pyrazol-10-yl)methanone; | 76.00 |
| 80 | racemic-(5-Cyclopropyl-1-(2-hydroxyethyl)-1H-pyrazol-4-yl)((5R,9S)-3-(3,5-difluorophenyl)-2-methyl-4,5,6,7,8,9-hexahydro-2H-5,9-epiminocycloocta[c]pyrazol-10-yl)methanone; | 74.71 |
| 81 | racemic-(3-Cyclopropyl-1-(2,2,2-trifluoroethyl)-1H-pyrazol-4-yl)((5R,9S)-3-(3,5-difluorophenyl)-2-methyl-4,5,6,7,8,9-hexahydro-2H-5,9-epiminocycloocta[c]pyrazol-10-yl)methanone; | 138.71 |
| 82 | racemic-(5-Cyclopropyl-1-phenyl-1H-pyrazol-4-yl)((5R,9S)-3-(3,5-difluorophenyl)-2-methyl-4,5,6,7,8,9-hexahydro-2H-5,9-epiminocycloocta[c]pyrazol-10-yl)methanone; | 264.61 |
| 83 | racemic-(5-Cyclopropyl-1-(3-(trifluoromethyl)phenyl)-1H-pyrazol-4-yl)((5R,9S)-3-(3,5-difluorophenyl)-2-methyl-4,5,6,7,8,9-hexahydro-2H-5,9-epiminocycloocta[c]pyrazol-10-yl)methanone; | 117.41 |
| 84 | racemic-((5R,9S)-3-(3,5-Difluorophenyl)-2-methyl-4,5,6,7,8,9-hexahydro-2H-5,9-epiminocycloocta[c]pyrazol-10-yl)(5-methyl-1-phenyl-1H-1,2,4-triazol-3-yl)methanone; | 9.52 |
| 85 | racemic-((5R,9S)-3-(3,5-Difluorophenyl)-2-methyl-4,5,6,7,8,9-hexahydro-2H-5,9-epiminocycloocta[c]pyrazol-10-yl)(1-(4-fluorophenyl)-5-methyl-1H-1,2,4-triazol-3-yl)methanone; | 81.10 |
| 86 | racemic-((5R,9S)-3-(3,5-Difluorophenyl)-2-methyl-4,5,6,7,8,9-hexahydro-2H-5,9-epiminocycloocta[c]pyrazol-10-yl)(5-ethyl-1-phenyl-1H-1,2,4-triazol-3-yl)methanone; | 2.82 |
| 87 | ((5R,9S)-3-(3,5-Difluorophenyl)-2-methyl-4,5,6,7,8,9-hexahydro-2H-5,9-epiminocycloocta[c]pyrazol-10-yl)(2-fluoropyridin-4-yl)methanone; | 101.25 |
| 88 | ((5R,9S)-3-(3,5-Difluorophenyl)-2-methyl-4,5,6,7,8,9-hexahydro-2H-5,9-epiminocycloocta[c]pyrazol-10-yl)(5-methoxypyridin-3-yl)methanone; | 36.47 |
| 89 | (5-Aminopyridin-2-yl)((5R,9S)-3-(3,5-difluorophenyl)-2-methyl-4,5,6,7,8,9-hexahydro-2H-5,9-epiminocycloocta[c]pyrazol-10-yl)methanone; | 129.99 |
| 90 | ((5R,9S)-3-(3,5-Difluorophenyl)-2-methyl-4,5,6,7,8,9-hexahydro-2H-5,9-epiminocycloocta[c]pyrazol-10-yl)(5-methoxybenzofuran-2-yl)methanone; | 63.69 |
| 91 | ((5R,9S)-3-(3,5-Difluorophenyl)-2-methyl-4,5,6,7,8,9-hexahydro-2H-5,9-epiminocycloocta[c]pyrazol-10-yl)(2-methylbenzo[d]oxazol-6-yl)methanone; | 0.64 |
| 92 | (2-Aminobenzo[d]oxazol-6-yl)((5R,9S)-3-(3,5-difluorophenyl)-2-methyl-4,5,6,7,8,9-hexahydro-2H-5,9-epiminocycloocta[c]pyrazol-10-yl)methanone; | 0.52 |
| 93 | ((5R,9S)-3-(3,5-Difluorophenyl)-2-methyl-4,5,6,7,8,9-hexahydro-2H-5,9-epiminocycloocta[c]pyrazol-10-yl)(furo[3,2-b]pyridin-2-yl)methanone; | 12.08 |
| 94 | ((5R,9S)-3-(3,5-Difluorophenyl)-2-methyl-4,5,6,7,8,9-hexahydro-2H-5,9-epiminocycloocta[c]pyrazol-10-yl)(furo[3,2-c]pyridin-4-yl)methanone; | 14.13 |
| 95 | ((5R,9S)-3-(3,5-Difluorophenyl)-2-methyl-4,5,6,7,8,9-hexahydro-2H-5,9-epiminocycloocta[c]pyrazol-10-yl)(1-methyl-1H-pyrazolo[3,4-b]pyridin-3-yl)methanone; | 3.59 |
| 96 | racemic-((5R,9S)-3-(3,5-Difluorophenyl)-2-methyl-4,5,6,7,8,9-hexahydro-2H-5,9-epiminocycloocta[c]pyrazol-10-yl)(quinolin-6-yl)methanone; | 2.47 |

TABLE 4-continued

| Ex # | Compound Name | MGL IC$_{50}$ (nM) |
|---|---|---|
| 97 | ((5R,9S)-3-(3,5-Difluorophenyl)-2-methyl-4,5,6,7,8,9-hexahydro-2H-5,9-epiminocycloocta[c]pyrazol-10-yl)(quinolin-6-yl)methanone; | 0.56 |
| 98 | ((5S,9R)-3-(3,5-Difluorophenyl)-2-methyl-4,5,6,7,8,9-hexahydro-2H-5,9-epiminocycloocta[c]pyrazol-10-yl)(quinolin-6-yl)methanone; | 554.12 |
| 99 | ((5R,9S)-3-(3,5-Difluorophenyl)-2-methyl-4,5,6,7,8,9-hexahydro-2H-5,9-epiminocycloocta[c]pyrazol-10-yl)(isoquinolin-3-yl)methanone; | 7.73 |
| 100 | ((5R,9S)-3-(3,5-Difluorophenyl)-2-methyl-4,5,6,7,8,9-hexahydro-2H-5,9-epiminocycloocta[c]pyrazol-10-yl)(quinolin-7-yl)methanone; | 1.19 |
| 101 | (4-Bromoquinolin-6-yl)((5R,9S)-3-(3,5-difluorophenyl)-2-methyl-4,5,6,7,8,9-hexahydro-2H-5,9-epiminocycloocta[c]pyrazol-10-yl)methanone; | 0.18 |
| 102 | (3-Bromoquinolin-6-yl)((5R,9S)-3-(3,5-difluorophenyl)-2-methyl-4,5,6,7,8,9-hexahydro-2H-5,9-epiminocycloocta[c]pyrazol-10-yl)methanone; | 7.62 |
| 103 | (8-Bromoquinolin-6-yl)((5R,9S)-3-(3,5-difluorophenyl)-2-methyl-4,5,6,7,8,9-hexahydro-2H-5,9-epiminocycloocta[c]pyrazol-10-yl)methanone; | 1.92 |
| 104 | (2-Chloroquinolin-6-yl)((5R,9S)-3-(3,5-difluorophenyl)-2-methyl-4,5,6,7,8,9-hexahydro-2H-5,9-epiminocycloocta[c]pyrazol-10-yl)methanone; | 38.00 |
| 105 | ((5R,9S)-3-(3,5-Difluorophenyl)-2-methyl-4,5,6,7,8,9-hexahydro-2H-5,9-epiminocycloocta[c]pyrazol-10-yl)(8-fluoroquinolin-5-yl)methanone; | 3.60 |
| 106 | ((5R,9S)-3-(3,5-Difluorophenyl)-2-methyl-4,5,6,7,8,9-hexahydro-2H-5,9-epiminocycloocta[c]pyrazol-10-yl)(8-fluoroquinolin-6-yl)methanone; | 1.64 |
| 107 | ((5R,9S)-3-(3,5-Difluorophenyl)-2-methyl-4,5,6,7,8,9-hexahydro-2H-5,9-epiminocycloocta[c]pyrazol-10-yl)(2-(trifluoromethyl)quinolin-6-yl)methanone; | 58.90 |
| 108 | ((5R,9S)-3-(3,5-Difluorophenyl)-2-methyl-4,5,6,7,8,9-hexahydro-2H-5,9-epiminocycloocta[c]pyrazol-10-yl)(8-hydroxyquinolin-6-yl)methanone; | 2.51 |
| 109 | ((5R,9S)-3-(3,5-Difluorophenyl)-2-methyl-4,5,6,7,8,9-hexahydro-2H-5,9-epiminocycloocta[c]pyrazol-10-yl)(5-methoxyquinolin-3-yl)methanone; | 0.53 |
| 110 | ((5R,9S)-3-(3,5-Difluorophenyl)-2-methyl-4,5,6,7,8,9-hexahydro-2H-5,9-epiminocycloocta[c]pyrazol-10-yl)(8-nitroquinolin-6-yl)methanone; | 4.07 |
| 111 | (8-Aminoquinolin-6-yl)((5R,9S)-3-(3,5-difluorophenyl)-2-methyl-4,5,6,7,8,9-hexahydro-2H-5,9-epiminocycloocta[c]pyrazol-10-yl)methanone; | 11.58 |
| 112 | ((5R,9S)-3-(3,5-Difluorophenyl)-2-methyl-4,5,6,7,8,9-hexahydro-2H-5,9-epiminocycloocta[c]pyrazol-10-yl)(quinazolin-7-yl)methanone; | 20.00 |
| 113 | ((5R,9S)-3-(3,5-Difluorophenyl)-2-methyl-4,5,6,7,8,9-hexahydro-2H-5,9-epiminocycloocta[c]pyrazol-10-yl)(quinoxalin-6-yl)methanone; | 2.66 |
| 114 | ((5R,9S)-3-(3,5-Difluorophenyl)-2-methyl-4,5,6,7,8,9-hexahydro-2H-5,9-epiminocycloocta[c]pyrazol-10-yl)(quinazolin-6-yl)methanone; | 29.95 |
| 115 | ((5R,9S)-3-(3,5-Difluorophenyl)-2-methyl-4,5,6,7,8,9-hexahydro-2H-5,9-epiminocycloocta[c]pyrazol-10-yl)(2-methylquinoxalin-6-yl)methanone; | 13.79 |
| 116 | ((5R,9S)-3-(3,5-Difluorophenyl)-2-methyl-4,5,6,7,8,9-hexahydro-2H-5,9-epiminocycloocta[c]pyrazol-10-yl)(7-fluoroquinoxalin-6-yl)methanone; | 1.00 |
| 117 | ((5R,9S)-3-(3,5-Difluorophenyl)-2-methyl-4,5,6,7,8,9-hexahydro-2H-5,9-epiminocycloocta[c]pyrazol-10-yl)(1,6-naphthyridin-5-yl)methanone; | 1.91 |
| 118 | ((5R,9S)-3-(3,5-Difluorophenyl)-2-methyl-4,5,6,7,8,9-hexahydro-2H-5,9-epiminocycloocta[c]pyrazol-10-yl)(1,8-naphthyridin-3-yl)methanone; | 19.50 |
| 119 | ((5R,9S)-3-(3,5-Difluorophenyl)-2-methyl-4,5,6,7,8,9-hexahydro-2H-5,9-epiminocycloocta[c]pyrazol-10-yl)(1,8-naphthyridin-4-yl)methanone; | 42.90 |
| 120 | ((5R,9S)-3-(3,5-Difluorophenyl)-2-methyl-4,5,6,7,8,9-hexahydro-2H-5,9-epiminocycloocta[c]pyrazol-10-yl)(1,7-naphthyridin-4-yl)methanone; | 19.64 |
| 121 | ((5R,9S)-3-(3,5-Difluorophenyl)-2-methyl-4,5,6,7,8,9-hexahydro-2H-5,9-epiminocycloocta[c]pyrazol-10-yl)(1,6-naphthyridin-4-yl)methanone; | 10.26 |

TABLE 4-continued

| Ex # | Compound Name | MGL IC$_{50}$ (nM) |
|---|---|---|
| 122 | ((5R,9S)-3-(3,5-Difluorophenyl)-2-methyl-4,5,6,7,8,9-hexahydro-2H-5,9-epiminocycloocta[c]pyrazol-10-yl)(1,5-naphthyridin-2-yl)methanone; | 15.00 |
| 123 | 6-((5R,9S)-3-(3,5-Difluorophenyl)-2-methyl-4,5,6,7,8,9-hexahydro-2H-5,9-epiminocycloocta[c]pyrazole-10-carbonyl)-1-(2-fluoroethyl)quinolin-4(1H)-one; | 11.51 |
| 124 | 6-((5R,9S)-3-(3,5-Difluorophenyl)-2-methyl-4,5,6,7,8,9-hexahydro-2H-5,9-epiminocycloocta[c]pyrazole-10-carbonyl)-4-methyl-2H-benzo[b][1,4]oxazin-3(4H)-one; | 8.01 |
| 125 | ((5R,9S)-3-(3,5-Difluorophenyl)-2-methyl-4,5,6,7,8,9-hexahydro-2H-5,9-epiminocycloocta[c]pyrazol-10-yl)(4-methyl-3,4-dihydro-2H-pyrido[3,2-b][1,4]oxazin-7-yl)methanone; | 5.31 |
| 126 | (2-(2H-1,2,3-Triazol-2-yl)phenyl)((5R,9S)-3-(3,4-difluorophenyl)-2-methyl-4,5,6,7,8,9-hexahydro-2H-5,9-epiminocycloocta[c]pyrazol-10-yl)methanone; | 7.44 |
| 127 | racemic-((5R,9S)-3-(3,4-Difluorophenyl)-2-methyl-4,5,6,7,8,9-hexahydro-2H-5,9-epiminocycloocta[c]pyrazol-10-yl)(quinolin-6-yl)methanone; | 24.31 |
| 128 | ((5R,9S)-3-(3,4-Difluorophenyl)-2-methyl-4,5,6,7,8,9-hexahydro-2H-5,9-epiminocycloocta[c]pyrazol-10-yl)(quinolin-6-yl)methanone; | 2.05 |
| 129 | racemic-((5R,9S)-3-(3,4-Difluorophenyl)-2-methyl-4,5,6,7,8,9-hexahydro-2H-5,9-epiminocycloocta[c]pyrazol-10-yl)(quinoxalin-6-yl)methanone; | 54.89 |
| 130 | ((5R,9S)-3-(3-Fluoro-5-methoxyphenyl)-2-methyl-4,5,6,7,8,9-hexahydro-2H-5,9-epiminocycloocta[c]pyrazol-10-yl)(quinoxalin-6-yl)methanone; | 17.07 |
| 131 | ((5R,9S)-3-(4-Chloro-3-fluorophenyl)-2-methyl-4,5,6,7,8,9-hexahydro-2H-5,9-epiminocycloocta[c]pyrazol-10-yl)(quinoxalin-6-yl)methanone; | 55.92 |
| 132 | ((5R,9S)-3-(3-Chloro-4-methoxyphenyl)-2-methyl-4,5,6,7,8,9-hexahydro-2H-5,9-epiminocycloocta[c]pyrazol-10-yl)(quinoxalin-6-yl)methanone; | 262.00 |
| 133 | (2-(2H-1,2,3-Triazol-2-yl)phenyl)((5R,9S)-3-(3-chloro-4-methoxyphenyl)-2-methyl-4,5,6,7,8,9-hexahydro-2H-5,9-epiminocycloocta[c]pyrazol-10-yl)methanone; | 55.89 |
| 134 | ((5R,9S)-3-(3-Chloro-4-methoxyphenyl)-2-methyl-4,5,6,7,8,9-hexahydro-2H-5,9-epiminocycloocta[c]pyrazol-10-yl)(1-methyl-1H-pyrazolo[3,4-b]pyridin-3-yl)methanone; | 110.79 |
| 135 | ((5R,9S)-3-(3-Chloro-4-methoxyphenyl)-2-methyl-4,5,6,7,8,9-hexahydro-2H-5,9-epiminocycloocta[c]pyrazol-10-yl)(quinolin-6-yl)methanone; | 27.15 |
| 136 | ((5R,9S)-3-(3-Chloro-5-methoxyphenyl)-2-methyl-4,5,6,7,8,9-hexahydro-2H-5,9-epiminocycloocta[c]pyrazol-10-yl)(2-methylbenzo[d]oxazol-6-yl)methanone; | 7.02 |
| 137 | ((5R,9S)-3-(3-Chloro-5-methoxyphenyl)-2-methyl-4,5,6,7,8,9-hexahydro-2H-5,9-epiminocycloocta[c]pyrazol-10-yl)(quinolin-6-yl)methanone; | 1.00 |
| 138 | ((5R,9S)-3-(3-Chloro-5-methoxyphenyl)-2-methyl-4,5,6,7,8,9-hexahydro-2H-5,9-epiminocycloocta[c]pyrazol-10-yl)(quinoxalin-6-yl)methanone; | 6.25 |
| 139 | ((5R,9S)-3-(3,5-Dimethoxyphenyl)-2-methyl-4,5,6,7,8,9-hexahydro-2H-5,9-epiminocycloocta[c]pyrazol-10-yl)(2-methylbenzo[d]oxazol-6-yl)methanone; | 188.50 |
| 140 | ((5R,9S)-3-(3,5-Dimethoxyphenyl)-2-methyl-4,5,6,7,8,9-hexahydro-2H-5,9-epiminocycloocta[c]pyrazol-10-yl)(quinoxalin-6-yl)methanone; | 147.71 |
| 141 | (3-(4H-1,2,4Ttriazol-4-yl)phenyl)((5R,9S)-3-(3,5-dichlorophenyl)-2-methyl-4,5,6,7,8,9-hexahydro-2H-5,9-epiminocycloocta[c]pyrazol-10-yl)methanone; | 3.67 |
| 142 | ((5R,9S)-3-(3,5-Dichlorophenyl)-2-methyl-4,5,6,7,8,9-hexahydro-2H-5,9-epiminocycloocta[c]pyrazol-10-yl)(4-methyl-3,4-dihydro-2H-pyrido[3,2-b][1,4]oxazin-7-yl)methanone; | 7.02 |
| 143 | ((5R,9S)-3-(3,5-Dichlorophenyl)-2-methyl-4,5,6,7,8,9-hexahydro-2H-5,9-epiminocycloocta[c]pyrazol-10-yl)(5-methoxy-1-methyl-1H-pyrazol-4-yl)methanone; | 10.96 |
| 144 | (5-Cyclopropyl-1-methyl-1H-pyrazol-4-yl)((5R,9S)-3-(3,5-dichlorophenyl)-2-methyl-4,5,6,7,8,9-hexahydro-2H-5,9-epiminocycloocta[c]pyrazol-10-yl)methanone; | 0.31 |
| 145 | ((5R,9S)-3-(3,5-Dichlorophenyl)-2-methyl-4,5,6,7,8,9-hexahydro-2H-5,9-epiminocycloocta[c]pyrazol-10-yl)(1-phenyl-1H-1,2,4-triazol-3-yl)methanone; | 3.00 |
| 146 | ((5R,9S)-3-(3,5-Dichlorophenyl)-2-methyl-4,5,6,7,8,9-hexahydro-2H-5,9-epiminocycloocta[c]pyrazol-10-yl)(5-methoxypyridin-3-yl)methanone; | 6.90 |

TABLE 4-continued

| Ex # | Compound Name | MGL IC$_{50}$ (nM) |
|---|---|---|
| 147 | ((5R,9S)-3-(3,5-Dichlorophenyl)-2-methyl-4,5,6,7,8,9-hexahydro-2H-5,9-epiminocycloocta[c]pyrazol-10-yl)(6-methyl-3-(2H-1,2,3-triazol-2-yl)pyridin-2-yl)methanone; | 18.12 |
| 148 | ((5R,9S)-3-(3,5-Dichlorophenyl)-2-methyl-4,5,6,7,8,9-hexahydro-2H-5,9-epiminocycloocta[c]pyrazol-10-yl)(2-methylbenzo[d]oxazol-6-yl)methanone; | 2.00 |
| 149 | ((5R,9S)-3-(3,5-Dichlorophenyl)-2-methyl-4,5,6,7,8,9-hexahydro-2H-5,9-epiminocycloocta[c]pyrazol-10-yl)(furo[3,2-b]pyridin-2-yl)methanone; | 19.71 |
| 150 | ((5R,9S)-3-(3,5-Dichlorophenyl)-2-methyl-4,5,6,7,8,9-hexahydro-2H-5,9-epiminocycloocta[c]pyrazol-10-yl)(imidazo[1,5-a]pyridin-8-yl)methanone; | 0.72 |
| 151 | ((5R,9S)-3-(3,5-Dichlorophenyl)-2-methyl-4,5,6,7,8,9-hexahydro-2H-5,9-epiminocycloocta[c]pyrazol-10-yl)(imidazo[1,2-a]pyridin-3-yl)methanone; | 3.55 |
| 152 | (4-Methoxy-2-(2H-1,2,3-triazol-2-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; | 0.49 |
| 153 | ((5R,9S)-3-(3,5-Dichlorophenyl)-2-methyl-4,5,6,7,8,9-hexahydro-2H-5,9-epiminocycloocta[c]pyrazol-10-yl)(quinoxalin-6-yl)methanone; | 1.19 |
| 154 | racemic-((5R,9S)-3-(3-(Difluoromethyl)-4-fluorophenyl)-2-methyl-4,5,6,7,8,9-hexahydro-2H-5,9-epiminocycloocta[c]pyrazol-10-yl)(quinolin-6-yl)methanone; | 38.43 |
| 155 | racemic-((5R,9S)-3-(3-(Difluoromethyl)-4-fluorophenyl)-2-methyl-4,5,6,7,8,9-hexahydro-2H-5,9-epiminocycloocta[c]pyrazol-10-yl)(quinoxalin-6-yl)methanone; | 120.34 |
| 156 | ((5R,9S)-3-(3-Fluoro-5-(trifluoromethyl)phenyl)-2-methyl-4,5,6,7,8,9-hexahydro-2H-5,9-epiminocycloocta[c]pyrazol-10-yl)(quinoxalin-6-yl)methanone; | 57.28 |
| 157 | (3-Chloro-5-methoxyphenyl)((5R,9S)-2-methyl-3-(3,4,5-trifluorophenyl)-4,5,6,7,8,9-hexahydro-2H-5,9-epiminocycloocta[c]pyrazol-10-yl)methanone; | 2.37 |
| 158 | N-(3-Methoxy-5-((5R,9S)-2-methyl-3-(3,4,5-trifluorophenyl)-4,5,6,7,8,9-hexahydro-2H-5,9-epiminocycloocta[c]pyrazole-10-carbonyl)phenyl)acetamide; | 2.56 |
| 159 | (3-(4H-1,2,4-Triazol-4-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; | 13.45 |
| 160 | (2-(4H-1,2,4-Triazol-4-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; | 7476.53 |
| 161 | (3-Fluoro-2-(1H-1,2,4-triazol-1-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; | 1.00 |
| 162 | (4-Fluoro-2-(1H-1,2,4-triazol-1-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; | 4.41 |
| 163 | (5-Fluoro-2-(1H-1,2,4-triazol-1-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; | 1.14 |
| 164 | (4-Methyl-2-(1H-1,2,4-triazol-1-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; | 1.66 |
| 165 | (5-Methyl-2-(1H-1,2,4-triazol-1-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; | 0.93 |
| 166 | (2-(1H-1,2,4-Triazol-1-yl)-5-(trifluoromethyl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; | 3.22 |
| 167 | ((5R,9S)-2-Methyl-3-(3,4,5-trifluorophenyl)-4,5,6,7,8,9-hexahydro-2H-5,9-epiminocycloocta[c]pyrazol-10-yl)(2-(3-(trifluoromethyl)-1H-1,2,4-triazol-1-yl)phenyl)methanone; | 39.13 |
| 168 | (2-(1H-Imidazol-1-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; | 20.77 |
| 169 | (5-Fluoro-2-(1H-pyrazol-1-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; | 2.77 |
| 170 | (3-(1-Methyl-1H-pyrazol-4-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; | 9.58 |
| 171 | (3-(4-Fluoro-1H-pyrazol-1-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; | 12.35 |

TABLE 4-continued

| Ex # | Compound Name | MGL IC$_{50}$ (nM) |
|---|---|---|
| 172 | ((5R,9S)-2-Methyl-3-(3,4,5-trifluorophenyl)-4,5,6,7,8,9-hexahydro-2H-5,9-epiminocycloocta[c]pyrazol-10-yl)(3-(4-(trifluoromethyl)-1H-pyrazol-1-yl)phenyl)methanone; | 13.46 |
| 173 | (3-(4-Methoxy-1H-pyrazol-1-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; | 18.42 |
| 174 | ((5R,9S)-2-Methyl-3-(3,4,5-trifluorophenyl)-4,5,6,7,8,9-hexahydro-2H-5,9-epiminocycloocta[c]pyrazol-10-yl)(3-(3-(trifluoromethyl)-1H-pyrazol-1-yl)phenyl)methanone; | 54.97 |
| 175 | (3-(2H-1,2,3-Triazol-2-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; | 1.78 |
| 176 | (5-Fluoro-2-(2H-1,2,3-triazol-2-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; | 3.24 |
| 177 | (3-Methyl-2-(2H-1,2,3-triazol-2-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; | 17.61 |
| 178 | (3-Methoxy-2-(2H-1,2,3-triazol-2-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; | 49.37 |
| 179 | (4-Methoxy-2-(2H-1,2,3-triazol-2-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; | 3.87 |
| 180 | (5-Methoxy-2-(2H-1,2,3-triazol-2-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; | 1.03 |
| 181 | (2-(2H-1,2,3-Triazol-2-yl)-4-(trifluoromethyl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; | 88.53 |
| 182 | (2-(2H-1,2,3-Triazol-2-yl)-5-(trifluoromethyl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; | 37.07 |
| 183 | (2-(1H-1,2,3-Triazol-1-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; | 76.05 |
| 184 | (3-Methoxy-2-(1H-1,2,3-triazol-1-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; | 152.51 |
| 185 | ((5R,9S)-2-Methyl-3-(3,4,5-trifluorophenyl)-4,5,6,7,8,9-hexahydro-2H-5,9-epiminocycloocta[c]pyrazol-10-yl)(4,5,6,7-tetrahydropyrazolo[1,5-a]pyridin-3-yl)methanone; | 5.05 |
| 186 | (3,4-Dihydro-2H-pyrano[3,2-b]pyridin-7-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 0.70 |
| 187 | (6,7-Dihydro-5H-pyrazolo[5,l-b][1,3]oxazin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 9.40 |
| 188 | ((5R,9S)-2-Methyl-3-(3,4,5-trifluorophenyl)-4,5,6,7,8,9-hexahydro-2H-5,9-epiminocycloocta[c]pyrazol-10-yl)(6-methyl-6,7-dihydro-5H-pyrazolo[5,1-b][1,3]oxazin-3-yl)methanone; | 26.91 |
| 189 | (6,7-Dihydro-5H-pyrazolo[5,l-b][1,3]oxazin-2-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 86.42 |
| 190 | ((5R,9S)-2-Methyl-3-(3,4,5-trifluorophenyl)-4,5,6,7,8,9-hexahydro-2H-5,9-epiminocycloocta[c]pyrazol-10-yl)(1-methyl-5-(trifluoromethyl)-1H-pyrazol-4-yl)methanone; | 3.03 |
| 191 | (1-(tert-Butyl)-5-(trifluoromethyl)-1H-pyrazol-4-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 14.22 |
| 192 | (5-Ethyl-1-phenyl-1H-1,2,4-triazol-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 1.88 |
| 193 | ((5R,9S)-2-Methyl-3-(3,4,5-trifluorophenyl)-4,5,6,7,8,9-hexahydro-2H-5,9-epiminocycloocta[c]pyrazol-10-yl)(1-phenyl-5-(trifluoromethyl)-1H-pyrazol-3-yl)methanone; | 32.14 |
| 194 | ((5R,9S)-2-Methyl-3-(3,4,5-trifluorophenyl)-4,5,6,7,8,9-hexahydro-2H-5,9-epiminocycloocta[c]pyrazol-10-yl)(1-phenyl-5-(trifluoromethyl)-1H-1,2,4-triazol-3-yl)methanone; | 18.49 |
| 195 | (5-Methoxy-1-phenyl-1H-1,2,4-triazol-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 1.53 |
| 196 | (1-(3-Fluorophenyl)-1H-1,2,4-triazol-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 13.69 |

TABLE 4-continued

| Ex # | Compound Name | MGL IC$_{50}$ (nM) |
|---|---|---|
| 197 | (1-(4-Fluorophenyl)-5-methyl-1H-1,2,4-triazol-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 19.03 |
| 198 | (1-(2-Methoxyphenyl)-1H-1,2,4-triazol-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 18.07 |
| 199 | (1-(3-Methoxyphenyl)-1H-1,2,4-triazol-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 258.29 |
| 200 | (4-Methoxypyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 26.04 |
| 201 | (6-Methoxypyridin-2-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 26.76 |
| 202 | (4-Methoxypyridin-2-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 75.93 |
| 203 | (5-Methoxypyridin-2-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 245.58 |
| 204 | (6-Methoxypyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 102.00 |
| 205 | (5-Isopropoxypyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 84.33 |
| 206 | ((5R,9S)-2-Methyl-3-(3,4,5-trifluorophenyl)-4,5,6,7,8,9-hexahydro-2H-5,9-epiminocycloocta[c]pyrazol-10-yl)(6-(trifluoromethoxy)pyridin-2-yl)methanone; | 51.40 |
| 207 | ((5R,9S)-2-Methyl-3-(3,4,5-trifluorophenyl)-4,5,6,7,8,9-hexahydro-2H-5,9-epiminocycloocta[c]pyrazol-10-yl)(5-(trifluoromethoxy)pyridin-2-yl)methanone; | 1124.86 |
| 208 | 6-((5R,9S)-2-Methyl-3-(3,4,5-trifluorophenyl)-4,5,6,7,8,9-hexahydro-2H-5,9-epiminocycloocta[c]pyrazole-10-carbonyl)picolinonitrile; | 294.10 |
| 209 | ((5R,9S)-2-Methyl-3-(3,4,5-trifluorophenyl)-4,5,6,7,8,9-hexahydro-2H-5,9-epiminocycloocta[c]pyrazol-10-yl)(pyrazin-2-yl)methanone; | 665.12 |
| 210 | ((5R,9S)-2-Methyl-3-(3,4,5-trifluorophenyl)-4,5,6,7,8,9-hexahydro-2H-5,9-epiminocycloocta[c]pyrazol-10-yl)(pyrimidin-4-yl)methanone; | 1768.07 |
| 211 | ((5R,9S)-2-Methyl-3-(3,4,5-trifluorophenyl)-4,5,6,7,8,9-hexahydro-2H-5,9-epiminocycloocta[c]pyrazol-10-yl)(pyridazin-4-yl)methanone; | 3199.63 |
| 212 | ((5R,9S)-2-Methyl-3-(3,4,5-trifluorophenyl)-4,5,6,7,8,9-hexahydro-2H-5,9-epiminocycloocta[c]pyrazol-10-yl)(pyrimidin-5-yl)methanone; | 3199.63 |
| 213 | (5-(1H-Pyrazol-1-yl)pyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 33.24 |
| 214 | (6-(1H-Pyrazol-1-yl)pyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 45.44 |
| 215 | (6-(1H-Pyrrol-1-yl)pyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 117.41 |
| 216 | (6-(1H-Imidazol-1-yl)pyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 151.71 |
| 217 | (6-Methyl-3-(2H-1,2,3-triazol-2-yl)pyridin-2-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 27.03 |
| 218 | ((5R,9S)-2-Methyl-3-(3,4,5-trifluorophenyl)-4,5,6,7,8,9-hexahydro-2H-5,9-epiminocycloocta[c]pyrazol-10-yl)(5-(pyrrolidin-1-yl)pyridin-3-yl)methanone; | 10.04 |
| 219 | 1-(5-((5R,9S)-2-Methyl-3-(3,4,5-trifluorophenyl)-4,5,6,7,8,9-hexahydro-2H-5,9-epiminocycloocta[c]pyrazole-10-carbonyl)pyridin-3-yl)pyrrolidin-2-one; | 139.09 |
| 220 | ((5R,9S)-2-Methyl-3-(3,4,5-trifluorophenyl)-4,5,6,7,8,9-hexahydro-2H-5,9-epiminocycloocta[c]pyrazol-10-yl)(5-morpholinopyridin-3-yl)methanone; | 55.89 |
| 221 | ((5R,9S)-2-Methyl-3-(3,4,5-trifluorophenyl)-4,5,6,7,8,9-hexahydro-2H-5,9-epiminocycloocta[c]pyrazol-10-yl)(2-methylindolizin-6-yl)methanone; | 142.10 |

TABLE 4-continued

| Ex # | Compound Name | MGL IC$_{50}$ (nM) |
|---|---|---|
| 222 | ((5R,9S)-2-Methyl-3-(3,4,5-trifluorophenyl)-4,5,6,7,8,9-hexahydro-2H-5,9-epiminocycloocta[c]pyrazol-10-yl)(2-methylbenzo[d]oxazol-6-yl)methanone; | 5.06 |
| 223 | ((5R,9S)-2-Methyl-3-(3,4,5-trifluorophenyl)-4,5,6,7,8,9-hexahydro-2H-5,9-epiminocycloocta[c]pyrazol-10-yl)(pyrazolo[1,5-a]pyridin-3-yl)methanone; | 1.49 |
| 224 | ((5R,9S)-2-Methyl-3-(3,4,5-trifluorophenyl)-4,5,6,7,8,9-hexahydro-2H-5,9-epiminocycloocta[c]pyrazol-10-yl)(5-methylpyrazolo[1,5-a]pyridin-3-yl)methanone; | 1.11 |
| 225 | ((5R,9S)-2-Methyl-3-(3,4,5-trifluorophenyl)-4,5,6,7,8,9-hexahydro-2H-5,9-epiminocycloocta[c]pyrazol-10-yl)(pyrazolo[1,5-a]pyridin-5-yl)methanone; | 8.95 |
| 226 | ((5R,9S)-2-Methyl-3-(3,4,5-trifluorophenyl)-4,5,6,7,8,9-hexahydro-2H-5,9-epiminocycloocta[c]pyrazol-10-yl)(pyrazolo[1,5-a]pyridin-6-yl)methanone; | 12.20 |
| 227 | ((5R,9S)-2-Methyl-3-(3,4,5-trifluorophenyl)-4,5,6,7,8,9-hexahydro-2H-5,9-epiminocycloocta[c]pyrazol-10-yl)(pyrazolo[1,5-a]pyridin-2-yl)methanone; | 28.00 |
| 228 | Imidazo[1,2-a]pyridin-5-yl((5R,9S)-2-methyl-3-(3,4,5-trifluorophenyl)-4,5,6,7,8,9-hexahydro-2H-5,9-epiminocycloocta[c]pyrazol-10-yl)methanone; | 13.20 |
| 229 | Imidazo[1,5-a]pyridin-5-yl((5R,9S)-2-methyl-3-(3,4,5-trifluorophenyl)-4,5,6,7,8,9-hexahydro-2H-5,9-epiminocycloocta[c]pyrazol-10-yl)methanone; | 15.73 |
| 230 | Imidazo[1,5-a]pyridin-6-yl((5R,9S)-2-methyl-3-(3,4,5-trifluorophenyl)-4,5,6,7,8,9-hexahydro-2H-5,9-epiminocycloocta[c]pyrazol-10-yl)methanone; | 15.30 |
| 231 | Imidazo[1,2-a]pyridin-6-yl((5R,9S)-2-methyl-3-(3,4,5-trifluorophenyl)-4,5,6,7,8,9-hexahydro-2H-5,9-epiminocycloocta[c]pyrazol-10-yl)methanone; | 20.31 |
| 232 | ((5R,9S)-2-Methyl-3-(3,4,5-trifluorophenyl)-4,5,6,7,8,9-hexahydro-2H-5,9-epiminocycloocta[c]pyrazol-10-yl)(7-methylimidazo[1,2-a]pyridin-3-yl)methanone; | 17.77 |
| 233 | (1-Methyl-1H-pyrrolo[2,3-b]pyridin-4-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 0.26 |
| 234 | (1-Methyl-1H-pyrrolo[2,3-b]pyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 14.63 |
| 235 | ((5R,9S)-2-Methyl-3-(3,4,5-trifluorophenyl)-4,5,6,7,8,9-hexahydro-2H-5,9-epiminocycloocta[c]pyrazol-10-yl)(pyrrolo[1,2-b]pyridazin-5-yl)methanone; | 1.14 |
| 236 | ((5R,9S)-2-Methyl-3-(3,4,5-trifluorophenyl)-4,5,6,7,8,9-hexahydro-2H-5,9-epiminocycloocta[c]pyrazol-10-yl)(pyrrolo[1,2-a]pyrazin-8-yl)methanone; | 1.26 |
| 237 | (4-Methoxy-1-methyl-1H-indazol-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 4.89 |
| 238 | (1-Methyl-1H-pyrazolo[3,4-b]pyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 5.36 |
| 239 | ((5R,9S)-2-Methyl-3-(3,4,5-trifluorophenyl)-4,5,6,7,8,9-hexahydro-2H-5,9-epiminocycloocta[c]pyrazol-10-yl)(pyrazolo[1,5-b]pyridazin-3-yl)methanone; | 17.03 |
| 240 | ((5R,9S)-2-Methyl-3-(3,4,5-trifluorophenyl)-4,5,6,7,8,9-hexahydro-2H-5,9-epiminocycloocta[c]pyrazol-10-yl)(pyrazolo[1,5-a]pyrimidin-2-yl)methanone; | 70.62 |
| 241 | ((5R,9S)-2-Methyl-3-(3,4,5-trifluorophenyl)-4,5,6,7,8,9-hexahydro-2H-5,9-epiminocycloocta[c]pyrazol-10-yl)(pyrazolo[1,5-a]pyrimidin-3-yl)methanone; | 23.31 |
| 242 | ((5R,9S)-2-Methyl-3-(3,4,5-trifluorophenyl)-4,5,6,7,8,9-hexahydro-2H-5,9-epiminocycloocta[c]pyrazol-10-yl)(6-methylpyrazolo[1,5-a]pyrimidin-3-yl)methanone; | 10.26 |
| 243 | ((5R,9S)-2-Methyl-3-(3,4,5-trifluorophenyl)-4,5,6,7,8,9-hexahydro-2H-5,9-epiminocycloocta[c]pyrazol-10-yl)(pyrazolo[1,5-a]pyrimidin-5-yl)methanone; | 73.60 |
| 244 | ((5R,9S)-2-Methyl-3-(3,4,5-trifluorophenyl)-4,5,6,7,8,9-hexahydro-2H-5,9-epiminocycloocta[c]pyrazol-10-yl)(pyrazolo[1,5-a]pyrazin-3-yl)methanone; | 16.41 |
| 245 | Imidazo[1,2-b]pyridazin-6-yl((5R,9S)-2-methyl-3-(3,4,5-trifluorophenyl)-4,5,6,7,8,9-hexahydro-2H-5,9-epiminocycloocta[c]pyrazol-10-yl)methanone; | 23.81 |
| 246 | Imidazo[1,2-b]pyridazin-3-yl((5R,9S)-2-methyl-3-(3,4,5-trifluorophenyl)-4,5,6,7,8,9-hexahydro-2H-5,9-epiminocycloocta[c]pyrazol-10-yl)methanone; | 3.23 |

TABLE 4-continued

| Ex # | Compound Name | MGL IC$_{50}$ (nM) |
|---|---|---|
| 247 | [1,2,4]Triazolo[1,5-a]pyridin-7-yl((5R,9S)-2-methyl-3-(3,4,5-trifluorophenyl)-4,5,6,7,8,9-hexahydro-2H-5,9-epiminocycloocta[c]pyrazol-10-yl)methanone; | 418.99 |
| 248 | ((5R,9S)-2-Methyl-3-(3,4,5-trifluorophenyl)-4,5,6,7,8,9-hexahydro-2H-5,9-epiminocycloocta[c]pyrazol-10-yl)(5-methyl-5H-pyrrolo[2,3-b]pyrazin-7-yl)methanone; | 97.16 |
| 249 | Imidazo[1,2-a]pyrimidin-3-yl((5R,9S)-2-methyl-3-(3,4,5-trifluorophenyl)-4,5,6,7,8,9-hexahydro-2H-5,9-epiminocycloocta[c]pyrazol-10-yl)methanone; | 221.00 |
| 250 | ((5R,9S)-2-Methyl-3-(3,4,5-trifluorophenyl)-4,5,6,7,8,9-hexahydro-2H-5,9-epiminocycloocta[c]pyrazol-10-yl)(quinolin-4-yl)methanone; | 0.29 |
| 251 | Isoquinolin-1-yl((5R,9S)-2-methyl-3-(3,4,5-trifluorophenyl)-4,5,6,7,8,9-hexahydro-2H-5,9-epiminocycloocta[c]pyrazol-10-yl)methanone; | 0.43 |
| 252 | ((5R,9S)-2-Methyl-3-(3,4,5-trifluorophenyl)-4,5,6,7,8,9-hexahydro-2H-5,9-epiminocycloocta[c]pyrazol-10-yl)(quinolin-6-yl)methanone; | 1.28 |
| 253 | ((5R,9S)-2-Methyl-3-(3,4,5-trifluorophenyl)-4,5,6,7,8,9-hexahydro-2H-5,9-epiminocycloocta[c]pyrazol-10-yl)(quinolin-7-yl)methanone; | 3.09 |
| 254 | ((5R,9S)-2-Methyl-3-(3,4,5-trifluorophenyl)-4,5,6,7,8,9-hexahydro-2H-5,9-epiminocycloocta[c]pyrazol-10-yl)(quinazolin-4-yl)methanone; | 0.43 |
| 255 | ((5R,9S)-2-Methyl-3-(3,4,5-trifluorophenyl)-4,5,6,7,8,9-hexahydro-2H-5,9-epiminocycloocta[c]pyrazol-10-yl)(quinoxalin-6-yl)methanone; | 5.56 |
| 256 | ((5R,9S)-2-Methyl-3-(3,4,5-trifluorophenyl)-4,5,6,7,8,9-hexahydro-2H-5,9-epiminocycloocta[c]pyrazol-10-yl)(2-methylquinoxalin-6-yl)methanone; | 15.78 |
| 257 | ((5R,9S)-2-Methyl-3-(3,4,5-trifluorophenyl)-4,5,6,7,8,9-hexahydro-2H-5,9-epiminocycloocta[c]pyrazol-10-yl)(quinoxalin-2-yl)methanone; | 16.00 |
| 258 | Cinnolin-3-yl((5R,9S)-2-methyl-3-(3,4,5-trifluorophenyl)-4,5,6,7,8,9-hexahydro-2H-5,9-epiminocycloocta[c]pyrazol-10-yl)methanone; | 20.34 |
| 259 | Cinnolin-6-yl((5R,9S)-2-methyl-3-(3,4,5-trifluorophenyl)-4,5,6,7,8,9-hexahydro-2H-5,9-epiminocycloocta[c]pyrazol-10-yl)methanone; | 28.46 |
| 260 | ((5R,9S)-2-Methyl-3-(3,4,5-trifluorophenyl)-4,5,6,7,8,9-hexahydro-2H-5,9-epiminocycloocta[c]pyrazol-10-yl)(1,5-naphthyridin-2-yl)methanone; | 12.41 |
| 261 | ((5R,9S)-2-Methyl-3-(3,4,5-trifluorophenyl)-4,5,6,7,8,9-hexahydro-2H-5,9-epiminocycloocta[c]pyrazol-10-yl)(1,5-naphthyridin-3-yl)methanone; | 53.24 |
| 262 | ((5R,9S)-2-Methyl-3-(3,4,5-trifluorophenyl)-4,5,6,7,8,9-hexahydro-2H-5,9-epiminocycloocta[c]pyrazol-10-yl)(1,6-naphthyridin-8-yl)methanone; | 2.16 |
| 263 | (2-(2H-1,2,3-Triazol-2-yl)phenyl)((5R,9S)-3-(3,5-difluoro-4-methoxyphenyl)-2-methyl-4,5,6,7,8,9-hexahydro-2H-5,9-epiminocycloocta[c]pyrazol-10-yl)methanone; | 120.50 |
| 264 | ((5R,9S)-3-(3,5-Difluoro-4-methoxyphenyl)-2-methyl-4,5,6,7,8,9-hexahydro-2H-5,9-epiminocycloocta[c]pyrazol-10-yl)(1-methyl-1H-pyrazolo[3,4-b]pyridin-3-yl)methanone; | 168.62 |
| 265 | ((5R,9S)-3-(3,5-Difluoro-4-methoxyphenyl)-2-methyl-4,5,6,7,8,9-hexahydro-2H-5,9-epiminocycloocta[c]pyrazol-10-yl)(quinolin-6-yl)methanone; | 68.99 |
| 266 | (2-(2H-1,2,3-Triazol-2-yl)phenyl)((5R,9S)-3-(3,5-difluoro-4-methoxyphenyl)-2-methyl-4,5,6,7,8,9-hexahydro-2H-5,9-epiminocycloocta[c]pyrazol-10-yl)methanone; | 14.57 |
| 267 | ((5R,9S)-3-(3,4-Difluoro-5-methoxyphenyl)-2-methyl-4,5,6,7,8,9-hexahydro-2H-5,9-epiminocycloocta[c]pyrazol-10-yl)(1-methyl-1H-pyrazolo[3,4-b]pyridin-3-yl)methanone; | 20.84 |
| 268 | ((5R,9S)-3-(3,4-Difluoro-5-methoxyphenyl)-2-methyl-4,5,6,7,8,9-hexahydro-2H-5,9-epiminocycloocta[c]pyrazol-10-yl)(quinolin-6-yl)methanone; | 5.32 |
| 269 | ((5R,9S)-2-Methyl-3-(1-methyl-1H-indol-2-yl)-4,5,6,7,8,9-hexahydro-2H-5,9-epiminocycloocta[c]pyrazol-10-yl)(quinolin-6-yl)methanone; | 34.87 |
| 270 | racemic-((5R,9S)-2-Methyl-3-(5-(trifluoromethyl)thiophen-2-yl)-4,5,6,7,8,9-hexahydro-2H-5,9-epiminocycloocta[c]pyrazol-10-yl)(quinolin-6-yl)methanone; | 54.92 |
| 271 | (4-Methoxyphenyl)((5R,9S)-2-methyl-3-(3,4,5-trifluorophenyl)-4,5,6,7,8,9-hexahydro-2H-5,9-epiminocycloocta[c]pyrazol-10-yl)methanone; | 20.42 |

TABLE 4-continued

| Ex # | Compound Name | MGL IC$_{50}$ (nM) |
|---|---|---|
| 272 | (2-Fluoro-4-methylphenyl)((5R,9S)-2-methyl-3-(3,4,5-trifluorophenyl)-4,5,6,7,8,9-hexahydro-2H-5,9-epiminocycloocta[c]pyrazol-10-yl)methanone; | 4.22 |
| 273 | (2-Fluoro-4-methoxyphenyl)((5R,9S)-2-methyl-3-(3,4,5-trifluorophenyl)-4,5,6,7,8,9-hexahydro-2H-5,9-epiminocycloocta[c]pyrazol-10-yl)methanone; | 6.39 |
| 274 | (3-Fluoro-5-(1H-pyrazol-1-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; | 7.30 |
| 275 | (3-Fluoro-5-(4H-1,2,4-triazol-4-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; | 18.07 |
| 276 | (4-Fluoro-3-(4H-1,2,4-triazol-4-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; | 329.91 |
| 277 | ((5R,9S)-2-Methyl-3-(3,4,5-trifluorophenyl)-4,5,6,7,8,9-hexahydro-2H-5,9-epiminocycloocta[c]pyrazol-10-yl)(4-methyl-3-(4H-1,2,4-triazol-4-yl)phenyl)methanone; | 352.78 |
| 278 | ((5R,9S)-2-Methyl-3-(3,4,5-trifluorophenyl)-4,5,6,7,8,9-hexahydro-2H-5,9-epiminocycloocta[c]pyrazol-10-yl)(3-methyl-5-(4H-1,2,4-triazol-4-yl)phenyl)methanone; | 21.66 |
| 279 | ((5R,9S)-2-Methyl-3-(3,4,5-trifluorophenyl)-4,5,6,7,8,9-hexahydro-2H-5,9-epiminocycloocta[c]pyrazol-10-yl)(2-methyl-3-(4H-1,2,4-triazol-4-yl)phenyl)methanone; | 43.04 |
| 280 | (2-(2H-1,2,3-Triazol-2-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; | 3.49 |
| 281 | (4-Fluoro-2-(2H-1,2,3-triazol-2-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; | 55.87 |
| 282 | (3-Fuoro-2-(2H-1,2,3-triazol-2-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; | 87.90 |
| 283 | (5-Fluoro-2-(2H-1,2,3-triazol-2-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; | 10.30 |
| 284 | (5-Methyl-2-(2H-1,2,3-triazol-2-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; | 19.45 |
| 285 | (2-(2H-1,2,3-Triazol-2-yl)-3-(trifluoromethyl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; | 319.89 |
| 286 | (2-(4-Methyl-2H-1,2,3-triazol-2-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; | 163.01 |
| 287 | ((5R,9S)-2-Methyl-3-(3,4,5-trifluorophenyl)-4,5,6,7,8,9-hexahydro-2H-5,9-epiminocycloocta[c]pyrazol-10-yl)(2-(4-(trifluoromethyl)-2H-1,2,3-triazol-2-yl)phenyl)methanone; | 368.21 |
| 288 | (5-Methoxy-2-(1H-1,2,4-triazol-1-yl)phenyl)((5R,9S)-2-methyl-3-(3,4,5-trifluorophenyl)-4,5,6,7,8,9-hexahydro-2H-5,9-epiminocycloocta[c]pyrazol-10-yl)methanone; | 2.77 |
| 289 | ((5R,9S)-2-Methyl-3-(3,4,5-trifluorophenyl)-4,5,6,7,8,9-hexahydro-2H-5,9-epiminocycloocta[c]pyrazol-10-yl)(2-(4-(trifluoromethyl)-1H-1,2,3-triazol-1-yl)phenyl)methanone; | 206.92 |
| 290 | (6-Isopropylpyrimidin-4-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 38.61 |
| 291 | (6-Methoxypyrimidin-4-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 296.89 |
| 292 | (6-(Dimethylamino)pyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 17.17 |
| 293 | (5-Methoxy-4-methylpyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 10.67 |
| 294 | (6-Methoxy-5-methylpyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 11.24 |
| 295 | (5-Fluoro-6-methoxypyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 67.92 |
| 296 | (5-Fluoro-2-methoxypyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 46.16 |

TABLE 4-continued

| Ex # | Compound Name | MGL IC$_{50}$ (nM) |
|---|---|---|
| 297 | (5,6-Dimethoxypyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 13.63 |
| 298 | (5,6-Dimethoxypyridin-2-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 31.07 |
| 299 | (3-Chloro-2-methoxypyridin-4-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 3.73 |
| 300 | (5-Chloro-6-methoxypyridin-2-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 35.46 |
| 301 | (4-Chloro-2-methylpyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 66.70 |
| 302 | (4-Chloro-5-methylpyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 3.26 |
| 303 | (3-Chloro-5-fluoropyridin-4-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 23.74 |
| 304 | (6-Cyclopropyl-2-methylpyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 92.56 |
| 305 | 1-(5-((5R,9S)-2-Methyl-3-(3,4,5-trifluorophenyl)-4,5,6,7,8,9-hexahydro-2H-5,9-epiminocycloocta[c]pyrazole-10-carbonyl)pyridin-2-yl)cyclopropane-1-carbonitrile; | 176.60 |
| 306 | (2-(1H-Pyrazol-1-yl)pyridin-4-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 62.85 |
| 307 | (4-(1H-Pyrazol-1-yl)pyridin-2-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 38.04 |
| 308 | (4-(1H-Pyrazol-1-yl)pyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 11.86 |
| 309 | (6-(1H-Pyrazol-1-yl)pyridin-2-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 9.64 |
| 310 | (6-Methyl-3-(1H-pyrazol-1-yl)pyridin-2-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 372.99 |
| 311 | (4-Methoxy-5-(1H-pyrazol-1-yl)pyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 618.44 |
| 312 | (6-Methyl-3-(1H-1,2,4-triazol-1-yl)pyridin-2-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 16.23 |
| 313 | (5-(4H-1,2,4-Triazol-4-yl)pyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 183.40 |
| 314 | (4-(4H-1,2,4-Triazol-4-yl)pyridin-2-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 48.55 |
| 315 | ((5R,9S)-2-Methyl-3-(3,4,5-trifluorophenyl)-4,5,6,7,8,9-hexahydro-2H-5,9-epiminocycloocta[c]pyrazol-10-yl)(6-methyl-4-(4H-1,2,4-triazol-4-yl)pyridin-2-yl)methanone; | 87.36 |
| 316 | (5-(2H-1,2,3-Triazol-2-yl)pyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 21.30 |
| 317 | (3-(2H-1,2,3-Triazol-2-yl)pyridin-2-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 12.08 |
| 318 | ((5R,9S)-2-Methyl-3-(3,4,5-trifluorophenyl)-4,5,6,7,8,9-hexahydro-2H-5,9-epiminocycloocta[c]pyrazol-10-yl)(6-methyl-4-(2H-1,2,3-triazol-2-yl)pyridin-2-yl)methanone; | 7.81 |
| 319 | (1,5-Dimethyl-1H-pyrazol-4-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 23.70 |
| 320 | (5-Ethyl-1-methyl-1H-pyrazol-4-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 185.70 |
| 321 | ((5R,9S)-2-Methyl-3-(3,4,5-trifluorophenyl)-4,5,6,7,8,9-hexahydro-2H-5,9-epiminocycloocta[c]pyrazol-10-yl)(1,3,5-trimethyl-1H-pyrazol-4-yl)methanone; | 21.04 |

TABLE 4-continued

| Ex # | Compound Name | MGL IC$_{50}$ (nM) |
|---|---|---|
| 322 | (5-Methoxy-1-methyl-1H-pyrazol-4-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 97.01 |
| 323 | (3-Methoxy-1-methyl-1H-pyrazol-4-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 213.30 |
| 324 | (3-Fluoro-1,5-dimethyl-1H-pyrazol-4-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 33.92 |
| 325 | (5-(Difluoromethyl)-1-methyl-1H-pyrazol-4-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 22.41 |
| 326 | (1-Cyclopropyl-5-methyl-1H-pyrazol-4-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 89.21 |
| 327 | (1-Cyclopropyl-3-methyl-1H-pyrazol-4-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 31.28 |
| 328 | (3-Cyclopropyl-1-methyl-1H-pyrazol-4-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 140.70 |
| 329 | Indolizin-7-yl((5R,9S)-2-methyl-3-(3,4,5-trifluorophenyl)-4,5,6,7,8,9-hexahydro-2H-5,9-epiminocycloocta[c]pyrazol-10-yl)methanone; | 6.68 |
| 330 | (4-Fluoropyrazolo[1,5-a]pyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 0.14 |
| 331 | (6-Fluoropyrazolo[1,5-a]pyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 3.93 |
| 332 | ((5R,9S)-2-Methyl-3-(3,4,5-trifluorophenyl)-4,5,6,7,8,9-hexahydro-2H-5,9-epiminocycloocta[c]pyrazol-10-yl)(7-methylpyrazolo[1,5-a]pyridin-3-yl)methanone; | 2.19 |
| 333 | (4-Methoxypyrazolo[1,5-a]pyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 0.87 |
| 334 | (6-Methoxypyrazolo[1,5-a]pyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 18.93 |
| 335 | Imidazo[1,5-a]pyridin-7-yl((5R,9S)-2-methyl-3-(3,4,5-trifluorophenyl)-4,5,6,7,8,9-hexahydro-2H-5,9-epiminocycloocta[c]pyrazol-10-yl)methanone; | 11.12 |
| 336 | ((5R,9S)-2-Methyl-3-(3,4,5-trifluorophenyl)-4,5,6,7,8,9-hexahydro-2H-5,9-epiminocycloocta[c]pyrazol-10-yl)(5-methylimidazo[1,5-a]pyridin-6-yl)methanone; | 8.76 |
| 337 | ((5R,9S)-2-Methyl-3-(3,4,5-trifluorophenyl)-4,5,6,7,8,9-hexahydro-2H-5,9-epiminocycloocta[c]pyrazol-10-yl)(3-methylimidazo[1,5-a]pyridin-6-yl)methanone; | 3.76 |
| 338 | ((5R,9S)-2-Methyl-3-(3,4,5-trifluorophenyl)-4,5,6,7,8,9-hexahydro-2H-5,9-epiminocycloocta[c]pyrazol-10-yl)(5-methylimidazo[1,2-a]pyridin-6-yl)methanone; | 7.88 |
| 339 | ((5R,9S)-2-Methyl-3-(3,4,5-trifluorophenyl)-4,5,6,7,8,9-hexahydro-2H-5,9-epiminocycloocta[c]pyrazol-10-yl)(7-methylimidazo[1,2-a]pyridin-5-yl)methanone; | 11.94 |
| 340 | ((5R,9S)-2-Methyl-3-(3,4,5-trifluorophenyl)-4,5,6,7,8,9-hexahydro-2H-5,9-epiminocycloocta[c]pyrazol-10-yl)(3-methylimidazo[1,2-a]pyridin-5-yl)methanone; | 4.86 |
| 341 | ((5R,9S)-2-Methyl-3-(3,4,5-trifluorophenyl)-4,5,6,7,8,9-hexahydro-2H-5,9-epiminocycloocta[c]pyrazol-10-yl)(3-methylimidazo[1,2-a]pyridin-6-yl)methanone; | 4.95 |
| 342 | ((5R,9S)-2-Methyl-3-(3,4,5-trifluorophenyl)-4,5,6,7,8,9-hexahydro-2H-5,9-epiminocycloocta[c]pyrazol-10-yl)(2-methylimidazo[1,2-a]pyridin-6-yl)methanone; | 139.99 |
| 343 | ((5R,9S)-2-Methyl-3-(3,4,5-trifluorophenyl)-4,5,6,7,8,9-hexahydro-2H-5,9-epiminocycloocta[c]pyrazol-10-yl)(2-methylimidazo[1,2-a]pyridin-5-yl)methanone; | 9.76 |
| 344 | Imidazo[1,2-a]pyridin-3-yl((5R,9S)-2-methyl-3-(3,4,5-trifluorophenyl)-4,5,6,7,8,9-hexahydro-2H-5,9-epiminocycloocta[c]pyrazol-10-yl)methanone; | 7.79 |
| 345 | (7-Fluoroimidazo[1,2-a]pyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 88.72 |
| 346 | (7-Chloroimidazo[1,2-a]pyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 187.28 |

TABLE 4-continued

| Ex # | Compound Name | MGL IC$_{50}$ (nM) |
| --- | --- | --- |
| 347 | ((5R,9S)-2-Methyl-3-(3,4,5-trifluorophenyl)-4,5,6,7,8,9-hexahydro-2H-5,9-epiminocycloocta[c]pyrazol-10-yl)(2-methylimidazo[1,2-a]pyridin-3-yl)methanone; | 0.68 |
| 348 | (2,7-Dimethylimidazo[1,2-a]pyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 11.76 |
| 349 | ((5R,9S)-3-(3-Fluoro-5-methylphenyl)-2-methyl-4,5,6,7,8,9-hexahydro-2H-5,9-epiminocycloocta[c]pyrazol-10-yl)(2-methylimidazo[1,2-a]pyridin-3-yl)methanone; | 2.73 |
| 350 | ((5R,9S)-2-Methyl-3-(3,4,5-trifluorophenyl)-4,5,6,7,8,9-hexahydro-2H-5,9-epiminocycloocta[c]pyrazol-10-yl)(5-methylimidazo[1,2-a]pyridin-3-yl)methanone; | 0.94 |
| 351 | ((5R,9S)-2-Methyl-3-(3,4,5-trifluorophenyl)-4,5,6,7,8,9-hexahydro-2H-5,9-epiminocycloocta[c]pyrazol-10-yl)(7-(trifluoromethyl)imidazo[1,2-a]pyridin-3-yl)methanone; | 91.18 |
| 352 | (2-(Difluoromethyl)imidazo[1,2-a]pyridin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 3.07 |
| 353 | (2-Methyl-2H-indazol-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 14.24 |
| 354 | (2,7-Dimethylpyrazolo[1,5-a]pyrimidin-5-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 6.96 |
| 355 | ((5R,9S)-2-Methyl-3-(3,4,5-trifluorophenyl)-4,5,6,7,8,9-hexahydro-2H-5,9-epiminocycloocta[c]pyrazol-10-yl)(7-methylpyrazolo[1,5-a]pyrimidin-6-yl)methanone; | 54.78 |
| 356 | (5-Isopropyl-3-methylpyrazolo[1,5-a]pyrimidin-7-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 1.76 |
| 357 | ((5R,9S)-2-Methyl-3-(3,4,5-trifluorophenyl)-4,5,6,7,8,9-hexahydro-2H-5,9-epiminocycloocta[c]pyrazol-10-yl)(2,3,5-trimethylpyrazolo[1,5-a]pyrimidin-7-yl)methanone; | 39.62 |
| 358 | (7-Cyclopropyl-2-methylpyrazolo[1,5-a]pyrimidin-5-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 9.15 |
| 359 | ((5R,9S)-2-Methyl-3-(3,4,5-trifluorophenyl)-4,5,6,7,8,9-hexahydro-2H-5,9-epiminocycloocta[c]pyrazol-10-yl)(2-methylpyrazolo[1,5-a]pyrimidin-3-yl)methanone; | 10.11 |
| 360 | ((5R,9S)-2-Methyl-3-(3,4,5-trifluorophenyl)-4,5,6,7,8,9-hexahydro-2H-5,9-epiminocycloocta[c]pyrazol-10-yl)(2-methylpyrazolo[1,5-b]pyridazin-3-yl)methanone; | 5.91 |
| 361 | ((5R,9S)-2-Methyl-3-(3,4,5-trifluorophenyl)-4,5,6,7,8,9-hexahydro-2H-5,9-epiminocycloocta[c]pyrazol-10-yl)(2-methylimidazo[1,2-a]pyrazin-8-yl)methanone; | 60.26 |
| 362 | ((5R,9S)-2-Methyl-3-(3,4,5-trifluorophenyl)-4,5,6,7,8,9-hexahydro-2H-5,9-epiminocycloocta[c]pyrazol-10-yl)(2,5,8-trimethylimidazo[1,2-a]pyrazin-3-yl)methanone; | 25.88 |
| 363 | ((5R,9S)-2-Methyl-3-(3,4,5-trifluorophenyl)-4,5,6,7,8,9-hexahydro-2H-5,9-epiminocycloocta[c]pyrazol-10-yl)(2-methylimidazo[1,2-b]pyridazin-3-yl)methanone; | 1.61 |
| 364 | (2,7-Dimethylimidazo[1,2-b]pyridazin-3-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 5.73 |
| 365 | ((5R,9S)-2-Methyl-3-(3,4,5-trifluorophenyl)-4,5,6,7,8,9-hexahydro-2H-5,9-epiminocycloocta[c]pyrazol-10-yl)(3-methyl-3H-imidazo[4,5-b]pyridin-7-yl)methanone; | 17.89 |
| 366 | ((5R,9S)-2-Methyl-3-(3,4,5-trifluorophenyl)-4,5,6,7,8,9-hexahydro-2H-5,9-epiminocycloocta[c]pyrazol-10-yl)(3-methyl-3H-imidazo[4,5-b]pyridin-6-yl)methanone; | 61.94 |
| 367 | ((5R,9S)-2-Methyl-3-(3,4,5-trifluorophenyl)-4,5,6,7,8,9-hexahydro-2H-5,9-epiminocycloocta[c]pyrazol-10-yl)(7-methyl-7H-pyrrolo[2,3-d]pyrimidin-4-yl)methanone; | 1.61 |
| 368 | (1-Methyl-1H-pyrazolo[3,4-b]pyridin-4-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 7.00 |
| 369 | (1-Methyl-1H-pyrazolo[3,4-d]pyrimidin-4-yl)((5R,9S)-2-methyl-3-(3,4,5-trifluorophenyl)-4,5,6,7,8,9-hexahydro-2H-5,9-epiminocycloocta[c]pyrazol-10-yl)methanone; | 6.49 |
| 370 | [1,2,4]Triazolo[4,3-a]pyridin-7-yl((5R,9S)-2-methyl-3-(3,4,5-trifluorophenyl)-4,5,6,7,8,9-hexahydro-2H-5,9-epiminocycloocta[c]pyrazol-10-yl)methanone; | 737.90 |
| 371 | ((5R,9S)-2-Methyl-3-(3,4,5-trifluorophenyl)-4,5,6,7,8,9-hexahydro-2H-5,9-epiminocycloocta[c]pyrazol-10-yl)(3-methylimidazo[1,5-a]pyrazin-1-yl)methanone; | 32.14 |

TABLE 4-continued

| Ex # | Compound Name | MGL IC$_{50}$ (nM) |
|---|---|---|
| 372 | ((5R,9S)-3-(3-Fluoro-5-methylphenyl)-2-methyl-4,5,6,7,8,9-hexahydro-2H-5,9-epiminocycloocta[c]pyrazol-10-yl)(quinolin-6-yl)methanone; | 2.68 |
| 373 | ((5R,9S)-2-Methyl-3-(3,4,5-trifluorophenyl)-4,5,6,7,8,9-hexahydro-2H-5,9-epiminocycloocta[c]pyrazol-10-yl)(4-methylquinolin-6-yl)methanone; | 0.46 |
| 374 | ((5R,9S)-3-(3,5-Difluorophenyl)-2-methyl-4,5,6,7,8,9-hexahydro-2H-5,9-epiminocycloocta[c]pyrazol-10-yl)(2-hydroxyquinolin-6-yl)methanone; | 8.98 |
| 375 | 6-((5R,9S)-3-(3,5-Difluorophenyl)-2-methyl-4,5,6,7,8,9-hexahydro-2H-5,9-epiminocycloocta[c]pyrazole-10-carbonyl)quinoline1-oxide; | 23.03 |
| 376 | ((5R,9S)-3-(3,5-Difluorophenyl)-2-methyl-4,5,6,7,8,9-hexahydro-2H-5,9-epiminocycloocta[c]pyrazol-10-yl)(quinolin-6-yl-4-t)methanone; | NT |
| 377 | ((5R,9S)-2-Methyl-3-(3,4,5-trifluorophenyl)-4,5,6,7,8,9-hexahydro-2H-5,9-epiminocycloocta[c]pyrazol-10-yl)(6-methylquinazolin-4-yl)methanone; | 9.17 |
| 378 | ((5R,9S)-2-Methyl-3-(3,4,5-trifluorophenyl)-4,5,6,7,8,9-hexahydro-2H-5,9-epiminocycloocta[c]pyrazol-10-yl)(quinoxalin-6-yl-2-d)methanone; | 2.08 |
| 379 | ((5R,9S)-2-Methyl-3-(3,4,5-trifluorophenyl)-4,5,6,7,8,9-hexahydro-2H-5,9-epiminocycloocta[c]pyrazol-10-yl)(quinoxalin-6-yl-2,3-d2)methanone; | 5.37 |
| 380 | ((5R,9S)-2-Methyl-3-(3,4,5-trifluorophenyl)-4,5,6,7,8,9-hexahydro-2H-5,9-epiminocycloocta[c]pyrazol-10-yl)(5-methyl-5,6,7,8-tetrahydroimidazo[1,2-a]pyridin-3-yl)methanone; | 155.60 |
| 381 | ((5R,9S)-2-Methyl-3-(3,4,5-trifluorophenyl)-4,5,6,7,8,9-hexahydro-2H-5,9-epiminocycloocta[c]pyrazol-10-yl)(5,6,7,8-tetrahydroimidazo[1,2-a]pyridin-3-yl)methanone; | 50.30 |
| 382 | ((5R,9S)-2-Methyl-3-(3,4,5-trifluorophenyl)-4,5,6,7,8,9-hexahydro-2H-5,9-epiminocycloocta[c]pyrazol-10-yl)(2,6,6-trimethyl-6,7-dihydro-4H-pyrazolo[5,1-c][1,4]oxazin-3-yl)methanone; | 250.50 |
| 383 | (3-Chlorophenyl)((5R,8S)-2-methyl-3-(3,4,5-trifluorophenyl)-2,4,5,6,7,8-hexahydro-5,8-epiminocyclohepta[c]pyrazol-9-yl)methanone; | 16.93 |
| 384 | (3-Methoxyphenyl)((5R,8S)-2-methyl-3-(3,4,5-trifluorophenyl)-2,4,5,6,7,8-hexahydro-5,8-epiminocyclohepta[c]pyrazol-9-yl)methanone; | 9.07 |
| 385 | ((5R,8S)-3-(2,5-Difluorophenyl)-2-methyl-2,4,5,6,7,8-hexahydro-5,8-epiminocyclohepta[c]pyrazol-9-yl)(3-methoxyphenyl)methanone; | 41.39 |
| 386 | (3-Methoxyphenyl)((5R,8S)-2-methyl-3-(2,4,5-trifluorophenyl)-2,4,5,6,7,8-hexahydro-5,8-epiminocyclohepta[c]pyrazol-9-yl)methanone; | 141.09 |
| 387 | ((5R,8S)-3-(2,3-Difluorophenyl)-2-methyl-2,4,5,6,7,8-hexahydro-5,8-epiminocyclohepta[c]pyrazol-9-yl)(3-methoxyphenyl)methanone; | 92.24 |
| 388 | (2,3-Dimethoxyphenyl)((5R,8S)-2-methyl-3-(3,4,5-trifluorophenyl)-2,4,5,6,7,8-hexahydro-5,8-epiminocyclohepta[c]pyrazol-9-yl)methanone; | 6.27 |
| 389 | (2-Fluoro-3-methoxyphenyl)((5R,8S)-2-methyl-3-(3,4,5-trifluorophenyl)-2,4,5,6,7,8-hexahydro-5,8-epiminocyclohepta[c]pyrazol-9-yl)methanone; | 7.47 |
| 390 | (2-Chloro-3-methoxyphenyl)((5R,8S)-2-methyl-3-(3,4,5-trifluorophenyl)-2,4,5,6,7,8-hexahydro-5,8-epiminocyclohepta[c]pyrazol-9-yl)methanone; | 1.19 |
| 391 | (6-Methoxypyridin-2-yl)((5R,8S)-2-methyl-3-(3,4,5-trifluorophenyl)-2,4,5,6,7,8-hexahydro-5,8-epiminocyclohepta[c]pyrazol-9-yl)methanone; | 309.89 |
| 392 | (1,5-Dimethyl-1H-pyrazol-4-yl)((5R,8S)-2-methyl-3-(3,4,5-trifluorophenyl)-2,4,5,6,7,8-hexahydro-5,8-epiminocyclohepta[c]pyrazol-9-yl)methanone; | 172.78 |
| 393 | (5-Cyclopropyl-1-methyl-1H-pyrazol-4-yl)((5R,8S)-3-(3-fluoro-5-methylphenyl)-2-methyl-2,4,5,6,7,8-hexahydro-5,8-epiminocyclohepta[c]pyrazol-9-yl)methanone; | 14.57 |
| 394 | (5-Cyclopropyl-1-methyl-1H-pyrazol-4-yl)((5R,8S)-2-methyl-3-phenyl-2,4,5,6,7,8-hexahydro-5,8-epiminocyclohepta[c]pyrazol-9-yl)methanone; | 27.30 |
| 395 | (5-Cyclopropyl-1-methyl-1H-pyrazol-4-yl)((5R,8S)-3-(3,4-difluorophenyl)-2-methyl-2,4,5,6,7,8-hexahydro-5,8-epiminocyclohepta[c]pyrazol-9-yl)methanone; | 22.25 |
| 396 | (5-Cyclopropyl-1-methyl-1H-pyrazol-4-yl)((5R,8S)-3-(2,4-difluorophenyl)-2-methyl-2,4,5,6,7,8-hexahydro-5,8-epiminocyclohepta[c]pyrazol-9-yl)methanone; | 197.52 |

TABLE 4-continued

| Ex # | Compound Name | MGL IC$_{50}$ (nM) |
|---|---|---|
| 397 | (5-Cyclopropyl-1-methyl-1H-pyrazol-4-yl)((5R,8S)-3-(3,5-difluorophenyl)-2-methyl-2,4,5,6,7,8-hexahydro-5,8-epiminocyclohepta[c]pyrazol-9-yl)methanone; | 4.94 |
| 398 | (5-Cyclopropyl-1-methyl-1H-pyrazol-4-yl)((5R,8S)-2-methyl-3-(2,3,4-trifluorophenyl)-2,4,5,6,7,8-hexahydro-5,8-epiminocyclohepta[c]pyrazol-9-yl)methanone; | 67.94 |
| 399 | (5-Cyclopropyl-1-methyl-1H-pyrazol-4-yl)((5R,8S)-2-methyl-3-(3,4,5-trifluorophenyl)-2,4,5,6,7,8-hexahydro-5,8-epiminocyclohepta[c]pyrazol-9-yl)methanone; | 25.85 |
| 400 | ((5R,8S)-2-Methyl-3-(3,4,5-trifluorophenyl)-2,4,5,6,7,8-hexahydro-5,8-epiminocyclohepta[c]pyrazol-9-yl)(2-methyl-4-(trifluoromethyl)-1H-imidazol-5-yl)methanone; | 576.90 |
| 401 | (1H-Indol-7-yl)((5R,8S)-2-methyl-3-(3,4,5-trifluorophenyl)-2,4,5,6,7,8-hexahydro-5,8-epiminocyclohepta[c]pyrazol-9-yl)methanone; | 68.44 |
| 402 | (6-Fluoro-1H-indol-7-yl)((5R,8S)-2-methyl-3-(3,4,5-trifluorophenyl)-2,4,5,6,7,8-hexahydro-5,8-epiminocyclohepta[c]pyrazol-9-yl)methanone; | 44.21 |
| 403 | (2,3-Dimethyl-1H-indol-7-yl)((5R,8S)-2-methyl-3-(3,4,5-trifluorophenyl)-2,4,5,6,7,8-hexahydro-5,8-epiminocyclohepta[c]pyrazol-9-yl)methanone; | 442.08 |
| 404 | (1H-Indazol-7-yl)((5R,8S)-2-methyl-3-(3,4,5-trifluorophenyl)-2,4,5,6,7,8-hexahydro-5,8-epiminocyclohepta[c]pyrazol-9-yl)methanone; | 107.70 |
| 405 | (1H-Benzo[d]imidazol-7-yl)((5R,8S)-2-methyl-3-(3,4,5-trifluorophenyl)-2,4,5,6,7,8-hexahydro-5,8-epiminocyclohepta[c]pyrazol-9-yl)methanone; | 323.00 |
| 406 | ((5R,8S)-2-Methyl-3-(3,4,5-trifluorophenyl)-2,4,5,6,7,8-hexahydro-5,8-epiminocyclohepta[c]pyrazol-9-yl)(2-methylbenzo[d]oxazol-6-yl)methanone; | 23.46 |
| 407 | Furo[3,2-c]pyridin-4-yl((5R,8S)-2-methyl-3-(3,4,5-trifluorophenyl)-2,4,5,6,7,8-hexahydro-5,8-epiminocyclohepta[c]pyrazol-9-yl)methanone; | 590.20 |
| 408 | (1-Methyl-1H-pyrrolo[2,3-b]pyridin-3-yl)((5R,8S)-2-methyl-3-phenyl-2,4,5,6,7,8-hexahydro-5,8-epiminocyclohepta[c]pyrazol-9-yl)methanone; | 198.61 |
| 409 | (1-Methyl-1H-pyrrolo[2,3-b]pyridin-3-yl)((5R,8S)-2-methyl-3-(3,4,5-trifluorophenyl)-2,4,5,6,7,8-hexahydro-5,8-epiminocyclohepta[c]pyrazol-9-yl)methanone; | 116.90 |
| 410 | Imidazo[1,2-a]pyridin-5-yl((5R,8S)-2-methyl-3-(3,4,5-trifluorophenyl)-2,4,5,6,7,8-hexahydro-5,8-epiminocyclohepta[c]pyrazol-9-yl)methanone; | 119.29 |
| 411 | Imidazo[1,2-a]pyridin-3-yl((5R,8S)-2-methyl-3-(3,4,5-trifluorophenyl)-2,4,5,6,7,8-hexahydro-5,8-epiminocyclohepta[c]pyrazol-9-yl)methanone; | 311.03 |
| 412 | (2-Chloroimidazo[1,2-a]pyridin-3-yl)((5R,8S)-2-methyl-3-(3,4,5-trifluorophenyl)-2,4,5,6,7,8-hexahydro-5,8-epiminocyclohepta[c]pyrazol-9-yl)methanone; | 5.91 |
| 413 | (7-Methoxyimidazo[1,2-a]pyridin-3-yl)((5R,8S)-2-methyl-3-(3,4,5-trifluorophenyl)-2,4,5,6,7,8-hexahydro-5,8-epiminocyclohepta[c]pyrazol-9-yl)methanone; | 721.61 |
| 414 | ((5R,8S)-2-Methyl-3-(3,4,5-trifluorophenyl)-2,4,5,6,7,8-hexahydro-5,8-epiminocyclohepta[c]pyrazol-9-yl)(2-methylimidazo[1,2-a]pyridin-3-yl)methanone; | 40.84 |
| 415 | (2,5-Dimethylimidazo[1,2-a]pyridin-3-yl)((5R,8S)-2-methyl-3-(3,4,5-trifluorophenyl)-2,4,5,6,7,8-hexahydro-5,8-epiminocyclohepta[c]pyrazol-9-yl)methanone; | 52.78 |
| 416 | (2,6-Dimethylimidazo[1,2-a]pyridin-3-yl)((5R,8S)-2-methyl-3-(3,4,5-trifluorophenyl)-2,4,5,6,7,8-hexahydro-5,8-epiminocyclohepta[c]pyrazol-9-yl)methanone; | 512.27 |
| 417 | ((5R,8S)-2-Methyl-3-(3,4,5-trifluorophenyl)-2,4,5,6,7,8-hexahydro-5,8-epiminocyclohepta[c]pyrazol-9-yl)(2-methylimidazo[1,2-a]pyridin-3-yl)methanone; | 156.71 |
| 418 | (5-Chloro-2-methylimidazo[1,2-a]pyridin-3-yl)((5R,8S)-2-methyl-3-(3,4,5-trifluorophenyl)-2,4,5,6,7,8-hexahydro-5,8-epiminocyclohepta[c]pyrazol-9-yl)methanone; | 320.33 |
| 419 | (2-(Difluoromethyl)imidazo[1,2-a]pyridin-3-yl)((5R,8S)-2-methyl-3-(3,4,5-trifluorophenyl)-2,4,5,6,7,8-hexahydro-5,8-epiminocyclohepta[c]pyrazol-9-yl)methanone; | 21.68 |
| 420 | ((5R,8S)-2-Methyl-3-(3,4,5-trifluorophenyl)-2,4,5,6,7,8-hexahydro-5,8-epiminocyclohepta[c]pyrazol-9-yl)(2-(trifluoromethyl)imidazo[1,2-a]pyridin-3-yl)methanone; | 16.27 |
| 421 | (5-Methyl-2-(trifluoromethyl)imidazo[1,2-a]pyridin-3-yl)((5R,8S)-2-methyl-3-(3,4,5-trifluorophenyl)-2,4,5,6,7,8-hexahydro-5,8-epiminocyclohepta[c]pyrazol-9-yl)methanone; | 33.13 |

TABLE 4-continued

| Ex # | Compound Name | MGL IC$_{50}$ (nM) |
|---|---|---|
| 422 | ((5R,8S)-2-Methyl-3-(3,4,5-trifluorophenyl)-2,4,5,6,7,8-hexahydro-5,8-epiminocyclohepta[c]pyrazol-9-yl)(pyrazolo[1,5-a]pyridin-3-yl)methanone; | 86.22 |
| 423 | ((5R,8S)-2-Methyl-3-(3,4,5-trifluorophenyl)-2,4,5,6,7,8-hexahydro-5,8-epiminocyclohepta[c]pyrazol-9-yl)(2-methylpyrazolo[1,5-a]pyridin-3-yl)methanone; | 15.19 |
| 433 | ((5S,8R)-2-Methyl-3-(3,4,5-trifluorophenyl)-2,4,5,6,7,8-hexahydro-5,8-epiminocyclohepta[c]pyrazol-9-yl)(quinolin-6-yl)methanone; | >10000 |
| 434 | ((5R,8S)-2-Methyl-3-(3,4,5-trifluorophenyl)-2,4,5,6,7,8-hexahydro-5,8-epiminocyclohepta[c]pyrazol-9-yl)(quinolin-6-yl)methanone; | 18.52 |
| 435 | (2,4-Dimethylquinolin-7-yl)((5R,8S)-2-methyl-3-(3,4,5-trifluorophenyl)-2,4,5,6,7,8-hexahydro-5,8-epiminocyclohepta[c]pyrazol-9-yl)methanone; | 52.46 |
| 436 | ((5R,8S)-2-Methyl-3-(3,4,5-trifluorophenyl)-2,4,5,6,7,8-hexahydro-5,8-epiminocyclohepta[c]pyrazol-9-yl)(6-methylquinolin-8-yl)methanone; | 5.44 |
| 437 | ((5R,8S)-2-Methyl-3-(3,4,5-trifluorophenyl)-2,4,5,6,7,8-hexahydro-5,8-epiminocyclohepta[c]pyrazol-9-yl)(quinoxalin-6-yl)methanone; | 9.93 |
| 438 | (2,3-Dimethylquinoxalin-6-yl)((5R,8S)-2-methyl-3-(3,4,5-trifluorophenyl)-2,4,5,6,7,8-hexahydro-5,8-epiminocyclohepta[c]pyrazol-9-yl)methanone; | 73.30 |
| 439 | ((5R,8S)-2-Methyl-3-phenyl-2,4,5,6,7,8-hexahydro-5,8-epiminocyclohepta[c]pyrazol-9-yl)(quinoxalin-5-yl)methanone; | 58.04 |
| 440 | ((5R,8S)-2-Methyl-3-(3,4,5-trifluorophenyl)-2,4,5,6,7,8-hexahydro-5,8-epiminocyclohepta[c]pyrazol-9-yl)(1,5-naphthyridin-3-yl)methanone; | 478.08 |
| 441 | ((5R,8S)-2-Methyl-3-(3,4,5-trifluorophenyl)-2,4,5,6,7,8-hexahydro-5,8-epiminocyclohepta[c]pyrazol-9-yl)(5-methyl-5,6,7,8-tetrahydroimidazo[1,2-a]pyridin-3-yl)methanone; | 183.11 |
| 442 | ((5R,8S)-2-Methyl-3-(3,4,5-trifluorophenyl)-2,4,5,6,7,8-hexahydro-5,8-epiminocyclohepta[c]pyrazol-9-yl)(5,6,7,8-tetrahydroimidazo[1,2-a]pyridin-3-yl)methanone; | 667.27 |
| 443 | Isochroman-7-yl((5R,8S)-2-methyl-3-(3,4,5-trifluorophenyl)-2,4,5,6,7,8-hexahydro-5,8-epiminocyclohepta[c]pyrazol-9-yl)methanone; and | 76.93 |
| 444 | (2,3-Dihydrobenzo[b][1,4]dioxin-6-yl)((5R,8S)-2-methyl-3-(3,4,5-trifluorophenyl)-2,4,5,6,7,8-hexahydro-5,8-epiminocyclohepta[c]pyrazol-9-yl)methanone. | 26.71 |

What is claimed is:

1. A method of treating a patient suffering from or diagnosed with a condition selected from the group consisting of major depressive disorder, treatment resistant depression, anxious depression and bipolar disorder, comprising administering to a patient in need thereof a compound, having the structure of Formula (I):

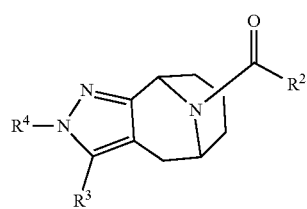

(I)

wherein
$R^2$ is selected from the group consisting of:
(a)

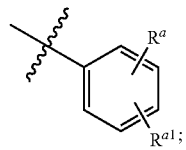

(b) 6-membered heteroaryl selected from the group consisting of: pyridazin-4-yl; pyrazin-2-yl; pyrimidinyl; pyrimidinyl substituted with $C_{1-4}$alkyl or $OC_{1-4}$alkyl; and pyridinyl, wherein the pyridinyl is substituted with one or two substituents each independently selected from the group consisting of: halo, $C_{1-4}$alkyl, $OC_{1-4}$ alkyl, $OC_{1-4}$haloalkyl, $C_{3-6}$cycloalkyl, $NH_2$, CN, $N(CH_3)_2$,

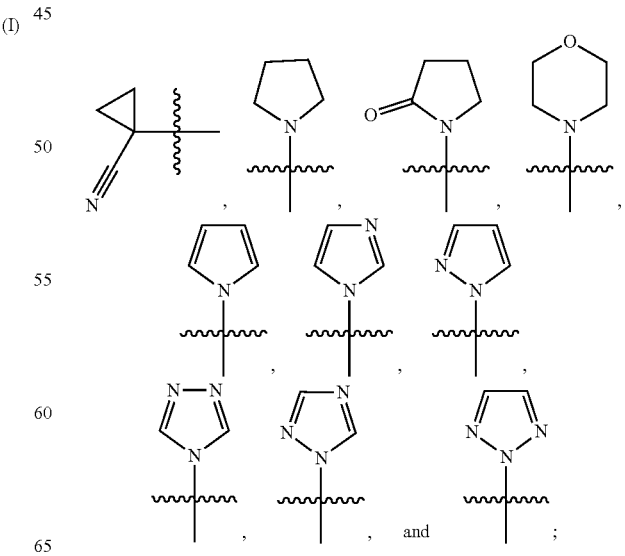

(c) 5-membered heteroaryl selected from the group consisting of:
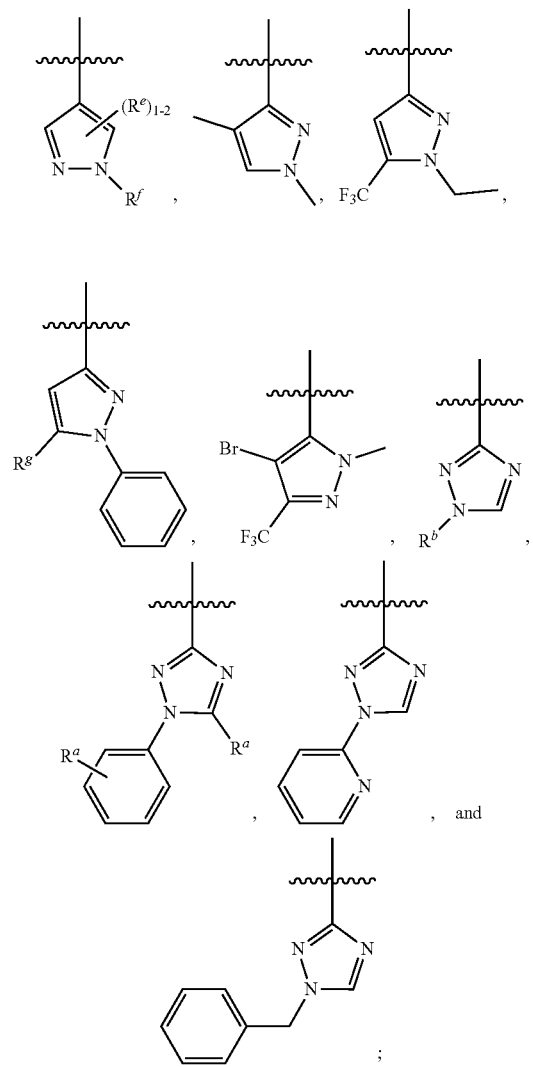
and
(d) 5,6-fused bicyclic heteroaryl or 6,5-fused bicyclic heteroaryl selected from the group consisting of:
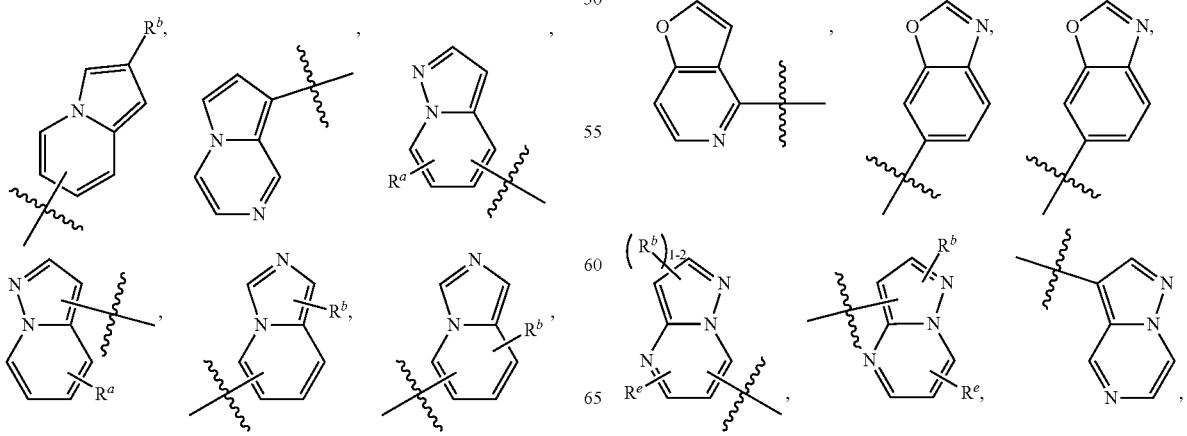
-continued
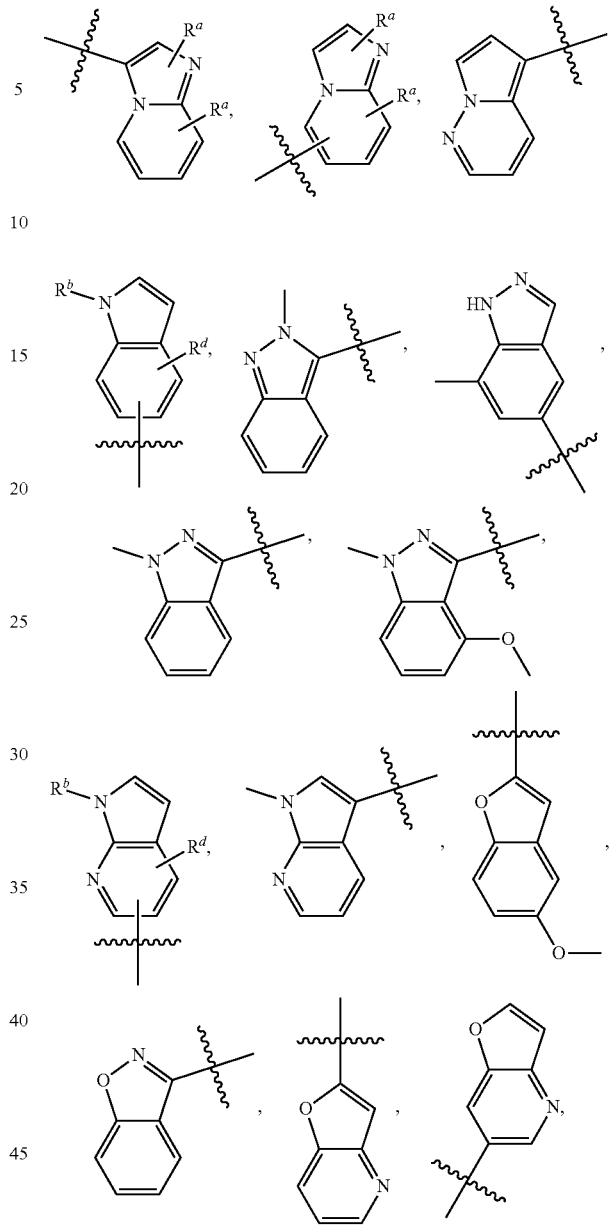
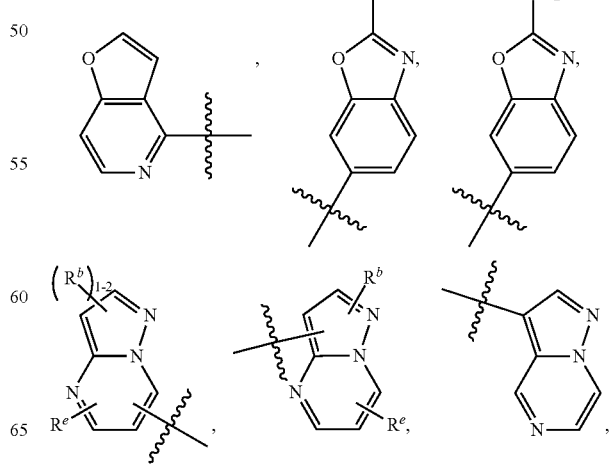

-continued
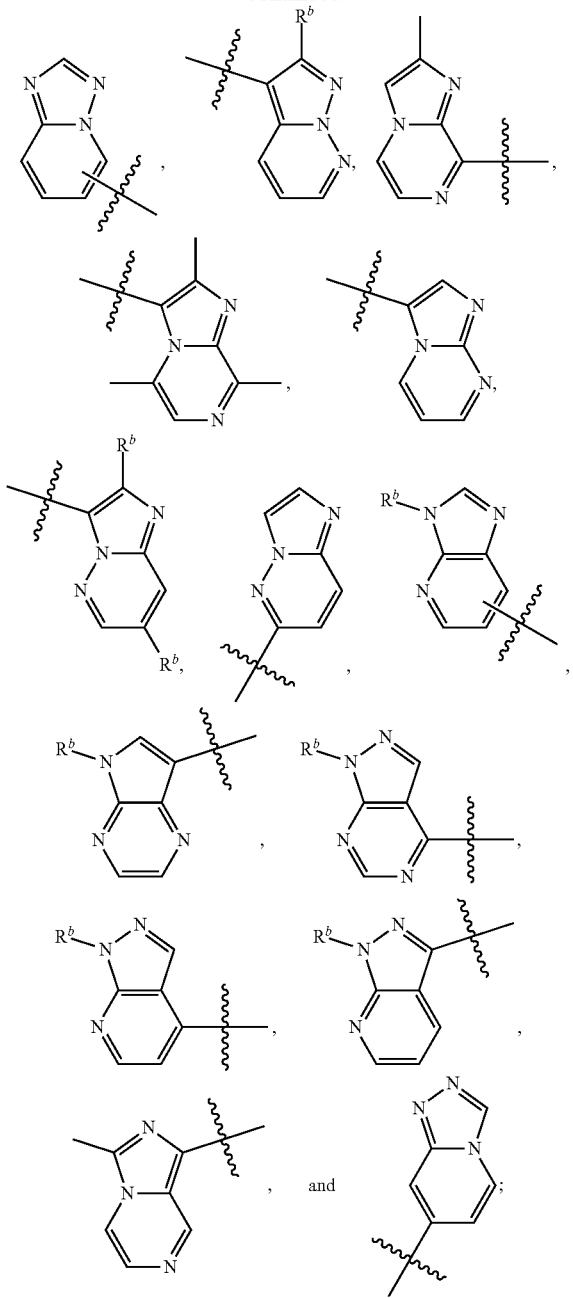
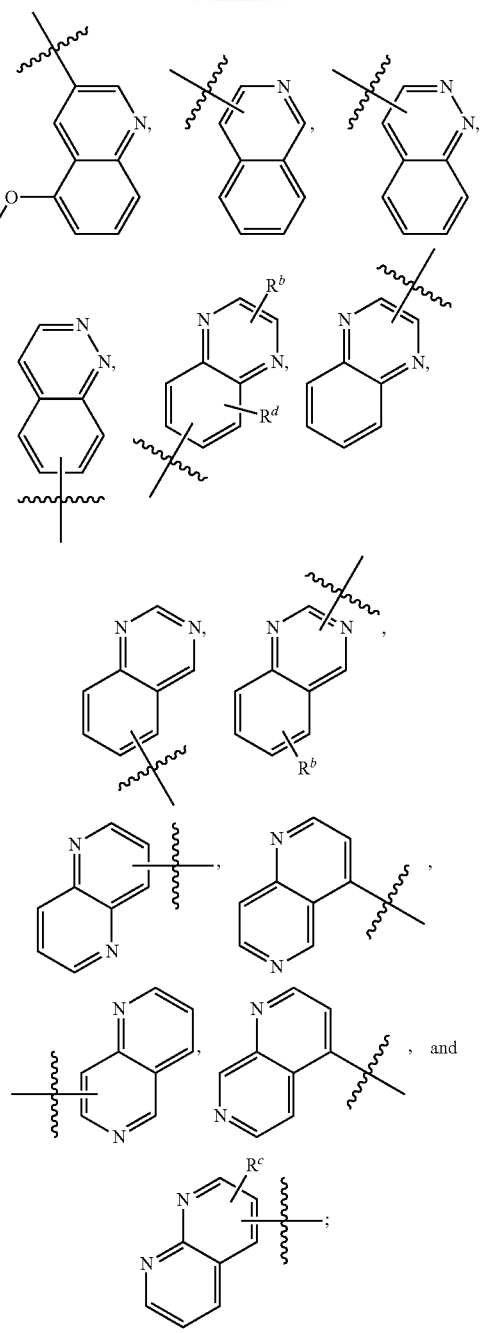
(e) 6,6-fused bicyclic heteroaryl selected from the group consisting of:
and
(f)
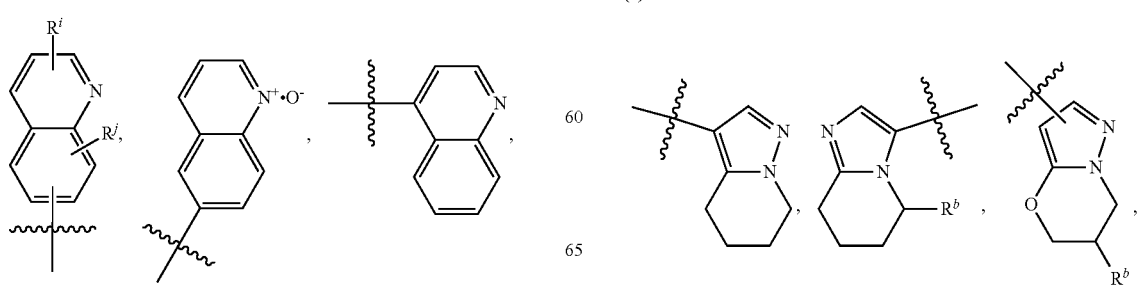

-continued

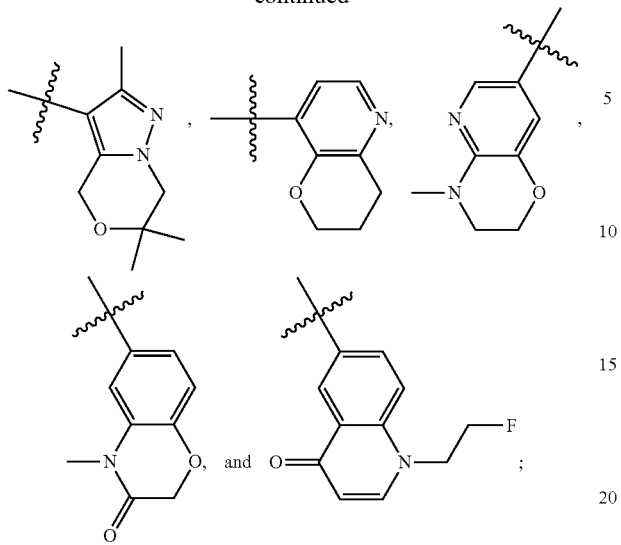

wherein
$R^a$ is selected from the group consisting of: H, halo, $C_{1-4}$alkyl, $OC_{1-4}$alkyl, $C_{1-4}$haloalkyl and $OC_{1-4}$haloalkyl;
$R^{a1}$ is selected from the group consisting of: $C_{1-4}$alkyl, $OC_{1-4}$alkyl, $OC_{1-4}$haloalkyl, $N(C=O)CH_3$, oxazol-2-yl, pyrimidin-2-yl, and 5-membered heteroaryl ring containing two, three, or four nitrogen members, wherein the 5-membered heteroaryl ring is optionally substituted with one $R^a$ member;
$R^b$ is H or $C_{1-4}$akyl;
$R^c$ is H or $C_{1-4}$haloalkyl;
$R^d$ is H or halo;
$R^e$ is selected from the group consisting of: H, halo, $C_{1-4}$akyl, $C_{1-4}$haloalkyl, $OC_{1-4}$alkyl, and $C_{3-6}$cycloalkyl;
$R^f$ is selected from the group consisting of: H, $C_{1-4}$alkyl, $CH_2CH_2OH$, $C_{1-4}$haloalkyl, cyclopropyl, phenyl, and phenyl substituted with $CF_3$;
$R^g$ is selected from the group consisting of: H, $OC_{1-4}$alkyl and $C_{1-4}$haloalkyl;
$R^i$ is H, halo, $C_{1-4}$alkyl, $C_{1-4}$haloalkyl, OH, $OC_{1-4}$alkyl, $OC_{1-4}$haloalkyl, $C_{3-6}$cycloalkyl;
$R^j$ is selected from the group consisting of: H, halo, $OCH_3$, OH, $NH_2$, and $NO_2$;
$R^3$ is selected from the group consisting of:
 (g) phenyl, wherein phenyl is independently substituted with one, two, or three members selected from the group consisting of: halo, $C_{1-4}$alkyl, $C_{1-4}$haloalkyl, and $OC_{1-4}$alkyl;
 (h) 5-(trifluoromethyl)-2-thienyl or 1-methylindol-2-yl; and
 (i) cyclopropyl; and
$R^4$ is $C_{1-4}$alkyl or $C_{3-4}$cycloalkyl;
and pharmaceutically acceptable salts thereof.

2. The method of claim 1, wherein $R^2$ is

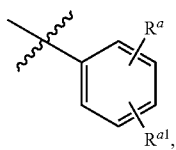

where $R^a$ is H, halo, $C_{1-4}$alkyl, or $OC_{1-4}$alkyl; and $R^{a1}$ is $C_{1-4}$alkyl, $OC_{1-4}$alkyl, $OC_{1-4}$haloalkyl, or $(C=O)NHCH_3$.

3. The method of claim 1, wherein $R^2$ is

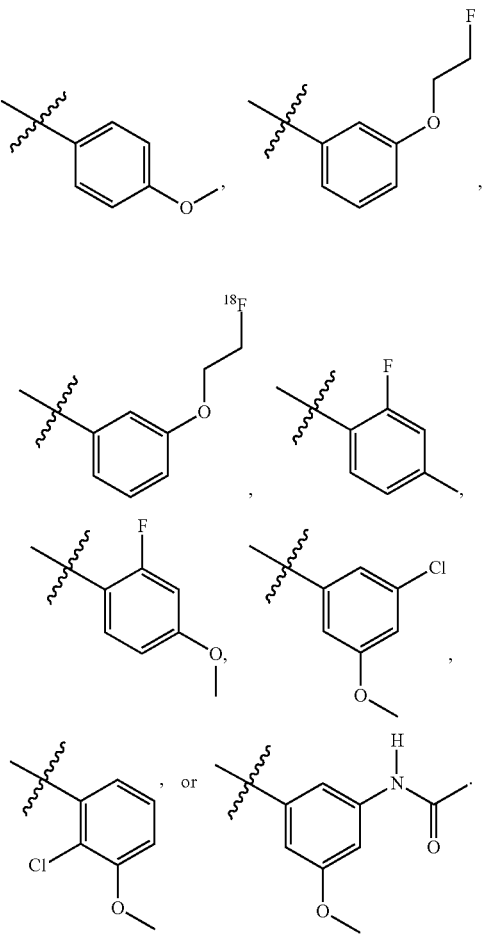

4. The method of claim 1, wherein $R^2$ is:

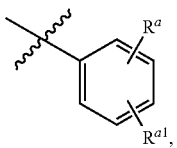

where $R^a$ is H, halo, $C_{1-4}$alkyl, $OC_{1-4}$alkyl, or $C_{1-4}$haloalkyl; and is

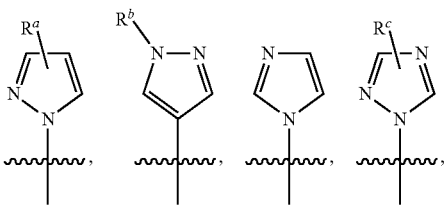

-continued
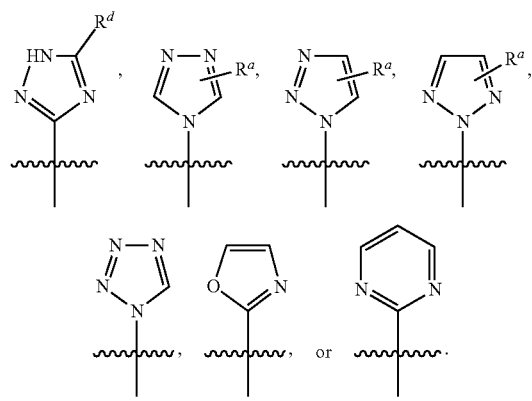
5. The method of claim 4, wherein is:
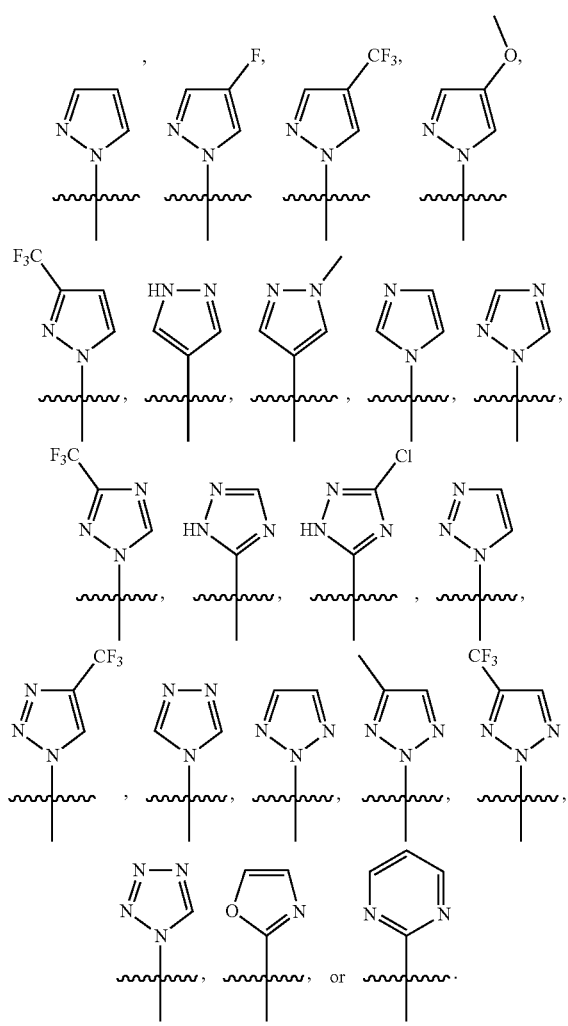
6. The method of claim 4, wherein $R^a$ is: H, Cl, F, $CH_3$, $CF_3$, or $OCH_3$.
7. The method of claim 4, wherein $R^b$ is: H or $CH_3$.
8. The method of claim 4, wherein $R^c$ is: H or $CF_3$.
9. The method of claim 4, wherein $R^d$ is: H, Cl, or F.
10. The method of claim 1, wherein $R^2$ is:
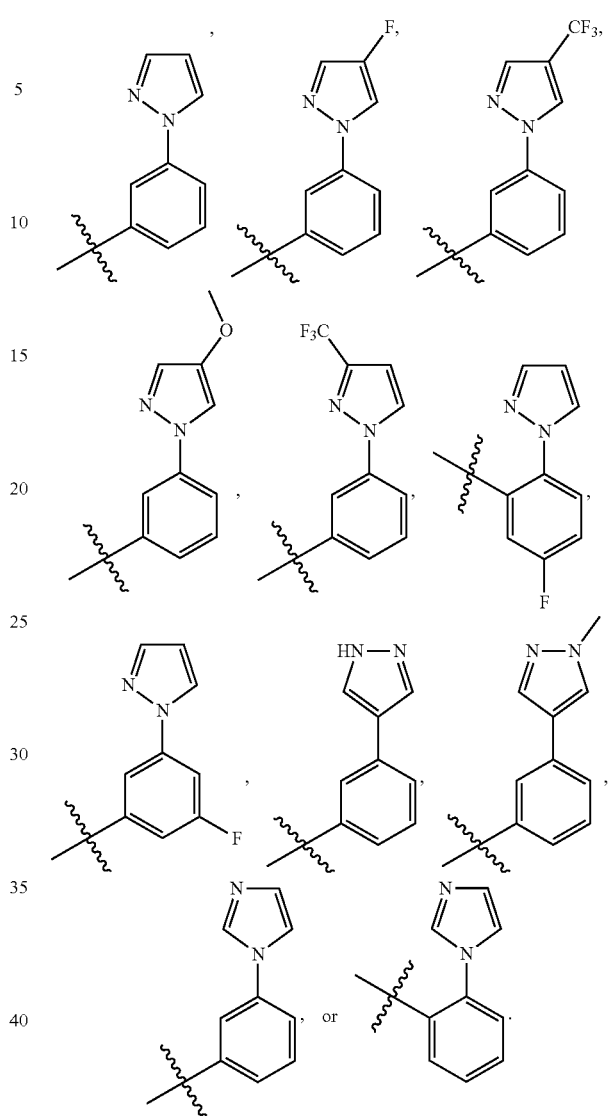
11. The method of claim 1, wherein $R^2$ is:
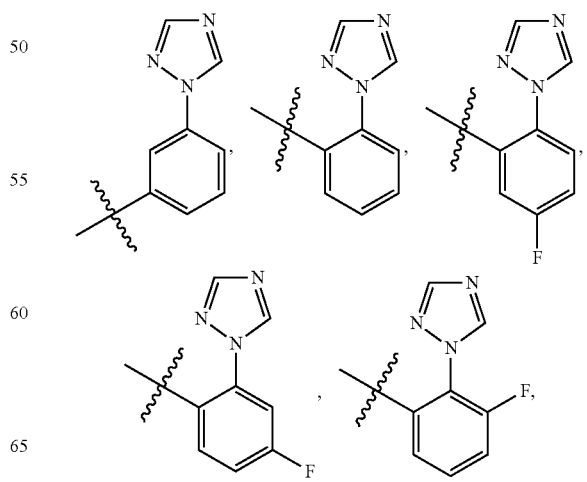

-continued
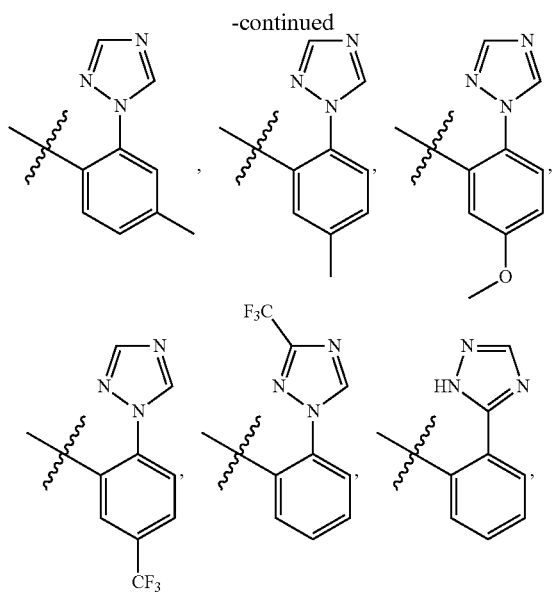
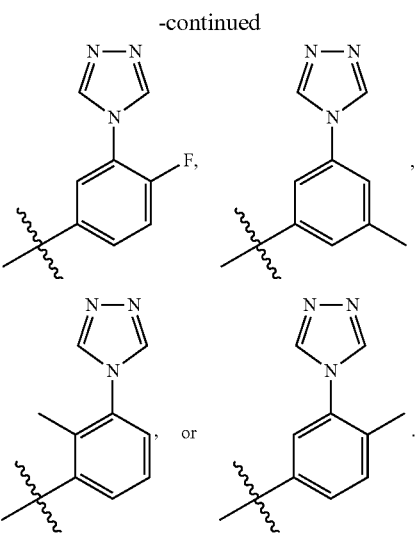
13. The method of claim 1, wherein R² is:
12. The method of claim 1, wherein R² is:
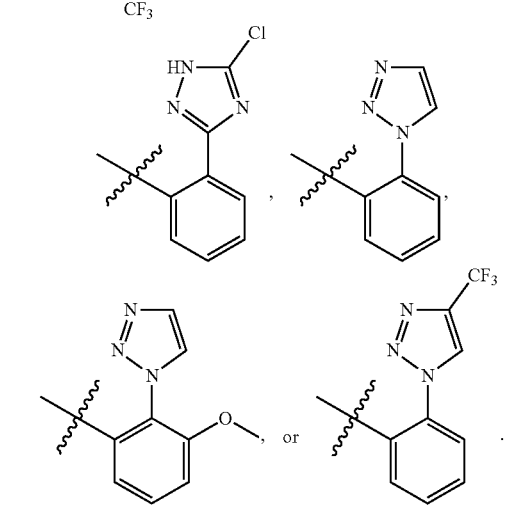
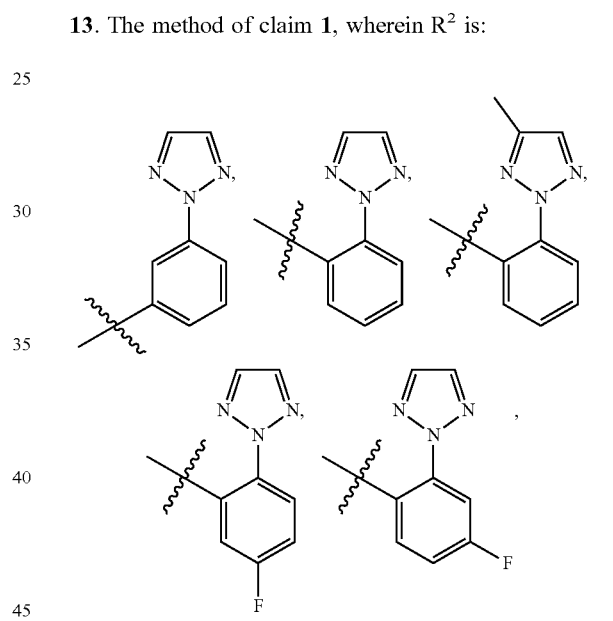
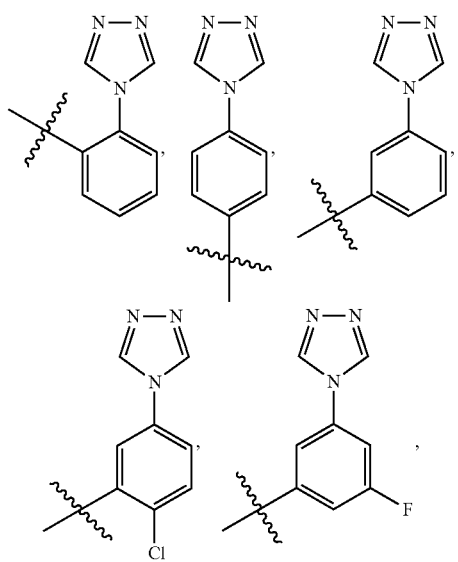
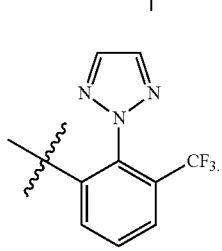

14. The method of claim 1, wherein R² is:

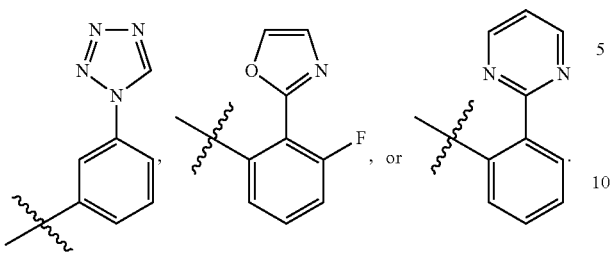

15. The method of claim 1, wherein R² is

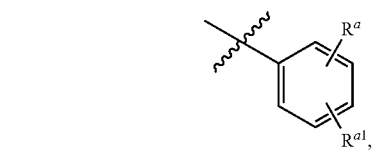

wherein Rᵃ is H, Cl, Br, F, or OCH₃, and Rᵃ¹ is OCH₃ or

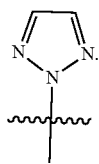 [SMILES: *n1nccn1]

16. The method of claim 1, wherein R² is:

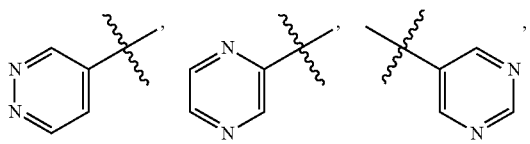

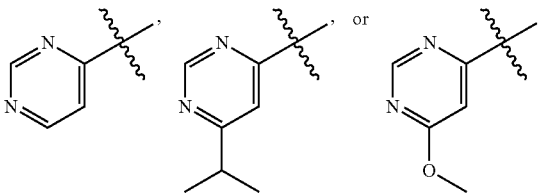

17. The method of claim 1, wherein the condition is major depressive disorder.

18. The method of claim 1, wherein the condition is treatment resistant depression.

19. The method of claim 1, wherein the condition is anxious depression.

20. The method of claim 1, wherein the condition is bipolar disorder.

* * * * *